(12) United States Patent
Lyne et al.

(10) Patent No.: US 7,358,054 B2
(45) Date of Patent: Apr. 15, 2008

(54) ANTIBODIES TO VLA-1

(75) Inventors: Paul D Lyne, Arlington, MA (US);
Ellen A Garber, Cambridge, MA (US);
Jose W Saldanha, Middlesex (GB);
Michael Karpusas, Upper Darby, PA (US)

(73) Assignee: Biogen Idec Ma Inc., Cambridge, MA (US)

( * ) Notice: Subject to any disclaimer, the term of this patent is extended or adjusted under 35 U.S.C. 154(b) by 0 days.

(21) Appl. No.: 10/474,832

(22) PCT Filed: Apr. 12, 2002

(86) PCT No.: PCT/US02/11521

§ 371 (c)(1),
(2), (4) Date: Oct. 14, 2003

(87) PCT Pub. No.: WO02/083854

PCT Pub. Date: Oct. 24, 2002

(65) Prior Publication Data

US 2004/0081651 A1    Apr. 29, 2004

Related U.S. Application Data

(60) Provisional application No. 60/283,794, filed on Apr. 13, 2001, provisional application No. 60/303,689, filed on Jul. 6, 2001.

(51) Int. Cl.
*G01N 33/53* (2006.01)
*C12N 5/20* (2006.01)
*C07K 16/46* (2006.01)
*C07K 16/28* (2006.01)

(52) U.S. Cl. ............... 435/7.1; 530/388.22; 530/387.3; 435/326

(58) Field of Classification Search ............ None
See application file for complete search history.

(56) References Cited

U.S. PATENT DOCUMENTS

| | | |
|---|---|---|
| 5,391,481 A | 2/1995 | Chess et al. |
| 5,565,332 A | 10/1996 | Hoogenboom et al. |
| 5,648,260 A | 7/1997 | Winter et al. |
| 5,733,743 A | 3/1998 | Johnson et al. |
| 5,788,966 A | 8/1998 | Chess et al. |
| 5,789,650 A | 8/1998 | Lonberg et al. |
| 5,798,230 A | 8/1998 | Bornkamm et al. |
| 5,827,690 A | 10/1998 | Meade et al. |
| 5,855,888 A | 1/1999 | Nishida et al. |
| 6,001,961 A | 12/1999 | Jonczyk et al. |
| 6,016,159 A | 1/2000 | Faris ............... 348/57 |
| 6,075,181 A | 6/2000 | Kucherlapati et al. |
| 6,127,524 A | 10/2000 | Casipit et al. ........ 530/387.3 |
| 6,150,584 A | 11/2000 | Kucherlapati et al. |
| 6,162,963 A | 12/2000 | Kucherlapati et al. |
| 6,180,370 B1 | 1/2001 | Queen et al. |
| 6,291,650 B1 | 9/2001 | Winter et al. |
| 6,300,064 B1 | 10/2001 | Knappik et al. |
| 6,303,313 B1 | 10/2001 | Wigler et al. |
| 6,307,026 B1 | 10/2001 | King et al. |
| 6,326,403 B1 | 12/2001 | Hölzemann et al. |
| 6,632,927 B2 * | 10/2003 | Adair et al. ............ 530/387.3 |

FOREIGN PATENT DOCUMENTS

| | | |
|---|---|---|
| EP | 0 239 400 A2 | 9/1987 |
| EP | 0 843 961 A1 | 5/1998 |
| JP | 08-131185 | 5/1996 |
| WO | WO 90/07861 A1 | 7/1990 |
| WO | WO 99/61040 A2 | 12/1999 |
| WO | WO 99/61040 A3 | 12/1999 |
| WO | WO 00/20459 A1 | 4/2000 |
| WO | WO 00/72881 A1 | 12/2000 |
| WO | WO 01/73444 A2 | 10/2001 |
| WO | WO 01/96365 A1 | 12/2001 |

OTHER PUBLICATIONS

Panka et al. Variable region framework differences result in decreased or increased affinity of variant anti-digoxin antibodies. Proc Natl Acad Sci U S A. May 1988;85(9):3080-4.*
R. Briesewitz et al., "Expression of Native and Truncated Forms of the Human Integrin α1 Subunit," *J. Bio. Chem.*, 268:2989-2996 (1993).
A. R. de Fougerolles et al., "Regulation of Inflammation by Collagen-Binding Integrins α1β1 and α2β1 in Models of Hypersensitivity and Arthritis," *J. Clin. Invest.*, 105:721-729 (2000).
M. Fabbri et al., "A Functional Monoclonal Antibody Recognizing the Human alpha1-Integrin I-Domain," *Tissue Antigens*, 48:47-51 (1996).
I. Bank et al., "Analysis of Recombinant Human α1 Integrin I-Domain with a Function-Blocking Monoclonal Antibody 1B3.1," *Isr. Med. Assoc. J.*, 2:19-20 (2000).
S.C.G. Brezinsky et al., "A Simple Method for Enriching Populations of Transfected CHO Cells for Cells of Higher Specific Productivity," *J. Immunol. Methods*, 277:141-155 (2003).
H. T. Cook et al., "Treatment with an Antibody to VLA-1 Integrin Reduces Glomerular and Tubulointerstitial Scarring in a Rat Model of Crescentic Glomerulonephritis," *Am. J. Pathol.*, 161:1265-1272 (2002).
T. O. Fischmann et al., "Crystallographic Refinement of the Three-Dimensional Structure of the FabD1.3-Lysozyme Complex at 2.5-Å Resolution," *J. Biol. Chem.*, 266:12915-12920 (1991).

(Continued)

*Primary Examiner*—Maher M. Haddad
(74) *Attorney, Agent, or Firm*—Lowrie, Lando & Anastasi, LLP

(57) ABSTRACT

Antibodies that specifically bind to VLA-1 integrin and methods of using these antibodies to treat immunological disorders in a subject. Also included are crystal structures of complexes formed by VLA-1 antibodies and their ligands, and VLA-1 antagonists and agonists identified by using the structure coordinates of these structures.

25 Claims, 131 Drawing Sheets

OTHER PUBLICATIONS

M. A. Holmes et al., "Conformational Correction Mechanisms Aiding Antigen Recognition by a Humanized Antibody," *J. Exp. Med.*, 187:479-485 (1998).

A. Ianaro et al., "Anti-Very Late Antigen-1 Monoclonal Antibody Modulates the Development of Secondary Lesion and T-Cell Response in Experimental Arthritis," *Lab. Invest.*, 80:73-80 (2000).

M. Karpusas et al., "Crystal Structure of the α1β1 Integrin I Domain in Complex with an Antibody Fab Fragment," *J. Mol. Biol.*, 327:1031-1041 (2003).

Y. Li et al., "Three-Dimensional Structures of the Free and Antigen-Bound Fab from Monoclonal Antilysozyme Antibody HyHEL-63," *Biochemistry*, 39:6296-6309 (2000).

N. S. Sampson et al., "Global Gene Expression Analysis Reveals a Role for the $α_1$ Integrin in Renal Pathogenesis," *J. Biol. Chem.*, 276:34182-34188 (2001).

E.T. Baldwin et al., "Cation Binding to the Integrin CD11b I Domain and Activation Model Assessment," *Structure*,6:923-935 (1998).

R. Briesewitz et al., "Expression of Native and Truncated Forms of the Human Integrin $α_1$ Subunit," *J. Biol. Chem.*, 268:2989-2996 (1993).

P. Carter et al., "Humanization of an Anti-p185$^{HER2}$ Antibody for Human Cancer Therapy," *Proc. Natl. Acad. Sci. USA*, 89:4285-4289 (1992).

C. Chothia et al., "Conformations of Immunoglobulin Hypervariable Regions," *Nature*, 342:877-883 (1989).

M.S. Co et al., "Humanized Antibodies for Antiviral Therapy," *Proc. Nat. Acad. Sci. USA*, 88:2869-2873 (1991).

A.L. Corbi et al., "The Human Leukocyte Adhesion Glycoprotein Mac-1 (Complement Receptor Type 3, CD11b) α Subunit," *J. Biol. Chem.*, 263:12403-12411 (1988).

A.L. Corbi et al., "cDNA Cloning and Complete Primary Structure of the α Subunit of a Leukocyte Adhesion Glycoprotein, P150,95," *EMBO J.*, 6:4023-4028 (1987).

D. Cosgrove, et al., "Integrin α1β1 and Transforming Growth Factor-β1 Play Distinct Roles in Alport Glomerular Pathogenesis and Serve as Dual Targets for Metabolic Therapy," *Am. J. Path.*, 157:1649-1659 (2000).

D.R. Davies and G.H. Cohen, "Interactions of Protein Antigens with Antibodies," *Proc. Natl. Acad. Sci. USA*, 93:7-12 (1996).

A.R. de Fougerolles et al., "Global Expression Analysis of Extracellular Matrix-Integrin Interactions in Monocytes," *Immunity*, 13:749-758 (2000).

C.P. Edwards et al., "Identification of Amino Acids in the CD11a I-domain Important for Binding of the Leukocyte Function-associated Antigen-1 (LFA-1) to Intercellular Adhesion Molecule-1 (ICAM-1)", *J. Biol. Chem.*, 270, 12635-12640 (1995).

C. Eigenbrot et al., "X-ray Structures of the Antigen-binding Domains from Three Variants of Humanized anti-p185$^{HER2}$ Antibody 4D5 and Comparison with Molecular Modeling," *J. Mol. Biol.*, 229:969-995 (1993).

J. Emsley et al., "Structural Basis of Collagen Recognition by Integrin α2β1," *Cell*, 100:47-56 (2000).

J. Emsley et al., "Crystal Structure of the I Domain from Integrin α2β1," *J. Biol. Chem.*, 272:28512-28517 (1997).

J. Foote and G. Winter, "Antibody Framework Residues Affecting the Conformation of the Hypervariable Loops," *J. Mol. Biol.*, 224:487-499 (1992).

A.A. Gaspari and S.I. Katz, "Contact Hypersensitivity," *Current Protocols in Immunology*. J.E. Coligan, A.M. Kruisbeek, D.H. Margulies, E.M. Shevach, and W. Strober, editors. John Wiley & Sons, New York. Section 4.2.1-4.2.5 (1991).

P.J. Gotwals et al., "Divalent Cations Stabilize the α1β1 Integrin I Domain," *Biochemistry*, 38:8280-8288 (1999).

P.J. Gotwals et al., "The α1β1 Integrin Is Expressed during Neointima Formation in Rat Arteries and Mediates Collagen Matrix Reorganization," *J. Clin. Invest.*, 97:2469-2477 (1996).

M.H. Grayson et al., "αdβ2 Integrin Is Expressed on Human Eosinophils and Functions as an Alternative Ligand for Vascular Cell Adhesion Molecule 1 (VCAM-1), *J. Exp. Med.*, 188:2187-2191 (1988).

L.L. Green et al., "Antigen-specific Human Monoclonal Antibodies From Mice Engineered With Human Ig Heavy and Light Chain YACs," *Nature Genetics*, 7:13-21 (1994).

M.E. Hemler et al., "Very Late Activation Antigens on Rheumatoid Synovial Fluid T Lymphocytes: Association with Stages of T Cell Activation," *J. Clin. Invest.*, 78:696-702 (1986).

M.E. Hemler et al., "VLA-1: A T Cell Surface Antigen which Defines a Novel Late Stage of Human T Cell Activation," *Eur. J. Immunol.*, 15:502-508 (1985).

C. Huang and B.D. Stollar, "A Majority of Ig H Chain cDNA of Normal Human Adult Blood Lymphocytes Resembles cDNA for Fetal Ig and Natural Autoantibodies," *J. Immunol.*, 151:5290-5300 (1993).

B. Hurtrel et al., "Different Time Course Patterns of Local Expression of Delayed-Type Hypersensitivity to Sheep Red Blood Cells In Mice," *Cell. Immunol.*, 142:252-263 (1992).

J.R. Huth et al., "NMR and Mutagenesis Evidence for an I Domain Allosteric Site that Regulates Lymphocyte Function-Associated Antigen 1 Ligand Binding," *Proc. Natl. Acad. Sci. U.S.A.*, 97:5231-5236 (2000).

M.J. Ignatius et al., "Molecular Cloning of the Rat Integrin $α_1$-Subunit: A Receptor for Laminin and Collagen," *J. Cell Biol.*, 111, 709-720 (1990).

S. Jones and J.M. Thornton, "Principles of Protein-Protein Interactions," *Proc. Natl. Acad. Sci. USA*, 93:13-20 (1996).

P.T. Jones et al., "Replacing the Complementarity-Determining Regions in a Human Antibody with Those from a Mouse," *Nature*, 321:522-525 (1986).

K. Kakimoto et al., "The Effect of Anti-adhesion Molecule Antibody on the Development of Collagen-Induced Arthritis," *Cell. Immunol.*, 142:326-337 (1992).

T. Kamata et al., "Critical Threonine and Aspartic Acid Residues within the I Domains of β2 Integrins for Interactions with Intercellular Adhesion Molecule 1 (ICAM-1) and C3bi," *J. Biol. Chem.*, 270:12531-12535 (1995).

P.J. Keely et al., "Alteration of Collagen-Dependent Adhesion, Motility, and Morphogenesis by the Expression of Antisense $α_2$ Integrin mRNA in Mammary Cells," *J. Cell Sci.*, 108:595-607 (1995).

A. Kern, et al., "The Role of the I Domain in Ligand Binding of the Human Integrin $α_1β_1$," *J. Biol. Chem.*, 269:22811-22816 (1994).

T. Kinashi and T.A. Springer, "Adhesion Molecules in Hematopoietic Cells," *Blood Cells*, 20:25-44 (1994).

S.L. King, et al., "Echovirus 1 Interaction with the Human Very Late Antigen-2 (Integrin α2β1) I Domain," *J. Biol. Chem.*, 272:28518-28522 (1997).

C.G. Knight et al., "The Collagen-binding A-domains of Integrins $α_1β_1$ and $α_2β_1$ Recognize the Same Specific Amino Acid Sequence, GFOGER, in Native (Triple-helical) Collagens," *J. Biol. Chem.*, 275:35-40 (2000).

F. Kolbinger et al., "Humanization of a Mouse Anti-human IgE Antibody: A Potential Therapeutic for IgE-mediated Allergies," *Protein Eng.*, 6:971-980 (1993).

O. Langholz et al., "Collagen and Collagenase Gene Expression in Three-dimensional Collagen Lattices Are Differentially Regulated by α1β1 and α2β1Integrins," *J. Cell Biol.*, 131:1903-1915 (1995).

R.S. Larson et al., "Primary Structure of the Leukocyte Function-associated Molecule-1 α Subunit: An Integrin with an Embedded Domain Defining a Protein Superfamily," *J. Cell Biol.*, 108:703-712 (1989).

J.-O. Lee et al., "Crystal Structure of the A Domain from the α Subunit of Integrin CR3 (CD11b/CD18)," *Cell*, 80:631-638 (1995).

J.-O. Lee et al., "Two Conformations of the Integrin A-domain (I-domain): A Pathway for Activation?" *Structure*, 3:1333-1340 (1995).

F. Mackay et al., "Lymphotoxin β Receptor Triggering Induces Activation of the Nuclear Factor κB Transcription Factor in Some Cell Types," *J. Biol. Chem.*, 271:24934-24938 (1996).

M.J. Mendez et al., "Functional Transplant of Megabase Human Immunoglobulin Loci Recapitulates Human Antibody. Response in Mice," *Nature Genetics*, 15:146-156 (1997).

D.L. Mendrick et al., "Glomerular Epithelial and Mesangial Cells Differentially Modulate the Binding Specificities of VLA-1 and VLA-2," *Lab. Invest.*, 72:367-375 (1995).

D.L. Mendrick and D.M. Kelly, "Temporal Expression of VLA-2 and Modulation of its Ligand Specificity by Rat Glomerular Epithelial Cells In vitro," *Lab. Invest.*, 69:690-702 (1993).

M. Michishita et al., "A Novel Divalent Cation-Binding Site in the A Domain of the β2 Integrin CR3 (CD11b/CD18) is Essential for Ligand Binding," *Cell*, 72:857-867 (1993).

S. Miyake et al., "β1 Integrin-mediated Interaction with Extracellular Matrix Proteins Regulates Cytokine Gene Expression in Synovial Fluid Cells of Rheumatoid Arthritis Patients," *J. Exp. Med.*, 177:863-868 (1993).

K. Miyake et al., "Evidence for a Role of the Integrin VLA-4 in Lympho-hemopoiesis," *J. Exp. Med.*, 173:599-607 (1991).

P. Mombaerts et al., "RAG-1-Deficient Mice Have No Mature B and T Lymphocytes," *Cell*, 68:869-877 (1992).

L. Mori et al., "Attenuation of Collagen-Induced Arthritis in 55-kDa TNF Receptor Type 1 (TNFR1)-IgG1-Treated and TNFR1-Deficient Mice," *J. Immunol.*, 157:3178-3182 (1996).

Y.A. Muller et al., "VEGF and the Fab Fragment of a Humanized Neutralizing Antibody: Crystal Structure of the Complex at 2.4 Å Resolution and Mutational Analysis of the Interface," *Structure*, 6:1153-1167 (1998).

M. Nolte et al., "Crystal Structure of the α1β1 Integrin I-Domain: Insights into Integrin I-Domain Function," *FEBS Lett.*, 452:379-385 (1999).

K. Noto et al., "Identification and Functional Characterization of Mouse CD29 with a mAb," *Int. Immunol.*, 7:835-842 (1995).

R. Orlandi et al., "Cloning Immunoglobulin Variable Domains for Expression by the Polymerase Chain Reaction," *Proc. Natl. Acad. Sci. USA*, 86:3833-3837 (1989).

D. Plows et al., "Mice Lacking Mature T and B Lymphocytes Develop Arthritic Lesions After Immunization with Type II Collagen," *J. Immunol.*, 162:1018-1023 (1999).

A. Qu and D.J. Leahy, "The Role of the Divalent Cation in the Structure of the I Domain from the CD11a/CD18 Integrin," *Structure*, 4:931-942 (1996).

A. Qu and D.J. Leahy, "Crystal Structure of the I-Domain from the CD11a/CD18 (LFA-1, $α_L β_2$) Integrin," *Proc. Natl. Acad. Sci. USA*, 92:10277-10281 (1995).

R.L. Rich et al., "Trench-shaped Binding Sites Promote Multiple Classes of Interactions between Collagen and the Adherence Receptors, $α_1 β_1$ Integrin and *Staphylococcus aureus* Cna MSCRAMM," *J. Biol. Chem.*, 274:24906-24913 (1999).

L. Riechmann et al., "Reshaping Human Antibodies for Therapy," *Nature*, 332:323-327 (1988).

T. Riikonen et al., "Transforming Growth Factor-β Regulates Collagen Gel Contraction by Increasing α2β1 Integrin Expression in Osteogenic Cells," *J. Biol. Chem.*, 270:376-382 (1995).

A. Scheynius et al. "Reduced Contact Sensitivity Reactions in Mice Treated with Monoclonal Antibodies to Leukocyte Function-Associated Molecule-1 and Intercellular Adhesion Molecule-1," *J. Immunol.*, 150:655-663 (1993).

J.A. Schiro et al., "Integrin $α^2 β_1$ (VLA-2) Mediates Reorganization and Contraction of Collagen Matrices by Human Cells," *Cell*, 67:403-410 (1991).

D. Seiffge, "Protective Effects of Monoclonal Antibody to VLA-4 on Leukocyte Adhesion and Course of Disease in Adjuvant Arthritis in Rats," *J. Rheumatol.*, 23:2086-2091 (1996).

S.K. Shaw et al., "Molecular Cloning of the Human Mucosal Lymphocyte Integrin $α^E$ Subunit," *J. Biol. Chem.*, 269:6016-6025 (1994).

A. Sonnenberg et al., "A Complex of Platelet Glycoproteins Ic and IIa Identified by a Rat Monoclonal Antibody," *J. Biol. Chem.*, 262:10376-10383 (1987).

T.A. Springer, "Adhesion Receptors of the Immune System," *Nature*, 346:425-434 (1990).

Y. Takada and M.E. Hemler, "The Primary Structure of the VLA-2/Collagen Receptor $α^2$ Subunit (Platelet GPIa): Homology to Other Integrins and the Presence of a Possible Collagen-binding Domain," *J. Cell Biol.*, 109:397-407 (1989).

P.C. Taylor et al., "Transfer of Type II Collagen-Induced Arthritis From DBA/1 to Severe Combined Immunodeficiency Mice Can Be Prevented by Blockage to Mac-1," *Immunology*, 88:315-321 (1996).

T.F. Tedder et al., "L-Selectin-deficient Mice Have Impaired Leukocyte Recruitment Into Inflammatory Sites," *J. Exp. Med.*, 181:2259-2264 (1995).

P.R. Tempest et al., "Reshaping a Human Monoclonal Antibody to Inhibit Human Respiratory Syncytial Virus Infection In vivo," *Bio/Technology*, 9:266-271 (1991).

M. Terashite et al., "Enhancement of Delayed-Type Hypersensitivity to Sheep Red Blood Cells in Mice by Granulocyte Colony-Stimulating Factor Administration at the Elicitation Phase," *J. Immunol.*, 156:4638-4643 (1996).

K. Terato et al., "Collagen-Induced Arthritis in Mice: Synergistic Effect of *E. coli* Lipopolysaccharide Bypasses Epitope Specificity in the Induction of Arthritis with Monoclonal Antibodies to Type II Collagen," *Autoimmunity*, 22:137-147 (1995).

K. Terato et al.,"Induction of Arthritis with Monoclonal Antibodies to Collagen," *J. Immunol.*, 148:2103-2108 (1992).

K. Tomizuka et al., "Functional Expression and Germline Transmission of a Human Chromosome Fragment in Chimaeric Mice," *Nature Genetics*, 16:133-143 (1997).

M. Verhoeyen et al., "Reshaping Human Antibodies: Grafting an Antilysozyme Activity," *Science*, 239:1534-1536 (1988).

E.S. Ward et al., "Binding Activities of a Repertoire of Single Immunoglobulin Variable Domains Secreted from *Escherichia coli*," *Nature*, 341:544-546 (1989).

M. Welschof et al., "Amino Acid Sequence based PCR Primers for Amplification of Rearranged Human Heavy and Light Chain Immunoglobulin Variable Region Genes," *J. Immunol. Meth.*, 179:203-214 (1995).

Shimoka,"Computational Design of an Integrin I Domain, etc.", Nature Structural Biology, vol. 7, No. 8 (Aug. 2000), pp. 674-678.

Bella Jordi,"Integrin-collagen complex:a metal glutamate handshake", Structure (London), vol. 8, No. 6 Jun. 15 2000), pp. R121-R126.

Leibiger et al., "Variable domain-linked oligosaccharides of a human monoclonal IgG: structure and influence on antigen binding," *Biochem. J.* 338:529-238, 1999.

Shakin-Eshleman et al., "The Amino Acid at the *X* Position of an Asn-*X*-Ser Sequon is an Important Determinant of N-Linked Coreglycosylation Efficiency," *J. Biol. Chem.* 271:6363-6366, 1996.

Wright and Morrison, "Effect of Altered $C_H2$-associated Carbohydrate Structure on the Functional Properties and In Vivo Fate of Chimeric Mouse-Human Immunoglobulin G1," *J. Exp. Med.* 180:1087-1096, 1994.

* cited by examiner

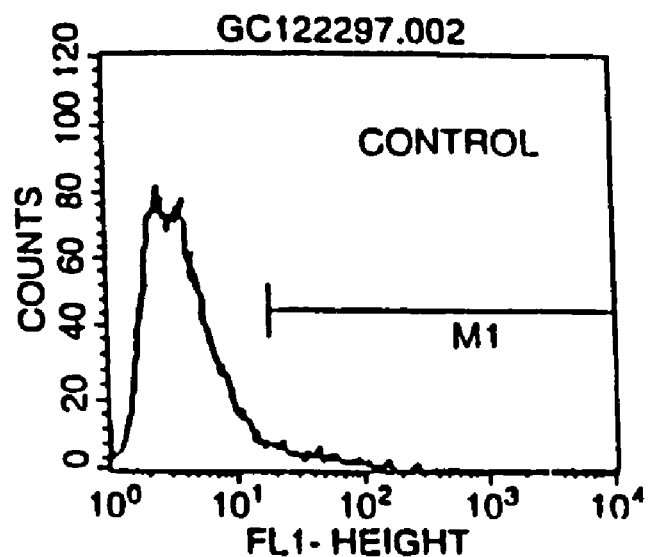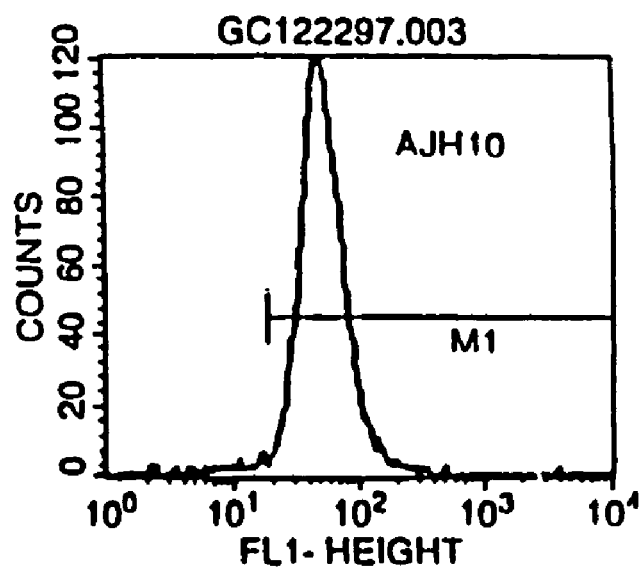
FIG. 14

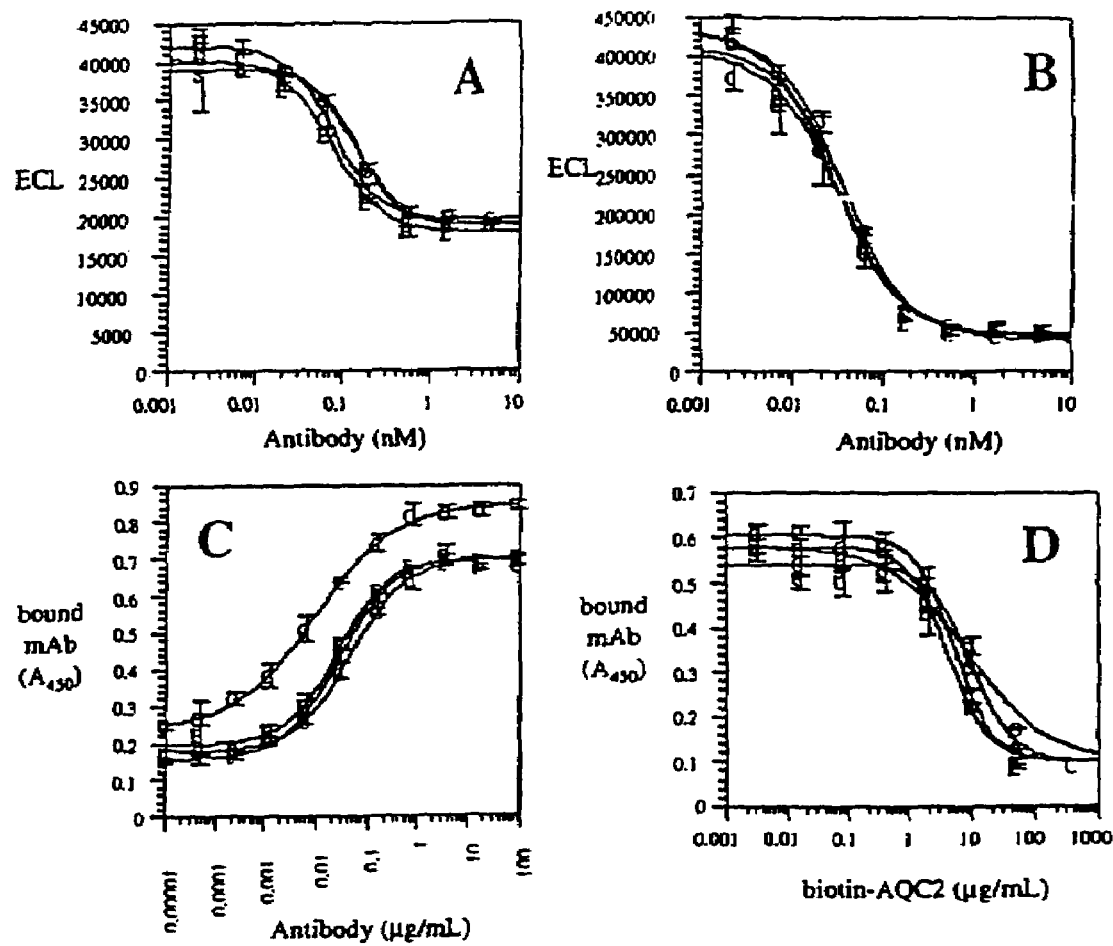
FIGS. 16 A, B, C, D

Fig. 19: A-1

| ATOM | 1 | CB | THR | 145 | 131.250 | 52.244 | -9.297 | 1.00 | 82.68 | A | C |
|---|---|---|---|---|---|---|---|---|---|---|---|
| ATOM | 2 | OG1 | THR | 145 | 131.373 | 51.127 | -10.191 | 1.00 | 82.68 | A | O |
| ATOM | 3 | CG2 | THR | 145 | 132.601 | 52.936 | -9.145 | 1.00 | 82.68 | A | C |
| ATOM | 4 | C | THR | 145 | 129.280 | 51.301 | -8.080 | 1.00 | 146.54 | A | C |
| ATOM | 5 | O | THR | 145 | 128.489 | 51.352 | -7.134 | 1.00 | 146.94 | A | O |
| ATOM | 6 | N | THR | 145 | 131.576 | 50.663 | -7.360 | 1.00 | 144.92 | A | N |
| ATOM | 7 | CA | THR | 145 | 130.726 | 51.757 | -7.915 | 1.00 | 144.52 | A | C |
| ATOM | 8 | N | GLN | 146 | 128.941 | 50.856 | -9.288 | 1.00 | 36.14 | A | N |
| ATOM | 9 | CA | GLN | 146 | 127.592 | 50.397 | -9.569 | 1.00 | 34.29 | A | C |
| ATOM | 10 | CB | GLN | 146 | 127.046 | 51.086 | -10.823 | 1.00 | 99.89 | A | C |
| ATOM | 11 | CG | GLN | 146 | 127.887 | 50.902 | -12.065 | 1.00 | 99.89 | A | C |
| ATOM | 12 | CD | GLN | 146 | 127.274 | 51.575 | -13.279 | 1.00 | 99.89 | A | C |
| ATOM | 13 | OE1 | GLN | 146 | 127.787 | 51.454 | -14.392 | 1.00 | 99.89 | A | O |
| ATOM | 14 | NE2 | GLN | 146 | 126.170 | 52.290 | -13.070 | 1.00 | 99.89 | A | N |
| ATOM | 15 | C | GLN | 146 | 127.535 | 48.883 | -9.721 | 1.00 | 34.71 | A | C |
| ATOM | 16 | O | GLN | 146 | 128.084 | 48.314 | -10.667 | 1.00 | 36.57 | A | O |
| ATOM | 17 | N | LEU | 147 | 126.876 | 48.240 | -8.762 | 1.00 | 33.54 | A | N |
| ATOM | 18 | CA | LEU | 147 | 126.718 | 46.794 | -8.767 | 1.00 | 32.67 | A | C |
| ATOM | 19 | CB | LEU | 147 | 127.491 | 46.143 | -7.609 | 1.00 | 35.25 | A | C |
| ATOM | 20 | CG | LEU | 147 | 128.963 | 46.398 | -7.301 | 1.00 | 35.44 | A | C |
| ATOM | 21 | CD1 | LEU | 147 | 129.205 | 47.877 | -7.087 | 1.00 | 30.65 | A | C |
| ATOM | 22 | CD2 | LEU | 147 | 129.325 | 45.637 | -6.037 | 1.00 | 35.29 | A | C |
| ATOM | 23 | C | LEU | 147 | 125.247 | 46.451 | -8.575 | 1.00 | 31.65 | A | C |
| ATOM | 24 | O | LEU | 147 | 124.506 | 47.194 | -7.939 | 1.00 | 32.95 | A | O |
| ATOM | 25 | N | ASP | 148 | 124.832 | 45.325 | -9.142 | 1.00 | 25.19 | A | N |
| ATOM | 26 | CA | ASP | 148 | 123.477 | 44.817 | -8.976 | 1.00 | 22.65 | A | C |
| ATOM | 27 | CB | ASP | 148 | 122.907 | 44.329 | -10.302 | 1.00 | 27.55 | A | C |
| ATOM | 28 | CG | ASP | 148 | 122.330 | 45.446 | -11.125 | 1.00 | 27.17 | A | C |
| ATOM | 29 | OD1 | ASP | 148 | 121.787 | 45.158 | -12.208 | 1.00 | 26.28 | A | O |
| ATOM | 30 | OD2 | ASP | 148 | 122.413 | 46.612 | -10.686 | 1.00 | 25.35 | A | O |
| ATOM | 31 | C | ASP | 148 | 123.664 | 43.638 | -8.025 | 1.00 | 19.03 | A | C |
| ATOM | 32 | O | ASP | 148 | 124.119 | 42.567 | -8.422 | 1.00 | 18.33 | A | O |
| ATOM | 33 | N | ILE | 149 | 123.341 | 43.848 | -6.760 | 1.00 | 16.75 | A | N |
| ATOM | 34 | CA | ILE | 149 | 123.502 | 42.809 | -5.761 | 1.00 | 15.69 | A | C |
| ATOM | 35 | CB | ILE | 149 | 124.041 | 43.391 | -4.442 | 1.00 | 18.53 | A | C |
| ATOM | 36 | CG2 | ILE | 149 | 124.401 | 42.269 | -3.485 | 1.00 | 13.54 | A | C |
| ATOM | 37 | CG1 | ILE | 149 | 125.271 | 44.251 | -4.718 | 1.00 | 14.25 | A | C |
| ATOM | 38 | CD1 | ILE | 149 | 125.819 | 44.932 | -3.497 | 1.00 | 17.00 | A | C |
| ATOM | 39 | C | ILE | 149 | 122.185 | 42.129 | -5.456 | 1.00 | 17.34 | A | C |
| ATOM | 40 | O | ILE | 149 | 121.191 | 42.794 | -5.181 | 1.00 | 17.74 | A | O |
| ATOM | 41 | N | VAL | 150 | 122.175 | 40.805 | -5.526 | 1.00 | 11.00 | A | N |
| ATOM | 42 | CA | VAL | 150 | 120.987 | 40.036 | -5.193 | 1.00 | 12.56 | A | C |
| ATOM | 43 | CB | VAL | 150 | 120.571 | 39.089 | -6.336 | 1.00 | 16.85 | A | C |
| ATOM | 44 | CG1 | VAL | 150 | 119.409 | 38.210 | -5.885 | 1.00 | 19.04 | A | C |
| ATOM | 45 | CG2 | VAL | 150 | 120.164 | 39.894 | -7.555 | 1.00 | 18.66 | A | C |
| ATOM | 46 | C | VAL | 150 | 121.367 | 39.212 | -3.970 | 1.00 | 10.12 | A | C |
| ATOM | 47 | O | VAL | 150 | 122.387 | 38.526 | -3.973 | 1.00 | 8.27 | A | O |
| ATOM | 48 | N | ILE | 151 | 120.573 | 39.303 | -2.912 | 1.00 | 20.50 | A | N |
| ATOM | 49 | CA | ILE | 151 | 120.856 | 38.537 | -1.699 | 1.00 | 19.30 | A | C |
| ATOM | 50 | CB | ILE | 151 | 120.653 | 39.392 | -0.439 | 1.00 | 14.22 | A | C |
| ATOM | 51 | CG2 | ILE | 151 | 121.039 | 38.601 | 0.785 | 1.00 | 10.58 | A | C |
| ATOM | 52 | CG1 | ILE | 151 | 121.515 | 40.659 | -0.532 | 1.00 | 12.64 | A | C |
| ATOM | 53 | CD1 | ILE | 151 | 121.283 | 41.660 | 0.593 | 1.00 | 14.62 | A | C |
| ATOM | 54 | C | ILE | 151 | 119.931 | 37.329 | -1.646 | 1.00 | 17.42 | A | C |
| ATOM | 55 | O | ILE | 151 | 118.715 | 37.459 | -1.777 | 1.00 | 17.66 | A | O |
| ATOM | 56 | N | VAL | 152 | 120.511 | 36.150 | -1.470 | 1.00 | 17.56 | A | N |
| ATOM | 57 | CA | VAL | 152 | 119.741 | 34.915 | -1.428 | 1.00 | 18.41 | A | C |
| ATOM | 58 | CB | VAL | 152 | 120.395 | 33.849 | -2.309 | 1.00 | 11.45 | A | C |
| ATOM | 59 | CG1 | VAL | 152 | 119.470 | 32.664 | -2.460 | 1.00 | 10.58 | A | C |
| ATOM | 60 | CG2 | VAL | 152 | 120.758 | 34.458 | -3.667 | 1.00 | 7.89 | A | C |
| ATOM | 61 | C | VAL | 152 | 119.675 | 34.404 | -0.003 | 1.00 | 16.31 | A | C |
| ATOM | 62 | O | VAL | 152 | 120.602 | 33.755 | 0.469 | 1.00 | 9.91 | A | O |
| ATOM | 63 | N | LEU | 153 | 118.568 | 34.692 | 0.672 | 1.00 | 19.79 | A | N |
| ATOM | 64 | CA | LEU | 153 | 118.367 | 34.297 | 2.061 | 1.00 | 19.90 | A | C |
| ATOM | 65 | CB | LEU | 153 | 117.530 | 35.361 | 2.766 | 1.00 | 21.44 | A | C |
| ATOM | 66 | CG | LEU | 153 | 118.250 | 36.403 | 3.623 | 1.00 | 23.22 | A | C |
| ATOM | 67 | CD1 | LEU | 153 | 119.699 | 36.561 | 3.185 | 1.00 | 23.73 | A | C |
| ATOM | 68 | CD2 | LEU | 153 | 117.494 | 37.721 | 3.530 | 1.00 | 25.76 | A | C |
| ATOM | 69 | C | LEU | 153 | 117.732 | 32.929 | 2.300 | 1.00 | 20.96 | A | C |
| ATOM | 70 | O | LEU | 153 | 116.724 | 32.574 | 1.690 | 1.00 | 19.96 | A | O |
| ATOM | 71 | N | ASP | 154 | 118.336 | 32.165 | 3.200 | 1.00 | 19.89 | A | N |
| ATOM | 72 | CA | ASP | 154 | 117.820 | 30.854 | 3.554 | 1.00 | 19.37 | A | C |
| ATOM | 73 | CB | ASP | 154 | 118.952 | 29.983 | 4.129 | 1.00 | 22.72 | A | C |

Fig. 19: A-2

| | | | | | | | | | | | |
|---|---|---|---|---|---|---|---|---|---|---|---|
| ATOM | 74 | CG | ASP | 154 | 118.486 | 28.601 | 4.546 | 1.00 | 21.92 | A | C |
| ATOM | 75 | OD1 | ASP | 154 | 117.266 | 28.363 | 4.537 | 1.00 | 25.43 | A | O |
| ATOM | 76 | OD2 | ASP | 154 | 119.340 | 27.754 | 4.893 | 1.00 | 18.24 | A | O |
| ATOM | 77 | C | ASP | 154 | 116.770 | 31.153 | 4.623 | 1.00 | 22.71 | A | C |
| ATOM | 78 | O | ASP | 154 | 117.062 | 31.802 | 5.630 | 1.00 | 19.03 | A | O |
| ATOM | 79 | N | GLY | 155 | 115.540 | 30.718 | 4.393 | 1.00 | 3.06 | A | N |
| ATOM | 80 | CA | GLY | 155 | 114.491 | 30.948 | 5.370 | 1.00 | 5.13 | A | C |
| ATOM | 81 | C | GLY | 155 | 113.840 | 29.638 | 5.788 | 1.00 | 6.39 | A | C |
| ATOM | 82 | O | GLY | 155 | 112.751 | 29.633 | 6.368 | 1.00 | 8.88 | A | O |
| ATOM | 83 | N | SER | 156 | 114.512 | 28.521 | 5.494 | 1.00 | 19.70 | A | N |
| ATOM | 84 | CA | SER | 156 | 114.011 | 27.191 | 5.832 | 1.00 | 24.28 | A | C |
| ATOM | 85 | CB | SER | 156 | 114.994 | 26.111 | 5.353 | 1.00 | 33.45 | A | C |
| ATOM | 86 | OG | SER | 156 | 116.261 | 26.252 | 5.967 | 1.00 | 36.37 | A | O |
| ATOM | 87 | C | SER | 156 | 113.773 | 27.054 | 7.330 | 1.00 | 21.27 | A | C |
| ATOM | 88 | O | SER | 156 | 114.270 | 27.843 | 8.128 | 1.00 | 24.45 | A | O |
| ATOM | 89 | N | ASN | 157 | 113.008 | 26.037 | 7.700 | 1.00 | 21.98 | A | N |
| ATOM | 90 | CA | ASN | 157 | 112.686 | 25.802 | 9.091 | 1.00 | 19.06 | A | C |
| ATOM | 91 | CB | ASN | 157 | 112.027 | 24.435 | 9.247 | 1.00 | 21.82 | A | C |
| ATOM | 92 | CG | ASN | 157 | 110.586 | 24.434 | 8.785 | 1.00 | 23.31 | A | C |
| ATOM | 93 | OD1 | ASN | 157 | 109.944 | 23.385 | 8.706 | 1.00 | 20.38 | A | O |
| ATOM | 94 | ND2 | ASN | 157 | 110.066 | 25.612 | 8.479 | 1.00 | 20.59 | A | N |
| ATOM | 95 | C | ASN | 157 | 113.859 | 25.913 | 10.048 | 1.00 | 17.03 | A | C |
| ATOM | 96 | O | ASN | 157 | 113.720 | 26.498 | 11.132 | 1.00 | 15.01 | A | O |
| ATOM | 97 | N | SER | 158 | 115.006 | 25.367 | 9.653 | 1.00 | 15.99 | A | N |
| ATOM | 98 | CA | SER | 158 | 116.179 | 25.378 | 10.510 | 1.00 | 14.20 | A | C |
| ATOM | 99 | CB | SER | 158 | 117.327 | 24.603 | 9.864 | 1.00 | 26.18 | A | C |
| ATOM | 100 | OG | SER | 158 | 117.597 | 25.067 | 8.562 | 1.00 | 28.89 | A | O |
| ATOM | 101 | C | SER | 158 | 116.656 | 26.753 | 10.941 | 1.00 | 14.97 | A | C |
| ATOM | 102 | O | SER | 158 | 117.053 | 26.930 | 12.097 | 1.00 | 12.14 | A | O |
| ATOM | 103 | N | ILE | 159 | 116.623 | 27.730 | 10.039 | 1.00 | 8.33 | A | N |
| ATOM | 104 | CA | ILE | 159 | 117.050 | 29.083 | 10.379 | 1.00 | 12.93 | A | C |
| ATOM | 105 | CB | ILE | 159 | 116.801 | 30.035 | 9.193 | 1.00 | 9.66 | A | C |
| ATOM | 106 | CG2 | ILE | 159 | 117.138 | 31.479 | 9.592 | 1.00 | 9.57 | A | C |
| ATOM | 107 | CG1 | ILE | 159 | 117.650 | 29.609 | 8.000 | 1.00 | 14.44 | A | C |
| ATOM | 108 | CD1 | ILE | 159 | 119.134 | 29.804 | 8.204 | 1.00 | 19.60 | A | C |
| ATOM | 109 | C | ILE | 159 | 116.292 | 29.604 | 11.616 | 1.00 | 17.24 | A | C |
| ATOM | 110 | O | ILE | 159 | 115.059 | 29.575 | 11.659 | 1.00 | 16.65 | A | O |
| ATOM | 111 | N | TYR | 160 | 117.032 | 30.084 | 12.611 | 1.00 | 29.54 | A | N |
| ATOM | 112 | CA | TYR | 160 | 116.438 | 30.600 | 13.849 | 1.00 | 31.67 | A | C |
| ATOM | 113 | CB | TYR | 160 | 115.775 | 29.455 | 14.639 | 1.00 | 16.89 | A | C |
| ATOM | 114 | CG | TYR | 160 | 115.094 | 29.869 | 15.941 | 1.00 | 13.65 | A | C |
| ATOM | 115 | CD1 | TYR | 160 | 113.717 | 30.089 | 15.993 | 1.00 | 16.07 | A | C |
| ATOM | 116 | CE1 | TYR | 160 | 113.088 | 30.466 | 17.186 | 1.00 | 13.67 | A | C |
| ATOM | 117 | CD2 | TYR | 160 | 115.828 | 30.038 | 17.116 | 1.00 | 11.30 | A | C |
| ATOM | 118 | CE2 | TYR | 160 | 115.211 | 30.416 | 18.304 | 1.00 | 15.01 | A | C |
| ATOM | 119 | CZ | TYR | 160 | 113.841 | 30.627 | 18.338 | 1.00 | 14.36 | A | C |
| ATOM | 120 | OH | TYR | 160 | 113.227 | 30.987 | 19.522 | 1.00 | 19.36 | A | O |
| ATOM | 121 | C | TYR | 160 | 117.498 | 31.264 | 14.734 | 1.00 | 33.39 | A | C |
| ATOM | 122 | O | TYR | 160 | 118.567 | 30.703 | 14.970 | 1.00 | 39.31 | A | O |
| ATOM | 123 | N | PRO | 161 | 117.206 | 32.467 | 15.248 | 1.00 | 31.87 | A | N |
| ATOM | 124 | CD | PRO | 161 | 117.988 | 33.002 | 16.380 | 1.00 | 14.17 | A | C |
| ATOM | 125 | CA | PRO | 161 | 115.969 | 33.234 | 15.055 | 1.00 | 30.15 | A | C |
| ATOM | 126 | CB | PRO | 161 | 115.831 | 33.976 | 16.379 | 1.00 | 18.55 | A | C |
| ATOM | 127 | CG | PRO | 161 | 117.278 | 34.291 | 16.703 | 1.00 | 21.71 | A | C |
| ATOM | 128 | C | PRO | 161 | 116.038 | 34.183 | 13.852 | 1.00 | 28.81 | A | C |
| ATOM | 129 | O | PRO | 161 | 117.074 | 34.792 | 13.580 | 1.00 | 28.13 | A | O |
| ATOM | 130 | N | TRP | 162 | 114.919 | 34.320 | 13.149 | 1.00 | 29.23 | A | N |
| ATOM | 131 | CA | TRP | 162 | 114.839 | 35.170 | 11.967 | 1.00 | 30.30 | A | C |
| ATOM | 132 | CB | TRP | 162 | 113.388 | 35.250 | 11.493 | 1.00 | 29.17 | A | C |
| ATOM | 133 | CG | TRP | 162 | 113.214 | 35.826 | 10.120 | 1.00 | 29.69 | A | C |
| ATOM | 134 | CD2 | TRP | 162 | 113.838 | 35.375 | 8.912 | 1.00 | 24.53 | A | C |
| ATOM | 135 | CE2 | TRP | 162 | 113.338 | 36.175 | 7.859 | 1.00 | 28.08 | A | C |
| ATOM | 136 | CE3 | TRP | 162 | 114.768 | 34.373 | 8.615 | 1.00 | 23.94 | A | C |
| ATOM | 137 | CD1 | TRP | 162 | 112.387 | 36.854 | 9.758 | 1.00 | 28.88 | A | C |
| ATOM | 138 | NE1 | TRP | 162 | 112.455 | 37.071 | 8.403 | 1.00 | 30.75 | A | N |
| ATOM | 139 | CZ2 | TRP | 162 | 113.741 | 36.000 | 6.532 | 1.00 | 26.62 | A | C |
| ATOM | 140 | CZ3 | TRP | 162 | 115.167 | 34.202 | 7.288 | 1.00 | 22.27 | A | C |
| ATOM | 141 | CH2 | TRP | 162 | 114.652 | 35.012 | 6.268 | 1.00 | 27.18 | A | C |
| ATOM | 142 | C | TRP | 162 | 115.381 | 36.579 | 12.210 | 1.00 | 32.08 | A | C |
| ATOM | 143 | O | TRP | 162 | 116.074 | 37.133 | 11.352 | 1.00 | 31.23 | A | O |
| ATOM | 144 | N | GLU | 163 | 115.077 | 37.147 | 13.381 | 1.00 | 25.22 | A | N |
| ATOM | 145 | CA | GLU | 163 | 115.510 | 38.504 | 13.734 | 1.00 | 27.00 | A | C |
| ATOM | 146 | CB | GLU | 163 | 115.108 | 38.857 | 15.172 | 1.00 | 105.95 | A | C |

Fig. 19: A-3

```
ATOM    147  CG   GLU   163     115.906   38.145   16.248  1.00   112.26   A  C
ATOM    148  CD   GLU   163     115.816   38.833   17.603  1.00   114.40   A  C
ATOM    149  OE1  GLU   163     116.310   39.975   17.732  1.00   116.11   A  O
ATOM    150  OE2  GLU   163     115.253   38.232   18.541  1.00   113.36   A  O
ATOM    151  C    GLU   163     117.008   38.723   13.557  1.00    26.66   A  C
ATOM    152  O    GLU   163     117.448   39.799   13.136  1.00    22.83   A  O
ATOM    153  N    SER   164     117.800   37.709   13.865  1.00    20.71   A  N
ATOM    154  CA   SER   164     119.241   37.850   13.715  1.00    17.90   A  C
ATOM    155  CB   SER   164     119.955   36.647   14.335  1.00    27.61   A  C
ATOM    156  OG   SER   164     119.716   36.582   15.731  1.00    33.50   A  O
ATOM    157  C    SER   164     119.601   37.988   12.235  1.00    18.66   A  C
ATOM    158  O    SER   164     120.436   38.813   11.863  1.00    21.86   A  O
ATOM    159  N    VAL   165     118.956   37.179   11.398  1.00     9.03   A  N
ATOM    160  CA   VAL   165     119.189   37.213    9.961  1.00     8.42   A  C
ATOM    161  CB   VAL   165     118.303   36.166    9.226  1.00    21.53   A  C
ATOM    162  CG1  VAL   165     118.296   36.430    7.721  1.00    22.92   A  C
ATOM    163  CG2  VAL   165     118.826   34.760    9.505  1.00    24.53   A  C
ATOM    164  C    VAL   165     118.873   38.595    9.411  1.00     9.58   A  C
ATOM    165  O    VAL   165     119.610   39.131    8.574  1.00    11.40   A  O
ATOM    166  N    ILE   166     117.772   39.169    9.887  1.00    17.73   A  N
ATOM    167  CA   ILE   166     117.351   40.482    9.427  1.00    17.05   A  C
ATOM    168  CB   ILE   166     115.903   40.763    9.840  1.00    21.02   A  C
ATOM    169  CG2  ILE   166     115.489   42.162    9.413  1.00    20.23   A  C
ATOM    170  CG1  ILE   166     114.997   39.737    9.164  1.00    20.88   A  C
ATOM    171  CD1  ILE   166     113.538   39.919    9.499  1.00    17.28   A  C
ATOM    172  C    ILE   166     118.281   41.564    9.929  1.00    16.50   A  C
ATOM    173  O    ILE   166     118.560   42.520    9.206  1.00    18.25   A  O
ATOM    174  N    ALA   167     118.774   41.413   11.157  1.00    25.46   A  N
ATOM    175  CA   ALA   167     119.711   42.391   11.710  1.00    26.06   A  C
ATOM    176  CB   ALA   167     120.095   42.021   13.100  1.00     7.73   A  C
ATOM    177  C    ALA   167     120.941   42.371   10.823  1.00    27.27   A  C
ATOM    178  O    ALA   167     121.546   43.414   10.544  1.00    23.87   A  O
ATOM    179  N    PHE   168     121.303   41.167   10.383  1.00    18.13   A  N
ATOM    180  CA   PHE   168     122.442   40.989    9.498  1.00    16.65   A  C
ATOM    181  CB   PHE   168     122.626   39.513    9.158  1.00    32.51   A  C
ATOM    182  CG   PHE   168     123.514   39.273    7.970  1.00    31.01   A  C
ATOM    183  CD1  PHE   168     122.968   39.066    6.701  1.00    32.61   A  C
ATOM    184  CD2  PHE   168     124.894   39.290    8.106  1.00    29.32   A  C
ATOM    185  CE1  PHE   168     123.792   38.882    5.585  1.00    31.09   A  C
ATOM    186  CE2  PHE   168     125.724   39.109    7.000  1.00    31.14   A  C
ATOM    187  CZ   PHE   168     125.173   38.906    5.738  1.00    33.63   A  C
ATOM    188  C    PHE   168     122.222   41.796    8.227  1.00    17.51   A  C
ATOM    189  O    PHE   168     123.139   42.475    7.750  1.00    13.95   A  O
ATOM    190  N    LEU   169     121.007   41.719    7.680  1.00    16.88   A  N
ATOM    191  CA   LEU   169     120.677   42.467    6.471  1.00    19.47   A  C
ATOM    192  CB   LEU   169     119.262   42.140    6.000  1.00    14.12   A  C
ATOM    193  CG   LEU   169     119.041   40.860    5.213  1.00    13.28   A  C
ATOM    194  CD1  LEU   169     117.662   40.952    4.603  1.00     9.74   A  C
ATOM    195  CD2  LEU   169     120.100   40.694    4.127  1.00    10.14   A  C
ATOM    196  C    LEU   169     120.777   43.966    6.731  1.00    21.77   A  C
ATOM    197  O    LEU   169     121.409   44.694    5.968  1.00    23.20   A  O
ATOM    198  N    ASN   170     120.150   44.419    7.815  1.00    20.45   A  N
ATOM    199  CA   ASN   170     120.159   45.832    8.175  1.00    17.58   A  C
ATOM    200  CB   ASN   170     119.534   46.018    9.562  1.00    31.53   A  C
ATOM    201  CG   ASN   170     119.017   47.426    9.791  1.00    34.95   A  C
ATOM    202  OD1  ASN   170     119.740   48.282   10.284  1.00    30.48   A  O
ATOM    203  ND2  ASN   170     117.762   47.671    9.421  1.00    32.86   A  N
ATOM    204  C    ASN   170     121.587   46.341    8.151  1.00    17.59   A  C
ATOM    205  O    ASN   170     121.941   47.174    7.321  1.00    17.80   A  O
ATOM    206  N    ASP   171     122.412   45.812    9.040  1.00    11.82   A  N
ATOM    207  CA   ASP   171     123.816   46.218    9.120  1.00    13.94   A  C
ATOM    208  CB   ASP   171     124.588   45.282   10.048  1.00    56.27   A  C
ATOM    209  CG   ASP   171     124.405   45.627   11.508  1.00    63.92   A  C
ATOM    210  OD1  ASP   171     123.248   45.689   11.971  1.00    66.14   A  O
ATOM    211  OD2  ASP   171     125.427   45.834   12.196  1.00    65.78   A  O
ATOM    212  C    ASP   171     124.509   46.244    7.760  1.00    15.43   A  C
ATOM    213  O    ASP   171     125.223   47.194    7.435  1.00    14.15   A  O
ATOM    214  N    LEU   172     124.289   45.200    6.966  1.00    15.45   A  N
ATOM    215  CA   LEU   172     124.910   45.099    5.650  1.00    16.13   A  C
ATOM    216  CB   LEU   172     124.633   43.717    5.047  1.00    10.67   A  C
ATOM    217  CG   LEU   172     125.667   43.058    4.123  1.00    10.16   A  C
ATOM    218  CD1  LEU   172     124.905   42.379    2.979  1.00     7.76   A  C
ATOM    219  CD2  LEU   172     126.672   44.070    3.594  1.00     8.33   A  C
```

Fig. 19: A-4

| ATOM | 220 | C | LEU | 172 | 124.401 | 46.178 | 4.699 | 1.00 | 16.47 | A | C |
|---|---|---|---|---|---|---|---|---|---|---|---|
| ATOM | 221 | O | LEU | 172 | 125.182 | 46.951 | 4.156 | 1.00 | 16.46 | A | O |
| ATOM | 222 | N | LEU | 173 | 123.088 | 46.226 | 4.509 | 1.00 | 30.03 | A | N |
| ATOM | 223 | CA | LEU | 173 | 122.475 | 47.193 | 3.609 | 1.00 | 32.78 | A | C |
| ATOM | 224 | CB | LEU | 173 | 120.967 | 46.932 | 3.474 | 1.00 | 23.11 | A | C |
| ATOM | 225 | CG | LEU | 173 | 120.357 | 45.803 | 2.627 | 1.00 | 24.46 | A | C |
| ATOM | 226 | CD1 | LEU | 173 | 121.069 | 45.702 | 1.292 | 1.00 | 27.98 | A | C |
| ATOM | 227 | CD2 | LEU | 173 | 120.456 | 44.501 | 3.353 | 1.00 | 25.01 | A | C |
| ATOM | 228 | C | LEU | 173 | 122.675 | 48.663 | 3.984 | 1.00 | 34.21 | A | C |
| ATOM | 229 | O | LEU | 173 | 122.937 | 49.495 | 3.105 | 1.00 | 30.93 | A | O |
| ATOM | 230 | N | LYS | 174 | 122.558 | 48.989 | 5.271 | 1.00 | 33.34 | A | N |
| ATOM | 231 | CA | LYS | 174 | 122.684 | 50.379 | 5.693 | 1.00 | 33.56 | A | C |
| ATOM | 232 | CB | LYS | 174 | 122.428 | 50.508 | 7.193 | 1.00 | 32.34 | A | C |
| ATOM | 233 | CG | LYS | 174 | 123.590 | 50.195 | 8.102 | 1.00 | 32.67 | A | C |
| ATOM | 234 | CD | LYS | 174 | 123.170 | 50.471 | 9.551 | 1.00 | 31.92 | A | C |
| ATOM | 235 | CE | LYS | 174 | 124.365 | 50.601 | 10.504 | 1.00 | 27.17 | A | C |
| ATOM | 236 | NZ | LYS | 174 | 125.178 | 49.351 | 10.664 | 1.00 | 23.64 | A | N |
| ATOM | 237 | C | LYS | 174 | 124.004 | 51.046 | 5.317 | 1.00 | 31.92 | A | C |
| ATOM | 238 | O | LYS | 174 | 124.060 | 52.256 | 5.142 | 1.00 | 32.79 | A | O |
| ATOM | 239 | N | ARG | 175 | 125.059 | 50.255 | 5.176 | 1.00 | 34.34 | A | N |
| ATOM | 240 | CA | ARG | 175 | 126.385 | 50.759 | 4.797 | 1.00 | 36.57 | A | C |
| ATOM | 241 | CB | ARG | 175 | 127.468 | 49.712 | 5.125 | 1.00 | 50.56 | A | C |
| ATOM | 242 | CG | ARG | 175 | 127.708 | 49.400 | 6.606 | 1.00 | 57.49 | A | C |
| ATOM | 243 | CD | ARG | 175 | 128.550 | 48.120 | 6.760 | 1.00 | 61.77 | A | C |
| ATOM | 244 | NE | ARG | 175 | 129.398 | 48.107 | 7.957 | 1.00 | 66.67 | A | N |
| ATOM | 245 | CZ | ARG | 175 | 128.954 | 48.049 | 9.211 | 1.00 | 70.25 | A | C |
| ATOM | 246 | NH1 | ARG | 175 | 127.653 | 47.997 | 9.461 | 1.00 | 70.45 | A | N |
| ATOM | 247 | NH2 | ARG | 175 | 129.819 | 48.039 | 10.219 | 1.00 | 71.15 | A | N |
| ATOM | 248 | C | ARG | 175 | 126.461 | 51.051 | 3.288 | 1.00 | 34.10 | A | C |
| ATOM | 249 | O | ARG | 175 | 127.487 | 51.522 | 2.796 | 1.00 | 33.94 | A | O |
| ATOM | 250 | N | MET | 176 | 125.384 | 50.766 | 2.557 | 1.00 | 18.81 | A | N |
| ATOM | 251 | CA | MET | 176 | 125.371 | 50.959 | 1.104 | 1.00 | 15.29 | A | C |
| ATOM | 252 | CB | MET | 176 | 124.758 | 49.728 | 0.431 | 1.00 | 45.67 | A | C |
| ATOM | 253 | CG | MET | 176 | 125.646 | 48.505 | 0.474 | 1.00 | 42.57 | A | C |
| ATOM | 254 | SD | MET | 176 | 124.887 | 47.063 | -0.292 | 1.00 | 46.71 | A | S |
| ATOM | 255 | CE | MET | 176 | 124.633 | 46.046 | 1.139 | 1.00 | 40.22 | A | C |
| ATOM | 256 | C | MET | 176 | 124.679 | 52.199 | 0.546 | 1.00 | 18.80 | A | C |
| ATOM | 257 | O | MET | 176 | 123.797 | 52.768 | 1.176 | 1.00 | 18.87 | A | O |
| ATOM | 258 | N | ASP | 177 | 125.098 | 52.605 | -0.652 | 1.00 | 31.75 | A | N |
| ATOM | 259 | CA | ASP | 177 | 124.504 | 53.744 | -1.344 | 1.00 | 34.24 | A | C |
| ATOM | 260 | CB | ASP | 177 | 125.584 | 54.671 | -1.903 | 1.00 | 129.70 | A | C |
| ATOM | 261 | CG | ASP | 177 | 126.196 | 55.556 | -0.838 | 1.00 | 132.65 | A | C |
| ATOM | 262 | OD1 | ASP | 177 | 127.004 | 56.437 | -1.194 | 1.00 | 132.32 | A | O |
| ATOM | 263 | OD2 | ASP | 177 | 125.869 | 55.372 | 0.354 | 1.00 | 134.30 | A | O |
| ATOM | 264 | C | ASP | 177 | 123.638 | 53.207 | -2.480 | 1.00 | 34.16 | A | C |
| ATOM | 265 | O | ASP | 177 | 124.085 | 53.107 | -3.617 | 1.00 | 33.88 | A | O |
| ATOM | 266 | N | ILE | 178 | 122.402 | 52.848 | -2.153 | 1.00 | 22.62 | A | N |
| ATOM | 267 | CA | ILE | 178 | 121.464 | 52.307 | -3.122 | 1.00 | 22.76 | A | C |
| ATOM | 268 | CB | ILE | 178 | 120.326 | 51.524 | -2.407 | 1.00 | 26.30 | A | C |
| ATOM | 269 | CG2 | ILE | 178 | 119.208 | 51.207 | -3.390 | 1.00 | 24.58 | A | C |
| ATOM | 270 | CG1 | ILE | 178 | 120.866 | 50.222 | -1.803 | 1.00 | 27.36 | A | C |
| ATOM | 271 | CD1 | ILE | 178 | 121.188 | 50.292 | -0.325 | 1.00 | 29.20 | A | C |
| ATOM | 272 | C | ILE | 178 | 120.848 | 53.398 | -4.009 | 1.00 | 21.90 | A | C |
| ATOM | 273 | O | ILE | 178 | 120.532 | 54.501 | -3.539 | 1.00 | 23.89 | A | O |
| ATOM | 274 | N | GLY | 179 | 120.669 | 53.077 | -5.292 | 1.00 | 18.17 | A | N |
| ATOM | 275 | CA | GLY | 179 | 120.091 | 54.029 | -6.226 | 1.00 | 17.89 | A | C |
| ATOM | 276 | C | GLY | 179 | 120.123 | 53.536 | -7.658 | 1.00 | 18.65 | A | C |
| ATOM | 277 | O | GLY | 179 | 121.019 | 52.786 | -8.023 | 1.00 | 16.80 | A | O |
| ATOM | 278 | N | PRO | 180 | 119.150 | 53.937 | -8.498 | 1.00 | 18.34 | A | N |
| ATOM | 279 | CD | PRO | 180 | 117.980 | 54.770 | -8.159 | 1.00 | 16.60 | A | C |
| ATOM | 280 | CA | PRO | 180 | 119.094 | 53.512 | -9.901 | 1.00 | 19.40 | A | C |
| ATOM | 281 | CB | PRO | 180 | 118.044 | 54.442 | -10.498 | 1.00 | 15.44 | A | C |
| ATOM | 282 | CG | PRO | 180 | 117.074 | 54.573 | -9.365 | 1.00 | 17.83 | A | C |
| ATOM | 283 | C | PRO | 180 | 120.432 | 53.622 | -10.597 | 1.00 | 21.18 | A | C |
| ATOM | 284 | O | PRO | 180 | 120.706 | 52.877 | -11.529 | 1.00 | 21.82 | A | O |
| ATOM | 285 | N | LYS | 181 | 121.262 | 54.553 | -10.139 | 1.00 | 25.85 | A | N |
| ATOM | 286 | CA | LYS | 181 | 122.581 | 54.751 | -10.732 | 1.00 | 26.27 | A | C |
| ATOM | 287 | CB | LYS | 181 | 122.737 | 56.187 | -11.253 | 1.00 | 26.21 | A | C |
| ATOM | 288 | CG | LYS | 181 | 121.801 | 56.557 | -12.403 | 1.00 | 26.81 | A | C |
| ATOM | 289 | CD | LYS | 181 | 122.014 | 55.683 | -13.627 | 1.00 | 25.67 | A | C |
| ATOM | 290 | CE | LYS | 181 | 121.014 | 56.031 | -14.719 | 1.00 | 28.19 | A | C |
| ATOM | 291 | NZ | LYS | 181 | 121.097 | 55.146 | -15.923 | 1.00 | 27.76 | A | N |
| ATOM | 292 | C | LYS | 181 | 123.684 | 54.451 | -9.729 | 1.00 | 25.62 | A | C |

Fig. 19: A-5

| | | | | | | | | | | |
|---|---|---|---|---|---|---|---|---|---|---|
| ATOM | 293 | O | LYS | 181 | 124.854 | 54.742 | -9.975 | 1.00 | 23.94 | A | O |
| ATOM | 294 | N | GLN | 182 | 123.300 | 53.870 | -8.599 | 1.00 | 34.95 | A | N |
| ATOM | 295 | CA | GLN | 182 | 124.246 | 53.513 | -7.548 | 1.00 | 33.61 | A | C |
| ATOM | 296 | CB | GLN | 182 | 123.797 | 54.096 | -6.207 | 1.00 | 89.66 | A | C |
| ATOM | 297 | CG | GLN | 182 | 123.331 | 55.528 | -6.251 | 1.00 | 90.94 | A | C |
| ATOM | 298 | CD | GLN | 182 | 124.443 | 56.478 | -6.597 | 1.00 | 92.56 | A | C |
| ATOM | 299 | OE1 | GLN | 182 | 125.007 | 56.418 | -7.686 | 1.00 | 93.40 | A | O |
| ATOM | 300 | NE2 | GLN | 182 | 124.772 | 57.364 | -5.667 | 1.00 | 93.92 | A | N |
| ATOM | 301 | C | GLN | 182 | 124.258 | 51.991 | -7.439 | 1.00 | 32.52 | A | C |
| ATOM | 302 | O | GLN | 182 | 124.398 | 51.278 | -8.429 | 1.00 | 36.85 | A | O |
| ATOM | 303 | N | THR | 183 | 124.096 | 51.507 | -6.216 | 1.00 | 26.87 | A | N |
| ATOM | 304 | CA | THR | 183 | 124.052 | 50.083 | -5.953 | 1.00 | 23.79 | A | C |
| ATOM | 305 | CB | THR | 183 | 124.642 | 49.767 | -4.584 | 1.00 | 30.55 | A | C |
| ATOM | 306 | OG1 | THR | 183 | 125.983 | 50.262 | -4.526 | 1.00 | 27.00 | A | O |
| ATOM | 307 | CG2 | THR | 183 | 124.629 | 48.274 | -4.331 | 1.00 | 28.23 | A | C |
| ATOM | 308 | C | THR | 183 | 122.590 | 49.687 | -5.944 | 1.00 | 23.45 | A | C |
| ATOM | 309 | O | THR | 183 | 121.752 | 50.380 | -5.368 | 1.00 | 21.98 | A | O |
| ATOM | 310 | N | GLN | 184 | 122.269 | 48.592 | -6.608 | 1.00 | 25.73 | A | N |
| ATOM | 311 | CA | GLN | 184 | 120.897 | 48.127 | -6.612 | 1.00 | 21.38 | A | C |
| ATOM | 312 | CB | GLN | 184 | 120.399 | 47.898 | -8.042 | 1.00 | 35.06 | A | C |
| ATOM | 313 | CG | GLN | 184 | 120.016 | 49.181 | -8.770 | 1.00 | 34.81 | A | C |
| ATOM | 314 | CD | GLN | 184 | 118.982 | 48.942 | -9.856 | 1.00 | 34.28 | A | C |
| ATOM | 315 | OE1 | GLN | 184 | 119.215 | 48.164 | -10.781 | 1.00 | 29.98 | A | O |
| ATOM | 316 | NE2 | GLN | 184 | 117.834 | 49.604 | -9.748 | 1.00 | 32.58 | A | N |
| ATOM | 317 | C | GLN | 184 | 120.862 | 46.839 | -5.800 | 1.00 | 21.76 | A | C |
| ATOM | 318 | O | GLN | 184 | 121.832 | 46.087 | -5.780 | 1.00 | 19.15 | A | O |
| ATOM | 319 | N | VAL | 185 | 119.753 | 46.599 | -5.112 | 1.00 | 33.23 | A | N |
| ATOM | 320 | CA | VAL | 185 | 119.634 | 45.408 | -4.298 | 1.00 | 31.60 | A | C |
| ATOM | 321 | CB | VAL | 185 | 119.868 | 45.742 | -2.810 | 1.00 | 20.42 | A | C |
| ATOM | 322 | CG1 | VAL | 185 | 119.572 | 44.535 | -1.938 | 1.00 | 20.41 | A | C |
| ATOM | 323 | CG2 | VAL | 185 | 121.294 | 46.148 | -2.614 | 1.00 | 6.28 | A | C |
| ATOM | 324 | C | VAL | 185 | 118.297 | 44.701 | -4.445 | 1.00 | 32.19 | A | C |
| ATOM | 325 | O | VAL | 185 | 117.237 | 45.322 | -4.469 | 1.00 | 29.34 | A | O |
| ATOM | 326 | N | GLY | 186 | 118.369 | 43.382 | -4.554 | 1.00 | 17.76 | A | N |
| ATOM | 327 | CA | GLY | 186 | 117.177 | 42.573 | -4.672 | 1.00 | 19.39 | A | C |
| ATOM | 328 | C | GLY | 186 | 117.355 | 41.424 | -3.711 | 1.00 | 17.37 | A | C |
| ATOM | 329 | O | GLY | 186 | 118.470 | 40.929 | -3.543 | 1.00 | 22.73 | A | O |
| ATOM | 330 | N | ILE | 187 | 116.278 | 40.995 | -3.073 | 1.00 | 15.41 | A | N |
| ATOM | 331 | CA | ILE | 187 | 116.395 | 39.906 | -2.133 | 1.00 | 14.00 | A | C |
| ATOM | 332 | CB | ILE | 187 | 116.117 | 40.403 | -0.675 | 1.00 | 10.12 | A | C |
| ATOM | 333 | CG2 | ILE | 187 | 116.053 | 39.225 | 0.299 | 1.00 | 7.45 | A | C |
| ATOM | 334 | CG1 | ILE | 187 | 117.232 | 41.364 | -0.253 | 1.00 | 10.64 | A | C |
| ATOM | 335 | CD1 | ILE | 187 | 117.156 | 41.817 | 1.176 | 1.00 | 11.69 | A | C |
| ATOM | 336 | C | ILE | 187 | 115.496 | 38.731 | -2.485 | 1.00 | 13.29 | A | C |
| ATOM | 337 | O | ILE | 187 | 114.301 | 38.896 | -2.768 | 1.00 | 12.19 | A | O |
| ATOM | 338 | N | VAL | 188 | 116.097 | 37.546 | -2.473 | 1.00 | 16.67 | A | N |
| ATOM | 339 | CA | VAL | 188 | 115.403 | 36.303 | -2.769 | 1.00 | 16.34 | A | C |
| ATOM | 340 | CB | VAL | 188 | 116.082 | 35.567 | -3.951 | 1.00 | 11.96 | A | C |
| ATOM | 341 | CG1 | VAL | 188 | 115.642 | 34.122 | -3.993 | 1.00 | 7.23 | A | C |
| ATOM | 342 | CG2 | VAL | 188 | 115.742 | 36.251 | -5.248 | 1.00 | 12.38 | A | C |
| ATOM | 343 | C | VAL | 188 | 115.464 | 35.404 | -1.536 | 1.00 | 14.88 | A | C |
| ATOM | 344 | O | VAL | 188 | 116.509 | 35.286 | -0.895 | 1.00 | 14.29 | A | O |
| ATOM | 345 | N | GLN | 189 | 114.348 | 34.774 | -1.194 | 1.00 | 30.23 | A | N |
| ATOM | 346 | CA | GLN | 189 | 114.335 | 33.873 | -0.049 | 1.00 | 29.91 | A | C |
| ATOM | 347 | CB | GLN | 189 | 113.374 | 34.363 | 1.039 | 1.00 | 26.02 | A | C |
| ATOM | 348 | CG | GLN | 189 | 113.277 | 33.399 | 2.210 | 1.00 | 23.53 | A | C |
| ATOM | 349 | CD | GLN | 189 | 112.257 | 33.807 | 3.267 | 1.00 | 24.24 | A | C |
| ATOM | 350 | OE1 | GLN | 189 | 111.891 | 32.998 | 4.125 | 1.00 | 25.46 | A | O |
| ATOM | 351 | NE2 | GLN | 189 | 111.800 | 35.058 | 3.219 | 1.00 | 25.28 | A | N |
| ATOM | 352 | C | GLN | 189 | 113.911 | 32.490 | -0.520 | 1.00 | 26.90 | A | C |
| ATOM | 353 | O | GLN | 189 | 113.056 | 32.366 | -1.401 | 1.00 | 25.26 | A | O |
| ATOM | 354 | N | TYR | 190 | 114.516 | 31.455 | 0.063 | 1.00 | 12.87 | A | N |
| ATOM | 355 | CA | TYR | 190 | 114.196 | 30.084 | -0.310 | 1.00 | 16.39 | A | C |
| ATOM | 356 | CB | TYR | 190 | 115.267 | 29.539 | -1.257 | 1.00 | 17.86 | A | C |
| ATOM | 357 | CG | TYR | 190 | 116.599 | 29.241 | -0.590 | 1.00 | 13.63 | A | C |
| ATOM | 358 | CD1 | TYR | 190 | 116.887 | 27.963 | -0.092 | 1.00 | 13.63 | A | C |
| ATOM | 359 | CE1 | TYR | 190 | 118.104 | 27.687 | 0.517 | 1.00 | 13.63 | A | C |
| ATOM | 360 | CD2 | TYR | 190 | 117.569 | 30.233 | -0.453 | 1.00 | 13.63 | A | C |
| ATOM | 361 | CE2 | TYR | 190 | 118.787 | 29.968 | 0.159 | 1.00 | 13.63 | A | C |
| ATOM | 362 | CZ | TYR | 190 | 119.053 | 28.698 | 0.640 | 1.00 | 13.63 | A | C |
| ATOM | 363 | OH | TYR | 190 | 120.278 | 28.442 | 1.228 | 1.00 | 13.63 | A | O |
| ATOM | 364 | C | TYR | 190 | 114.035 | 29.135 | 0.878 | 1.00 | 18.24 | A | C |
| ATOM | 365 | O | TYR | 190 | 114.456 | 29.424 | 2.003 | 1.00 | 18.32 | A | O |

Fig. 19: A-6

| ATOM | 366 | N   | GLY | 191 | 113.417 | 27.994 | 0.588  | 1.00 | 15.40 | A | N |
|------|-----|-----|-----|-----|---------|--------|--------|------|-------|---|---|
| ATOM | 367 | CA  | GLY | 191 | 113.171 | 26.954 | 1.572  | 1.00 | 13.15 | A | C |
| ATOM | 368 | C   | GLY | 191 | 112.683 | 25.776 | 0.764  | 1.00 | 14.59 | A | C |
| ATOM | 369 | O   | GLY | 191 | 113.482 | 25.084 | 0.139  | 1.00 | 17.97 | A | O |
| ATOM | 370 | N   | GLU | 192 | 111.371 | 25.552 | 0.769  | 1.00 | 27.03 | A | N |
| ATOM | 371 | CA  | GLU | 192 | 110.764 | 24.475 | -0.020 | 1.00 | 29.04 | A | C |
| ATOM | 372 | CB  | GLU | 192 | 109.400 | 24.089 | 0.537  | 1.00 | 28.96 | A | C |
| ATOM | 373 | CG  | GLU | 192 | 109.412 | 23.507 | 1.929  | 1.00 | 29.34 | A | C |
| ATOM | 374 | CD  | GLU | 192 | 108.020 | 23.089 | 2.390  | 1.00 | 29.53 | A | C |
| ATOM | 375 | OE1 | GLU | 192 | 107.890 | 22.532 | 3.505  | 1.00 | 32.42 | A | O |
| ATOM | 376 | OE2 | GLU | 192 | 107.051 | 23.322 | 1.633  | 1.00 | 27.40 | A | O |
| ATOM | 377 | C   | GLU | 192 | 110.562 | 25.062 | -1.410 | 1.00 | 28.85 | A | C |
| ATOM | 378 | O   | GLU | 192 | 110.692 | 24.380 | -2.422 | 1.00 | 30.22 | A | O |
| ATOM | 379 | N   | ASN | 193 | 110.236 | 26.350 | -1.433 | 1.00 | 34.68 | A | N |
| ATOM | 380 | CA  | ASN | 193 | 110.019 | 27.088 | -2.668 | 1.00 | 35.89 | A | C |
| ATOM | 381 | CB  | ASN | 193 | 108.566 | 27.527 | -2.769 | 1.00 | 60.91 | A | C |
| ATOM | 382 | CG  | ASN | 193 | 107.606 | 26.388 | -2.564 | 1.00 | 64.08 | A | C |
| ATOM | 383 | OD1 | ASN | 193 | 107.545 | 25.804 | -1.488 | 1.00 | 68.19 | A | O |
| ATOM | 384 | ND2 | ASN | 193 | 106.849 | 26.058 | -3.601 | 1.00 | 66.19 | A | N |
| ATOM | 385 | C   | ASN | 193 | 110.910 | 28.315 | -2.640 | 1.00 | 34.07 | A | C |
| ATOM | 386 | O   | ASN | 193 | 111.759 | 28.459 | -1.760 | 1.00 | 35.07 | A | O |
| ATOM | 387 | N   | VAL | 194 | 110.712 | 29.206 | -3.598 | 1.00 | 31.94 | A | N |
| ATOM | 388 | CA  | VAL | 194 | 111.511 | 30.423 | -3.660 | 1.00 | 34.28 | A | C |
| ATOM | 389 | CB  | VAL | 194 | 112.524 | 30.365 | -4.803 | 1.00 | 32.89 | A | C |
| ATOM | 390 | CG1 | VAL | 194 | 113.514 | 31.495 | -4.671 | 1.00 | 33.92 | A | C |
| ATOM | 391 | CG2 | VAL | 194 | 113.227 | 29.036 | -4.799 | 1.00 | 30.16 | A | C |
| ATOM | 392 | C   | VAL | 194 | 110.601 | 31.608 | -3.914 | 1.00 | 32.05 | A | C |
| ATOM | 393 | O   | VAL | 194 | 109.651 | 31.507 | -4.688 | 1.00 | 30.17 | A | O |
| ATOM | 394 | N   | THR | 195 | 110.877 | 32.730 | -3.261 | 1.00 | 26.46 | A | N |
| ATOM | 395 | CA  | THR | 195 | 110.058 | 33.915 | -3.474 | 1.00 | 27.64 | A | C |
| ATOM | 396 | CB  | THR | 195 | 109.050 | 34.135 | -2.307 | 1.00 | 36.45 | A | C |
| ATOM | 397 | OG1 | THR | 195 | 109.728 | 34.654 | -1.163 | 1.00 | 40.46 | A | O |
| ATOM | 398 | CG2 | THR | 195 | 108.396 | 32.820 | -1.918 | 1.00 | 38.08 | A | C |
| ATOM | 399 | C   | THR | 195 | 110.927 | 35.161 | -3.656 | 1.00 | 28.48 | A | C |
| ATOM | 400 | O   | THR | 195 | 111.977 | 35.309 | -3.032 | 1.00 | 31.07 | A | O |
| ATOM | 401 | N   | HIS | 196 | 110.492 | 36.040 | -4.545 | 1.00 | 36.83 | A | N |
| ATOM | 402 | CA  | HIS | 196 | 111.196 | 37.281 | -4.819 | 1.00 | 36.93 | A | C |
| ATOM | 403 | CB  | HIS | 196 | 110.843 | 37.772 | -6.225 | 1.00 | 33.18 | A | C |
| ATOM | 404 | CG  | HIS | 196 | 111.434 | 36.951 | -7.326 | 1.00 | 29.68 | A | C |
| ATOM | 405 | CD2 | HIS | 196 | 110.933 | 35.910 | -8.032 | 1.00 | 30.31 | A | C |
| ATOM | 406 | ND1 | HIS | 196 | 112.707 | 37.169 | -7.813 | 1.00 | 28.33 | A | N |
| ATOM | 407 | CE1 | HIS | 196 | 112.965 | 36.296 | -8.772 | 1.00 | 25.05 | A | C |
| ATOM | 408 | NE2 | HIS | 196 | 111.905 | 35.521 | -8.924 | 1.00 | 23.26 | A | N |
| ATOM | 409 | C   | HIS | 196 | 110.730 | 38.315 | -3.802 | 1.00 | 36.79 | A | C |
| ATOM | 410 | O   | HIS | 196 | 109.687 | 38.933 | -3.997 | 1.00 | 35.45 | A | O |
| ATOM | 411 | N   | GLU | 197 | 111.480 | 38.508 | -2.721 | 1.00 | 21.51 | A | N |
| ATOM | 412 | CA  | GLU | 197 | 111.069 | 39.488 | -1.732 | 1.00 | 18.84 | A | C |
| ATOM | 413 | CB  | GLU | 197 | 112.091 | 39.588 | -0.604 | 1.00 | 43.52 | A | C |
| ATOM | 414 | CG  | GLU | 197 | 112.094 | 38.384 | 0.339  | 1.00 | 43.86 | A | C |
| ATOM | 415 | CD  | GLU | 197 | 110.717 | 38.043 | 0.882  | 1.00 | 42.93 | A | C |
| ATOM | 416 | OE1 | GLU | 197 | 109.909 | 38.967 | 1.100  | 1.00 | 41.51 | A | O |
| ATOM | 417 | OE2 | GLU | 197 | 110.444 | 36.847 | 1.111  | 1.00 | 44.59 | A | O |
| ATOM | 418 | C   | GLU | 197 | 110.882 | 40.832 | -2.442 | 1.00 | 16.31 | A | C |
| ATOM | 419 | O   | GLU | 197 | 109.802 | 41.419 | -2.403 | 1.00 | 21.51 | A | O |
| ATOM | 420 | N   | PHE | 198 | 111.921 | 41.325 | -3.098 | 1.00 | 11.53 | A | N |
| ATOM | 421 | CA  | PHE | 198 | 111.786 | 42.562 | -3.845 | 1.00 | 13.33 | A | C |
| ATOM | 422 | CB  | PHE | 198 | 111.803 | 43.785 | -2.901 | 1.00 | 15.90 | A | C |
| ATOM | 423 | CG  | PHE | 198 | 113.092 | 44.003 | -2.153 | 1.00 | 14.15 | A | C |
| ATOM | 424 | CD1 | PHE | 198 | 114.262 | 44.390 | -2.823 | 1.00 | 20.29 | A | C |
| ATOM | 425 | CD2 | PHE | 198 | 113.115 | 43.912 | -0.756 | 1.00 | 10.34 | A | C |
| ATOM | 426 | CE1 | PHE | 198 | 115.427 | 44.685 | -2.113 | 1.00 | 16.32 | A | C |
| ATOM | 427 | CE2 | PHE | 198 | 114.274 | 44.208 | -0.039 | 1.00 | 14.80 | A | C |
| ATOM | 428 | CZ  | PHE | 198 | 115.431 | 44.594 | -0.719 | 1.00 | 18.60 | A | C |
| ATOM | 429 | C   | PHE | 198 | 112.829 | 42.652 | -4.956 | 1.00 | 16.01 | A | C |
| ATOM | 430 | O   | PHE | 198 | 113.974 | 42.239 | -4.771 | 1.00 | 17.30 | A | O |
| ATOM | 431 | N   | ASN | 199 | 112.418 | 43.152 | -6.123 | 1.00 | 19.42 | A | N |
| ATOM | 432 | CA  | ASN | 199 | 113.321 | 43.265 | -7.276 | 1.00 | 19.71 | A | C |
| ATOM | 433 | CB  | ASN | 199 | 112.540 | 43.562 | -8.548 | 1.00 | 30.06 | A | C |
| ATOM | 434 | CG  | ASN | 199 | 111.465 | 42.548 | -8.824 | 1.00 | 31.32 | A | C |
| ATOM | 435 | OD1 | ASN | 199 | 111.726 | 41.350 | -8.934 | 1.00 | 32.85 | A | O |
| ATOM | 436 | ND2 | ASN | 199 | 110.236 | 43.029 | -8.948 | 1.00 | 30.20 | A | N |
| ATOM | 437 | C   | ASN | 199 | 114.458 | 44.288 | -7.173 | 1.00 | 22.17 | A | C |
| ATOM | 438 | O   | ASN | 199 | 114.430 | 45.215 | -6.351 | 1.00 | 19.98 | A | O |

Fig. 19: A-7

```
ATOM    439  N    LEU  200     115.445  44.107  -8.044  1.00   18.99    A  N
ATOM    440  CA   LEU  200     116.619  44.958  -8.078  1.00   20.95    A  C
ATOM    441  CB   LEU  200     117.556  44.524  -9.212  1.00   24.87    A  C
ATOM    442  CG   LEU  200     118.631  43.490  -8.869  1.00   22.72    A  C
ATOM    443  CD1  LEU  200     119.348  43.048 -10.130  1.00   27.84    A  C
ATOM    444  CD2  LEU  200     119.617  44.089  -7.869  1.00   23.89    A  C
ATOM    445  C    LEU  200     116.282  46.415  -8.246  1.00   21.35    A  C
ATOM    446  O    LEU  200     116.960  47.274  -7.688  1.00   22.37    A  O
ATOM    447  N    ASN  201     115.231  46.691  -9.011  1.00   18.94    A  N
ATOM    448  CA   ASN  201     114.816  48.061  -9.284  1.00   20.79    A  C
ATOM    449  CB   ASN  201     114.546  48.208 -10.773  1.00   21.69    A  C
ATOM    450  CG   ASN  201     113.401  47.336 -11.236  1.00   23.97    A  C
ATOM    451  OD1  ASN  201     113.119  47.246 -12.424  1.00   24.11    A  O
ATOM    452  ND2  ASN  201     112.727  46.684 -10.292  1.00   21.81    A  N
ATOM    453  C    ASN  201     113.572  48.510  -8.509  1.00   20.84    A  C
ATOM    454  O    ASN  201     112.969  49.522  -8.851  1.00   16.74    A  O
ATOM    455  N    LYS  202     113.182  47.770  -7.477  1.00   23.30    A  N
ATOM    456  CA   LYS  202     111.998  48.137  -6.710  1.00   23.42    A  C
ATOM    457  CB   LYS  202     111.621  47.022  -5.741  1.00   34.18    A  C
ATOM    458  CG   LYS  202     110.337  47.265  -4.944  1.00   35.72    A  C
ATOM    459  CD   LYS  202     109.099  47.092  -5.803  1.00   37.63    A  C
ATOM    460  CE   LYS  202     109.162  45.813  -6.678  1.00   43.38    A  C
ATOM    461  NZ   LYS  202     109.316  44.491  -5.962  1.00   42.40    A  N
ATOM    462  C    LYS  202     112.188  49.428  -5.930  1.00   22.29    A  C
ATOM    463  O    LYS  202     111.338  50.313  -5.984  1.00   19.57    A  O
ATOM    464  N    TYR  203     113.292  49.538  -5.203  1.00   24.72    A  N
ATOM    465  CA   TYR  203     113.538  50.731  -4.407  1.00   24.40    A  C
ATOM    466  CB   TYR  203     113.769  50.348  -2.942  1.00   32.57    A  C
ATOM    467  CG   TYR  203     112.679  49.461  -2.396  1.00   31.24    A  C
ATOM    468  CD1  TYR  203     112.869  48.086  -2.282  1.00   31.85    A  C
ATOM    469  CE1  TYR  203     111.842  47.251  -1.844  1.00   28.32    A  C
ATOM    470  CD2  TYR  203     111.427  49.986  -2.050  1.00   34.13    A  C
ATOM    471  CE2  TYR  203     110.393  49.161  -1.611  1.00   36.88    A  C
ATOM    472  CZ   TYR  203     110.607  47.794  -1.512  1.00   36.50    A  C
ATOM    473  OH   TYR  203     109.590  46.962  -1.095  1.00   41.50    A  O
ATOM    474  C    TYR  203     114.713  51.541  -4.938  1.00   25.04    A  C
ATOM    475  O    TYR  203     115.755  50.986  -5.280  1.00   23.21    A  O
ATOM    476  N    SER  204     114.536  52.861  -4.998  1.00   28.94    A  N
ATOM    477  CA   SER  204     115.557  53.764  -5.513  1.00   30.79    A  C
ATOM    478  CB   SER  204     114.892  54.863  -6.338  1.00   29.83    A  C
ATOM    479  OG   SER  204     113.945  55.577  -5.558  1.00   31.66    A  O
ATOM    480  C    SER  204     116.372  54.402  -4.412  1.00   33.37    A  C
ATOM    481  O    SER  204     117.247  55.214  -4.680  1.00   33.88    A  O
ATOM    482  N    SER  205     116.089  54.027  -3.173  1.00   27.33    A  N
ATOM    483  CA   SER  205     116.787  54.615  -2.048  1.00   26.99    A  C
ATOM    484  CB   SER  205     115.874  55.628  -1.378  1.00   50.70    A  C
ATOM    485  OG   SER  205     116.409  56.032  -0.137  1.00   56.19    A  O
ATOM    486  C    SER  205     117.251  53.608  -1.016  1.00   25.12    A  C
ATOM    487  O    SER  205     116.650  52.551  -0.857  1.00   21.38    A  O
ATOM    488  N    THR  206     118.318  53.949  -0.301  1.00   23.44    A  N
ATOM    489  CA   THR  206     118.854  53.075   0.735  1.00   24.79    A  C
ATOM    490  CB   THR  206     120.176  53.614   1.286  1.00   12.85    A  C
ATOM    491  OG1  THR  206     121.137  53.683   0.227  1.00   11.66    A  O
ATOM    492  CG2  THR  206     120.696  52.712   2.392  1.00   11.22    A  C
ATOM    493  C    THR  206     117.889  52.879   1.900  1.00   25.38    A  C
ATOM    494  O    THR  206     117.798  51.785   2.447  1.00   28.17    A  O
ATOM    495  N    GLU  207     117.173  53.926   2.299  1.00   23.18    A  N
ATOM    496  CA   GLU  207     116.238  53.746   3.394  1.00   22.34    A  C
ATOM    497  CB   GLU  207     115.800  55.083   3.986  1.00  114.79    A  C
ATOM    498  CG   GLU  207     115.317  56.095   2.992  1.00  115.51    A  C
ATOM    499  CD   GLU  207     114.757  57.325   3.675  1.00  116.92    A  C
ATOM    500  OE1  GLU  207     115.428  57.857   4.587  1.00  116.15    A  O
ATOM    501  OE2  GLU  207     113.648  57.761   3.302  1.00  115.82    A  O
ATOM    502  C    GLU  207     115.038  52.937   2.908  1.00   22.84    A  C
ATOM    503  O    GLU  207     114.515  52.094   3.640  1.00   22.79    A  O
ATOM    504  N    GLU  208     114.614  53.163   1.668  1.00   31.71    A  N
ATOM    505  CA   GLU  208     113.485  52.412   1.126  1.00   33.44    A  C
ATOM    506  CB   GLU  208     113.168  52.841  -0.308  1.00   38.62    A  C
ATOM    507  CG   GLU  208     112.661  54.265  -0.441  1.00   36.09    A  C
ATOM    508  CD   GLU  208     112.288  54.633  -1.875  1.00   35.61    A  C
ATOM    509  OE1  GLU  208     111.943  55.811  -2.111  1.00   41.38    A  O
ATOM    510  OE2  GLU  208     112.338  53.757  -2.767  1.00   34.33    A  O
ATOM    511  C    GLU  208     113.808  50.920   1.148  1.00   34.14    A  C
```

Fig. 19: A-8

| | | | | | | | | | | |
|---|---|---|---|---|---|---|---|---|---|---|
| ATOM | 512 | O | GLU | 208 | 112.942 | 50.093 | 1.426 | 1.00 | 35.14 | A O |
| ATOM | 513 | N | VAL | 209 | 115.057 | 50.575 | 0.855 | 1.00 | 17.60 | A N |
| ATOM | 514 | CA | VAL | 209 | 115.472 | 49.180 | 0.853 | 1.00 | 16.52 | A C |
| ATOM | 515 | CB | VAL | 209 | 116.790 | 48.982 | 0.077 | 1.00 | 10.63 | A C |
| ATOM | 516 | CG1 | VAL | 209 | 117.501 | 47.719 | 0.538 | 1.00 | 10.96 | A C |
| ATOM | 517 | CG2 | VAL | 209 | 116.491 | 48.889 | 1.398 | 1.00 | 11.65 | A C |
| ATOM | 518 | C | VAL | 209 | 115.656 | 48.691 | 2.276 | 1.00 | 14.54 | A C |
| ATOM | 519 | O | VAL | 209 | 115.278 | 47.558 | 2.596 | 1.00 | 13.50 | A O |
| ATOM | 520 | N | LEU | 210 | 116.230 | 49.548 | 3.123 | 1.00 | 19.45 | A N |
| ATOM | 521 | CA | LEU | 210 | 116.459 | 49.205 | 4.521 | 1.00 | 19.78 | A C |
| ATOM | 522 | CB | LEU | 210 | 117.148 | 50.354 | 5.242 | 1.00 | 21.61 | A C |
| ATOM | 523 | CG | LEU | 210 | 118.589 | 50.100 | 5.683 | 1.00 | 21.85 | A C |
| ATOM | 524 | CD1 | LEU | 210 | 119.093 | 51.347 | 6.358 | 1.00 | 18.40 | A C |
| ATOM | 525 | CD2 | LEU | 210 | 118.687 | 48.916 | 6.632 | 1.00 | 15.30 | A C |
| ATOM | 526 | C | LEU | 210 | 115.148 | 48.894 | 5.223 | 1.00 | 18.04 | A C |
| ATOM | 527 | O | LEU | 210 | 115.078 | 48.022 | 6.093 | 1.00 | 18.81 | A O |
| ATOM | 528 | N | VAL | 211 | 114.107 | 49.618 | 4.839 | 1.00 | 25.49 | A N |
| ATOM | 529 | CA | VAL | 211 | 112.798 | 49.443 | 5.432 | 1.00 | 25.25 | A C |
| ATOM | 530 | CB | VAL | 211 | 111.916 | 50.685 | 5.175 | 1.00 | 19.83 | A C |
| ATOM | 531 | CG1 | VAL | 211 | 110.457 | 50.391 | 5.537 | 1.00 | 22.01 | A C |
| ATOM | 532 | CG2 | VAL | 211 | 112.446 | 51.859 | 5.989 | 1.00 | 20.44 | A C |
| ATOM | 533 | C | VAL | 211 | 112.107 | 48.214 | 4.871 | 1.00 | 24.50 | A C |
| ATOM | 534 | O | VAL | 211 | 111.437 | 47.483 | 5.593 | 1.00 | 25.18 | A O |
| ATOM | 535 | N | ALA | 212 | 112.262 | 47.986 | 3.577 | 1.00 | 29.23 | A N |
| ATOM | 536 | CA | ALA | 212 | 111.624 | 46.839 | 2.964 | 1.00 | 28.21 | A C |
| ATOM | 537 | CB | ALA | 212 | 111.725 | 46.935 | 1.439 | 1.00 | 1.87 | A C |
| ATOM | 538 | C | ALA | 212 | 112.275 | 45.559 | 3.465 | 1.00 | 26.02 | A C |
| ATOM | 539 | O | ALA | 212 | 111.603 | 44.543 | 3.657 | 1.00 | 25.96 | A O |
| ATOM | 540 | N | ALA | 213 | 113.587 | 45.618 | 3.680 | 1.00 | 33.07 | A N |
| ATOM | 541 | CA | ALA | 213 | 114.339 | 44.464 | 4.147 | 1.00 | 34.24 | A C |
| ATOM | 542 | CB | ALA | 213 | 115.803 | 44.787 | 4.176 | 1.00 | 20.72 | A C |
| ATOM | 543 | C | ALA | 213 | 113.875 | 44.011 | 5.522 | 1.00 | 33.04 | A C |
| ATOM | 544 | O | ALA | 213 | 113.659 | 42.824 | 5.746 | 1.00 | 30.67 | A O |
| ATOM | 545 | N | ASN | 214 | 113.723 | 44.952 | 6.446 | 1.00 | 10.19 | A N |
| ATOM | 546 | CA | ASN | 214 | 113.268 | 44.608 | 7.788 | 1.00 | 14.06 | A C |
| ATOM | 547 | CB | ASN | 214 | 113.357 | 45.817 | 8.713 | 1.00 | 18.34 | A C |
| ATOM | 548 | CG | ASN | 214 | 114.763 | 46.094 | 9.158 | 1.00 | 20.07 | A C |
| ATOM | 549 | OD1 | ASN | 214 | 115.597 | 46.563 | 8.377 | 1.00 | 22.00 | A O |
| ATOM | 550 | ND2 | ASN | 214 | 115.045 | 45.794 | 10.425 | 1.00 | 20.49 | A N |
| ATOM | 551 | C | ASN | 214 | 111.847 | 44.081 | 7.828 | 1.00 | 16.45 | A C |
| ATOM | 552 | O | ASN | 214 | 111.448 | 43.500 | 8.825 | 1.00 | 17.17 | A O |
| ATOM | 553 | N | LYS | 215 | 111.080 | 44.289 | 6.764 | 1.00 | 16.88 | A N |
| ATOM | 554 | CA | LYS | 215 | 109.705 | 43.817 | 6.744 | 1.00 | 17.32 | A C |
| ATOM | 555 | CB | LYS | 215 | 108.804 | 44.772 | 5.926 | 1.00 | 20.45 | A C |
| ATOM | 556 | CG | LYS | 215 | 108.670 | 46.176 | 6.531 | 1.00 | 28.03 | A C |
| ATOM | 557 | CD | LYS | 215 | 107.387 | 46.902 | 6.115 | 1.00 | 31.57 | A C |
| ATOM | 558 | CE | LYS | 215 | 107.304 | 47.155 | 4.607 | 1.00 | 35.03 | A C |
| ATOM | 559 | NZ | LYS | 215 | 106.135 | 48.007 | 4.237 | 1.00 | 36.02 | A N |
| ATOM | 560 | C | LYS | 215 | 109.617 | 42.399 | 6.193 | 1.00 | 15.45 | A C |
| ATOM | 561 | O | LYS | 215 | 108.529 | 41.825 | 6.124 | 1.00 | 16.67 | A O |
| ATOM | 562 | N | ILE | 216 | 110.757 | 41.824 | 5.812 | 1.00 | 28.84 | A N |
| ATOM | 563 | CA | ILE | 216 | 110.754 | 40.475 | 5.262 | 1.00 | 25.66 | A C |
| ATOM | 564 | CB | ILE | 216 | 112.088 | 40.123 | 4.594 | 1.00 | 13.08 | A C |
| ATOM | 565 | CG2 | ILE | 216 | 112.088 | 38.681 | 4.163 | 1.00 | 9.86 | A C |
| ATOM | 566 | CG1 | ILE | 216 | 112.298 | 41.002 | 3.362 | 1.00 | 9.76 | A C |
| ATOM | 567 | CD1 | ILE | 216 | 113.597 | 40.713 | 2.626 | 1.00 | 6.72 | A C |
| ATOM | 568 | C | ILE | 216 | 110.459 | 39.445 | 6.333 | 1.00 | 24.10 | A C |
| ATOM | 569 | O | ILE | 216 | 111.076 | 39.441 | 7.404 | 1.00 | 24.80 | A O |
| ATOM | 570 | N | VAL | 217 | 109.503 | 38.574 | 6.017 | 1.00 | 14.68 | A N |
| ATOM | 571 | CA | VAL | 217 | 109.065 | 37.511 | 6.904 | 1.00 | 16.45 | A C |
| ATOM | 572 | CB | VAL | 217 | 107.535 | 37.425 | 6.901 | 1.00 | 9.81 | A C |
| ATOM | 573 | CG1 | VAL | 217 | 107.065 | 36.144 | 7.569 | 1.00 | 9.81 | A C |
| ATOM | 574 | CG2 | VAL | 217 | 106.967 | 38.647 | 7.626 | 1.00 | 9.81 | A C |
| ATOM | 575 | C | VAL | 217 | 109.641 | 36.173 | 6.483 | 1.00 | 17.61 | A C |
| ATOM | 576 | O | VAL | 217 | 109.794 | 35.895 | 5.298 | 1.00 | 17.07 | A O |
| ATOM | 577 | N | GLN | 218 | 109.959 | 35.348 | 7.474 | 1.00 | 15.74 | A N |
| ATOM | 578 | CA | GLN | 218 | 110.512 | 34.024 | 7.234 | 1.00 | 16.40 | A C |
| ATOM | 579 | CB | GLN | 218 | 111.064 | 33.446 | 8.531 | 1.00 | 14.26 | A C |
| ATOM | 580 | CG | GLN | 218 | 111.752 | 32.109 | 8.372 | 1.00 | 14.26 | A C |
| ATOM | 581 | CD | GLN | 218 | 112.331 | 31.589 | 9.675 | 1.00 | 14.26 | A C |
| ATOM | 582 | OE1 | GLN | 218 | 113.166 | 30.685 | 9.668 | 1.00 | 14.26 | A O |
| ATOM | 583 | NE2 | GLN | 218 | 111.887 | 32.156 | 10.802 | 1.00 | 14.26 | A N |
| ATOM | 584 | C | GLN | 218 | 109.392 | 33.151 | 6.719 | 1.00 | 15.85 | A C |

Fig. 19: A-9

| | | | | | | | | | | | |
|---|---|---|---|---|---|---|---|---|---|---|---|
| ATOM | 585 | O | GLN | 218 | 108.335 | 33.103 | 7.328 | 1.00 | 19.60 | A | O |
| ATOM | 586 | N | ARG | 219 | 109.622 | 32.464 | 5.604 | 1.00 | 16.04 | A | N |
| ATOM | 587 | CA | ARG | 219 | 108.599 | 31.602 | 5.005 | 1.00 | 15.69 | A | C |
| ATOM | 588 | CB | ARG | 219 | 108.595 | 31.786 | 3.489 | 1.00 | 43.49 | A | C |
| ATOM | 589 | CG | ARG | 219 | 109.053 | 33.163 | 3.054 | 1.00 | 43.49 | A | C |
| ATOM | 590 | CD | ARG | 219 | 108.719 | 33.421 | 1.606 | 1.00 | 43.49 | A | C |
| ATOM | 591 | NE | ARG | 219 | 107.365 | 33.952 | 1.454 | 1.00 | 43.49 | A | N |
| ATOM | 592 | CZ | ARG | 219 | 107.042 | 35.232 | 1.606 | 1.00 | 43.49 | A | C |
| ATOM | 593 | NH1 | ARG | 219 | 107.978 | 36.122 | 1.915 | 1.00 | 43.49 | A | N |
| ATOM | 594 | NH2 | ARG | 219 | 105.786 | 35.621 | 1.443 | 1.00 | 43.49 | A | N |
| ATOM | 595 | C | ARG | 219 | 108.814 | 30.127 | 5.350 | 1.00 | 16.90 | A | C |
| ATOM | 596 | O | ARG | 219 | 108.073 | 29.253 | 4.886 | 1.00 | 16.91 | A | O |
| ATOM | 597 | N | GLY | 220 | 109.838 | 29.867 | 6.160 | 1.00 | 9.58 | A | N |
| ATOM | 598 | CA | GLY | 220 | 110.148 | 28.513 | 6.567 | 1.00 | 9.19 | A | C |
| ATOM | 599 | C | GLY | 220 | 110.442 | 27.562 | 5.422 | 1.00 | 8.86 | A | C |
| ATOM | 600 | O | GLY | 220 | 110.682 | 27.993 | 4.288 | 1.00 | 7.20 | A | O |
| ATOM | 601 | N | GLY | 221 | 110.435 | 26.266 | 5.730 | 1.00 | 16.50 | A | N |
| ATOM | 602 | CA | GLY | 221 | 110.682 | 25.265 | 4.718 | 1.00 | 15.07 | A | C |
| ATOM | 603 | C | GLY | 221 | 111.117 | 23.954 | 5.314 | 1.00 | 15.49 | A | C |
| ATOM | 604 | O | GLY | 221 | 112.038 | 23.928 | 6.124 | 1.00 | 12.29 | A | O |
| ATOM | 605 | N | ARG | 222 | 110.459 | 22.865 | 4.927 | 1.00 | 35.34 | A | N |
| ATOM | 606 | CA | ARG | 222 | 110.815 | 21.543 | 5.433 | 1.00 | 36.05 | A | C |
| ATOM | 607 | CB | ARG | 222 | 109.652 | 20.567 | 5.235 | 1.00 | 22.30 | A | C |
| ATOM | 608 | CG | ARG | 222 | 108.505 | 20.791 | 6.201 | 1.00 | 22.30 | A | C |
| ATOM | 609 | CD | ARG | 222 | 107.252 | 20.047 | 5.779 | 1.00 | 22.30 | A | C |
| ATOM | 610 | NE | ARG | 222 | 106.621 | 20.647 | 4.614 | 1.00 | 22.30 | A | N |
| ATOM | 611 | CZ | ARG | 222 | 105.459 | 20.247 | 4.103 | 1.00 | 22.30 | A | C |
| ATOM | 612 | NH1 | ARG | 222 | 104.795 | 19.241 | 4.654 | 1.00 | 22.30 | A | N |
| ATOM | 613 | NH2 | ARG | 222 | 104.951 | 20.857 | 3.042 | 1.00 | 22.30 | A | N |
| ATOM | 614 | C | ARG | 222 | 112.062 | 21.036 | 4.723 | 1.00 | 36.10 | A | C |
| ATOM | 615 | O | ARG | 222 | 112.626 | 20.017 | 5.107 | 1.00 | 36.87 | A | O |
| ATOM | 616 | N | GLN | 223 | 112.473 | 21.750 | 3.678 | 1.00 | 27.48 | A | N |
| ATOM | 617 | CA | GLN | 223 | 113.672 | 21.428 | 2.912 | 1.00 | 25.77 | A | C |
| ATOM | 618 | CB | GLN | 223 | 113.328 | 20.858 | 1.535 | 1.00 | 13.17 | A | C |
| ATOM | 619 | CG | GLN | 223 | 112.830 | 19.417 | 1.508 | 1.00 | 14.61 | A | C |
| ATOM | 620 | CD | GLN | 223 | 111.346 | 19.312 | 1.790 | 1.00 | 15.02 | A | C |
| ATOM | 621 | OE1 | GLN | 223 | 110.533 | 20.016 | 1.190 | 1.00 | 15.42 | A | O |
| ATOM | 622 | NE2 | GLN | 223 | 110.981 | 18.417 | 2.698 | 1.00 | 15.46 | A | N |
| ATOM | 623 | C | GLN | 223 | 114.498 | 22.706 | 2.724 | 1.00 | 26.51 | A | C |
| ATOM | 624 | O | GLN | 223 | 114.057 | 23.799 | 3.069 | 1.00 | 25.99 | A | O |
| ATOM | 625 | N | THR | 224 | 115.696 | 22.567 | 2.172 | 1.00 | 24.40 | A | N |
| ATOM | 626 | CA | THR | 224 | 116.581 | 23.704 | 1.948 | 1.00 | 22.28 | A | C |
| ATOM | 627 | CB | THR | 224 | 117.795 | 23.633 | 2.897 | 1.00 | 14.98 | A | C |
| ATOM | 628 | OG1 | THR | 224 | 117.328 | 23.565 | 4.246 | 1.00 | 14.97 | A | O |
| ATOM | 629 | CG2 | THR | 224 | 118.683 | 24.849 | 2.747 | 1.00 | 11.28 | A | C |
| ATOM | 630 | C | THR | 224 | 117.061 | 23.662 | 0.500 | 1.00 | 19.29 | A | C |
| ATOM | 631 | O | THR | 224 | 118.122 | 23.129 | 0.202 | 1.00 | 15.78 | A | O |
| ATOM | 632 | N | MET | 225 | 116.272 | 24.234 | -0.395 | 1.00 | 14.15 | A | N |
| ATOM | 633 | CA | MET | 225 | 116.607 | 24.236 | -1.810 | 1.00 | 15.04 | A | C |
| ATOM | 634 | CB | MET | 225 | 115.346 | 24.481 | -2.636 | 1.00 | 22.98 | A | C |
| ATOM | 635 | CG | MET | 225 | 114.183 | 23.602 | -2.267 | 1.00 | 20.41 | A | C |
| ATOM | 636 | SD | MET | 225 | 114.421 | 21.883 | -2.704 | 1.00 | 28.15 | A | S |
| ATOM | 637 | CE | MET | 225 | 112.675 | 21.302 | -2.554 | 1.00 | 24.73 | A | C |
| ATOM | 638 | C | MET | 225 | 117.653 | 25.275 | -2.204 | 1.00 | 16.07 | A | C |
| ATOM | 639 | O | MET | 225 | 117.426 | 26.054 | -3.136 | 1.00 | 17.53 | A | O |
| ATOM | 640 | N | THR | 226 | 118.791 | 25.297 | -1.513 | 1.00 | 16.19 | A | N |
| ATOM | 641 | CA | THR | 226 | 119.841 | 26.259 | -1.840 | 1.00 | 15.66 | A | C |
| ATOM | 642 | CB | THR | 226 | 121.155 | 25.905 | -1.129 | 1.00 | 25.30 | A | C |
| ATOM | 643 | OG1 | THR | 226 | 120.925 | 25.825 | 0.284 | 1.00 | 27.32 | A | O |
| ATOM | 644 | CG2 | THR | 226 | 122.216 | 26.959 | -1.414 | 1.00 | 23.02 | A | C |
| ATOM | 645 | C | THR | 226 | 120.100 | 26.337 | -3.356 | 1.00 | 14.26 | A | C |
| ATOM | 646 | O | THR | 226 | 120.229 | 27.418 | -3.917 | 1.00 | 8.95 | A | O |
| ATOM | 647 | N | ALA | 227 | 120.158 | 25.190 | -4.019 | 1.00 | 9.41 | A | N |
| ATOM | 648 | CA | ALA | 227 | 120.408 | 25.162 | -5.448 | 1.00 | 8.35 | A | C |
| ATOM | 649 | CB | ALA | 227 | 120.422 | 23.738 | -5.939 | 1.00 | 23.80 | A | C |
| ATOM | 650 | C | ALA | 227 | 119.342 | 25.951 | -6.188 | 1.00 | 9.01 | A | C |
| ATOM | 651 | O | ALA | 227 | 119.644 | 26.759 | -7.067 | 1.00 | 9.81 | A | O |
| ATOM | 652 | N | LEU | 228 | 118.085 | 25.711 | -5.842 | 1.00 | 28.18 | A | N |
| ATOM | 653 | CA | LEU | 228 | 116.985 | 26.410 | -6.489 | 1.00 | 26.62 | A | C |
| ATOM | 654 | CB | LEU | 228 | 115.649 | 25.860 | -5.988 | 1.00 | 14.81 | A | C |
| ATOM | 655 | CG | LEU | 228 | 114.372 | 26.485 | -6.557 | 1.00 | 22.70 | A | C |
| ATOM | 656 | CD1 | LEU | 228 | 114.356 | 26.363 | -8.080 | 1.00 | 20.29 | A | C |
| ATOM | 657 | CD2 | LEU | 228 | 113.163 | 25.801 | -5.947 | 1.00 | 19.75 | A | C |

Fig. 19: A-10

| | | | | | | | | | | |
|---|---|---|---|---|---|---|---|---|---|---|
| ATOM | 658 | C | LEU | 228 | 117.067 | 27.909 | -6.221 | 1.00 | 25.80 | A C |
| ATOM | 659 | O | LEU | 228 | 116.885 | 28.719 | -7.129 | 1.00 | 28.78 | A O |
| ATOM | 660 | N | GLY | 229 | 117.341 | 28.274 | -4.971 | 1.00 | 23.50 | A N |
| ATOM | 661 | CA | GLY | 229 | 117.449 | 29.679 | -4.624 | 1.00 | 25.86 | A C |
| ATOM | 662 | C | GLY | 229 | 118.464 | 30.407 | -5.495 | 1.00 | 28.42 | A C |
| ATOM | 663 | O | GLY | 229 | 118.149 | 31.428 | -6.108 | 1.00 | 29.01 | A O |
| ATOM | 664 | N | ILE | 230 | 119.682 | 29.876 | -5.562 | 1.00 | 20.49 | A N |
| ATOM | 665 | CA | ILE | 230 | 120.736 | 30.498 | -6.354 | 1.00 | 21.82 | A C |
| ATOM | 666 | CB | ILE | 230 | 122.096 | 29.779 | -6.195 | 1.00 | 2.66 | A C |
| ATOM | 667 | CG2 | ILE | 230 | 123.168 | 30.546 | -6.953 | 1.00 | 2.66 | A C |
| ATOM | 668 | CG1 | ILE | 230 | 122.486 | 29.692 | -4.720 | 1.00 | 2.66 | A C |
| ATOM | 669 | CD1 | ILE | 230 | 123.773 | 28.920 | -4.474 | 1.00 | 2.66 | A C |
| ATOM | 670 | C | ILE | 230 | 120.386 | 30.508 | -7.830 | 1.00 | 22.08 | A C |
| ATOM | 671 | O | ILE | 230 | 120.614 | 31.498 | -8.511 | 1.00 | 20.01 | A O |
| ATOM | 672 | N | ASP | 231 | 119.841 | 29.409 | -8.333 | 1.00 | 32.19 | A N |
| ATOM | 673 | CA | ASP | 231 | 119.473 | 29.352 | -9.743 | 1.00 | 30.59 | A C |
| ATOM | 674 | CB | ASP | 231 | 118.959 | 27.958 | -10.103 | 1.00 | 35.41 | A C |
| ATOM | 675 | CG | ASP | 231 | 118.860 | 27.739 | -11.604 | 1.00 | 42.41 | A C |
| ATOM | 676 | OD1 | ASP | 231 | 119.910 | 27.778 | -12.281 | 1.00 | 41.17 | A O |
| ATOM | 677 | OD2 | ASP | 231 | 117.735 | 27.525 | -12.103 | 1.00 | 45.95 | A O |
| ATOM | 678 | C | ASP | 231 | 118.392 | 30.395 | -10.048 | 1.00 | 31.57 | A C |
| ATOM | 679 | O | ASP | 231 | 118.429 | 31.048 | -11.090 | 1.00 | 28.79 | A O |
| ATOM | 680 | N | THR | 232 | 117.443 | 30.554 | -9.126 | 1.00 | 18.29 | A N |
| ATOM | 681 | CA | THR | 232 | 116.347 | 31.510 | -9.296 | 1.00 | 17.08 | A C |
| ATOM | 682 | CB | THR | 232 | 115.287 | 31.347 | -8.194 | 1.00 | 20.70 | A C |
| ATOM | 683 | OG1 | THR | 232 | 114.714 | 30.041 | -8.279 | 1.00 | 19.21 | A O |
| ATOM | 684 | CG2 | THR | 232 | 114.191 | 32.370 | -8.358 | 1.00 | 14.24 | A C |
| ATOM | 685 | C | THR | 232 | 116.859 | 32.937 | -9.264 | 1.00 | 17.71 | A C |
| ATOM | 686 | O | THR | 232 | 116.390 | 33.801 | -10.010 | 1.00 | 17.88 | A O |
| ATOM | 687 | N | ALA | 233 | 117.815 | 33.187 | -8.379 | 1.00 | 19.66 | A N |
| ATOM | 688 | CA | ALA | 233 | 118.395 | 34.517 | -8.270 | 1.00 | 22.31 | A C |
| ATOM | 689 | CB | ALA | 233 | 119.364 | 34.580 | -7.099 | 1.00 | 15.15 | A C |
| ATOM | 690 | C | ALA | 233 | 119.125 | 34.796 | -9.575 | 1.00 | 24.62 | A C |
| ATOM | 691 | O | ALA | 233 | 119.187 | 35.929 | -10.031 | 1.00 | 26.53 | A O |
| ATOM | 692 | N | ARG | 234 | 119.666 | 33.746 | -10.180 | 1.00 | 30.19 | A N |
| ATOM | 693 | CA | ARG | 234 | 120.390 | 33.879 | -11.434 | 1.00 | 33.29 | A C |
| ATOM | 694 | CB | ARG | 234 | 121.241 | 32.637 | -11.693 | 1.00 | 15.32 | A C |
| ATOM | 695 | CG | ARG | 234 | 122.345 | 32.875 | -12.693 | 1.00 | 15.32 | A C |
| ATOM | 696 | CD | ARG | 234 | 122.760 | 31.617 | -13.460 | 1.00 | 15.32 | A C |
| ATOM | 697 | NE | ARG | 234 | 121.839 | 31.311 | -14.554 | 1.00 | 15.32 | A N |
| ATOM | 698 | CZ | ARG | 234 | 120.875 | 30.405 | -14.481 | 1.00 | 15.32 | A C |
| ATOM | 699 | NH1 | ARG | 234 | 120.708 | 29.713 | -13.368 | 1.00 | 15.32 | A N |
| ATOM | 700 | NH2 | ARG | 234 | 120.078 | 30.188 | -15.511 | 1.00 | 15.32 | A N |
| ATOM | 701 | C | ARG | 234 | 119.446 | 34.083 | -12.619 | 1.00 | 35.42 | A C |
| ATOM | 702 | O | ARG | 234 | 119.409 | 35.153 | -13.215 | 1.00 | 35.47 | A O |
| ATOM | 703 | N | LYS | 235 | 118.666 | 33.057 | -12.941 | 1.00 | 67.48 | A N |
| ATOM | 704 | CA | LYS | 235 | 117.767 | 33.124 | -14.085 | 1.00 | 67.43 | A C |
| ATOM | 705 | CB | LYS | 235 | 117.204 | 31.730 | -14.397 | 1.00 | 53.18 | A C |
| ATOM | 706 | CG | LYS | 235 | 115.965 | 31.308 | -13.615 | 1.00 | 54.33 | A C |
| ATOM | 707 | CD | LYS | 235 | 115.583 | 29.867 | -13.970 | 1.00 | 54.15 | A C |
| ATOM | 708 | CE | LYS | 235 | 114.146 | 29.517 | -13.590 | 1.00 | 54.95 | A C |
| ATOM | 709 | NZ | LYS | 235 | 113.873 | 29.660 | -12.135 | 1.00 | 55.71 | A N |
| ATOM | 710 | C | LYS | 235 | 116.628 | 34.134 | -14.017 | 1.00 | 67.57 | A C |
| ATOM | 711 | O | LYS | 235 | 116.074 | 34.500 | -15.054 | 1.00 | 67.91 | A O |
| ATOM | 712 | N | GLU | 236 | 116.277 | 34.596 | -12.822 | 1.00 | 98.68 | A N |
| ATOM | 713 | CA | GLU | 236 | 115.186 | 35.558 | -12.693 | 1.00 | 100.30 | A C |
| ATOM | 714 | CB | GLU | 236 | 114.087 | 34.999 | -11.781 | 1.00 | 50.64 | A C |
| ATOM | 715 | CG | GLU | 236 | 113.008 | 34.192 | -12.510 | 1.00 | 53.41 | A C |
| ATOM | 716 | CD | GLU | 236 | 112.199 | 33.276 | -11.582 | 1.00 | 55.89 | A C |
| ATOM | 717 | OE1 | GLU | 236 | 111.660 | 33.760 | -10.565 | 1.00 | 55.98 | A O |
| ATOM | 718 | OE2 | GLU | 236 | 112.098 | 32.065 | -11.875 | 1.00 | 55.73 | A O |
| ATOM | 719 | C | GLU | 236 | 115.627 | 36.917 | -12.174 | 1.00 | 98.85 | A C |
| ATOM | 720 | O | GLU | 236 | 115.638 | 37.900 | -12.912 | 1.00 | 100.28 | A O |
| ATOM | 721 | N | ALA | 237 | 115.991 | 36.969 | -10.899 | 1.00 | 71.25 | A N |
| ATOM | 722 | CA | ALA | 237 | 116.405 | 38.218 | -10.276 | 1.00 | 68.72 | A C |
| ATOM | 723 | CB | ALA | 237 | 117.046 | 37.934 | -8.932 | 1.00 | 56.85 | A C |
| ATOM | 724 | C | ALA | 237 | 117.349 | 39.046 | -11.139 | 1.00 | 67.56 | A C |
| ATOM | 725 | O | ALA | 237 | 117.225 | 40.267 | -11.200 | 1.00 | 65.98 | A O |
| ATOM | 726 | N | PHE | 238 | 118.283 | 38.385 | -11.812 | 1.00 | 41.81 | A N |
| ATOM | 727 | CA | PHE | 238 | 119.256 | 39.080 | -12.651 | 1.00 | 41.24 | A C |
| ATOM | 728 | CB | PHE | 238 | 120.606 | 38.369 | -12.591 | 1.00 | 47.57 | A C |
| ATOM | 729 | CG | PHE | 238 | 121.413 | 38.696 | -11.378 | 1.00 | 46.60 | A C |
| ATOM | 730 | CD1 | PHE | 238 | 121.686 | 37.725 | -10.419 | 1.00 | 47.83 | A C |

Fig. 19: A-11

| ATOM | 731 | CD2 | PHE | 238 | 121.931 | 39.970 | -11.208 | 1.00 | 44.20 | A | C |
|------|-----|-----|-----|-----|---------|--------|---------|------|-------|---|---|
| ATOM | 732 | CE1 | PHE | 238 | 122.476 | 38.023 | -9.298 | 1.00 | 45.63 | A | C |
| ATOM | 733 | CE2 | PHE | 238 | 122.719 | 40.282 | -10.094 | 1.00 | 50.51 | A | C |
| ATOM | 734 | CZ | PHE | 238 | 122.993 | 39.305 | -9.137 | 1.00 | 51.93 | A | C |
| ATOM | 735 | C | PHE | 238 | 118.861 | 39.252 | -14.116 | 1.00 | 43.09 | A | C |
| ATOM | 736 | O | PHE | 238 | 119.699 | 39.129 | -15.017 | 1.00 | 43.19 | A | O |
| ATOM | 737 | N | THR | 239 | 117.586 | 39.520 | -14.362 | 1.00 | 28.84 | A | N |
| ATOM | 738 | CA | THR | 239 | 117.117 | 39.744 | -15.724 | 1.00 | 32.78 | A | C |
| ATOM | 739 | CB | THR | 239 | 115.952 | 38.821 | -16.086 | 1.00 | 22.29 | A | C |
| ATOM | 740 | OG1 | THR | 239 | 114.866 | 39.059 | -15.191 | 1.00 | 20.25 | A | O |
| ATOM | 741 | CG2 | THR | 239 | 116.363 | 37.382 | -15.988 | 1.00 | 25.20 | A | C |
| ATOM | 742 | C | THR | 239 | 116.655 | 41.202 | -15.798 | 1.00 | 33.04 | A | C |
| ATOM | 743 | O | THR | 239 | 115.955 | 41.695 | -14.902 | 1.00 | 33.54 | A | O |
| ATOM | 744 | N | GLU | 240 | 117.067 | 41.881 | -16.868 | 1.00 | 73.11 | A | N |
| ATOM | 745 | CA | GLU | 240 | 116.755 | 43.291 | -17.085 | 1.00 | 73.36 | A | C |
| ATOM | 746 | CB | GLU | 240 | 116.995 | 43.654 | -18.549 | 1.00 | 97.49 | A | C |
| ATOM | 747 | CG | GLU | 240 | 117.147 | 45.141 | -18.793 | 1.00 | 102.13 | A | C |
| ATOM | 748 | CD | GLU | 240 | 117.738 | 45.441 | -20.152 | 1.00 | 105.04 | A | C |
| ATOM | 749 | OE1 | GLU | 240 | 118.794 | 44.858 | -20.483 | 1.00 | 105.14 | A | O |
| ATOM | 750 | OE2 | GLU | 240 | 117.151 | 46.263 | -20.885 | 1.00 | 105.11 | A | O |
| ATOM | 751 | C | GLU | 240 | 115.336 | 43.665 | -16.689 | 1.00 | 74.71 | A | C |
| ATOM | 752 | O | GLU | 240 | 115.083 | 44.772 | -16.210 | 1.00 | 75.92 | A | O |
| ATOM | 753 | N | ALA | 241 | 114.417 | 42.730 | -16.885 | 1.00 | 32.59 | A | N |
| ATOM | 754 | CA | ALA | 241 | 113.016 | 42.952 | -16.552 | 1.00 | 33.44 | A | C |
| ATOM | 755 | CB | ALA | 241 | 112.170 | 41.769 | -17.051 | 1.00 | 4.05 | A | C |
| ATOM | 756 | C | ALA | 241 | 112.802 | 43.165 | -15.044 | 1.00 | 32.91 | A | C |
| ATOM | 757 | O | ALA | 241 | 111.809 | 43.759 | -14.622 | 1.00 | 34.37 | A | O |
| ATOM | 758 | N | ARG | 242 | 113.725 | 42.678 | -14.223 | 1.00 | 31.60 | A | N |
| ATOM | 759 | CA | ARG | 242 | 113.585 | 42.851 | -12.786 | 1.00 | 31.34 | A | C |
| ATOM | 760 | CB | ARG | 242 | 113.757 | 41.500 | -12.079 | 1.00 | 27.81 | A | C |
| ATOM | 761 | CG | ARG | 242 | 112.489 | 40.658 | -12.052 | 1.00 | 28.01 | A | C |
| ATOM | 762 | CD | ARG | 242 | 112.669 | 39.440 | -11.160 | 1.00 | 28.87 | A | C |
| ATOM | 763 | NE | ARG | 242 | 111.425 | 39.010 | -10.515 | 1.00 | 30.07 | A | N |
| ATOM | 764 | CZ | ARG | 242 | 110.582 | 38.106 | -11.011 | 1.00 | 29.27 | A | C |
| ATOM | 765 | NH1 | ARG | 242 | 110.846 | 37.525 | -12.176 | 1.00 | 28.32 | A | N |
| ATOM | 766 | NH2 | ARG | 242 | 109.485 | 37.769 | -10.334 | 1.00 | 31.29 | A | N |
| ATOM | 767 | C | ARG | 242 | 114.557 | 43.898 | -12.231 | 1.00 | 32.54 | A | C |
| ATOM | 768 | O | ARG | 242 | 114.824 | 43.954 | -11.026 | 1.00 | 35.55 | A | O |
| ATOM | 769 | N | GLY | 243 | 115.080 | 44.733 | -13.122 | 1.00 | 38.70 | A | N |
| ATOM | 770 | CA | GLY | 243 | 115.996 | 45.775 | -12.706 | 1.00 | 36.85 | A | C |
| ATOM | 771 | C | GLY | 243 | 117.468 | 45.462 | -12.890 | 1.00 | 35.13 | A | C |
| ATOM | 772 | O | GLY | 243 | 118.318 | 46.139 | -12.308 | 1.00 | 34.75 | A | O |
| ATOM | 773 | N | ALA | 244 | 117.792 | 44.447 | -13.683 | 1.00 | 32.25 | A | N |
| ATOM | 774 | CA | ALA | 244 | 119.190 | 44.119 | -13.896 | 1.00 | 30.25 | A | C |
| ATOM | 775 | CB | ALA | 244 | 119.326 | 42.709 | -14.442 | 1.00 | 67.28 | A | C |
| ATOM | 776 | C | ALA | 244 | 119.750 | 45.130 | -14.886 | 1.00 | 32.13 | A | C |
| ATOM | 777 | O | ALA | 244 | 119.437 | 45.088 | -16.068 | 1.00 | 31.59 | A | O |
| ATOM | 778 | N | ARG | 245 | 120.566 | 46.054 | -14.401 | 1.00 | 18.96 | A | N |
| ATOM | 779 | CA | ARG | 245 | 121.154 | 47.074 | -15.258 | 1.00 | 19.79 | A | C |
| ATOM | 780 | CB | ARG | 245 | 121.853 | 48.130 | -14.399 | 1.00 | 36.60 | A | C |
| ATOM | 781 | CG | ARG | 245 | 120.888 | 49.043 | -13.655 | 1.00 | 39.07 | A | C |
| ATOM | 782 | CD | ARG | 245 | 121.614 | 49.991 | -12.741 | 1.00 | 39.28 | A | C |
| ATOM | 783 | NE | ARG | 245 | 122.309 | 49.254 | -11.701 | 1.00 | 33.70 | A | N |
| ATOM | 784 | CZ | ARG | 245 | 122.997 | 49.824 | -10.726 | 1.00 | 33.52 | A | C |
| ATOM | 785 | NH1 | ARG | 245 | 123.084 | 51.145 | -10.662 | 1.00 | 32.72 | A | N |
| ATOM | 786 | NH2 | ARG | 245 | 123.590 | 49.075 | -9.810 | 1.00 | 30.81 | A | N |
| ATOM | 787 | C | ARG | 245 | 122.131 | 46.493 | -16.266 | 1.00 | 18.16 | A | C |
| ATOM | 788 | O | ARG | 245 | 123.003 | 45.710 | -15.911 | 1.00 | 14.27 | A | O |
| ATOM | 789 | N | ARG | 246 | 121.985 | 46.896 | -17.525 | 1.00 | 55.16 | A | N |
| ATOM | 790 | CA | ARG | 246 | 122.848 | 46.429 | -18.607 | 1.00 | 57.95 | A | C |
| ATOM | 791 | CB | ARG | 246 | 122.447 | 47.078 | -19.928 | 1.00 | 115.62 | A | C |
| ATOM | 792 | CG | ARG | 246 | 123.405 | 46.764 | -21.067 | 1.00 | 120.98 | A | C |
| ATOM | 793 | CD | ARG | 246 | 123.057 | 47.546 | -22.318 | 1.00 | 126.90 | A | C |
| ATOM | 794 | NE | ARG | 246 | 121.637 | 47.444 | -22.641 | 1.00 | 129.81 | A | N |
| ATOM | 795 | CZ | ARG | 246 | 120.981 | 46.298 | -22.804 | 1.00 | 132.92 | A | C |
| ATOM | 796 | NH1 | ARG | 246 | 121.615 | 45.138 | -22.676 | 1.00 | 132.61 | A | N |
| ATOM | 797 | NH2 | ARG | 246 | 119.685 | 46.314 | -23.094 | 1.00 | 133.70 | A | N |
| ATOM | 798 | C | ARG | 246 | 124.313 | 46.736 | -18.364 | 1.00 | 55.77 | A | C |
| ATOM | 799 | O | ARG | 246 | 124.671 | 47.879 | -18.092 | 1.00 | 58.40 | A | O |
| ATOM | 800 | N | GLY | 247 | 125.151 | 45.711 | -18.475 | 1.00 | 47.75 | A | N |
| ATOM | 801 | CA | GLY | 247 | 126.587 | 45.878 | -18.302 | 1.00 | 50.33 | A | C |
| ATOM | 802 | C | GLY | 247 | 127.097 | 46.294 | -16.934 | 1.00 | 50.40 | A | C |
| ATOM | 803 | O | GLY | 247 | 128.129 | 46.958 | -16.824 | 1.00 | 53.36 | A | O |

Fig. 19: A-12

```
ATOM    804  N    VAL 248    126.382  45.911 -15.887  1.00  40.38  A  N
ATOM    805  CA   VAL 248    126.790  46.248 -14.535  1.00  38.39  A  C
ATOM    806  CB   VAL 248    125.653  46.928 -13.780  1.00  41.70  A  C
ATOM    807  CG1  VAL 248    126.049  47.136 -12.331  1.00  39.35  A  C
ATOM    808  CG2  VAL 248    125.331  48.250 -14.436  1.00  33.47  A  C
ATOM    809  C    VAL 248    127.173  44.970 -13.807  1.00  41.41  A  C
ATOM    810  O    VAL 248    126.530  43.936 -13.993  1.00  45.46  A  O
ATOM    811  N    LYS 249    128.208  45.036 -12.975  1.00  30.45  A  N
ATOM    812  CA   LYS 249    128.645  43.852 -12.250  1.00  31.36  A  C
ATOM    813  CB   LYS 249    129.799  44.186 -11.299  1.00  85.59  A  C
ATOM    814  CG   LYS 249    130.426  42.940 -10.690  1.00  91.11  A  C
ATOM    815  CD   LYS 249    130.844  41.943 -11.782  1.00  92.18  A  C
ATOM    816  CE   LYS 249    131.040  40.539 -11.224  1.00  94.54  A  C
ATOM    817  NZ   LYS 249    131.548  39.546 -12.218  1.00  97.36  A  N
ATOM    818  C    LYS 249    127.503  43.190 -11.473  1.00  30.02  A  C
ATOM    819  O    LYS 249    126.706  43.862 -10.815  1.00  29.84  A  O
ATOM    820  N    LYS 250    127.432  41.864 -11.559  1.00  29.51  A  N
ATOM    821  CA   LYS 250    126.396  41.110 -10.879  1.00  29.16  A  C
ATOM    822  CB   LYS 250    125.763  40.134 -11.871  1.00  45.59  A  C
ATOM    823  CG   LYS 250    125.050  40.864 -12.996  1.00  44.19  A  C
ATOM    824  CD   LYS 250    124.892  40.022 -14.263  1.00  45.74  A  C
ATOM    825  CE   LYS 250    123.827  38.928 -14.135  1.00  44.90  A  C
ATOM    826  NZ   LYS 250    123.513  38.274 -15.453  1.00  46.72  A  N
ATOM    827  C    LYS 250    126.979  40.391  -9.663  1.00  28.51  A  C
ATOM    828  O    LYS 250    127.849  39.541  -9.804  1.00  28.19  A  O
ATOM    829  N    VAL 251    126.493  40.754  -8.474  1.00  23.05  A  N
ATOM    830  CA   VAL 251    126.954  40.173  -7.219  1.00  22.96  A  C
ATOM    831  CB   VAL 251    127.504  41.263  -6.307  1.00  28.85  A  C
ATOM    832  CG1  VAL 251    127.901  40.676  -4.959  1.00  27.00  A  C
ATOM    833  CG2  VAL 251    128.678  41.928  -6.974  1.00  30.06  A  C
ATOM    834  C    VAL 251    125.863  39.421  -6.451  1.00  21.44  A  C
ATOM    835  O    VAL 251    124.778  39.945  -6.232  1.00  17.44  A  O
ATOM    836  N    MET 252    126.168  38.199  -6.023  1.00  19.32  A  N
ATOM    837  CA   MET 252    125.212  37.383  -5.278  1.00  20.30  A  C
ATOM    838  CB   MET 252    124.949  36.073  -6.024  1.00  19.49  A  C
ATOM    839  CG   MET 252    123.850  35.212  -5.425  1.00  18.18  A  C
ATOM    840  SD   MET 252    123.556  33.701  -6.379  1.00  22.23  A  S
ATOM    841  CE   MET 252    123.009  34.366  -7.960  1.00  13.54  A  C
ATOM    842  C    MET 252    125.730  37.072  -3.875  1.00  19.32  A  C
ATOM    843  O    MET 252    126.880  36.675  -3.704  1.00  21.69  A  O
ATOM    844  N    VAL 253    124.886  37.261  -2.869  1.00  11.70  A  N
ATOM    845  CA   VAL 253    125.286  36.971  -1.505  1.00  12.85  A  C
ATOM    846  CB   VAL 253    125.173  38.221  -0.593  1.00   5.67  A  C
ATOM    847  CG1  VAL 253    125.508  37.856   0.842  1.00   7.09  A  C
ATOM    848  CG2  VAL 253    126.118  39.310  -1.079  1.00   5.31  A  C
ATOM    849  C    VAL 253    124.370  35.881  -0.974  1.00  12.42  A  C
ATOM    850  O    VAL 253    123.166  36.093  -0.870  1.00  10.86  A  O
ATOM    851  N    ILE 254    124.936  34.716  -0.649  1.00  26.88  A  N
ATOM    852  CA   ILE 254    124.142  33.597  -0.126  1.00  23.78  A  C
ATOM    853  CB   ILE 254    124.457  32.266  -0.847  1.00  10.72  A  C
ATOM    854  CG2  ILE 254    123.584  31.171  -0.294  1.00   7.19  A  C
ATOM    855  CG1  ILE 254    124.220  32.397  -2.352  1.00   9.30  A  C
ATOM    856  CD1  ILE 254    125.307  33.140  -3.078  1.00   8.93  A  C
ATOM    857  C    ILE 254    124.379  33.370   1.359  1.00  21.87  A  C
ATOM    858  O    ILE 254    125.508  33.431   1.833  1.00  23.74  A  O
ATOM    859  N    VAL 255    123.300  33.105   2.084  1.00  38.19  A  N
ATOM    860  CA   VAL 255    123.379  32.858   3.516  1.00  36.93  A  C
ATOM    861  CB   VAL 255    122.733  33.994   4.328  1.00  13.80  A  C
ATOM    862  CG1  VAL 255    123.224  33.949   5.753  1.00  12.25  A  C
ATOM    863  CG2  VAL 255    123.056  35.325   3.713  1.00  14.44  A  C
ATOM    864  C    VAL 255    122.592  31.594   3.798  1.00  34.68  A  C
ATOM    865  O    VAL 255    121.431  31.491   3.403  1.00  36.68  A  O
ATOM    866  N    THR 256    123.210  30.632   4.474  1.00  19.22  A  N
ATOM    867  CA   THR 256    122.514  29.387   4.798  1.00  20.04  A  C
ATOM    868  CB   THR 256    122.477  28.457   3.566  1.00  10.08  A  C
ATOM    869  OG1  THR 256    122.032  27.147   3.952  1.00   6.12  A  O
ATOM    870  CG2  THR 256    123.851  28.387   2.926  1.00   8.93  A  C
ATOM    871  C    THR 256    123.128  28.650   5.995  1.00  23.52  A  C
ATOM    872  O    THR 256    124.303  28.831   6.310  1.00  19.68  A  O
ATOM    873  N    ASP 257    122.323  27.829   6.663  1.00  46.58  A  N
ATOM    874  CA   ASP 257    122.794  27.097   7.830  1.00  46.96  A  C
ATOM    875  CB   ASP 257    122.069  27.585   9.091  1.00  21.89  A  C
ATOM    876  CG   ASP 257    120.655  27.009   9.225  1.00  27.25  A  C
```

Fig. 19: A-13

| | | | | | | | | | | | |
|---|---|---|---|---|---|---|---|---|---|---|---|
| ATOM | 877 | OD1 | ASP | 257 | 120.089 | 26.573 | 8.191 | 1.00 | 27.72 | A | O |
| ATOM | 878 | OD2 | ASP | 257 | 120.110 | 27.006 | 10.362 | 1.00 | 32.52 | A | O |
| ATOM | 879 | C | ASP | 257 | 122.599 | 25.596 | 7.693 | 1.00 | 43.55 | A | C |
| ATOM | 880 | O | ASP | 257 | 122.525 | 24.883 | 8.695 | 1.00 | 42.79 | A | O |
| ATOM | 881 | N | GLY | 258 | 122.510 | 25.106 | 6.461 | 1.00 | 42.38 | A | N |
| ATOM | 882 | CA | GLY | 258 | 122.330 | 23.678 | 6.283 | 1.00 | 44.80 | A | C |
| ATOM | 883 | C | GLY | 258 | 122.618 | 23.150 | 4.896 | 1.00 | 48.62 | A | C |
| ATOM | 884 | O | GLY | 258 | 122.523 | 23.871 | 3.903 | 1.00 | 44.34 | A | O |
| ATOM | 885 | N | GLU | 259 | 122.984 | 21.876 | 4.832 | 1.00 | 88.78 | A | N |
| ATOM | 886 | CA | GLU | 259 | 123.265 | 21.230 | 3.562 | 1.00 | 90.66 | A | C |
| ATOM | 887 | CB | GLU | 259 | 123.650 | 19.770 | 3.782 | 1.00 | 87.02 | A | C |
| ATOM | 888 | CG | GLU | 259 | 124.983 | 19.588 | 4.461 | 1.00 | 94.80 | A | C |
| ATOM | 889 | CD | GLU | 259 | 125.130 | 18.214 | 5.070 | 1.00 | 98.61 | A | C |
| ATOM | 890 | OE1 | GLU | 259 | 126.256 | 17.861 | 5.481 | 1.00 | 105.36 | A | O |
| ATOM | 891 | OE2 | GLU | 259 | 124.115 | 17.490 | 5.147 | 1.00 | 98.63 | A | O |
| ATOM | 892 | C | GLU | 259 | 122.004 | 21.298 | 2.727 | 1.00 | 89.52 | A | C |
| ATOM | 893 | O | GLU | 259 | 120.927 | 20.906 | 3.174 | 1.00 | 86.69 | A | O |
| ATOM | 894 | N | SER | 260 | 122.140 | 21.815 | 1.517 | 1.00 | 31.72 | A | N |
| ATOM | 895 | CA | SER | 260 | 121.007 | 21.922 | 0.615 | 1.00 | 34.88 | A | C |
| ATOM | 896 | CB | SER | 260 | 121.435 | 22.606 | -0.685 | 1.00 | 104.64 | A | C |
| ATOM | 897 | OG | SER | 260 | 122.467 | 21.872 | -1.325 | 1.00 | 105.15 | A | O |
| ATOM | 898 | C | SER | 260 | 120.489 | 20.526 | 0.304 | 1.00 | 34.78 | A | C |
| ATOM | 899 | O | SER | 260 | 121.257 | 19.571 | 0.315 | 1.00 | 30.81 | A | O |
| ATOM | 900 | N | HIS | 261 | 119.192 | 20.409 | 0.039 | 1.00 | 119.42 | A | N |
| ATOM | 901 | CA | HIS | 261 | 118.609 | 19.114 | -0.284 | 1.00 | 123.77 | A | C |
| ATOM | 902 | CB | HIS | 261 | 117.107 | 19.116 | 0.020 | 1.00 | 89.56 | A | C |
| ATOM | 903 | CG | HIS | 261 | 116.789 | 19.030 | 1.482 | 1.00 | 92.76 | A | C |
| ATOM | 904 | CD2 | HIS | 261 | 116.610 | 19.997 | 2.413 | 1.00 | 91.87 | A | C |
| ATOM | 905 | ND1 | HIS | 261 | 116.648 | 17.830 | 2.147 | 1.00 | 94.24 | A | N |
| ATOM | 906 | CE1 | HIS | 261 | 116.393 | 18.065 | 3.422 | 1.00 | 94.31 | A | C |
| ATOM | 907 | NE2 | HIS | 261 | 116.365 | 19.372 | 3.610 | 1.00 | 91.58 | A | N |
| ATOM | 908 | C | HIS | 261 | 118.866 | 18.815 | -1.754 | 1.00 | 124.83 | A | C |
| ATOM | 909 | O | HIS | 261 | 118.732 | 17.676 | -2.203 | 1.00 | 122.05 | A | O |
| ATOM | 910 | N | ASP | 262 | 119.251 | 19.850 | -2.495 | 1.00 | 94.20 | A | N |
| ATOM | 911 | CA | ASP | 262 | 119.556 | 19.709 | -3.913 | 1.00 | 99.17 | A | C |
| ATOM | 912 | CB | ASP | 262 | 118.838 | 20.798 | -4.732 | 1.00 | 77.35 | A | C |
| ATOM | 913 | CG | ASP | 262 | 118.558 | 22.065 | -3.929 | 1.00 | 77.35 | A | C |
| ATOM | 914 | OD1 | ASP | 262 | 119.382 | 22.429 | -3.067 | 1.00 | 77.35 | A | O |
| ATOM | 915 | OD2 | ASP | 262 | 117.515 | 22.708 | -4.179 | 1.00 | 77.35 | A | O |
| ATOM | 916 | C | ASP | 262 | 121.065 | 19.758 | -4.191 | 1.00 | 99.22 | A | C |
| ATOM | 917 | O | ASP | 262 | 121.510 | 20.456 | -5.104 | 1.00 | 99.08 | A | O |
| ATOM | 918 | N | ASN | 263 | 121.842 | 19.009 | -3.406 | 1.00 | 48.33 | A | N |
| ATOM | 919 | CA | ASN | 263 | 123.300 | 18.956 | -3.558 | 1.00 | 49.50 | A | C |
| ATOM | 920 | CB | ASN | 263 | 123.896 | 17.820 | -2.719 | 1.00 | 78.20 | A | C |
| ATOM | 921 | CG | ASN | 263 | 123.359 | 17.781 | -1.303 | 1.00 | 82.57 | A | C |
| ATOM | 922 | OD1 | ASN | 263 | 123.578 | 18.703 | -0.511 | 1.00 | 84.07 | A | O |
| ATOM | 923 | ND2 | ASN | 263 | 122.651 | 16.702 | -0.974 | 1.00 | 77.07 | A | N |
| ATOM | 924 | C | ASN | 263 | 123.657 | 18.684 | -5.012 | 1.00 | 50.14 | A | C |
| ATOM | 925 | O | ASN | 263 | 124.574 | 19.286 | -5.572 | 1.00 | 49.04 | A | O |
| ATOM | 926 | N | TYR | 264 | 122.915 | 17.754 | -5.601 | 1.00 | 83.05 | A | N |
| ATOM | 927 | CA | TYR | 264 | 123.112 | 17.330 | -6.976 | 1.00 | 80.90 | A | C |
| ATOM | 928 | CB | TYR | 264 | 121.905 | 16.512 | -7.431 | 1.00 | 165.37 | A | C |
| ATOM | 929 | CG | TYR | 264 | 121.684 | 15.297 | -6.568 | 1.00 | 165.37 | A | C |
| ATOM | 930 | CD1 | TYR | 264 | 121.294 | 15.427 | -5.234 | 1.00 | 165.37 | A | C |
| ATOM | 931 | CE1 | TYR | 264 | 121.137 | 14.312 | -4.419 | 1.00 | 165.37 | A | C |
| ATOM | 932 | CD2 | TYR | 264 | 121.909 | 14.016 | -7.067 | 1.00 | 165.37 | A | C |
| ATOM | 933 | CE2 | TYR | 264 | 121.753 | 12.892 | -6.262 | 1.00 | 165.37 | A | C |
| ATOM | 934 | CZ | TYR | 264 | 121.369 | 13.048 | -4.939 | 1.00 | 165.37 | A | C |
| ATOM | 935 | OH | TYR | 264 | 121.224 | 11.940 | -4.139 | 1.00 | 165.37 | A | O |
| ATOM | 936 | C | TYR | 264 | 123.396 | 18.439 | -7.977 | 1.00 | 79.55 | A | C |
| ATOM | 937 | O | TYR | 264 | 124.509 | 18.536 | -8.498 | 1.00 | 76.68 | A | O |
| ATOM | 938 | N | ARG | 265 | 122.406 | 19.283 | -8.245 | 1.00 | 83.26 | A | N |
| ATOM | 939 | CA | ARG | 265 | 122.605 | 20.340 | -9.224 | 1.00 | 82.16 | A | C |
| ATOM | 940 | CB | ARG | 265 | 121.297 | 20.636 | -9.957 | 1.00 | 36.62 | A | C |
| ATOM | 941 | CG | ARG | 265 | 120.182 | 21.225 | -9.142 | 1.00 | 37.07 | A | C |
| ATOM | 942 | CD | ARG | 265 | 119.267 | 21.953 | -10.110 | 1.00 | 38.90 | A | C |
| ATOM | 943 | NE | ARG | 265 | 118.140 | 22.620 | -9.464 | 1.00 | 44.29 | A | N |
| ATOM | 944 | CZ | ARG | 265 | 117.562 | 23.714 | -9.947 | 1.00 | 44.46 | A | C |
| ATOM | 945 | NH1 | ARG | 265 | 118.016 | 24.257 | -11.071 | 1.00 | 49.09 | A | N |
| ATOM | 946 | NH2 | ARG | 265 | 116.528 | 24.258 | -9.321 | 1.00 | 48.43 | A | N |
| ATOM | 947 | C | ARG | 265 | 123.211 | 21.644 | -8.720 | 1.00 | 81.41 | A | C |
| ATOM | 948 | O | ARG | 265 | 123.137 | 22.668 | -9.396 | 1.00 | 82.72 | A | O |
| ATOM | 949 | N | LEU | 266 | 123.819 | 21.614 | -7.543 | 1.00 | 27.19 | A | N |

Fig. 19: A-14

```
ATOM    950  CA   LEU  266     124.435   22.815   -7.003  1.00   28.76   A  C
ATOM    951  CB   LEU  266     124.798   22.601   -5.539  1.00    4.24   A  C
ATOM    952  CG   LEU  266     125.336   23.820   -4.797  1.00    3.45   A  C
ATOM    953  CD1  LEU  266     124.393   24.999   -4.976  1.00    5.79   A  C
ATOM    954  CD2  LEU  266     125.502   23.466   -3.320  1.00    1.87   A  C
ATOM    955  C    LEU  266     125.684   23.084   -7.828  1.00   31.58   A  C
ATOM    956  O    LEU  266     126.086   24.226   -8.022  1.00   31.46   A  O
ATOM    957  N    LYS  267     126.286   22.007   -8.317  1.00   45.65   A  N
ATOM    958  CA   LYS  267     127.479   22.088   -9.149  1.00   47.96   A  C
ATOM    959  CB   LYS  267     127.949   20.673   -9.497  1.00   72.30   A  C
ATOM    960  CG   LYS  267     129.239   20.583  -10.298  1.00   72.30   A  C
ATOM    961  CD   LYS  267     130.428   20.277   -9.403  1.00   72.30   A  C
ATOM    962  CE   LYS  267     131.649   19.894  -10.230  1.00   72.30   A  C
ATOM    963  NZ   LYS  267     132.793   19.452   -9.381  1.00   72.30   A  N
ATOM    964  C    LYS  267     127.103   22.842  -10.427  1.00   47.45   A  C
ATOM    965  O    LYS  267     127.763   23.810  -10.809  1.00   46.97   A  O
ATOM    966  N    GLN  268     126.032   22.389  -11.074  1.00   32.65   A  N
ATOM    967  CA   GLN  268     125.553   22.999  -12.303  1.00   31.62   A  C
ATOM    968  CB   GLN  268     124.292   22.295  -12.798  1.00   88.56   A  C
ATOM    969  CG   GLN  268     124.449   20.845  -13.182  1.00   88.56   A  C
ATOM    970  CD   GLN  268     123.119   20.227  -13.576  1.00   88.56   A  C
ATOM    971  OE1  GLN  268     123.059   19.078  -14.010  1.00   88.56   A  O
ATOM    972  NE2  GLN  268     122.041   20.992  -13.423  1.00   88.56   A  N
ATOM    973  C    GLN  268     125.221   24.474  -12.100  1.00   27.37   A  C
ATOM    974  O    GLN  268     125.678   25.332  -12.851  1.00   28.55   A  O
ATOM    975  N    VAL  269     124.410   24.767  -11.089  1.00   11.19   A  N
ATOM    976  CA   VAL  269     124.007   26.140  -10.830  1.00    8.94   A  C
ATOM    977  CB   VAL  269     123.088   26.223   -9.598  1.00   22.95   A  C
ATOM    978  CG1  VAL  269     122.650   27.667   -9.374  1.00   18.60   A  C
ATOM    979  CG2  VAL  269     121.872   25.334   -9.801  1.00   20.81   A  C
ATOM    980  C    VAL  269     125.198   27.076  -10.649  1.00    8.53   A  C
ATOM    981  O    VAL  269     125.286   28.093  -11.318  1.00   11.37   A  O
ATOM    982  N    ILE  270     126.114   26.744   -9.746  1.00    5.57   A  N
ATOM    983  CA   ILE  270     127.291   27.585   -9.535  1.00    6.19   A  C
ATOM    984  CB   ILE  270     128.281   26.944   -8.533  1.00   12.81   A  C
ATOM    985  CG2  ILE  270     129.592   27.731   -8.504  1.00    7.43   A  C
ATOM    986  CG1  ILE  270     127.671   26.926   -7.135  1.00   10.37   A  C
ATOM    987  CD1  ILE  270     127.367   28.317   -6.591  1.00   11.49   A  C
ATOM    988  C    ILE  270     128.001   27.775  -10.870  1.00   10.06   A  C
ATOM    989  O    ILE  270     128.549   28.838  -11.140  1.00    8.84   A  O
ATOM    990  N    GLN  271     127.981   26.729  -11.696  1.00    7.96   A  N
ATOM    991  CA   GLN  271     128.605   26.751  -13.011  1.00   10.02   A  C
ATOM    992  CB   GLN  271     128.434   25.394  -13.698  1.00   84.89   A  C
ATOM    993  CG   GLN  271     129.267   25.214  -14.947  1.00   86.79   A  C
ATOM    994  CD   GLN  271     130.744   25.366  -14.665  1.00   89.29   A  C
ATOM    995  OE1  GLN  271     131.244   26.477  -14.506  1.00   89.62   A  O
ATOM    996  NE2  GLN  271     131.451   24.243  -14.583  1.00   90.86   A  N
ATOM    997  C    GLN  271     127.962   27.842  -13.860  1.00   12.48   A  C
ATOM    998  O    GLN  271     128.644   28.733  -14.348  1.00   15.17   A  O
ATOM    999  N    ASP  272     126.648   27.770  -14.031  1.00   33.57   A  N
ATOM   1000  CA   ASP  272     125.929   28.758  -14.818  1.00   34.85   A  C
ATOM   1001  CB   ASP  272     124.430   28.459  -14.786  1.00   74.39   A  C
ATOM   1002  CG   ASP  272     124.084   27.142  -15.454  1.00   76.01   A  C
ATOM   1003  OD1  ASP  272     123.000   26.589  -15.163  1.00   78.08   A  O
ATOM   1004  OD2  ASP  272     124.893   26.665  -16.278  1.00   82.27   A  O
ATOM   1005  C    ASP  272     126.194   30.163  -14.283  1.00   35.65   A  C
ATOM   1006  O    ASP  272     126.190   31.131  -15.042  1.00   33.10   A  O
ATOM   1007  N    CYS  273     126.426   30.280  -12.978  1.00   42.88   A  N
ATOM   1008  CA   CYS  273     126.698   31.582  -12.387  1.00   41.31   A  C
ATOM   1009  CB   CYS  273     126.630   31.516  -10.862  1.00   24.14   A  C
ATOM   1010  SG   CYS  273     124.940   31.489  -10.191  1.00   22.24   A  S
ATOM   1011  C    CYS  273     128.059   32.090  -12.826  1.00   41.68   A  C
ATOM   1012  O    CYS  273     128.244   33.288  -13.008  1.00   35.99   A  O
ATOM   1013  N    GLU  274     129.010   31.178  -12.994  1.00   20.07   A  N
ATOM   1014  CA   GLU  274     130.364   31.531  -13.440  1.00   22.87   A  C
ATOM   1015  CB   GLU  274     131.317   30.338  -13.298  1.00   39.18   A  C
ATOM   1016  CG   GLU  274     132.090   30.309  -11.989  1.00   44.30   A  C
ATOM   1017  CD   GLU  274     133.041   31.490  -11.836  1.00   49.41   A  C
ATOM   1018  OE1  GLU  274     133.622   31.659  -10.740  1.00   51.28   A  O
ATOM   1019  OE2  GLU  274     133.212   32.251  -12.812  1.00   53.97   A  O
ATOM   1020  C    GLU  274     130.345   31.984  -14.893  1.00   25.29   A  C
ATOM   1021  O    GLU  274     131.031   32.931  -15.266  1.00   27.49   A  O
ATOM   1022  N    ASP  275     129.550   31.298  -15.707  1.00   41.03   A  N
```

Fig. 19: A-15

| ATOM | 1023 | CA | ASP | 275 | 129.421 | 31.625 | -17.119 | 1.00 | 39.77 | A | C |
|---|---|---|---|---|---|---|---|---|---|---|---|
| ATOM | 1024 | CB | ASP | 275 | 128.538 | 30.594 | -17.822 | 1.00 | 63.42 | A | C |
| ATOM | 1025 | CG | ASP | 275 | 129.106 | 29.203 | -17.757 | 1.00 | 64.69 | A | C |
| ATOM | 1026 | OD1 | ASP | 275 | 129.987 | 28.959 | -16.906 | 1.00 | 68.39 | A | O |
| ATOM | 1027 | OD2 | ASP | 275 | 128.657 | 28.352 | -18.551 | 1.00 | 66.35 | A | O |
| ATOM | 1028 | C | ASP | 275 | 128.789 | 32.996 | -17.295 | 1.00 | 38.76 | A | C |
| ATOM | 1029 | O | ASP | 275 | 128.883 | 33.595 | -18.367 | 1.00 | 34.31 | A | O |
| ATOM | 1030 | N | GLU | 276 | 128.137 | 33.485 | -16.247 | 1.00 | 28.36 | A | N |
| ATOM | 1031 | CA | GLU | 276 | 127.479 | 34.771 | -16.328 | 1.00 | 28.01 | A | C |
| ATOM | 1032 | CB | GLU | 276 | 126.019 | 34.617 | -15.913 | 1.00 | 53.33 | A | C |
| ATOM | 1033 | CG | GLU | 276 | 125.310 | 33.520 | -16.700 | 1.00 | 53.20 | A | C |
| ATOM | 1034 | CD | GLU | 276 | 123.807 | 33.493 | -16.487 | 1.00 | 54.30 | A | C |
| ATOM | 1035 | OE1 | GLU | 276 | 123.150 | 32.629 | -17.102 | 1.00 | 55.01 | A | O |
| ATOM | 1036 | OE2 | GLU | 276 | 123.280 | 34.330 | -15.717 | 1.00 | 51.24 | A | O |
| ATOM | 1037 | C | GLU | 276 | 128.172 | 35.841 | -15.504 | 1.00 | 26.84 | A | C |
| ATOM | 1038 | O | GLU | 276 | 127.621 | 36.919 | -15.288 | 1.00 | 27.95 | A | O |
| ATOM | 1039 | N | ASN | 277 | 129.382 | 35.535 | -15.050 | 1.00 | 28.50 | A | N |
| ATOM | 1040 | CA | ASN | 277 | 130.185 | 36.472 | -14.268 | 1.00 | 28.47 | A | C |
| ATOM | 1041 | CB | ASN | 277 | 130.607 | 37.655 | -15.140 | 1.00 | 86.35 | A | C |
| ATOM | 1042 | CG | ASN | 277 | 131.230 | 37.218 | -16.439 | 1.00 | 91.27 | A | C |
| ATOM | 1043 | OD1 | ASN | 277 | 132.263 | 36.548 | -16.451 | 1.00 | 91.09 | A | O |
| ATOM | 1044 | ND2 | ASN | 277 | 130.601 | 37.589 | -17.550 | 1.00 | 90.23 | A | N |
| ATOM | 1045 | C | ASN | 277 | 129.493 | 37.014 | -13.018 | 1.00 | 24.82 | A | C |
| ATOM | 1046 | O | ASN | 277 | 129.476 | 38.226 | -12.790 | 1.00 | 25.80 | A | O |
| ATOM | 1047 | N | ILE | 278 | 128.925 | 36.127 | -12.207 | 1.00 | 15.37 | A | N |
| ATOM | 1048 | CA | ILE | 278 | 128.261 | 36.560 | -10.989 | 1.00 | 15.82 | A | C |
| ATOM | 1049 | CB | ILE | 278 | 126.963 | 35.773 | -10.747 | 1.00 | 17.43 | A | C |
| ATOM | 1050 | CG2 | ILE | 278 | 126.304 | 36.243 | -9.454 | 1.00 | 18.82 | A | C |
| ATOM | 1051 | CG1 | ILE | 278 | 126.016 | 35.949 | -11.932 | 1.00 | 14.88 | A | C |
| ATOM | 1052 | CD1 | ILE | 278 | 124.742 | 35.153 | -11.796 | 1.00 | 17.16 | A | C |
| ATOM | 1053 | C | ILE | 278 | 129.168 | 36.345 | -9.780 | 1.00 | 16.42 | A | C |
| ATOM | 1054 | O | ILE | 278 | 129.363 | 35.212 | -9.354 | 1.00 | 16.76 | A | O |
| ATOM | 1055 | N | GLN | 279 | 129.737 | 37.426 | -9.244 | 1.00 | 26.25 | A | N |
| ATOM | 1056 | CA | GLN | 279 | 130.578 | 37.335 | -8.053 | 1.00 | 25.85 | A | C |
| ATOM | 1057 | CB | GLN | 279 | 131.035 | 38.716 | -7.605 | 1.00 | 41.76 | A | C |
| ATOM | 1058 | CG | GLN | 279 | 131.959 | 39.382 | -8.574 | 1.00 | 47.54 | A | C |
| ATOM | 1059 | CD | GLN | 279 | 133.158 | 38.524 | -8.894 | 1.00 | 51.46 | A | C |
| ATOM | 1060 | OE1 | GLN | 279 | 133.992 | 38.255 | -8.023 | 1.00 | 45.70 | A | O |
| ATOM | 1061 | NE2 | GLN | 279 | 133.252 | 38.078 | -10.146 | 1.00 | 51.05 | A | N |
| ATOM | 1062 | C | GLN | 279 | 129.716 | 36.736 | -6.958 | 1.00 | 23.72 | A | C |
| ATOM | 1063 | O | GLN | 279 | 128.609 | 37.216 | -6.692 | 1.00 | 20.64 | A | O |
| ATOM | 1064 | N | ARG | 280 | 130.214 | 35.697 | -6.310 | 1.00 | 16.06 | A | N |
| ATOM | 1065 | CA | ARG | 280 | 129.440 | 35.054 | -5.258 | 1.00 | 17.58 | A | C |
| ATOM | 1066 | CB | ARG | 280 | 129.107 | 33.620 | -5.661 | 1.00 | 19.51 | A | C |
| ATOM | 1067 | CG | ARG | 280 | 128.413 | 33.488 | -6.997 | 1.00 | 18.14 | A | C |
| ATOM | 1068 | CD | ARG | 280 | 128.274 | 32.021 | -7.371 | 1.00 | 17.81 | A | C |
| ATOM | 1069 | NE | ARG | 280 | 129.576 | 31.365 | -7.441 | 1.00 | 14.86 | A | N |
| ATOM | 1070 | CZ | ARG | 280 | 130.427 | 31.489 | -8.452 | 1.00 | 18.77 | A | C |
| ATOM | 1071 | NH1 | ARG | 280 | 130.131 | 32.241 | -9.493 | 1.00 | 21.69 | A | N |
| ATOM | 1072 | NH2 | ARG | 280 | 131.579 | 30.846 | -8.422 | 1.00 | 23.71 | A | N |
| ATOM | 1073 | C | ARG | 280 | 130.123 | 35.037 | -3.892 | 1.00 | 17.24 | A | C |
| ATOM | 1074 | O | ARG | 280 | 131.269 | 34.592 | -3.750 | 1.00 | 16.97 | A | O |
| ATOM | 1075 | N | PHE | 281 | 129.406 | 35.539 | -2.894 | 1.00 | 21.33 | A | N |
| ATOM | 1076 | CA | PHE | 281 | 129.889 | 35.538 | -1.527 | 1.00 | 23.32 | A | C |
| ATOM | 1077 | CB | PHE | 281 | 129.848 | 36.933 | -0.924 | 1.00 | 12.67 | A | C |
| ATOM | 1078 | CG | PHE | 281 | 130.754 | 37.900 | -1.603 | 1.00 | 15.70 | A | C |
| ATOM | 1079 | CD1 | PHE | 281 | 130.419 | 38.434 | -2.837 | 1.00 | 19.55 | A | C |
| ATOM | 1080 | CD2 | PHE | 281 | 131.968 | 38.250 | -1.024 | 1.00 | 17.43 | A | C |
| ATOM | 1081 | CE1 | PHE | 281 | 131.281 | 39.305 | -3.487 | 1.00 | 19.61 | A | C |
| ATOM | 1082 | CE2 | PHE | 281 | 132.842 | 39.120 | -1.665 | 1.00 | 15.16 | A | C |
| ATOM | 1083 | CZ | PHE | 281 | 132.498 | 39.650 | -2.900 | 1.00 | 16.59 | A | C |
| ATOM | 1084 | C | PHE | 281 | 128.925 | 34.646 | -0.785 | 1.00 | 24.03 | A | C |
| ATOM | 1085 | O | PHE | 281 | 127.710 | 34.867 | -0.821 | 1.00 | 26.40 | A | O |
| ATOM | 1086 | N | SER | 282 | 129.449 | 33.613 | -0.141 | 1.00 | 13.47 | A | N |
| ATOM | 1087 | CA | SER | 282 | 128.594 | 32.705 | 0.602 | 1.00 | 15.32 | A | C |
| ATOM | 1088 | CB | SER | 282 | 128.746 | 31.272 | 0.084 | 1.00 | 11.38 | A | C |
| ATOM | 1089 | OG | SER | 282 | 130.081 | 30.816 | 0.216 | 1.00 | 7.93 | A | O |
| ATOM | 1090 | C | SER | 282 | 128.947 | 32.782 | 2.069 | 1.00 | 17.20 | A | C |
| ATOM | 1091 | O | SER | 282 | 130.066 | 33.135 | 2.435 | 1.00 | 21.06 | A | O |
| ATOM | 1092 | N | ILE | 283 | 127.969 | 32.477 | 2.908 | 1.00 | 24.08 | A | N |
| ATOM | 1093 | CA | ILE | 283 | 128.164 | 32.504 | 4.343 | 1.00 | 22.00 | A | C |
| ATOM | 1094 | CB | ILE | 283 | 127.517 | 33.733 | 4.968 | 1.00 | 17.91 | A | C |
| ATOM | 1095 | CG2 | ILE | 283 | 127.843 | 33.791 | 6.442 | 1.00 | 18.72 | A | C |

Fig. 19: A-16

| ATOM | 1096 | CG1 | ILE | 283 | 128.045 | 34.986 | 4.281 | 1.00 | 14.38 | A | C |
|---|---|---|---|---|---|---|---|---|---|---|---|
| ATOM | 1097 | CD1 | ILE | 283 | 127.103 | 36.171 | 4.383 | 1.00 | 17.94 | A | C |
| ATOM | 1098 | C | ILE | 283 | 127.510 | 31.273 | 4.912 | 1.00 | 21.07 | A | C |
| ATOM | 1099 | O | ILE | 283 | 126.394 | 30.917 | 4.536 | 1.00 | 20.93 | A | O |
| ATOM | 1100 | N | ALA | 284 | 128.204 | 30.618 | 5.823 | 1.00 | 29.93 | A | N |
| ATOM | 1101 | CA | ALA | 284 | 127.663 | 29.421 | 6.412 | 1.00 | 29.95 | A | C |
| ATOM | 1102 | CB | ALA | 284 | 128.548 | 28.253 | 6.070 | 1.00 | 1.87 | A | C |
| ATOM | 1103 | C | ALA | 284 | 127.507 | 29.536 | 7.920 | 1.00 | 28.08 | A | C |
| ATOM | 1104 | O | ALA | 284 | 128.482 | 29.740 | 8.641 | 1.00 | 26.74 | A | O |
| ATOM | 1105 | N | ILE | 285 | 126.270 | 29.422 | 8.389 | 1.00 | 31.23 | A | N |
| ATOM | 1106 | CA | ILE | 285 | 125.997 | 29.457 | 9.817 | 1.00 | 25.43 | A | C |
| ATOM | 1107 | CB | ILE | 285 | 124.529 | 29.859 | 10.107 | 1.00 | 43.54 | A | C |
| ATOM | 1108 | CG2 | ILE | 285 | 124.187 | 29.569 | 11.555 | 1.00 | 38.36 | A | C |
| ATOM | 1109 | CG1 | ILE | 285 | 124.306 | 31.344 | 9.791 | 1.00 | 38.87 | A | C |
| ATOM | 1110 | CD1 | ILE | 285 | 124.206 | 31.670 | 8.315 | 1.00 | 40.01 | A | C |
| ATOM | 1111 | C | ILE | 285 | 126.227 | 28.022 | 10.296 | 1.00 | 28.75 | A | C |
| ATOM | 1112 | O | ILE | 285 | 125.523 | 27.106 | 9.872 | 1.00 | 30.49 | A | O |
| ATOM | 1113 | N | LEU | 286 | 127.205 | 27.818 | 11.169 | 1.00 | 38.23 | A | N |
| ATOM | 1114 | CA | LEU | 286 | 127.497 | 26.471 | 11.649 | 1.00 | 38.71 | A | C |
| ATOM | 1115 | CB | LEU | 286 | 128.999 | 26.313 | 11.876 | 1.00 | 50.51 | A | C |
| ATOM | 1116 | CG | LEU | 286 | 129.917 | 26.722 | 10.727 | 1.00 | 53.33 | A | C |
| ATOM | 1117 | CD1 | LEU | 286 | 131.340 | 26.363 | 11.105 | 1.00 | 55.89 | A | C |
| ATOM | 1118 | CD2 | LEU | 286 | 129.513 | 26.019 | 9.441 | 1.00 | 55.00 | A | C |
| ATOM | 1119 | C | LEU | 286 | 126.760 | 26.069 | 12.923 | 1.00 | 39.16 | A | C |
| ATOM | 1120 | O | LEU | 286 | 127.068 | 25.036 | 13.517 | 1.00 | 40.00 | A | O |
| ATOM | 1121 | N | GLY | 287 | 125.789 | 26.875 | 13.339 | 1.00 | 72.80 | A | N |
| ATOM | 1122 | CA | GLY | 287 | 125.042 | 26.579 | 14.551 | 1.00 | 71.58 | A | C |
| ATOM | 1123 | C | GLY | 287 | 124.586 | 25.139 | 14.700 | 1.00 | 69.16 | A | C |
| ATOM | 1124 | O | GLY | 287 | 125.056 | 24.419 | 15.583 | 1.00 | 73.26 | A | O |
| ATOM | 1125 | N | THR | 296 | 131.112 | 19.210 | 10.542 | 1.00 | 87.02 | A | N |
| ATOM | 1126 | CA | THR | 296 | 130.609 | 20.333 | 9.766 | 1.00 | 87.06 | A | C |
| ATOM | 1127 | CB | THR | 296 | 130.702 | 21.652 | 10.554 | 1.00 | 100.17 | A | C |
| ATOM | 1128 | OG1 | THR | 296 | 132.071 | 21.903 | 10.895 | 1.00 | 105.23 | A | O |
| ATOM | 1129 | CG2 | THR | 296 | 129.861 | 21.592 | 11.817 | 1.00 | 100.04 | A | C |
| ATOM | 1130 | C | THR | 296 | 131.387 | 20.535 | 8.479 | 1.00 | 88.04 | A | C |
| ATOM | 1131 | O | THR | 296 | 130.985 | 21.331 | 7.631 | 1.00 | 86.85 | A | O |
| ATOM | 1132 | N | GLU | 297 | 132.497 | 19.825 | 8.322 | 1.00 | 78.34 | A | N |
| ATOM | 1133 | CA | GLU | 297 | 133.304 | 20.020 | 7.128 | 1.00 | 81.80 | A | C |
| ATOM | 1134 | CB | GLU | 297 | 134.577 | 19.171 | 7.169 | 1.00 | 125.47 | A | C |
| ATOM | 1135 | CG | GLU | 297 | 134.403 | 17.709 | 6.851 | 1.00 | 132.50 | A | C |
| ATOM | 1136 | CD | GLU | 297 | 135.690 | 17.103 | 6.342 | 1.00 | 133.75 | A | C |
| ATOM | 1137 | OE1 | GLU | 297 | 135.709 | 15.886 | 6.067 | 1.00 | 135.24 | A | O |
| ATOM | 1138 | OE2 | GLU | 297 | 136.682 | 17.853 | 6.212 | 1.00 | 137.19 | A | O |
| ATOM | 1139 | C | GLU | 297 | 132.550 | 19.770 | 5.832 | 1.00 | 79.84 | A | C |
| ATOM | 1140 | O | GLU | 297 | 132.581 | 20.609 | 4.931 | 1.00 | 79.34 | A | O |
| ATOM | 1141 | N | LYS | 298 | 131.865 | 18.638 | 5.728 | 1.00 | 42.69 | A | N |
| ATOM | 1142 | CA | LYS | 298 | 131.125 | 18.352 | 4.505 | 1.00 | 42.69 | A | C |
| ATOM | 1143 | CB | LYS | 298 | 130.281 | 17.087 | 4.678 | 1.00 | 102.63 | A | C |
| ATOM | 1144 | CG | LYS | 298 | 129.695 | 16.562 | 3.376 | 1.00 | 111.34 | A | C |
| ATOM | 1145 | CD | LYS | 298 | 129.117 | 15.166 | 3.545 | 1.00 | 113.06 | A | C |
| ATOM | 1146 | CE | LYS | 298 | 130.167 | 14.187 | 4.057 | 1.00 | 116.88 | A | C |
| ATOM | 1147 | NZ | LYS | 298 | 131.378 | 14.159 | 3.195 | 1.00 | 121.20 | A | N |
| ATOM | 1148 | C | LYS | 298 | 130.228 | 19.547 | 4.143 | 1.00 | 40.29 | A | C |
| ATOM | 1149 | O | LYS | 298 | 130.032 | 19.853 | 2.964 | 1.00 | 41.17 | A | O |
| ATOM | 1150 | N | PHE | 299 | 129.700 | 20.218 | 5.167 | 1.00 | 38.43 | A | N |
| ATOM | 1151 | CA | PHE | 299 | 128.839 | 21.380 | 4.978 | 1.00 | 36.67 | A | C |
| ATOM | 1152 | CB | PHE | 299 | 128.100 | 21.712 | 6.283 | 1.00 | 55.97 | A | C |
| ATOM | 1153 | CG | PHE | 299 | 127.256 | 22.967 | 6.209 | 1.00 | 48.41 | A | C |
| ATOM | 1154 | CD1 | PHE | 299 | 126.319 | 23.146 | 5.186 | 1.00 | 44.86 | A | C |
| ATOM | 1155 | CD2 | PHE | 299 | 127.400 | 23.970 | 7.160 | 1.00 | 46.14 | A | C |
| ATOM | 1156 | CE1 | PHE | 299 | 125.545 | 24.307 | 5.117 | 1.00 | 44.27 | A | C |
| ATOM | 1157 | CE2 | PHE | 299 | 126.627 | 25.132 | 7.095 | 1.00 | 40.55 | A | C |
| ATOM | 1158 | CZ | PHE | 299 | 125.701 | 25.299 | 6.073 | 1.00 | 39.06 | A | C |
| ATOM | 1159 | C | PHE | 299 | 129.684 | 22.573 | 4.544 | 1.00 | 37.02 | A | C |
| ATOM | 1160 | O | PHE | 299 | 129.439 | 23.190 | 3.504 | 1.00 | 32.83 | A | O |
| ATOM | 1161 | N | VAL | 300 | 130.682 | 22.896 | 5.352 | 1.00 | 13.94 | A | N |
| ATOM | 1162 | CA | VAL | 300 | 131.551 | 24.010 | 5.034 | 1.00 | 18.89 | A | C |
| ATOM | 1163 | CB | VAL | 300 | 132.752 | 24.068 | 5.993 | 1.00 | 40.51 | A | C |
| ATOM | 1164 | CG1 | VAL | 300 | 133.769 | 25.076 | 5.493 | 1.00 | 44.08 | A | C |
| ATOM | 1165 | CG2 | VAL | 300 | 132.282 | 24.451 | 7.382 | 1.00 | 44.52 | A | C |
| ATOM | 1166 | C | VAL | 300 | 132.061 | 23.893 | 3.607 | 1.00 | 17.53 | A | C |
| ATOM | 1167 | O | VAL | 300 | 132.177 | 24.889 | 2.906 | 1.00 | 18.03 | A | O |
| ATOM | 1168 | N | GLU | 301 | 132.365 | 22.679 | 3.164 | 1.00 | 18.30 | A | N |

Fig. 19: A-17

| | | | | | | | | | | |
|---|---|---|---|---|---|---|---|---|---|---|
| ATOM | 1169 | CA | GLU | 301 | 132.866 | 22.513 | 1.808 | 1.00 | 18.96 | A C |
| ATOM | 1170 | CB | GLU | 301 | 133.407 | 21.094 | 1.605 | 1.00 | 40.16 | A C |
| ATOM | 1171 | CG | GLU | 301 | 134.058 | 20.854 | 0.243 | 1.00 | 42.43 | A C |
| ATOM | 1172 | CD | GLU | 301 | 135.049 | 21.943 | -0.155 | 1.00 | 48.24 | A C |
| ATOM | 1173 | OE1 | GLU | 301 | 135.956 | 22.267 | 0.645 | 1.00 | 47.79 | A O |
| ATOM | 1174 | OE2 | GLU | 301 | 134.918 | 22.469 | -1.282 | 1.00 | 50.51 | A O |
| ATOM | 1175 | C | GLU | 301 | 131.770 | 22.832 | 0.791 | 1.00 | 17.53 | A C |
| ATOM | 1176 | O | GLU | 301 | 132.034 | 23.458 | -0.242 | 1.00 | 15.61 | A O |
| ATOM | 1177 | N | GLU | 302 | 130.541 | 22.420 | 1.097 | 1.00 | 32.12 | A N |
| ATOM | 1178 | CA | GLU | 302 | 129.412 | 22.667 | 0.210 | 1.00 | 31.93 | A C |
| ATOM | 1179 | CB | GLU | 302 | 128.127 | 22.084 | 0.801 | 1.00 | 76.04 | A C |
| ATOM | 1180 | CG | GLU | 302 | 126.894 | 22.274 | -0.071 | 1.00 | 75.79 | A C |
| ATOM | 1181 | CD | GLU | 302 | 125.659 | 21.594 | 0.501 | 1.00 | 72.72 | A C |
| ATOM | 1182 | OE1 | GLU | 302 | 125.651 | 20.349 | 0.584 | 1.00 | 72.70 | A O |
| ATOM | 1183 | OE2 | GLU | 302 | 124.698 | 22.302 | 0.872 | 1.00 | 77.14 | A O |
| ATOM | 1184 | C | GLU | 302 | 129.237 | 24.158 | -0.033 | 1.00 | 35.00 | A C |
| ATOM | 1185 | O | GLU | 302 | 129.040 | 24.580 | -1.170 | 1.00 | 34.26 | A O |
| ATOM | 1186 | N | ILE | 303 | 129.334 | 24.953 | 1.031 | 1.00 | 23.69 | A N |
| ATOM | 1187 | CA | ILE | 303 | 129.171 | 26.405 | 0.936 | 1.00 | 23.74 | A C |
| ATOM | 1188 | CB | ILE | 303 | 128.933 | 27.019 | 2.326 | 1.00 | 28.42 | A C |
| ATOM | 1189 | CG2 | ILE | 303 | 128.556 | 28.480 | 2.199 | 1.00 | 23.60 | A C |
| ATOM | 1190 | CG1 | ILE | 303 | 127.823 | 26.245 | 3.046 | 1.00 | 26.02 | A C |
| ATOM | 1191 | CD1 | ILE | 303 | 126.599 | 25.926 | 2.183 | 1.00 | 22.48 | A C |
| ATOM | 1192 | C | ILE | 303 | 130.340 | 27.129 | 0.267 | 1.00 | 25.77 | A C |
| ATOM | 1193 | O | ILE | 303 | 130.133 | 28.036 | -0.553 | 1.00 | 28.26 | A O |
| ATOM | 1194 | N | LYS | 304 | 131.564 | 26.740 | 0.612 | 1.00 | 28.18 | A N |
| ATOM | 1195 | CA | LYS | 304 | 132.733 | 27.363 | 0.003 | 1.00 | 28.98 | A C |
| ATOM | 1196 | CB | LYS | 304 | 134.018 | 26.713 | 0.501 | 1.00 | 31.11 | A C |
| ATOM | 1197 | CG | LYS | 304 | 134.415 | 27.051 | 1.915 | 1.00 | 37.78 | A C |
| ATOM | 1198 | CD | LYS | 304 | 135.810 | 26.502 | 2.190 | 1.00 | 39.31 | A C |
| ATOM | 1199 | CE | LYS | 304 | 136.298 | 26.803 | 3.599 | 1.00 | 42.04 | A C |
| ATOM | 1200 | NZ | LYS | 304 | 137.673 | 26.262 | 3.857 | 1.00 | 44.22 | A N |
| ATOM | 1201 | C | LYS | 304 | 132.665 | 27.210 | -1.512 | 1.00 | 25.07 | A C |
| ATOM | 1202 | O | LYS | 304 | 133.033 | 28.118 | -2.252 | 1.00 | 29.15 | A O |
| ATOM | 1203 | N | SER | 305 | 132.195 | 26.054 | -1.965 | 1.00 | 30.32 | A N |
| ATOM | 1204 | CA | SER | 305 | 132.100 | 25.785 | -3.386 | 1.00 | 27.48 | A C |
| ATOM | 1205 | CB | SER | 305 | 131.702 | 24.329 | -3.635 | 1.00 | 18.09 | A C |
| ATOM | 1206 | OG | SER | 305 | 130.352 | 24.088 | -3.293 | 1.00 | 14.77 | A O |
| ATOM | 1207 | C | SER | 305 | 131.094 | 26.709 | -4.044 | 1.00 | 28.00 | A C |
| ATOM | 1208 | O | SER | 305 | 131.137 | 26.917 | -5.263 | 1.00 | 30.57 | A O |
| ATOM | 1209 | N | ILE | 306 | 130.181 | 27.258 | -3.247 | 1.00 | 37.08 | A N |
| ATOM | 1210 | CA | ILE | 306 | 129.180 | 28.176 | -3.783 | 1.00 | 33.83 | A C |
| ATOM | 1211 | CB | ILE | 306 | 127.990 | 28.319 | -2.831 | 1.00 | 15.00 | A C |
| ATOM | 1212 | CG2 | ILE | 306 | 127.190 | 29.565 | -3.167 | 1.00 | 15.73 | A C |
| ATOM | 1213 | CG1 | ILE | 306 | 127.118 | 27.069 | -2.929 | 1.00 | 17.63 | A C |
| ATOM | 1214 | CD1 | ILE | 306 | 125.993 | 27.029 | -1.916 | 1.00 | 15.34 | A C |
| ATOM | 1215 | C | ILE | 306 | 129.812 | 29.544 | -4.008 | 1.00 | 31.59 | A C |
| ATOM | 1216 | O | ILE | 306 | 129.361 | 30.333 | -4.851 | 1.00 | 32.12 | A O |
| ATOM | 1217 | N | ALA | 307 | 130.874 | 29.805 | -3.251 | 1.00 | 20.26 | A N |
| ATOM | 1218 | CA | ALA | 307 | 131.584 | 31.062 | -3.349 | 1.00 | 22.45 | A C |
| ATOM | 1219 | CB | ALA | 307 | 132.444 | 31.260 | -2.118 | 1.00 | 5.65 | A C |
| ATOM | 1220 | C | ALA | 307 | 132.441 | 31.113 | -4.611 | 1.00 | 22.11 | A C |
| ATOM | 1221 | O | ALA | 307 | 132.622 | 30.103 | -5.302 | 1.00 | 21.10 | A O |
| ATOM | 1222 | N | SER | 308 | 132.953 | 32.307 | -4.906 | 1.00 | 24.29 | A N |
| ATOM | 1223 | CA | SER | 308 | 133.796 | 32.533 | -6.072 | 1.00 | 27.22 | A C |
| ATOM | 1224 | CB | SER | 308 | 133.489 | 33.899 | -6.700 | 1.00 | 15.61 | A C |
| ATOM | 1225 | OG | SER | 308 | 132.299 | 33.860 | -7.460 | 1.00 | 19.00 | A O |
| ATOM | 1226 | C | SER | 308 | 135.264 | 32.482 | -5.690 | 1.00 | 30.87 | A C |
| ATOM | 1227 | O | SER | 308 | 135.625 | 32.797 | -4.555 | 1.00 | 28.21 | A O |
| ATOM | 1228 | N | GLU | 309 | 136.103 | 32.069 | -6.640 | 1.00 | 26.43 | A N |
| ATOM | 1229 | CA | GLU | 309 | 137.542 | 32.008 | -6.418 | 1.00 | 29.92 | A C |
| ATOM | 1230 | CB | GLU | 309 | 138.224 | 31.266 | -7.569 | 1.00 | 73.14 | A C |
| ATOM | 1231 | CG | GLU | 309 | 137.811 | 29.809 | -7.737 | 1.00 | 78.51 | A C |
| ATOM | 1232 | CD | GLU | 309 | 138.181 | 28.950 | -6.541 | 1.00 | 81.27 | A C |
| ATOM | 1233 | OE1 | GLU | 309 | 138.103 | 27.708 | -6.651 | 1.00 | 83.60 | A O |
| ATOM | 1234 | OE2 | GLU | 309 | 138.544 | 29.514 | -5.487 | 1.00 | 85.42 | A O |
| ATOM | 1235 | C | GLU | 309 | 138.009 | 33.461 | -6.396 | 1.00 | 30.67 | A C |
| ATOM | 1236 | O | GLU | 309 | 137.580 | 34.257 | -7.230 | 1.00 | 32.32 | A O |
| ATOM | 1237 | N | PRO | 310 | 138.882 | 33.834 | -5.442 | 1.00 | 19.51 | A N |
| ATOM | 1238 | CD | PRO | 310 | 139.395 | 35.217 | -5.381 | 1.00 | 49.07 | A C |
| ATOM | 1239 | CA | PRO | 310 | 139.483 | 33.029 | -4.377 | 1.00 | 19.70 | A C |
| ATOM | 1240 | CB | PRO | 310 | 140.703 | 33.851 | -3.982 | 1.00 | 50.90 | A C |
| ATOM | 1241 | CG | PRO | 310 | 140.182 | 35.231 | -4.065 | 1.00 | 50.46 | A C |

Fig. 19: A-18

| ATOM | 1242 | C | PRO | 310 | 138.569 | 32.751 | -3.178 | 1.00 | 20.19 | A | C |
|---|---|---|---|---|---|---|---|---|---|---|---|
| ATOM | 1243 | O | PRO | 310 | 138.229 | 33.654 | -2.394 | 1.00 | 16.98 | A | O |
| ATOM | 1244 | N | THR | 311 | 138.197 | 31.483 | -3.043 | 1.00 | 25.93 | A | N |
| ATOM | 1245 | CA | THR | 311 | 137.352 | 31.013 | -1.957 | 1.00 | 26.80 | A | C |
| ATOM | 1246 | CB | THR | 311 | 137.618 | 29.521 | -1.695 | 1.00 | 73.61 | A | C |
| ATOM | 1247 | OG1 | THR | 311 | 137.053 | 29.145 | -0.434 | 1.00 | 77.77 | A | O |
| ATOM | 1248 | CG2 | THR | 311 | 139.118 | 29.244 | -1.696 | 1.00 | 76.69 | A | C |
| ATOM | 1249 | C | THR | 311 | 137.521 | 31.781 | -0.643 | 1.00 | 28.67 | A | C |
| ATOM | 1250 | O | THR | 311 | 136.535 | 32.173 | -0.025 | 1.00 | 29.84 | A | O |
| ATOM | 1251 | N | GLU | 312 | 138.759 | 32.009 | -0.223 | 1.00 | 47.89 | A | N |
| ATOM | 1252 | CA | GLU | 312 | 139.007 | 32.713 | 1.029 | 1.00 | 46.51 | A | C |
| ATOM | 1253 | CB | GLU | 312 | 140.506 | 32.751 | 1.340 | 1.00 | 98.24 | A | C |
| ATOM | 1254 | CG | GLU | 312 | 141.354 | 33.411 | 0.268 | 1.00 | 100.00 | A | C |
| ATOM | 1255 | CD | GLU | 312 | 142.621 | 34.031 | 0.825 | 1.00 | 99.11 | A | C |
| ATOM | 1256 | OE1 | GLU | 312 | 143.491 | 34.431 | 0.024 | 1.00 | 102.46 | A | O |
| ATOM | 1257 | OE2 | GLU | 312 | 142.742 | 34.130 | 2.065 | 1.00 | 99.98 | A | O |
| ATOM | 1258 | C | GLU | 312 | 138.453 | 34.134 | 1.092 | 1.00 | 45.13 | A | C |
| ATOM | 1259 | O | GLU | 312 | 137.997 | 34.576 | 2.147 | 1.00 | 45.09 | A | O |
| ATOM | 1260 | N | LYS | 313 | 138.490 | 34.856 | -0.021 | 1.00 | 49.11 | A | N |
| ATOM | 1261 | CA | LYS | 313 | 137.990 | 36.226 | -0.024 | 1.00 | 48.31 | A | C |
| ATOM | 1262 | CB | LYS | 313 | 138.797 | 37.091 | -1.000 | 1.00 | 91.02 | A | C |
| ATOM | 1263 | CG | LYS | 313 | 140.171 | 37.508 | -0.486 | 1.00 | 90.90 | A | C |
| ATOM | 1264 | CD | LYS | 313 | 140.081 | 38.565 | 0.620 | 1.00 | 87.20 | A | C |
| ATOM | 1265 | CE | LYS | 313 | 139.966 | 39.982 | 0.066 | 1.00 | 89.24 | A | C |
| ATOM | 1266 | NZ | LYS | 313 | 138.804 | 40.159 | -0.842 | 1.00 | 93.72 | A | N |
| ATOM | 1267 | C | LYS | 313 | 136.511 | 36.307 | -0.374 | 1.00 | 49.46 | A | C |
| ATOM | 1268 | O | LYS | 313 | 135.973 | 37.397 | -0.580 | 1.00 | 51.78 | A | O |
| ATOM | 1269 | N | HIS | 314 | 135.849 | 35.159 | -0.427 | 1.00 | 27.67 | A | N |
| ATOM | 1270 | CA | HIS | 314 | 134.437 | 35.137 | -0.775 | 1.00 | 28.52 | A | C |
| ATOM | 1271 | CB | HIS | 314 | 134.274 | 34.652 | -2.212 | 1.00 | 32.51 | A | C |
| ATOM | 1272 | CG | HIS | 314 | 134.872 | 35.574 | -3.224 | 1.00 | 29.37 | A | C |
| ATOM | 1273 | CD2 | HIS | 314 | 136.073 | 35.552 | -3.849 | 1.00 | 28.84 | A | C |
| ATOM | 1274 | ND1 | HIS | 314 | 134.220 | 36.697 | -3.683 | 1.00 | 28.95 | A | N |
| ATOM | 1275 | CE1 | HIS | 314 | 134.992 | 37.326 | -4.551 | 1.00 | 28.24 | A | C |
| ATOM | 1276 | NE2 | HIS | 314 | 136.122 | 36.652 | -4.669 | 1.00 | 28.63 | A | N |
| ATOM | 1277 | C | HIS | 314 | 133.587 | 34.277 | 0.141 | 1.00 | 28.65 | A | C |
| ATOM | 1278 | O | HIS | 314 | 132.366 | 34.238 | -0.008 | 1.00 | 32.05 | A | O |
| ATOM | 1279 | N | PHE | 315 | 134.230 | 33.591 | 1.081 | 1.00 | 32.99 | A | N |
| ATOM | 1280 | CA | PHE | 315 | 133.519 | 32.723 | 2.013 | 1.00 | 32.79 | A | C |
| ATOM | 1281 | CB | PHE | 315 | 134.045 | 31.294 | 1.878 | 1.00 | 35.38 | A | C |
| ATOM | 1282 | CG | PHE | 315 | 133.476 | 30.339 | 2.884 | 1.00 | 30.36 | A | C |
| ATOM | 1283 | CD1 | PHE | 315 | 132.123 | 30.026 | 2.877 | 1.00 | 32.20 | A | C |
| ATOM | 1284 | CD2 | PHE | 315 | 134.298 | 29.749 | 3.839 | 1.00 | 28.44 | A | C |
| ATOM | 1285 | CE1 | PHE | 315 | 131.592 | 29.144 | 3.800 | 1.00 | 27.15 | A | C |
| ATOM | 1286 | CE2 | PHE | 315 | 133.783 | 28.866 | 4.769 | 1.00 | 29.14 | A | C |
| ATOM | 1287 | CZ | PHE | 315 | 132.421 | 28.560 | 4.749 | 1.00 | 30.81 | A | C |
| ATOM | 1288 | C | PHE | 315 | 133.640 | 33.198 | 3.466 | 1.00 | 33.51 | A | C |
| ATOM | 1289 | O | PHE | 315 | 134.706 | 33.643 | 3.896 | 1.00 | 34.91 | A | O |
| ATOM | 1290 | N | PHE | 316 | 132.539 | 33.104 | 4.210 | 1.00 | 26.09 | A | N |
| ATOM | 1291 | CA | PHE | 316 | 132.513 | 33.516 | 5.610 | 1.00 | 23.14 | A | C |
| ATOM | 1292 | CB | PHE | 316 | 131.707 | 34.803 | 5.780 | 1.00 | 27.51 | A | C |
| ATOM | 1293 | CG | PHE | 316 | 132.343 | 36.008 | 5.155 | 1.00 | 31.13 | A | C |
| ATOM | 1294 | CD1 | PHE | 316 | 132.125 | 36.312 | 3.822 | 1.00 | 26.72 | A | C |
| ATOM | 1295 | CD2 | PHE | 316 | 133.182 | 36.827 | 5.903 | 1.00 | 27.98 | A | C |
| ATOM | 1296 | CE1 | PHE | 316 | 132.737 | 37.420 | 3.237 | 1.00 | 29.29 | A | C |
| ATOM | 1297 | CE2 | PHE | 316 | 133.799 | 37.931 | 5.334 | 1.00 | 31.09 | A | C |
| ATOM | 1298 | CZ | PHE | 316 | 133.577 | 38.230 | 3.998 | 1.00 | 31.32 | A | C |
| ATOM | 1299 | C | PHE | 316 | 131.909 | 32.438 | 6.497 | 1.00 | 21.07 | A | C |
| ATOM | 1300 | O | PHE | 316 | 130.901 | 31.831 | 6.153 | 1.00 | 20.31 | A | O |
| ATOM | 1301 | N | ASN | 317 | 132.533 | 32.220 | 7.647 | 1.00 | 37.16 | A | N |
| ATOM | 1302 | CA | ASN | 317 | 132.093 | 31.214 | 8.599 | 1.00 | 38.38 | A | C |
| ATOM | 1303 | CB | ASN | 317 | 133.288 | 30.385 | 9.047 | 1.00 | 74.28 | A | C |
| ATOM | 1304 | CG | ASN | 317 | 133.055 | 28.919 | 8.888 | 1.00 | 77.27 | A | C |
| ATOM | 1305 | OD1 | ASN | 317 | 131.954 | 28.433 | 9.138 | 1.00 | 79.20 | A | O |
| ATOM | 1306 | ND2 | ASN | 317 | 134.088 | 28.190 | 8.478 | 1.00 | 75.53 | A | N |
| ATOM | 1307 | C | ASN | 317 | 131.487 | 31.893 | 9.817 | 1.00 | 39.34 | A | C |
| ATOM | 1308 | O | ASN | 317 | 132.001 | 32.902 | 10.285 | 1.00 | 40.20 | A | O |
| ATOM | 1309 | N | VAL | 318 | 130.398 | 31.348 | 10.336 | 1.00 | 30.64 | A | N |
| ATOM | 1310 | CA | VAL | 318 | 129.763 | 31.924 | 11.521 | 1.00 | 29.27 | A | C |
| ATOM | 1311 | CB | VAL | 318 | 128.531 | 32.778 | 11.144 | 1.00 | 70.89 | A | C |
| ATOM | 1312 | CG1 | VAL | 318 | 127.896 | 33.349 | 12.386 | 1.00 | 71.02 | A | C |
| ATOM | 1313 | CG2 | VAL | 318 | 128.942 | 33.899 | 10.223 | 1.00 | 70.87 | A | C |
| ATOM | 1314 | C | VAL | 318 | 129.331 | 30.808 | 12.482 | 1.00 | 24.42 | A | C |

Fig. 19: A-19

| | | | | | | | | | | |
|---|---|---|---|---|---|---|---|---|---|---|
| ATOM | 1315 | O | VAL | 318 | 128.872 | 29.744 | 12.053 | 1.00 | 25.09 | A | O |
| ATOM | 1316 | N | SER | 319 | 129.482 | 31.045 | 13.779 | 1.00 | 32.47 | A | N |
| ATOM | 1317 | CA | SER | 319 | 129.108 | 30.035 | 14.752 | 1.00 | 31.73 | A | C |
| ATOM | 1318 | CB | SER | 319 | 129.669 | 30.384 | 16.134 | 1.00 | 29.19 | A | C |
| ATOM | 1319 | OG | SER | 319 | 129.289 | 31.687 | 16.538 | 1.00 | 41.14 | A | O |
| ATOM | 1320 | C | SER | 319 | 127.600 | 29.840 | 14.831 | 1.00 | 30.33 | A | C |
| ATOM | 1321 | O | SER | 319 | 127.132 | 28.716 | 14.963 | 1.00 | 28.40 | A | O |
| ATOM | 1322 | N | ASP | 320 | 126.839 | 30.926 | 14.741 | 1.00 | 32.33 | A | N |
| ATOM | 1323 | CA | ASP | 320 | 125.382 | 30.846 | 14.816 | 1.00 | 32.31 | A | C |
| ATOM | 1324 | CB | ASP | 320 | 124.934 | 30.632 | 16.275 | 1.00 | 63.91 | A | C |
| ATOM | 1325 | CG | ASP | 320 | 125.369 | 31.760 | 17.209 | 1.00 | 62.36 | A | C |
| ATOM | 1326 | OD1 | ASP | 320 | 126.586 | 31.992 | 17.364 | 1.00 | 61.04 | A | O |
| ATOM | 1327 | OD2 | ASP | 320 | 124.486 | 32.412 | 17.801 | 1.00 | 62.91 | A | O |
| ATOM | 1328 | C | ASP | 320 | 124.698 | 32.088 | 14.237 | 1.00 | 30.68 | A | C |
| ATOM | 1329 | O | ASP | 320 | 125.367 | 33.072 | 13.905 | 1.00 | 30.46 | A | O |
| ATOM | 1330 | N | GLU | 321 | 123.371 | 32.042 | 14.110 | 1.00 | 35.58 | A | N |
| ATOM | 1331 | CA | GLU | 321 | 122.614 | 33.173 | 13.569 | 1.00 | 36.56 | A | C |
| ATOM | 1332 | CB | GLU | 321 | 121.126 | 33.029 | 13.889 | 1.00 | 84.00 | A | C |
| ATOM | 1333 | CG | GLU | 321 | 120.285 | 32.398 | 12.796 | 1.00 | 77.84 | A | C |
| ATOM | 1334 | CD | GLU | 321 | 120.602 | 30.938 | 12.569 | 1.00 | 77.59 | A | C |
| ATOM | 1335 | OE1 | GLU | 321 | 120.595 | 30.164 | 13.549 | 1.00 | 79.02 | A | O |
| ATOM | 1336 | OE2 | GLU | 321 | 120.849 | 30.565 | 11.404 | 1.00 | 81.63 | A | O |
| ATOM | 1337 | C | GLU | 321 | 123.101 | 34.500 | 14.134 | 1.00 | 40.55 | A | C |
| ATOM | 1338 | O | GLU | 321 | 123.278 | 35.475 | 13.397 | 1.00 | 37.31 | A | O |
| ATOM | 1339 | N | LEU | 322 | 123.323 | 34.519 | 15.447 | 1.00 | 25.97 | A | N |
| ATOM | 1340 | CA | LEU | 322 | 123.769 | 35.717 | 16.155 | 1.00 | 28.66 | A | C |
| ATOM | 1341 | CB | LEU | 322 | 123.925 | 35.407 | 17.648 | 1.00 | 49.06 | A | C |
| ATOM | 1342 | CG | LEU | 322 | 122.646 | 35.281 | 18.477 | 1.00 | 47.69 | A | C |
| ATOM | 1343 | CD1 | LEU | 322 | 121.935 | 36.625 | 18.486 | 1.00 | 49.43 | A | C |
| ATOM | 1344 | CD2 | LEU | 322 | 121.745 | 34.194 | 17.917 | 1.00 | 52.74 | A | C |
| ATOM | 1345 | C | LEU | 322 | 125.052 | 36.368 | 15.644 | 1.00 | 30.25 | A | C |
| ATOM | 1346 | O | LEU | 322 | 125.106 | 37.580 | 15.459 | 1.00 | 33.60 | A | O |
| ATOM | 1347 | N | ALA | 323 | 126.080 | 35.558 | 15.424 | 1.00 | 27.12 | A | N |
| ATOM | 1348 | CA | ALA | 323 | 127.358 | 36.071 | 14.965 | 1.00 | 27.55 | A | C |
| ATOM | 1349 | CB | ALA | 323 | 128.420 | 34.994 | 15.112 | 1.00 | 20.92 | A | C |
| ATOM | 1350 | C | ALA | 323 | 127.368 | 36.631 | 13.539 | 1.00 | 27.96 | A | C |
| ATOM | 1351 | O | ALA | 323 | 128.363 | 37.227 | 13.120 | 1.00 | 27.98 | A | O |
| ATOM | 1352 | N | LEU | 324 | 126.280 | 36.451 | 12.794 | 1.00 | 44.60 | A | N |
| ATOM | 1353 | CA | LEU | 324 | 126.231 | 36.961 | 11.427 | 1.00 | 43.08 | A | C |
| ATOM | 1354 | CB | LEU | 324 | 124.807 | 36.875 | 10.867 | 1.00 | 12.96 | A | C |
| ATOM | 1355 | CG | LEU | 324 | 124.398 | 35.546 | 10.215 | 1.00 | 11.69 | A | C |
| ATOM | 1356 | CD1 | LEU | 324 | 122.900 | 35.547 | 9.935 | 1.00 | 10.83 | A | C |
| ATOM | 1357 | CD2 | LEU | 324 | 125.197 | 35.331 | 8.938 | 1.00 | 9.62 | A | C |
| ATOM | 1358 | C | LEU | 324 | 126.734 | 38.400 | 11.346 | 1.00 | 46.61 | A | C |
| ATOM | 1359 | O | LEU | 324 | 127.545 | 38.735 | 10.484 | 1.00 | 43.15 | A | O |
| ATOM | 1360 | N | VAL | 325 | 126.257 | 39.244 | 12.252 | 1.00 | 37.14 | A | N |
| ATOM | 1361 | CA | VAL | 325 | 126.657 | 40.645 | 12.297 | 1.00 | 40.67 | A | C |
| ATOM | 1362 | CB | VAL | 325 | 126.111 | 41.328 | 13.549 | 1.00 | 15.02 | A | C |
| ATOM | 1363 | CG1 | VAL | 325 | 124.613 | 41.517 | 13.425 | 1.00 | 15.13 | A | C |
| ATOM | 1364 | CG2 | VAL | 325 | 126.453 | 40.503 | 14.773 | 1.00 | 18.41 | A | C |
| ATOM | 1365 | C | VAL | 325 | 128.168 | 40.840 | 12.304 | 1.00 | 43.49 | A | C |
| ATOM | 1366 | O | VAL | 325 | 128.706 | 41.663 | 11.560 | 1.00 | 45.55 | A | O |
| ATOM | 1367 | N | THR | 326 | 128.844 | 40.088 | 13.161 | 1.00 | 37.74 | A | N |
| ATOM | 1368 | CA | THR | 326 | 130.289 | 40.164 | 13.286 | 1.00 | 39.15 | A | C |
| ATOM | 1369 | CB | THR | 326 | 130.768 | 39.218 | 14.391 | 1.00 | 28.63 | A | C |
| ATOM | 1370 | OG1 | THR | 326 | 130.648 | 37.863 | 13.944 | 1.00 | 30.54 | A | O |
| ATOM | 1371 | CG2 | THR | 326 | 129.911 | 39.398 | 15.643 | 1.00 | 31.00 | A | C |
| ATOM | 1372 | C | THR | 326 | 130.996 | 39.790 | 11.985 | 1.00 | 39.16 | A | C |
| ATOM | 1373 | O | THR | 326 | 132.105 | 39.268 | 12.005 | 1.00 | 37.98 | A | O |
| ATOM | 1374 | N | ILE | 327 | 130.358 | 40.065 | 10.854 | 1.00 | 29.50 | A | N |
| ATOM | 1375 | CA | ILE | 327 | 130.922 | 39.739 | 9.552 | 1.00 | 29.69 | A | C |
| ATOM | 1376 | CB | ILE | 327 | 130.407 | 38.343 | 9.098 | 1.00 | 36.77 | A | C |
| ATOM | 1377 | CG2 | ILE | 327 | 129.867 | 38.372 | 7.679 | 1.00 | 37.54 | A | C |
| ATOM | 1378 | CG1 | ILE | 327 | 131.539 | 37.335 | 9.199 | 1.00 | 37.13 | A | C |
| ATOM | 1379 | CD1 | ILE | 327 | 131.100 | 35.928 | 8.903 | 1.00 | 36.80 | A | C |
| ATOM | 1380 | C | ILE | 327 | 130.572 | 40.816 | 8.520 | 1.00 | 30.20 | A | C |
| ATOM | 1381 | O | ILE | 327 | 131.284 | 41.008 | 7.530 | 1.00 | 30.45 | A | O |
| ATOM | 1382 | N | VAL | 328 | 129.478 | 41.527 | 8.766 | 1.00 | 25.26 | A | N |
| ATOM | 1383 | CA | VAL | 328 | 129.040 | 42.565 | 7.851 | 1.00 | 27.40 | A | C |
| ATOM | 1384 | CB | VAL | 328 | 127.851 | 43.363 | 8.436 | 1.00 | 56.37 | A | C |
| ATOM | 1385 | CG1 | VAL | 328 | 126.752 | 42.408 | 8.838 | 1.00 | 58.32 | A | C |
| ATOM | 1386 | CG2 | VAL | 328 | 128.301 | 44.197 | 9.626 | 1.00 | 57.64 | A | C |
| ATOM | 1387 | C | VAL | 328 | 130.159 | 43.539 | 7.485 | 1.00 | 27.32 | A | C |

Fig. 19: A-20

| ATOM | 1388 | O | VAL | 328 | 130.220 | 44.017 | 6.355 | 1.00 | 26.60 | A | O |
|---|---|---|---|---|---|---|---|---|---|---|---|
| ATOM | 1389 | N | LYS | 329 | 131.047 | 43.837 | 8.426 | 1.00 | 32.39 | A | N |
| ATOM | 1390 | CA | LYS | 329 | 132.121 | 44.773 | 8.124 | 1.00 | 31.60 | A | C |
| ATOM | 1391 | CB | LYS | 329 | 132.949 | 45.076 | 9.378 | 1.00 | 67.11 | A | C |
| ATOM | 1392 | CG | LYS | 329 | 133.861 | 46.291 | 9.242 | 1.00 | 68.66 | A | C |
| ATOM | 1393 | CD | LYS | 329 | 134.737 | 46.454 | 10.474 | 1.00 | 70.98 | A | C |
| ATOM | 1394 | CE | LYS | 329 | 135.540 | 47.746 | 10.437 | 1.00 | 74.02 | A | C |
| ATOM | 1395 | NZ | LYS | 329 | 134.660 | 48.952 | 10.496 | 1.00 | 77.70 | A | N |
| ATOM | 1396 | C | LYS | 329 | 133.014 | 44.194 | 7.036 | 1.00 | 29.77 | A | C |
| ATOM | 1397 | O | LYS | 329 | 133.205 | 44.802 | 5.978 | 1.00 | 30.98 | A | O |
| ATOM | 1398 | N | ALA | 330 | 133.551 | 43.008 | 7.293 | 1.00 | 29.12 | A | N |
| ATOM | 1399 | CA | ALA | 330 | 134.425 | 42.365 | 6.331 | 1.00 | 29.15 | A | C |
| ATOM | 1400 | CB | ALA | 330 | 134.997 | 41.091 | 6.922 | 1.00 | 30.19 | A | C |
| ATOM | 1401 | C | ALA | 330 | 133.681 | 42.056 | 5.043 | 1.00 | 30.30 | A | C |
| ATOM | 1402 | O | ALA | 330 | 134.207 | 42.269 | 3.955 | 1.00 | 30.20 | A | O |
| ATOM | 1403 | N | LEU | 331 | 132.457 | 41.551 | 5.168 | 1.00 | 22.22 | A | N |
| ATOM | 1404 | CA | LEU | 331 | 131.661 | 41.206 | 3.994 | 1.00 | 19.86 | A | C |
| ATOM | 1405 | CB | LEU | 331 | 130.284 | 40.667 | 4.403 | 1.00 | 36.97 | A | C |
| ATOM | 1406 | CG | LEU | 331 | 129.567 | 39.761 | 3.389 | 1.00 | 33.39 | A | C |
| ATOM | 1407 | CD1 | LEU | 331 | 128.110 | 39.600 | 3.787 | 1.00 | 35.02 | A | C |
| ATOM | 1408 | CD2 | LEU | 331 | 129.658 | 40.343 | 1.996 | 1.00 | 29.08 | A | C |
| ATOM | 1409 | C | LEU | 331 | 131.483 | 42.467 | 3.162 | 1.00 | 19.89 | A | C |
| ATOM | 1410 | O | LEU | 331 | 131.741 | 42.468 | 1.961 | 1.00 | 19.24 | A | O |
| ATOM | 1411 | N | GLY | 332 | 131.045 | 43.535 | 3.830 | 1.00 | 15.82 | A | N |
| ATOM | 1412 | CA | GLY | 332 | 130.824 | 44.811 | 3.179 | 1.00 | 16.92 | A | C |
| ATOM | 1413 | C | GLY | 332 | 132.024 | 45.309 | 2.402 | 1.00 | 17.18 | A | C |
| ATOM | 1414 | O | GLY | 332 | 131.911 | 45.651 | 1.224 | 1.00 | 21.05 | A | O |
| ATOM | 1415 | N | GLU | 333 | 133.185 | 45.347 | 3.045 | 1.00 | 34.74 | A | N |
| ATOM | 1416 | CA | GLU | 333 | 134.369 | 45.831 | 2.362 | 1.00 | 32.80 | A | C |
| ATOM | 1417 | CB | GLU | 333 | 135.472 | 46.165 | 3.371 | 1.00 | 75.29 | A | C |
| ATOM | 1418 | CG | GLU | 333 | 136.139 | 44.968 | 4.005 | 1.00 | 73.66 | A | C |
| ATOM | 1419 | CD | GLU | 333 | 137.251 | 45.363 | 4.959 | 1.00 | 73.68 | A | C |
| ATOM | 1420 | OE1 | GLU | 333 | 137.953 | 44.459 | 5.456 | 1.00 | 75.73 | A | O |
| ATOM | 1421 | OE2 | GLU | 333 | 137.421 | 46.575 | 5.215 | 1.00 | 67.80 | A | O |
| ATOM | 1422 | C | GLU | 333 | 134.888 | 44.841 | 1.322 | 1.00 | 31.78 | A | C |
| ATOM | 1423 | O | GLU | 333 | 135.370 | 45.236 | 0.261 | 1.00 | 31.40 | A | O |
| ATOM | 1424 | N | ARG | 334 | 134.781 | 43.552 | 1.610 | 1.00 | 50.02 | A | N |
| ATOM | 1425 | CA | ARG | 334 | 135.275 | 42.563 | 0.669 | 1.00 | 53.40 | A | C |
| ATOM | 1426 | CB | ARG | 334 | 135.064 | 41.152 | 1.215 | 1.00 | 83.27 | A | C |
| ATOM | 1427 | CG | ARG | 334 | 136.000 | 40.123 | 0.607 | 1.00 | 82.56 | A | C |
| ATOM | 1428 | CD | ARG | 334 | 136.564 | 39.198 | 1.677 | 1.00 | 81.32 | A | C |
| ATOM | 1429 | NE | ARG | 334 | 137.441 | 39.901 | 2.612 | 1.00 | 76.87 | A | N |
| ATOM | 1430 | CZ | ARG | 334 | 137.888 | 39.383 | 3.753 | 1.00 | 80.96 | A | C |
| ATOM | 1431 | NH1 | ARG | 334 | 137.537 | 38.148 | 4.108 | 1.00 | 77.70 | A | N |
| ATOM | 1432 | NH2 | ARG | 334 | 138.686 | 40.097 | 4.539 | 1.00 | 87.10 | A | N |
| ATOM | 1433 | C | ARG | 334 | 134.556 | 42.757 | -0.654 | 1.00 | 54.70 | A | C |
| ATOM | 1434 | O | ARG | 334 | 135.170 | 42.716 | -1.716 | 1.00 | 51.62 | A | O |
| ATOM | 1435 | N | ILE | 335 | 133.253 | 42.988 | -0.591 | 1.00 | 36.48 | A | N |
| ATOM | 1436 | CA | ILE | 335 | 132.473 | 43.214 | -1.803 | 1.00 | 36.41 | A | C |
| ATOM | 1437 | CB | ILE | 335 | 130.940 | 42.967 | -1.539 | 1.00 | 33.09 | A | C |
| ATOM | 1438 | CG2 | ILE | 335 | 130.524 | 43.522 | -0.203 | 1.00 | 35.87 | A | C |
| ATOM | 1439 | CG1 | ILE | 335 | 130.094 | 43.611 | -2.630 | 1.00 | 34.31 | A | C |
| ATOM | 1440 | CD1 | ILE | 335 | 128.612 | 43.520 | -2.368 | 1.00 | 37.10 | A | C |
| ATOM | 1441 | C | ILE | 335 | 132.742 | 44.663 | -2.215 | 1.00 | 34.70 | A | C |
| ATOM | 1442 | O | ILE | 335 | 132.421 | 45.092 | -3.326 | 1.00 | 37.30 | A | O |
| ATOM | 1443 | N | PHE | 336 | 133.392 | 45.377 | -1.299 | 1.00 | 108.43 | A | N |
| ATOM | 1444 | CA | PHE | 336 | 133.744 | 46.789 | -1.419 | 1.00 | 108.06 | A | C |
| ATOM | 1445 | CB | PHE | 336 | 135.092 | 46.989 | -2.157 | 1.00 | 57.00 | A | C |
| ATOM | 1446 | CG | PHE | 336 | 135.114 | 46.540 | -3.601 | 1.00 | 53.32 | A | C |
| ATOM | 1447 | CD1 | PHE | 336 | 134.135 | 46.941 | -4.508 | 1.00 | 52.74 | A | C |
| ATOM | 1448 | CD2 | PHE | 336 | 136.178 | 45.779 | -4.073 | 1.00 | 51.27 | A | C |
| ATOM | 1449 | CE1 | PHE | 336 | 134.219 | 46.589 | -5.868 | 1.00 | 43.07 | A | C |
| ATOM | 1450 | CE2 | PHE | 336 | 136.271 | 45.426 | -5.422 | 1.00 | 45.63 | A | C |
| ATOM | 1451 | CZ | PHE | 336 | 135.292 | 45.832 | -6.319 | 1.00 | 46.09 | A | C |
| ATOM | 1452 | C | PHE | 336 | 132.662 | 47.670 | -2.020 | 1.00 | 108.09 | A | C |
| ATOM | 1453 | O | PHE | 336 | 131.623 | 47.131 | -2.453 | 1.00 | 87.71 | A | O |
| ATOM | 1454 | OXT | PHE | 336 | 132.864 | 48.902 | -2.024 | 1.00 | 40.49 | A | O |
| ATOM | 1455 | CB | GLU | 1 | 119.537 | 12.185 | 27.786 | 1.00 | 88.08 | H | C |
| ATOM | 1456 | CG | GLU | 1 | 118.650 | 11.120 | 28.419 | 1.00 | 88.08 | H | C |
| ATOM | 1457 | CD | GLU | 1 | 119.399 | 10.237 | 29.409 | 1.00 | 88.08 | H | C |
| ATOM | 1458 | OE1 | GLU | 1 | 120.127 | 10.777 | 30.271 | 1.00 | 88.08 | H | O |
| ATOM | 1459 | OE2 | GLU | 1 | 119.251 | 8.998 | 29.324 | 1.00 | 88.08 | H | O |
| ATOM | 1460 | C | GLU | 1 | 118.366 | 14.360 | 28.176 | 1.00 | 62.78 | H | C |

Fig. 19: A-21

| ATOM | 1461 | O | GLU | 1 | 117.763 | 15.033 | 29.012 | 1.00 | 62.78 | H | O |
|---|---|---|---|---|---|---|---|---|---|---|---|
| ATOM | 1462 | N | GLU | 1 | 119.687 | 13.262 | 30.016 | 1.00 | 62.78 | H | N |
| ATOM | 1463 | CA | GLU | 1 | 119.580 | 13.515 | 28.553 | 1.00 | 62.78 | H | C |
| ATOM | 1464 | N | VAL | 2 | 118.019 | 14.312 | 26.896 | 1.00 | 44.26 | H | N |
| ATOM | 1465 | CA | VAL | 2 | 116.896 | 15.064 | 26.359 | 1.00 | 44.26 | H | C |
| ATOM | 1466 | CB | VAL | 2 | 117.154 | 15.460 | 24.909 | 1.00 | 15.14 | H | C |
| ATOM | 1467 | CG1 | VAL | 2 | 118.610 | 15.840 | 24.732 | 1.00 | 15.14 | H | C |
| ATOM | 1468 | CG2 | VAL | 2 | 116.807 | 14.309 | 23.997 | 1.00 | 15.14 | H | C |
| ATOM | 1469 | C | VAL | 2 | 115.677 | 14.174 | 26.353 | 1.00 | 44.26 | H | C |
| ATOM | 1470 | O | VAL | 2 | 115.803 | 12.951 | 26.347 | 1.00 | 44.26 | H | O |
| ATOM | 1471 | N | GLN | 3 | 114.497 | 14.780 | 26.340 | 1.00 | 25.45 | H | N |
| ATOM | 1472 | CA | GLN | 3 | 113.280 | 13.984 | 26.288 | 1.00 | 25.45 | H | C |
| ATOM | 1473 | CB | GLN | 3 | 113.191 | 13.046 | 27.494 | 1.00 | 105.15 | H | C |
| ATOM | 1474 | CG | GLN | 3 | 113.307 | 13.707 | 28.841 | 1.00 | 105.15 | H | C |
| ATOM | 1475 | CD | GLN | 3 | 113.015 | 12.733 | 29.961 | 1.00 | 105.15 | H | C |
| ATOM | 1476 | OE1 | GLN | 3 | 113.554 | 11.623 | 29.990 | 1.00 | 105.15 | H | O |
| ATOM | 1477 | NE2 | GLN | 3 | 112.157 | 13.139 | 30.892 | 1.00 | 105.15 | H | N |
| ATOM | 1478 | C | GLN | 3 | 111.961 | 14.708 | 26.119 | 1.00 | 25.45 | H | C |
| ATOM | 1479 | O | GLN | 3 | 111.809 | 15.887 | 26.438 | 1.00 | 25.45 | H | O |
| ATOM | 1480 | N | LEU | 4 | 111.009 | 13.959 | 25.588 | 1.00 | 27.88 | H | N |
| ATOM | 1481 | CA | LEU | 4 | 109.668 | 14.446 | 25.339 | 1.00 | 27.88 | H | C |
| ATOM | 1482 | CB | LEU | 4 | 109.347 | 14.369 | 23.842 | 1.00 | 33.14 | H | C |
| ATOM | 1483 | CG | LEU | 4 | 110.367 | 14.924 | 22.847 | 1.00 | 33.14 | H | C |
| ATOM | 1484 | CD1 | LEU | 4 | 109.821 | 14.772 | 21.438 | 1.00 | 33.14 | H | C |
| ATOM | 1485 | CD2 | LEU | 4 | 110.646 | 16.385 | 23.155 | 1.00 | 33.14 | H | C |
| ATOM | 1486 | C | LEU | 4 | 108.755 | 13.507 | 26.095 | 1.00 | 27.88 | H | C |
| ATOM | 1487 | O | LEU | 4 | 108.871 | 12.282 | 25.960 | 1.00 | 27.88 | H | O |
| ATOM | 1488 | N | VAL | 5 | 107.858 | 14.061 | 26.901 | 1.00 | 26.47 | H | N |
| ATOM | 1489 | CA | VAL | 5 | 106.942 | 13.215 | 27.656 | 1.00 | 26.47 | H | C |
| ATOM | 1490 | CB | VAL | 5 | 107.176 | 13.329 | 29.197 | 1.00 | 25.39 | H | C |
| ATOM | 1491 | CG1 | VAL | 5 | 107.281 | 14.772 | 29.606 | 1.00 | 25.39 | H | C |
| ATOM | 1492 | CG2 | VAL | 5 | 106.046 | 12.654 | 29.947 | 1.00 | 25.39 | H | C |
| ATOM | 1493 | C | VAL | 5 | 105.520 | 13.578 | 27.297 | 1.00 | 26.47 | H | C |
| ATOM | 1494 | O | VAL | 5 | 105.031 | 14.664 | 27.635 | 1.00 | 26.47 | H | O |
| ATOM | 1495 | N | GLU | 6 | 104.868 | 12.650 | 26.601 | 1.00 | 23.78 | H | N |
| ATOM | 1496 | CA | GLU | 6 | 103.495 | 12.835 | 26.133 | 1.00 | 23.78 | H | C |
| ATOM | 1497 | CB | GLU | 6 | 103.258 | 11.995 | 24.885 | 1.00 | 29.58 | H | C |
| ATOM | 1498 | CG | GLU | 6 | 104.409 | 12.017 | 23.933 | 1.00 | 29.58 | H | C |
| ATOM | 1499 | CD | GLU | 6 | 104.188 | 11.109 | 22.756 | 1.00 | 29.58 | H | C |
| ATOM | 1500 | OE1 | GLU | 6 | 105.194 | 10.664 | 22.168 | 1.00 | 29.58 | H | O |
| ATOM | 1501 | OE2 | GLU | 6 | 103.013 | 10.846 | 22.413 | 1.00 | 29.58 | H | O |
| ATOM | 1502 | C | GLU | 6 | 102.429 | 12.485 | 27.155 | 1.00 | 23.78 | H | C |
| ATOM | 1503 | O | GLU | 6 | 102.680 | 11.740 | 28.101 | 1.00 | 23.78 | H | O |
| ATOM | 1504 | N | SER | 7 | 101.242 | 13.047 | 26.937 | 1.00 | 26.30 | H | N |
| ATOM | 1505 | CA | SER | 7 | 100.061 | 12.823 | 27.766 | 1.00 | 26.30 | H | C |
| ATOM | 1506 | CB | SER | 7 | 100.177 | 13.535 | 29.102 | 1.00 | 32.56 | H | C |
| ATOM | 1507 | OG | SER | 7 | 100.574 | 14.871 | 28.906 | 1.00 | 32.56 | H | O |
| ATOM | 1508 | C | SER | 7 | 98.886 | 13.381 | 26.998 | 1.00 | 26.30 | H | C |
| ATOM | 1509 | O | SER | 7 | 99.060 | 14.248 | 26.136 | 1.00 | 26.30 | H | O |
| ATOM | 1510 | N | GLY | 8 | 97.693 | 12.872 | 27.287 | 1.00 | 41.74 | H | N |
| ATOM | 1511 | CA | GLY | 8 | 96.514 | 13.360 | 26.598 | 1.00 | 41.74 | H | C |
| ATOM | 1512 | C | GLY | 8 | 95.807 | 12.321 | 25.752 | 1.00 | 41.74 | H | C |
| ATOM | 1513 | O | GLY | 8 | 94.745 | 12.603 | 25.201 | 1.00 | 41.74 | H | O |
| ATOM | 1514 | N | GLY | 9 | 96.383 | 11.127 | 25.637 | 1.00 | 47.50 | H | N |
| ATOM | 1515 | CA | GLY | 9 | 95.751 | 10.079 | 24.851 | 1.00 | 47.50 | H | C |
| ATOM | 1516 | C | GLY | 9 | 94.431 | 9.601 | 25.446 | 1.00 | 47.50 | H | C |
| ATOM | 1517 | O | GLY | 9 | 94.038 | 10.020 | 26.536 | 1.00 | 47.50 | H | O |
| ATOM | 1518 | N | GLY | 10 | 93.732 | 8.723 | 24.735 | 1.00 | 16.50 | H | N |
| ATOM | 1519 | CA | GLY | 10 | 92.469 | 8.225 | 25.244 | 1.00 | 16.50 | H | C |
| ATOM | 1520 | C | GLY | 10 | 91.485 | 7.806 | 24.169 | 1.00 | 16.50 | H | C |
| ATOM | 1521 | O | GLY | 10 | 91.830 | 7.701 | 22.990 | 1.00 | 16.50 | H | O |
| ATOM | 1522 | N | LEU | 11 | 90.251 | 7.559 | 24.595 | 1.00 | 37.61 | H | N |
| ATOM | 1523 | CA | LEU | 11 | 89.175 | 7.137 | 23.710 | 1.00 | 37.61 | H | C |
| ATOM | 1524 | CB | LEU | 11 | 88.388 | 6.003 | 24.365 | 1.00 | 18.32 | H | C |
| ATOM | 1525 | CG | LEU | 11 | 86.959 | 5.715 | 23.885 | 1.00 | 18.32 | H | C |
| ATOM | 1526 | CD1 | LEU | 11 | 86.962 | 5.148 | 22.463 | 1.00 | 18.32 | H | C |
| ATOM | 1527 | CD2 | LEU | 11 | 86.313 | 4.729 | 24.856 | 1.00 | 18.32 | H | C |
| ATOM | 1528 | C | LEU | 11 | 88.235 | 8.292 | 23.436 | 1.00 | 37.61 | H | C |
| ATOM | 1529 | O | LEU | 11 | 87.769 | 8.943 | 24.365 | 1.00 | 37.61 | H | O |
| ATOM | 1530 | N | VAL | 12 | 87.961 | 8.550 | 22.165 | 1.00 | 31.23 | H | N |
| ATOM | 1531 | CA | VAL | 12 | 87.048 | 9.624 | 21.792 | 1.00 | 31.23 | H | C |
| ATOM | 1532 | CB | VAL | 12 | 87.794 | 10.800 | 21.144 | 1.00 | 52.64 | H | C |
| ATOM | 1533 | CG1 | VAL | 12 | 88.609 | 11.532 | 22.192 | 1.00 | 52.64 | H | C |

Fig. 19: A-22

| | | | | | | | | | | |
|---|---|---|---|---|---|---|---|---|---|---|
| ATOM | 1534 | CG2 | VAL | 12 | 88.699 | 10.290 | 20.039 | 1.00 | 52.64 | H C |
| ATOM | 1535 | C | VAL | 12 | 86.062 | 9.045 | 20.794 | 1.00 | 31.23 | H C |
| ATOM | 1536 | O | VAL | 12 | 86.365 | 8.057 | 20.138 | 1.00 | 31.23 | H O |
| ATOM | 1537 | N | GLN | 13 | 84.882 | 9.640 | 20.681 | 1.00 | 27.32 | H N |
| ATOM | 1538 | CA | GLN | 13 | 83.894 | 9.126 | 19.741 | 1.00 | 27.32 | H C |
| ATOM | 1539 | CB | GLN | 13 | 82.493 | 9.391 | 20.270 | 1.00 | 92.40 | H C |
| ATOM | 1540 | CG | GLN | 13 | 82.206 | 8.652 | 21.553 | 1.00 | 92.40 | H C |
| ATOM | 1541 | CD | GLN | 13 | 80.808 | 8.906 | 22.056 | 1.00 | 92.40 | H C |
| ATOM | 1542 | OE1 | GLN | 13 | 79.836 | 8.766 | 21.310 | 1.00 | 92.40 | H O |
| ATOM | 1543 | NE2 | GLN | 13 | 80.693 | 9.276 | 23.329 | 1.00 | 92.40 | H N |
| ATOM | 1544 | C | GLN | 13 | 84.063 | 9.747 | 18.356 | 1.00 | 27.32 | H C |
| ATOM | 1545 | O | GLN | 13 | 84.400 | 10.924 | 18.227 | 1.00 | 27.32 | H O |
| ATOM | 1546 | N | PRO | 14 | 83.834 | 8.955 | 17.298 | 1.00 | 39.48 | H N |
| ATOM | 1547 | CD | PRO | 14 | 83.418 | 7.539 | 17.302 | 1.00 | 31.44 | H C |
| ATOM | 1548 | CA | PRO | 14 | 83.971 | 9.452 | 15.929 | 1.00 | 39.48 | H C |
| ATOM | 1549 | CB | PRO | 14 | 83.219 | 8.406 | 15.118 | 1.00 | 31.44 | H C |
| ATOM | 1550 | CG | PRO | 14 | 83.584 | 7.145 | 15.837 | 1.00 | 31.44 | H C |
| ATOM | 1551 | C | PRO | 14 | 83.401 | 10.849 | 15.766 | 1.00 | 39.48 | H C |
| ATOM | 1552 | O | PRO | 14 | 82.235 | 11.076 | 16.053 | 1.00 | 39.48 | H O |
| ATOM | 1553 | N | GLY | 15 | 84.233 | 11.784 | 15.319 | 1.00 | 28.44 | H N |
| ATOM | 1554 | CA | GLY | 15 | 83.788 | 13.154 | 15.130 | 1.00 | 28.44 | H C |
| ATOM | 1555 | C | GLY | 15 | 84.048 | 14.065 | 16.323 | 1.00 | 28.44 | H C |
| ATOM | 1556 | O | GLY | 15 | 83.759 | 15.265 | 16.269 | 1.00 | 28.44 | H O |
| ATOM | 1557 | N | GLY | 16 | 84.588 | 13.496 | 17.401 | 1.00 | 22.09 | H N |
| ATOM | 1558 | CA | GLY | 16 | 84.880 | 14.266 | 18.601 | 1.00 | 22.09 | H C |
| ATOM | 1559 | C | GLY | 16 | 86.286 | 14.826 | 18.571 | 1.00 | 22.09 | H C |
| ATOM | 1560 | O | GLY | 16 | 86.900 | 14.912 | 17.507 | 1.00 | 22.09 | H O |
| ATOM | 1561 | N | SER | 17 | 86.819 | 15.202 | 19.726 | 1.00 | 31.69 | H N |
| ATOM | 1562 | CA | SER | 17 | 88.161 | 15.762 | 19.749 | 1.00 | 31.69 | H C |
| ATOM | 1563 | CB | SER | 17 | 88.085 | 17.272 | 19.592 | 1.00 | 54.23 | H C |
| ATOM | 1564 | OG | SER | 17 | 87.308 | 17.829 | 20.625 | 1.00 | 54.23 | H O |
| ATOM | 1565 | C | SER | 17 | 88.953 | 15.416 | 21.000 | 1.00 | 31.69 | H C |
| ATOM | 1566 | O | SER | 17 | 88.427 | 14.824 | 21.944 | 1.00 | 31.69 | H O |
| ATOM | 1567 | N | LEU | 18 | 90.227 | 15.794 | 20.995 | 1.00 | 31.76 | H N |
| ATOM | 1568 | CA | LEU | 18 | 91.132 | 15.515 | 22.105 | 1.00 | 31.76 | H C |
| ATOM | 1569 | CB | LEU | 18 | 91.452 | 14.019 | 22.124 | 1.00 | 63.56 | H C |
| ATOM | 1570 | CG | LEU | 18 | 92.462 | 13.465 | 23.124 | 1.00 | 63.56 | H C |
| ATOM | 1571 | CD1 | LEU | 18 | 92.121 | 13.932 | 24.536 | 1.00 | 63.56 | H C |
| ATOM | 1572 | CD2 | LEU | 18 | 92.462 | 11.942 | 23.017 | 1.00 | 63.56 | H C |
| ATOM | 1573 | C | LEU | 18 | 92.407 | 16.334 | 21.899 | 1.00 | 31.76 | H C |
| ATOM | 1574 | O | LEU | 18 | 92.622 | 16.884 | 20.815 | 1.00 | 31.76 | H O |
| ATOM | 1575 | N | ARG | 19 | 93.243 | 16.443 | 22.928 | 1.00 | 39.26 | H N |
| ATOM | 1576 | CA | ARG | 19 | 94.475 | 17.207 | 22.781 | 1.00 | 39.26 | H C |
| ATOM | 1577 | CB | ARG | 19 | 94.303 | 18.650 | 23.258 | 1.00 | 32.50 | H C |
| ATOM | 1578 | CG | ARG | 19 | 95.571 | 19.474 | 23.063 | 1.00 | 32.50 | H C |
| ATOM | 1579 | CD | ARG | 19 | 95.481 | 20.862 | 23.667 | 1.00 | 32.50 | H C |
| ATOM | 1580 | NE | ARG | 19 | 95.387 | 20.846 | 25.125 | 1.00 | 32.50 | H N |
| ATOM | 1581 | CZ | ARG | 19 | 95.262 | 21.936 | 25.879 | 1.00 | 32.50 | H C |
| ATOM | 1582 | NH1 | ARG | 19 | 95.220 | 23.138 | 25.322 | 1.00 | 32.50 | H N |
| ATOM | 1583 | NH2 | ARG | 19 | 95.162 | 21.824 | 27.193 | 1.00 | 32.50 | H N |
| ATOM | 1584 | C | ARG | 19 | 95.668 | 16.606 | 23.500 | 1.00 | 39.26 | H C |
| ATOM | 1585 | O | ARG | 19 | 95.687 | 16.469 | 24.732 | 1.00 | 39.26 | H O |
| ATOM | 1586 | N | LEU | 20 | 96.677 | 16.266 | 22.709 | 1.00 | 36.74 | H N |
| ATOM | 1587 | CA | LEU | 20 | 97.896 | 15.695 | 23.241 | 1.00 | 36.74 | H C |
| ATOM | 1588 | CB | LEU | 20 | 98.534 | 14.737 | 22.222 | 1.00 | 31.69 | H C |
| ATOM | 1589 | CG | LEU | 20 | 97.601 | 13.846 | 21.390 | 1.00 | 31.69 | H C |
| ATOM | 1590 | CD1 | LEU | 20 | 98.426 | 12.870 | 20.555 | 1.00 | 31.69 | H C |
| ATOM | 1591 | CD2 | LEU | 20 | 96.659 | 13.093 | 22.292 | 1.00 | 31.69 | H C |
| ATOM | 1592 | C | LEU | 20 | 98.854 | 16.838 | 23.533 | 1.00 | 36.74 | H C |
| ATOM | 1593 | O | LEU | 20 | 98.866 | 17.856 | 22.840 | 1.00 | 36.74 | H O |
| ATOM | 1594 | N | SER | 21 | 99.638 | 16.664 | 24.584 | 1.00 | 25.68 | H N |
| ATOM | 1595 | CA | SER | 21 | 100.635 | 17.640 | 24.974 | 1.00 | 25.68 | H C |
| ATOM | 1596 | CB | SER | 21 | 100.273 | 18.278 | 26.307 | 1.00 | 13.03 | H C |
| ATOM | 1597 | OG | SER | 21 | 99.718 | 17.320 | 27.175 | 1.00 | 13.03 | H O |
| ATOM | 1598 | C | SER | 21 | 101.901 | 16.838 | 25.099 | 1.00 | 25.68 | H C |
| ATOM | 1599 | O | SER | 21 | 101.851 | 15.635 | 25.336 | 1.00 | 25.68 | H O |
| ATOM | 1600 | N | CYS | 22 | 103.036 | 17.498 | 24.931 | 1.00 | 22.18 | H N |
| ATOM | 1601 | CA | CYS | 22 | 104.321 | 16.822 | 25.008 | 1.00 | 22.18 | H C |
| ATOM | 1602 | C | CYS | 22 | 105.255 | 17.765 | 25.713 | 1.00 | 22.18 | H C |
| ATOM | 1603 | O | CYS | 22 | 105.491 | 18.863 | 25.229 | 1.00 | 22.18 | H O |
| ATOM | 1604 | CB | CYS | 22 | 104.804 | 16.543 | 23.603 | 1.00 | 57.35 | H C |
| ATOM | 1605 | SG | CYS | 22 | 106.473 | 15.867 | 23.383 | 1.00 | 57.35 | H S |
| ATOM | 1606 | N | ALA | 23 | 105.769 | 17.349 | 26.867 | 1.00 | 26.87 | H N |

Fig. 19: A-23

| | | | | | | | | | | | |
|---|---|---|---|---|---|---|---|---|---|---|---|
| ATOM | 1607 | CA | ALA | 23 | 106.669 | 18.191 | 27.654 | 1.00 | 26.87 | H | C |
| ATOM | 1608 | CB | ALA | 23 | 106.470 | 17.937 | 29.141 | 1.00 | 9.84 | H | C |
| ATOM | 1609 | C | ALA | 23 | 108.125 | 17.989 | 27.284 | 1.00 | 26.87 | H | C |
| ATOM | 1610 | O | ALA | 23 | 108.683 | 16.899 | 27.437 | 1.00 | 26.87 | H | O |
| ATOM | 1611 | N | ALA | 24 | 108.738 | 19.058 | 26.800 | 1.00 | 13.29 | H | N |
| ATOM | 1612 | CA | ALA | 24 | 110.124 | 18.988 | 26.409 | 1.00 | 13.29 | H | C |
| ATOM | 1613 | CB | ALA | 24 | 110.357 | 19.851 | 25.183 | 1.00 | 45.62 | H | C |
| ATOM | 1614 | C | ALA | 24 | 111.023 | 19.432 | 27.552 | 1.00 | 13.29 | H | C |
| ATOM | 1615 | O | ALA | 24 | 110.664 | 20.304 | 28.356 | 1.00 | 13.29 | H | O |
| ATOM | 1616 | N | SER | 25 | 112.194 | 18.819 | 27.617 | 1.00 | 22.11 | H | N |
| ATOM | 1617 | CA | SER | 25 | 113.168 | 19.152 | 28.634 | 1.00 | 22.11 | H | C |
| ATOM | 1618 | CB | SER | 25 | 112.731 | 18.582 | 29.982 | 1.00 | 51.20 | H | C |
| ATOM | 1619 | OG | SER | 25 | 112.401 | 17.214 | 29.862 | 1.00 | 51.20 | H | O |
| ATOM | 1620 | C | SER | 25 | 114.526 | 18.591 | 28.232 | 1.00 | 22.11 | H | C |
| ATOM | 1621 | O | SER | 25 | 114.614 | 17.539 | 27.590 | 1.00 | 22.11 | H | O |
| ATOM | 1622 | N | GLY | 26 | 115.582 | 19.306 | 28.591 | 1.00 | 10.76 | H | N |
| ATOM | 1623 | CA | GLY | 26 | 116.914 | 18.844 | 28.263 | 1.00 | 10.76 | H | C |
| ATOM | 1624 | C | GLY | 26 | 117.553 | 19.585 | 27.107 | 1.00 | 10.76 | H | C |
| ATOM | 1625 | O | GLY | 26 | 118.728 | 19.367 | 26.809 | 1.00 | 10.76 | H | O |
| ATOM | 1626 | N | PHE | 27 | 116.794 | 20.458 | 26.448 | 1.00 | 18.08 | H | N |
| ATOM | 1627 | CA | PHE | 27 | 117.325 | 21.207 | 25.318 | 1.00 | 18.08 | H | C |
| ATOM | 1628 | CB | PHE | 27 | 117.241 | 20.373 | 24.031 | 1.00 | 16.53 | H | C |
| ATOM | 1629 | CG | PHE | 27 | 115.842 | 19.974 | 23.651 | 1.00 | 16.53 | H | C |
| ATOM | 1630 | CD1 | PHE | 27 | 115.089 | 19.140 | 24.476 | 1.00 | 16.53 | H | C |
| ATOM | 1631 | CD2 | PHE | 27 | 115.269 | 20.448 | 22.476 | 1.00 | 16.53 | H | C |
| ATOM | 1632 | CE1 | PHE | 27 | 113.770 | 18.782 | 24.137 | 1.00 | 16.53 | H | C |
| ATOM | 1633 | CE2 | PHE | 27 | 113.958 | 20.101 | 22.125 | 1.00 | 16.53 | H | C |
| ATOM | 1634 | CZ | PHE | 27 | 113.203 | 19.268 | 22.954 | 1.00 | 16.53 | H | C |
| ATOM | 1635 | C | PHE | 27 | 116.592 | 22.528 | 25.135 | 1.00 | 18.08 | H | C |
| ATOM | 1636 | O | PHE | 27 | 115.566 | 22.780 | 25.763 | 1.00 | 18.08 | H | O |
| ATOM | 1637 | N | THR | 28 | 117.139 | 23.377 | 24.276 | 1.00 | 42.88 | H | N |
| ATOM | 1638 | CA | THR | 28 | 116.544 | 24.672 | 24.017 | 1.00 | 42.88 | H | C |
| ATOM | 1639 | CB | THR | 28 | 117.575 | 25.604 | 23.381 | 1.00 | 53.65 | H | C |
| ATOM | 1640 | OG1 | THR | 28 | 118.841 | 25.399 | 24.018 | 1.00 | 53.65 | H | O |
| ATOM | 1641 | CG2 | THR | 28 | 117.168 | 27.056 | 23.561 | 1.00 | 53.65 | H | C |
| ATOM | 1642 | C | THR | 28 | 115.369 | 24.463 | 23.074 | 1.00 | 42.88 | H | C |
| ATOM | 1643 | O | THR | 28 | 115.484 | 24.666 | 21.868 | 1.00 | 42.88 | H | O |
| ATOM | 1644 | N | PHE | 29 | 114.239 | 24.051 | 23.644 | 1.00 | 29.92 | H | N |
| ATOM | 1645 | CA | PHE | 29 | 113.004 | 23.772 | 22.901 | 1.00 | 29.92 | H | C |
| ATOM | 1646 | CB | PHE | 29 | 111.855 | 23.614 | 23.906 | 1.00 | 3.95 | H | C |
| ATOM | 1647 | CG | PHE | 29 | 110.503 | 23.347 | 23.276 | 1.00 | 3.95 | H | C |
| ATOM | 1648 | CD1 | PHE | 29 | 110.208 | 22.102 | 22.696 | 1.00 | 3.95 | H | C |
| ATOM | 1649 | CD2 | PHE | 29 | 109.504 | 24.336 | 23.283 | 1.00 | 3.95 | H | C |
| ATOM | 1650 | CE1 | PHE | 29 | 108.939 | 21.852 | 22.139 | 1.00 | 3.95 | H | C |
| ATOM | 1651 | CE2 | PHE | 29 | 108.234 | 24.092 | 22.727 | 1.00 | 3.95 | H | C |
| ATOM | 1652 | CZ | PHE | 29 | 107.953 | 22.860 | 22.160 | 1.00 | 3.95 | H | C |
| ATOM | 1653 | C | PHE | 29 | 112.611 | 24.777 | 21.797 | 1.00 | 29.92 | H | C |
| ATOM | 1654 | O | PHE | 29 | 112.390 | 24.389 | 20.647 | 1.00 | 29.92 | H | O |
| ATOM | 1655 | N | SER | 30 | 112.539 | 26.058 | 22.144 | 1.00 | 32.50 | H | N |
| ATOM | 1656 | CA | SER | 30 | 112.139 | 27.105 | 21.199 | 1.00 | 32.50 | H | C |
| ATOM | 1657 | CB | SER | 30 | 112.335 | 28.473 | 21.852 | 1.00 | 67.50 | H | C |
| ATOM | 1658 | OG | SER | 30 | 113.644 | 28.591 | 22.372 | 1.00 | 67.50 | H | O |
| ATOM | 1659 | C | SER | 30 | 112.799 | 27.107 | 19.812 | 1.00 | 32.50 | H | C |
| ATOM | 1660 | O | SER | 30 | 112.191 | 27.504 | 18.816 | 1.00 | 32.50 | H | O |
| ATOM | 1661 | N | ARG | 31 | 114.037 | 26.649 | 19.751 | 1.00 | 18.89 | H | N |
| ATOM | 1662 | CA | ARG | 31 | 114.801 | 26.636 | 18.515 | 1.00 | 18.89 | H | C |
| ATOM | 1663 | CB | ARG | 31 | 116.292 | 26.604 | 18.886 | 1.00 | 48.17 | H | C |
| ATOM | 1664 | CG | ARG | 31 | 117.217 | 25.955 | 17.887 | 1.00 | 48.17 | H | C |
| ATOM | 1665 | CD | ARG | 31 | 118.650 | 26.425 | 18.112 | 1.00 | 48.17 | H | C |
| ATOM | 1666 | NE | ARG | 31 | 119.135 | 26.203 | 19.476 | 1.00 | 48.17 | H | N |
| ATOM | 1667 | CZ | ARG | 31 | 120.228 | 26.777 | 19.980 | 1.00 | 48.17 | H | C |
| ATOM | 1668 | NH1 | ARG | 31 | 120.950 | 27.608 | 19.238 | 1.00 | 48.17 | H | N |
| ATOM | 1669 | NH2 | ARG | 31 | 120.604 | 26.524 | 21.226 | 1.00 | 48.17 | H | N |
| ATOM | 1670 | C | ARG | 31 | 114.463 | 25.523 | 17.521 | 1.00 | 18.89 | H | C |
| ATOM | 1671 | O | ARG | 31 | 114.520 | 25.723 | 16.313 | 1.00 | 18.89 | H | O |
| ATOM | 1672 | N | TYR | 32 | 114.095 | 24.353 | 18.027 | 1.00 | 15.47 | H | N |
| ATOM | 1673 | CA | TYR | 32 | 113.791 | 23.200 | 17.179 | 1.00 | 15.47 | H | C |
| ATOM | 1674 | CB | TYR | 32 | 113.949 | 21.922 | 17.996 | 1.00 | 6.03 | H | C |
| ATOM | 1675 | CG | TYR | 32 | 115.367 | 21.653 | 18.426 | 1.00 | 6.03 | H | C |
| ATOM | 1676 | CD1 | TYR | 32 | 115.934 | 22.336 | 19.500 | 1.00 | 6.03 | H | C |
| ATOM | 1677 | CE1 | TYR | 32 | 117.249 | 22.097 | 19.889 | 1.00 | 6.03 | H | C |
| ATOM | 1678 | CD2 | TYR | 32 | 116.153 | 20.722 | 17.747 | 1.00 | 6.03 | H | C |
| ATOM | 1679 | CE2 | TYR | 32 | 117.467 | 20.477 | 18.122 | 1.00 | 6.03 | H | C |

Fig. 19: A-24

| | | | | | | | | | | |
|---|---|---|---|---|---|---|---|---|---|---|
| ATOM | 1680 | CZ | TYR | 32 | 118.013 | 21.165 | 19.198 | 1.00 | 6.03 | H C |
| ATOM | 1681 | OH | TYR | 32 | 119.317 | 20.907 | 19.597 | 1.00 | 6.03 | H O |
| ATOM | 1682 | C | TYR | 32 | 112.426 | 23.184 | 16.534 | 1.00 | 15.47 | H C |
| ATOM | 1683 | O | TYR | 32 | 111.480 | 23.748 | 17.058 | 1.00 | 15.47 | H O |
| ATOM | 1684 | N | THR | 33 | 112.309 | 22.545 | 15.382 | 1.00 | 10.91 | H N |
| ATOM | 1685 | CA | THR | 33 | 110.988 | 22.451 | 14.792 | 1.00 | 10.91 | H C |
| ATOM | 1686 | CB | THR | 33 | 111.032 | 22.556 | 13.230 | 1.00 | 11.96 | H C |
| ATOM | 1687 | OG1 | THR | 33 | 111.079 | 21.259 | 12.639 | 1.00 | 11.96 | H O |
| ATOM | 1688 | CG2 | THR | 33 | 112.251 | 23.338 | 12.786 | 1.00 | 11.96 | H C |
| ATOM | 1689 | C | THR | 33 | 110.501 | 21.082 | 15.303 | 1.00 | 10.91 | H C |
| ATOM | 1690 | O | THR | 33 | 111.188 | 20.061 | 15.157 | 1.00 | 10.91 | H O |
| ATOM | 1691 | N | MET | 34 | 109.348 | 21.070 | 15.960 | 1.00 | 21.14 | H N |
| ATOM | 1692 | CA | MET | 34 | 108.815 | 19.835 | 16.518 | 1.00 | 21.14 | H C |
| ATOM | 1693 | CB | MET | 34 | 108.188 | 20.094 | 17.888 | 1.00 | 16.88 | H C |
| ATOM | 1694 | CG | MET | 34 | 109.035 | 20.899 | 18.847 | 1.00 | 16.88 | H C |
| ATOM | 1695 | SD | MET | 34 | 110.603 | 20.131 | 19.122 | 1.00 | 16.88 | H S |
| ATOM | 1696 | CE | MET | 34 | 110.155 | 18.770 | 20.240 | 1.00 | 16.88 | H C |
| ATOM | 1697 | C | MET | 34 | 107.760 | 19.218 | 15.614 | 1.00 | 21.14 | H C |
| ATOM | 1698 | O | MET | 34 | 107.160 | 19.905 | 14.781 | 1.00 | 21.14 | H O |
| ATOM | 1699 | N | SER | 35 | 107.519 | 17.925 | 15.802 | 1.00 | 15.88 | H N |
| ATOM | 1700 | CA | SER | 35 | 106.533 | 17.232 | 14.997 | 1.00 | 15.88 | H C |
| ATOM | 1701 | CB | SER | 35 | 107.205 | 16.581 | 13.794 | 1.00 | 13.53 | H C |
| ATOM | 1702 | OG | SER | 35 | 107.895 | 17.550 | 13.034 | 1.00 | 13.53 | H O |
| ATOM | 1703 | C | SER | 35 | 105.767 | 16.168 | 15.763 | 1.00 | 15.88 | H C |
| ATOM | 1704 | O | SER | 35 | 106.058 | 15.867 | 16.926 | 1.00 | 15.88 | H O |
| ATOM | 1705 | N | TRP | 36 | 104.765 | 15.617 | 15.087 | 1.00 | 13.73 | H N |
| ATOM | 1706 | CA | TRP | 36 | 103.948 | 14.556 | 15.626 | 1.00 | 13.73 | H C |
| ATOM | 1707 | CB | TRP | 36 | 102.510 | 15.023 | 15.849 | 1.00 | 20.04 | H C |
| ATOM | 1708 | CG | TRP | 36 | 102.337 | 15.903 | 17.039 | 1.00 | 20.04 | H C |
| ATOM | 1709 | CD2 | TRP | 36 | 102.259 | 15.489 | 18.406 | 1.00 | 20.04 | H C |
| ATOM | 1710 | CE2 | TRP | 36 | 102.112 | 16.654 | 19.186 | 1.00 | 20.04 | H C |
| ATOM | 1711 | CE3 | TRP | 36 | 102.301 | 14.248 | 19.046 | 1.00 | 20.04 | H C |
| ATOM | 1712 | CD1 | TRP | 36 | 102.236 | 17.255 | 17.045 | 1.00 | 20.04 | H C |
| ATOM | 1713 | NE1 | TRP | 36 | 102.100 | 17.716 | 18.329 | 1.00 | 20.04 | H N |
| ATOM | 1714 | CZ2 | TRP | 36 | 102.004 | 16.622 | 20.576 | 1.00 | 20.04 | H C |
| ATOM | 1715 | CZ3 | TRP | 36 | 102.192 | 14.211 | 20.442 | 1.00 | 20.04 | H C |
| ATOM | 1716 | CH2 | TRP | 36 | 102.044 | 15.396 | 21.190 | 1.00 | 20.04 | H C |
| ATOM | 1717 | C | TRP | 36 | 103.978 | 13.470 | 14.565 | 1.00 | 13.73 | H C |
| ATOM | 1718 | O | TRP | 36 | 103.879 | 13.769 | 13.373 | 1.00 | 13.73 | H O |
| ATOM | 1719 | N | VAL | 37 | 104.138 | 12.221 | 15.006 | 1.00 | 21.09 | H N |
| ATOM | 1720 | CA | VAL | 37 | 104.179 | 11.054 | 14.125 | 1.00 | 21.09 | H C |
| ATOM | 1721 | CB | VAL | 37 | 105.622 | 10.464 | 14.053 | 1.00 | 6.36 | H C |
| ATOM | 1722 | CG1 | VAL | 37 | 105.591 | 9.017 | 13.642 | 1.00 | 6.36 | H C |
| ATOM | 1723 | CG2 | VAL | 37 | 106.461 | 11.253 | 13.057 | 1.00 | 6.36 | H C |
| ATOM | 1724 | C | VAL | 37 | 103.229 | 10.041 | 14.748 | 1.00 | 21.09 | H C |
| ATOM | 1725 | O | VAL | 37 | 103.144 | 9.940 | 15.963 | 1.00 | 21.09 | H O |
| ATOM | 1726 | N | ARG | 38 | 102.508 | 9.294 | 13.929 | 1.00 | 17.98 | H N |
| ATOM | 1727 | CA | ARG | 38 | 101.562 | 8.309 | 14.454 | 1.00 | 17.98 | H C |
| ATOM | 1728 | CB | ARG | 38 | 100.133 | 8.697 | 14.058 | 1.00 | 13.99 | H C |
| ATOM | 1729 | CG | ARG | 38 | 100.106 | 9.210 | 12.633 | 1.00 | 13.99 | H C |
| ATOM | 1730 | CD | ARG | 38 | 98.899 | 8.817 | 11.839 | 1.00 | 13.99 | H C |
| ATOM | 1731 | NE | ARG | 38 | 97.664 | 9.434 | 12.289 | 1.00 | 13.99 | H N |
| ATOM | 1732 | CZ | ARG | 38 | 96.652 | 9.707 | 11.470 | 1.00 | 13.99 | H C |
| ATOM | 1733 | NH1 | ARG | 38 | 96.744 | 9.432 | 10.171 | 1.00 | 13.99 | H N |
| ATOM | 1734 | NH2 | ARG | 38 | 95.533 | 10.224 | 11.960 | 1.00 | 13.99 | H N |
| ATOM | 1735 | C | ARG | 38 | 101.856 | 6.925 | 13.895 | 1.00 | 17.98 | H C |
| ATOM | 1736 | O | ARG | 38 | 102.468 | 6.785 | 12.840 | 1.00 | 17.98 | H O |
| ATOM | 1737 | N | GLN | 39 | 101.386 | 5.909 | 14.604 | 1.00 | 17.63 | H N |
| ATOM | 1738 | CA | GLN | 39 | 101.560 | 4.521 | 14.200 | 1.00 | 17.63 | H C |
| ATOM | 1739 | CB | GLN | 39 | 102.659 | 3.866 | 15.051 | 1.00 | 12.11 | H C |
| ATOM | 1740 | CG | GLN | 39 | 102.976 | 2.424 | 14.712 | 1.00 | 12.11 | H C |
| ATOM | 1741 | CD | GLN | 39 | 104.396 | 2.025 | 15.134 | 1.00 | 12.11 | H C |
| ATOM | 1742 | OE1 | GLN | 39 | 104.811 | 2.262 | 16.272 | 1.00 | 12.11 | H O |
| ATOM | 1743 | NE2 | GLN | 39 | 105.143 | 1.414 | 14.212 | 1.00 | 12.11 | H N |
| ATOM | 1744 | C | GLN | 39 | 100.206 | 3.847 | 14.429 | 1.00 | 17.63 | H C |
| ATOM | 1745 | O | GLN | 39 | 99.712 | 3.770 | 15.562 | 1.00 | 17.63 | H O |
| ATOM | 1746 | N | ALA | 40 | 99.590 | 3.399 | 13.344 | 1.00 | 55.11 | H N |
| ATOM | 1747 | CA | ALA | 40 | 98.300 | 2.737 | 13.436 | 1.00 | 55.11 | H C |
| ATOM | 1748 | CB | ALA | 40 | 97.605 | 2.754 | 12.088 | 1.00 | 43.12 | H C |
| ATOM | 1749 | C | ALA | 40 | 98.536 | 1.302 | 13.881 | 1.00 | 55.11 | H C |
| ATOM | 1750 | O | ALA | 40 | 99.626 | 0.762 | 13.687 | 1.00 | 55.11 | H O |
| ATOM | 1751 | N | PRO | 41 | 97.517 | 0.670 | 14.491 | 1.00 | 55.83 | H N |
| ATOM | 1752 | CD | PRO | 41 | 96.189 | 1.237 | 14.782 | 1.00 | 86.02 | H C |

Fig. 19: A-25

| | | | | | | | | | | | |
|---|---|---|---|---|---|---|---|---|---|---|---|
| ATOM | 1753 | CA | PRO | 41 | 97.600 | -0.712 | 14.969 | 1.00 | 55.83 | H | C |
| ATOM | 1754 | CB | PRO | 41 | 96.169 | -1.009 | 15.400 | 1.00 | 86.02 | H | C |
| ATOM | 1755 | CG | PRO | 41 | 95.681 | 0.315 | 15.859 | 1.00 | 86.02 | H | C |
| ATOM | 1756 | C | PRO | 41 | 98.057 | -1.624 | 13.838 | 1.00 | 55.83 | H | C |
| ATOM | 1757 | O | PRO | 41 | 97.423 | -1.670 | 12.781 | 1.00 | 55.83 | H | O |
| ATOM | 1758 | N | GLY | 42 | 99.160 | -2.335 | 14.061 | 1.00 | 43.01 | H | N |
| ATOM | 1759 | CA | GLY | 42 | 99.684 | -3.227 | 13.042 | 1.00 | 43.01 | H | C |
| ATOM | 1760 | C | GLY | 42 | 100.227 | -2.529 | 11.800 | 1.00 | 43.01 | H | C |
| ATOM | 1761 | O | GLY | 42 | 100.480 | -3.175 | 10.775 | 1.00 | 43.01 | H | O |
| ATOM | 1762 | N | LYS | 43 | 100.415 | -1.212 | 11.882 | 1.00 | 46.16 | H | N |
| ATOM | 1763 | CA | LYS | 43 | 100.922 | -0.446 | 10.750 | 1.00 | 46.16 | H | C |
| ATOM | 1764 | CB | LYS | 43 | 99.896 | 0.612 | 10.334 | 1.00 | 59.60 | H | C |
| ATOM | 1765 | CG | LYS | 43 | 98.800 | 0.081 | 9.421 | 1.00 | 59.60 | H | C |
| ATOM | 1766 | CD | LYS | 43 | 98.003 | -1.023 | 10.079 | 1.00 | 59.60 | H | C |
| ATOM | 1767 | CE | LYS | 43 | 97.230 | -1.831 | 9.047 | 1.00 | 59.60 | H | C |
| ATOM | 1768 | NZ | LYS | 43 | 98.125 | -2.590 | 8.124 | 1.00 | 59.60 | H | N |
| ATOM | 1769 | C | LYS | 43 | 102.278 | 0.215 | 10.994 | 1.00 | 46.16 | H | C |
| ATOM | 1770 | O | LYS | 43 | 102.889 | 0.060 | 12.063 | 1.00 | 46.16 | H | O |
| ATOM | 1771 | N | GLY | 44 | 102.742 | 0.942 | 9.976 | 1.00 | 50.42 | H | N |
| ATOM | 1772 | CA | GLY | 44 | 104.016 | 1.631 | 10.054 | 1.00 | 50.42 | H | C |
| ATOM | 1773 | C | GLY | 44 | 103.916 | 3.004 | 10.691 | 1.00 | 50.42 | H | C |
| ATOM | 1774 | O | GLY | 44 | 103.001 | 3.281 | 11.462 | 1.00 | 50.42 | H | O |
| ATOM | 1775 | N | LEU | 45 | 104.862 | 3.870 | 10.347 | 1.00 | 25.59 | H | N |
| ATOM | 1776 | CA | LEU | 45 | 104.933 | 5.229 | 10.883 | 1.00 | 25.59 | H | C |
| ATOM | 1777 | CB | LEU | 45 | 106.387 | 5.544 | 11.224 | 1.00 | 8.94 | H | C |
| ATOM | 1778 | CG | LEU | 45 | 107.011 | 4.480 | 12.118 | 1.00 | 8.94 | H | C |
| ATOM | 1779 | CD1 | LEU | 45 | 108.520 | 4.578 | 12.054 | 1.00 | 8.94 | H | C |
| ATOM | 1780 | CD2 | LEU | 45 | 106.481 | 4.638 | 13.541 | 1.00 | 8.94 | H | C |
| ATOM | 1781 | C | LEU | 45 | 104.394 | 6.259 | 9.893 | 1.00 | 25.59 | H | C |
| ATOM | 1782 | O | LEU | 45 | 104.613 | 6.142 | 8.684 | 1.00 | 25.59 | H | O |
| ATOM | 1783 | N | GLU | 46 | 103.698 | 7.268 | 10.411 | 1.00 | 28.67 | H | N |
| ATOM | 1784 | CA | GLU | 46 | 103.111 | 8.308 | 9.569 | 1.00 | 28.67 | H | C |
| ATOM | 1785 | CB | GLU | 46 | 101.617 | 8.045 | 9.370 | 1.00 | 21.38 | H | C |
| ATOM | 1786 | CG | GLU | 46 | 100.977 | 8.902 | 8.304 | 1.00 | 21.38 | H | C |
| ATOM | 1787 | CD | GLU | 46 | 99.555 | 8.471 | 7.972 | 1.00 | 21.38 | H | C |
| ATOM | 1788 | OE1 | GLU | 46 | 98.711 | 8.399 | 8.903 | 1.00 | 21.38 | H | O |
| ATOM | 1789 | OE2 | GLU | 46 | 99.283 | 8.214 | 6.776 | 1.00 | 21.38 | H | O |
| ATOM | 1790 | C | GLU | 46 | 103.304 | 9.698 | 10.152 | 1.00 | 28.67 | H | C |
| ATOM | 1791 | O | GLU | 46 | 102.942 | 9.962 | 11.301 | 1.00 | 28.67 | H | O |
| ATOM | 1792 | N | TRP | 47 | 103.887 | 10.579 | 9.347 | 1.00 | 2.61 | H | N |
| ATOM | 1793 | CA | TRP | 47 | 104.132 | 11.944 | 9.758 | 1.00 | 2.61 | H | C |
| ATOM | 1794 | CB | TRP | 47 | 105.055 | 12.618 | 8.757 | 1.00 | 14.19 | H | C |
| ATOM | 1795 | CG | TRP | 47 | 105.068 | 14.095 | 8.904 | 1.00 | 14.19 | H | C |
| ATOM | 1796 | CD2 | TRP | 47 | 104.446 | 15.035 | 8.036 | 1.00 | 14.19 | H | C |
| ATOM | 1797 | CE2 | TRP | 47 | 104.681 | 16.323 | 8.578 | 1.00 | 14.19 | H | C |
| ATOM | 1798 | CE3 | TRP | 47 | 103.709 | 14.919 | 6.852 | 1.00 | 14.19 | H | C |
| ATOM | 1799 | CD1 | TRP | 47 | 105.644 | 14.824 | 9.914 | 1.00 | 14.19 | H | C |
| ATOM | 1800 | NE1 | TRP | 47 | 105.418 | 16.161 | 9.723 | 1.00 | 14.19 | H | N |
| ATOM | 1801 | CZ2 | TRP | 47 | 104.201 | 17.490 | 7.969 | 1.00 | 14.19 | H | C |
| ATOM | 1802 | CZ3 | TRP | 47 | 103.233 | 16.074 | 6.248 | 1.00 | 14.19 | H | C |
| ATOM | 1803 | CH2 | TRP | 47 | 103.480 | 17.344 | 6.808 | 1.00 | 14.19 | H | C |
| ATOM | 1804 | C | TRP | 47 | 102.791 | 12.673 | 9.802 | 1.00 | 2.61 | H | C |
| ATOM | 1805 | O | TRP | 47 | 102.083 | 12.752 | 8.796 | 1.00 | 2.61 | H | O |
| ATOM | 1806 | N | VAL | 48 | 102.443 | 13.215 | 10.962 | 1.00 | 34.26 | H | N |
| ATOM | 1807 | CA | VAL | 48 | 101.165 | 13.895 | 11.114 | 1.00 | 34.26 | H | C |
| ATOM | 1808 | CB | VAL | 48 | 100.576 | 13.639 | 12.523 | 1.00 | 16.29 | H | C |
| ATOM | 1809 | CG1 | VAL | 48 | 99.137 | 14.148 | 12.623 | 1.00 | 16.29 | H | C |
| ATOM | 1810 | CG2 | VAL | 48 | 100.624 | 12.187 | 12.812 | 1.00 | 16.29 | H | C |
| ATOM | 1811 | C | VAL | 48 | 101.246 | 15.393 | 10.884 | 1.00 | 34.26 | H | C |
| ATOM | 1812 | O | VAL | 48 | 100.563 | 15.932 | 10.015 | 1.00 | 34.26 | H | O |
| ATOM | 1813 | N | ALA | 49 | 102.078 | 16.068 | 11.665 | 1.00 | 19.79 | H | N |
| ATOM | 1814 | CA | ALA | 49 | 102.198 | 17.505 | 11.533 | 1.00 | 19.79 | H | C |
| ATOM | 1815 | CB | ALA | 49 | 101.052 | 18.193 | 12.288 | 1.00 | 1.87 | H | C |
| ATOM | 1816 | C | ALA | 49 | 103.542 | 17.994 | 12.041 | 1.00 | 19.79 | H | C |
| ATOM | 1817 | O | ALA | 49 | 104.295 | 17.244 | 12.645 | 1.00 | 19.79 | H | O |
| ATOM | 1818 | N | THR | 50 | 103.816 | 19.271 | 11.795 | 1.00 | 29.76 | H | N |
| ATOM | 1819 | CA | THR | 50 | 105.067 | 19.906 | 12.184 | 1.00 | 29.76 | H | C |
| ATOM | 1820 | CB | THR | 50 | 106.142 | 19.637 | 11.127 | 1.00 | 20.69 | H | C |
| ATOM | 1821 | OG1 | THR | 50 | 106.390 | 18.232 | 11.065 | 1.00 | 20.69 | H | O |
| ATOM | 1822 | CG2 | THR | 50 | 107.422 | 20.357 | 11.460 | 1.00 | 20.69 | H | C |
| ATOM | 1823 | C | THR | 50 | 104.897 | 21.416 | 12.327 | 1.00 | 29.76 | H | C |
| ATOM | 1824 | O | THR | 50 | 104.113 | 22.035 | 11.616 | 1.00 | 29.76 | H | O |
| ATOM | 1825 | N | ILE | 51 | 105.649 | 21.994 | 13.258 | 1.00 | 20.54 | H | N |

Fig. 19: A-26

| ATOM | 1826 | CA | ILE | 51 | 105.626 | 23.424 | 13.530 | 1.00 | 20.54 | H | C |
|------|------|-----|-----|----|---------|--------|--------|------|-------|---|---|
| ATOM | 1827 | CB | ILE | 51 | 104.824 | 23.714 | 14.816 | 1.00 | 27.11 | H | C |
| ATOM | 1828 | CG2 | ILE | 51 | 105.430 | 22.955 | 15.975 | 1.00 | 27.11 | H | C |
| ATOM | 1829 | CG1 | ILE | 51 | 104.805 | 25.217 | 15.108 | 1.00 | 27.11 | H | C |
| ATOM | 1830 | CD1 | ILE | 51 | 104.073 | 25.593 | 16.389 | 1.00 | 27.11 | H | C |
| ATOM | 1831 | C | ILE | 51 | 107.090 | 23.813 | 13.723 | 1.00 | 20.54 | H | C |
| ATOM | 1832 | O | ILE | 51 | 107.781 | 23.208 | 14.533 | 1.00 | 20.54 | H | O |
| ATOM | 1833 | N | SER | 52 | 107.565 | 24.803 | 12.970 | 1.00 | 28.49 | H | N |
| ATOM | 1834 | CA | SER | 52 | 108.962 | 25.234 | 13.047 | 1.00 | 28.49 | H | C |
| ATOM | 1835 | CB | SER | 52 | 109.356 | 26.018 | 11.797 | 1.00 | 35.37 | H | C |
| ATOM | 1836 | OG | SER | 52 | 108.819 | 27.332 | 11.832 | 1.00 | 35.37 | H | O |
| ATOM | 1837 | C | SER | 52 | 109.236 | 26.105 | 14.256 | 1.00 | 28.49 | H | C |
| ATOM | 1838 | O | SER | 52 | 108.316 | 26.461 | 14.994 | 1.00 | 28.49 | H | O |
| ATOM | 1839 | N | GLY | 53 | 110.509 | 26.452 | 14.451 | 1.00 | 16.74 | H | N |
| ATOM | 1840 | CA | GLY | 53 | 110.864 | 27.295 | 15.568 | 1.00 | 16.74 | H | C |
| ATOM | 1841 | C | GLY | 53 | 110.203 | 28.651 | 15.410 | 1.00 | 16.74 | H | C |
| ATOM | 1842 | O | GLY | 53 | 110.093 | 29.412 | 16.369 | 1.00 | 16.74 | H | O |
| ATOM | 1843 | N | GLY | 54 | 109.746 | 28.939 | 14.192 | 1.00 | 26.55 | H | N |
| ATOM | 1844 | CA | GLY | 54 | 109.120 | 30.218 | 13.907 | 1.00 | 26.55 | H | C |
| ATOM | 1845 | C | GLY | 54 | 107.605 | 30.253 | 13.815 | 1.00 | 26.55 | H | C |
| ATOM | 1846 | O | GLY | 54 | 107.020 | 31.317 | 13.607 | 1.00 | 26.55 | H | O |
| ATOM | 1847 | N | GLY | 55 | 106.953 | 29.105 | 13.948 | 1.00 | 34.83 | H | N |
| ATOM | 1848 | CA | GLY | 55 | 105.505 | 29.105 | 13.889 | 1.00 | 34.83 | H | C |
| ATOM | 1849 | C | GLY | 55 | 104.878 | 28.610 | 12.604 | 1.00 | 34.83 | H | C |
| ATOM | 1850 | O | GLY | 55 | 103.657 | 28.663 | 12.458 | 1.00 | 34.83 | H | O |
| ATOM | 1851 | N | HIS | 56 | 105.683 | 28.149 | 11.655 | 1.00 | 20.17 | H | N |
| ATOM | 1852 | CA | HIS | 56 | 105.091 | 27.643 | 10.426 | 1.00 | 20.17 | H | C |
| ATOM | 1853 | CB | HIS | 56 | 106.117 | 27.522 | 9.302 | 1.00 | 75.35 | H | C |
| ATOM | 1854 | CG | HIS | 56 | 106.829 | 28.797 | 8.996 | 1.00 | 75.35 | H | C |
| ATOM | 1855 | CD2 | HIS | 56 | 106.561 | 29.773 | 8.096 | 1.00 | 75.35 | H | C |
| ATOM | 1856 | ND1 | HIS | 56 | 107.959 | 29.201 | 9.677 | 1.00 | 75.35 | H | N |
| ATOM | 1857 | CE1 | HIS | 56 | 108.356 | 30.370 | 9.209 | 1.00 | 75.35 | H | C |
| ATOM | 1858 | NE2 | HIS | 56 | 107.525 | 30.739 | 8.250 | 1.00 | 75.35 | H | N |
| ATOM | 1859 | C | HIS | 56 | 104.585 | 26.266 | 10.774 | 1.00 | 20.17 | H | C |
| ATOM | 1860 | O | HIS | 56 | 105.309 | 25.465 | 11.350 | 1.00 | 20.17 | H | O |
| ATOM | 1861 | N | THR | 57 | 103.331 | 25.994 | 10.458 | 1.00 | 9.30 | H | N |
| ATOM | 1862 | CA | THR | 57 | 102.793 | 24.676 | 10.728 | 1.00 | 9.30 | H | C |
| ATOM | 1863 | CB | THR | 57 | 101.437 | 24.766 | 11.475 | 1.00 | 25.93 | H | C |
| ATOM | 1864 | OG1 | THR | 57 | 100.483 | 25.493 | 10.691 | 1.00 | 25.93 | H | O |
| ATOM | 1865 | CG2 | THR | 57 | 101.624 | 25.460 | 12.821 | 1.00 | 25.93 | H | C |
| ATOM | 1866 | C | THR | 57 | 102.657 | 23.911 | 9.403 | 1.00 | 9.30 | H | C |
| ATOM | 1867 | O | THR | 57 | 102.437 | 24.503 | 8.348 | 1.00 | 9.30 | H | O |
| ATOM | 1868 | N | TYR | 58 | 102.849 | 22.598 | 9.463 | 1.00 | 10.35 | H | N |
| ATOM | 1869 | CA | TYR | 58 | 102.739 | 21.729 | 8.293 | 1.00 | 10.35 | H | C |
| ATOM | 1870 | CB | TYR | 58 | 104.115 | 21.217 | 7.912 | 1.00 | 22.31 | H | C |
| ATOM | 1871 | CG | TYR | 58 | 105.023 | 22.324 | 7.485 | 1.00 | 22.31 | H | C |
| ATOM | 1872 | CD1 | TYR | 58 | 105.051 | 22.744 | 6.167 | 1.00 | 22.31 | H | C |
| ATOM | 1873 | CE1 | TYR | 58 | 105.871 | 23.765 | 5.768 | 1.00 | 22.31 | H | C |
| ATOM | 1874 | CD2 | TYR | 58 | 105.843 | 22.967 | 8.399 | 1.00 | 22.31 | H | C |
| ATOM | 1875 | CE2 | TYR | 58 | 106.667 | 23.997 | 8.007 | 1.00 | 22.31 | H | C |
| ATOM | 1876 | CZ | TYR | 58 | 106.674 | 24.388 | 6.689 | 1.00 | 22.31 | H | C |
| ATOM | 1877 | OH | TYR | 58 | 107.478 | 25.419 | 6.279 | 1.00 | 22.31 | H | O |
| ATOM | 1878 | C | TYR | 58 | 101.812 | 20.565 | 8.635 | 1.00 | 10.35 | H | C |
| ATOM | 1879 | O | TYR | 58 | 101.699 | 20.164 | 9.801 | 1.00 | 10.35 | H | O |
| ATOM | 1880 | N | TYR | 59 | 101.147 | 20.007 | 7.634 | 1.00 | 15.64 | H | N |
| ATOM | 1881 | CA | TYR | 59 | 100.219 | 18.936 | 7.931 | 1.00 | 15.64 | H | C |
| ATOM | 1882 | CB | TYR | 59 | 98.843 | 19.542 | 8.203 | 1.00 | 11.32 | H | C |
| ATOM | 1883 | CG | TYR | 59 | 98.803 | 20.511 | 9.360 | 1.00 | 11.32 | H | C |
| ATOM | 1884 | CD1 | TYR | 59 | 98.625 | 20.058 | 10.661 | 1.00 | 11.32 | H | C |
| ATOM | 1885 | CE1 | TYR | 59 | 98.540 | 20.942 | 11.731 | 1.00 | 11.32 | H | C |
| ATOM | 1886 | CD2 | TYR | 59 | 98.912 | 21.886 | 9.148 | 1.00 | 11.32 | H | C |
| ATOM | 1887 | CE2 | TYR | 59 | 98.835 | 22.783 | 10.208 | 1.00 | 11.32 | H | C |
| ATOM | 1888 | CZ | TYR | 59 | 98.640 | 22.302 | 11.502 | 1.00 | 11.32 | H | C |
| ATOM | 1889 | OH | TYR | 59 | 98.498 | 23.177 | 12.557 | 1.00 | 11.32 | H | O |
| ATOM | 1890 | C | TYR | 59 | 100.071 | 17.883 | 6.856 | 1.00 | 15.64 | H | C |
| ATOM | 1891 | O | TYR | 59 | 100.150 | 18.182 | 5.666 | 1.00 | 15.64 | H | O |
| ATOM | 1892 | N | LEU | 60 | 99.854 | 16.644 | 7.286 | 1.00 | 33.81 | H | N |
| ATOM | 1893 | CA | LEU | 60 | 99.616 | 15.539 | 6.366 | 1.00 | 33.81 | H | C |
| ATOM | 1894 | CB | LEU | 60 | 99.625 | 14.217 | 7.135 | 1.00 | 13.27 | H | C |
| ATOM | 1895 | CG | LEU | 60 | 99.371 | 12.896 | 6.406 | 1.00 | 13.27 | H | C |
| ATOM | 1896 | CD1 | LEU | 60 | 100.681 | 12.371 | 5.800 | 1.00 | 13.27 | H | C |
| ATOM | 1897 | CD2 | LEU | 60 | 98.804 | 11.882 | 7.397 | 1.00 | 13.27 | H | C |
| ATOM | 1898 | C | LEU | 60 | 98.198 | 15.861 | 5.869 | 1.00 | 33.81 | H | C |

Fig. 19: A-27

| ATOM | 1899 | O | LEU | 60 | 97.329 | 16.255 | 6.659 | 1.00 | 33.81 | H | O |
|---|---|---|---|---|---|---|---|---|---|---|---|
| ATOM | 1900 | N | ASP | 61 | 97.962 | 15.710 | 4.573 | 1.00 | 24.56 | H | N |
| ATOM | 1901 | CA | ASP | 61 | 96.659 | 16.028 | 3.991 | 1.00 | 24.56 | H | C |
| ATOM | 1902 | CB | ASP | 61 | 96.639 | 15.579 | 2.530 | 1.00 | 55.35 | H | C |
| ATOM | 1903 | CG | ASP | 61 | 97.719 | 16.260 | 1.708 | 1.00 | 55.35 | H | C |
| ATOM | 1904 | OD1 | ASP | 61 | 98.919 | 16.083 | 2.023 | 1.00 | 55.35 | H | O |
| ATOM | 1905 | OD2 | ASP | 61 | 97.374 | 16.981 | 0.754 | 1.00 | 55.35 | H | O |
| ATOM | 1906 | C | ASP | 61 | 95.436 | 15.495 | 4.731 | 1.00 | 24.56 | H | C |
| ATOM | 1907 | O | ASP | 61 | 94.515 | 16.254 | 5.043 | 1.00 | 24.56 | H | O |
| ATOM | 1908 | N | SER | 62 | 95.432 | 14.198 | 5.024 | 1.00 | 20.78 | H | N |
| ATOM | 1909 | CA | SER | 62 | 94.317 | 13.567 | 5.717 | 1.00 | 20.78 | H | C |
| ATOM | 1910 | CB | SER | 62 | 94.630 | 12.085 | 5.955 | 1.00 | 31.68 | H | C |
| ATOM | 1911 | OG | SER | 62 | 95.820 | 11.902 | 6.708 | 1.00 | 31.68 | H | O |
| ATOM | 1912 | C | SER | 62 | 93.882 | 14.216 | 7.044 | 1.00 | 20.78 | H | C |
| ATOM | 1913 | O | SER | 62 | 92.732 | 14.053 | 7.475 | 1.00 | 20.78 | H | O |
| ATOM | 1914 | N | VAL | 63 | 94.779 | 14.949 | 7.695 | 1.00 | 24.27 | H | N |
| ATOM | 1915 | CA | VAL | 63 | 94.439 | 15.567 | 8.968 | 1.00 | 24.27 | H | C |
| ATOM | 1916 | CB | VAL | 63 | 95.478 | 15.202 | 10.049 | 1.00 | 45.54 | H | C |
| ATOM | 1917 | CG1 | VAL | 63 | 95.642 | 13.698 | 10.110 | 1.00 | 45.54 | H | C |
| ATOM | 1918 | CG2 | VAL | 63 | 96.812 | 15.873 | 9.752 | 1.00 | 45.54 | H | C |
| ATOM | 1919 | C | VAL | 63 | 94.374 | 17.083 | 8.839 | 1.00 | 24.27 | H | C |
| ATOM | 1920 | O | VAL | 63 | 94.112 | 17.812 | 9.823 | 1.00 | 24.27 | H | O |
| ATOM | 1921 | N | LYS | 64 | 94.611 | 17.556 | 7.618 | 1.00 | 38.99 | H | N |
| ATOM | 1922 | CA | LYS | 64 | 94.611 | 18.985 | 7.348 | 1.00 | 38.99 | H | C |
| ATOM | 1923 | CB | LYS | 64 | 94.983 | 19.235 | 5.889 | 1.00 | 39.16 | H | C |
| ATOM | 1924 | CG | LYS | 64 | 95.736 | 20.528 | 5.671 | 1.00 | 39.16 | H | C |
| ATOM | 1925 | CD | LYS | 64 | 96.417 | 20.521 | 4.309 | 1.00 | 39.16 | H | C |
| ATOM | 1926 | CE | LYS | 64 | 97.432 | 19.380 | 4.176 | 1.00 | 39.16 | H | C |
| ATOM | 1927 | NZ | LYS | 64 | 98.011 | 19.296 | 2.803 | 1.00 | 39.16 | H | N |
| ATOM | 1928 | C | LYS | 64 | 93.262 | 19.607 | 7.667 | 1.00 | 38.99 | H | C |
| ATOM | 1929 | O | LYS | 64 | 92.240 | 19.212 | 7.121 | 1.00 | 38.99 | H | O |
| ATOM | 1930 | N | GLY | 65 | 93.263 | 20.577 | 8.567 | 1.00 | 28.42 | H | N |
| ATOM | 1931 | CA | GLY | 65 | 92.019 | 21.219 | 8.918 | 1.00 | 28.42 | H | C |
| ATOM | 1932 | C | GLY | 65 | 91.277 | 20.501 | 10.021 | 1.00 | 28.42 | H | C |
| ATOM | 1933 | O | GLY | 65 | 90.271 | 21.005 | 10.509 | 1.00 | 28.42 | H | O |
| ATOM | 1934 | N | ARG | 66 | 91.751 | 19.324 | 10.414 | 1.00 | 48.07 | H | N |
| ATOM | 1935 | CA | ARG | 66 | 91.098 | 18.588 | 11.488 | 1.00 | 48.07 | H | C |
| ATOM | 1936 | CB | ARG | 66 | 90.783 | 17.154 | 11.064 | 1.00 | 36.61 | H | C |
| ATOM | 1937 | CG | ARG | 66 | 89.845 | 17.052 | 9.887 | 1.00 | 36.61 | H | C |
| ATOM | 1938 | CD | ARG | 66 | 89.484 | 15.608 | 9.571 | 1.00 | 36.61 | H | C |
| ATOM | 1939 | NE | ARG | 66 | 90.654 | 14.750 | 9.346 | 1.00 | 36.61 | H | N |
| ATOM | 1940 | CZ | ARG | 66 | 91.133 | 13.877 | 10.236 | 1.00 | 36.61 | H | C |
| ATOM | 1941 | NH1 | ARG | 66 | 90.545 | 13.739 | 11.421 | 1.00 | 36.61 | H | N |
| ATOM | 1942 | NH2 | ARG | 66 | 92.203 | 13.144 | 9.944 | 1.00 | 36.61 | H | N |
| ATOM | 1943 | C | ARG | 66 | 92.018 | 18.568 | 12.687 | 1.00 | 48.07 | H | C |
| ATOM | 1944 | O | ARG | 66 | 91.584 | 18.312 | 13.808 | 1.00 | 48.07 | H | O |
| ATOM | 1945 | N | PHE | 67 | 93.296 | 18.839 | 12.438 | 1.00 | 31.81 | H | N |
| ATOM | 1946 | CA | PHE | 67 | 94.304 | 18.854 | 13.490 | 1.00 | 31.81 | H | C |
| ATOM | 1947 | CB | PHE | 67 | 95.372 | 17.802 | 13.211 | 1.00 | 34.94 | H | C |
| ATOM | 1948 | CG | PHE | 67 | 94.937 | 16.394 | 13.444 | 1.00 | 34.94 | H | C |
| ATOM | 1949 | CD1 | PHE | 67 | 93.763 | 15.907 | 12.902 | 1.00 | 34.94 | H | C |
| ATOM | 1950 | CD2 | PHE | 67 | 95.748 | 15.530 | 14.158 | 1.00 | 34.94 | H | C |
| ATOM | 1951 | CE1 | PHE | 67 | 93.400 | 14.564 | 13.063 | 1.00 | 34.94 | H | C |
| ATOM | 1952 | CE2 | PHE | 67 | 95.400 | 14.192 | 14.326 | 1.00 | 34.94 | H | C |
| ATOM | 1953 | CZ | PHE | 67 | 94.222 | 13.706 | 13.777 | 1.00 | 34.94 | H | C |
| ATOM | 1954 | C | PHE | 67 | 94.989 | 20.209 | 13.520 | 1.00 | 31.81 | H | C |
| ATOM | 1955 | O | PHE | 67 | 95.054 | 20.899 | 12.501 | 1.00 | 31.81 | H | O |
| ATOM | 1956 | N | THR | 68 | 95.511 | 20.587 | 14.683 | 1.00 | 27.20 | H | N |
| ATOM | 1957 | CA | THR | 68 | 96.233 | 21.851 | 14.804 | 1.00 | 27.20 | H | C |
| ATOM | 1958 | CB | THR | 68 | 95.344 | 22.998 | 15.384 | 1.00 | 14.56 | H | C |
| ATOM | 1959 | OG1 | THR | 68 | 94.400 | 23.434 | 14.399 | 1.00 | 14.56 | H | O |
| ATOM | 1960 | CG2 | THR | 68 | 96.196 | 24.192 | 15.758 | 1.00 | 14.56 | H | C |
| ATOM | 1961 | C | THR | 68 | 97.466 | 21.680 | 15.689 | 1.00 | 27.20 | H | C |
| ATOM | 1962 | O | THR | 68 | 97.355 | 21.393 | 16.882 | 1.00 | 27.20 | H | O |
| ATOM | 1963 | N | ILE | 69 | 98.643 | 21.847 | 15.099 | 1.00 | 22.74 | H | N |
| ATOM | 1964 | CA | ILE | 69 | 99.869 | 21.718 | 15.861 | 1.00 | 22.74 | H | C |
| ATOM | 1965 | CB | ILE | 69 | 100.991 | 21.084 | 15.020 | 1.00 | 13.28 | H | C |
| ATOM | 1966 | CG2 | ILE | 69 | 101.417 | 22.022 | 13.933 | 1.00 | 13.28 | H | C |
| ATOM | 1967 | CG1 | ILE | 69 | 102.188 | 20.736 | 15.908 | 1.00 | 13.28 | H | C |
| ATOM | 1968 | CD1 | ILE | 69 | 103.226 | 19.848 | 15.206 | 1.00 | 13.28 | H | C |
| ATOM | 1969 | C | ILE | 69 | 100.287 | 23.096 | 16.336 | 1.00 | 22.74 | H | C |
| ATOM | 1970 | O | ILE | 69 | 100.282 | 24.065 | 15.578 | 1.00 | 22.74 | H | O |
| ATOM | 1971 | N | SER | 70 | 100.632 | 23.188 | 17.608 | 1.00 | 15.22 | H | N |

Fig. 19: A-28

| | | | | | | | | | | | |
|---|---|---|---|---|---|---|---|---|---|---|---|
| ATOM | 1972 | CA | SER | 70 | 101.032 | 24.460 | 18.183 | 1.00 | 15.22 | H | C |
| ATOM | 1973 | CB | SER | 70 | 99.834 | 25.147 | 18.851 | 1.00 | 3.12 | H | C |
| ATOM | 1974 | OG | SER | 70 | 99.588 | 24.606 | 20.144 | 1.00 | 3.12 | H | O |
| ATOM | 1975 | C | SER | 70 | 102.088 | 24.203 | 19.235 | 1.00 | 15.22 | H | C |
| ATOM | 1976 | O | SER | 70 | 102.392 | 23.053 | 19.557 | 1.00 | 15.22 | H | O |
| ATOM | 1977 | N | ARG | 71 | 102.636 | 25.281 | 19.780 | 1.00 | 42.13 | H | N |
| ATOM | 1978 | CA | ARG | 71 | 103.640 | 25.158 | 20.813 | 1.00 | 42.13 | H | C |
| ATOM | 1979 | CB | ARG | 71 | 105.039 | 25.089 | 20.210 | 1.00 | 12.52 | H | C |
| ATOM | 1980 | CG | ARG | 71 | 105.417 | 26.296 | 19.388 | 1.00 | 12.52 | H | C |
| ATOM | 1981 | CD | ARG | 71 | 106.906 | 26.507 | 19.436 | 1.00 | 12.52 | H | C |
| ATOM | 1982 | NE | ARG | 71 | 107.644 | 25.627 | 18.540 | 1.00 | 12.52 | H | N |
| ATOM | 1983 | CZ | ARG | 71 | 108.844 | 25.114 | 18.816 | 1.00 | 12.52 | H | C |
| ATOM | 1984 | NH1 | ARG | 71 | 109.444 | 25.380 | 19.970 | 1.00 | 12.52 | H | N |
| ATOM | 1985 | NH2 | ARG | 71 | 109.456 | 24.354 | 17.924 | 1.00 | 12.52 | H | N |
| ATOM | 1986 | C | ARG | 71 | 103.568 | 26.341 | 21.739 | 1.00 | 42.13 | H | C |
| ATOM | 1987 | O | ARG | 71 | 103.115 | 27.416 | 21.352 | 1.00 | 42.13 | H | O |
| ATOM | 1988 | N | ASP | 72 | 104.003 | 26.131 | 22.973 | 1.00 | 26.38 | H | N |
| ATOM | 1989 | CA | ASP | 72 | 104.034 | 27.197 | 23.954 | 1.00 | 26.38 | H | C |
| ATOM | 1990 | CB | ASP | 72 | 102.949 | 27.026 | 25.007 | 1.00 | 47.03 | H | C |
| ATOM | 1991 | CG | ASP | 72 | 103.003 | 28.108 | 26.050 | 1.00 | 47.03 | H | C |
| ATOM | 1992 | OD1 | ASP | 72 | 102.157 | 28.112 | 26.964 | 1.00 | 47.03 | H | O |
| ATOM | 1993 | OD2 | ASP | 72 | 103.907 | 28.959 | 25.953 | 1.00 | 47.03 | H | O |
| ATOM | 1994 | C | ASP | 72 | 105.402 | 27.159 | 24.607 | 1.00 | 26.38 | H | C |
| ATOM | 1995 | O | ASP | 72 | 105.618 | 26.508 | 25.633 | 1.00 | 26.38 | H | O |
| ATOM | 1996 | N | ASN | 73 | 106.325 | 27.868 | 23.979 | 1.00 | 50.64 | H | N |
| ATOM | 1997 | CA | ASN | 73 | 107.692 | 27.939 | 24.441 | 1.00 | 50.64 | H | C |
| ATOM | 1998 | CB | ASN | 73 | 108.522 | 28.747 | 23.446 | 1.00 | 30.24 | H | C |
| ATOM | 1999 | CG | ASN | 73 | 108.584 | 28.091 | 22.086 | 1.00 | 30.24 | H | C |
| ATOM | 2000 | OD1 | ASN | 73 | 109.170 | 28.625 | 21.149 | 1.00 | 30.24 | H | O |
| ATOM | 2001 | ND2 | ASN | 73 | 107.984 | 26.917 | 21.974 | 1.00 | 30.24 | H | N |
| ATOM | 2002 | C | ASN | 73 | 107.827 | 28.516 | 25.841 | 1.00 | 50.64 | H | C |
| ATOM | 2003 | O | ASN | 73 | 108.898 | 28.436 | 26.438 | 1.00 | 50.64 | H | O |
| ATOM | 2004 | N | SER | 74 | 106.758 | 29.097 | 26.376 | 1.00 | 33.75 | H | N |
| ATOM | 2005 | CA | SER | 74 | 106.848 | 29.644 | 27.723 | 1.00 | 33.75 | H | C |
| ATOM | 2006 | CB | SER | 74 | 105.593 | 30.429 | 28.093 | 1.00 | 48.57 | H | C |
| ATOM | 2007 | OG | SER | 74 | 104.534 | 29.556 | 28.444 | 1.00 | 48.57 | H | O |
| ATOM | 2008 | C | SER | 74 | 106.979 | 28.456 | 28.653 | 1.00 | 33.75 | H | C |
| ATOM | 2009 | O | SER | 74 | 107.681 | 28.530 | 29.660 | 1.00 | 33.75 | H | O |
| ATOM | 2010 | N | LYS | 75 | 106.312 | 27.354 | 28.302 | 1.00 | 39.57 | H | N |
| ATOM | 2011 | CA | LYS | 75 | 106.352 | 26.142 | 29.119 | 1.00 | 39.57 | H | C |
| ATOM | 2012 | CB | LYS | 75 | 104.973 | 25.889 | 29.732 | 1.00 | 42.48 | H | C |
| ATOM | 2013 | CG | LYS | 75 | 103.842 | 25.924 | 28.731 | 1.00 | 42.48 | H | C |
| ATOM | 2014 | CD | LYS | 75 | 102.482 | 25.985 | 29.418 | 1.00 | 42.48 | H | C |
| ATOM | 2015 | CE | LYS | 75 | 102.156 | 27.393 | 29.918 | 1.00 | 42.48 | H | C |
| ATOM | 2016 | NZ | LYS | 75 | 103.090 | 27.928 | 30.963 | 1.00 | 42.48 | H | N |
| ATOM | 2017 | C | LYS | 75 | 106.843 | 24.894 | 28.380 | 1.00 | 39.57 | H | C |
| ATOM | 2018 | O | LYS | 75 | 106.497 | 23.767 | 28.744 | 1.00 | 39.57 | H | O |
| ATOM | 2019 | N | ASN | 76 | 107.660 | 25.110 | 27.353 | 1.00 | 44.84 | H | N |
| ATOM | 2020 | CA | ASN | 76 | 108.245 | 24.043 | 26.539 | 1.00 | 44.84 | H | C |
| ATOM | 2021 | CB | ASN | 76 | 109.572 | 23.608 | 27.139 | 1.00 | 31.30 | H | C |
| ATOM | 2022 | CG | ASN | 76 | 110.528 | 24.766 | 27.312 | 1.00 | 31.30 | H | C |
| ATOM | 2023 | OD1 | ASN | 76 | 111.666 | 24.593 | 27.739 | 1.00 | 31.30 | H | O |
| ATOM | 2024 | ND2 | ASN | 76 | 110.067 | 25.965 | 26.979 | 1.00 | 31.30 | H | N |
| ATOM | 2025 | C | ASN | 76 | 107.362 | 22.827 | 26.322 | 1.00 | 44.84 | H | C |
| ATOM | 2026 | O | ASN | 76 | 107.793 | 21.681 | 26.479 | 1.00 | 44.84 | H | O |
| ATOM | 2027 | N | THR | 77 | 106.121 | 23.090 | 25.941 | 1.00 | 30.42 | H | N |
| ATOM | 2028 | CA | THR | 77 | 105.181 | 22.032 | 25.686 | 1.00 | 30.42 | H | C |
| ATOM | 2029 | CB | THR | 77 | 103.989 | 22.131 | 26.628 | 1.00 | 46.49 | H | C |
| ATOM | 2030 | OG1 | THR | 77 | 104.446 | 21.977 | 27.974 | 1.00 | 46.49 | H | O |
| ATOM | 2031 | CG2 | THR | 77 | 102.975 | 21.045 | 26.319 | 1.00 | 46.49 | H | C |
| ATOM | 2032 | C | THR | 77 | 104.708 | 22.182 | 24.254 | 1.00 | 30.42 | H | C |
| ATOM | 2033 | O | THR | 77 | 104.488 | 23.291 | 23.786 | 1.00 | 30.42 | H | O |
| ATOM | 2034 | N | LEU | 78 | 104.583 | 21.056 | 23.563 | 1.00 | 20.66 | H | N |
| ATOM | 2035 | CA | LEU | 78 | 104.135 | 21.017 | 22.185 | 1.00 | 20.66 | H | C |
| ATOM | 2036 | CB | LEU | 78 | 104.978 | 20.024 | 21.394 | 1.00 | 19.59 | H | C |
| ATOM | 2037 | CG | LEU | 78 | 104.550 | 19.758 | 19.953 | 1.00 | 19.59 | H | C |
| ATOM | 2038 | CD1 | LEU | 78 | 104.575 | 21.055 | 19.166 | 1.00 | 19.59 | H | C |
| ATOM | 2039 | CD2 | LEU | 78 | 105.470 | 18.731 | 19.320 | 1.00 | 19.59 | H | C |
| ATOM | 2040 | C | LEU | 78 | 102.716 | 20.520 | 22.298 | 1.00 | 20.66 | H | C |
| ATOM | 2041 | O | LEU | 78 | 102.368 | 19.921 | 23.312 | 1.00 | 20.66 | H | O |
| ATOM | 2042 | N | TYR | 79 | 101.902 | 20.753 | 21.271 | 1.00 | 30.75 | H | N |
| ATOM | 2043 | CA | TYR | 79 | 100.498 | 20.333 | 21.294 | 1.00 | 30.75 | H | C |
| ATOM | 2044 | CB | TYR | 79 | 99.591 | 21.494 | 21.728 | 1.00 | 47.95 | H | C |

Fig. 19: A-29

| ATOM | 2045 | CG | TYR | 79 | 99.809 | 22.008 | 23.119 | 1.00 | 47.95 | H | C |
|------|------|-----|-----|----|--------|--------|--------|------|-------|---|---|
| ATOM | 2046 | CD1 | TYR | 79 | 99.166 | 21.430 | 24.205 | 1.00 | 47.95 | H | C |
| ATOM | 2047 | CE1 | TYR | 79 | 99.357 | 21.916 | 25.491 | 1.00 | 47.95 | H | C |
| ATOM | 2048 | CD2 | TYR | 79 | 100.655 | 23.085 | 23.349 | 1.00 | 47.95 | H | C |
| ATOM | 2049 | CE2 | TYR | 79 | 100.857 | 23.579 | 24.628 | 1.00 | 47.95 | H | C |
| ATOM | 2050 | CZ | TYR | 79 | 100.204 | 22.991 | 25.695 | 1.00 | 47.95 | H | C |
| ATOM | 2051 | OH | TYR | 79 | 100.404 | 23.493 | 26.958 | 1.00 | 47.95 | H | O |
| ATOM | 2052 | C | TYR | 79 | 99.966 | 19.863 | 19.950 | 1.00 | 30.75 | H | C |
| ATOM | 2053 | O | TYR | 79 | 100.418 | 20.316 | 18.898 | 1.00 | 30.75 | H | O |
| ATOM | 2054 | N | LEU | 80 | 98.981 | 18.969 | 20.003 | 1.00 | 19.83 | H | N |
| ATOM | 2055 | CA | LEU | 80 | 98.308 | 18.472 | 18.811 | 1.00 | 19.83 | H | C |
| ATOM | 2056 | CB | LEU | 80 | 98.776 | 17.070 | 18.397 | 1.00 | 5.08 | H | C |
| ATOM | 2057 | CG | LEU | 80 | 98.132 | 16.598 | 17.076 | 1.00 | 5.08 | H | C |
| ATOM | 2058 | CD1 | LEU | 80 | 98.706 | 17.386 | 15.914 | 1.00 | 5.08 | H | C |
| ATOM | 2059 | CD2 | LEU | 80 | 98.352 | 15.111 | 16.874 | 1.00 | 5.08 | H | C |
| ATOM | 2060 | C | LEU | 80 | 96.838 | 18.411 | 19.182 | 1.00 | 19.83 | H | C |
| ATOM | 2061 | O | LEU | 80 | 96.398 | 17.503 | 19.879 | 1.00 | 19.83 | H | O |
| ATOM | 2062 | N | GLN | 81 | 96.091 | 19.412 | 18.742 | 1.00 | 24.43 | H | N |
| ATOM | 2063 | CA | GLN | 81 | 94.671 | 19.463 | 19.004 | 1.00 | 24.43 | H | C |
| ATOM | 2064 | CB | GLN | 81 | 94.169 | 20.911 | 18.966 | 1.00 | 60.73 | H | C |
| ATOM | 2065 | CG | GLN | 81 | 92.710 | 21.093 | 19.399 | 1.00 | 60.73 | H | C |
| ATOM | 2066 | CD | GLN | 81 | 92.505 | 20.974 | 20.911 | 1.00 | 60.73 | H | C |
| ATOM | 2067 | OE1 | GLN | 81 | 92.981 | 21.810 | 21.691 | 1.00 | 60.73 | H | O |
| ATOM | 2068 | NE2 | GLN | 81 | 91.787 | 19.935 | 21.328 | 1.00 | 60.73 | H | N |
| ATOM | 2069 | C | GLN | 81 | 94.064 | 18.672 | 17.867 | 1.00 | 24.43 | H | C |
| ATOM | 2070 | O | GLN | 81 | 94.376 | 18.921 | 16.698 | 1.00 | 24.43 | H | O |
| ATOM | 2071 | N | MET | 82 | 93.205 | 17.718 | 18.210 | 1.00 | 35.69 | H | N |
| ATOM | 2072 | CA | MET | 82 | 92.559 | 16.878 | 17.211 | 1.00 | 35.69 | H | C |
| ATOM | 2073 | CB | MET | 82 | 92.989 | 15.424 | 17.383 | 1.00 | 24.95 | H | C |
| ATOM | 2074 | CG | MET | 82 | 94.481 | 15.209 | 17.363 | 1.00 | 24.95 | H | C |
| ATOM | 2075 | SD | MET | 82 | 94.896 | 13.491 | 17.609 | 1.00 | 24.95 | H | S |
| ATOM | 2076 | CE | MET | 82 | 94.985 | 13.427 | 19.373 | 1.00 | 24.95 | H | C |
| ATOM | 2077 | C | MET | 82 | 91.051 | 16.957 | 17.316 | 1.00 | 35.69 | H | C |
| ATOM | 2078 | O | MET | 82 | 90.479 | 16.599 | 18.338 | 1.00 | 35.69 | H | O |
| ATOM | 2079 | N | ASN | 83 | 90.414 | 17.416 | 16.247 | 1.00 | 28.29 | H | N |
| ATOM | 2080 | CA | ASN | 83 | 88.968 | 17.536 | 16.204 | 1.00 | 28.29 | H | C |
| ATOM | 2081 | CB | ASN | 83 | 88.550 | 18.989 | 15.985 | 1.00 | 66.28 | H | C |
| ATOM | 2082 | CG | ASN | 83 | 89.274 | 19.943 | 16.899 | 1.00 | 66.28 | H | C |
| ATOM | 2083 | OD1 | ASN | 83 | 89.213 | 19.819 | 18.121 | 1.00 | 66.28 | H | O |
| ATOM | 2084 | ND2 | ASN | 83 | 89.970 | 20.910 | 16.309 | 1.00 | 66.28 | H | N |
| ATOM | 2085 | C | ASN | 83 | 88.502 | 16.728 | 15.025 | 1.00 | 28.29 | H | C |
| ATOM | 2086 | O | ASN | 83 | 89.306 | 16.348 | 14.185 | 1.00 | 28.29 | H | O |
| ATOM | 2087 | N | SER | 84 | 87.199 | 16.486 | 14.954 | 1.00 | 57.41 | H | N |
| ATOM | 2088 | CA | SER | 84 | 86.618 | 15.739 | 13.847 | 1.00 | 57.41 | H | C |
| ATOM | 2089 | CB | SER | 84 | 86.648 | 16.584 | 12.574 | 1.00 | 29.12 | H | C |
| ATOM | 2090 | OG | SER | 84 | 86.027 | 17.836 | 12.786 | 1.00 | 29.12 | H | O |
| ATOM | 2091 | C | SER | 84 | 87.374 | 14.450 | 13.603 | 1.00 | 57.41 | H | C |
| ATOM | 2092 | O | SER | 84 | 87.642 | 14.085 | 12.456 | 1.00 | 57.41 | H | O |
| ATOM | 2093 | N | LEU | 85 | 87.725 | 13.769 | 14.687 | 1.00 | 32.34 | H | N |
| ATOM | 2094 | CA | LEU | 85 | 88.452 | 12.513 | 14.595 | 1.00 | 32.34 | H | C |
| ATOM | 2095 | CB | LEU | 85 | 88.818 | 12.009 | 15.990 | 1.00 | 15.22 | H | C |
| ATOM | 2096 | CG | LEU | 85 | 89.913 | 12.880 | 16.600 | 1.00 | 15.22 | H | C |
| ATOM | 2097 | CD1 | LEU | 85 | 90.082 | 12.594 | 18.078 | 1.00 | 15.22 | H | C |
| ATOM | 2098 | CD2 | LEU | 85 | 91.204 | 12.636 | 15.828 | 1.00 | 15.22 | H | C |
| ATOM | 2099 | C | LEU | 85 | 87.641 | 11.460 | 13.877 | 1.00 | 32.34 | H | C |
| ATOM | 2100 | O | LEU | 85 | 86.434 | 11.369 | 14.050 | 1.00 | 32.34 | H | O |
| ATOM | 2101 | N | ARG | 86 | 88.319 | 10.680 | 13.049 | 1.00 | 24.27 | H | N |
| ATOM | 2102 | CA | ARG | 86 | 87.686 | 9.604 | 12.316 | 1.00 | 24.27 | H | C |
| ATOM | 2103 | CB | ARG | 86 | 87.858 | 9.801 | 10.815 | 1.00 | 51.87 | H | C |
| ATOM | 2104 | CG | ARG | 86 | 87.146 | 11.026 | 10.286 | 1.00 | 51.87 | H | C |
| ATOM | 2105 | CD | ARG | 86 | 86.864 | 10.887 | 8.808 | 1.00 | 51.87 | H | C |
| ATOM | 2106 | NE | ARG | 86 | 87.237 | 12.088 | 8.076 | 1.00 | 51.87 | H | N |
| ATOM | 2107 | CZ | ARG | 86 | 88.470 | 12.581 | 8.043 | 1.00 | 51.87 | H | C |
| ATOM | 2108 | NH1 | ARG | 86 | 89.444 | 11.967 | 8.707 | 1.00 | 51.87 | H | N |
| ATOM | 2109 | NH2 | ARG | 86 | 88.733 | 13.676 | 7.334 | 1.00 | 51.87 | H | N |
| ATOM | 2110 | C | ARG | 86 | 88.387 | 8.343 | 12.769 | 1.00 | 24.27 | H | C |
| ATOM | 2111 | O | ARG | 86 | 89.367 | 8.416 | 13.514 | 1.00 | 24.27 | H | O |
| ATOM | 2112 | N | ALA | 87 | 87.894 | 7.191 | 12.335 | 1.00 | 40.98 | H | N |
| ATOM | 2113 | CA | ALA | 87 | 88.499 | 5.928 | 12.733 | 1.00 | 40.98 | H | C |
| ATOM | 2114 | CB | ALA | 87 | 87.678 | 4.763 | 12.196 | 1.00 | 28.01 | H | C |
| ATOM | 2115 | C | ALA | 87 | 89.937 | 5.833 | 12.242 | 1.00 | 40.98 | H | C |
| ATOM | 2116 | O | ALA | 87 | 90.824 | 5.425 | 12.989 | 1.00 | 40.98 | H | O |
| ATOM | 2117 | N | GLU | 88 | 90.169 | 6.222 | 10.993 | 1.00 | 32.24 | H | N |

Fig. 19: A-30

```
ATOM   2118  CA  GLU  88    91.511   6.157  10.433  1.00  32.24  H  C
ATOM   2119  CB  GLU  88    91.583   6.890   9.094  1.00  72.38  H  C
ATOM   2120  CG  GLU  88    90.432   6.614   8.169  1.00  72.38  H  C
ATOM   2121  CD  GLU  88    89.327   7.623   8.336  1.00  72.38  H  C
ATOM   2122  OE1 GLU  88    89.529   8.792   7.937  1.00  72.38  H  O
ATOM   2123  OE2 GLU  88    88.265   7.246   8.874  1.00  72.38  H  O
ATOM   2124  C   GLU  88    92.529   6.780  11.372  1.00  32.24  H  C
ATOM   2125  O   GLU  88    93.691   6.370  11.417  1.00  32.24  H  O
ATOM   2126  N   ASP  89    92.080   7.772  12.128  1.00  18.63  H  N
ATOM   2127  CA  ASP  89    92.935   8.497  13.054  1.00  18.63  H  C
ATOM   2128  CB  ASP  89    92.212   9.764  13.507  1.00  29.25  H  C
ATOM   2129  CG  ASP  89    92.073  10.775  12.392  1.00  29.25  H  C
ATOM   2130  OD1 ASP  89    91.297  11.732  12.553  1.00  29.25  H  O
ATOM   2131  OD2 ASP  89    92.748  10.622  11.355  1.00  29.25  H  O
ATOM   2132  C   ASP  89    93.434   7.724  14.268  1.00  18.63  H  C
ATOM   2133  O   ASP  89    94.391   8.149  14.922  1.00  18.63  H  O
ATOM   2134  N   THR  90    92.817   6.588  14.575  1.00  29.66  H  N
ATOM   2135  CA  THR  90    93.261   5.845  15.749  1.00  29.66  H  C
ATOM   2136  CB  THR  90    92.303   4.668  16.113  1.00  30.61  H  C
ATOM   2137  OG1 THR  90    92.601   3.537  15.293  1.00  30.61  H  O
ATOM   2138  CG2 THR  90    90.828   5.072  15.903  1.00  30.61  H  C
ATOM   2139  C   THR  90    94.664   5.311  15.527  1.00  29.66  H  C
ATOM   2140  O   THR  90    94.961   4.727  14.492  1.00  29.66  H  O
ATOM   2141  N   ALA  91    95.532   5.553  16.499  1.00  11.25  H  N
ATOM   2142  CA  ALA  91    96.918   5.094  16.451  1.00  11.25  H  C
ATOM   2143  CB  ALA  91    97.629   5.690  15.259  1.00   1.87  H  C
ATOM   2144  C   ALA  91    97.611   5.536  17.729  1.00  11.25  H  C
ATOM   2145  O   ALA  91    96.972   6.044  18.646  1.00  11.25  H  O
ATOM   2146  N   VAL  92    98.915   5.312  17.797  1.00  22.44  H  N
ATOM   2147  CA  VAL  92    99.694   5.755  18.947  1.00  22.44  H  C
ATOM   2148  CB  VAL  92   100.654   4.665  19.465  1.00  21.44  H  C
ATOM   2149  CG1 VAL  92   101.306   3.966  18.298  1.00  21.44  H  C
ATOM   2150  CG2 VAL  92   101.716   5.284  20.346  1.00  21.44  H  C
ATOM   2151  C   VAL  92   100.482   6.913  18.363  1.00  22.44  H  C
ATOM   2152  O   VAL  92   101.107   6.771  17.310  1.00  22.44  H  O
ATOM   2153  N   TYR  93   100.413   8.066  19.019  1.00  21.58  H  N
ATOM   2154  CA  TYR  93   101.105   9.261  18.538  1.00  21.58  H  C
ATOM   2155  CB  TYR  93   100.161  10.470  18.585  1.00  12.38  H  C
ATOM   2156  CG  TYR  93    99.000  10.385  17.624  1.00  12.38  H  C
ATOM   2157  CD1 TYR  93    98.023   9.399  17.759  1.00  12.38  H  C
ATOM   2158  CE1 TYR  93    96.975   9.287  16.836  1.00  12.38  H  C
ATOM   2159  CD2 TYR  93    98.899  11.264  16.553  1.00  12.38  H  C
ATOM   2160  CE2 TYR  93    97.863  11.165  15.634  1.00  12.38  H  C
ATOM   2161  CZ  TYR  93    96.908  10.173  15.773  1.00  12.38  H  C
ATOM   2162  OH  TYR  93    95.915  10.043  14.827  1.00  12.38  H  O
ATOM   2163  C   TYR  93   102.384   9.577  19.312  1.00  21.58  H  C
ATOM   2164  O   TYR  93   102.466   9.401  20.531  1.00  21.58  H  O
ATOM   2165  N   TYR  94   103.381  10.049  18.579  1.00  19.04  H  N
ATOM   2166  CA  TYR  94   104.668  10.409  19.151  1.00  19.04  H  C
ATOM   2167  CB  TYR  94   105.789   9.576  18.533  1.00  29.80  H  C
ATOM   2168  CG  TYR  94   105.548   8.101  18.431  1.00  29.80  H  C
ATOM   2169  CD1 TYR  94   105.948   7.237  19.454  1.00  29.80  H  C
ATOM   2170  CE1 TYR  94   105.768   5.876  19.345  1.00  29.80  H  C
ATOM   2171  CD2 TYR  94   104.958   7.563  17.298  1.00  29.80  H  C
ATOM   2172  CE2 TYR  94   104.773   6.204  17.177  1.00  29.80  H  C
ATOM   2173  CZ  TYR  94   105.179   5.363  18.202  1.00  29.80  H  C
ATOM   2174  OH  TYR  94   104.996   4.007  18.071  1.00  29.80  H  O
ATOM   2175  C   TYR  94   104.991  11.853  18.805  1.00  19.04  H  C
ATOM   2176  O   TYR  94   104.867  12.244  17.642  1.00  19.04  H  O
ATOM   2177  N   CYS  95   105.383  12.654  19.791  1.00  25.07  H  N
ATOM   2178  CA  CYS  95   105.806  14.000  19.466  1.00  25.07  H  C
ATOM   2179  C   CYS  95   107.228  13.689  19.096  1.00  25.07  H  C
ATOM   2180  O   CYS  95   107.716  12.584  19.342  1.00  25.07  H  O
ATOM   2181  CB  CYS  95   105.784  14.942  20.647  1.00  46.53  H  C
ATOM   2182  SG  CYS  95   106.112  14.206  22.267  1.00  46.53  H  S
ATOM   2183  N   THR  96   107.931  14.657  18.549  1.00  31.61  H  N
ATOM   2184  CA  THR  96   109.253  14.331  18.115  1.00  31.61  H  C
ATOM   2185  CB  THR  96   109.088  13.445  16.861  1.00  32.15  H  C
ATOM   2186  OG1 THR  96   110.331  12.862  16.494  1.00  32.15  H  O
ATOM   2187  CG2 THR  96   108.554  14.260  15.708  1.00  32.15  H  C
ATOM   2188  C   THR  96   110.045  15.591  17.830  1.00  31.61  H  C
ATOM   2189  O   THR  96   109.530  16.548  17.260  1.00  31.61  H  O
ATOM   2190  N   ARG  97   111.292  15.610  18.270  1.00  26.02  H  N
```

Fig. 19: A-31

| ATOM | 2191 | CA | ARG | 97 | 112.135 | 16.759 | 17.996 | 1.00 | 26.02 | H | C |
|------|------|-----|-----|-----|---------|--------|--------|------|-------|---|---|
| ATOM | 2192 | CB | ARG | 97 | 113.220 | 16.959 | 19.053 | 1.00 | 22.53 | H | C |
| ATOM | 2193 | CG | ARG | 97 | 114.076 | 18.184 | 18.766 | 1.00 | 22.53 | H | C |
| ATOM | 2194 | CD | ARG | 97 | 115.204 | 18.345 | 19.764 | 1.00 | 22.53 | H | C |
| ATOM | 2195 | NE | ARG | 97 | 116.357 | 17.532 | 19.411 | 1.00 | 22.53 | H | N |
| ATOM | 2196 | CZ | ARG | 97 | 117.494 | 17.509 | 20.099 | 1.00 | 22.53 | H | C |
| ATOM | 2197 | NH1 | ARG | 97 | 117.635 | 18.257 | 21.183 | 1.00 | 22.53 | H | N |
| ATOM | 2198 | NH2 | ARG | 97 | 118.494 | 16.739 | 19.704 | 1.00 | 22.53 | H | N |
| ATOM | 2199 | C | ARG | 97 | 112.799 | 16.473 | 16.665 | 1.00 | 26.02 | H | C |
| ATOM | 2200 | O | ARG | 97 | 113.145 | 15.322 | 16.357 | 1.00 | 26.02 | H | O |
| ATOM | 2201 | N | GLY | 98 | 112.980 | 17.528 | 15.882 | 1.00 | 13.43 | H | N |
| ATOM | 2202 | CA | GLY | 98 | 113.586 | 17.367 | 14.582 | 1.00 | 13.43 | H | C |
| ATOM | 2203 | C | GLY | 98 | 114.947 | 17.995 | 14.496 | 1.00 | 13.43 | H | C |
| ATOM | 2204 | O | GLY | 98 | 115.308 | 18.850 | 15.281 | 1.00 | 13.43 | H | O |
| ATOM | 2205 | N | PHE | 99 | 115.719 | 17.537 | 13.534 | 1.00 | 20.13 | H | N |
| ATOM | 2206 | CA | PHE | 99 | 117.038 | 18.065 | 13.315 | 1.00 | 20.13 | H | C |
| ATOM | 2207 | CB | PHE | 99 | 118.018 | 16.902 | 13.211 | 1.00 | 25.23 | H | C |
| ATOM | 2208 | CG | PHE | 99 | 119.338 | 17.271 | 12.628 | 1.00 | 25.23 | H | C |
| ATOM | 2209 | CD1 | PHE | 99 | 119.587 | 17.079 | 11.279 | 1.00 | 25.23 | H | C |
| ATOM | 2210 | CD2 | PHE | 99 | 120.326 | 17.828 | 13.420 | 1.00 | 25.23 | H | C |
| ATOM | 2211 | CE1 | PHE | 99 | 120.804 | 17.437 | 10.721 | 1.00 | 25.23 | H | C |
| ATOM | 2212 | CE2 | PHE | 99 | 121.543 | 18.191 | 12.875 | 1.00 | 25.23 | H | C |
| ATOM | 2213 | CZ | PHE | 99 | 121.784 | 17.994 | 11.517 | 1.00 | 25.23 | H | C |
| ATOM | 2214 | C | PHE | 99 | 116.887 | 18.819 | 11.996 | 1.00 | 20.13 | H | C |
| ATOM | 2215 | O | PHE | 99 | 115.950 | 18.551 | 11.241 | 1.00 | 20.13 | H | O |
| ATOM | 2216 | N | GLY | 100 | 117.768 | 19.774 | 11.719 | 1.00 | 15.08 | H | N |
| ATOM | 2217 | CA | GLY | 100 | 117.655 | 20.513 | 10.469 | 1.00 | 15.08 | H | C |
| ATOM | 2218 | C | GLY | 100 | 116.285 | 21.139 | 10.274 | 1.00 | 15.08 | H | C |
| ATOM | 2219 | O | GLY | 100 | 115.682 | 21.636 | 11.216 | 1.00 | 15.08 | H | O |
| ATOM | 2220 | N | ASP | 101 | 115.779 | 21.128 | 9.050 | 1.00 | 7.89 | H | N |
| ATOM | 2221 | CA | ASP | 101 | 114.462 | 21.692 | 8.812 | 1.00 | 7.89 | H | C |
| ATOM | 2222 | CB | ASP | 101 | 114.195 | 21.848 | 7.302 | 1.00 | 13.13 | H | C |
| ATOM | 2223 | CG | ASP | 101 | 115.328 | 22.587 | 6.564 | 1.00 | 13.13 | H | C |
| ATOM | 2224 | OD1 | ASP | 101 | 115.921 | 23.558 | 7.105 | 1.00 | 13.13 | H | O |
| ATOM | 2225 | OD2 | ASP | 101 | 115.616 | 22.190 | 5.417 | 1.00 | 13.13 | H | O |
| ATOM | 2226 | C | ASP | 101 | 113.406 | 20.785 | 9.460 | 1.00 | 7.89 | H | C |
| ATOM | 2227 | O | ASP | 101 | 112.222 | 20.844 | 9.124 | 1.00 | 7.89 | H | O |
| ATOM | 2228 | N | GLY | 102 | 113.854 | 19.924 | 10.374 | 1.00 | 22.31 | H | N |
| ATOM | 2229 | CA | GLY | 102 | 112.952 | 19.043 | 11.100 | 1.00 | 22.31 | H | C |
| ATOM | 2230 | C | GLY | 102 | 112.588 | 17.674 | 10.562 | 1.00 | 22.31 | H | C |
| ATOM | 2231 | O | GLY | 102 | 111.927 | 16.915 | 11.263 | 1.00 | 22.31 | H | O |
| ATOM | 2232 | N | GLY | 103 | 113.001 | 17.347 | 9.343 | 1.00 | 25.09 | H | N |
| ATOM | 2233 | CA | GLY | 103 | 112.662 | 16.054 | 8.772 | 1.00 | 25.09 | H | C |
| ATOM | 2234 | C | GLY | 103 | 113.342 | 14.844 | 9.403 | 1.00 | 25.09 | H | C |
| ATOM | 2235 | O | GLY | 103 | 112.948 | 13.703 | 9.156 | 1.00 | 25.09 | H | O |
| ATOM | 2236 | N | TYR | 104 | 114.376 | 15.071 | 10.202 | 1.00 | 22.52 | H | N |
| ATOM | 2237 | CA | TYR | 104 | 115.070 | 13.961 | 10.844 | 1.00 | 22.52 | H | C |
| ATOM | 2238 | CB | TYR | 104 | 116.578 | 14.114 | 10.715 | 1.00 | 15.87 | H | C |
| ATOM | 2239 | CG | TYR | 104 | 117.342 | 13.175 | 11.599 | 1.00 | 15.87 | H | C |
| ATOM | 2240 | CD1 | TYR | 104 | 118.507 | 13.600 | 12.233 | 1.00 | 15.87 | H | C |
| ATOM | 2241 | CE1 | TYR | 104 | 119.198 | 12.776 | 13.100 | 1.00 | 15.87 | H | C |
| ATOM | 2242 | CD2 | TYR | 104 | 116.884 | 11.880 | 11.844 | 1.00 | 15.87 | H | C |
| ATOM | 2243 | CE2 | TYR | 104 | 117.575 | 11.034 | 12.713 | 1.00 | 15.87 | H | C |
| ATOM | 2244 | CZ | TYR | 104 | 118.734 | 11.498 | 13.343 | 1.00 | 15.87 | H | C |
| ATOM | 2245 | OH | TYR | 104 | 119.417 | 10.713 | 14.239 | 1.00 | 15.87 | H | O |
| ATOM | 2246 | C | TYR | 104 | 114.665 | 13.991 | 12.296 | 1.00 | 22.52 | H | C |
| ATOM | 2247 | O | TYR | 104 | 114.933 | 14.956 | 13.001 | 1.00 | 22.52 | H | O |
| ATOM | 2248 | N | PHE | 105 | 114.036 | 12.909 | 12.733 | 1.00 | 16.00 | H | N |
| ATOM | 2249 | CA | PHE | 105 | 113.501 | 12.806 | 14.073 | 1.00 | 16.00 | H | C |
| ATOM | 2250 | CB | PHE | 105 | 112.292 | 11.890 | 14.031 | 1.00 | 16.01 | H | C |
| ATOM | 2251 | CG | PHE | 105 | 111.269 | 12.327 | 13.020 | 1.00 | 16.01 | H | C |
| ATOM | 2252 | CD1 | PHE | 105 | 110.782 | 13.627 | 13.038 | 1.00 | 16.01 | H | C |
| ATOM | 2253 | CD2 | PHE | 105 | 110.827 | 11.459 | 12.023 | 1.00 | 16.01 | H | C |
| ATOM | 2254 | CE1 | PHE | 105 | 109.880 | 14.059 | 12.091 | 1.00 | 16.01 | H | C |
| ATOM | 2255 | CE2 | PHE | 105 | 109.918 | 11.885 | 11.067 | 1.00 | 16.01 | H | C |
| ATOM | 2256 | CZ | PHE | 105 | 109.443 | 13.190 | 11.101 | 1.00 | 16.01 | H | C |
| ATOM | 2257 | C | PHE | 105 | 114.442 | 12.433 | 15.179 | 1.00 | 16.00 | H | C |
| ATOM | 2258 | O | PHE | 105 | 114.543 | 11.283 | 15.595 | 1.00 | 16.00 | H | O |
| ATOM | 2259 | N | ASP | 106 | 115.105 | 13.481 | 15.642 | 1.00 | 29.40 | H | N |
| ATOM | 2260 | CA | ASP | 106 | 116.089 | 13.519 | 16.714 | 1.00 | 29.40 | H | C |
| ATOM | 2261 | CB | ASP | 106 | 116.251 | 14.976 | 17.117 | 1.00 | 39.43 | H | C |
| ATOM | 2262 | CG | ASP | 106 | 117.656 | 15.400 | 17.133 | 1.00 | 39.43 | H | C |
| ATOM | 2263 | OD1 | ASP | 106 | 118.492 | 14.528 | 17.433 | 1.00 | 39.43 | H | O |

Fig. 19: A-32

| | | | | | | | | | | |
|---|---|---|---|---|---|---|---|---|---|---|
| ATOM | 2264 | OD2 | ASP | 106 | 117.922 | 16.591 | 16.859 | 1.00 | 39.43 | H | O |
| ATOM | 2265 | C | ASP | 106 | 115.797 | 12.728 | 17.993 | 1.00 | 29.40 | H | C |
| ATOM | 2266 | O | ASP | 106 | 116.567 | 11.861 | 18.396 | 1.00 | 29.40 | H | O |
| ATOM | 2267 | N | VAL | 107 | 114.687 | 13.094 | 18.635 | 1.00 | 7.69 | H | N |
| ATOM | 2268 | CA | VAL | 107 | 114.248 | 12.533 | 19.906 | 1.00 | 7.69 | H | C |
| ATOM | 2269 | CB | VAL | 107 | 114.402 | 13.600 | 21.026 | 1.00 | 10.61 | H | C |
| ATOM | 2270 | CG1 | VAL | 107 | 113.985 | 13.045 | 22.374 | 1.00 | 10.61 | H | C |
| ATOM | 2271 | CG2 | VAL | 107 | 115.838 | 14.116 | 21.048 | 1.00 | 10.61 | H | C |
| ATOM | 2272 | C | VAL | 107 | 112.778 | 12.199 | 19.765 | 1.00 | 7.69 | H | C |
| ATOM | 2273 | O | VAL | 107 | 112.107 | 12.835 | 18.970 | 1.00 | 7.69 | H | O |
| ATOM | 2274 | N | TRP | 108 | 112.285 | 11.224 | 20.540 | 1.00 | 26.84 | H | N |
| ATOM | 2275 | CA | TRP | 108 | 110.871 | 10.795 | 20.510 | 1.00 | 26.84 | H | C |
| ATOM | 2276 | CB | TRP | 108 | 110.729 | 9.405 | 19.868 | 1.00 | 1.87 | H | C |
| ATOM | 2277 | CG | TRP | 108 | 111.201 | 9.329 | 18.468 | 1.00 | 1.87 | H | C |
| ATOM | 2278 | CD2 | TRP | 108 | 110.431 | 8.950 | 17.328 | 1.00 | 1.87 | H | C |
| ATOM | 2279 | CE2 | TRP | 108 | 111.287 | 9.020 | 16.201 | 1.00 | 1.87 | H | C |
| ATOM | 2280 | CE3 | TRP | 108 | 109.102 | 8.557 | 17.142 | 1.00 | 1.87 | H | C |
| ATOM | 2281 | CD1 | TRP | 108 | 112.460 | 9.606 | 18.008 | 1.00 | 1.87 | H | C |
| ATOM | 2282 | NE1 | TRP | 108 | 112.520 | 9.422 | 16.648 | 1.00 | 1.87 | H | N |
| ATOM | 2283 | CZ2 | TRP | 108 | 110.854 | 8.710 | 14.904 | 1.00 | 1.87 | H | C |
| ATOM | 2284 | CZ3 | TRP | 108 | 108.667 | 8.244 | 15.836 | 1.00 | 1.87 | H | C |
| ATOM | 2285 | CH2 | TRP | 108 | 109.547 | 8.325 | 14.742 | 1.00 | 1.87 | H | C |
| ATOM | 2286 | C | TRP | 108 | 110.204 | 10.724 | 21.881 | 1.00 | 26.84 | H | C |
| ATOM | 2287 | O | TRP | 108 | 110.859 | 10.503 | 22.899 | 1.00 | 26.84 | H | O |
| ATOM | 2288 | N | GLY | 109 | 108.889 | 10.907 | 21.889 | 1.00 | 15.55 | H | N |
| ATOM | 2289 | CA | GLY | 109 | 108.134 | 10.811 | 23.125 | 1.00 | 15.55 | H | C |
| ATOM | 2290 | C | GLY | 109 | 107.896 | 9.331 | 23.386 | 1.00 | 15.55 | H | C |
| ATOM | 2291 | O | GLY | 109 | 108.170 | 8.502 | 22.511 | 1.00 | 15.55 | H | O |
| ATOM | 2292 | N | GLN | 110 | 107.393 | 8.971 | 24.563 | 1.00 | 21.92 | H | N |
| ATOM | 2293 | CA | GLN | 110 | 107.161 | 7.554 | 24.852 | 1.00 | 21.92 | H | C |
| ATOM | 2294 | CB | GLN | 110 | 106.800 | 7.338 | 26.325 | 1.00 | 44.26 | H | C |
| ATOM | 2295 | CG | GLN | 110 | 105.404 | 7.798 | 26.703 | 1.00 | 44.26 | H | C |
| ATOM | 2296 | CD | GLN | 110 | 105.321 | 9.283 | 26.957 | 1.00 | 44.26 | H | C |
| ATOM | 2297 | OE1 | GLN | 110 | 105.573 | 10.102 | 26.071 | 1.00 | 44.26 | H | O |
| ATOM | 2298 | NE2 | GLN | 110 | 104.967 | 9.642 | 28.181 | 1.00 | 44.26 | H | N |
| ATOM | 2299 | C | GLN | 110 | 106.051 | 6.979 | 23.973 | 1.00 | 21.92 | H | C |
| ATOM | 2300 | O | GLN | 110 | 106.054 | 5.798 | 23.651 | 1.00 | 21.92 | H | O |
| ATOM | 2301 | N | GLY | 111 | 105.114 | 7.824 | 23.574 | 1.00 | 22.63 | H | N |
| ATOM | 2302 | CA | GLY | 111 | 104.014 | 7.361 | 22.761 | 1.00 | 22.63 | H | C |
| ATOM | 2303 | C | GLY | 111 | 102.758 | 7.463 | 23.597 | 1.00 | 22.63 | H | C |
| ATOM | 2304 | O | GLY | 111 | 102.834 | 7.414 | 24.827 | 1.00 | 22.63 | H | O |
| ATOM | 2305 | N | THR | 112 | 101.611 | 7.619 | 22.938 | 1.00 | 17.52 | H | N |
| ATOM | 2306 | CA | THR | 112 | 100.333 | 7.740 | 23.630 | 1.00 | 17.52 | H | C |
| ATOM | 2307 | CB | THR | 112 | 100.058 | 9.211 | 24.030 | 1.00 | 34.98 | H | C |
| ATOM | 2308 | OG1 | THR | 112 | 98.958 | 9.261 | 24.939 | 1.00 | 34.98 | H | O |
| ATOM | 2309 | CG2 | THR | 112 | 99.734 | 10.055 | 22.809 | 1.00 | 34.98 | H | C |
| ATOM | 2310 | C | THR | 112 | 99.228 | 7.203 | 22.717 | 1.00 | 17.52 | H | C |
| ATOM | 2311 | O | THR | 112 | 99.133 | 7.559 | 21.533 | 1.00 | 17.52 | H | O |
| ATOM | 2312 | N | LEU | 113 | 98.396 | 6.340 | 23.292 | 1.00 | 32.82 | H | N |
| ATOM | 2313 | CA | LEU | 113 | 97.318 | 5.668 | 22.576 | 1.00 | 32.82 | H | C |
| ATOM | 2314 | CB | LEU | 113 | 96.953 | 4.374 | 23.328 | 1.00 | 26.98 | H | C |
| ATOM | 2315 | CG | LEU | 113 | 95.842 | 3.431 | 22.856 | 1.00 | 26.98 | H | C |
| ATOM | 2316 | CD1 | LEU | 113 | 94.455 | 4.057 | 23.105 | 1.00 | 26.98 | H | C |
| ATOM | 2317 | CD2 | LEU | 113 | 96.055 | 3.115 | 21.392 | 1.00 | 26.98 | H | C |
| ATOM | 2318 | C | LEU | 113 | 96.073 | 6.498 | 22.354 | 1.00 | 32.82 | H | C |
| ATOM | 2319 | O | LEU | 113 | 95.448 | 6.964 | 23.299 | 1.00 | 32.82 | H | O |
| ATOM | 2320 | N | VAL | 114 | 95.708 | 6.671 | 21.094 | 1.00 | 38.48 | H | N |
| ATOM | 2321 | CA | VAL | 114 | 94.506 | 7.419 | 20.767 | 1.00 | 38.48 | H | C |
| ATOM | 2322 | CB | VAL | 114 | 94.809 | 8.658 | 19.870 | 1.00 | 53.69 | H | C |
| ATOM | 2323 | CG1 | VAL | 114 | 93.518 | 9.420 | 19.571 | 1.00 | 53.69 | H | C |
| ATOM | 2324 | CG2 | VAL | 114 | 95.798 | 9.575 | 20.562 | 1.00 | 53.69 | H | C |
| ATOM | 2325 | C | VAL | 114 | 93.557 | 6.484 | 20.022 | 1.00 | 38.48 | H | C |
| ATOM | 2326 | O | VAL | 114 | 93.859 | 6.003 | 18.928 | 1.00 | 38.48 | H | O |
| ATOM | 2327 | N | THR | 115 | 92.411 | 6.216 | 20.629 | 1.00 | 29.76 | H | N |
| ATOM | 2328 | CA | THR | 115 | 91.414 | 5.356 | 20.012 | 1.00 | 29.76 | H | C |
| ATOM | 2329 | CB | THR | 115 | 91.081 | 4.125 | 20.916 | 1.00 | 30.84 | H | C |
| ATOM | 2330 | OG1 | THR | 115 | 92.292 | 3.453 | 21.300 | 1.00 | 30.84 | H | O |
| ATOM | 2331 | CG2 | THR | 115 | 90.180 | 3.151 | 20.170 | 1.00 | 30.84 | H | C |
| ATOM | 2332 | C | THR | 115 | 90.133 | 6.164 | 19.803 | 1.00 | 29.76 | H | C |
| ATOM | 2333 | O | THR | 115 | 89.700 | 6.905 | 20.694 | 1.00 | 29.76 | H | O |
| ATOM | 2334 | N | VAL | 116 | 89.543 | 6.056 | 18.619 | 1.00 | 38.29 | H | N |
| ATOM | 2335 | CA | VAL | 116 | 88.289 | 6.747 | 18.371 | 1.00 | 38.29 | H | C |
| ATOM | 2336 | CB | VAL | 116 | 88.395 | 7.822 | 17.240 | 1.00 | 10.28 | H | C |

Fig. 19: A-33

| | | | | | | | | | | | |
|---|---|---|---|---|---|---|---|---|---|---|---|
| ATOM | 2337 | CG1 | VAL | 116 | 89.861 | 8.088 | 16.922 | 1.00 | 10.28 | H | C |
| ATOM | 2338 | CG2 | VAL | 116 | 87.575 | 7.415 | 15.994 | 1.00 | 10.28 | H | C |
| ATOM | 2339 | C | VAL | 116 | 87.303 | 5.656 | 17.996 | 1.00 | 38.29 | H | C |
| ATOM | 2340 | O | VAL | 116 | 87.545 | 4.888 | 17.063 | 1.00 | 38.29 | H | O |
| ATOM | 2341 | N | SER | 117 | 86.207 | 5.579 | 18.746 | 1.00 | 41.53 | H | N |
| ATOM | 2342 | CA | SER | 117 | 85.193 | 4.565 | 18.517 | 1.00 | 41.53 | H | C |
| ATOM | 2343 | CB | SER | 117 | 85.768 | 3.182 | 18.851 | 1.00 | 61.62 | H | C |
| ATOM | 2344 | OG | SER | 117 | 84.788 | 2.165 | 18.751 | 1.00 | 61.62 | H | O |
| ATOM | 2345 | C | SER | 117 | 83.959 | 4.815 | 19.366 | 1.00 | 41.53 | H | C |
| ATOM | 2346 | O | SER | 117 | 84.049 | 5.336 | 20.482 | 1.00 | 41.53 | H | O |
| ATOM | 2347 | N | SER | 118 | 82.808 | 4.431 | 18.828 | 1.00 | 36.79 | H | N |
| ATOM | 2348 | CA | SER | 118 | 81.538 | 4.581 | 19.525 | 1.00 | 36.79 | H | C |
| ATOM | 2349 | CB | SER | 118 | 80.401 | 4.226 | 18.579 | 1.00 | 49.30 | H | C |
| ATOM | 2350 | OG | SER | 118 | 80.598 | 2.919 | 18.069 | 1.00 | 49.30 | H | O |
| ATOM | 2351 | C | SER | 118 | 81.510 | 3.649 | 20.740 | 1.00 | 36.79 | H | C |
| ATOM | 2352 | O | SER | 118 | 80.753 | 3.853 | 21.685 | 1.00 | 35.84 | H | O |
| ATOM | 2353 | N | ALA | 119 | 82.339 | 2.616 | 20.707 | 1.00 | 26.31 | H | N |
| ATOM | 2354 | CA | ALA | 119 | 82.412 | 1.679 | 21.815 | 1.00 | 26.31 | H | C |
| ATOM | 2355 | CB | ALA | 119 | 83.569 | 0.707 | 21.617 | 1.00 | 20.55 | H | C |
| ATOM | 2356 | C | ALA | 119 | 82.611 | 2.461 | 23.100 | 1.00 | 26.31 | H | C |
| ATOM | 2357 | O | ALA | 119 | 83.319 | 3.477 | 23.124 | 1.00 | 26.31 | H | O |
| ATOM | 2358 | N | SER | 120 | 81.988 | 1.975 | 24.166 | 1.00 | 39.08 | H | N |
| ATOM | 2359 | CA | SER | 120 | 82.074 | 2.621 | 25.462 | 1.00 | 39.08 | H | C |
| ATOM | 2360 | CB | SER | 120 | 80.711 | 2.597 | 26.151 | 1.00 | 57.76 | H | C |
| ATOM | 2361 | OG | SER | 120 | 79.720 | 3.179 | 25.329 | 1.00 | 57.76 | H | O |
| ATOM | 2362 | C | SER | 120 | 83.086 | 1.938 | 26.353 | 1.00 | 39.08 | H | C |
| ATOM | 2363 | O | SER | 120 | 83.194 | 0.715 | 26.362 | 1.00 | 39.08 | H | O |
| ATOM | 2364 | N | THR | 121 | 83.837 | 2.734 | 27.100 | 1.00 | 26.62 | H | N |
| ATOM | 2365 | CA | THR | 121 | 84.813 | 2.188 | 28.023 | 1.00 | 25.63 | H | C |
| ATOM | 2366 | CB | THR | 121 | 85.274 | 3.267 | 29.002 | 1.00 | 27.79 | H | C |
| ATOM | 2367 | OG1 | THR | 121 | 85.860 | 4.353 | 28.268 | 1.00 | 32.58 | H | O |
| ATOM | 2368 | CG2 | THR | 121 | 86.273 | 2.691 | 30.007 | 1.00 | 25.52 | H | C |
| ATOM | 2369 | C | THR | 121 | 84.108 | 1.078 | 28.801 | 1.00 | 26.35 | H | C |
| ATOM | 2370 | O | THR | 121 | 82.919 | 1.189 | 29.098 | 1.00 | 29.95 | H | O |
| ATOM | 2371 | N | LYS | 122 | 84.828 | 0.007 | 29.116 | 1.00 | 53.26 | H | N |
| ATOM | 2372 | CA | LYS | 122 | 84.243 | -1.102 | 29.864 | 1.00 | 50.64 | H | C |
| ATOM | 2373 | CB | LYS | 122 | 83.333 | -1.930 | 28.947 | 1.00 | 42.70 | H | C |
| ATOM | 2374 | CG | LYS | 122 | 83.009 | -3.347 | 29.437 | 1.00 | 44.07 | H | C |
| ATOM | 2375 | CD | LYS | 122 | 82.469 | -3.373 | 30.864 | 1.00 | 47.16 | H | C |
| ATOM | 2376 | CE | LYS | 122 | 82.216 | -4.805 | 31.337 | 1.00 | 51.36 | H | C |
| ATOM | 2377 | NZ | LYS | 122 | 81.986 | -4.880 | 32.809 | 1.00 | 50.23 | H | N |
| ATOM | 2378 | C | LYS | 122 | 85.301 | -1.991 | 30.496 | 1.00 | 52.40 | H | C |
| ATOM | 2379 | O | LYS | 122 | 86.154 | -2.548 | 29.809 | 1.00 | 54.02 | H | O |
| ATOM | 2380 | N | GLY | 123 | 85.240 | -2.114 | 31.817 | 1.00 | 42.56 | H | N |
| ATOM | 2381 | CA | GLY | 123 | 86.188 | -2.952 | 32.530 | 1.00 | 42.89 | H | C |
| ATOM | 2382 | C | GLY | 123 | 86.213 | -4.396 | 32.035 | 1.00 | 44.35 | H | C |
| ATOM | 2383 | O | GLY | 123 | 85.222 | -4.907 | 31.503 | 1.00 | 40.33 | H | O |
| ATOM | 2384 | N | PRO | 124 | 87.346 | -5.090 | 32.198 | 1.00 | 44.81 | H | N |
| ATOM | 2385 | CD | PRO | 124 | 88.680 | -4.632 | 32.633 | 1.00 | 21.78 | H | C |
| ATOM | 2386 | CA | PRO | 124 | 87.397 | -6.472 | 31.731 | 1.00 | 46.19 | H | C |
| ATOM | 2387 | CB | PRO | 124 | 88.868 | -6.668 | 31.439 | 1.00 | 22.93 | H | C |
| ATOM | 2388 | CG | PRO | 124 | 89.504 | -5.905 | 32.561 | 1.00 | 22.69 | H | C |
| ATOM | 2389 | C | PRO | 124 | 86.899 | -7.461 | 32.764 | 1.00 | 45.69 | H | C |
| ATOM | 2390 | O | PRO | 124 | 86.854 | -7.170 | 33.961 | 1.00 | 46.94 | H | O |
| ATOM | 2391 | N | SER | 125 | 86.507 | -8.631 | 32.287 | 1.00 | 43.49 | H | N |
| ATOM | 2392 | CA | SER | 125 | 86.053 | -9.678 | 33.176 | 1.00 | 38.23 | H | C |
| ATOM | 2393 | CB | SER | 125 | 84.858 | -10.416 | 32.579 | 1.00 | 23.34 | H | C |
| ATOM | 2394 | OG | SER | 125 | 83.756 | -9.544 | 32.402 | 1.00 | 25.34 | H | O |
| ATOM | 2395 | C | SER | 125 | 87.262 | -10.576 | 33.200 | 1.00 | 33.52 | H | C |
| ATOM | 2396 | O | SER | 125 | 87.738 | -10.972 | 32.139 | 1.00 | 32.91 | H | O |
| ATOM | 2397 | N | VAL | 126 | 87.787 | -10.873 | 34.386 | 1.00 | 23.96 | H | N |
| ATOM | 2398 | CA | VAL | 126 | 88.962 | -11.727 | 34.452 | 1.00 | 20.86 | H | C |
| ATOM | 2399 | CB | VAL | 126 | 90.135 | -11.003 | 35.174 | 1.00 | 22.19 | H | C |
| ATOM | 2400 | CG1 | VAL | 126 | 89.894 | -9.504 | 35.113 | 1.00 | 17.46 | H | C |
| ATOM | 2401 | CG2 | VAL | 126 | 90.331 | -11.507 | 36.597 | 1.00 | 22.90 | H | C |
| ATOM | 2402 | C | VAL | 126 | 88.666 | -13.091 | 35.065 | 1.00 | 20.51 | H | C |
| ATOM | 2403 | O | VAL | 126 | 88.382 | -13.227 | 36.256 | 1.00 | 24.79 | H | O |
| ATOM | 2404 | N | PHE | 127 | 88.713 | -14.105 | 34.213 | 1.00 | 27.15 | H | N |
| ATOM | 2405 | CA | PHE | 127 | 88.443 | -15.464 | 34.625 | 1.00 | 29.56 | H | C |
| ATOM | 2406 | CB | PHE | 127 | 87.628 | -16.167 | 33.544 | 1.00 | 16.06 | H | C |
| ATOM | 2407 | CG | PHE | 127 | 86.392 | -15.419 | 33.141 | 1.00 | 12.41 | H | C |
| ATOM | 2408 | CD1 | PHE | 127 | 85.380 | -15.167 | 34.071 | 1.00 | 11.21 | H | C |
| ATOM | 2409 | CD2 | PHE | 127 | 86.255 | -14.922 | 31.840 | 1.00 | 10.06 | H | C |

Fig. 19: A-34

| | | | | | | | | | | |
|---|---|---|---|---|---|---|---|---|---|---|
| ATOM | 2410 | CE1 | PHE | 127 | 84.254 | -14.428 | 33.721 | 1.00 | 12.93 | H C |
| ATOM | 2411 | CE2 | PHE | 127 | 85.126 | -14.174 | 31.470 | 1.00 | 6.89 | H C |
| ATOM | 2412 | CZ | PHE | 127 | 84.125 | -13.925 | 32.413 | 1.00 | 6.94 | H C |
| ATOM | 2413 | C | PHE | 127 | 89.763 | -16.183 | 34.825 | 1.00 | 31.37 | H C |
| ATOM | 2414 | O | PHE | 127 | 90.806 | -15.733 | 34.351 | 1.00 | 34.05 | H O |
| ATOM | 2415 | N | PRO | 128 | 89.743 | -17.310 | 35.540 | 1.00 | 21.35 | H N |
| ATOM | 2416 | CD | PRO | 128 | 88.681 | -17.812 | 36.434 | 1.00 | 32.37 | H C |
| ATOM | 2417 | CA | PRO | 128 | 90.996 | -18.039 | 35.752 | 1.00 | 22.25 | H C |
| ATOM | 2418 | CB | PRO | 128 | 90.823 | -18.577 | 37.161 | 1.00 | 34.03 | H C |
| ATOM | 2419 | CG | PRO | 128 | 89.358 | -18.983 | 37.130 | 1.00 | 33.18 | H C |
| ATOM | 2420 | C | PRO | 128 | 91.198 | -19.176 | 34.739 | 1.00 | 21.65 | H C |
| ATOM | 2421 | O | PRO | 128 | 90.235 | -19.770 | 34.244 | 1.00 | 21.29 | H O |
| ATOM | 2422 | N | LEU | 129 | 92.457 | -19.457 | 34.432 | 1.00 | 17.17 | H N |
| ATOM | 2423 | CA | LEU | 129 | 92.811 | -20.557 | 33.545 | 1.00 | 19.61 | H C |
| ATOM | 2424 | CB | LEU | 129 | 93.683 | -20.061 | 32.396 | 1.00 | 18.81 | H C |
| ATOM | 2425 | CG | LEU | 129 | 93.086 | -18.872 | 31.635 | 1.00 | 18.17 | H C |
| ATOM | 2426 | CD1 | LEU | 129 | 94.115 | -18.254 | 30.696 | 1.00 | 16.12 | H C |
| ATOM | 2427 | CD2 | LEU | 129 | 91.886 | -19.341 | 30.870 | 1.00 | 11.94 | H C |
| ATOM | 2428 | C | LEU | 129 | 93.601 | -21.457 | 34.497 | 1.00 | 23.45 | H C |
| ATOM | 2429 | O | LEU | 129 | 94.824 | -21.481 | 34.499 | 1.00 | 25.82 | H O |
| ATOM | 2430 | N | ALA | 130 | 92.870 | -22.179 | 35.332 | 1.00 | 16.93 | H N |
| ATOM | 2431 | CA | ALA | 130 | 93.455 | -23.046 | 36.341 | 1.00 | 18.97 | H C |
| ATOM | 2432 | CB | ALA | 130 | 92.363 | -23.561 | 37.256 | 1.00 | 49.82 | H C |
| ATOM | 2433 | C | ALA | 130 | 94.280 | -24.219 | 35.846 | 1.00 | 18.88 | H C |
| ATOM | 2434 | O | ALA | 130 | 93.928 | -24.876 | 34.869 | 1.00 | 20.61 | H O |
| ATOM | 2435 | N | PRO | 131 | 95.401 | -24.490 | 36.534 | 1.00 | 29.98 | H N |
| ATOM | 2436 | CD | PRO | 131 | 95.929 | -23.703 | 37.665 | 1.00 | 16.68 | H C |
| ATOM | 2437 | CA | PRO | 131 | 96.301 | -25.595 | 36.198 | 1.00 | 27.20 | H C |
| ATOM | 2438 | CB | PRO | 131 | 97.453 | -25.424 | 37.196 | 1.00 | 12.88 | H C |
| ATOM | 2439 | CG | PRO | 131 | 96.815 | -24.691 | 38.354 | 1.00 | 15.86 | H C |
| ATOM | 2440 | C | PRO | 131 | 95.534 | -26.897 | 36.405 | 1.00 | 26.68 | H C |
| ATOM | 2441 | O | PRO | 131 | 94.666 | -26.978 | 37.274 | 1.00 | 27.16 | H O |
| ATOM | 2442 | N | SER | 132 | 95.838 | -27.912 | 35.607 | 1.00 | 64.88 | H N |
| ATOM | 2443 | CA | SER | 132 | 95.138 | -29.187 | 35.720 | 1.00 | 67.56 | H C |
| ATOM | 2444 | CB | SER | 132 | 93.745 | -29.075 | 35.086 | 1.00 | 44.77 | H C |
| ATOM | 2445 | OG | SER | 132 | 93.824 | -28.747 | 33.704 | 1.00 | 46.53 | H O |
| ATOM | 2446 | C | SER | 132 | 95.918 | -30.284 | 35.020 | 1.00 | 69.15 | H C |
| ATOM | 2447 | O | SER | 132 | 97.107 | -30.139 | 34.757 | 1.00 | 69.80 | H O |
| ATOM | 2448 | N | SER | 133 | 95.247 | -31.391 | 34.732 | 1.00 | 58.75 | H N |
| ATOM | 2449 | CA | SER | 133 | 95.894 | -32.483 | 34.024 | 1.00 | 61.13 | H C |
| ATOM | 2450 | CB | SER | 133 | 95.007 | -33.738 | 34.068 | 1.00 | 91.14 | H C |
| ATOM | 2451 | OG | SER | 133 | 93.668 | -33.456 | 33.684 | 1.00 | 100.88 | H O |
| ATOM | 2452 | C | SER | 133 | 96.121 | -32.017 | 32.576 | 1.00 | 60.76 | H C |
| ATOM | 2453 | O | SER | 133 | 97.091 | -32.413 | 31.927 | 1.00 | 61.01 | H O |
| ATOM | 2454 | N | LYS | 134 | 95.220 | -31.156 | 32.095 | 1.00 | 101.65 | H N |
| ATOM | 2455 | CA | LYS | 134 | 95.285 | -30.605 | 30.739 | 1.00 | 102.79 | H C |
| ATOM | 2456 | CB | LYS | 134 | 93.951 | -29.962 | 30.341 | 1.00 | 44.82 | H C |
| ATOM | 2457 | CG | LYS | 134 | 92.703 | -30.784 | 30.609 | 1.00 | 52.94 | H C |
| ATOM | 2458 | CD | LYS | 134 | 92.058 | -30.452 | 31.959 | 1.00 | 55.86 | H C |
| ATOM | 2459 | CE | LYS | 134 | 90.686 | -31.127 | 32.091 | 1.00 | 53.71 | H C |
| ATOM | 2460 | NZ | LYS | 134 | 89.988 | -30.792 | 33.367 | 1.00 | 52.28 | H N |
| ATOM | 2461 | C | LYS | 134 | 96.364 | -29.531 | 30.655 | 1.00 | 102.96 | H C |
| ATOM | 2462 | O | LYS | 134 | 96.932 | -29.284 | 29.589 | 1.00 | 104.03 | H O |
| ATOM | 2463 | N | SER | 135 | 96.619 | -28.885 | 31.791 | 1.00 | 77.03 | H N |
| ATOM | 2464 | CA | SER | 135 | 97.611 | -27.818 | 31.896 | 1.00 | 76.76 | H C |
| ATOM | 2465 | CB | SER | 135 | 97.069 | -26.698 | 32.784 | 1.00 | 81.66 | H C |
| ATOM | 2466 | OG | SER | 135 | 95.726 | -26.390 | 32.443 | 1.00 | 81.07 | H O |
| ATOM | 2467 | C | SER | 135 | 98.911 | -28.358 | 32.488 | 1.00 | 71.98 | H C |
| ATOM | 2468 | O | SER | 135 | 99.733 | -27.601 | 33.006 | 1.00 | 72.29 | H O |
| ATOM | 2469 | N | THR | 136 | 99.075 | -29.676 | 32.418 | 1.00 | 86.02 | H N |
| ATOM | 2470 | CA | THR | 136 | 100.262 | -30.351 | 32.932 | 1.00 | 86.44 | H C |
| ATOM | 2471 | CB | THR | 136 | 99.897 | -31.391 | 34.036 | 1.00 | 47.16 | H C |
| ATOM | 2472 | OG1 | THR | 136 | 99.491 | -30.715 | 35.237 | 1.00 | 47.25 | H O |
| ATOM | 2473 | CG2 | THR | 136 | 101.096 | -32.281 | 34.354 | 1.00 | 50.70 | H C |
| ATOM | 2474 | C | THR | 136 | 100.977 | -31.072 | 31.788 | 1.00 | 86.90 | H C |
| ATOM | 2475 | O | THR | 136 | 100.334 | -31.615 | 30.885 | 1.00 | 85.81 | H O |
| ATOM | 2476 | N | SER | 137 | 102.309 | -31.059 | 31.836 | 1.00 | 82.54 | H N |
| ATOM | 2477 | CA | SER | 137 | 103.164 | -31.700 | 30.834 | 1.00 | 82.34 | H C |
| ATOM | 2478 | CB | SER | 137 | 103.113 | -30.942 | 29.495 | 1.00 | 65.40 | H C |
| ATOM | 2479 | OG | SER | 137 | 101.863 | -31.097 | 28.841 | 1.00 | 66.87 | H O |
| ATOM | 2480 | C | SER | 137 | 104.600 | -31.715 | 31.352 | 1.00 | 82.68 | H C |
| ATOM | 2481 | O | SER | 137 | 105.321 | -30.722 | 31.244 | 1.00 | 84.11 | H O |
| ATOM | 2482 | N | GLY | 138 | 105.016 | -32.845 | 31.911 | 1.00 | 62.73 | H N |

Fig. 19: A-35

| | | | | | | | | | | |
|---|---|---|---|---|---|---|---|---|---|---|
| ATOM | 2483 | CA | GLY | 138 | 106.361 | -32.941 | 32.438 | 1.00 | 62.79 | H C |
| ATOM | 2484 | C | GLY | 138 | 106.394 | -32.371 | 33.840 | 1.00 | 65.01 | H C |
| ATOM | 2485 | O | GLY | 138 | 105.392 | -32.410 | 34.555 | 1.00 | 65.52 | H O |
| ATOM | 2486 | N | GLY | 139 | 107.537 | -31.827 | 34.237 | 1.00 | 45.62 | H N |
| ATOM | 2487 | CA | GLY | 139 | 107.645 | -31.267 | 35.570 | 1.00 | 45.97 | H C |
| ATOM | 2488 | C | GLY | 139 | 107.037 | -29.884 | 35.680 | 1.00 | 46.52 | H C |
| ATOM | 2489 | O | GLY | 139 | 107.020 | -29.297 | 36.762 | 1.00 | 50.66 | H O |
| ATOM | 2490 | N | THR | 140 | 106.527 | -29.365 | 34.568 | 1.00 | 41.37 | H N |
| ATOM | 2491 | CA | THR | 140 | 105.941 | -28.030 | 34.571 | 1.00 | 35.80 | H C |
| ATOM | 2492 | CB | THR | 140 | 106.626 | -27.108 | 33.533 | 1.00 | 32.97 | H C |
| ATOM | 2493 | OG1 | THR | 140 | 105.886 | -27.138 | 32.311 | 1.00 | 30.01 | H O |
| ATOM | 2494 | CG2 | THR | 140 | 108.052 | -27.574 | 33.250 | 1.00 | 33.92 | H C |
| ATOM | 2495 | C | THR | 140 | 104.434 | -27.993 | 34.299 | 1.00 | 32.68 | H C |
| ATOM | 2496 | O | THR | 140 | 103.884 | -28.820 | 33.560 | 1.00 | 31.27 | H O |
| ATOM | 2497 | N | ALA | 141 | 103.777 | -27.013 | 34.914 | 1.00 | 23.19 | H N |
| ATOM | 2498 | CA | ALA | 141 | 102.350 | -26.817 | 34.752 | 1.00 | 23.90 | H C |
| ATOM | 2499 | CB | ALA | 141 | 101.647 | -26.986 | 36.087 | 1.00 | 31.87 | H C |
| ATOM | 2500 | C | ALA | 141 | 102.121 | -25.408 | 34.206 | 1.00 | 24.06 | H C |
| ATOM | 2501 | O | ALA | 141 | 102.930 | -24.498 | 34.415 | 1.00 | 28.34 | H O |
| ATOM | 2502 | N | ALA | 142 | 101.022 | -25.239 | 33.487 | 1.00 | 36.28 | H N |
| ATOM | 2503 | CA | ALA | 142 | 100.685 | -23.948 | 32.924 | 1.00 | 31.12 | H C |
| ATOM | 2504 | CB | ALA | 142 | 100.507 | -24.062 | 31.419 | 1.00 | 1.87 | H C |
| ATOM | 2505 | C | ALA | 142 | 99.389 | -23.519 | 33.588 | 1.00 | 29.11 | H C |
| ATOM | 2506 | O | ALA | 142 | 98.565 | -24.359 | 33.961 | 1.00 | 33.50 | H O |
| ATOM | 2507 | N | LEU | 143 | 99.233 | -22.211 | 33.751 | 1.00 | 27.06 | H N |
| ATOM | 2508 | CA | LEU | 143 | 98.054 | -21.611 | 34.372 | 1.00 | 31.22 | H C |
| ATOM | 2509 | CB | LEU | 143 | 98.154 | -21.670 | 35.900 | 1.00 | 28.24 | H C |
| ATOM | 2510 | CG | LEU | 143 | 99.269 | -20.865 | 36.582 | 1.00 | 30.55 | H C |
| ATOM | 2511 | CD1 | LEU | 143 | 98.702 | -19.526 | 36.991 | 1.00 | 23.14 | H C |
| ATOM | 2512 | CD2 | LEU | 143 | 99.817 | -21.596 | 37.809 | 1.00 | 37.29 | H C |
| ATOM | 2513 | C | LEU | 143 | 98.068 | -20.169 | 33.913 | 1.00 | 34.46 | H C |
| ATOM | 2514 | O | LEU | 143 | 99.069 | -19.700 | 33.364 | 1.00 | 32.14 | H O |
| ATOM | 2515 | N | GLY | 144 | 96.970 | -19.458 | 34.128 | 1.00 | 25.78 | H N |
| ATOM | 2516 | CA | GLY | 144 | 96.922 | -18.074 | 33.694 | 1.00 | 28.57 | H C |
| ATOM | 2517 | C | GLY | 144 | 95.578 | -17.425 | 33.896 | 1.00 | 31.81 | H C |
| ATOM | 2518 | O | GLY | 144 | 94.693 | -17.985 | 34.543 | 1.00 | 35.57 | H O |
| ATOM | 2519 | N | CYS | 145 | 95.420 | -16.235 | 33.335 | 1.00 | 24.76 | H N |
| ATOM | 2520 | CA | CYS | 145 | 94.177 | -15.501 | 33.471 | 1.00 | 23.67 | H C |
| ATOM | 2521 | C | CYS | 145 | 93.665 | -15.071 | 32.122 | 1.00 | 21.65 | H C |
| ATOM | 2522 | O | CYS | 145 | 94.437 | -14.868 | 31.188 | 1.00 | 22.23 | H O |
| ATOM | 2523 | CB | CYS | 145 | 94.385 | -14.273 | 34.363 | 1.00 | 28.67 | H C |
| ATOM | 2524 | SG | CYS | 145 | 94.354 | -14.658 | 36.141 | 1.00 | 36.96 | H S |
| ATOM | 2525 | N | LEU | 146 | 92.351 | -14.940 | 32.024 | 1.00 | 43.52 | H N |
| ATOM | 2526 | CA | LEU | 146 | 91.712 | -14.512 | 30.792 | 1.00 | 43.76 | H C |
| ATOM | 2527 | CB | LEU | 146 | 90.715 | -15.580 | 30.314 | 1.00 | 38.89 | H C |
| ATOM | 2528 | CG | LEU | 146 | 89.754 | -15.245 | 29.164 | 1.00 | 28.77 | H C |
| ATOM | 2529 | CD1 | LEU | 146 | 90.519 | -14.669 | 27.982 | 1.00 | 25.69 | H C |
| ATOM | 2530 | CD2 | LEU | 146 | 88.989 | -16.489 | 28.755 | 1.00 | 35.84 | H C |
| ATOM | 2531 | C | LEU | 146 | 90.997 | -13.188 | 31.055 | 1.00 | 45.61 | H C |
| ATOM | 2532 | O | LEU | 146 | 89.943 | -13.160 | 31.690 | 1.00 | 45.79 | H O |
| ATOM | 2533 | N | VAL | 147 | 91.609 | -12.098 | 30.593 | 1.00 | 12.91 | H N |
| ATOM | 2534 | CA | VAL | 147 | 91.069 | -10.732 | 30.716 | 1.00 | 12.94 | H C |
| ATOM | 2535 | CB | VAL | 147 | 92.231 | -9.696 | 30.638 | 1.00 | 24.21 | H C |
| ATOM | 2536 | CG1 | VAL | 147 | 91.703 | -8.291 | 30.722 | 1.00 | 25.32 | H C |
| ATOM | 2537 | CG2 | VAL | 147 | 93.212 | -9.947 | 31.778 | 1.00 | 13.52 | H C |
| ATOM | 2538 | C | VAL | 147 | 90.101 | -10.563 | 29.532 | 1.00 | 18.31 | H C |
| ATOM | 2539 | O | VAL | 147 | 90.532 | -10.460 | 28.381 | 1.00 | 18.59 | H O |
| ATOM | 2540 | N | LYS | 148 | 88.798 | -10.519 | 29.806 | 1.00 | 25.16 | H N |
| ATOM | 2541 | CA | LYS | 148 | 87.835 | -10.467 | 28.709 | 1.00 | 29.22 | H C |
| ATOM | 2542 | CB | LYS | 148 | 87.140 | -11.827 | 28.609 | 1.00 | 15.56 | H C |
| ATOM | 2543 | CG | LYS | 148 | 86.353 | -12.032 | 27.348 | 1.00 | 22.92 | H C |
| ATOM | 2544 | CD | LYS | 148 | 85.731 | -13.405 | 27.355 | 1.00 | 22.16 | H C |
| ATOM | 2545 | CE | LYS | 148 | 84.795 | -13.570 | 26.190 | 1.00 | 24.54 | H C |
| ATOM | 2546 | NZ | LYS | 148 | 85.514 | -13.308 | 24.928 | 1.00 | 22.92 | H N |
| ATOM | 2547 | C | LYS | 148 | 86.777 | -9.372 | 28.646 | 1.00 | 32.79 | H C |
| ATOM | 2548 | O | LYS | 148 | 86.332 | -8.844 | 29.664 | 1.00 | 33.18 | H O |
| ATOM | 2549 | N | ASP | 149 | 86.387 | -9.069 | 27.409 | 1.00 | 55.13 | H N |
| ATOM | 2550 | CA | ASP | 149 | 85.381 | -8.070 | 27.078 | 1.00 | 53.92 | H C |
| ATOM | 2551 | CB | ASP | 149 | 83.993 | -8.595 | 27.429 | 1.00 | 38.49 | H C |
| ATOM | 2552 | CG | ASP | 149 | 83.635 | -9.853 | 26.661 | 1.00 | 42.52 | H C |
| ATOM | 2553 | OD1 | ASP | 149 | 83.797 | -9.882 | 25.421 | 1.00 | 46.52 | H O |
| ATOM | 2554 | OD2 | ASP | 149 | 83.181 | -10.817 | 27.305 | 1.00 | 41.08 | H O |
| ATOM | 2555 | C | ASP | 149 | 85.585 | -6.690 | 27.698 | 1.00 | 56.06 | H C |

Fig. 19: A-36

| ATOM | 2556 | O | ASP | 149 | 84.720 | -6.175 | 28.415 | 1.00 | 57.30 | H | O |
|---|---|---|---|---|---|---|---|---|---|---|---|
| ATOM | 2557 | N | TYR | 150 | 86.734 | -6.091 | 27.399 | 1.00 | 33.00 | H | N |
| ATOM | 2558 | CA | TYR | 150 | 87.072 | -4.770 | 27.897 | 1.00 | 33.34 | H | C |
| ATOM | 2559 | CB | TYR | 150 | 88.306 | -4.844 | 28.797 | 1.00 | 39.19 | H | C |
| ATOM | 2560 | CG | TYR | 150 | 89.622 | -5.155 | 28.097 | 1.00 | 44.75 | H | C |
| ATOM | 2561 | CD1 | TYR | 150 | 90.405 | -4.137 | 27.556 | 1.00 | 44.06 | H | C |
| ATOM | 2562 | CE1 | TYR | 150 | 91.653 | -4.401 | 26.994 | 1.00 | 46.40 | H | C |
| ATOM | 2563 | CD2 | TYR | 150 | 90.121 | -6.457 | 28.046 | 1.00 | 44.23 | H | C |
| ATOM | 2564 | CE2 | TYR | 150 | 91.369 | -6.730 | 27.483 | 1.00 | 43.19 | H | C |
| ATOM | 2565 | CZ | TYR | 150 | 92.130 | -5.694 | 26.963 | 1.00 | 45.07 | H | C |
| ATOM | 2566 | OH | TYR | 150 | 93.376 | -5.942 | 26.431 | 1.00 | 42.66 | H | O |
| ATOM | 2567 | C | TYR | 150 | 87.331 | -3.838 | 26.723 | 1.00 | 34.19 | H | C |
| ATOM | 2568 | O | TYR | 150 | 87.420 | -4.275 | 25.569 | 1.00 | 36.79 | H | O |
| ATOM | 2569 | N | PHE | 151 | 87.450 | -2.549 | 27.034 | 1.00 | 53.36 | H | N |
| ATOM | 2570 | CA | PHE | 151 | 87.686 | -1.522 | 26.034 | 1.00 | 51.06 | H | C |
| ATOM | 2571 | CB | PHE | 151 | 86.520 | -1.506 | 25.038 | 1.00 | 22.52 | H | C |
| ATOM | 2572 | CG | PHE | 151 | 86.663 | -0.500 | 23.923 | 1.00 | 22.34 | H | C |
| ATOM | 2573 | CD1 | PHE | 151 | 86.509 | 0.865 | 24.164 | 1.00 | 21.58 | H | C |
| ATOM | 2574 | CD2 | PHE | 151 | 86.896 | -0.923 | 22.616 | 1.00 | 24.08 | H | C |
| ATOM | 2575 | CE1 | PHE | 151 | 86.576 | 1.789 | 23.117 | 1.00 | 22.62 | H | C |
| ATOM | 2576 | CE2 | PHE | 151 | 86.968 | -0.003 | 21.558 | 1.00 | 25.39 | H | C |
| ATOM | 2577 | CZ | PHE | 151 | 86.805 | 1.351 | 21.809 | 1.00 | 25.56 | H | C |
| ATOM | 2578 | C | PHE | 151 | 87.819 | -0.175 | 26.734 | 1.00 | 48.17 | H | C |
| ATOM | 2579 | O | PHE | 151 | 87.161 | 0.084 | 27.737 | 1.00 | 47.45 | H | O |
| ATOM | 2580 | N | PRO | 152 | 88.712 | 0.685 | 26.232 | 1.00 | 46.09 | H | N |
| ATOM | 2581 | CD | PRO | 152 | 88.959 | 2.055 | 26.730 | 1.00 | 7.14 | H | C |
| ATOM | 2582 | CA | PRO | 152 | 89.554 | 0.388 | 25.065 | 1.00 | 47.66 | H | C |
| ATOM | 2583 | CB | PRO | 152 | 89.773 | 1.765 | 24.464 | 1.00 | 12.39 | H | C |
| ATOM | 2584 | CG | PRO | 152 | 90.017 | 2.594 | 25.730 | 1.00 | 9.55 | H | C |
| ATOM | 2585 | C | PRO | 152 | 90.835 | -0.199 | 25.636 | 1.00 | 47.42 | H | C |
| ATOM | 2586 | O | PRO | 152 | 90.826 | -0.716 | 26.748 | 1.00 | 49.63 | H | O |
| ATOM | 2587 | N | GLU | 153 | 91.933 | -0.128 | 24.894 | 1.00 | 48.37 | H | N |
| ATOM | 2588 | CA | GLU | 153 | 93.200 | -0.620 | 25.422 | 1.00 | 45.01 | H | C |
| ATOM | 2589 | CB | GLU | 153 | 94.232 | -0.788 | 24.308 | 1.00 | 35.76 | H | C |
| ATOM | 2590 | CG | GLU | 153 | 93.983 | -1.951 | 23.370 | 1.00 | 41.71 | H | C |
| ATOM | 2591 | CD | GLU | 153 | 94.465 | -3.279 | 23.920 | 1.00 | 49.73 | H | C |
| ATOM | 2592 | OE1 | GLU | 153 | 94.329 | -4.276 | 23.191 | 1.00 | 53.96 | H | O |
| ATOM | 2593 | OE2 | GLU | 153 | 94.979 | -3.337 | 25.062 | 1.00 | 49.06 | H | O |
| ATOM | 2594 | C | GLU | 153 | 93.667 | 0.487 | 26.355 | 1.00 | 40.62 | H | C |
| ATOM | 2595 | O | GLU | 153 | 93.160 | 1.611 | 26.288 | 1.00 | 43.09 | H | O |
| ATOM | 2596 | N | PRO | 154 | 94.626 | 0.193 | 27.242 | 1.00 | 31.67 | H | N |
| ATOM | 2597 | CD | PRO | 154 | 95.605 | 1.250 | 27.562 | 1.00 | 24.24 | H | C |
| ATOM | 2598 | CA | PRO | 154 | 95.266 | -1.107 | 27.404 | 1.00 | 32.01 | H | C |
| ATOM | 2599 | CB | PRO | 154 | 96.707 | -0.803 | 27.072 | 1.00 | 23.56 | H | C |
| ATOM | 2600 | CG | PRO | 154 | 96.899 | 0.447 | 27.855 | 1.00 | 23.31 | H | C |
| ATOM | 2601 | C | PRO | 154 | 95.127 | -1.577 | 28.846 | 1.00 | 37.33 | H | C |
| ATOM | 2602 | O | PRO | 154 | 94.929 | -0.788 | 29.770 | 1.00 | 40.93 | H | O |
| ATOM | 2603 | N | VAL | 155 | 95.270 | -2.874 | 29.029 | 1.00 | 27.89 | H | N |
| ATOM | 2604 | CA | VAL | 155 | 95.171 | -3.468 | 30.339 | 1.00 | 28.93 | H | C |
| ATOM | 2605 | CB | VAL | 155 | 94.167 | -4.647 | 30.309 | 1.00 | 32.63 | H | C |
| ATOM | 2606 | CG1 | VAL | 155 | 94.624 | -5.699 | 29.306 | 1.00 | 39.44 | H | C |
| ATOM | 2607 | CG2 | VAL | 155 | 94.030 | -5.243 | 31.690 | 1.00 | 38.09 | H | C |
| ATOM | 2608 | C | VAL | 155 | 96.561 | -3.969 | 30.715 | 1.00 | 29.75 | H | C |
| ATOM | 2609 | O | VAL | 155 | 97.319 | -4.427 | 29.856 | 1.00 | 34.58 | H | O |
| ATOM | 2610 | N | THR | 156 | 96.898 | -3.864 | 31.995 | 1.00 | 30.47 | H | N |
| ATOM | 2611 | CA | THR | 156 | 98.195 | -4.322 | 32.482 | 1.00 | 30.67 | H | C |
| ATOM | 2612 | CB | THR | 156 | 98.855 | -3.316 | 33.458 | 1.00 | 37.06 | H | C |
| ATOM | 2613 | OG1 | THR | 156 | 98.554 | -3.699 | 34.810 | 1.00 | 41.96 | H | O |
| ATOM | 2614 | CG2 | THR | 156 | 98.346 | -1.895 | 33.213 | 1.00 | 35.30 | H | C |
| ATOM | 2615 | C | THR | 156 | 97.956 | -5.589 | 33.276 | 1.00 | 28.26 | H | C |
| ATOM | 2616 | O | THR | 156 | 96.915 | -5.736 | 33.906 | 1.00 | 24.33 | H | O |
| ATOM | 2617 | N | VAL | 157 | 98.914 | -6.501 | 33.250 | 1.00 | 20.40 | H | N |
| ATOM | 2618 | CA | VAL | 157 | 98.784 | -7.731 | 34.014 | 1.00 | 23.86 | H | C |
| ATOM | 2619 | CB | VAL | 157 | 98.263 | -8.918 | 33.149 | 1.00 | 6.55 | H | C |
| ATOM | 2620 | CG1 | VAL | 157 | 98.307 | -10.191 | 33.970 | 1.00 | 2.70 | H | C |
| ATOM | 2621 | CG2 | VAL | 157 | 96.817 | -8.649 | 32.662 | 1.00 | 8.40 | H | C |
| ATOM | 2622 | C | VAL | 157 | 100.122 | -8.142 | 34.618 | 1.00 | 25.91 | H | C |
| ATOM | 2623 | O | VAL | 157 | 101.130 | -8.220 | 33.918 | 1.00 | 28.24 | H | O |
| ATOM | 2624 | N | SER | 158 | 100.127 | -8.401 | 35.918 | 1.00 | 37.92 | H | N |
| ATOM | 2625 | CA | SER | 158 | 101.333 | -8.840 | 36.606 | 1.00 | 38.42 | H | C |
| ATOM | 2626 | CB | SER | 158 | 101.852 | -7.738 | 37.521 | 1.00 | 26.79 | H | C |
| ATOM | 2627 | OG | SER | 158 | 101.008 | -7.591 | 38.648 | 1.00 | 29.78 | H | O |
| ATOM | 2628 | C | SER | 158 | 100.947 | -10.064 | 37.439 | 1.00 | 37.35 | H | C |

Fig. 19: A-37

| ATOM | 2629 | O | SER | 158 | 99.765 | -10.366 | 37.583 | 1.00 | 35.45 | H | O |
|---|---|---|---|---|---|---|---|---|---|---|---|
| ATOM | 2630 | N | TRP | 159 | 101.926 | -10.772 | 37.989 | 1.00 | 38.23 | H | N |
| ATOM | 2631 | CA | TRP | 159 | 101.604 | -11.945 | 38.790 | 1.00 | 38.96 | H | C |
| ATOM | 2632 | CB | TRP | 159 | 102.060 | -13.224 | 38.074 | 1.00 | 33.06 | H | C |
| ATOM | 2633 | CG | TRP | 159 | 101.197 | -13.555 | 36.899 | 1.00 | 30.80 | H | C |
| ATOM | 2634 | CD2 | TRP | 159 | 100.089 | -14.463 | 36.879 | 1.00 | 31.04 | H | C |
| ATOM | 2635 | CE2 | TRP | 159 | 99.540 | -14.423 | 35.577 | 1.00 | 29.21 | H | C |
| ATOM | 2636 | CE3 | TRP | 159 | 99.507 | -15.307 | 37.836 | 1.00 | 31.84 | H | C |
| ATOM | 2637 | CD1 | TRP | 159 | 101.271 | -13.015 | 35.649 | 1.00 | 26.46 | H | C |
| ATOM | 2638 | NE1 | TRP | 159 | 100.280 | -13.531 | 34.848 | 1.00 | 30.17 | H | N |
| ATOM | 2639 | CZ2 | TRP | 159 | 98.439 | -15.196 | 35.204 | 1.00 | 33.73 | H | C |
| ATOM | 2640 | CZ3 | TRP | 159 | 98.407 | -16.079 | 37.465 | 1.00 | 33.56 | H | C |
| ATOM | 2641 | CH2 | TRP | 159 | 97.887 | -16.018 | 36.158 | 1.00 | 34.95 | H | C |
| ATOM | 2642 | C | TRP | 159 | 102.166 | -11.908 | 40.203 | 1.00 | 41.53 | H | C |
| ATOM | 2643 | O | TRP | 159 | 103.355 | -11.670 | 40.412 | 1.00 | 40.45 | H | O |
| ATOM | 2644 | N | ASN | 160 | 101.295 | -12.163 | 41.170 | 1.00 | 50.63 | H | N |
| ATOM | 2645 | CA | ASN | 160 | 101.699 | -12.153 | 42.557 | 1.00 | 51.18 | H | C |
| ATOM | 2646 | CB | ASN | 160 | 102.753 | -13.230 | 42.814 | 1.00 | 31.23 | H | C |
| ATOM | 2647 | CG | ASN | 160 | 102.145 | -14.619 | 42.946 | 1.00 | 28.65 | H | C |
| ATOM | 2648 | OD1 | ASN | 160 | 100.924 | -14.784 | 42.911 | 1.00 | 22.55 | H | O |
| ATOM | 2649 | ND2 | ASN | 160 | 103.000 | -15.630 | 43.107 | 1.00 | 28.71 | H | N |
| ATOM | 2650 | C | ASN | 160 | 102.245 | -10.777 | 42.891 | 1.00 | 53.56 | H | C |
| ATOM | 2651 | O | ASN | 160 | 103.277 | -10.637 | 43.554 | 1.00 | 51.84 | H | O |
| ATOM | 2652 | N | SER | 161 | 101.548 | -9.758 | 42.397 | 1.00 | 57.36 | H | N |
| ATOM | 2653 | CA | SER | 161 | 101.915 | -8.372 | 42.651 | 1.00 | 58.07 | H | C |
| ATOM | 2654 | CB | SER | 161 | 101.833 | -8.106 | 44.161 | 1.00 | 44.49 | H | C |
| ATOM | 2655 | OG | SER | 161 | 100.611 | -8.586 | 44.713 | 1.00 | 48.26 | H | O |
| ATOM | 2656 | C | SER | 161 | 103.305 | -7.997 | 42.118 | 1.00 | 57.98 | H | C |
| ATOM | 2657 | O | SER | 161 | 103.779 | -6.883 | 42.329 | 1.00 | 58.91 | H | O |
| ATOM | 2658 | N | GLY | 162 | 103.957 | -8.927 | 41.431 | 1.00 | 43.40 | H | N |
| ATOM | 2659 | CA | GLY | 162 | 105.271 | -8.641 | 40.886 | 1.00 | 41.61 | H | C |
| ATOM | 2660 | C | GLY | 162 | 106.343 | -9.670 | 41.195 | 1.00 | 41.13 | H | C |
| ATOM | 2661 | O | GLY | 162 | 107.340 | -9.756 | 40.475 | 1.00 | 41.89 | H | O |
| ATOM | 2662 | N | ALA | 163 | 106.144 | -10.460 | 42.248 | 1.00 | 32.79 | H | N |
| ATOM | 2663 | CA | ALA | 163 | 107.135 | -11.462 | 42.644 | 1.00 | 33.15 | H | C |
| ATOM | 2664 | CB | ALA | 163 | 106.845 | -11.956 | 44.065 | 1.00 | 7.75 | H | C |
| ATOM | 2665 | C | ALA | 163 | 107.265 | -12.651 | 41.702 | 1.00 | 33.69 | H | C |
| ATOM | 2666 | O | ALA | 163 | 108.154 | -13.473 | 41.868 | 1.00 | 36.52 | H | O |
| ATOM | 2667 | N | LEU | 164 | 106.378 | -12.750 | 40.722 | 1.00 | 33.04 | H | N |
| ATOM | 2668 | CA | LEU | 164 | 106.412 | -13.847 | 39.755 | 1.00 | 28.09 | H | C |
| ATOM | 2669 | CB | LEU | 164 | 105.146 | -14.701 | 39.869 | 1.00 | 29.67 | H | C |
| ATOM | 2670 | CG | LEU | 164 | 105.008 | -15.851 | 38.870 | 1.00 | 27.43 | H | C |
| ATOM | 2671 | CD1 | LEU | 164 | 105.976 | -16.963 | 39.215 | 1.00 | 24.01 | H | C |
| ATOM | 2672 | CD2 | LEU | 164 | 103.605 | -16.370 | 38.903 | 1.00 | 22.28 | H | C |
| ATOM | 2673 | C | LEU | 164 | 106.483 | -13.227 | 38.370 | 1.00 | 26.00 | H | C |
| ATOM | 2674 | O | LEU | 164 | 105.492 | -12.663 | 37.893 | 1.00 | 20.06 | H | O |
| ATOM | 2675 | N | THR | 165 | 107.656 | -13.326 | 37.740 | 1.00 | 28.49 | H | N |
| ATOM | 2676 | CA | THR | 165 | 107.893 | -12.758 | 36.410 | 1.00 | 32.54 | H | C |
| ATOM | 2677 | CB | THR | 165 | 108.927 | -11.613 | 36.462 | 1.00 | 18.33 | H | C |
| ATOM | 2678 | OG1 | THR | 165 | 110.114 | -12.057 | 37.139 | 1.00 | 21.15 | H | O |
| ATOM | 2679 | CG2 | THR | 165 | 108.348 | -10.419 | 37.184 | 1.00 | 20.86 | H | C |
| ATOM | 2680 | C | THR | 165 | 108.394 | -13.770 | 35.397 | 1.00 | 33.42 | H | C |
| ATOM | 2681 | O | THR | 165 | 108.028 | -13.717 | 34.227 | 1.00 | 34.44 | H | O |
| ATOM | 2682 | N | SER | 166 | 109.244 | -14.683 | 35.849 | 1.00 | 63.46 | H | N |
| ATOM | 2683 | CA | SER | 166 | 109.804 | -15.702 | 34.973 | 1.00 | 62.93 | H | C |
| ATOM | 2684 | CB | SER | 166 | 110.901 | -16.472 | 35.710 | 1.00 | 37.10 | H | C |
| ATOM | 2685 | OG | SER | 166 | 111.503 | -17.442 | 34.870 | 1.00 | 42.11 | H | O |
| ATOM | 2686 | C | SER | 166 | 108.748 | -16.678 | 34.458 | 1.00 | 60.85 | H | C |
| ATOM | 2687 | O | SER | 166 | 107.955 | -17.226 | 35.227 | 1.00 | 60.31 | H | O |
| ATOM | 2688 | N | GLY | 167 | 108.744 | -16.895 | 33.148 | 1.00 | 58.61 | H | N |
| ATOM | 2689 | CA | GLY | 167 | 107.784 | -17.812 | 32.566 | 1.00 | 55.44 | H | C |
| ATOM | 2690 | C | GLY | 167 | 106.425 | -17.181 | 32.332 | 1.00 | 49.55 | H | C |
| ATOM | 2691 | O | GLY | 167 | 105.462 | -17.878 | 32.010 | 1.00 | 51.52 | H | O |
| ATOM | 2692 | N | VAL | 168 | 106.340 | -15.864 | 32.491 | 1.00 | 12.32 | H | N |
| ATOM | 2693 | CA | VAL | 168 | 105.081 | -15.183 | 32.280 | 1.00 | 12.04 | H | C |
| ATOM | 2694 | CB | VAL | 168 | 104.933 | -13.970 | 33.190 | 1.00 | 2.74 | H | C |
| ATOM | 2695 | CG1 | VAL | 168 | 103.590 | -13.273 | 32.906 | 1.00 | 2.74 | H | C |
| ATOM | 2696 | CG2 | VAL | 168 | 105.070 | -14.398 | 34.630 | 1.00 | 2.83 | H | C |
| ATOM | 2697 | C | VAL | 168 | 104.965 | -14.687 | 30.852 | 1.00 | 11.82 | H | C |
| ATOM | 2698 | O | VAL | 168 | 105.894 | -14.087 | 30.319 | 1.00 | 11.28 | H | O |
| ATOM | 2699 | N | HIS | 169 | 103.807 | -14.931 | 30.253 | 1.00 | 28.24 | H | N |
| ATOM | 2700 | CA | HIS | 169 | 103.518 | -14.512 | 28.891 | 1.00 | 24.96 | H | C |
| ATOM | 2701 | CB | HIS | 169 | 103.566 | -15.695 | 27.924 | 1.00 | 1.87 | H | C |

Fig. 19: A-38

| | | | | | | | | | | |
|---|---|---|---|---|---|---|---|---|---|---|
| ATOM | 2702 | CG | HIS | 169 | 104.935 | -16.209 | 27.634 | 1.00 | 1.87 | H | C |
| ATOM | 2703 | CD2 | HIS | 169 | 105.456 | -17.452 | 27.739 | 1.00 | 10.72 | H | C |
| ATOM | 2704 | ND1 | HIS | 169 | 105.935 | -15.415 | 27.114 | 1.00 | 4.04 | H | N |
| ATOM | 2705 | CE1 | HIS | 169 | 107.015 | -16.147 | 26.912 | 1.00 | 11.56 | H | C |
| ATOM | 2706 | NE2 | HIS | 169 | 106.750 | -17.387 | 27.282 | 1.00 | 3.03 | H | N |
| ATOM | 2707 | C | HIS | 169 | 102.106 | -13.934 | 28.818 | 1.00 | 26.88 | H | C |
| ATOM | 2708 | O | HIS | 169 | 101.143 | -14.679 | 28.610 | 1.00 | 27.44 | H | O |
| ATOM | 2709 | N | THR | 170 | 101.960 | -12.628 | 28.995 | 1.00 | 15.52 | H | N |
| ATOM | 2710 | CA | THR | 170 | 100.637 | -12.030 | 28.885 | 1.00 | 14.61 | H | C |
| ATOM | 2711 | CB | THR | 170 | 100.472 | -10.872 | 29.894 | 1.00 | 20.19 | H | C |
| ATOM | 2712 | OG1 | THR | 170 | 99.403 | -10.021 | 29.470 | 1.00 | 14.32 | H | O |
| ATOM | 2713 | CG2 | THR | 170 | 101.760 | -10.096 | 30.042 | 1.00 | 25.14 | H | C |
| ATOM | 2714 | C | THR | 170 | 100.487 | -11.553 | 27.433 | 1.00 | 15.32 | H | C |
| ATOM | 2715 | O | THR | 170 | 101.023 | -10.532 | 27.053 | 1.00 | 11.65 | H | O |
| ATOM | 2716 | N | PHE | 171 | 99.762 | -12.324 | 26.630 | 1.00 | 23.28 | H | N |
| ATOM | 2717 | CA | PHE | 171 | 99.587 | -12.046 | 25.206 | 1.00 | 17.85 | H | C |
| ATOM | 2718 | CB | PHE | 171 | 98.695 | -13.110 | 24.554 | 1.00 | 15.23 | H | C |
| ATOM | 2719 | CG | PHE | 171 | 99.138 | -14.521 | 24.806 | 1.00 | 7.97 | H | C |
| ATOM | 2720 | CD1 | PHE | 171 | 98.731 | -15.195 | 25.955 | 1.00 | 8.65 | H | C |
| ATOM | 2721 | CD2 | PHE | 171 | 99.978 | -15.174 | 23.903 | 1.00 | 7.84 | H | C |
| ATOM | 2722 | CE1 | PHE | 171 | 99.153 | -16.492 | 26.202 | 1.00 | 17.36 | H | C |
| ATOM | 2723 | CE2 | PHE | 171 | 100.407 | -16.473 | 24.144 | 1.00 | 15.22 | H | C |
| ATOM | 2724 | CZ | PHE | 171 | 99.993 | -17.133 | 25.295 | 1.00 | 16.34 | H | C |
| ATOM | 2725 | C | PHE | 171 | 99.032 | -10.692 | 24.793 | 1.00 | 18.20 | H | C |
| ATOM | 2726 | O | PHE | 171 | 98.344 | -10.015 | 25.552 | 1.00 | 23.73 | H | O |
| ATOM | 2727 | N | PRO | 172 | 99.341 | -10.278 | 23.557 | 1.00 | 21.77 | H | N |
| ATOM | 2728 | CD | PRO | 172 | 100.227 | -10.890 | 22.550 | 1.00 | 20.32 | H | C |
| ATOM | 2729 | CA | PRO | 172 | 98.827 | -8.999 | 23.088 | 1.00 | 23.20 | H | C |
| ATOM | 2730 | CB | PRO | 172 | 99.595 | -8.775 | 21.782 | 1.00 | 20.71 | H | C |
| ATOM | 2731 | CG | PRO | 172 | 99.834 | -10.148 | 21.287 | 1.00 | 18.82 | H | C |
| ATOM | 2732 | C | PRO | 172 | 97.339 | -9.235 | 22.876 | 1.00 | 25.11 | H | C |
| ATOM | 2733 | O | PRO | 172 | 96.916 | -10.364 | 22.645 | 1.00 | 23.46 | H | O |
| ATOM | 2734 | N | ALA | 173 | 96.551 | -8.172 | 22.960 | 1.00 | 24.67 | H | N |
| ATOM | 2735 | CA | ALA | 173 | 95.104 | -8.267 | 22.815 | 1.00 | 27.18 | H | C |
| ATOM | 2736 | CB | ALA | 173 | 94.439 | -7.079 | 23.498 | 1.00 | 1.87 | H | C |
| ATOM | 2737 | C | ALA | 173 | 94.604 | -8.379 | 21.391 | 1.00 | 30.18 | H | C |
| ATOM | 2738 | O | ALA | 173 | 95.304 | -8.080 | 20.426 | 1.00 | 32.13 | H | O |
| ATOM | 2739 | N | VAL | 174 | 93.365 | -8.820 | 21.277 | 1.00 | 21.72 | H | N |
| ATOM | 2740 | CA | VAL | 174 | 92.753 | -8.964 | 19.984 | 1.00 | 23.16 | H | C |
| ATOM | 2741 | CB | VAL | 174 | 92.841 | -10.406 | 19.511 | 1.00 | 28.95 | H | C |
| ATOM | 2742 | CG1 | VAL | 174 | 92.103 | -10.566 | 18.201 | 1.00 | 32.21 | H | C |
| ATOM | 2743 | CG2 | VAL | 174 | 94.305 | -10.797 | 19.356 | 1.00 | 26.32 | H | C |
| ATOM | 2744 | C | VAL | 174 | 91.302 | -8.508 | 20.058 | 1.00 | 25.36 | H | C |
| ATOM | 2745 | O | VAL | 174 | 90.611 | -8.718 | 21.069 | 1.00 | 25.35 | H | O |
| ATOM | 2746 | N | LEU | 175 | 90.860 | -7.856 | 18.987 | 1.00 | 41.55 | H | N |
| ATOM | 2747 | CA | LEU | 175 | 89.504 | -7.338 | 18.890 | 1.00 | 40.23 | H | C |
| ATOM | 2748 | CB | LEU | 175 | 89.443 | -6.276 | 17.787 | 1.00 | 23.29 | H | C |
| ATOM | 2749 | CG | LEU | 175 | 88.728 | -4.928 | 17.990 | 1.00 | 20.94 | H | C |
| ATOM | 2750 | CD1 | LEU | 175 | 88.634 | -4.511 | 19.463 | 1.00 | 21.45 | H | C |
| ATOM | 2751 | CD2 | LEU | 175 | 89.518 | -3.900 | 17.186 | 1.00 | 22.78 | H | C |
| ATOM | 2752 | C | LEU | 175 | 88.539 | -8.474 | 18.588 | 1.00 | 42.85 | H | C |
| ATOM | 2753 | O | LEU | 175 | 88.738 | -9.233 | 17.638 | 1.00 | 45.50 | H | O |
| ATOM | 2754 | N | GLN | 176 | 87.500 | -8.592 | 19.407 | 1.00 | 41.11 | H | N |
| ATOM | 2755 | CA | GLN | 176 | 86.514 | -9.645 | 19.228 | 1.00 | 42.33 | H | C |
| ATOM | 2756 | CB | GLN | 176 | 85.852 | -9.990 | 20.564 | 1.00 | 38.15 | H | C |
| ATOM | 2757 | CG | GLN | 176 | 86.817 | -10.276 | 21.703 | 1.00 | 37.93 | H | C |
| ATOM | 2758 | CD | GLN | 176 | 86.109 | -10.801 | 22.939 | 1.00 | 36.82 | H | C |
| ATOM | 2759 | OE1 | GLN | 176 | 85.562 | -11.899 | 22.923 | 1.00 | 36.67 | H | O |
| ATOM | 2760 | NE2 | GLN | 176 | 86.108 | -10.014 | 24.011 | 1.00 | 33.13 | H | N |
| ATOM | 2761 | C | GLN | 176 | 85.439 | -9.207 | 18.245 | 1.00 | 44.39 | H | C |
| ATOM | 2762 | O | GLN | 176 | 85.274 | -8.018 | 17.969 | 1.00 | 34.09 | H | O |
| ATOM | 2763 | N | SER | 177 | 84.708 | -10.182 | 17.718 | 1.00 | 59.83 | H | N |
| ATOM | 2764 | CA | SER | 177 | 83.624 | -9.902 | 16.790 | 1.00 | 58.61 | H | C |
| ATOM | 2765 | CB | SER | 177 | 82.804 | -11.177 | 16.558 | 1.00 | 104.21 | H | C |
| ATOM | 2766 | OG | SER | 177 | 81.708 | -10.945 | 15.689 | 1.00 | 104.01 | H | O |
| ATOM | 2767 | C | SER | 177 | 82.759 | -8.832 | 17.448 | 1.00 | 60.09 | H | C |
| ATOM | 2768 | O | SER | 177 | 82.169 | -7.985 | 16.778 | 1.00 | 62.26 | H | O |
| ATOM | 2769 | N | SER | 178 | 82.722 | -8.877 | 18.778 | 1.00 | 34.26 | H | N |
| ATOM | 2770 | CA | SER | 178 | 81.942 | -7.952 | 19.596 | 1.00 | 32.97 | H | C |
| ATOM | 2771 | CB | SER | 178 | 81.798 | -8.510 | 21.019 | 1.00 | 67.89 | H | C |
| ATOM | 2772 | OG | SER | 178 | 83.057 | -8.636 | 21.663 | 1.00 | 66.22 | H | O |
| ATOM | 2773 | C | SER | 178 | 82.538 | -6.554 | 19.671 | 1.00 | 32.95 | H | C |
| ATOM | 2774 | O | SER | 178 | 81.921 | -5.640 | 20.210 | 1.00 | 35.05 | H | O |

Fig. 19: A-39

| | | | | | | | | | | | |
|---|---|---|---|---|---|---|---|---|---|---|---|
| ATOM | 2775 | N | GLY | 179 | 83.738 | -6.382 | 19.135 | 1.00 | 43.45 | H | N |
| ATOM | 2776 | CA | GLY | 179 | 84.357 | -5.072 | 19.191 | 1.00 | 46.81 | H | C |
| ATOM | 2777 | C | GLY | 179 | 84.972 | -4.821 | 20.552 | 1.00 | 50.21 | H | C |
| ATOM | 2778 | O | GLY | 179 | 85.380 | -3.707 | 20.869 | 1.00 | 50.30 | H | O |
| ATOM | 2779 | N | LEU | 180 | 85.020 | -5.862 | 21.369 | 1.00 | 30.24 | H | N |
| ATOM | 2780 | CA | LEU | 180 | 85.620 | -5.749 | 22.686 | 1.00 | 32.27 | H | C |
| ATOM | 2781 | CB | LEU | 180 | 84.706 | -6.380 | 23.730 | 1.00 | 33.41 | H | C |
| ATOM | 2782 | CG | LEU | 180 | 83.485 | -5.524 | 24.054 | 1.00 | 32.78 | H | C |
| ATOM | 2783 | CD1 | LEU | 180 | 82.513 | -6.292 | 24.902 | 1.00 | 27.00 | H | C |
| ATOM | 2784 | CD2 | LEU | 180 | 83.943 | -4.278 | 24.781 | 1.00 | 32.58 | H | C |
| ATOM | 2785 | C | LEU | 180 | 86.974 | -6.442 | 22.672 | 1.00 | 32.86 | H | C |
| ATOM | 2786 | O | LEU | 180 | 87.135 | -7.488 | 22.054 | 1.00 | 36.18 | H | O |
| ATOM | 2787 | N | TYR | 181 | 87.952 | -5.843 | 23.336 | 1.00 | 31.41 | H | N |
| ATOM | 2788 | CA | TYR | 181 | 89.293 | -6.409 | 23.387 | 1.00 | 32.68 | H | C |
| ATOM | 2789 | CB | TYR | 181 | 90.297 | -5.323 | 23.792 | 1.00 | 57.58 | H | C |
| ATOM | 2790 | CG | TYR | 181 | 90.773 | -4.445 | 22.651 | 1.00 | 56.39 | H | C |
| ATOM | 2791 | CD1 | TYR | 181 | 91.591 | -4.961 | 21.647 | 1.00 | 57.58 | H | C |
| ATOM | 2792 | CE1 | TYR | 181 | 92.063 | -4.155 | 20.605 | 1.00 | 57.08 | H | C |
| ATOM | 2793 | CD2 | TYR | 181 | 90.430 | -3.092 | 22.585 | 1.00 | 56.67 | H | C |
| ATOM | 2794 | CE2 | TYR | 181 | 90.899 | -2.273 | 21.543 | 1.00 | 57.48 | H | C |
| ATOM | 2795 | CZ | TYR | 181 | 91.717 | -2.816 | 20.559 | 1.00 | 58.33 | H | C |
| ATOM | 2796 | OH | TYR | 181 | 92.202 | -2.033 | 19.533 | 1.00 | 62.35 | H | O |
| ATOM | 2797 | C | TYR | 181 | 89.361 | -7.573 | 24.375 | 1.00 | 31.73 | H | C |
| ATOM | 2798 | O | TYR | 181 | 88.581 | -7.638 | 25.324 | 1.00 | 32.08 | H | O |
| ATOM | 2799 | N | SER | 182 | 90.287 | -8.499 | 24.149 | 1.00 | 35.13 | H | N |
| ATOM | 2800 | CA | SER | 182 | 90.446 | -9.642 | 25.045 | 1.00 | 32.04 | H | C |
| ATOM | 2801 | CB | SER | 182 | 89.439 | -10.741 | 24.700 | 1.00 | 65.40 | H | C |
| ATOM | 2802 | OG | SER | 182 | 89.612 | -11.868 | 25.543 | 1.00 | 59.63 | H | O |
| ATOM | 2803 | C | SER | 182 | 91.860 | -10.209 | 24.970 | 1.00 | 33.65 | H | C |
| ATOM | 2804 | O | SER | 182 | 92.494 | -10.187 | 23.906 | 1.00 | 37.13 | H | O |
| ATOM | 2805 | N | LEU | 183 | 92.351 | -10.713 | 26.101 | 1.00 | 28.98 | H | N |
| ATOM | 2806 | CA | LEU | 183 | 93.689 | -11.290 | 26.152 | 1.00 | 24.91 | H | C |
| ATOM | 2807 | CB | LEU | 183 | 94.753 | -10.179 | 26.189 | 1.00 | 31.36 | H | C |
| ATOM | 2808 | CG | LEU | 183 | 94.913 | -9.263 | 27.414 | 1.00 | 23.12 | H | C |
| ATOM | 2809 | CD1 | LEU | 183 | 95.475 | -10.014 | 28.625 | 1.00 | 27.02 | H | C |
| ATOM | 2810 | CD2 | LEU | 183 | 95.849 | -8.148 | 27.036 | 1.00 | 19.84 | H | C |
| ATOM | 2811 | C | LEU | 183 | 93.898 | -12.209 | 27.342 | 1.00 | 24.58 | H | C |
| ATOM | 2812 | O | LEU | 183 | 93.179 | -12.135 | 28.326 | 1.00 | 18.76 | H | O |
| ATOM | 2813 | N | SER | 184 | 94.894 | -13.077 | 27.250 | 1.00 | 26.13 | H | N |
| ATOM | 2814 | CA | SER | 184 | 95.205 | -13.967 | 28.357 | 1.00 | 26.65 | H | C |
| ATOM | 2815 | CB | SER | 184 | 95.000 | -15.445 | 27.968 | 1.00 | 16.60 | H | C |
| ATOM | 2816 | OG | SER | 184 | 93.638 | -15.750 | 27.710 | 1.00 | 22.49 | H | O |
| ATOM | 2817 | C | SER | 184 | 96.660 | -13.752 | 28.784 | 1.00 | 22.47 | H | C |
| ATOM | 2818 | O | SER | 184 | 97.546 | -13.511 | 27.953 | 1.00 | 21.27 | H | O |
| ATOM | 2819 | N | SER | 185 | 96.896 | -13.786 | 30.087 | 1.00 | 27.49 | H | N |
| ATOM | 2820 | CA | SER | 185 | 98.251 | -13.670 | 30.575 | 1.00 | 25.55 | H | C |
| ATOM | 2821 | CB | SER | 185 | 98.389 | -12.634 | 31.678 | 1.00 | 27.24 | H | C |
| ATOM | 2822 | OG | SER | 185 | 99.760 | -12.516 | 32.031 | 1.00 | 25.68 | H | O |
| ATOM | 2823 | C | SER | 185 | 98.460 | -15.060 | 31.123 | 1.00 | 23.97 | H | C |
| ATOM | 2824 | O | SER | 185 | 97.652 | -15.551 | 31.912 | 1.00 | 25.28 | H | O |
| ATOM | 2825 | N | VAL | 186 | 99.533 | -15.699 | 30.679 | 1.00 | 29.81 | H | N |
| ATOM | 2826 | CA | VAL | 186 | 99.830 | -17.060 | 31.064 | 1.00 | 29.28 | H | C |
| ATOM | 2827 | CB | VAL | 186 | 99.717 | -17.966 | 29.831 | 1.00 | 20.56 | H | C |
| ATOM | 2828 | CG1 | VAL | 186 | 100.305 | -19.306 | 30.112 | 1.00 | 20.80 | H | C |
| ATOM | 2829 | CG2 | VAL | 186 | 98.253 | -18.121 | 29.446 | 1.00 | 19.74 | H | C |
| ATOM | 2830 | C | VAL | 186 | 101.204 | -17.193 | 31.664 | 1.00 | 30.42 | H | C |
| ATOM | 2831 | O | VAL | 186 | 102.097 | -16.416 | 31.357 | 1.00 | 31.20 | H | O |
| ATOM | 2832 | N | VAL | 187 | 101.359 | -18.179 | 32.540 | 1.00 | 29.47 | H | N |
| ATOM | 2833 | CA | VAL | 187 | 102.645 | -18.457 | 33.178 | 1.00 | 26.42 | H | C |
| ATOM | 2834 | CB | VAL | 187 | 102.739 | -17.797 | 34.586 | 1.00 | 27.93 | H | C |
| ATOM | 2835 | CG1 | VAL | 187 | 101.681 | -18.385 | 35.507 | 1.00 | 26.86 | H | C |
| ATOM | 2836 | CG2 | VAL | 187 | 104.134 | -17.994 | 35.180 | 1.00 | 26.29 | H | C |
| ATOM | 2837 | C | VAL | 187 | 102.842 | -19.975 | 33.309 | 1.00 | 20.75 | H | C |
| ATOM | 2838 | O | VAL | 187 | 101.882 | -20.743 | 33.316 | 1.00 | 22.47 | H | O |
| ATOM | 2839 | N | THR | 188 | 104.098 | -20.397 | 33.377 | 1.00 | 5.29 | H | N |
| ATOM | 2840 | CA | THR | 188 | 104.441 | -21.807 | 33.539 | 1.00 | 7.86 | H | C |
| ATOM | 2841 | CB | THR | 188 | 105.280 | -22.327 | 32.366 | 1.00 | 35.20 | H | C |
| ATOM | 2842 | OG1 | THR | 188 | 106.425 | -21.487 | 32.194 | 1.00 | 33.26 | H | O |
| ATOM | 2843 | CG2 | THR | 188 | 104.453 | -22.337 | 31.078 | 1.00 | 39.96 | H | C |
| ATOM | 2844 | C | THR | 188 | 105.270 | -21.870 | 34.802 | 1.00 | 13.86 | H | C |
| ATOM | 2845 | O | THR | 188 | 106.194 | -21.077 | 34.975 | 1.00 | 18.45 | H | O |
| ATOM | 2846 | N | VAL | 189 | 104.921 | -22.799 | 35.688 | 1.00 | 28.00 | H | N |
| ATOM | 2847 | CA | VAL | 189 | 105.613 | -22.963 | 36.965 | 1.00 | 25.42 | H | C |

Fig. 19: A-40

| | | | | | | | | | | |
|---|---|---|---|---|---|---|---|---|---|---|
| ATOM | 2848 | CB | VAL | 189 | 104.755 | -22.412 | 38.137 | 1.00 | 24.28 | H | C |
| ATOM | 2849 | CG1 | VAL | 189 | 104.399 | -20.951 | 37.904 | 1.00 | 17.23 | H | C |
| ATOM | 2850 | CG2 | VAL | 189 | 103.478 | -23.234 | 38.270 | 1.00 | 17.84 | H | C |
| ATOM | 2851 | C | VAL | 189 | 105.875 | -24.439 | 37.242 | 1.00 | 32.15 | H | C |
| ATOM | 2852 | O | VAL | 189 | 105.386 | -25.309 | 36.523 | 1.00 | 35.18 | H | O |
| ATOM | 2853 | N | PRO | 190 | 106.671 | -24.738 | 38.280 | 1.00 | 50.39 | H | N |
| ATOM | 2854 | CD | PRO | 190 | 107.545 | -23.823 | 39.036 | 1.00 | 32.03 | H | C |
| ATOM | 2855 | CA | PRO | 190 | 106.962 | -26.133 | 38.624 | 1.00 | 50.40 | H | C |
| ATOM | 2856 | CB | PRO | 190 | 107.911 | -26.001 | 39.814 | 1.00 | 29.50 | H | C |
| ATOM | 2857 | CG | PRO | 190 | 108.651 | -24.746 | 39.514 | 1.00 | 29.72 | H | C |
| ATOM | 2858 | C | PRO | 190 | 105.650 | -26.801 | 39.018 | 1.00 | 50.46 | H | C |
| ATOM | 2859 | O | PRO | 190 | 104.899 | -26.267 | 39.834 | 1.00 | 48.43 | H | O |
| ATOM | 2860 | N | SER | 191 | 105.357 | -27.953 | 38.436 | 1.00 | 54.29 | H | N |
| ATOM | 2861 | CA | SER | 191 | 104.122 | -28.638 | 38.774 | 1.00 | 60.79 | H | C |
| ATOM | 2862 | CB | SER | 191 | 104.111 | -30.036 | 38.157 | 1.00 | 30.49 | H | C |
| ATOM | 2863 | OG | SER | 191 | 104.076 | -29.980 | 36.740 | 1.00 | 31.07 | H | O |
| ATOM | 2864 | C | SER | 191 | 104.009 | -28.730 | 40.297 | 1.00 | 63.91 | H | C |
| ATOM | 2865 | O | SER | 191 | 102.986 | -28.361 | 40.882 | 1.00 | 66.82 | H | O |
| ATOM | 2866 | N | SER | 192 | 105.084 | -29.201 | 40.924 | 1.00 | 39.50 | H | N |
| ATOM | 2867 | CA | SER | 192 | 105.177 | -29.374 | 42.376 | 1.00 | 40.99 | H | C |
| ATOM | 2868 | CB | SER | 192 | 106.602 | -29.776 | 42.739 | 1.00 | 41.75 | H | C |
| ATOM | 2869 | OG | SER | 192 | 107.475 | -28.675 | 42.565 | 1.00 | 41.65 | H | O |
| ATOM | 2870 | C | SER | 192 | 104.795 | -28.150 | 43.220 | 1.00 | 42.26 | H | C |
| ATOM | 2871 | O | SER | 192 | 104.403 | -28.286 | 44.381 | 1.00 | 48.17 | H | O |
| ATOM | 2872 | N | SER | 193 | 104.923 | -26.960 | 42.645 | 1.00 | 20.64 | H | N |
| ATOM | 2873 | CA | SER | 193 | 104.601 | -25.733 | 43.365 | 1.00 | 22.36 | H | C |
| ATOM | 2874 | CB | SER | 193 | 105.396 | -24.567 | 42.771 | 1.00 | 39.90 | H | C |
| ATOM | 2875 | OG | SER | 193 | 104.973 | -24.284 | 41.447 | 1.00 | 36.65 | H | O |
| ATOM | 2876 | C | SER | 193 | 103.097 | -25.380 | 43.392 | 1.00 | 22.92 | H | C |
| ATOM | 2877 | O | SER | 193 | 102.697 | -24.363 | 43.963 | 1.00 | 25.84 | H | O |
| ATOM | 2878 | N | LEU | 194 | 102.268 | -26.218 | 42.776 | 1.00 | 41.78 | H | N |
| ATOM | 2879 | CA | LEU | 194 | 100.827 | -25.974 | 42.741 | 1.00 | 45.87 | H | C |
| ATOM | 2880 | CB | LEU | 194 | 100.172 | -26.850 | 41.677 | 1.00 | 23.80 | H | C |
| ATOM | 2881 | CG | LEU | 194 | 100.533 | -26.605 | 40.216 | 1.00 | 21.31 | H | C |
| ATOM | 2882 | CD1 | LEU | 194 | 99.975 | -27.739 | 39.377 | 1.00 | 19.27 | H | C |
| ATOM | 2883 | CD2 | LEU | 194 | 99.973 | -25.246 | 39.757 | 1.00 | 15.31 | H | C |
| ATOM | 2884 | C | LEU | 194 | 100.177 | -26.276 | 44.080 | 1.00 | 49.01 | H | C |
| ATOM | 2885 | O | LEU | 194 | 99.209 | -25.623 | 44.478 | 1.00 | 48.38 | H | O |
| ATOM | 2886 | N | GLY | 195 | 100.718 | -27.272 | 44.770 | 1.00 | 65.65 | H | N |
| ATOM | 2887 | CA | GLY | 195 | 100.160 | -27.676 | 46.043 | 1.00 | 68.76 | H | C |
| ATOM | 2888 | C | GLY | 195 | 100.625 | -26.877 | 47.235 | 1.00 | 66.22 | H | C |
| ATOM | 2889 | O | GLY | 195 | 100.051 | -26.992 | 48.314 | 1.00 | 68.30 | H | O |
| ATOM | 2890 | N | THR | 196 | 101.659 | -26.067 | 47.053 | 1.00 | 33.26 | H | N |
| ATOM | 2891 | CA | THR | 196 | 102.175 | -25.265 | 48.155 | 1.00 | 32.73 | H | C |
| ATOM | 2892 | CB | THR | 196 | 103.575 | -25.763 | 48.585 | 1.00 | 30.77 | H | C |
| ATOM | 2893 | OG1 | THR | 196 | 104.489 | -25.676 | 47.478 | 1.00 | 28.63 | H | O |
| ATOM | 2894 | CG2 | THR | 196 | 103.488 | -27.213 | 49.071 | 1.00 | 27.23 | H | C |
| ATOM | 2895 | C | THR | 196 | 102.251 | -23.786 | 47.813 | 1.00 | 35.97 | H | C |
| ATOM | 2896 | O | THR | 196 | 102.179 | -22.933 | 48.695 | 1.00 | 36.72 | H | O |
| ATOM | 2897 | N | GLN | 197 | 102.389 | -23.488 | 46.527 | 1.00 | 53.90 | H | N |
| ATOM | 2898 | CA | GLN | 197 | 102.478 | -22.110 | 46.060 | 1.00 | 54.25 | H | C |
| ATOM | 2899 | CB | GLN | 197 | 103.480 | -22.031 | 44.906 | 1.00 | 42.12 | H | C |
| ATOM | 2900 | CG | GLN | 197 | 104.561 | -20.975 | 45.045 | 1.00 | 45.66 | H | C |
| ATOM | 2901 | CD | GLN | 197 | 104.051 | -19.587 | 44.765 | 1.00 | 49.49 | H | C |
| ATOM | 2902 | OE1 | GLN | 197 | 103.257 | -19.032 | 45.528 | 1.00 | 50.05 | H | O |
| ATOM | 2903 | NE2 | GLN | 197 | 104.500 | -19.013 | 43.656 | 1.00 | 49.01 | H | N |
| ATOM | 2904 | C | GLN | 197 | 101.105 | -21.617 | 45.604 | 1.00 | 52.98 | H | C |
| ATOM | 2905 | O | GLN | 197 | 100.314 | -22.382 | 45.050 | 1.00 | 55.53 | H | O |
| ATOM | 2906 | N | THR | 198 | 100.829 | -20.338 | 45.847 | 1.00 | 30.38 | H | N |
| ATOM | 2907 | CA | THR | 198 | 99.559 | -19.719 | 45.470 | 1.00 | 29.29 | H | C |
| ATOM | 2908 | CB | THR | 198 | 98.922 | -18.970 | 46.677 | 1.00 | 45.77 | H | C |
| ATOM | 2909 | OG1 | THR | 198 | 97.546 | -18.682 | 46.404 | 1.00 | 43.55 | H | O |
| ATOM | 2910 | CG2 | THR | 198 | 99.643 | -17.644 | 46.929 | 1.00 | 47.95 | H | C |
| ATOM | 2911 | C | THR | 198 | 99.811 | -18.719 | 44.338 | 1.00 | 27.94 | H | C |
| ATOM | 2912 | O | THR | 198 | 100.722 | -17.891 | 44.413 | 1.00 | 31.22 | H | O |
| ATOM | 2913 | N | TYR | 199 | 99.008 | -18.789 | 43.285 | 1.00 | 40.84 | H | N |
| ATOM | 2914 | CA | TYR | 199 | 99.191 | -17.874 | 42.168 | 1.00 | 31.26 | H | C |
| ATOM | 2915 | CB | TYR | 199 | 99.402 | -18.681 | 40.880 | 1.00 | 39.46 | H | C |
| ATOM | 2916 | CG | TYR | 199 | 100.677 | -19.496 | 40.904 | 1.00 | 33.83 | H | C |
| ATOM | 2917 | CD1 | TYR | 199 | 101.911 | -18.901 | 40.630 | 1.00 | 31.63 | H | C |
| ATOM | 2918 | CE1 | TYR | 199 | 103.107 | -19.626 | 40.735 | 1.00 | 31.28 | H | C |
| ATOM | 2919 | CD2 | TYR | 199 | 100.662 | -20.847 | 41.282 | 1.00 | 32.94 | H | C |
| ATOM | 2920 | CE2 | TYR | 199 | 101.850 | -21.590 | 41.392 | 1.00 | 33.91 | H | C |

Fig. 19: A-41

```
ATOM   2921  CZ   TYR  199     103.069  -20.972   41.118  1.00   33.40      H  C
ATOM   2922  OH   TYR  199     104.244  -21.685   41.223  1.00   37.29      H  O
ATOM   2923  C    TYR  199      98.029  -16.897   42.014  1.00   31.50      H  C
ATOM   2924  O    TYR  199      96.876  -17.302   41.913  1.00   32.18      H  O
ATOM   2925  N    ILE  200      98.342  -15.605   42.026  1.00   38.61      H  N
ATOM   2926  CA   ILE  200      97.329  -14.566   41.858  1.00   39.11      H  C
ATOM   2927  CB   ILE  200      97.265  -13.574   43.051  1.00   27.10      H  C
ATOM   2928  CG2  ILE  200      96.185  -12.540   42.793  1.00   26.36      H  C
ATOM   2929  CG1  ILE  200      96.978  -14.301   44.363  1.00   30.59      H  C
ATOM   2930  CD1  ILE  200      98.119  -15.184   44.842  1.00   36.15      H  C
ATOM   2931  C    ILE  200      97.730  -13.736   40.649  1.00   41.59      H  C
ATOM   2932  O    ILE  200      98.916  -13.517   40.415  1.00   45.01      H  O
ATOM   2933  N    CYS  201      96.758  -13.283   39.867  1.00   30.01      H  N
ATOM   2934  CA   CYS  201      97.092  -12.434   38.735  1.00   27.23      H  C
ATOM   2935  C    CYS  201      96.476  -11.075   39.011  1.00   24.60      H  C
ATOM   2936  O    CYS  201      95.307  -10.967   39.386  1.00   22.36      H  O
ATOM   2937  CB   CYS  201      96.577  -12.997   37.394  1.00   42.80      H  C
ATOM   2938  SG   CYS  201      94.784  -12.909   37.090  1.00   39.16      H  S
ATOM   2939  N    ASN  202      97.282  -10.035   38.849  1.00   26.40      H  N
ATOM   2940  CA   ASN  202      96.819   -8.683   39.080  1.00   32.39      H  C
ATOM   2941  CB   ASN  202      97.884   -7.902   39.846  1.00   36.85      H  C
ATOM   2942  CG   ASN  202      98.507   -8.720   40.954  1.00   39.80      H  C
ATOM   2943  OD1  ASN  202      99.570   -9.314   40.779  1.00   38.11      H  O
ATOM   2944  ND2  ASN  202      97.837   -8.776   42.097  1.00   41.02      H  N
ATOM   2945  C    ASN  202      96.530   -8.025   37.743  1.00   36.08      H  C
ATOM   2946  O    ASN  202      97.419   -7.867   36.911  1.00   40.34      H  O
ATOM   2947  N    VAL  203      95.273   -7.668   37.533  1.00   28.99      H  N
ATOM   2948  CA   VAL  203      94.868   -7.017   36.295  1.00   29.18      H  C
ATOM   2949  CB   VAL  203      93.691   -7.781   35.624  1.00   21.70      H  C
ATOM   2950  CG1  VAL  203      93.321   -7.134   34.274  1.00   17.35      H  C
ATOM   2951  CG2  VAL  203      94.067   -9.236   35.450  1.00   25.16      H  C
ATOM   2952  C    VAL  203      94.443   -5.580   36.615  1.00   32.31      H  C
ATOM   2953  O    VAL  203      93.808   -5.320   37.643  1.00   27.84      H  O
ATOM   2954  N    ASN  204      94.799   -4.648   35.741  1.00   45.86      H  N
ATOM   2955  CA   ASN  204      94.442   -3.266   35.979  1.00   50.50      H  C
ATOM   2956  CB   ASN  204      95.565   -2.570   36.739  1.00   59.79      H  C
ATOM   2957  CG   ASN  204      95.186   -1.176   37.164  1.00   65.34      H  C
ATOM   2958  OD1  ASN  204      94.801   -0.347   36.338  1.00   69.10      H  O
ATOM   2959  ND2  ASN  204      95.287   -0.906   38.459  1.00   65.59      H  N
ATOM   2960  C    ASN  204      94.109   -2.486   34.709  1.00   51.54      H  C
ATOM   2961  O    ASN  204      94.985   -2.164   33.905  1.00   51.77      H  O
ATOM   2962  N    HIS  205      92.828   -2.176   34.550  1.00   30.40      H  N
ATOM   2963  CA   HIS  205      92.338   -1.431   33.396  1.00   29.10      H  C
ATOM   2964  CB   HIS  205      90.994   -1.998   32.957  1.00   20.87      H  C
ATOM   2965  CG   HIS  205      90.444   -1.371   31.718  1.00   25.68      H  C
ATOM   2966  CD2  HIS  205      89.209   -0.889   31.437  1.00   28.69      H  C
ATOM   2967  ND1  HIS  205      91.165   -1.282   30.548  1.00   23.44      H  N
ATOM   2968  CE1  HIS  205      90.396   -0.780   29.597  1.00   25.19      H  C
ATOM   2969  NE2  HIS  205      89.203   -0.534   30.110  1.00   28.16      H  N
ATOM   2970  C    HIS  205      92.157    0.022   33.793  1.00   30.12      H  C
ATOM   2971  O    HIS  205      91.057    0.429   34.173  1.00   28.02      H  O
ATOM   2972  N    LYS  206      93.228    0.805   33.714  1.00   50.94      H  N
ATOM   2973  CA   LYS  206      93.138    2.209   34.084  1.00   49.11      H  C
ATOM   2974  CB   LYS  206      94.486    2.906   33.867  1.00   50.82      H  C
ATOM   2975  CG   LYS  206      95.536    2.476   34.895  1.00   57.82      H  C
ATOM   2976  CD   LYS  206      96.809    3.325   34.857  1.00   61.64      H  C
ATOM   2977  CE   LYS  206      97.793    2.906   35.959  1.00   63.00      H  C
ATOM   2978  NZ   LYS  206      99.049    3.715   35.960  1.00   66.30      H  N
ATOM   2979  C    LYS  206      92.017    2.949   33.353  1.00   47.68      H  C
ATOM   2980  O    LYS  206      91.318    3.765   33.955  1.00   46.73      H  O
ATOM   2981  N    PRO  207      91.810    2.650   32.057  1.00   33.42      H  N
ATOM   2982  CD   PRO  207      92.613    1.722   31.239  1.00   21.52      H  C
ATOM   2983  CA   PRO  207      90.770    3.285   31.241  1.00   34.06      H  C
ATOM   2984  CB   PRO  207      90.831    2.501   29.936  1.00   21.18      H  C
ATOM   2985  CG   PRO  207      92.286    2.156   29.831  1.00   24.69      H  C
ATOM   2986  C    PRO  207      89.366    3.280   31.846  1.00   34.36      H  C
ATOM   2987  O    PRO  207      88.452    3.927   31.311  1.00   32.31      H  O
ATOM   2988  N    SER  208      89.190    2.545   32.944  1.00   25.18      H  N
ATOM   2989  CA   SER  208      87.893    2.481   33.628  1.00   28.11      H  C
ATOM   2990  CB   SER  208      87.055    1.320   33.094  1.00   29.27      H  C
ATOM   2991  OG   SER  208      87.724    0.096   33.315  1.00   27.44      H  O
ATOM   2992  C    SER  208      88.120    2.314   35.126  1.00   31.08      H  C
ATOM   2993  O    SER  208      87.266    1.789   35.846  1.00   34.78      H  O
```

Fig. 19: A-42

| | | | | | | | | | | | |
|---|---|---|---|---|---|---|---|---|---|---|---|
| ATOM | 2994 | N | ASN | 209 | 89.284 | 2.777 | 35.573 | 1.00 | 68.02 | H | N |
| ATOM | 2995 | CA | ASN | 209 | 89.678 | 2.701 | 36.970 | 1.00 | 70.18 | H | C |
| ATOM | 2996 | CB | ASN | 209 | 89.073 | 3.879 | 37.741 | 1.00 | 49.77 | H | C |
| ATOM | 2997 | CG | ASN | 209 | 89.673 | 4.044 | 39.125 | 1.00 | 56.50 | H | C |
| ATOM | 2998 | OD1 | ASN | 209 | 90.885 | 3.963 | 39.301 | 1.00 | 62.08 | H | O |
| ATOM | 2999 | ND2 | ASN | 209 | 88.824 | 4.290 | 40.114 | 1.00 | 57.03 | H | N |
| ATOM | 3000 | C | ASN | 209 | 89.267 | 1.360 | 37.593 | 1.00 | 68.80 | H | C |
| ATOM | 3001 | O | ASN | 209 | 88.708 | 1.304 | 38.690 | 1.00 | 68.05 | H | O |
| ATOM | 3002 | N | THR | 210 | 89.555 | 0.282 | 36.871 | 1.00 | 35.45 | H | N |
| ATOM | 3003 | CA | THR | 210 | 89.246 | -1.061 | 37.322 | 1.00 | 37.08 | H | C |
| ATOM | 3004 | CB | THR | 210 | 88.640 | -1.883 | 36.201 | 1.00 | 55.80 | H | C |
| ATOM | 3005 | OG1 | THR | 210 | 87.416 | -1.273 | 35.787 | 1.00 | 56.14 | H | O |
| ATOM | 3006 | CG2 | THR | 210 | 88.367 | -3.303 | 36.668 | 1.00 | 57.05 | H | C |
| ATOM | 3007 | C | THR | 210 | 90.538 | -1.719 | 37.762 | 1.00 | 36.35 | H | C |
| ATOM | 3008 | O | THR | 210 | 91.613 | -1.388 | 37.266 | 1.00 | 34.79 | H | O |
| ATOM | 3009 | N | LYS | 211 | 90.426 | -2.655 | 38.692 | 1.00 | 33.96 | H | N |
| ATOM | 3010 | CA | LYS | 211 | 91.588 | -3.352 | 39.207 | 1.00 | 34.09 | H | C |
| ATOM | 3011 | CB | LYS | 211 | 92.366 | -2.422 | 40.154 | 1.00 | 52.60 | H | C |
| ATOM | 3012 | CG | LYS | 211 | 93.360 | -3.095 | 41.117 | 1.00 | 57.40 | H | C |
| ATOM | 3013 | CD | LYS | 211 | 94.338 | -4.040 | 40.416 | 1.00 | 62.07 | H | C |
| ATOM | 3014 | CE | LYS | 211 | 95.636 | -4.228 | 41.216 | 1.00 | 64.56 | H | C |
| ATOM | 3015 | NZ | LYS | 211 | 95.432 | -4.548 | 42.660 | 1.00 | 65.70 | H | N |
| ATOM | 3016 | C | LYS | 211 | 91.147 | -4.609 | 39.935 | 1.00 | 32.12 | H | C |
| ATOM | 3017 | O | LYS | 211 | 90.611 | -4.525 | 41.036 | 1.00 | 32.03 | H | O |
| ATOM | 3018 | N | VAL | 212 | 91.357 | -5.772 | 39.322 | 1.00 | 43.02 | H | N |
| ATOM | 3019 | CA | VAL | 212 | 90.971 | -7.017 | 39.973 | 1.00 | 37.80 | H | C |
| ATOM | 3020 | CB | VAL | 212 | 89.728 | -7.685 | 39.308 | 1.00 | 28.95 | H | C |
| ATOM | 3021 | CG1 | VAL | 212 | 88.671 | -6.639 | 39.021 | 1.00 | 26.33 | H | C |
| ATOM | 3022 | CG2 | VAL | 212 | 90.125 | -8.431 | 38.059 | 1.00 | 26.83 | H | C |
| ATOM | 3023 | C | VAL | 212 | 92.086 | -8.042 | 40.020 | 1.00 | 39.84 | H | C |
| ATOM | 3024 | O | VAL | 212 | 92.832 | -8.224 | 39.057 | 1.00 | 39.92 | H | O |
| ATOM | 3025 | N | ASP | 213 | 92.184 | -8.709 | 41.162 | 1.00 | 52.39 | H | N |
| ATOM | 3026 | CA | ASP | 213 | 93.177 | -9.743 | 41.376 | 1.00 | 49.02 | H | C |
| ATOM | 3027 | CB | ASP | 213 | 93.900 | -9.493 | 42.692 | 1.00 | 46.86 | H | C |
| ATOM | 3028 | CG | ASP | 213 | 94.548 | -8.128 | 42.740 | 1.00 | 52.80 | H | C |
| ATOM | 3029 | OD1 | ASP | 213 | 95.420 | -7.852 | 41.887 | 1.00 | 56.11 | H | O |
| ATOM | 3030 | OD2 | ASP | 213 | 94.182 | -7.329 | 43.626 | 1.00 | 57.38 | H | O |
| ATOM | 3031 | C | ASP | 213 | 92.433 | -11.067 | 41.423 | 1.00 | 46.03 | H | C |
| ATOM | 3032 | O | ASP | 213 | 91.537 | -11.248 | 42.236 | 1.00 | 45.16 | H | O |
| ATOM | 3033 | N | LYS | 214 | 92.796 | -11.993 | 40.548 | 1.00 | 33.42 | H | N |
| ATOM | 3034 | CA | LYS | 214 | 92.124 | -13.282 | 40.502 | 1.00 | 29.46 | H | C |
| ATOM | 3035 | CB | LYS | 214 | 91.732 | -13.602 | 39.055 | 0.00 | 52.86 | H | C |
| ATOM | 3036 | CG | LYS | 214 | 90.422 | -14.370 | 38.875 | 0.00 | 47.62 | H | C |
| ATOM | 3037 | CD | LYS | 214 | 90.398 | -15.699 | 39.614 | 0.00 | 43.68 | H | C |
| ATOM | 3038 | CE | LYS | 214 | 89.852 | -15.541 | 41.024 | 0.00 | 41.24 | H | C |
| ATOM | 3039 | NZ | LYS | 214 | 88.452 | -15.037 | 41.021 | 0.00 | 39.27 | H | N |
| ATOM | 3040 | C | LYS | 214 | 93.027 | -14.377 | 41.047 | 1.00 | 29.68 | H | C |
| ATOM | 3041 | O | LYS | 214 | 94.160 | -14.549 | 40.585 | 1.00 | 27.06 | H | O |
| ATOM | 3042 | N | LYS | 215 | 92.533 | -15.103 | 42.045 | 1.00 | 38.49 | H | N |
| ATOM | 3043 | CA | LYS | 215 | 93.289 | -16.207 | 42.617 | 1.00 | 34.59 | H | C |
| ATOM | 3044 | CB | LYS | 215 | 92.788 | -16.531 | 44.032 | 0.00 | 48.10 | H | C |
| ATOM | 3045 | CG | LYS | 215 | 92.812 | -15.343 | 44.987 | 0.00 | 42.43 | H | C |
| ATOM | 3046 | CD | LYS | 215 | 92.403 | -15.737 | 46.401 | 0.00 | 38.17 | H | C |
| ATOM | 3047 | CE | LYS | 215 | 93.458 | -16.597 | 47.089 | 0.00 | 35.48 | H | C |
| ATOM | 3048 | NZ | LYS | 215 | 93.695 | -17.895 | 46.397 | 0.00 | 33.32 | H | N |
| ATOM | 3049 | C | LYS | 215 | 93.042 | -17.391 | 41.675 | 1.00 | 36.50 | H | C |
| ATOM | 3050 | O | LYS | 215 | 91.901 | -17.770 | 41.413 | 1.00 | 38.63 | H | O |
| ATOM | 3051 | N | VAL | 216 | 94.113 | -17.939 | 41.122 | 1.00 | 32.15 | H | N |
| ATOM | 3052 | CA | VAL | 216 | 93.996 | -19.081 | 40.224 | 1.00 | 32.08 | H | C |
| ATOM | 3053 | CB | VAL | 216 | 94.801 | -18.850 | 38.923 | 1.00 | 21.03 | H | C |
| ATOM | 3054 | CG1 | VAL | 216 | 94.435 | -19.912 | 37.880 | 1.00 | 20.14 | H | C |
| ATOM | 3055 | CG2 | VAL | 216 | 94.482 | -17.480 | 38.375 | 1.00 | 18.92 | H | C |
| ATOM | 3056 | C | VAL | 216 | 94.504 | -20.334 | 40.948 | 1.00 | 33.21 | H | C |
| ATOM | 3057 | O | VAL | 216 | 95.696 | -20.441 | 41.248 | 1.00 | 33.32 | H | O |
| ATOM | 3058 | N | GLU | 217 | 93.586 | -21.269 | 41.219 | 1.00 | 45.06 | H | N |
| ATOM | 3059 | CA | GLU | 217 | 93.871 | -22.508 | 41.949 | 1.00 | 48.19 | H | C |
| ATOM | 3060 | CB | GLU | 217 | 93.065 | -22.532 | 43.250 | 1.00 | 91.11 | H | C |
| ATOM | 3061 | CG | GLU | 217 | 93.114 | -21.248 | 44.065 | 1.00 | 95.99 | H | C |
| ATOM | 3062 | CD | GLU | 217 | 91.872 | -21.005 | 44.901 | 1.00 | 101.94 | H | C |
| ATOM | 3063 | OE1 | GLU | 217 | 90.757 | -21.353 | 44.453 | 1.00 | 105.02 | H | O |
| ATOM | 3064 | OE2 | GLU | 217 | 92.013 | -20.475 | 46.029 | 1.00 | 105.37 | H | O |
| ATOM | 3065 | C | GLU | 217 | 93.426 | -23.720 | 41.109 | 1.00 | 48.96 | H | C |
| ATOM | 3066 | O | GLU | 217 | 92.500 | -23.643 | 40.332 | 1.00 | 51.24 | H | O |

Fig. 19: A-43

| ATOM | 3067 | N | PRO | 218 | 94.078 | -24.870 | 41.265 | 1.00 | 42.53 | H | N |
|---|---|---|---|---|---|---|---|---|---|---|---|
| ATOM | 3068 | CD | PRO | 218 | 95.339 | -25.074 | 41.993 | 1.00 | 48.02 | H | C |
| ATOM | 3069 | CA | PRO | 218 | 93.711 | -26.079 | 40.509 | 1.00 | 40.69 | H | C |
| ATOM | 3070 | CB | PRO | 218 | 94.962 | -26.924 | 40.609 | 1.00 | 42.70 | H | C |
| ATOM | 3071 | CG | PRO | 218 | 95.482 | -26.557 | 41.957 | 1.00 | 44.19 | H | C |
| ATOM | 3072 | C | PRO | 218 | 92.544 | -26.782 | 41.183 | 1.00 | 41.85 | H | C |
| ATOM | 3073 | O | PRO | 218 | 92.513 | -26.844 | 42.403 | 1.00 | 45.36 | H | O |
| ATOM | 3074 | N | LYS | 219 | 91.638 | -27.354 | 40.396 | 1.00 | 112.06 | H | N |
| ATOM | 3075 | CA | LYS | 219 | 90.475 | -28.045 | 40.934 | 1.00 | 111.92 | H | C |
| ATOM | 3076 | CB | LYS | 219 | 89.635 | -28.618 | 39.794 | 0.00 | 52.93 | H | C |
| ATOM | 3077 | CG | LYS | 219 | 89.522 | -27.658 | 38.654 | 0.00 | 47.21 | H | C |
| ATOM | 3078 | CD | LYS | 219 | 88.205 | -27.801 | 37.948 | 0.00 | 42.71 | H | C |
| ATOM | 3079 | CE | LYS | 219 | 88.174 | -26.793 | 36.845 | 0.00 | 39.84 | H | C |
| ATOM | 3080 | NZ | LYS | 219 | 86.847 | -26.599 | 36.249 | 0.00 | 37.57 | H | N |
| ATOM | 3081 | C | LYS | 219 | 90.867 | -29.169 | 41.892 | 1.00 | 116.73 | H | C |
| ATOM | 3082 | O | LYS | 219 | 90.330 | -29.223 | 43.021 | 1.00 | 116.18 | H | O |
| ATOM | 3083 | OXT | LYS | 219 | 91.705 | -30.007 | 41.503 | 1.00 | 36.39 | H | O |
| ATOM | 3084 | CB | ILE | 2 | 109.298 | 10.543 | -2.157 | 1.00 | 31.85 | L | C |
| ATOM | 3085 | CG2 | ILE | 2 | 110.285 | 9.382 | -2.130 | 1.00 | 31.85 | L | C |
| ATOM | 3086 | CG1 | ILE | 2 | 109.803 | 11.664 | -3.069 | 1.00 | 31.85 | L | C |
| ATOM | 3087 | CD1 | ILE | 2 | 111.143 | 12.240 | -2.656 | 1.00 | 31.85 | L | C |
| ATOM | 3088 | C | ILE | 2 | 107.518 | 8.858 | -1.778 | 1.00 | 41.66 | L | C |
| ATOM | 3089 | O | ILE | 2 | 107.155 | 9.019 | -0.613 | 1.00 | 41.66 | L | O |
| ATOM | 3090 | N | ILE | 2 | 106.898 | 11.133 | -2.646 | 1.00 | 41.66 | L | N |
| ATOM | 3091 | CA | ILE | 2 | 107.922 | 10.043 | -2.648 | 1.00 | 41.66 | L | C |
| ATOM | 3092 | N | GLN | 3 | 107.597 | 7.665 | -2.361 | 1.00 | 28.81 | L | N |
| ATOM | 3093 | CA | GLN | 3 | 107.244 | 6.433 | -1.669 | 1.00 | 28.81 | L | C |
| ATOM | 3094 | CB | GLN | 3 | 106.206 | 5.677 | -2.484 | 1.00 | 56.92 | L | C |
| ATOM | 3095 | CG | GLN | 3 | 105.708 | 4.412 | -1.837 | 1.00 | 56.92 | L | C |
| ATOM | 3096 | CD | GLN | 3 | 104.579 | 3.778 | -2.622 | 1.00 | 56.92 | L | C |
| ATOM | 3097 | OE1 | GLN | 3 | 104.124 | 2.681 | -2.298 | 1.00 | 56.92 | L | O |
| ATOM | 3098 | NE2 | GLN | 3 | 104.116 | 4.469 | -3.661 | 1.00 | 56.92 | L | N |
| ATOM | 3099 | C | GLN | 3 | 108.482 | 5.557 | -1.428 | 1.00 | 28.81 | L | C |
| ATOM | 3100 | O | GLN | 3 | 109.297 | 5.322 | -2.327 | 1.00 | 28.81 | L | O |
| ATOM | 3101 | N | LEU | 4 | 108.615 | 5.088 | -0.195 | 1.00 | 39.62 | L | N |
| ATOM | 3102 | CA | LEU | 4 | 109.744 | 4.260 | 0.198 | 1.00 | 39.62 | L | C |
| ATOM | 3103 | CB | LEU | 4 | 110.377 | 4.820 | 1.469 | 1.00 | 19.64 | L | C |
| ATOM | 3104 | CG | LEU | 4 | 111.546 | 5.792 | 1.348 | 1.00 | 19.64 | L | C |
| ATOM | 3105 | CD1 | LEU | 4 | 111.407 | 6.643 | 0.092 | 1.00 | 19.64 | L | C |
| ATOM | 3106 | CD2 | LEU | 4 | 111.614 | 6.640 | 2.617 | 1.00 | 19.64 | L | C |
| ATOM | 3107 | C | LEU | 4 | 109.323 | 2.823 | 0.445 | 1.00 | 39.62 | L | C |
| ATOM | 3108 | O | LEU | 4 | 108.470 | 2.548 | 1.289 | 1.00 | 39.62 | L | O |
| ATOM | 3109 | N | THR | 5 | 109.935 | 1.903 | -0.289 | 1.00 | 16.92 | L | N |
| ATOM | 3110 | CA | THR | 5 | 109.634 | 0.485 | -0.152 | 1.00 | 16.92 | L | C |
| ATOM | 3111 | CB | THR | 5 | 108.945 | -0.038 | -1.437 | 1.00 | 21.45 | L | C |
| ATOM | 3112 | OG1 | THR | 5 | 109.307 | -1.402 | -1.651 | 1.00 | 21.45 | L | O |
| ATOM | 3113 | CG2 | THR | 5 | 109.324 | 0.802 | -2.641 | 1.00 | 21.45 | L | C |
| ATOM | 3114 | C | THR | 5 | 110.908 | -0.312 | 0.186 | 1.00 | 16.92 | L | C |
| ATOM | 3115 | O | THR | 5 | 111.849 | -0.382 | -0.601 | 1.00 | 16.92 | L | O |
| ATOM | 3116 | N | GLN | 6 | 110.919 | -0.880 | 1.391 | 1.00 | 17.69 | L | N |
| ATOM | 3117 | CA | GLN | 6 | 112.040 | -1.661 | 1.933 | 1.00 | 17.69 | L | C |
| ATOM | 3118 | CB | GLN | 6 | 112.078 | -1.544 | 3.468 | 1.00 | 15.96 | L | C |
| ATOM | 3119 | CG | GLN | 6 | 111.898 | -0.138 | 4.014 | 1.00 | 15.96 | L | C |
| ATOM | 3120 | CD | GLN | 6 | 112.007 | -0.060 | 5.535 | 1.00 | 15.96 | L | C |
| ATOM | 3121 | OE1 | GLN | 6 | 111.626 | 0.944 | 6.139 | 1.00 | 15.96 | L | O |
| ATOM | 3122 | NE2 | GLN | 6 | 112.541 | -1.115 | 6.158 | 1.00 | 15.96 | L | N |
| ATOM | 3123 | C | GLN | 6 | 111.962 | -3.143 | 1.588 | 1.00 | 17.69 | L | C |
| ATOM | 3124 | O | GLN | 6 | 110.882 | -3.675 | 1.352 | 1.00 | 17.69 | L | O |
| ATOM | 3125 | N | SER | 7 | 113.107 | -3.814 | 1.595 | 1.00 | 44.56 | L | N |
| ATOM | 3126 | CA | SER | 7 | 113.148 | -5.238 | 1.293 | 1.00 | 44.56 | L | C |
| ATOM | 3127 | CB | SER | 7 | 113.109 | -5.470 | -0.214 | 1.00 | 33.18 | L | C |
| ATOM | 3128 | OG | SER | 7 | 114.194 | -4.813 | -0.837 | 1.00 | 33.18 | L | O |
| ATOM | 3129 | C | SER | 7 | 114.394 | -5.898 | 1.855 | 1.00 | 44.56 | L | C |
| ATOM | 3130 | O | SER | 7 | 115.480 | -5.328 | 1.811 | 1.00 | 44.56 | L | O |
| ATOM | 3131 | N | PRO | 8 | 114.246 | -7.107 | 2.415 | 1.00 | 19.10 | L | N |
| ATOM | 3132 | CD | PRO | 8 | 115.292 | -7.921 | 3.063 | 1.00 | 16.76 | L | C |
| ATOM | 3133 | CA | PRO | 8 | 112.945 | -7.771 | 2.494 | 1.00 | 19.10 | L | C |
| ATOM | 3134 | CB | PRO | 8 | 113.303 | -9.161 | 3.004 | 1.00 | 16.76 | L | C |
| ATOM | 3135 | CG | PRO | 8 | 114.481 | -8.882 | 3.905 | 1.00 | 16.76 | L | C |
| ATOM | 3136 | C | PRO | 8 | 112.068 | -7.023 | 3.479 | 1.00 | 19.10 | L | C |
| ATOM | 3137 | O | PRO | 8 | 112.517 | -6.069 | 4.125 | 1.00 | 19.10 | L | O |
| ATOM | 3138 | N | SER | 9 | 110.822 | -7.460 | 3.589 | 1.00 | 12.41 | L | N |
| ATOM | 3139 | CA | SER | 9 | 109.885 | -6.851 | 4.516 | 1.00 | 12.41 | L | C |

Fig. 19: A-44

| ATOM | 3140 | CB | SER | 9 | 108.466 | -7.059 | 4.023 | 1.00 | 25.43 | L | C |
|---|---|---|---|---|---|---|---|---|---|---|---|
| ATOM | 3141 | OG | SER | 9 | 108.345 | -6.555 | 2.707 | 1.00 | 25.43 | L | O |
| ATOM | 3142 | C | SER | 9 | 110.083 | -7.558 | 5.837 | 1.00 | 12.41 | L | C |
| ATOM | 3143 | O | SER | 9 | 109.904 | -6.983 | 6.904 | 1.00 | 12.41 | L | O |
| ATOM | 3144 | N | SER | 10 | 110.492 | -8.817 | 5.745 | 1.00 | 33.63 | L | N |
| ATOM | 3145 | CA | SER | 10 | 110.720 | -9.645 | 6.910 | 1.00 | 33.63 | L | C |
| ATOM | 3146 | CB | SER | 10 | 109.490 | -10.517 | 7.144 | 1.00 | 43.13 | L | C |
| ATOM | 3147 | OG | SER | 10 | 109.614 | -11.248 | 8.338 | 1.00 | 43.13 | L | O |
| ATOM | 3148 | C | SER | 10 | 111.942 | -10.504 | 6.624 | 1.00 | 33.63 | L | C |
| ATOM | 3149 | O | SER | 10 | 112.226 | -10.814 | 5.470 | 1.00 | 33.63 | L | O |
| ATOM | 3150 | N | LEU | 11 | 112.677 | -10.880 | 7.666 | 1.00 | 38.19 | L | N |
| ATOM | 3151 | CA | LEU | 11 | 113.867 | -11.709 | 7.484 | 1.00 | 38.19 | L | C |
| ATOM | 3152 | CB | LEU | 11 | 115.020 | -10.880 | 6.894 | 1.00 | 33.64 | L | C |
| ATOM | 3153 | CG | LEU | 11 | 115.721 | -9.849 | 7.793 | 1.00 | 33.64 | L | C |
| ATOM | 3154 | CD1 | LEU | 11 | 116.757 | -10.532 | 8.667 | 1.00 | 33.64 | L | C |
| ATOM | 3155 | CD2 | LEU | 11 | 116.401 | -8.807 | 6.927 | 1.00 | 33.64 | L | C |
| ATOM | 3156 | C | LEU | 11 | 114.319 | -12.335 | 8.792 | 1.00 | 38.19 | L | C |
| ATOM | 3157 | O | LEU | 11 | 114.365 | -11.672 | 9.829 | 1.00 | 38.19 | L | O |
| ATOM | 3158 | N | SER | 12 | 114.661 | -13.616 | 8.736 | 1.00 | 42.98 | L | N |
| ATOM | 3159 | CA | SER | 12 | 115.128 | -14.320 | 9.916 | 1.00 | 42.98 | L | C |
| ATOM | 3160 | CB | SER | 12 | 114.334 | -15.612 | 10.103 | 1.00 | 67.78 | L | C |
| ATOM | 3161 | OG | SER | 12 | 114.474 | -16.092 | 11.426 | 1.00 | 67.78 | L | O |
| ATOM | 3162 | C | SER | 12 | 116.611 | -14.628 | 9.738 | 1.00 | 42.98 | L | C |
| ATOM | 3163 | O | SER | 12 | 117.031 | -15.118 | 8.697 | 1.00 | 42.98 | L | O |
| ATOM | 3164 | N | ALA | 13 | 117.407 | -14.320 | 10.749 | 1.00 | 25.03 | L | N |
| ATOM | 3165 | CA | ALA | 13 | 118.836 | -14.575 | 10.667 | 1.00 | 25.03 | L | C |
| ATOM | 3166 | CB | ALA | 13 | 119.556 | -13.340 | 10.124 | 1.00 | 41.64 | L | C |
| ATOM | 3167 | C | ALA | 13 | 119.390 | -14.952 | 12.037 | 1.00 | 25.03 | L | C |
| ATOM | 3168 | O | ALA | 13 | 118.829 | -14.571 | 13.067 | 1.00 | 25.03 | L | O |
| ATOM | 3169 | N | SER | 14 | 120.493 | -15.701 | 12.045 | 1.00 | 32.48 | L | N |
| ATOM | 3170 | CA | SER | 14 | 121.111 | -16.132 | 13.294 | 1.00 | 32.48 | L | C |
| ATOM | 3171 | CB | SER | 14 | 121.594 | -17.569 | 13.160 | 1.00 | 77.12 | L | C |
| ATOM | 3172 | OG | SER | 14 | 122.348 | -17.721 | 11.975 | 1.00 | 77.12 | L | O |
| ATOM | 3173 | C | SER | 14 | 122.269 | -15.231 | 13.691 | 1.00 | 32.48 | L | C |
| ATOM | 3174 | O | SER | 14 | 122.893 | -14.595 | 12.841 | 1.00 | 32.48 | L | O |
| ATOM | 3175 | N | VAL | 15 | 122.545 | -15.166 | 14.988 | 1.00 | 47.29 | L | N |
| ATOM | 3176 | CA | VAL | 15 | 123.637 | -14.336 | 15.470 | 1.00 | 47.29 | L | C |
| ATOM | 3177 | CB | VAL | 15 | 123.996 | -14.657 | 16.937 | 1.00 | 53.16 | L | C |
| ATOM | 3178 | CG1 | VAL | 15 | 123.121 | -13.847 | 17.881 | 1.00 | 53.16 | L | C |
| ATOM | 3179 | CG2 | VAL | 15 | 123.808 | -16.148 | 17.198 | 1.00 | 53.16 | L | C |
| ATOM | 3180 | C | VAL | 15 | 124.858 | -14.575 | 14.606 | 1.00 | 47.29 | L | C |
| ATOM | 3181 | O | VAL | 15 | 125.164 | -15.712 | 14.250 | 1.00 | 47.29 | L | O |
| ATOM | 3182 | N | GLY | 16 | 125.537 | -13.495 | 14.247 | 1.00 | 32.44 | L | N |
| ATOM | 3183 | CA | GLY | 16 | 126.728 | -13.615 | 13.431 | 1.00 | 32.44 | L | C |
| ATOM | 3184 | C | GLY | 16 | 126.506 | -13.463 | 11.945 | 1.00 | 32.44 | L | C |
| ATOM | 3185 | O | GLY | 16 | 127.467 | -13.306 | 11.191 | 1.00 | 32.44 | L | O |
| ATOM | 3186 | N | ASP | 17 | 125.255 | -13.524 | 11.510 | 1.00 | 32.03 | L | N |
| ATOM | 3187 | CA | ASP | 17 | 124.959 | -13.367 | 10.092 | 1.00 | 32.03 | L | C |
| ATOM | 3188 | CB | ASP | 17 | 123.533 | -13.814 | 9.788 | 1.00 | 55.01 | L | C |
| ATOM | 3189 | CG | ASP | 17 | 123.344 | -15.291 | 9.961 | 1.00 | 55.01 | L | C |
| ATOM | 3190 | OD1 | ASP | 17 | 122.211 | -15.771 | 9.739 | 1.00 | 55.01 | L | O |
| ATOM | 3191 | OD2 | ASP | 17 | 124.331 | -15.965 | 10.320 | 1.00 | 55.01 | L | O |
| ATOM | 3192 | C | ASP | 17 | 125.109 | -11.905 | 9.677 | 1.00 | 32.03 | L | C |
| ATOM | 3193 | O | ASP | 17 | 125.041 | -10.997 | 10.517 | 1.00 | 32.03 | L | O |
| ATOM | 3194 | N | ARG | 18 | 125.324 | -11.680 | 8.385 | 1.00 | 40.86 | L | N |
| ATOM | 3195 | CA | ARG | 18 | 125.447 | -10.325 | 7.875 | 1.00 | 40.86 | L | C |
| ATOM | 3196 | CB | ARG | 18 | 126.587 | -10.231 | 6.865 | 1.00 | 78.37 | L | C |
| ATOM | 3197 | CG | ARG | 18 | 126.790 | -8.842 | 6.293 | 1.00 | 78.37 | L | C |
| ATOM | 3198 | CD | ARG | 18 | 128.223 | -8.662 | 5.812 | 1.00 | 78.37 | L | C |
| ATOM | 3199 | NE | ARG | 18 | 128.413 | -7.408 | 5.087 | 1.00 | 78.37 | L | N |
| ATOM | 3200 | CZ | ARG | 18 | 127.841 | -7.131 | 3.918 | 1.00 | 78.37 | L | C |
| ATOM | 3201 | NH1 | ARG | 18 | 127.042 | -8.021 | 3.336 | 1.00 | 78.37 | L | N |
| ATOM | 3202 | NH2 | ARG | 18 | 128.064 | -5.960 | 3.334 | 1.00 | 78.37 | L | N |
| ATOM | 3203 | C | ARG | 18 | 124.116 | -9.986 | 7.220 | 1.00 | 40.86 | L | C |
| ATOM | 3204 | O | ARG | 18 | 123.690 | -10.656 | 6.284 | 1.00 | 40.86 | L | O |
| ATOM | 3205 | N | VAL | 19 | 123.455 | -8.948 | 7.721 | 1.00 | 26.42 | L | N |
| ATOM | 3206 | CA | VAL | 19 | 122.157 | -8.549 | 7.193 | 1.00 | 26.42 | L | C |
| ATOM | 3207 | CB | VAL | 19 | 121.154 | -8.426 | 8.335 | 1.00 | 32.94 | L | C |
| ATOM | 3208 | CG1 | VAL | 19 | 119.768 | -8.214 | 7.783 | 1.00 | 32.94 | L | C |
| ATOM | 3209 | CG2 | VAL | 19 | 121.204 | -9.678 | 9.194 | 1.00 | 32.94 | L | C |
| ATOM | 3210 | C | VAL | 19 | 122.200 | -7.235 | 6.420 | 1.00 | 26.42 | L | C |
| ATOM | 3211 | O | VAL | 19 | 122.902 | -6.306 | 6.798 | 1.00 | 26.42 | L | O |
| ATOM | 3212 | N | THR | 20 | 121.443 | -7.160 | 5.333 | 1.00 | 42.24 | L | N |

Fig. 19: A-45

| | | | | | | | | | | |
|---|---|---|---|---|---|---|---|---|---|---|
| ATOM | 3213 | CA | THR | 20 | 121.408 | -5.950 | 4.519 | 1.00 | 42.24 | L | C |
| ATOM | 3214 | CB | THR | 20 | 122.310 | -6.097 | 3.289 | 1.00 | 29.90 | L | C |
| ATOM | 3215 | OG1 | THR | 20 | 123.680 | -6.127 | 3.714 | 1.00 | 29.90 | L | O |
| ATOM | 3216 | CG2 | THR | 20 | 122.099 | -4.944 | 2.326 | 1.00 | 29.90 | L | C |
| ATOM | 3217 | C | THR | 20 | 120.008 | -5.582 | 4.050 | 1.00 | 42.24 | L | C |
| ATOM | 3218 | O | THR | 20 | 119.477 | -6.202 | 3.127 | 1.00 | 42.24 | L | O |
| ATOM | 3219 | N | ILE | 21 | 119.418 | -4.568 | 4.683 | 1.00 | 13.95 | L | N |
| ATOM | 3220 | CA | ILE | 21 | 118.077 | -4.114 | 4.326 | 1.00 | 13.95 | L | C |
| ATOM | 3221 | CB | ILE | 21 | 117.349 | -3.486 | 5.541 | 1.00 | 24.11 | L | C |
| ATOM | 3222 | CG2 | ILE | 21 | 115.892 | -3.176 | 5.186 | 1.00 | 24.11 | L | C |
| ATOM | 3223 | CG1 | ILE | 21 | 117.390 | -4.457 | 6.720 | 1.00 | 24.11 | L | C |
| ATOM | 3224 | CD1 | ILE | 21 | 116.709 | -3.936 | 7.960 | 1.00 | 24.11 | L | C |
| ATOM | 3225 | C | ILE | 21 | 118.180 | -3.081 | 3.217 | 1.00 | 13.95 | L | C |
| ATOM | 3226 | O | ILE | 21 | 119.036 | -2.208 | 3.251 | 1.00 | 13.95 | L | O |
| ATOM | 3227 | N | THR | 22 | 117.305 | -3.190 | 2.230 | 1.00 | 27.07 | L | N |
| ATOM | 3228 | CA | THR | 22 | 117.304 | -2.266 | 1.107 | 1.00 | 27.07 | L | C |
| ATOM | 3229 | CB | THR | 22 | 117.335 | -3.022 | -0.239 | 1.00 | 29.03 | L | C |
| ATOM | 3230 | OG1 | THR | 22 | 118.613 | -3.642 | -0.404 | 1.00 | 29.03 | L | O |
| ATOM | 3231 | CG2 | THR | 22 | 117.084 | -2.084 | -1.391 | 1.00 | 29.03 | L | C |
| ATOM | 3232 | C | THR | 22 | 116.067 | -1.385 | 1.123 | 1.00 | 27.07 | L | C |
| ATOM | 3233 | O | THR | 22 | 114.951 | -1.871 | 1.313 | 1.00 | 27.07 | L | O |
| ATOM | 3234 | N | CYS | 23 | 116.281 | -0.089 | 0.916 | 1.00 | 32.83 | L | N |
| ATOM | 3235 | CA | CYS | 23 | 115.203 | 0.896 | 0.882 | 1.00 | 32.83 | L | C |
| ATOM | 3236 | C | CYS | 23 | 115.259 | 1.546 | -0.489 | 1.00 | 32.83 | L | C |
| ATOM | 3237 | O | CYS | 23 | 116.250 | 2.187 | -0.837 | 1.00 | 32.83 | L | O |
| ATOM | 3238 | CB | CYS | 23 | 115.424 | 1.947 | 1.973 | 1.00 | 18.66 | L | C |
| ATOM | 3239 | SG | CYS | 23 | 114.216 | 3.310 | 2.141 | 1.00 | 18.66 | L | S |
| ATOM | 3240 | N | SER | 24 | 114.199 | 1.355 | -1.268 | 1.00 | 11.34 | L | N |
| ATOM | 3241 | CA | SER | 24 | 114.110 | 1.924 | -2.612 | 1.00 | 11.34 | L | C |
| ATOM | 3242 | CB | SER | 24 | 113.696 | 0.853 | -3.614 | 1.00 | 28.67 | L | C |
| ATOM | 3243 | OG | SER | 24 | 114.642 | -0.190 | -3.632 | 1.00 | 28.67 | L | O |
| ATOM | 3244 | C | SER | 24 | 113.096 | 3.058 | -2.641 | 1.00 | 11.34 | L | C |
| ATOM | 3245 | O | SER | 24 | 111.971 | 2.910 | -2.154 | 1.00 | 11.34 | L | O |
| ATOM | 3246 | N | ALA | 25 | 113.496 | 4.186 | -3.217 | 1.00 | 32.05 | L | N |
| ATOM | 3247 | CA | ALA | 25 | 112.617 | 5.343 | -3.286 | 1.00 | 32.05 | L | C |
| ATOM | 3248 | CB | ALA | 25 | 113.312 | 6.567 | -2.707 | 1.00 | 44.86 | L | C |
| ATOM | 3249 | C | ALA | 25 | 112.139 | 5.633 | -4.699 | 1.00 | 32.05 | L | C |
| ATOM | 3250 | O | ALA | 25 | 112.918 | 5.619 | -5.658 | 1.00 | 32.05 | L | O |
| ATOM | 3251 | N | SER | 26 | 110.839 | 5.901 | -4.803 | 1.00 | 26.80 | L | N |
| ATOM | 3252 | CA | SER | 26 | 110.179 | 6.204 | -6.070 | 1.00 | 26.80 | L | C |
| ATOM | 3253 | CB | SER | 26 | 108.717 | 6.572 | -5.814 | 1.00 | 23.33 | L | C |
| ATOM | 3254 | OG | SER | 26 | 108.617 | 7.713 | -4.984 | 1.00 | 23.33 | L | O |
| ATOM | 3255 | C | SER | 26 | 110.866 | 7.338 | -6.813 | 1.00 | 26.80 | L | C |
| ATOM | 3256 | O | SER | 26 | 110.814 | 7.404 | -8.032 | 1.00 | 26.80 | L | O |
| ATOM | 3257 | N | SER | 27 | 111.496 | 8.234 | -6.066 | 1.00 | 22.71 | L | N |
| ATOM | 3258 | CA | SER | 27 | 112.210 | 9.363 | -6.644 | 1.00 | 22.71 | L | C |
| ATOM | 3259 | CB | SER | 27 | 111.439 | 10.661 | -6.406 | 1.00 | 47.74 | L | C |
| ATOM | 3260 | OG | SER | 27 | 110.105 | 10.552 | -6.862 | 1.00 | 47.74 | L | O |
| ATOM | 3261 | C | SER | 27 | 113.547 | 9.438 | -5.934 | 1.00 | 22.71 | L | C |
| ATOM | 3262 | O | SER | 27 | 113.666 | 8.982 | -4.805 | 1.00 | 22.71 | L | O |
| ATOM | 3263 | N | SER | 28 | 114.555 | 10.004 | -6.586 | 1.00 | 37.73 | L | N |
| ATOM | 3264 | CA | SER | 28 | 115.874 | 10.121 | -5.972 | 1.00 | 37.73 | L | C |
| ATOM | 3265 | CB | SER | 28 | 116.890 | 10.583 | -7.010 | 1.00 | 36.75 | L | C |
| ATOM | 3266 | OG | SER | 28 | 116.486 | 11.818 | -7.573 | 1.00 | 36.75 | L | O |
| ATOM | 3267 | C | SER | 28 | 115.846 | 11.106 | -4.804 | 1.00 | 37.73 | L | C |
| ATOM | 3268 | O | SER | 28 | 115.043 | 12.038 | -4.775 | 1.00 | 37.73 | L | O |
| ATOM | 3269 | N | VAL | 29 | 116.726 | 10.890 | -3.838 | 1.00 | 35.34 | L | N |
| ATOM | 3270 | CA | VAL | 29 | 116.807 | 11.753 | -2.669 | 1.00 | 35.34 | L | C |
| ATOM | 3271 | CB | VAL | 29 | 116.002 | 11.154 | -1.484 | 1.00 | 39.96 | L | C |
| ATOM | 3272 | CG1 | VAL | 29 | 114.521 | 11.097 | -1.842 | 1.00 | 39.96 | L | C |
| ATOM | 3273 | CG2 | VAL | 29 | 116.506 | 9.755 | -1.147 | 1.00 | 39.96 | L | C |
| ATOM | 3274 | C | VAL | 29 | 118.277 | 11.895 | -2.289 | 1.00 | 35.34 | L | C |
| ATOM | 3275 | O | VAL | 29 | 119.076 | 11.001 | -2.571 | 1.00 | 35.34 | L | O |
| ATOM | 3276 | N | ASN | 30 | 118.641 | 13.007 | -1.658 | 1.00 | 55.44 | L | N |
| ATOM | 3277 | CA | ASN | 30 | 120.033 | 13.236 | -1.278 | 1.00 | 55.44 | L | C |
| ATOM | 3278 | CB | ASN | 30 | 120.252 | 14.722 | -0.974 | 1.00 | 66.75 | L | C |
| ATOM | 3279 | CG | ASN | 30 | 119.176 | 15.292 | -0.071 | 1.00 | 66.75 | L | C |
| ATOM | 3280 | OD1 | ASN | 30 | 118.006 | 15.359 | -0.453 | 1.00 | 66.75 | L | O |
| ATOM | 3281 | ND2 | ASN | 30 | 119.561 | 15.694 | 1.138 | 1.00 | 66.75 | L | N |
| ATOM | 3282 | C | ASN | 30 | 120.510 | 12.386 | -0.095 | 1.00 | 55.44 | L | C |
| ATOM | 3283 | O | ASN | 30 | 121.705 | 12.099 | 0.033 | 1.00 | 55.44 | L | O |
| ATOM | 3284 | N | HIS | 31 | 119.586 | 11.985 | 0.770 | 1.00 | 34.66 | L | N |
| ATOM | 3285 | CA | HIS | 31 | 119.947 | 11.172 | 1.923 | 1.00 | 34.66 | L | C |

Fig. 19: A-46

| | | | | | | | | | | | |
|---|---|---|---|---|---|---|---|---|---|---|---|
| ATOM | 3286 | CB | HIS | 31 | 120.290 | 12.049 | 3.132 | 1.00 | 51.96 | L | C |
| ATOM | 3287 | CG | HIS | 31 | 121.623 | 12.725 | 3.042 | 1.00 | 51.96 | L | C |
| ATOM | 3288 | CD2 | HIS | 31 | 122.763 | 12.534 | 3.744 | 1.00 | 51.96 | L | C |
| ATOM | 3289 | ND1 | HIS | 31 | 121.879 | 13.763 | 2.172 | 1.00 | 51.96 | L | N |
| ATOM | 3290 | CE1 | HIS | 31 | 123.118 | 14.186 | 2.345 | 1.00 | 51.96 | L | C |
| ATOM | 3291 | NE2 | HIS | 31 | 123.676 | 13.457 | 3.294 | 1.00 | 51.96 | L | N |
| ATOM | 3292 | C | HIS | 31 | 118.811 | 10.241 | 2.316 | 1.00 | 34.66 | L | C |
| ATOM | 3293 | O | HIS | 31 | 117.736 | 10.267 | 1.707 | 1.00 | 34.66 | L | O |
| ATOM | 3294 | N | MET | 32 | 119.070 | 9.415 | 3.332 | 1.00 | 24.85 | L | N |
| ATOM | 3295 | CA | MET | 32 | 118.081 | 8.489 | 3.864 | 1.00 | 24.85 | L | C |
| ATOM | 3296 | CB | MET | 32 | 118.189 | 7.126 | 3.187 | 1.00 | 22.87 | L | C |
| ATOM | 3297 | CG | MET | 32 | 116.961 | 6.226 | 3.394 | 1.00 | 22.87 | L | C |
| ATOM | 3298 | SD | MET | 32 | 115.381 | 6.922 | 2.757 | 1.00 | 22.87 | L | S |
| ATOM | 3299 | CE | MET | 32 | 115.727 | 7.028 | 1.012 | 1.00 | 22.87 | L | C |
| ATOM | 3300 | C | MET | 32 | 118.316 | 8.340 | 5.360 | 1.00 | 24.85 | L | C |
| ATOM | 3301 | O | MET | 32 | 119.454 | 8.377 | 5.831 | 1.00 | 24.85 | L | O |
| ATOM | 3302 | N | PHE | 33 | 117.244 | 8.180 | 6.118 | 1.00 | 7.47 | L | N |
| ATOM | 3303 | CA | PHE | 33 | 117.391 | 8.029 | 7.554 | 1.00 | 7.47 | L | C |
| ATOM | 3304 | CB | PHE | 33 | 116.693 | 9.171 | 8.285 | 1.00 | 11.22 | L | C |
| ATOM | 3305 | CG | PHE | 33 | 117.205 | 10.533 | 7.901 | 1.00 | 11.22 | L | C |
| ATOM | 3306 | CD1 | PHE | 33 | 116.901 | 11.078 | 6.652 | 1.00 | 11.22 | L | C |
| ATOM | 3307 | CD2 | PHE | 33 | 118.017 | 11.259 | 8.776 | 1.00 | 11.22 | L | C |
| ATOM | 3308 | CE1 | PHE | 33 | 117.399 | 12.325 | 6.275 | 1.00 | 11.22 | L | C |
| ATOM | 3309 | CE2 | PHE | 33 | 118.519 | 12.501 | 8.407 | 1.00 | 11.22 | L | C |
| ATOM | 3310 | CZ | PHE | 33 | 118.207 | 13.035 | 7.149 | 1.00 | 11.22 | L | C |
| ATOM | 3311 | C | PHE | 33 | 116.817 | 6.702 | 7.994 | 1.00 | 7.47 | L | C |
| ATOM | 3312 | O | PHE | 33 | 115.959 | 6.150 | 7.320 | 1.00 | 7.47 | L | O |
| ATOM | 3313 | N | TRP | 34 | 117.301 | 6.186 | 9.118 | 1.00 | 15.67 | L | N |
| ATOM | 3314 | CA | TRP | 34 | 116.815 | 4.912 | 9.618 | 1.00 | 15.67 | L | C |
| ATOM | 3315 | CB | TRP | 34 | 117.859 | 3.818 | 9.414 | 1.00 | 16.49 | L | C |
| ATOM | 3316 | CG | TRP | 34 | 118.217 | 3.590 | 7.992 | 1.00 | 16.49 | L | C |
| ATOM | 3317 | CD2 | TRP | 34 | 117.671 | 2.592 | 7.123 | 1.00 | 16.49 | L | C |
| ATOM | 3318 | CE2 | TRP | 34 | 118.315 | 2.732 | 5.872 | 1.00 | 16.49 | L | C |
| ATOM | 3319 | CE3 | TRP | 34 | 116.702 | 1.596 | 7.279 | 1.00 | 16.49 | L | C |
| ATOM | 3320 | CD1 | TRP | 34 | 119.137 | 4.278 | 7.259 | 1.00 | 16.49 | L | C |
| ATOM | 3321 | NE1 | TRP | 34 | 119.205 | 3.767 | 5.984 | 1.00 | 16.49 | L | N |
| ATOM | 3322 | CZ2 | TRP | 34 | 118.024 | 1.914 | 4.782 | 1.00 | 16.49 | L | C |
| ATOM | 3323 | CZ3 | TRP | 34 | 116.409 | 0.780 | 6.194 | 1.00 | 16.49 | L | C |
| ATOM | 3324 | CH2 | TRP | 34 | 117.069 | 0.945 | 4.960 | 1.00 | 16.49 | L | C |
| ATOM | 3325 | C | TRP | 34 | 116.459 | 4.960 | 11.086 | 1.00 | 15.67 | L | C |
| ATOM | 3326 | O | TRP | 34 | 117.149 | 5.593 | 11.882 | 1.00 | 15.67 | L | O |
| ATOM | 3327 | N | TYR | 35 | 115.370 | 4.288 | 11.437 | 1.00 | 19.71 | L | N |
| ATOM | 3328 | CA | TYR | 35 | 114.939 | 4.229 | 12.820 | 1.00 | 19.71 | L | C |
| ATOM | 3329 | CB | TYR | 35 | 113.591 | 4.922 | 13.007 | 1.00 | 25.75 | L | C |
| ATOM | 3330 | CG | TYR | 35 | 113.623 | 6.381 | 12.621 | 1.00 | 25.75 | L | C |
| ATOM | 3331 | CD1 | TYR | 35 | 113.255 | 6.790 | 11.344 | 1.00 | 25.75 | L | C |
| ATOM | 3332 | CE1 | TYR | 35 | 113.310 | 8.124 | 10.980 | 1.00 | 25.75 | L | C |
| ATOM | 3333 | CD2 | TYR | 35 | 114.052 | 7.353 | 13.527 | 1.00 | 25.75 | L | C |
| ATOM | 3334 | CE2 | TYR | 35 | 114.110 | 8.685 | 13.173 | 1.00 | 25.75 | L | C |
| ATOM | 3335 | CZ | TYR | 35 | 113.737 | 9.064 | 11.899 | 1.00 | 25.75 | L | C |
| ATOM | 3336 | OH | TYR | 35 | 113.776 | 10.384 | 11.540 | 1.00 | 25.75 | L | O |
| ATOM | 3337 | C | TYR | 35 | 114.821 | 2.781 | 13.207 | 1.00 | 19.71 | L | C |
| ATOM | 3338 | O | TYR | 35 | 114.508 | 1.937 | 12.373 | 1.00 | 19.71 | L | O |
| ATOM | 3339 | N | GLN | 36 | 115.100 | 2.491 | 14.468 | 1.00 | 30.18 | L | N |
| ATOM | 3340 | CA | GLN | 36 | 114.987 | 1.136 | 14.964 | 1.00 | 30.18 | L | C |
| ATOM | 3341 | CB | GLN | 36 | 116.292 | 0.659 | 15.597 | 1.00 | 33.56 | L | C |
| ATOM | 3342 | CG | GLN | 36 | 116.109 | -0.625 | 16.387 | 1.00 | 33.56 | L | C |
| ATOM | 3343 | CD | GLN | 36 | 117.154 | -0.806 | 17.464 | 1.00 | 33.56 | L | C |
| ATOM | 3344 | OE1 | GLN | 36 | 118.296 | -1.161 | 17.179 | 1.00 | 33.56 | L | O |
| ATOM | 3345 | NE2 | GLN | 36 | 116.770 | -0.550 | 18.716 | 1.00 | 33.56 | L | N |
| ATOM | 3346 | C | GLN | 36 | 113.902 | 1.124 | 16.017 | 1.00 | 30.18 | L | C |
| ATOM | 3347 | O | GLN | 36 | 113.986 | 1.852 | 17.008 | 1.00 | 30.18 | L | O |
| ATOM | 3348 | N | GLN | 37 | 112.877 | 0.311 | 15.803 | 1.00 | 31.84 | L | N |
| ATOM | 3349 | CA | GLN | 37 | 111.811 | 0.209 | 16.778 | 1.00 | 31.84 | L | C |
| ATOM | 3350 | CB | GLN | 37 | 110.467 | 0.599 | 16.162 | 1.00 | 26.28 | L | C |
| ATOM | 3351 | CG | GLN | 37 | 109.335 | 0.494 | 17.165 | 1.00 | 26.28 | L | C |
| ATOM | 3352 | CD | GLN | 37 | 108.003 | 0.979 | 16.632 | 1.00 | 26.28 | L | C |
| ATOM | 3353 | OE1 | GLN | 37 | 107.573 | 0.597 | 15.537 | 1.00 | 26.28 | L | O |
| ATOM | 3354 | NE2 | GLN | 37 | 107.328 | 1.819 | 17.417 | 1.00 | 26.28 | L | N |
| ATOM | 3355 | C | GLN | 37 | 111.729 | -1.201 | 17.360 | 1.00 | 31.84 | L | C |
| ATOM | 3356 | O | GLN | 37 | 111.571 | -2.189 | 16.637 | 1.00 | 31.84 | L | O |
| ATOM | 3357 | N | LYS | 38 | 111.861 | -1.285 | 18.676 | 1.00 | 33.78 | L | N |
| ATOM | 3358 | CA | LYS | 38 | 111.776 | -2.561 | 19.366 | 1.00 | 33.78 | L | C |

Fig. 19: A-47

| ATOM | 3359 | CB | LYS | 38 | 112.784 | -2.618 | 20.519 | 1.00 | 38.31 | L | C |
| --- | --- | --- | --- | --- | --- | --- | --- | --- | --- | --- | --- |
| ATOM | 3360 | CG | LYS | 38 | 114.209 | -2.306 | 20.094 | 1.00 | 38.31 | L | C |
| ATOM | 3361 | CD | LYS | 38 | 115.224 | -2.552 | 21.207 | 1.00 | 38.31 | L | C |
| ATOM | 3362 | CE | LYS | 38 | 115.494 | -4.034 | 21.402 | 1.00 | 38.31 | L | C |
| ATOM | 3363 | NZ | LYS | 38 | 115.954 | -4.720 | 20.154 | 1.00 | 38.31 | L | N |
| ATOM | 3364 | C | LYS | 38 | 110.346 | -2.671 | 19.889 | 1.00 | 33.78 | L | C |
| ATOM | 3365 | O | LYS | 38 | 109.770 | -1.690 | 20.354 | 1.00 | 33.78 | L | O |
| ATOM | 3366 | N | PRO | 39 | 109.757 | -3.873 | 19.818 | 1.00 | 36.51 | L | N |
| ATOM | 3367 | CD | PRO | 39 | 110.419 | -5.128 | 19.422 | 1.00 | 56.09 | L | C |
| ATOM | 3368 | CA | PRO | 39 | 108.389 | -4.139 | 20.271 | 1.00 | 36.51 | L | C |
| ATOM | 3369 | CB | PRO | 39 | 108.376 | -5.652 | 20.409 | 1.00 | 56.09 | L | C |
| ATOM | 3370 | CG | PRO | 39 | 109.254 | -6.072 | 19.283 | 1.00 | 56.09 | L | C |
| ATOM | 3371 | C | PRO | 39 | 107.976 | -3.434 | 21.559 | 1.00 | 36.51 | L | C |
| ATOM | 3372 | O | PRO | 39 | 108.664 | -3.523 | 22.573 | 1.00 | 36.51 | L | O |
| ATOM | 3373 | N | GLY | 40 | 106.846 | -2.735 | 21.503 | 1.00 | 29.94 | L | N |
| ATOM | 3374 | CA | GLY | 40 | 106.330 | -2.036 | 22.667 | 1.00 | 29.94 | L | C |
| ATOM | 3375 | C | GLY | 40 | 107.025 | -0.738 | 23.034 | 1.00 | 29.94 | L | C |
| ATOM | 3376 | O | GLY | 40 | 106.669 | -0.119 | 24.037 | 1.00 | 29.94 | L | O |
| ATOM | 3377 | N | LYS | 41 | 108.019 | -0.332 | 22.243 | 1.00 | 32.57 | L | N |
| ATOM | 3378 | CA | LYS | 41 | 108.754 | 0.903 | 22.503 | 1.00 | 32.57 | L | C |
| ATOM | 3379 | CB | LYS | 41 | 110.231 | 0.611 | 22.804 | 1.00 | 82.45 | L | C |
| ATOM | 3380 | CG | LYS | 41 | 110.466 | -0.251 | 24.040 | 1.00 | 82.45 | L | C |
| ATOM | 3381 | CD | LYS | 41 | 111.905 | -0.157 | 24.579 | 1.00 | 82.45 | L | C |
| ATOM | 3382 | CE | LYS | 41 | 112.977 | -0.603 | 23.575 | 1.00 | 82.45 | L | C |
| ATOM | 3383 | NZ | LYS | 41 | 113.257 | 0.396 | 22.496 | 1.00 | 82.45 | L | N |
| ATOM | 3384 | C | LYS | 41 | 108.656 | 1.860 | 21.319 | 1.00 | 32.57 | L | C |
| ATOM | 3385 | O | LYS | 41 | 108.243 | 1.480 | 20.227 | 1.00 | 32.57 | L | O |
| ATOM | 3386 | N | ALA | 42 | 109.029 | 3.112 | 21.547 | 1.00 | 30.66 | L | N |
| ATOM | 3387 | CA | ALA | 42 | 108.990 | 4.126 | 20.502 | 1.00 | 30.66 | L | C |
| ATOM | 3388 | CB | ALA | 42 | 108.980 | 5.513 | 21.129 | 1.00 | 32.87 | L | C |
| ATOM | 3389 | C | ALA | 42 | 110.209 | 3.973 | 19.606 | 1.00 | 30.66 | L | C |
| ATOM | 3390 | O | ALA | 42 | 111.235 | 3.436 | 20.028 | 1.00 | 30.66 | L | O |
| ATOM | 3391 | N | PRO | 43 | 110.112 | 4.435 | 18.351 | 1.00 | 23.79 | L | N |
| ATOM | 3392 | CD | PRO | 43 | 108.939 | 4.976 | 17.647 | 1.00 | 7.10 | L | C |
| ATOM | 3393 | CA | PRO | 43 | 111.248 | 4.323 | 17.440 | 1.00 | 23.79 | L | C |
| ATOM | 3394 | CB | PRO | 43 | 110.727 | 4.980 | 16.170 | 1.00 | 7.10 | L | C |
| ATOM | 3395 | CG | PRO | 43 | 109.275 | 4.677 | 16.212 | 1.00 | 7.10 | L | C |
| ATOM | 3396 | C | PRO | 43 | 112.476 | 5.042 | 18.007 | 1.00 | 23.79 | L | C |
| ATOM | 3397 | O | PRO | 43 | 112.359 | 5.903 | 18.877 | 1.00 | 23.79 | L | O |
| ATOM | 3398 | N | LYS | 44 | 113.652 | 4.678 | 17.514 | 1.00 | 26.42 | L | N |
| ATOM | 3399 | CA | LYS | 44 | 114.888 | 5.283 | 17.972 | 1.00 | 26.42 | L | C |
| ATOM | 3400 | CB | LYS | 44 | 115.656 | 4.289 | 18.843 | 1.00 | 45.11 | L | C |
| ATOM | 3401 | CG | LYS | 44 | 115.840 | 4.724 | 20.288 | 1.00 | 45.11 | L | C |
| ATOM | 3402 | CD | LYS | 44 | 116.535 | 3.651 | 21.131 | 1.00 | 45.11 | L | C |
| ATOM | 3403 | CE | LYS | 44 | 115.656 | 2.400 | 21.338 | 1.00 | 45.11 | L | C |
| ATOM | 3404 | NZ | LYS | 44 | 115.359 | 1.613 | 20.087 | 1.00 | 45.11 | L | N |
| ATOM | 3405 | C | LYS | 44 | 115.741 | 5.673 | 16.767 | 1.00 | 26.42 | L | C |
| ATOM | 3406 | O | LYS | 44 | 115.898 | 4.888 | 15.829 | 1.00 | 26.42 | L | O |
| ATOM | 3407 | N | PRO | 45 | 116.287 | 6.902 | 16.764 | 1.00 | 19.50 | L | N |
| ATOM | 3408 | CD | PRO | 45 | 116.146 | 7.943 | 17.794 | 1.00 | 7.61 | L | C |
| ATOM | 3409 | CA | PRO | 45 | 117.132 | 7.362 | 15.649 | 1.00 | 19.50 | L | C |
| ATOM | 3410 | CB | PRO | 45 | 117.638 | 8.720 | 16.120 | 1.00 | 7.61 | L | C |
| ATOM | 3411 | CG | PRO | 45 | 116.547 | 9.180 | 17.041 | 1.00 | 7.61 | L | C |
| ATOM | 3412 | C | PRO | 45 | 118.273 | 6.367 | 15.542 | 1.00 | 19.50 | L | C |
| ATOM | 3413 | O | PRO | 45 | 118.925 | 6.082 | 16.549 | 1.00 | 19.50 | L | O |
| ATOM | 3414 | N | TRP | 46 | 118.521 | 5.848 | 14.342 | 1.00 | 23.41 | L | N |
| ATOM | 3415 | CA | TRP | 46 | 119.581 | 4.861 | 14.158 | 1.00 | 23.41 | L | C |
| ATOM | 3416 | CB | TRP | 46 | 118.980 | 3.559 | 13.643 | 1.00 | 20.77 | L | C |
| ATOM | 3417 | CG | TRP | 46 | 119.662 | 2.382 | 14.178 | 1.00 | 20.77 | L | C |
| ATOM | 3418 | CD2 | TRP | 46 | 119.738 | 2.007 | 15.554 | 1.00 | 20.77 | L | C |
| ATOM | 3419 | CE2 | TRP | 46 | 120.509 | 0.829 | 15.624 | 1.00 | 20.77 | L | C |
| ATOM | 3420 | CE3 | TRP | 46 | 119.229 | 2.554 | 16.737 | 1.00 | 20.77 | L | C |
| ATOM | 3421 | CD1 | TRP | 46 | 120.365 | 1.446 | 13.481 | 1.00 | 20.77 | L | C |
| ATOM | 3422 | NE1 | TRP | 46 | 120.879 | 0.504 | 14.345 | 1.00 | 20.77 | L | N |
| ATOM | 3423 | CZ2 | TRP | 46 | 120.786 | 0.191 | 16.834 | 1.00 | 20.77 | L | C |
| ATOM | 3424 | CZ3 | TRP | 46 | 119.505 | 1.918 | 17.938 | 1.00 | 20.77 | L | C |
| ATOM | 3425 | CH2 | TRP | 46 | 120.276 | 0.750 | 17.977 | 1.00 | 20.77 | L | C |
| ATOM | 3426 | C | TRP | 46 | 120.691 | 5.302 | 13.209 | 1.00 | 23.41 | L | C |
| ATOM | 3427 | O | TRP | 46 | 121.871 | 5.174 | 13.507 | 1.00 | 23.41 | L | O |
| ATOM | 3428 | N | ILE | 47 | 120.306 | 5.806 | 12.048 | 1.00 | 21.62 | L | N |
| ATOM | 3429 | CA | ILE | 47 | 121.275 | 6.248 | 11.073 | 1.00 | 21.62 | L | C |
| ATOM | 3430 | CB | ILE | 47 | 121.515 | 5.160 | 10.008 | 1.00 | 12.16 | L | C |
| ATOM | 3431 | CG2 | ILE | 47 | 122.473 | 5.668 | 8.929 | 1.00 | 12.16 | L | C |

Fig. 19: A-48

| | | | | | | | | | | | |
|---|---|---|---|---|---|---|---|---|---|---|---|
| ATOM | 3432 | CG1 | ILE | 47 | 122.067 | 3.902 | 10.670 | 1.00 | 12.16 | L | C |
| ATOM | 3433 | CD1 | ILE | 47 | 122.301 | 2.746 | 9.686 | 1.00 | 12.16 | L | C |
| ATOM | 3434 | C | ILE | 47 | 120.694 | 7.482 | 10.408 | 1.00 | 21.62 | L | C |
| ATOM | 3435 | O | ILE | 47 | 119.600 | 7.424 | 9.840 | 1.00 | 21.62 | L | O |
| ATOM | 3436 | N | TYR | 48 | 121.408 | 8.603 | 10.510 | 1.00 | 27.63 | L | N |
| ATOM | 3437 | CA | TYR | 48 | 120.961 | 9.842 | 9.887 | 1.00 | 27.63 | L | C |
| ATOM | 3438 | CB | TYR | 48 | 120.899 | 10.992 | 10.892 | 1.00 | 47.89 | L | C |
| ATOM | 3439 | CG | TYR | 48 | 122.206 | 11.318 | 11.564 | 1.00 | 47.89 | L | C |
| ATOM | 3440 | CD1 | TYR | 48 | 122.762 | 10.454 | 12.502 | 1.00 | 47.89 | L | C |
| ATOM | 3441 | CE1 | TYR | 48 | 123.961 | 10.766 | 13.143 | 1.00 | 47.89 | L | C |
| ATOM | 3442 | CD2 | TYR | 48 | 122.881 | 12.503 | 11.277 | 1.00 | 47.89 | L | C |
| ATOM | 3443 | CE2 | TYR | 48 | 124.078 | 12.827 | 11.907 | 1.00 | 47.89 | L | C |
| ATOM | 3444 | CZ | TYR | 48 | 124.617 | 11.957 | 12.843 | 1.00 | 47.89 | L | C |
| ATOM | 3445 | OH | TYR | 48 | 125.803 | 12.269 | 13.483 | 1.00 | 47.89 | L | O |
| ATOM | 3446 | C | TYR | 48 | 121.922 | 10.181 | 8.766 | 1.00 | 27.63 | L | C |
| ATOM | 3447 | O | TYR | 48 | 122.992 | 9.575 | 8.646 | 1.00 | 27.63 | L | O |
| ATOM | 3448 | N | LEU | 49 | 121.535 | 11.150 | 7.948 | 1.00 | 28.95 | L | N |
| ATOM | 3449 | CA | LEU | 49 | 122.344 | 11.550 | 6.811 | 1.00 | 28.95 | L | C |
| ATOM | 3450 | CB | LEU | 49 | 123.421 | 12.568 | 7.232 | 1.00 | 11.18 | L | C |
| ATOM | 3451 | CG | LEU | 49 | 123.051 | 14.040 | 7.473 | 1.00 | 11.18 | L | C |
| ATOM | 3452 | CD1 | LEU | 49 | 122.174 | 14.552 | 6.344 | 1.00 | 11.18 | L | C |
| ATOM | 3453 | CD2 | LEU | 49 | 122.333 | 14.178 | 8.780 | 1.00 | 11.18 | L | C |
| ATOM | 3454 | C | LEU | 49 | 122.997 | 10.350 | 6.117 | 1.00 | 28.95 | L | C |
| ATOM | 3455 | O | LEU | 49 | 124.204 | 10.323 | 5.920 | 1.00 | 28.95 | L | O |
| ATOM | 3456 | N | THR | 50 | 122.192 | 9.351 | 5.777 | 1.00 | 29.56 | L | N |
| ATOM | 3457 | CA | THR | 50 | 122.666 | 8.165 | 5.072 | 1.00 | 29.56 | L | C |
| ATOM | 3458 | CB | THR | 50 | 123.352 | 8.566 | 3.770 | 1.00 | 23.05 | L | C |
| ATOM | 3459 | OG1 | THR | 50 | 122.490 | 9.434 | 3.040 | 1.00 | 23.05 | L | O |
| ATOM | 3460 | CG2 | THR | 50 | 123.647 | 7.335 | 2.923 | 1.00 | 23.05 | L | C |
| ATOM | 3461 | C | THR | 50 | 123.582 | 7.152 | 5.767 | 1.00 | 29.56 | L | C |
| ATOM | 3462 | O | THR | 50 | 123.229 | 5.976 | 5.888 | 1.00 | 29.56 | L | O |
| ATOM | 3463 | N | SER | 51 | 124.757 | 7.586 | 6.203 | 1.00 | 25.90 | L | N |
| ATOM | 3464 | CA | SER | 51 | 125.697 | 6.670 | 6.839 | 1.00 | 25.90 | L | C |
| ATOM | 3465 | CB | SER | 51 | 126.976 | 6.594 | 6.003 | 1.00 | 41.07 | L | C |
| ATOM | 3466 | OG | SER | 51 | 127.467 | 7.893 | 5.715 | 1.00 | 41.07 | L | O |
| ATOM | 3467 | C | SER | 51 | 126.049 | 6.998 | 8.287 | 1.00 | 25.90 | L | C |
| ATOM | 3468 | O | SER | 51 | 126.578 | 6.160 | 9.015 | 1.00 | 25.90 | L | O |
| ATOM | 3469 | N | ASN | 52 | 125.749 | 8.211 | 8.712 | 1.00 | 36.32 | L | N |
| ATOM | 3470 | CA | ASN | 52 | 126.050 | 8.615 | 10.075 | 1.00 | 36.32 | L | C |
| ATOM | 3471 | CB | ASN | 52 | 125.741 | 10.092 | 10.247 | 1.00 | 35.00 | L | C |
| ATOM | 3472 | CG | ASN | 52 | 126.708 | 10.954 | 9.499 | 1.00 | 35.00 | L | C |
| ATOM | 3473 | OD1 | ASN | 52 | 127.881 | 11.022 | 9.857 | 1.00 | 35.00 | L | O |
| ATOM | 3474 | ND2 | ASN | 52 | 126.236 | 11.608 | 8.439 | 1.00 | 35.00 | L | N |
| ATOM | 3475 | C | ASN | 52 | 125.288 | 7.815 | 11.109 | 1.00 | 36.32 | L | C |
| ATOM | 3476 | O | ASN | 52 | 124.059 | 7.766 | 11.078 | 1.00 | 36.32 | L | O |
| ATOM | 3477 | N | LEU | 53 | 126.018 | 7.190 | 12.027 | 1.00 | 27.25 | L | N |
| ATOM | 3478 | CA | LEU | 53 | 125.387 | 6.408 | 13.080 | 1.00 | 27.25 | L | C |
| ATOM | 3479 | CB | LEU | 53 | 126.355 | 5.366 | 13.631 | 1.00 | 36.82 | L | C |
| ATOM | 3480 | CG | LEU | 53 | 126.949 | 4.324 | 12.682 | 1.00 | 36.82 | L | C |
| ATOM | 3481 | CD1 | LEU | 53 | 127.640 | 3.266 | 13.531 | 1.00 | 36.82 | L | C |
| ATOM | 3482 | CD2 | LEU | 53 | 125.876 | 3.674 | 11.822 | 1.00 | 36.82 | L | C |
| ATOM | 3483 | C | LEU | 53 | 124.938 | 7.312 | 14.219 | 1.00 | 27.25 | L | C |
| ATOM | 3484 | O | LEU | 53 | 125.643 | 8.241 | 14.581 | 1.00 | 27.25 | L | O |
| ATOM | 3485 | N | ALA | 54 | 123.763 | 7.043 | 14.779 | 1.00 | 46.43 | L | N |
| ATOM | 3486 | CA | ALA | 54 | 123.251 | 7.827 | 15.897 | 1.00 | 46.43 | L | C |
| ATOM | 3487 | CB | ALA | 54 | 121.938 | 7.272 | 16.373 | 1.00 | 9.56 | L | C |
| ATOM | 3488 | C | ALA | 54 | 124.267 | 7.728 | 17.008 | 1.00 | 46.43 | L | C |
| ATOM | 3489 | O | ALA | 54 | 125.380 | 7.254 | 16.794 | 1.00 | 46.43 | L | O |
| ATOM | 3490 | N | SER | 55 | 123.891 | 8.140 | 18.208 | 1.00 | 82.41 | L | N |
| ATOM | 3491 | CA | SER | 55 | 124.847 | 8.081 | 19.290 | 1.00 | 82.41 | L | C |
| ATOM | 3492 | CB | SER | 55 | 124.439 | 9.036 | 20.406 | 1.00 | 85.12 | L | C |
| ATOM | 3493 | OG | SER | 55 | 125.561 | 9.342 | 21.215 | 1.00 | 85.12 | L | O |
| ATOM | 3494 | C | SER | 55 | 125.049 | 6.675 | 19.850 | 1.00 | 82.41 | L | C |
| ATOM | 3495 | O | SER | 55 | 126.187 | 6.226 | 20.004 | 1.00 | 82.41 | L | O |
| ATOM | 3496 | N | GLY | 56 | 123.957 | 5.970 | 20.137 | 1.00 | 57.94 | L | N |
| ATOM | 3497 | CA | GLY | 56 | 124.074 | 4.632 | 20.701 | 1.00 | 57.94 | L | C |
| ATOM | 3498 | C | GLY | 56 | 124.408 | 3.486 | 19.758 | 1.00 | 57.94 | L | C |
| ATOM | 3499 | O | GLY | 56 | 125.101 | 2.545 | 20.136 | 1.00 | 57.94 | L | O |
| ATOM | 3500 | N | VAL | 57 | 123.914 | 3.562 | 18.530 | 1.00 | 69.56 | L | N |
| ATOM | 3501 | CA | VAL | 57 | 124.131 | 2.519 | 17.530 | 1.00 | 69.56 | L | C |
| ATOM | 3502 | CB | VAL | 57 | 123.809 | 3.053 | 16.108 | 1.00 | 49.85 | L | C |
| ATOM | 3503 | CG1 | VAL | 57 | 123.682 | 1.898 | 15.128 | 1.00 | 49.85 | L | C |
| ATOM | 3504 | CG2 | VAL | 57 | 122.529 | 3.875 | 16.139 | 1.00 | 49.85 | L | C |

Fig. 19: A-49

| | | | | | | | | | | |
|---|---|---|---|---|---|---|---|---|---|---|
| ATOM | 3505 | C | VAL | 57 | 125.544 | 1.929 | 17.513 | 1.00 | 69.56 | L C |
| ATOM | 3506 | O | VAL | 57 | 126.515 | 2.637 | 17.244 | 1.00 | 69.56 | L O |
| ATOM | 3507 | N | PRO | 58 | 125.674 | 0.618 | 17.799 | 1.00 | 24.22 | L N |
| ATOM | 3508 | CD | PRO | 58 | 124.609 | -0.342 | 18.141 | 1.00 | 44.23 | L C |
| ATOM | 3509 | CA | PRO | 58 | 126.978 | -0.046 | 17.802 | 1.00 | 24.22 | L C |
| ATOM | 3510 | CB | PRO | 58 | 126.638 | -1.472 | 18.237 | 1.00 | 44.23 | L C |
| ATOM | 3511 | CG | PRO | 58 | 125.244 | -1.653 | 17.772 | 1.00 | 44.23 | L C |
| ATOM | 3512 | C | PRO | 58 | 127.609 | 0.017 | 16.415 | 1.00 | 24.22 | L C |
| ATOM | 3513 | O | PRO | 58 | 126.903 | -0.083 | 15.400 | 1.00 | 24.22 | L O |
| ATOM | 3514 | N | SER | 59 | 128.935 | 0.174 | 16.381 | 1.00 | 54.17 | L N |
| ATOM | 3515 | CA | SER | 59 | 129.691 | 0.295 | 15.134 | 1.00 | 54.17 | L C |
| ATOM | 3516 | CB | SER | 59 | 131.184 | 0.489 | 15.438 | 1.00 | 118.98 | L C |
| ATOM | 3517 | OG | SER | 59 | 131.729 | -0.615 | 16.139 | 1.00 | 118.98 | L O |
| ATOM | 3518 | C | SER | 59 | 129.528 | -0.815 | 14.096 | 1.00 | 54.17 | L C |
| ATOM | 3519 | O | SER | 59 | 130.015 | -0.672 | 12.970 | 1.00 | 54.17 | L O |
| ATOM | 3520 | N | ARG | 60 | 128.861 | -1.914 | 14.449 | 1.00 | 62.94 | L N |
| ATOM | 3521 | CA | ARG | 60 | 128.659 | -2.983 | 13.473 | 1.00 | 62.94 | L C |
| ATOM | 3522 | CB | ARG | 60 | 128.247 | -4.291 | 14.159 | 1.00 | 67.90 | L C |
| ATOM | 3523 | CG | ARG | 60 | 127.110 | -4.165 | 15.136 | 1.00 | 67.90 | L C |
| ATOM | 3524 | CD | ARG | 60 | 126.572 | -5.533 | 15.506 | 1.00 | 67.90 | L C |
| ATOM | 3525 | NE | ARG | 60 | 125.638 | -5.453 | 16.621 | 1.00 | 67.90 | L N |
| ATOM | 3526 | CZ | ARG | 60 | 125.978 | -5.050 | 17.840 | 1.00 | 67.90 | L C |
| ATOM | 3527 | NH1 | ARG | 60 | 127.230 | -4.696 | 18.093 | 1.00 | 67.90 | L N |
| ATOM | 3528 | NH2 | ARG | 60 | 125.070 | -5.002 | 18.807 | 1.00 | 67.90 | L N |
| ATOM | 3529 | C | ARG | 60 | 127.596 | -2.555 | 12.459 | 1.00 | 62.94 | L C |
| ATOM | 3530 | O | ARG | 60 | 127.471 | -3.146 | 11.382 | 1.00 | 62.94 | L O |
| ATOM | 3531 | N | PHE | 61 | 126.839 | -1.517 | 12.814 | 1.00 | 65.80 | L N |
| ATOM | 3532 | CA | PHE | 61 | 125.799 | -0.979 | 11.943 | 1.00 | 65.80 | L C |
| ATOM | 3533 | CB | PHE | 61 | 124.718 | -0.270 | 12.752 | 1.00 | 20.54 | L C |
| ATOM | 3534 | CG | PHE | 61 | 123.650 | -1.177 | 13.278 | 1.00 | 20.54 | L C |
| ATOM | 3535 | CD1 | PHE | 61 | 123.613 | -1.519 | 14.628 | 1.00 | 20.54 | L C |
| ATOM | 3536 | CD2 | PHE | 61 | 122.656 | -1.662 | 12.428 | 1.00 | 20.54 | L C |
| ATOM | 3537 | CE1 | PHE | 61 | 122.593 | -2.330 | 15.133 | 1.00 | 20.54 | L C |
| ATOM | 3538 | CE2 | PHE | 61 | 121.627 | -2.476 | 12.914 | 1.00 | 20.54 | L C |
| ATOM | 3539 | CZ | PHE | 61 | 121.594 | -2.809 | 14.270 | 1.00 | 20.54 | L C |
| ATOM | 3540 | C | PHE | 61 | 126.389 | 0.019 | 10.964 | 1.00 | 65.80 | L C |
| ATOM | 3541 | O | PHE | 61 | 127.300 | 0.773 | 11.300 | 1.00 | 65.80 | L O |
| ATOM | 3542 | N | SER | 62 | 125.851 | 0.030 | 9.754 | 1.00 | 31.43 | L N |
| ATOM | 3543 | CA | SER | 62 | 126.317 | 0.941 | 8.722 | 1.00 | 31.43 | L C |
| ATOM | 3544 | CB | SER | 62 | 127.530 | 0.355 | 8.001 | 1.00 | 48.53 | L C |
| ATOM | 3545 | OG | SER | 62 | 127.212 | -0.890 | 7.412 | 1.00 | 48.53 | L O |
| ATOM | 3546 | C | SER | 62 | 125.211 | 1.216 | 7.714 | 1.00 | 31.43 | L C |
| ATOM | 3547 | O | SER | 62 | 124.402 | 0.340 | 7.395 | 1.00 | 31.43 | L O |
| ATOM | 3548 | N | GLY | 63 | 125.177 | 2.443 | 7.216 | 1.00 | 26.27 | L N |
| ATOM | 3549 | CA | GLY | 63 | 124.168 | 2.802 | 6.244 | 1.00 | 26.27 | L C |
| ATOM | 3550 | C | GLY | 63 | 124.870 | 3.245 | 4.988 | 1.00 | 26.27 | L C |
| ATOM | 3551 | O | GLY | 63 | 126.032 | 3.634 | 5.044 | 1.00 | 26.27 | L O |
| ATOM | 3552 | N | SER | 64 | 124.177 | 3.201 | 3.860 | 1.00 | 35.51 | L N |
| ATOM | 3553 | CA | SER | 64 | 124.789 | 3.605 | 2.610 | 1.00 | 35.51 | L C |
| ATOM | 3554 | CB | SER | 64 | 125.824 | 2.565 | 2.193 | 1.00 | 33.46 | L C |
| ATOM | 3555 | OG | SER | 64 | 126.422 | 2.920 | 0.964 | 1.00 | 33.46 | L O |
| ATOM | 3556 | C | SER | 64 | 123.772 | 3.783 | 1.495 | 1.00 | 35.51 | L C |
| ATOM | 3557 | O | SER | 64 | 122.614 | 3.371 | 1.622 | 1.00 | 35.51 | L O |
| ATOM | 3558 | N | GLY | 65 | 124.209 | 4.401 | 0.401 | 1.00 | 29.14 | L N |
| ATOM | 3559 | CA | GLY | 65 | 123.318 | 4.594 | -0.727 | 1.00 | 29.14 | L C |
| ATOM | 3560 | C | GLY | 65 | 123.334 | 5.963 | -1.370 | 1.00 | 29.14 | L C |
| ATOM | 3561 | O | GLY | 65 | 124.127 | 6.837 | -1.024 | 1.00 | 29.14 | L O |
| ATOM | 3562 | N | SER | 66 | 122.439 | 6.137 | -2.329 | 1.00 | 15.93 | L N |
| ATOM | 3563 | CA | SER | 66 | 122.305 | 7.389 | -3.052 | 1.00 | 15.93 | L C |
| ATOM | 3564 | CB | SER | 66 | 123.623 | 7.750 | -3.741 | 1.00 | 32.28 | L C |
| ATOM | 3565 | OG | SER | 66 | 124.127 | 6.657 | -4.482 | 1.00 | 32.28 | L O |
| ATOM | 3566 | C | SER | 66 | 121.171 | 7.264 | -4.076 | 1.00 | 15.93 | L C |
| ATOM | 3567 | O | SER | 66 | 120.609 | 6.184 | -4.284 | 1.00 | 15.93 | L O |
| ATOM | 3568 | N | GLY | 67 | 120.812 | 8.378 | -4.690 | 1.00 | 33.97 | L N |
| ATOM | 3569 | CA | GLY | 67 | 119.751 | 8.349 | -5.673 | 1.00 | 33.97 | L C |
| ATOM | 3570 | C | GLY | 67 | 118.469 | 7.706 | -5.194 | 1.00 | 33.97 | L C |
| ATOM | 3571 | O | GLY | 67 | 117.757 | 8.262 | -4.361 | 1.00 | 33.97 | L O |
| ATOM | 3572 | N | THR | 68 | 118.182 | 6.521 | -5.715 | 1.00 | 25.46 | L N |
| ATOM | 3573 | CA | THR | 68 | 116.954 | 5.828 | -5.366 | 1.00 | 25.46 | L C |
| ATOM | 3574 | CB | THR | 68 | 116.176 | 5.455 | -6.633 | 1.00 | 47.05 | L C |
| ATOM | 3575 | OG1 | THR | 68 | 117.003 | 4.636 | -7.471 | 1.00 | 47.05 | L O |
| ATOM | 3576 | CG2 | THR | 68 | 115.772 | 6.704 | -7.395 | 1.00 | 47.05 | L C |
| ATOM | 3577 | C | THR | 68 | 117.132 | 4.559 | -4.539 | 1.00 | 25.46 | L C |

Fig. 19: A-50

| ATOM | 3578 | O | THR | 68 | 116.144 | 3.963 | -4.103 | 1.00 | 25.46 | L | O |
|---|---|---|---|---|---|---|---|---|---|---|---|
| ATOM | 3579 | N | ASP | 69 | 118.374 | 4.134 | -4.327 | 1.00 | 17.04 | L | N |
| ATOM | 3580 | CA | ASP | 69 | 118.614 | 2.921 | -3.554 | 1.00 | 17.04 | L | C |
| ATOM | 3581 | CB | ASP | 69 | 119.156 | 1.812 | -4.463 | 1.00 | 63.22 | L | C |
| ATOM | 3582 | CG | ASP | 69 | 118.129 | 1.354 | -5.490 | 1.00 | 63.22 | L | C |
| ATOM | 3583 | OD1 | ASP | 69 | 117.087 | 0.791 | -5.083 | 1.00 | 63.22 | L | O |
| ATOM | 3584 | OD2 | ASP | 69 | 118.356 | 1.565 | -6.703 | 1.00 | 63.22 | L | O |
| ATOM | 3585 | C | ASP | 69 | 119.544 | 3.146 | -2.372 | 1.00 | 17.04 | L | C |
| ATOM | 3586 | O | ASP | 69 | 120.684 | 3.567 | -2.535 | 1.00 | 17.04 | L | O |
| ATOM | 3587 | N | TYR | 70 | 119.030 | 2.866 | -1.177 | 1.00 | 19.76 | L | N |
| ATOM | 3588 | CA | TYR | 70 | 119.778 | 3.037 | 0.061 | 1.00 | 19.76 | L | C |
| ATOM | 3589 | CB | TYR | 70 | 119.130 | 4.151 | 0.895 | 1.00 | 24.73 | L | C |
| ATOM | 3590 | CG | TYR | 70 | 119.424 | 5.544 | 0.369 | 1.00 | 24.73 | L | C |
| ATOM | 3591 | CD1 | TYR | 70 | 120.547 | 6.255 | 0.809 | 1.00 | 24.73 | L | C |
| ATOM | 3592 | CE1 | TYR | 70 | 120.865 | 7.511 | 0.281 | 1.00 | 24.73 | L | C |
| ATOM | 3593 | CD2 | TYR | 70 | 118.620 | 6.129 | -0.616 | 1.00 | 24.73 | L | C |
| ATOM | 3594 | CE2 | TYR | 70 | 118.931 | 7.384 | -1.153 | 1.00 | 24.73 | L | C |
| ATOM | 3595 | CZ | TYR | 70 | 120.053 | 8.062 | -0.700 | 1.00 | 24.73 | L | C |
| ATOM | 3596 | OH | TYR | 70 | 120.371 | 9.275 | -1.247 | 1.00 | 24.73 | L | O |
| ATOM | 3597 | C | TYR | 70 | 119.812 | 1.727 | 0.840 | 1.00 | 19.76 | L | C |
| ATOM | 3598 | O | TYR | 70 | 118.997 | 0.828 | 0.599 | 1.00 | 19.76 | L | O |
| ATOM | 3599 | N | THR | 71 | 120.751 | 1.603 | 1.772 | 1.00 | 26.87 | L | N |
| ATOM | 3600 | CA | THR | 71 | 120.837 | 0.366 | 2.535 | 1.00 | 26.87 | L | C |
| ATOM | 3601 | CB | THR | 71 | 121.754 | -0.661 | 1.828 | 1.00 | 34.85 | L | C |
| ATOM | 3602 | OG1 | THR | 71 | 123.107 | -0.192 | 1.860 | 1.00 | 34.85 | L | O |
| ATOM | 3603 | CG2 | THR | 71 | 121.329 | -0.863 | 0.376 | 1.00 | 34.85 | L | C |
| ATOM | 3604 | C | THR | 71 | 121.333 | 0.483 | 3.977 | 1.00 | 26.87 | L | C |
| ATOM | 3605 | O | THR | 71 | 122.160 | 1.335 | 4.306 | 1.00 | 26.87 | L | O |
| ATOM | 3606 | N | LEU | 72 | 120.800 | -0.385 | 4.829 | 1.00 | 24.40 | L | N |
| ATOM | 3607 | CA | LEU | 72 | 121.204 | -0.467 | 6.222 | 1.00 | 24.40 | L | C |
| ATOM | 3608 | CB | LEU | 72 | 119.987 | -0.412 | 7.150 | 1.00 | 25.91 | L | C |
| ATOM | 3609 | CG | LEU | 72 | 120.183 | -0.827 | 8.614 | 1.00 | 25.91 | L | C |
| ATOM | 3610 | CD1 | LEU | 72 | 121.539 | -0.387 | 9.105 | 1.00 | 25.91 | L | C |
| ATOM | 3611 | CD2 | LEU | 72 | 119.097 | -0.207 | 9.470 | 1.00 | 25.91 | L | C |
| ATOM | 3612 | C | LEU | 72 | 121.875 | -1.837 | 6.296 | 1.00 | 24.40 | L | C |
| ATOM | 3613 | O | LEU | 72 | 121.386 | -2.803 | 5.707 | 1.00 | 24.40 | L | O |
| ATOM | 3614 | N | THR | 73 | 123.000 | -1.930 | 6.990 | 1.00 | 38.15 | L | N |
| ATOM | 3615 | CA | THR | 73 | 123.695 | -3.204 | 7.066 | 1.00 | 38.15 | L | C |
| ATOM | 3616 | CB | THR | 73 | 124.907 | -3.217 | 6.110 | 1.00 | 35.63 | L | C |
| ATOM | 3617 | OG1 | THR | 73 | 124.556 | -2.566 | 4.885 | 1.00 | 35.63 | L | O |
| ATOM | 3618 | CG2 | THR | 73 | 125.328 | -4.649 | 5.797 | 1.00 | 35.63 | L | C |
| ATOM | 3619 | C | THR | 73 | 124.189 | -3.542 | 8.467 | 1.00 | 38.15 | L | C |
| ATOM | 3620 | O | THR | 73 | 124.719 | -2.690 | 9.177 | 1.00 | 38.15 | L | O |
| ATOM | 3621 | N | ILE | 74 | 123.997 | -4.791 | 8.866 | 1.00 | 31.55 | L | N |
| ATOM | 3622 | CA | ILE | 74 | 124.467 | -5.246 | 10.158 | 1.00 | 31.55 | L | C |
| ATOM | 3623 | CB | ILE | 74 | 123.342 | -5.884 | 10.988 | 1.00 | 39.02 | L | C |
| ATOM | 3624 | CG2 | ILE | 74 | 123.734 | -5.878 | 12.461 | 1.00 | 39.02 | L | C |
| ATOM | 3625 | CG1 | ILE | 74 | 122.041 | -5.099 | 10.821 | 1.00 | 39.02 | L | C |
| ATOM | 3626 | CD1 | ILE | 74 | 120.870 | -5.663 | 11.635 | 1.00 | 39.02 | L | C |
| ATOM | 3627 | C | ILE | 74 | 125.504 | -6.313 | 9.814 | 1.00 | 31.55 | L | C |
| ATOM | 3628 | O | ILE | 74 | 125.146 | -7.434 | 9.440 | 1.00 | 31.55 | L | O |
| ATOM | 3629 | N | SER | 75 | 126.782 | -5.951 | 9.921 | 1.00 | 48.74 | L | N |
| ATOM | 3630 | CA | SER | 75 | 127.888 | -6.857 | 9.605 | 1.00 | 48.74 | L | C |
| ATOM | 3631 | CB | SER | 75 | 129.209 | -6.106 | 9.727 | 1.00 | 44.70 | L | C |
| ATOM | 3632 | OG | SER | 75 | 129.306 | -5.485 | 10.994 | 1.00 | 44.70 | L | O |
| ATOM | 3633 | C | SER | 75 | 127.940 | -8.129 | 10.456 | 1.00 | 48.74 | L | C |
| ATOM | 3634 | O | SER | 75 | 128.346 | -9.184 | 9.970 | 1.00 | 48.74 | L | O |
| ATOM | 3635 | N | SER | 76 | 127.544 | -8.021 | 11.722 | 1.00 | 53.77 | L | N |
| ATOM | 3636 | CA | SER | 76 | 127.530 | -9.165 | 12.635 | 1.00 | 53.77 | L | C |
| ATOM | 3637 | CB | SER | 76 | 128.773 | -9.166 | 13.521 | 1.00 | 79.21 | L | C |
| ATOM | 3638 | OG | SER | 76 | 128.707 | -10.224 | 14.463 | 1.00 | 79.21 | L | O |
| ATOM | 3639 | C | SER | 76 | 126.288 | -9.102 | 13.515 | 1.00 | 53.77 | L | C |
| ATOM | 3640 | O | SER | 76 | 126.306 | -8.533 | 14.604 | 1.00 | 53.77 | L | O |
| ATOM | 3641 | N | LEU | 77 | 125.211 | -9.704 | 13.036 | 1.00 | 35.38 | L | N |
| ATOM | 3642 | CA | LEU | 77 | 123.946 | -9.691 | 13.756 | 1.00 | 35.38 | L | C |
| ATOM | 3643 | CB | LEU | 77 | 122.955 | -10.639 | 13.085 | 1.00 | 37.68 | L | C |
| ATOM | 3644 | CG | LEU | 77 | 121.514 | -10.154 | 12.995 | 1.00 | 37.68 | L | C |
| ATOM | 3645 | CD1 | LEU | 77 | 120.623 | -11.329 | 12.638 | 1.00 | 37.68 | L | C |
| ATOM | 3646 | CD2 | LEU | 77 | 121.080 | -9.548 | 14.317 | 1.00 | 37.68 | L | C |
| ATOM | 3647 | C | LEU | 77 | 124.096 | -10.080 | 15.215 | 1.00 | 35.38 | L | C |
| ATOM | 3648 | O | LEU | 77 | 124.714 | -11.086 | 15.531 | 1.00 | 35.38 | L | O |
| ATOM | 3649 | N | GLN | 78 | 123.527 | -9.279 | 16.105 | 1.00 | 50.91 | L | N |
| ATOM | 3650 | CA | GLN | 78 | 123.589 | -9.577 | 17.527 | 1.00 | 50.91 | L | C |

Fig. 19: A-51

| ATOM | 3651 | CB | GLN | 78 | 124.201 | -8.408 | 18.290 | 1.00 | 82.93 | L | C |
|------|------|-----|-----|----|---------|--------|--------|------|-------|---|---|
| ATOM | 3652 | CG | GLN | 78 | 125.653 | -8.159 | 17.938 | 1.00 | 82.93 | L | C |
| ATOM | 3653 | CD | GLN | 78 | 126.525 | -9.385 | 18.135 | 1.00 | 82.93 | L | C |
| ATOM | 3654 | OE1 | GLN | 78 | 126.509 | -10.007 | 19.200 | 1.00 | 82.93 | L | O |
| ATOM | 3655 | NE2 | GLN | 78 | 127.299 | -9.736 | 17.109 | 1.00 | 82.93 | L | N |
| ATOM | 3656 | C | GLN | 78 | 122.192 | -9.880 | 18.062 | 1.00 | 50.91 | L | C |
| ATOM | 3657 | O | GLN | 78 | 121.197 | -9.411 | 17.519 | 1.00 | 50.91 | L | O |
| ATOM | 3658 | N | PRO | 79 | 122.104 | -10.680 | 19.135 | 1.00 | 74.65 | L | N |
| ATOM | 3659 | CD | PRO | 79 | 123.228 | -11.171 | 19.952 | 1.00 | 43.98 | L | C |
| ATOM | 3660 | CA | PRO | 79 | 120.821 | -11.049 | 19.743 | 1.00 | 74.65 | L | C |
| ATOM | 3661 | CB | PRO | 79 | 121.243 | -11.963 | 20.887 | 1.00 | 43.98 | L | C |
| ATOM | 3662 | CG | PRO | 79 | 122.577 | -11.373 | 21.284 | 1.00 | 43.98 | L | C |
| ATOM | 3663 | C | PRO | 79 | 120.033 | -9.830 | 20.224 | 1.00 | 74.65 | L | C |
| ATOM | 3664 | O | PRO | 79 | 118.855 | -9.922 | 20.577 | 1.00 | 74.65 | L | O |
| ATOM | 3665 | N | GLU | 80 | 120.697 | -8.685 | 20.221 | 1.00 | 42.25 | L | N |
| ATOM | 3666 | CA | GLU | 80 | 120.080 | -7.451 | 20.659 | 1.00 | 42.25 | L | C |
| ATOM | 3667 | CB | GLU | 80 | 121.085 | -6.697 | 21.527 | 1.00 | 40.93 | L | C |
| ATOM | 3668 | CG | GLU | 80 | 122.485 | -6.700 | 20.958 | 1.00 | 40.93 | L | C |
| ATOM | 3669 | CD | GLU | 80 | 123.424 | -5.786 | 21.726 | 1.00 | 40.93 | L | C |
| ATOM | 3670 | OE1 | GLU | 80 | 123.013 | -4.648 | 22.033 | 1.00 | 40.93 | L | O |
| ATOM | 3671 | OE2 | GLU | 80 | 124.572 | -6.197 | 22.009 | 1.00 | 40.93 | L | O |
| ATOM | 3672 | C | GLU | 80 | 119.602 | -6.575 | 19.489 | 1.00 | 42.25 | L | C |
| ATOM | 3673 | O | GLU | 80 | 118.723 | -5.726 | 19.656 | 1.00 | 42.25 | L | O |
| ATOM | 3674 | N | ASP | 81 | 120.189 | -6.787 | 18.312 | 1.00 | 42.48 | L | N |
| ATOM | 3675 | CA | ASP | 81 | 119.835 | -6.037 | 17.108 | 1.00 | 42.48 | L | C |
| ATOM | 3676 | CB | ASP | 81 | 120.867 | -6.254 | 16.005 | 1.00 | 43.12 | L | C |
| ATOM | 3677 | CG | ASP | 81 | 122.262 | -5.914 | 16.441 | 1.00 | 43.12 | L | C |
| ATOM | 3678 | OD1 | ASP | 81 | 122.422 | -5.003 | 17.281 | 1.00 | 43.12 | L | O |
| ATOM | 3679 | OD2 | ASP | 81 | 123.205 | -6.549 | 15.924 | 1.00 | 43.12 | L | O |
| ATOM | 3680 | C | ASP | 81 | 118.495 | -6.488 | 16.564 | 1.00 | 42.48 | L | C |
| ATOM | 3681 | O | ASP | 81 | 118.086 | -6.063 | 15.488 | 1.00 | 42.48 | L | O |
| ATOM | 3682 | N | PHE | 82 | 117.810 | -7.351 | 17.299 | 1.00 | 48.53 | L | N |
| ATOM | 3683 | CA | PHE | 82 | 116.544 | -7.856 | 16.822 | 1.00 | 48.53 | L | C |
| ATOM | 3684 | CB | PHE | 82 | 116.337 | -9.265 | 17.368 | 1.00 | 189.91 | L | C |
| ATOM | 3685 | CG | PHE | 82 | 117.320 | -10.260 | 16.810 | 1.00 | 189.91 | L | C |
| ATOM | 3686 | CD1 | PHE | 82 | 117.227 | -10.676 | 15.485 | 1.00 | 189.91 | L | C |
| ATOM | 3687 | CD2 | PHE | 82 | 118.369 | -10.741 | 17.587 | 1.00 | 189.91 | L | C |
| ATOM | 3688 | CE1 | PHE | 82 | 118.164 | -11.554 | 14.940 | 1.00 | 189.91 | L | C |
| ATOM | 3689 | CE2 | PHE | 82 | 119.311 | -11.622 | 17.048 | 1.00 | 189.91 | L | C |
| ATOM | 3690 | CZ | PHE | 82 | 119.207 | -12.027 | 15.725 | 1.00 | 189.91 | L | C |
| ATOM | 3691 | C | PHE | 82 | 115.359 | -6.953 | 17.094 | 1.00 | 48.53 | L | C |
| ATOM | 3692 | O | PHE | 82 | 114.857 | -6.863 | 18.216 | 1.00 | 48.53 | L | O |
| ATOM | 3693 | N | ALA | 83 | 114.939 | -6.271 | 16.032 | 1.00 | 31.52 | L | N |
| ATOM | 3694 | CA | ALA | 83 | 113.813 | -5.350 | 16.052 | 1.00 | 31.52 | L | C |
| ATOM | 3695 | CB | ALA | 83 | 114.217 | -4.051 | 16.723 | 1.00 | 63.37 | L | C |
| ATOM | 3696 | C | ALA | 83 | 113.398 | -5.090 | 14.605 | 1.00 | 31.52 | L | C |
| ATOM | 3697 | O | ALA | 83 | 113.816 | -5.808 | 13.693 | 1.00 | 31.52 | L | O |
| ATOM | 3698 | N | THR | 84 | 112.565 | -4.075 | 14.395 | 1.00 | 28.09 | L | N |
| ATOM | 3699 | CA | THR | 84 | 112.124 | -3.733 | 13.045 | 1.00 | 28.09 | L | C |
| ATOM | 3700 | CB | THR | 84 | 110.572 | -3.799 | 12.928 | 1.00 | 15.50 | L | C |
| ATOM | 3701 | OG1 | THR | 84 | 110.127 | -3.002 | 11.822 | 1.00 | 15.50 | L | O |
| ATOM | 3702 | CG2 | THR | 84 | 109.922 | -3.332 | 14.207 | 1.00 | 15.50 | L | C |
| ATOM | 3703 | C | THR | 84 | 112.664 | -2.346 | 12.659 | 1.00 | 28.09 | L | C |
| ATOM | 3704 | O | THR | 84 | 112.505 | -1.373 | 13.400 | 1.00 | 28.09 | L | O |
| ATOM | 3705 | N | TYR | 85 | 113.316 | -2.282 | 11.496 | 1.00 | 21.31 | L | N |
| ATOM | 3706 | CA | TYR | 85 | 113.935 | -1.055 | 11.000 | 1.00 | 21.31 | L | C |
| ATOM | 3707 | CB | TYR | 85 | 115.367 | -1.338 | 10.517 | 1.00 | 19.63 | L | C |
| ATOM | 3708 | CG | TYR | 85 | 116.240 | -1.976 | 11.566 | 1.00 | 19.63 | L | C |
| ATOM | 3709 | CD1 | TYR | 85 | 115.988 | -3.279 | 12.021 | 1.00 | 19.63 | L | C |
| ATOM | 3710 | CE1 | TYR | 85 | 116.718 | -3.834 | 13.061 | 1.00 | 19.63 | L | C |
| ATOM | 3711 | CD2 | TYR | 85 | 117.255 | -1.259 | 12.174 | 1.00 | 19.63 | L | C |
| ATOM | 3712 | CE2 | TYR | 85 | 117.990 | -1.807 | 13.217 | 1.00 | 19.63 | L | C |
| ATOM | 3713 | CZ | TYR | 85 | 117.711 | -3.087 | 13.655 | 1.00 | 19.63 | L | C |
| ATOM | 3714 | OH | TYR | 85 | 118.405 | -3.592 | 14.722 | 1.00 | 19.63 | L | O |
| ATOM | 3715 | C | TYR | 85 | 113.173 | -0.365 | 9.882 | 1.00 | 21.31 | L | C |
| ATOM | 3716 | O | TYR | 85 | 112.768 | -0.996 | 8.900 | 1.00 | 21.31 | L | O |
| ATOM | 3717 | N | TYR | 86 | 113.015 | 0.948 | 10.046 | 1.00 | 18.01 | L | N |
| ATOM | 3718 | CA | TYR | 86 | 112.321 | 1.806 | 9.090 | 1.00 | 18.01 | L | C |
| ATOM | 3719 | CB | TYR | 86 | 111.242 | 2.632 | 9.790 | 1.00 | 24.73 | L | C |
| ATOM | 3720 | CG | TYR | 86 | 110.130 | 1.846 | 10.421 | 1.00 | 24.73 | L | C |
| ATOM | 3721 | CD1 | TYR | 86 | 109.020 | 1.459 | 9.679 | 1.00 | 24.73 | L | C |
| ATOM | 3722 | CE1 | TYR | 86 | 107.971 | 0.756 | 10.278 | 1.00 | 24.73 | L | C |
| ATOM | 3723 | CD2 | TYR | 86 | 110.177 | 1.508 | 11.773 | 1.00 | 24.73 | L | C |

Fig. 19: A-52

| ATOM | 3724 | CE2 | TYR | 86 | 109.140 | 0.804 | 12.378 | 1.00 | 24.73 | L | C |
|---|---|---|---|---|---|---|---|---|---|---|---|
| ATOM | 3725 | CZ | TYR | 86 | 108.042 | 0.438 | 11.628 | 1.00 | 24.73 | L | C |
| ATOM | 3726 | OH | TYR | 86 | 107.002 | -0.204 | 12.238 | 1.00 | 24.73 | L | O |
| ATOM | 3727 | C | TYR | 86 | 113.280 | 2.798 | 8.465 | 1.00 | 18.01 | L | C |
| ATOM | 3728 | O | TYR | 86 | 114.110 | 3.378 | 9.158 | 1.00 | 18.01 | L | O |
| ATOM | 3729 | N | CYS | 87 | 113.170 | 2.996 | 7.158 | 1.00 | 20.53 | L | N |
| ATOM | 3730 | CA | CYS | 87 | 113.989 | 3.999 | 6.494 | 1.00 | 20.53 | L | C |
| ATOM | 3731 | C | CYS | 87 | 113.021 | 5.156 | 6.335 | 1.00 | 20.53 | L | C |
| ATOM | 3732 | O | CYS | 87 | 111.806 | 4.954 | 6.351 | 1.00 | 20.53 | L | O |
| ATOM | 3733 | CB | CYS | 87 | 114.509 | 3.527 | 5.133 | 1.00 | 17.33 | L | C |
| ATOM | 3734 | SG | CYS | 87 | 113.306 | 2.900 | 3.921 | 1.00 | 17.33 | L | S |
| ATOM | 3735 | N | GLN | 88 | 113.545 | 6.363 | 6.212 | 1.00 | 10.63 | L | N |
| ATOM | 3736 | CA | GLN | 88 | 112.696 | 7.534 | 6.083 | 1.00 | 10.63 | L | C |
| ATOM | 3737 | CB | GLN | 88 | 112.393 | 8.083 | 7.482 | 1.00 | 18.09 | L | C |
| ATOM | 3738 | CG | GLN | 88 | 111.509 | 9.303 | 7.525 | 1.00 | 18.09 | L | C |
| ATOM | 3739 | CD | GLN | 88 | 112.256 | 10.547 | 7.971 | 1.00 | 18.09 | L | C |
| ATOM | 3740 | OE1 | GLN | 88 | 112.946 | 10.539 | 8.987 | 1.00 | 18.09 | L | O |
| ATOM | 3741 | NE2 | GLN | 88 | 112.106 | 11.627 | 7.219 | 1.00 | 18.09 | L | N |
| ATOM | 3742 | C | GLN | 88 | 113.390 | 8.583 | 5.219 | 1.00 | 10.63 | L | C |
| ATOM | 3743 | O | GLN | 88 | 114.626 | 8.680 | 5.198 | 1.00 | 10.63 | L | O |
| ATOM | 3744 | N | GLN | 89 | 112.600 | 9.357 | 4.483 | 1.00 | 11.94 | L | N |
| ATOM | 3745 | CA | GLN | 89 | 113.171 | 10.386 | 3.625 | 1.00 | 11.94 | L | C |
| ATOM | 3746 | CB | GLN | 89 | 112.877 | 10.073 | 2.152 | 1.00 | 25.01 | L | C |
| ATOM | 3747 | CG | GLN | 89 | 111.407 | 10.008 | 1.776 | 1.00 | 25.01 | L | C |
| ATOM | 3748 | CD | GLN | 89 | 110.786 | 11.377 | 1.579 | 1.00 | 25.01 | L | C |
| ATOM | 3749 | OE1 | GLN | 89 | 111.373 | 12.247 | 0.935 | 1.00 | 25.01 | L | O |
| ATOM | 3750 | NE2 | GLN | 89 | 109.591 | 11.571 | 2.119 | 1.00 | 25.01 | L | N |
| ATOM | 3751 | C | GLN | 89 | 112.606 | 11.732 | 4.023 | 1.00 | 11.94 | L | C |
| ATOM | 3752 | O | GLN | 89 | 111.498 | 11.802 | 4.552 | 1.00 | 11.94 | L | O |
| ATOM | 3753 | N | TRP | 90 | 113.375 | 12.794 | 3.792 | 1.00 | 19.62 | L | N |
| ATOM | 3754 | CA | TRP | 90 | 112.948 | 14.144 | 4.145 | 1.00 | 19.62 | L | C |
| ATOM | 3755 | CB | TRP | 90 | 113.773 | 14.667 | 5.336 | 1.00 | 17.27 | L | C |
| ATOM | 3756 | CG | TRP | 90 | 115.220 | 15.018 | 5.023 | 1.00 | 17.27 | L | C |
| ATOM | 3757 | CD2 | TRP | 90 | 116.174 | 15.611 | 5.918 | 1.00 | 17.27 | L | C |
| ATOM | 3758 | CE2 | TRP | 90 | 117.373 | 15.797 | 5.189 | 1.00 | 17.27 | L | C |
| ATOM | 3759 | CE3 | TRP | 90 | 116.132 | 16.005 | 7.267 | 1.00 | 17.27 | L | C |
| ATOM | 3760 | CD1 | TRP | 90 | 115.869 | 14.867 | 3.823 | 1.00 | 17.27 | L | C |
| ATOM | 3761 | NE1 | TRP | 90 | 117.156 | 15.334 | 3.918 | 1.00 | 17.27 | L | N |
| ATOM | 3762 | CZ2 | TRP | 90 | 118.522 | 16.363 | 5.759 | 1.00 | 17.27 | L | C |
| ATOM | 3763 | CZ3 | TRP | 90 | 117.284 | 16.570 | 7.839 | 1.00 | 17.27 | L | C |
| ATOM | 3764 | CH2 | TRP | 90 | 118.462 | 16.741 | 7.080 | 1.00 | 17.27 | L | C |
| ATOM | 3765 | C | TRP | 90 | 113.074 | 15.093 | 2.947 | 1.00 | 19.62 | L | C |
| ATOM | 3766 | O | TRP | 90 | 112.783 | 16.289 | 3.048 | 1.00 | 19.62 | L | O |
| ATOM | 3767 | N | SER | 91 | 113.494 | 14.552 | 1.807 | 1.00 | 12.71 | L | N |
| ATOM | 3768 | CA | SER | 91 | 113.662 | 15.359 | 0.600 | 1.00 | 12.71 | L | C |
| ATOM | 3769 | CB | SER | 91 | 114.504 | 14.587 | -0.414 | 1.00 | 23.55 | L | C |
| ATOM | 3770 | OG | SER | 91 | 115.762 | 14.248 | 0.137 | 1.00 | 23.55 | L | O |
| ATOM | 3771 | C | SER | 91 | 112.344 | 15.800 | -0.054 | 1.00 | 12.71 | L | C |
| ATOM | 3772 | O | SER | 91 | 112.284 | 16.860 | -0.680 | 1.00 | 12.71 | L | O |
| ATOM | 3773 | N | GLY | 92 | 111.297 | 14.986 | 0.096 | 1.00 | 23.24 | L | N |
| ATOM | 3774 | CA | GLY | 92 | 110.008 | 15.310 | -0.493 | 1.00 | 23.24 | L | C |
| ATOM | 3775 | C | GLY | 92 | 108.867 | 15.347 | 0.509 | 1.00 | 23.24 | L | C |
| ATOM | 3776 | O | GLY | 92 | 108.931 | 16.218 | 1.567 | 1.00 | 23.24 | L | O |
| ATOM | 3777 | N | ASN | 93 | 107.811 | 16.078 | 0.169 | 1.00 | 31.94 | L | N |
| ATOM | 3778 | CA | ASN | 93 | 106.663 | 16.206 | 1.048 | 1.00 | 31.94 | L | C |
| ATOM | 3779 | CB | ASN | 93 | 106.307 | 17.670 | 1.203 | 1.00 | 23.71 | L | C |
| ATOM | 3780 | CG | ASN | 93 | 107.400 | 18.448 | 1.896 | 1.00 | 23.71 | L | C |
| ATOM | 3781 | OD1 | ASN | 93 | 107.790 | 19.525 | 1.445 | 1.00 | 23.71 | L | O |
| ATOM | 3782 | ND2 | ASN | 93 | 107.905 | 17.905 | 3.006 | 1.00 | 23.71 | L | N |
| ATOM | 3783 | C | ASN | 93 | 105.478 | 15.454 | 0.507 | 1.00 | 31.94 | L | C |
| ATOM | 3784 | O | ASN | 93 | 105.227 | 15.478 | -0.692 | 1.00 | 31.94 | L | O |
| ATOM | 3785 | N | PRO | 94 | 104.724 | 14.779 | 1.386 | 1.00 | 29.10 | L | N |
| ATOM | 3786 | CD | PRO | 94 | 103.575 | 13.939 | 1.009 | 1.00 | 1.87 | L | C |
| ATOM | 3787 | CA | PRO | 94 | 104.950 | 14.713 | 2.830 | 1.00 | 29.10 | L | C |
| ATOM | 3788 | CB | PRO | 94 | 103.651 | 14.113 | 3.340 | 1.00 | 1.87 | L | C |
| ATOM | 3789 | CG | PRO | 94 | 103.336 | 13.137 | 2.269 | 1.00 | 1.87 | L | C |
| ATOM | 3790 | C | PRO | 94 | 106.131 | 13.823 | 3.167 | 1.00 | 29.10 | L | C |
| ATOM | 3791 | O | PRO | 94 | 106.516 | 12.987 | 2.361 | 1.00 | 29.10 | L | O |
| ATOM | 3792 | N | TRP | 95 | 106.711 | 14.011 | 4.349 | 1.00 | 16.41 | L | N |
| ATOM | 3793 | CA | TRP | 95 | 107.810 | 13.155 | 4.772 | 1.00 | 16.41 | L | C |
| ATOM | 3794 | CB | TRP | 95 | 108.425 | 13.629 | 6.094 | 1.00 | 13.37 | L | C |
| ATOM | 3795 | CG | TRP | 95 | 109.201 | 14.906 | 5.979 | 1.00 | 13.37 | L | C |
| ATOM | 3796 | CD2 | TRP | 95 | 109.284 | 15.950 | 6.954 | 1.00 | 13.37 | L | C |

Fig. 19: A-53

| ATOM | 3797 | CE2 | TRP | 95 | 110.104 | 16.960 | 6.412 | 1.00 | 13.37 | L | C |
|---|---|---|---|---|---|---|---|---|---|---|---|
| ATOM | 3798 | CE3 | TRP | 95 | 108.743 | 16.132 | 8.229 | 1.00 | 13.37 | L | C |
| ATOM | 3799 | CD1 | TRP | 95 | 109.963 | 15.312 | 4.917 | 1.00 | 13.37 | L | C |
| ATOM | 3800 | NE1 | TRP | 95 | 110.504 | 16.543 | 5.168 | 1.00 | 13.37 | L | N |
| ATOM | 3801 | CZ2 | TRP | 95 | 110.394 | 18.144 | 7.107 | 1.00 | 13.37 | L | C |
| ATOM | 3802 | CZ3 | TRP | 95 | 109.030 | 17.305 | 8.919 | 1.00 | 13.37 | L | C |
| ATOM | 3803 | CH2 | TRP | 95 | 109.845 | 18.297 | 8.358 | 1.00 | 13.37 | L | C |
| ATOM | 3804 | C | TRP | 95 | 107.226 | 11.751 | 4.942 | 1.00 | 16.41 | L | C |
| ATOM | 3805 | O | TRP | 95 | 106.136 | 11.575 | 5.484 | 1.00 | 16.41 | L | O |
| ATOM | 3806 | N | THR | 96 | 107.956 | 10.748 | 4.481 | 1.00 | 6.71 | L | N |
| ATOM | 3807 | CA | THR | 96 | 107.465 | 9.388 | 4.563 | 1.00 | 6.71 | L | C |
| ATOM | 3808 | CB | THR | 96 | 106.963 | 8.932 | 3.172 | 1.00 | 11.59 | L | C |
| ATOM | 3809 | OG1 | THR | 96 | 108.045 | 8.991 | 2.235 | 1.00 | 11.59 | L | O |
| ATOM | 3810 | CG2 | THR | 96 | 105.859 | 9.852 | 2.674 | 1.00 | 11.59 | L | C |
| ATOM | 3811 | C | THR | 96 | 108.489 | 8.369 | 5.087 | 1.00 | 6.71 | L | C |
| ATOM | 3812 | O | THR | 96 | 109.703 | 8.621 | 5.121 | 1.00 | 6.71 | L | O |
| ATOM | 3813 | N | PHE | 97 | 107.966 | 7.222 | 5.513 | 1.00 | 24.36 | L | N |
| ATOM | 3814 | CA | PHE | 97 | 108.777 | 6.119 | 6.013 | 1.00 | 24.36 | L | C |
| ATOM | 3815 | CB | PHE | 97 | 108.327 | 5.689 | 7.418 | 1.00 | 11.10 | L | C |
| ATOM | 3816 | CG | PHE | 97 | 108.422 | 6.762 | 8.461 | 1.00 | 11.10 | L | C |
| ATOM | 3817 | CD1 | PHE | 97 | 107.541 | 7.831 | 8.460 | 1.00 | 11.10 | L | C |
| ATOM | 3818 | CD2 | PHE | 97 | 109.391 | 6.685 | 9.470 | 1.00 | 11.10 | L | C |
| ATOM | 3819 | CE1 | PHE | 97 | 107.612 | 8.821 | 9.453 | 1.00 | 11.10 | L | C |
| ATOM | 3820 | CE2 | PHE | 97 | 109.475 | 7.665 | 10.468 | 1.00 | 11.10 | L | C |
| ATOM | 3821 | CZ | PHE | 97 | 108.577 | 8.738 | 10.456 | 1.00 | 11.10 | L | C |
| ATOM | 3822 | C | PHE | 97 | 108.532 | 4.950 | 5.062 | 1.00 | 24.36 | L | C |
| ATOM | 3823 | O | PHE | 97 | 107.613 | 4.990 | 4.241 | 1.00 | 24.36 | L | O |
| ATOM | 3824 | N | GLY | 98 | 109.362 | 3.919 | 5.168 | 1.00 | 21.54 | L | N |
| ATOM | 3825 | CA | GLY | 98 | 109.183 | 2.727 | 4.350 | 1.00 | 21.54 | L | C |
| ATOM | 3826 | C | GLY | 98 | 108.266 | 1.849 | 5.184 | 1.00 | 21.54 | L | C |
| ATOM | 3827 | O | GLY | 98 | 107.977 | 2.196 | 6.339 | 1.00 | 21.54 | L | O |
| ATOM | 3828 | N | GLN | 99 | 107.796 | 0.728 | 4.645 | 1.00 | 11.59 | L | N |
| ATOM | 3829 | CA | GLN | 99 | 106.894 | -0.114 | 5.442 | 1.00 | 11.59 | L | C |
| ATOM | 3830 | CB | GLN | 99 | 106.211 | -1.197 | 4.593 | 1.00 | 37.88 | L | C |
| ATOM | 3831 | CG | GLN | 99 | 106.810 | -1.403 | 3.238 | 1.00 | 37.88 | L | C |
| ATOM | 3832 | CD | GLN | 99 | 108.266 | -1.748 | 3.319 | 1.00 | 37.88 | L | C |
| ATOM | 3833 | OE1 | GLN | 99 | 108.638 | -2.821 | 3.796 | 1.00 | 37.88 | L | O |
| ATOM | 3834 | NE2 | GLN | 99 | 109.110 | -0.832 | 2.866 | 1.00 | 37.88 | L | N |
| ATOM | 3835 | C | GLN | 99 | 107.586 | -0.758 | 6.634 | 1.00 | 11.59 | L | C |
| ATOM | 3836 | O | GLN | 99 | 106.943 | -1.317 | 7.508 | 1.00 | 11.59 | L | O |
| ATOM | 3837 | N | GLY | 100 | 108.902 | -0.640 | 6.684 | 1.00 | 24.72 | L | N |
| ATOM | 3838 | CA | GLY | 100 | 109.633 | -1.225 | 7.785 | 1.00 | 24.72 | L | C |
| ATOM | 3839 | C | GLY | 100 | 110.055 | -2.630 | 7.425 | 1.00 | 24.72 | L | C |
| ATOM | 3840 | O | GLY | 100 | 109.402 | -3.279 | 6.606 | 1.00 | 24.72 | L | O |
| ATOM | 3841 | N | THR | 101 | 111.157 | -3.084 | 8.017 | 1.00 | 23.77 | L | N |
| ATOM | 3842 | CA | THR | 101 | 111.685 | -4.424 | 7.780 | 1.00 | 23.77 | L | C |
| ATOM | 3843 | CB | THR | 101 | 113.019 | -4.382 | 7.040 | 1.00 | 10.18 | L | C |
| ATOM | 3844 | OG1 | THR | 101 | 112.790 | -4.076 | 5.659 | 1.00 | 10.18 | L | O |
| ATOM | 3845 | CG2 | THR | 101 | 113.735 | -5.716 | 7.173 | 1.00 | 10.18 | L | C |
| ATOM | 3846 | C | THR | 101 | 111.908 | -5.076 | 9.129 | 1.00 | 23.77 | L | C |
| ATOM | 3847 | O | THR | 101 | 112.689 | -4.582 | 9.942 | 1.00 | 23.77 | L | O |
| ATOM | 3848 | N | LYS | 102 | 111.223 | -6.188 | 9.365 | 1.00 | 19.34 | L | N |
| ATOM | 3849 | CA | LYS | 102 | 111.347 | -6.858 | 10.641 | 1.00 | 19.34 | L | C |
| ATOM | 3850 | CB | LYS | 102 | 110.009 | -7.496 | 11.027 | 1.00 | 36.70 | L | C |
| ATOM | 3851 | CG | LYS | 102 | 109.872 | -7.774 | 12.521 | 1.00 | 36.70 | L | C |
| ATOM | 3852 | CD | LYS | 102 | 108.464 | -8.244 | 12.876 | 1.00 | 36.70 | L | C |
| ATOM | 3853 | CE | LYS | 102 | 108.313 | -8.467 | 14.372 | 1.00 | 36.70 | L | C |
| ATOM | 3854 | NZ | LYS | 102 | 108.632 | -7.218 | 15.120 | 1.00 | 36.70 | L | N |
| ATOM | 3855 | C | LYS | 102 | 112.449 | -7.907 | 10.608 | 1.00 | 19.34 | L | C |
| ATOM | 3856 | O | LYS | 102 | 112.530 | -8.703 | 9.661 | 1.00 | 19.34 | L | O |
| ATOM | 3857 | N | VAL | 103 | 113.304 | -7.894 | 11.634 | 1.00 | 20.01 | L | N |
| ATOM | 3858 | CA | VAL | 103 | 114.378 | -8.868 | 11.714 | 1.00 | 20.01 | L | C |
| ATOM | 3859 | CB | VAL | 103 | 115.793 | -8.188 | 11.567 | 1.00 | 24.69 | L | C |
| ATOM | 3860 | CG1 | VAL | 103 | 115.696 | -6.991 | 10.636 | 1.00 | 24.69 | L | C |
| ATOM | 3861 | CG2 | VAL | 103 | 116.361 | -7.780 | 12.908 | 1.00 | 24.69 | L | C |
| ATOM | 3862 | C | VAL | 103 | 114.280 | -9.654 | 13.031 | 1.00 | 20.01 | L | C |
| ATOM | 3863 | O | VAL | 103 | 114.380 | -9.075 | 14.117 | 1.00 | 20.01 | L | O |
| ATOM | 3864 | N | GLU | 104 | 114.047 | -10.969 | 12.927 | 1.00 | 25.78 | L | N |
| ATOM | 3865 | CA | GLU | 104 | 113.948 | -11.831 | 14.106 | 1.00 | 25.78 | L | C |
| ATOM | 3866 | CB | GLU | 104 | 112.662 | -12.666 | 14.098 | 1.00 | 117.28 | L | C |
| ATOM | 3867 | CG | GLU | 104 | 112.589 | -13.728 | 13.022 | 1.00 | 117.28 | L | C |
| ATOM | 3868 | CD | GLU | 104 | 112.095 | -13.176 | 11.705 | 1.00 | 117.28 | L | C |
| ATOM | 3869 | OE1 | GLU | 104 | 112.047 | -13.942 | 10.717 | 1.00 | 117.28 | L | O |

Fig. 19: A-54

| | | | | | | | | | | |
|---|---|---|---|---|---|---|---|---|---|---|
| ATOM | 3870 | OE2 | GLU | 104 | 111.747 | -11.975 | 11.660 | 1.00 | 117.28 | L | O |
| ATOM | 3871 | C | GLU | 104 | 115.148 | -12.759 | 14.179 | 1.00 | 25.78 | L | C |
| ATOM | 3872 | O | GLU | 104 | 115.852 | -12.955 | 13.185 | 1.00 | 25.78 | L | O |
| ATOM | 3873 | N | ILE | 105 | 115.368 | -13.324 | 15.365 | 1.00 | 16.82 | L | N |
| ATOM | 3874 | CA | ILE | 105 | 116.489 | -14.228 | 15.621 | 1.00 | 16.82 | L | C |
| ATOM | 3875 | CB | ILE | 105 | 116.771 | -14.386 | 17.124 | 1.00 | 41.57 | L | C |
| ATOM | 3876 | CG2 | ILE | 105 | 118.226 | -14.701 | 17.335 | 1.00 | 41.57 | L | C |
| ATOM | 3877 | CG1 | ILE | 105 | 116.372 | -13.111 | 17.873 | 1.00 | 41.57 | L | C |
| ATOM | 3878 | CD1 | ILE | 105 | 116.594 | -13.151 | 19.385 | 1.00 | 41.57 | L | C |
| ATOM | 3879 | C | ILE | 105 | 116.204 | -15.611 | 15.102 | 1.00 | 16.82 | L | C |
| ATOM | 3880 | O | ILE | 105 | 115.251 | -16.250 | 15.543 | 1.00 | 16.82 | L | O |
| ATOM | 3881 | N | LYS | 106 | 117.008 | -16.076 | 14.153 | 1.00 | 39.65 | L | N |
| ATOM | 3882 | CA | LYS | 106 | 116.807 | -17.422 | 13.653 | 1.00 | 39.65 | L | C |
| ATOM | 3883 | CB | LYS | 106 | 117.310 | -17.587 | 12.217 | 1.00 | 48.57 | L | C |
| ATOM | 3884 | CG | LYS | 106 | 116.947 | -18.952 | 11.631 | 1.00 | 48.57 | L | C |
| ATOM | 3885 | CD | LYS | 106 | 117.401 | -19.148 | 10.179 | 1.00 | 48.57 | L | C |
| ATOM | 3886 | CE | LYS | 106 | 117.087 | -20.579 | 9.702 | 1.00 | 48.57 | L | C |
| ATOM | 3887 | NZ | LYS | 106 | 117.672 | -20.948 | 8.369 | 1.00 | 48.57 | L | N |
| ATOM | 3888 | C | LYS | 106 | 117.598 | -18.310 | 14.600 | 1.00 | 39.65 | L | C |
| ATOM | 3889 | O | LYS | 106 | 118.804 | -18.122 | 14.782 | 1.00 | 38.70 | L | O |
| ATOM | 3890 | N | ARG | 107 | 116.894 | -19.242 | 15.235 | 1.00 | 14.86 | L | N |
| ATOM | 3891 | CA | ARG | 107 | 117.492 | -20.178 | 16.174 | 1.00 | 14.86 | L | C |
| ATOM | 3892 | CB | ARG | 107 | 117.158 | -19.771 | 17.605 | 1.00 | 20.96 | L | C |
| ATOM | 3893 | CG | ARG | 107 | 115.687 | -19.532 | 17.832 | 1.00 | 20.96 | L | C |
| ATOM | 3894 | CD | ARG | 107 | 115.296 | -19.930 | 19.239 | 1.00 | 20.96 | L | C |
| ATOM | 3895 | NE | ARG | 107 | 115.615 | -21.335 | 19.502 | 1.00 | 20.96 | L | N |
| ATOM | 3896 | CZ | ARG | 107 | 115.513 | -21.910 | 20.692 | 1.00 | 20.96 | L | C |
| ATOM | 3897 | NH1 | ARG | 107 | 115.096 | -21.206 | 21.732 | 1.00 | 20.96 | L | N |
| ATOM | 3898 | NH2 | ARG | 107 | 115.843 | -23.182 | 20.840 | 1.00 | 20.96 | L | N |
| ATOM | 3899 | C | ARG | 107 | 116.986 | -21.595 | 15.899 | 1.00 | 14.86 | L | C |
| ATOM | 3900 | O | ARG | 107 | 116.062 | -21.796 | 15.107 | 1.00 | 14.86 | L | O |
| ATOM | 3901 | N | THR | 108 | 117.606 | -22.575 | 16.545 | 1.00 | 15.74 | L | N |
| ATOM | 3902 | CA | THR | 108 | 117.220 | -23.963 | 16.354 | 1.00 | 15.74 | L | C |
| ATOM | 3903 | CB | THR | 108 | 118.025 | -24.921 | 17.260 | 1.00 | 26.88 | L | C |
| ATOM | 3904 | OG1 | THR | 108 | 118.232 | -24.320 | 18.548 | 1.00 | 26.88 | L | O |
| ATOM | 3905 | CG2 | THR | 108 | 119.347 | -25.257 | 16.618 | 1.00 | 26.88 | L | C |
| ATOM | 3906 | C | THR | 108 | 115.756 | -24.161 | 16.653 | 1.00 | 15.74 | L | C |
| ATOM | 3907 | O | THR | 108 | 115.179 | -23.450 | 17.481 | 1.00 | 15.74 | L | O |
| ATOM | 3908 | N | VAL | 109 | 115.170 | -25.134 | 15.963 | 1.00 | 14.98 | L | N |
| ATOM | 3909 | CA | VAL | 109 | 113.775 | -25.469 | 16.136 | 1.00 | 12.60 | L | C |
| ATOM | 3910 | CB | VAL | 109 | 113.368 | -26.593 | 15.189 | 1.00 | 15.46 | L | C |
| ATOM | 3911 | CG1 | VAL | 109 | 111.987 | -27.105 | 15.527 | 1.00 | 14.41 | L | C |
| ATOM | 3912 | CG2 | VAL | 109 | 113.383 | -26.074 | 13.789 | 1.00 | 13.59 | L | C |
| ATOM | 3913 | C | VAL | 109 | 113.517 | -25.909 | 17.565 | 1.00 | 13.54 | L | C |
| ATOM | 3914 | O | VAL | 109 | 114.393 | -26.477 | 18.236 | 1.00 | 21.28 | L | O |
| ATOM | 3915 | N | ALA | 110 | 112.313 | -25.637 | 18.036 | 1.00 | 11.81 | L | N |
| ATOM | 3916 | CA | ALA | 110 | 111.953 | -26.001 | 19.383 | 1.00 | 12.99 | L | C |
| ATOM | 3917 | CB | ALA | 110 | 112.312 | -24.878 | 20.330 | 1.00 | 8.30 | L | C |
| ATOM | 3918 | C | ALA | 110 | 110.463 | -26.281 | 19.426 | 1.00 | 13.63 | L | C |
| ATOM | 3919 | O | ALA | 110 | 109.654 | -25.390 | 19.158 | 1.00 | 15.92 | L | O |
| ATOM | 3920 | N | ALA | 111 | 110.112 | -27.525 | 19.758 | 1.00 | 25.70 | L | N |
| ATOM | 3921 | CA | ALA | 111 | 108.715 | -27.951 | 19.838 | 1.00 | 26.75 | L | C |
| ATOM | 3922 | CB | ALA | 111 | 108.641 | -29.446 | 20.087 | 1.00 | 23.32 | L | C |
| ATOM | 3923 | C | ALA | 111 | 107.981 | -27.198 | 20.936 | 1.00 | 25.59 | L | C |
| ATOM | 3924 | O | ALA | 111 | 108.525 | -26.926 | 22.008 | 1.00 | 29.44 | L | O |
| ATOM | 3925 | N | PRO | 112 | 106.720 | -26.857 | 20.686 | 1.00 | 20.76 | L | N |
| ATOM | 3926 | CD | PRO | 112 | 105.901 | -27.063 | 19.477 | 1.00 | 26.01 | L | C |
| ATOM | 3927 | CA | PRO | 112 | 105.975 | -26.125 | 21.707 | 1.00 | 26.81 | L | C |
| ATOM | 3928 | CB | PRO | 112 | 104.938 | -25.381 | 20.882 | 1.00 | 26.37 | L | C |
| ATOM | 3929 | CG | PRO | 112 | 104.550 | -26.457 | 19.876 | 1.00 | 24.71 | L | C |
| ATOM | 3930 | C | PRO | 112 | 105.322 | -27.058 | 22.703 | 1.00 | 30.67 | L | C |
| ATOM | 3931 | O | PRO | 112 | 104.936 | -28.166 | 22.353 | 1.00 | 31.28 | L | O |
| ATOM | 3932 | N | SER | 113 | 105.220 | -26.618 | 23.947 | 1.00 | 12.97 | L | N |
| ATOM | 3933 | CA | SER | 113 | 104.530 | -27.410 | 24.944 | 1.00 | 16.57 | L | C |
| ATOM | 3934 | CB | SER | 113 | 105.027 | -27.079 | 26.334 | 1.00 | 14.96 | L | C |
| ATOM | 3935 | OG | SER | 113 | 106.427 | -27.168 | 26.370 | 1.00 | 27.37 | L | O |
| ATOM | 3936 | C | SER | 113 | 103.099 | -26.913 | 24.815 | 1.00 | 15.10 | L | C |
| ATOM | 3937 | O | SER | 113 | 102.884 | -25.708 | 24.770 | 1.00 | 12.98 | L | O |
| ATOM | 3938 | N | VAL | 114 | 102.111 | -27.792 | 24.731 | 1.00 | 10.23 | L | N |
| ATOM | 3939 | CA | VAL | 114 | 100.766 | -27.258 | 24.630 | 1.00 | 9.98 | L | C |
| ATOM | 3940 | CB | VAL | 114 | 99.989 | -27.808 | 23.413 | 1.00 | 7.82 | L | C |
| ATOM | 3941 | CG1 | VAL | 114 | 100.921 | -27.972 | 22.212 | 1.00 | 4.17 | L | C |
| ATOM | 3942 | CG2 | VAL | 114 | 99.331 | -29.100 | 23.777 | 1.00 | 9.35 | L | C |

Fig. 19: A-55

| ATOM | 3943 | C | VAL | 114 | 99.992 | -27.558 | 25.899 | 1.00 | 9.84 | L | C |
|---|---|---|---|---|---|---|---|---|---|---|---|
| ATOM | 3944 | O | VAL | 114 | 100.318 | -28.494 | 26.628 | 1.00 | 12.49 | L | O |
| ATOM | 3945 | N | PHE | 115 | 98.981 | -26.728 | 26.153 | 1.00 | 26.11 | L | N |
| ATOM | 3946 | CA | PHE | 115 | 98.109 | -26.840 | 27.318 | 1.00 | 30.12 | L | C |
| ATOM | 3947 | CB | PHE | 115 | 98.581 | -25.896 | 28.416 | 1.00 | 36.06 | L | C |
| ATOM | 3948 | CG | PHE | 115 | 100.030 | -26.015 | 28.706 | 1.00 | 35.84 | L | C |
| ATOM | 3949 | CD1 | PHE | 115 | 100.505 | -27.040 | 29.513 | 1.00 | 38.16 | L | C |
| ATOM | 3950 | CD2 | PHE | 115 | 100.935 | -25.146 | 28.115 | 1.00 | 34.45 | L | C |
| ATOM | 3951 | CE1 | PHE | 115 | 101.854 | -27.203 | 29.723 | 1.00 | 41.30 | L | C |
| ATOM | 3952 | CE2 | PHE | 115 | 102.287 | -25.302 | 28.319 | 1.00 | 38.56 | L | C |
| ATOM | 3953 | CZ | PHE | 115 | 102.749 | -26.335 | 29.126 | 1.00 | 39.82 | L | C |
| ATOM | 3954 | C | PHE | 115 | 96.727 | -26.410 | 26.873 | 1.00 | 32.06 | L | C |
| ATOM | 3955 | O | PHE | 115 | 96.590 | -25.543 | 26.017 | 1.00 | 32.56 | L | O |
| ATOM | 3956 | N | ILE | 116 | 95.694 | -27.018 | 27.432 | 1.00 | 24.34 | L | N |
| ATOM | 3957 | CA | ILE | 116 | 94.354 | -26.608 | 27.069 | 1.00 | 18.54 | L | C |
| ATOM | 3958 | CB | ILE | 116 | 93.606 | -27.735 | 26.309 | 1.00 | 15.62 | L | C |
| ATOM | 3959 | CG2 | ILE | 116 | 93.239 | -28.855 | 27.249 | 1.00 | 4.34 | L | C |
| ATOM | 3960 | CG1 | ILE | 116 | 92.377 | -27.145 | 25.615 | 1.00 | 12.45 | L | C |
| ATOM | 3961 | CD1 | ILE | 116 | 91.695 | -28.089 | 24.646 | 1.00 | 4.28 | L | C |
| ATOM | 3962 | C | ILE | 116 | 93.661 | -26.233 | 28.371 | 1.00 | 19.64 | L | C |
| ATOM | 3963 | O | ILE | 116 | 93.931 | -26.834 | 29.412 | 1.00 | 19.05 | L | O |
| ATOM | 3964 | N | PHE | 117 | 92.802 | -25.217 | 28.308 | 1.00 | 17.52 | L | N |
| ATOM | 3965 | CA | PHE | 117 | 92.066 | -24.715 | 29.475 | 1.00 | 21.17 | L | C |
| ATOM | 3966 | CB | PHE | 117 | 92.501 | -23.295 | 29.828 | 1.00 | 22.98 | L | C |
| ATOM | 3967 | CG | PHE | 117 | 93.922 | -23.177 | 30.280 | 1.00 | 26.62 | L | C |
| ATOM | 3968 | CD1 | PHE | 117 | 94.293 | -23.562 | 31.559 | 1.00 | 29.31 | L | C |
| ATOM | 3969 | CD2 | PHE | 117 | 94.882 | -22.653 | 29.433 | 1.00 | 28.01 | L | C |
| ATOM | 3970 | CE1 | PHE | 117 | 95.599 | -23.421 | 31.988 | 1.00 | 28.27 | L | C |
| ATOM | 3971 | CE2 | PHE | 117 | 96.186 | -22.511 | 29.854 | 1.00 | 26.58 | L | C |
| ATOM | 3972 | CZ | PHE | 117 | 96.550 | -22.895 | 31.134 | 1.00 | 28.58 | L | C |
| ATOM | 3973 | C | PHE | 117 | 90.585 | -24.642 | 29.194 | 1.00 | 24.71 | L | C |
| ATOM | 3974 | O | PHE | 117 | 90.167 | -23.964 | 28.261 | 1.00 | 29.18 | L | O |
| ATOM | 3975 | N | PRO | 118 | 89.768 | -25.323 | 30.007 | 1.00 | 23.78 | L | N |
| ATOM | 3976 | CD | PRO | 118 | 90.235 | -26.376 | 30.926 | 1.00 | 9.40 | L | C |
| ATOM | 3977 | CA | PRO | 118 | 88.300 | -25.354 | 29.883 | 1.00 | 26.26 | L | C |
| ATOM | 3978 | CB | PRO | 118 | 87.907 | -26.568 | 30.718 | 1.00 | 9.92 | L | C |
| ATOM | 3979 | CG | PRO | 118 | 89.159 | -27.404 | 30.763 | 1.00 | 12.26 | L | C |
| ATOM | 3980 | C | PRO | 118 | 87.660 | -24.081 | 30.455 | 1.00 | 29.72 | L | C |
| ATOM | 3981 | O | PRO | 118 | 88.231 | -23.440 | 31.338 | 1.00 | 31.19 | L | O |
| ATOM | 3982 | N | PRO | 119 | 86.464 | -23.699 | 29.966 | 1.00 | 9.50 | L | N |
| ATOM | 3983 | CD | PRO | 119 | 85.678 | -24.330 | 28.892 | 1.00 | 26.21 | L | C |
| ATOM | 3984 | CA | PRO | 119 | 85.787 | -22.493 | 30.479 | 1.00 | 9.82 | L | C |
| ATOM | 3985 | CB | PRO | 119 | 84.413 | -22.555 | 29.826 | 1.00 | 24.20 | L | C |
| ATOM | 3986 | CG | PRO | 119 | 84.703 | -23.219 | 28.519 | 1.00 | 27.52 | L | C |
| ATOM | 3987 | C | PRO | 119 | 85.682 | -22.566 | 32.001 | 1.00 | 15.21 | L | C |
| ATOM | 3988 | O | PRO | 119 | 85.463 | -23.630 | 32.561 | 1.00 | 17.89 | L | O |
| ATOM | 3989 | N | SER | 120 | 85.843 | -21.435 | 32.665 | 1.00 | 31.09 | L | N |
| ATOM | 3990 | CA | SER | 120 | 85.765 | -21.378 | 34.118 | 1.00 | 35.08 | L | C |
| ATOM | 3991 | CB | SER | 120 | 86.299 | -20.027 | 34.586 | 1.00 | 17.54 | L | C |
| ATOM | 3992 | OG | SER | 120 | 85.709 | -18.983 | 33.832 | 1.00 | 27.86 | L | O |
| ATOM | 3993 | C | SER | 120 | 84.334 | -21.550 | 34.623 | 1.00 | 35.73 | L | C |
| ATOM | 3994 | O | SER | 120 | 83.370 | -21.381 | 33.869 | 1.00 | 35.32 | L | O |
| ATOM | 3995 | N | ASP | 121 | 84.185 | -21.896 | 35.897 | 1.00 | 24.20 | L | N |
| ATOM | 3996 | CA | ASP | 121 | 82.842 | -22.015 | 36.465 | 1.00 | 27.07 | L | C |
| ATOM | 3997 | CB | ASP | 121 | 82.897 | -22.458 | 37.937 | 1.00 | 55.35 | L | C |
| ATOM | 3998 | CG | ASP | 121 | 83.160 | -23.950 | 38.101 | 1.00 | 60.98 | L | C |
| ATOM | 3999 | OD1 | ASP | 121 | 82.573 | -24.736 | 37.331 | 1.00 | 62.35 | L | O |
| ATOM | 4000 | OD2 | ASP | 121 | 83.934 | -24.337 | 39.008 | 1.00 | 63.66 | L | O |
| ATOM | 4001 | C | ASP | 121 | 82.194 | -20.627 | 36.384 | 1.00 | 26.11 | L | C |
| ATOM | 4002 | O | ASP | 121 | 81.053 | -20.474 | 35.941 | 1.00 | 23.12 | L | O |
| ATOM | 4003 | N | GLU | 122 | 82.954 | -19.617 | 36.794 | 1.00 | 48.87 | L | N |
| ATOM | 4004 | CA | GLU | 122 | 82.490 | -18.234 | 36.797 | 1.00 | 47.43 | L | C |
| ATOM | 4005 | CB | GLU | 122 | 83.596 | -17.328 | 37.348 | 1.00 | 56.26 | L | C |
| ATOM | 4006 | CG | GLU | 122 | 83.180 | -15.870 | 37.529 | 1.00 | 59.80 | L | C |
| ATOM | 4007 | CD | GLU | 122 | 84.328 | -14.966 | 37.984 | 1.00 | 63.49 | L | C |
| ATOM | 4008 | OE1 | GLU | 122 | 84.099 | -13.741 | 38.109 | 1.00 | 64.12 | L | O |
| ATOM | 4009 | OE2 | GLU | 122 | 85.453 | -15.472 | 38.213 | 1.00 | 63.98 | L | O |
| ATOM | 4010 | C | GLU | 122 | 82.018 | -17.703 | 35.434 | 1.00 | 47.22 | L | C |
| ATOM | 4011 | O | GLU | 122 | 80.884 | -17.232 | 35.303 | 1.00 | 45.96 | L | O |
| ATOM | 4012 | N | GLN | 123 | 82.881 | -17.774 | 34.424 | 1.00 | 34.52 | L | N |
| ATOM | 4013 | CA | GLN | 123 | 82.523 | -17.273 | 33.102 | 1.00 | 32.32 | L | C |
| ATOM | 4014 | CB | GLN | 123 | 83.643 | -17.511 | 32.097 | 1.00 | 23.68 | L | C |
| ATOM | 4015 | CG | GLN | 123 | 83.286 | -17.000 | 30.723 | 1.00 | 24.85 | L | C |

Fig. 19: A-56

| | | | | | | | | | | |
|---|---|---|---|---|---|---|---|---|---|---|
| ATOM | 4016 | CD | GLN | 123 | 84.089 | -17.644 | 29.635 | 1.00 | 26.94 | L | C |
| ATOM | 4017 | OE1 | GLN | 123 | 83.877 | -17.369 | 28.463 | 1.00 | 23.36 | L | O |
| ATOM | 4018 | NE2 | GLN | 123 | 85.017 | -18.511 | 30.010 | 1.00 | 24.66 | L | N |
| ATOM | 4019 | C | GLN | 123 | 81.256 | -17.909 | 32.565 | 1.00 | 32.32 | L | C |
| ATOM | 4020 | O | GLN | 123 | 80.424 | -17.233 | 31.969 | 1.00 | 29.27 | L | O |
| ATOM | 4021 | N | LEU | 124 | 81.128 | -19.218 | 32.745 | 1.00 | 36.22 | L | N |
| ATOM | 4022 | CA | LEU | 124 | 79.938 | -19.926 | 32.288 | 1.00 | 37.57 | L | C |
| ATOM | 4023 | CB | LEU | 124 | 80.075 | -21.425 | 32.570 | 1.00 | 20.16 | L | C |
| ATOM | 4024 | CG | LEU | 124 | 80.878 | -22.173 | 31.498 | 1.00 | 19.96 | L | C |
| ATOM | 4025 | CD1 | LEU | 124 | 81.099 | -23.623 | 31.892 | 1.00 | 15.21 | L | C |
| ATOM | 4026 | CD2 | LEU | 124 | 80.123 | -22.085 | 30.176 | 1.00 | 18.53 | L | C |
| ATOM | 4027 | C | LEU | 124 | 78.722 | -19.355 | 33.003 | 1.00 | 41.33 | L | C |
| ATOM | 4028 | O | LEU | 124 | 77.648 | -19.204 | 32.417 | 1.00 | 43.14 | L | O |
| ATOM | 4029 | N | LYS | 125 | 78.912 | -19.022 | 34.274 | 1.00 | 101.23 | L | N |
| ATOM | 4030 | CA | LYS | 125 | 77.856 | -18.441 | 35.090 | 1.00 | 102.45 | L | C |
| ATOM | 4031 | CB | LYS | 125 | 78.355 | -18.285 | 36.534 | 1.00 | 60.11 | L | C |
| ATOM | 4032 | CG | LYS | 125 | 77.286 | -18.376 | 37.612 | 1.00 | 62.95 | L | C |
| ATOM | 4033 | CD | LYS | 125 | 76.737 | -19.797 | 37.713 | 1.00 | 68.67 | L | C |
| ATOM | 4034 | CE | LYS | 125 | 75.726 | -19.942 | 38.847 | 1.00 | 73.14 | L | C |
| ATOM | 4035 | NZ | LYS | 125 | 75.101 | -21.299 | 38.895 | 1.00 | 74.11 | L | N |
| ATOM | 4036 | C | LYS | 125 | 77.545 | -17.065 | 34.494 | 1.00 | 104.22 | L | C |
| ATOM | 4037 | O | LYS | 125 | 77.004 | -16.195 | 35.168 | 1.00 | 105.97 | L | O |
| ATOM | 4038 | N | SER | 126 | 77.892 | -16.880 | 33.222 | 1.00 | 44.02 | L | N |
| ATOM | 4039 | CA | SER | 126 | 77.693 | -15.614 | 32.522 | 1.00 | 43.14 | L | C |
| ATOM | 4040 | CB | SER | 126 | 79.045 | -14.925 | 32.308 | 1.00 | 48.89 | L | C |
| ATOM | 4041 | OG | SER | 126 | 78.953 | -13.915 | 31.324 | 1.00 | 52.18 | L | O |
| ATOM | 4042 | C | SER | 126 | 76.995 | -15.769 | 31.176 | 1.00 | 41.22 | L | C |
| ATOM | 4043 | O | SER | 126 | 76.469 | -14.802 | 30.631 | 1.00 | 40.32 | L | O |
| ATOM | 4044 | N | GLY | 127 | 77.007 | -16.978 | 30.626 | 1.00 | 29.57 | L | N |
| ATOM | 4045 | CA | GLY | 127 | 76.340 | -17.190 | 29.355 | 1.00 | 30.30 | L | C |
| ATOM | 4046 | C | GLY | 127 | 77.266 | -17.332 | 28.168 | 1.00 | 29.68 | L | C |
| ATOM | 4047 | O | GLY | 127 | 76.818 | -17.391 | 27.022 | 1.00 | 30.41 | L | O |
| ATOM | 4048 | N | THR | 128 | 78.564 | -17.375 | 28.432 | 1.00 | 60.53 | L | N |
| ATOM | 4049 | CA | THR | 128 | 79.530 | -17.531 | 27.360 | 1.00 | 57.77 | L | C |
| ATOM | 4050 | CB | THR | 128 | 80.105 | -16.180 | 26.921 | 1.00 | 55.78 | L | C |
| ATOM | 4051 | OG1 | THR | 128 | 79.080 | -15.424 | 26.264 | 1.00 | 56.94 | L | O |
| ATOM | 4052 | CG2 | THR | 128 | 81.259 | -16.381 | 25.960 | 1.00 | 54.81 | L | C |
| ATOM | 4053 | C | THR | 128 | 80.643 | -18.434 | 27.830 | 1.00 | 56.24 | L | C |
| ATOM | 4054 | O | THR | 128 | 80.979 | -18.446 | 29.015 | 1.00 | 51.99 | L | O |
| ATOM | 4055 | N | ALA | 129 | 81.201 | -19.203 | 26.901 | 1.00 | 18.93 | L | N |
| ATOM | 4056 | CA | ALA | 129 | 82.275 | -20.125 | 27.232 | 1.00 | 17.83 | L | C |
| ATOM | 4057 | CB | ALA | 129 | 81.779 | -21.558 | 27.108 | 1.00 | 65.23 | L | C |
| ATOM | 4058 | C | ALA | 129 | 83.512 | -19.937 | 26.374 | 1.00 | 17.59 | L | C |
| ATOM | 4059 | O | ALA | 129 | 83.443 | -19.993 | 25.148 | 1.00 | 23.96 | L | O |
| ATOM | 4060 | N | SER | 130 | 84.652 | -19.729 | 27.020 | 1.00 | 24.31 | L | N |
| ATOM | 4061 | CA | SER | 130 | 85.905 | -19.560 | 26.298 | 1.00 | 19.76 | L | C |
| ATOM | 4062 | CB | SER | 130 | 86.565 | -18.256 | 26.741 | 1.00 | 18.21 | L | C |
| ATOM | 4063 | OG | SER | 130 | 85.724 | -17.142 | 26.477 | 1.00 | 20.32 | L | O |
| ATOM | 4064 | C | SER | 130 | 86.835 | -20.755 | 26.573 | 1.00 | 16.63 | L | C |
| ATOM | 4065 | O | SER | 130 | 87.037 | -21.141 | 27.732 | 1.00 | 19.43 | L | O |
| ATOM | 4066 | N | VAL | 131 | 87.370 | -21.371 | 25.521 | 1.00 | 11.62 | L | N |
| ATOM | 4067 | CA | VAL | 131 | 88.294 | -22.502 | 25.686 | 1.00 | 9.15 | L | C |
| ATOM | 4068 | CB | VAL | 131 | 87.848 | -23.743 | 24.872 | 1.00 | 17.04 | L | C |
| ATOM | 4069 | CG1 | VAL | 131 | 88.738 | -24.927 | 25.196 | 1.00 | 21.32 | L | C |
| ATOM | 4070 | CG2 | VAL | 131 | 86.413 | -24.081 | 25.180 | 1.00 | 16.62 | L | C |
| ATOM | 4071 | C | VAL | 131 | 89.647 | -22.030 | 25.156 | 1.00 | 9.42 | L | C |
| ATOM | 4072 | O | VAL | 131 | 89.731 | -21.557 | 24.025 | 1.00 | 13.02 | L | O |
| ATOM | 4073 | N | VAL | 132 | 90.704 | -22.146 | 25.956 | 1.00 | 21.24 | L | N |
| ATOM | 4074 | CA | VAL | 132 | 92.011 | -21.677 | 25.501 | 1.00 | 16.30 | L | C |
| ATOM | 4075 | CB | VAL | 132 | 92.573 | -20.538 | 26.414 | 1.00 | 43.77 | L | C |
| ATOM | 4076 | CG1 | VAL | 132 | 93.958 | -20.122 | 25.934 | 1.00 | 47.77 | L | C |
| ATOM | 4077 | CG2 | VAL | 132 | 91.645 | -19.324 | 26.393 | 1.00 | 44.24 | L | C |
| ATOM | 4078 | C | VAL | 132 | 93.081 | -22.743 | 25.374 | 1.00 | 17.14 | L | C |
| ATOM | 4079 | O | VAL | 132 | 93.372 | -23.482 | 26.320 | 1.00 | 14.49 | L | O |
| ATOM | 4080 | N | CYS | 133 | 93.662 | -22.793 | 24.178 | 1.00 | 23.86 | L | N |
| ATOM | 4081 | CA | CYS | 133 | 94.737 | -23.713 | 23.822 | 1.00 | 24.13 | L | C |
| ATOM | 4082 | C | CYS | 133 | 96.034 | -22.880 | 23.891 | 1.00 | 24.10 | L | C |
| ATOM | 4083 | O | CYS | 133 | 96.072 | -21.744 | 23.425 | 1.00 | 27.83 | L | O |
| ATOM | 4084 | CB | CYS | 133 | 94.486 | -24.219 | 22.399 | 1.00 | 19.56 | L | C |
| ATOM | 4085 | SG | CYS | 133 | 95.558 | -25.537 | 21.738 | 1.00 | 32.96 | L | S |
| ATOM | 4086 | N | LEU | 134 | 97.085 | -23.432 | 24.482 | 1.00 | 36.02 | L | N |
| ATOM | 4087 | CA | LEU | 134 | 98.343 | -22.709 | 24.591 | 1.00 | 34.35 | L | C |
| ATOM | 4088 | CB | LEU | 134 | 98.658 | -22.383 | 26.058 | 1.00 | 16.71 | L | C |

Fig. 19: A-57

| | | | | | | | | | | |
|---|---|---|---|---|---|---|---|---|---|---|
| ATOM | 4089 | CG | LEU | 134 | 100.079 | -21.843 | 26.376 | 1.00 | 12.52 | L | C |
| ATOM | 4090 | CD1 | LEU | 134 | 100.297 | -20.468 | 25.729 | 1.00 | 9.26 | L | C |
| ATOM | 4091 | CD2 | LEU | 134 | 100.275 | -21.746 | 27.892 | 1.00 | 9.75 | L | C |
| ATOM | 4092 | C | LEU | 134 | 99.532 | -23.457 | 24.001 | 1.00 | 33.88 | L | C |
| ATOM | 4093 | O | LEU | 134 | 99.820 | -24.595 | 24.378 | 1.00 | 33.96 | L | O |
| ATOM | 4094 | N | LEU | 135 | 100.206 | -22.802 | 23.060 | 1.00 | 23.69 | L | N |
| ATOM | 4095 | CA | LEU | 135 | 101.406 | -23.336 | 22.441 | 1.00 | 29.22 | L | C |
| ATOM | 4096 | CB | LEU | 135 | 101.353 | -23.150 | 20.926 | 1.00 | 1.87 | L | C |
| ATOM | 4097 | CG | LEU | 135 | 100.337 | -24.016 | 20.168 | 1.00 | 4.32 | L | C |
| ATOM | 4098 | CD1 | LEU | 135 | 98.962 | -23.751 | 20.672 | 1.00 | 5.12 | L | C |
| ATOM | 4099 | CD2 | LEU | 135 | 100.392 | -23.713 | 18.681 | 1.00 | 3.70 | L | C |
| ATOM | 4100 | C | LEU | 135 | 102.454 | -22.437 | 23.097 | 1.00 | 29.43 | L | C |
| ATOM | 4101 | O | LEU | 135 | 102.401 | -21.216 | 22.977 | 1.00 | 30.81 | L | O |
| ATOM | 4102 | N | ASN | 136 | 103.394 | -23.047 | 23.810 | 1.00 | 17.75 | L | N |
| ATOM | 4103 | CA | ASN | 136 | 104.393 | -22.299 | 24.550 | 1.00 | 20.05 | L | C |
| ATOM | 4104 | CB | ASN | 136 | 104.179 | -22.576 | 26.016 | 1.00 | 15.03 | L | C |
| ATOM | 4105 | CG | ASN | 136 | 104.905 | -21.615 | 26.885 | 1.00 | 19.57 | L | C |
| ATOM | 4106 | OD1 | ASN | 136 | 105.767 | -22.017 | 27.666 | 1.00 | 25.01 | L | O |
| ATOM | 4107 | ND2 | ASN | 136 | 104.569 | -20.327 | 26.769 | 1.00 | 19.54 | L | N |
| ATOM | 4108 | C | ASN | 136 | 105.856 | -22.526 | 24.212 | 1.00 | 18.78 | L | C |
| ATOM | 4109 | O | ASN | 136 | 106.283 | -23.651 | 23.963 | 1.00 | 17.25 | L | O |
| ATOM | 4110 | N | ASN | 137 | 106.619 | -21.436 | 24.240 | 1.00 | 28.11 | L | N |
| ATOM | 4111 | CA | ASN | 137 | 108.053 | -21.425 | 23.950 | 1.00 | 27.19 | L | C |
| ATOM | 4112 | CB | ASN | 137 | 108.869 | -21.844 | 25.173 | 1.00 | 13.82 | L | C |
| ATOM | 4113 | CG | ASN | 137 | 108.594 | -20.986 | 26.387 | 1.00 | 24.17 | L | C |
| ATOM | 4114 | OD1 | ASN | 137 | 108.027 | -19.901 | 26.281 | 1.00 | 19.30 | L | O |
| ATOM | 4115 | ND2 | ASN | 137 | 109.009 | -21.468 | 27.558 | 1.00 | 29.25 | L | N |
| ATOM | 4116 | C | ASN | 137 | 108.486 | -22.292 | 22.783 | 1.00 | 25.42 | L | C |
| ATOM | 4117 | O | ASN | 137 | 109.125 | -23.324 | 22.977 | 1.00 | 28.31 | L | O |
| ATOM | 4118 | N | PHE | 138 | 108.152 | -21.880 | 21.571 | 1.00 | 45.01 | L | N |
| ATOM | 4119 | CA | PHE | 138 | 108.557 | -22.652 | 20.412 | 1.00 | 41.21 | L | C |
| ATOM | 4120 | CB | PHE | 138 | 107.362 | -23.361 | 19.777 | 1.00 | 23.11 | L | C |
| ATOM | 4121 | CG | PHE | 138 | 106.230 | -22.452 | 19.442 | 1.00 | 20.89 | L | C |
| ATOM | 4122 | CD1 | PHE | 138 | 105.342 | -22.043 | 20.433 | 1.00 | 18.63 | L | C |
| ATOM | 4123 | CD2 | PHE | 138 | 106.055 | -21.993 | 18.137 | 1.00 | 19.93 | L | C |
| ATOM | 4124 | CE1 | PHE | 138 | 104.289 | -21.189 | 20.134 | 1.00 | 11.59 | L | C |
| ATOM | 4125 | CE2 | PHE | 138 | 105.010 | -21.138 | 17.818 | 1.00 | 16.52 | L | C |
| ATOM | 4126 | CZ | PHE | 138 | 104.118 | -20.730 | 18.818 | 1.00 | 14.07 | L | C |
| ATOM | 4127 | C | PHE | 138 | 109.248 | -21.794 | 19.369 | 1.00 | 36.81 | L | C |
| ATOM | 4128 | O | PHE | 138 | 109.456 | -20.594 | 19.559 | 1.00 | 35.37 | L | O |
| ATOM | 4129 | N | TYR | 139 | 109.606 | -22.437 | 18.267 | 1.00 | 17.70 | L | N |
| ATOM | 4130 | CA | TYR | 139 | 110.283 | -21.797 | 17.159 | 1.00 | 20.93 | L | C |
| ATOM | 4131 | CB | TYR | 139 | 111.660 | -21.300 | 17.579 | 1.00 | 31.56 | L | C |
| ATOM | 4132 | CG | TYR | 139 | 112.317 | -20.472 | 16.502 | 1.00 | 31.46 | L | C |
| ATOM | 4133 | CD1 | TYR | 139 | 112.207 | -19.083 | 16.502 | 1.00 | 26.49 | L | C |
| ATOM | 4134 | CE1 | TYR | 139 | 112.725 | -18.327 | 15.462 | 1.00 | 25.20 | L | C |
| ATOM | 4135 | CD2 | TYR | 139 | 112.974 | -21.093 | 15.428 | 1.00 | 25.20 | L | C |
| ATOM | 4136 | CE2 | TYR | 139 | 113.490 | -20.336 | 14.386 | 1.00 | 25.20 | L | C |
| ATOM | 4137 | CZ | TYR | 139 | 113.358 | -18.960 | 14.407 | 1.00 | 25.20 | L | C |
| ATOM | 4138 | OH | TYR | 139 | 113.820 | -18.216 | 13.353 | 1.00 | 28.00 | L | O |
| ATOM | 4139 | C | TYR | 139 | 110.447 | -22.917 | 16.166 | 1.00 | 20.32 | L | C |
| ATOM | 4140 | O | TYR | 139 | 110.798 | -24.022 | 16.550 | 1.00 | 25.25 | L | O |
| ATOM | 4141 | N | PRO | 140 | 110.223 | -22.662 | 14.876 | 1.00 | 34.32 | L | N |
| ATOM | 4142 | CD | PRO | 140 | 110.342 | -23.783 | 13.937 | 1.00 | 6.42 | L | C |
| ATOM | 4143 | CA | PRO | 140 | 109.824 | -21.443 | 14.171 | 1.00 | 30.02 | L | C |
| ATOM | 4144 | CB | PRO | 140 | 109.691 | -21.901 | 12.723 | 1.00 | 2.76 | L | C |
| ATOM | 4145 | CG | PRO | 140 | 110.570 | -23.070 | 12.643 | 1.00 | 4.42 | L | C |
| ATOM | 4146 | C | PRO | 140 | 108.502 | -20.939 | 14.685 | 1.00 | 31.53 | L | C |
| ATOM | 4147 | O | PRO | 140 | 107.830 | -21.612 | 15.466 | 1.00 | 29.36 | L | O |
| ATOM | 4148 | N | ARG | 141 | 108.119 | -19.764 | 14.203 | 1.00 | 22.83 | L | N |
| ATOM | 4149 | CA | ARG | 141 | 106.871 | -19.115 | 14.588 | 1.00 | 27.99 | L | C |
| ATOM | 4150 | CB | ARG | 141 | 106.931 | -17.657 | 14.148 | 1.00 | 21.70 | L | C |
| ATOM | 4151 | CG | ARG | 141 | 105.753 | -16.783 | 14.473 | 1.00 | 25.87 | L | C |
| ATOM | 4152 | CD | ARG | 141 | 106.157 | -15.358 | 14.129 | 1.00 | 37.20 | L | C |
| ATOM | 4153 | NE | ARG | 141 | 105.187 | -14.366 | 14.564 | 1.00 | 43.19 | L | N |
| ATOM | 4154 | CZ | ARG | 141 | 104.001 | -14.188 | 13.995 | 1.00 | 43.90 | L | C |
| ATOM | 4155 | NH1 | ARG | 141 | 103.642 | -14.941 | 12.960 | 1.00 | 39.57 | L | N |
| ATOM | 4156 | NH2 | ARG | 141 | 103.173 | -13.262 | 14.464 | 1.00 | 42.44 | L | N |
| ATOM | 4157 | C | ARG | 141 | 105.668 | -19.798 | 13.960 | 1.00 | 30.81 | L | C |
| ATOM | 4158 | O | ARG | 141 | 104.585 | -19.815 | 14.537 | 1.00 | 34.71 | L | O |
| ATOM | 4159 | N | GLU | 142 | 105.860 | -20.365 | 12.776 | 1.00 | 28.20 | L | N |
| ATOM | 4160 | CA | GLU | 142 | 104.756 | -21.013 | 12.091 | 1.00 | 24.33 | L | C |
| ATOM | 4161 | CB | GLU | 142 | 105.171 | -21.552 | 10.725 | 1.00 | 7.98 | L | C |

Fig. 19: A-58

| | | | | | | | | | | |
|---|---|---|---|---|---|---|---|---|---|---|
| ATOM | 4162 | CG | GLU | 142 | 105.741 | -20.523 | 9.781 | 1.00 | 19.00 | L | C |
| ATOM | 4163 | CD | GLU | 142 | 107.096 | -20.051 | 10.217 | 1.00 | 27.12 | L | C |
| ATOM | 4164 | OE1 | GLU | 142 | 107.152 | -18.970 | 10.837 | 1.00 | 31.02 | L | O |
| ATOM | 4165 | OE2 | GLU | 142 | 108.095 | -20.772 | 9.952 | 1.00 | 33.88 | L | O |
| ATOM | 4166 | C | GLU | 142 | 104.154 | -22.151 | 12.878 | 1.00 | 22.94 | L | C |
| ATOM | 4167 | O | GLU | 142 | 104.753 | -23.220 | 13.021 | 1.00 | 26.95 | L | O |
| ATOM | 4168 | N | ALA | 143 | 102.958 | -21.909 | 13.386 | 1.00 | 30.55 | L | N |
| ATOM | 4169 | CA | ALA | 143 | 102.238 | -22.914 | 14.130 | 1.00 | 32.81 | L | C |
| ATOM | 4170 | CB | ALA | 143 | 102.260 | -22.593 | 15.640 | 1.00 | 21.32 | L | C |
| ATOM | 4171 | C | ALA | 143 | 100.819 | -22.862 | 13.579 | 1.00 | 34.94 | L | C |
| ATOM | 4172 | O | ALA | 143 | 100.373 | -21.832 | 13.058 | 1.00 | 38.69 | L | O |
| ATOM | 4173 | N | LYS | 144 | 100.120 | -23.981 | 13.677 | 1.00 | 46.96 | L | N |
| ATOM | 4174 | CA | LYS | 144 | 98.761 | -24.047 | 13.197 | 1.00 | 49.64 | L | C |
| ATOM | 4175 | CB | LYS | 144 | 98.734 | -24.807 | 11.870 | 1.00 | 34.36 | L | C |
| ATOM | 4176 | CG | LYS | 144 | 97.631 | -24.370 | 10.922 | 1.00 | 44.31 | L | C |
| ATOM | 4177 | CD | LYS | 144 | 97.441 | -25.358 | 9.772 | 1.00 | 55.06 | L | C |
| ATOM | 4178 | CE | LYS | 144 | 96.888 | -26.699 | 10.279 | 1.00 | 57.35 | L | C |
| ATOM | 4179 | NZ | LYS | 144 | 96.807 | -27.761 | 9.225 | 1.00 | 58.76 | L | N |
| ATOM | 4180 | C | LYS | 144 | 97.934 | -24.771 | 14.266 | 1.00 | 52.97 | L | C |
| ATOM | 4181 | O | LYS | 144 | 98.340 | -25.822 | 14.775 | 1.00 | 51.55 | L | O |
| ATOM | 4182 | N | VAL | 145 | 96.791 | -24.194 | 14.630 | 1.00 | 15.87 | L | N |
| ATOM | 4183 | CA | VAL | 145 | 95.927 | -24.813 | 15.629 | 1.00 | 21.71 | L | C |
| ATOM | 4184 | CB | VAL | 145 | 95.790 | -23.937 | 16.905 | 1.00 | 8.53 | L | C |
| ATOM | 4185 | CG1 | VAL | 145 | 94.817 | -24.597 | 17.889 | 1.00 | 7.53 | L | C |
| ATOM | 4186 | CG2 | VAL | 145 | 97.151 | -23.769 | 17.570 | 1.00 | 8.28 | L | C |
| ATOM | 4187 | C | VAL | 145 | 94.536 | -25.074 | 15.073 | 1.00 | 25.32 | L | C |
| ATOM | 4188 | O | VAL | 145 | 93.909 | -24.193 | 14.497 | 1.00 | 27.49 | L | O |
| ATOM | 4189 | N | GLN | 146 | 94.055 | -26.296 | 15.231 | 1.00 | 39.17 | L | N |
| ATOM | 4190 | CA | GLN | 146 | 92.729 | -26.611 | 14.743 | 1.00 | 38.70 | L | C |
| ATOM | 4191 | CB | GLN | 146 | 92.798 | -27.679 | 13.653 | 1.00 | 72.09 | L | C |
| ATOM | 4192 | CG | GLN | 146 | 93.678 | -27.281 | 12.482 | 1.00 | 76.00 | L | C |
| ATOM | 4193 | CD | GLN | 146 | 93.630 | -28.276 | 11.339 | 1.00 | 75.94 | L | C |
| ATOM | 4194 | OE1 | GLN | 146 | 92.616 | -28.399 | 10.654 | 1.00 | 76.92 | L | O |
| ATOM | 4195 | NE2 | GLN | 146 | 94.730 | -28.997 | 11.130 | 1.00 | 77.33 | L | N |
| ATOM | 4196 | C | GLN | 146 | 91.880 | -27.094 | 15.904 | 1.00 | 37.70 | L | C |
| ATOM | 4197 | O | GLN | 146 | 92.302 | -27.965 | 16.667 | 1.00 | 34.46 | L | O |
| ATOM | 4198 | N | TRP | 147 | 90.699 | -26.498 | 16.048 | 1.00 | 30.86 | L | N |
| ATOM | 4199 | CA | TRP | 147 | 89.777 | -26.878 | 17.102 | 1.00 | 30.91 | L | C |
| ATOM | 4200 | CB | TRP | 147 | 88.947 | -25.687 | 17.556 | 1.00 | 36.68 | L | C |
| ATOM | 4201 | CG | TRP | 147 | 89.689 | -24.788 | 18.432 | 1.00 | 34.29 | L | C |
| ATOM | 4202 | CD2 | TRP | 147 | 89.927 | -24.969 | 19.825 | 1.00 | 32.37 | L | C |
| ATOM | 4203 | CE2 | TRP | 147 | 90.723 | -23.885 | 20.258 | 1.00 | 33.31 | L | C |
| ATOM | 4204 | CE3 | TRP | 147 | 89.552 | -25.943 | 20.752 | 1.00 | 31.13 | L | C |
| ATOM | 4205 | CD1 | TRP | 147 | 90.326 | -23.641 | 18.077 | 1.00 | 36.68 | L | C |
| ATOM | 4206 | NE1 | TRP | 147 | 90.951 | -23.086 | 19.168 | 1.00 | 33.41 | L | N |
| ATOM | 4207 | CZ2 | TRP | 147 | 91.150 | -23.747 | 21.587 | 1.00 | 31.66 | L | C |
| ATOM | 4208 | CZ3 | TRP | 147 | 89.977 | -25.808 | 22.073 | 1.00 | 33.39 | L | C |
| ATOM | 4209 | CH2 | TRP | 147 | 90.767 | -24.716 | 22.476 | 1.00 | 33.58 | L | C |
| ATOM | 4210 | C | TRP | 147 | 88.844 | -27.963 | 16.611 | 1.00 | 33.36 | L | C |
| ATOM | 4211 | O | TRP | 147 | 88.440 | -27.968 | 15.453 | 1.00 | 34.42 | L | O |
| ATOM | 4212 | N | LYS | 148 | 88.495 | -28.877 | 17.501 | 1.00 | 28.86 | L | N |
| ATOM | 4213 | CA | LYS | 148 | 87.609 | -29.958 | 17.147 | 1.00 | 29.96 | L | C |
| ATOM | 4214 | CB | LYS | 148 | 88.431 | -31.196 | 16.787 | 1.00 | 35.94 | L | C |
| ATOM | 4215 | CG | LYS | 148 | 88.353 | -31.585 | 15.320 | 1.00 | 39.31 | L | C |
| ATOM | 4216 | CD | LYS | 148 | 89.726 | -31.865 | 14.715 | 1.00 | 45.24 | L | C |
| ATOM | 4217 | CE | LYS | 148 | 90.421 | -33.078 | 15.337 | 1.00 | 45.54 | L | C |
| ATOM | 4218 | NZ | LYS | 148 | 91.826 | -33.267 | 14.818 | 1.00 | 44.96 | L | N |
| ATOM | 4219 | C | LYS | 148 | 86.712 | -30.227 | 18.340 | 1.00 | 32.40 | L | C |
| ATOM | 4220 | O | LYS | 148 | 87.197 | -30.505 | 19.438 | 1.00 | 31.51 | L | O |
| ATOM | 4221 | N | VAL | 149 | 85.404 | -30.124 | 18.118 | 1.00 | 22.85 | L | N |
| ATOM | 4222 | CA | VAL | 149 | 84.406 | -30.352 | 19.161 | 1.00 | 20.04 | L | C |
| ATOM | 4223 | CB | VAL | 149 | 83.453 | -29.167 | 19.269 | 1.00 | 1.90 | L | C |
| ATOM | 4224 | CG1 | VAL | 149 | 82.408 | -29.440 | 20.364 | 1.00 | 1.90 | L | C |
| ATOM | 4225 | CG2 | VAL | 149 | 84.242 | -27.899 | 19.563 | 1.00 | 1.90 | L | C |
| ATOM | 4226 | C | VAL | 149 | 83.580 | -31.605 | 18.862 | 1.00 | 23.24 | L | C |
| ATOM | 4227 | O | VAL | 149 | 82.835 | -31.642 | 17.883 | 1.00 | 24.43 | L | O |
| ATOM | 4228 | N | ASP | 150 | 83.679 | -32.611 | 19.731 | 1.00 | 18.00 | L | N |
| ATOM | 4229 | CA | ASP | 150 | 82.974 | -33.863 | 19.502 | 1.00 | 21.30 | L | C |
| ATOM | 4230 | CB | ASP | 150 | 81.464 | -33.661 | 19.459 | 1.00 | 45.33 | L | C |
| ATOM | 4231 | CG | ASP | 150 | 80.862 | -33.543 | 20.840 | 1.00 | 50.39 | L | C |
| ATOM | 4232 | OD1 | ASP | 150 | 81.334 | -34.248 | 21.760 | 1.00 | 51.76 | L | O |
| ATOM | 4233 | OD2 | ASP | 150 | 79.910 | -32.756 | 21.007 | 1.00 | 53.67 | L | O |
| ATOM | 4234 | C | ASP | 150 | 83.487 | -34.293 | 18.152 | 1.00 | 22.51 | L | C |

Fig. 19: A-59

| ATOM | 4235 | O | ASP | 150 | 82.737 | -34.683 | 17.268 | 1.00 | 23.76 | L | O |
|---|---|---|---|---|---|---|---|---|---|---|---|
| ATOM | 4236 | N | ASN | 151 | 84.800 | -34.161 | 18.007 | 1.00 | 36.79 | L | N |
| ATOM | 4237 | CA | ASN | 151 | 85.493 | -34.524 | 16.789 | 1.00 | 39.62 | L | C |
| ATOM | 4238 | CB | ASN | 151 | 85.425 | -36.041 | 16.614 | 1.00 | 29.22 | L | C |
| ATOM | 4239 | CG | ASN | 151 | 86.220 | -36.776 | 17.683 | 1.00 | 38.58 | L | C |
| ATOM | 4240 | OD1 | ASN | 151 | 87.450 | -36.736 | 17.686 | 1.00 | 42.16 | L | O |
| ATOM | 4241 | ND2 | ASN | 151 | 85.522 | -37.430 | 18.608 | 1.00 | 39.63 | L | N |
| ATOM | 4242 | C | ASN | 151 | 84.985 | -33.778 | 15.557 | 1.00 | 37.90 | L | C |
| ATOM | 4243 | O | ASN | 151 | 85.224 | -34.183 | 14.425 | 1.00 | 41.98 | L | O |
| ATOM | 4244 | N | ALA | 152 | 84.293 | -32.672 | 15.793 | 1.00 | 26.76 | L | N |
| ATOM | 4245 | CA | ALA | 152 | 83.802 | -31.838 | 14.703 | 1.00 | 29.16 | L | C |
| ATOM | 4246 | CB | ALA | 152 | 82.421 | -31.261 | 15.034 | 1.00 | 1.87 | L | C |
| ATOM | 4247 | C | ALA | 152 | 84.801 | -30.698 | 14.501 | 1.00 | 30.47 | L | C |
| ATOM | 4248 | O | ALA | 152 | 84.940 | -29.813 | 15.355 | 1.00 | 32.16 | L | O |
| ATOM | 4249 | N | LEU | 153 | 85.502 | -30.724 | 13.375 | 1.00 | 37.66 | L | N |
| ATOM | 4250 | CA | LEU | 153 | 86.470 | -29.684 | 13.073 | 1.00 | 38.47 | L | C |
| ATOM | 4251 | CB | LEU | 153 | 87.021 | -29.896 | 11.656 | 1.00 | 33.69 | L | C |
| ATOM | 4252 | CG | LEU | 153 | 87.944 | -28.864 | 11.005 | 1.00 | 36.76 | L | C |
| ATOM | 4253 | CD1 | LEU | 153 | 87.112 | -27.705 | 10.466 | 1.00 | 35.54 | L | C |
| ATOM | 4254 | CD2 | LEU | 153 | 88.999 | -28.394 | 12.004 | 1.00 | 35.80 | L | C |
| ATOM | 4255 | C | LEU | 153 | 85.796 | -28.315 | 13.206 | 1.00 | 37.05 | L | C |
| ATOM | 4256 | O | LEU | 153 | 84.632 | -28.150 | 12.870 | 1.00 | 37.53 | L | O |
| ATOM | 4257 | N | GLN | 154 | 86.524 | -27.342 | 13.732 | 1.00 | 42.87 | L | N |
| ATOM | 4258 | CA | GLN | 154 | 85.984 | -26.006 | 13.885 | 1.00 | 41.76 | L | C |
| ATOM | 4259 | CB | GLN | 154 | 86.346 | -25.438 | 15.255 | 1.00 | 24.84 | L | C |
| ATOM | 4260 | CG | GLN | 154 | 85.653 | -26.133 | 16.403 | 1.00 | 25.94 | L | C |
| ATOM | 4261 | CD | GLN | 154 | 84.146 | -26.162 | 16.225 | 1.00 | 28.42 | L | C |
| ATOM | 4262 | OE1 | GLN | 154 | 83.495 | -25.115 | 16.127 | 1.00 | 30.98 | L | O |
| ATOM | 4263 | NE2 | GLN | 154 | 83.584 | -27.365 | 16.176 | 1.00 | 27.76 | L | N |
| ATOM | 4264 | C | GLN | 154 | 86.574 | -25.139 | 12.793 | 1.00 | 40.20 | L | C |
| ATOM | 4265 | O | GLN | 154 | 87.702 | -25.363 | 12.350 | 1.00 | 39.24 | L | O |
| ATOM | 4266 | N | SER | 155 | 85.813 | -24.146 | 12.359 | 1.00 | 42.27 | L | N |
| ATOM | 4267 | CA | SER | 155 | 86.269 | -23.257 | 11.306 | 1.00 | 44.34 | L | C |
| ATOM | 4268 | CB | SER | 155 | 85.770 | -23.768 | 9.952 | 1.00 | 47.84 | L | C |
| ATOM | 4269 | OG | SER | 155 | 86.319 | -23.035 | 8.872 | 1.00 | 49.98 | L | O |
| ATOM | 4270 | C | SER | 155 | 85.693 | -21.888 | 11.600 | 1.00 | 40.94 | L | C |
| ATOM | 4271 | O | SER | 155 | 86.208 | -20.864 | 11.160 | 1.00 | 39.18 | L | O |
| ATOM | 4272 | N | GLY | 156 | 84.621 | -21.877 | 12.374 | 1.00 | 21.85 | L | N |
| ATOM | 4273 | CA | GLY | 156 | 83.986 | -20.619 | 12.702 | 1.00 | 22.33 | L | C |
| ATOM | 4274 | C | GLY | 156 | 84.732 | -19.585 | 13.544 | 1.00 | 22.19 | L | C |
| ATOM | 4275 | O | GLY | 156 | 85.518 | -18.793 | 13.032 | 1.00 | 19.16 | L | O |
| ATOM | 4276 | N | ASN | 157 | 84.484 | -19.595 | 14.850 | 1.00 | 39.06 | L | N |
| ATOM | 4277 | CA | ASN | 157 | 85.088 | -18.595 | 15.697 | 1.00 | 40.50 | L | C |
| ATOM | 4278 | CB | ASN | 157 | 83.992 | -17.700 | 16.281 | 1.00 | 106.22 | L | C |
| ATOM | 4279 | CG | ASN | 157 | 83.201 | -16.977 | 15.200 | 1.00 | 109.22 | L | C |
| ATOM | 4280 | OD1 | ASN | 157 | 83.779 | -16.402 | 14.277 | 1.00 | 109.54 | L | O |
| ATOM | 4281 | ND2 | ASN | 157 | 81.874 | -16.999 | 15.313 | 1.00 | 114.95 | L | N |
| ATOM | 4282 | C | ASN | 157 | 86.059 | -18.997 | 16.790 | 1.00 | 41.01 | L | C |
| ATOM | 4283 | O | ASN | 157 | 85.713 | -19.566 | 17.827 | 1.00 | 40.41 | L | O |
| ATOM | 4284 | N | SER | 158 | 87.299 | -18.635 | 16.520 | 1.00 | 42.44 | L | N |
| ATOM | 4285 | CA | SER | 158 | 88.409 | -18.862 | 17.405 | 1.00 | 35.84 | L | C |
| ATOM | 4286 | CB | SER | 158 | 89.078 | -20.173 | 17.047 | 1.00 | 10.55 | L | C |
| ATOM | 4287 | OG | SER | 158 | 89.643 | -20.069 | 15.757 | 1.00 | 10.12 | L | O |
| ATOM | 4288 | C | SER | 158 | 89.326 | -17.691 | 17.059 | 1.00 | 34.29 | L | C |
| ATOM | 4289 | O | SER | 158 | 89.197 | -17.092 | 15.992 | 1.00 | 32.27 | L | O |
| ATOM | 4290 | N | GLN | 159 | 90.238 | -17.345 | 17.952 | 1.00 | 34.35 | L | N |
| ATOM | 4291 | CA | GLN | 159 | 91.133 | -16.250 | 17.652 | 1.00 | 31.73 | L | C |
| ATOM | 4292 | CB | GLN | 159 | 90.538 | -14.932 | 18.130 | 1.00 | 20.18 | L | C |
| ATOM | 4293 | CG | GLN | 159 | 89.399 | -14.413 | 17.266 | 1.00 | 21.46 | L | C |
| ATOM | 4294 | CD | GLN | 159 | 89.053 | -12.981 | 17.608 | 1.00 | 25.67 | L | C |
| ATOM | 4295 | OE1 | GLN | 159 | 88.796 | -12.658 | 18.762 | 1.00 | 28.88 | L | O |
| ATOM | 4296 | NE2 | GLN | 159 | 89.051 | -12.114 | 16.606 | 1.00 | 25.13 | L | N |
| ATOM | 4297 | C | GLN | 159 | 92.502 | -16.452 | 18.255 | 1.00 | 29.74 | L | C |
| ATOM | 4298 | O | GLN | 159 | 92.647 | -16.711 | 19.449 | 1.00 | 28.24 | L | O |
| ATOM | 4299 | N | GLU | 160 | 93.514 | -16.327 | 17.414 | 1.00 | 31.36 | L | N |
| ATOM | 4300 | CA | GLU | 160 | 94.872 | -16.510 | 17.865 | 1.00 | 24.49 | L | C |
| ATOM | 4301 | CB | GLU | 160 | 95.646 | -17.703 | 16.834 | 1.00 | 58.94 | L | C |
| ATOM | 4302 | CG | GLU | 160 | 94.977 | -18.617 | 16.476 | 1.00 | 59.06 | L | C |
| ATOM | 4303 | CD | GLU | 160 | 95.890 | -19.506 | 15.678 | 1.00 | 67.10 | L | C |
| ATOM | 4304 | OE1 | GLU | 160 | 95.463 | -20.619 | 15.285 | 1.00 | 71.37 | L | O |
| ATOM | 4305 | OE2 | GLU | 160 | 97.043 | -19.078 | 15.452 | 1.00 | 65.02 | L | O |
| ATOM | 4306 | C | GLU | 160 | 95.591 | -15.199 | 18.140 | 1.00 | 20.89 | L | C |
| ATOM | 4307 | O | GLU | 160 | 95.211 | -14.141 | 17.654 | 1.00 | 14.39 | L | O |

Fig. 19: A-60

| | | | | | | | | | | | |
|---|---|---|---|---|---|---|---|---|---|---|---|
| ATOM | 4308 | N | SER | 161 | 96.639 | -15.293 | 18.941 | 1.00 | 19.35 | L | N |
| ATOM | 4309 | CA | SER | 161 | 97.456 | -14.151 | 19.310 | 1.00 | 16.36 | L | C |
| ATOM | 4310 | CB | SER | 161 | 96.953 | -13.486 | 20.597 | 1.00 | 26.12 | L | C |
| ATOM | 4311 | OG | SER | 161 | 97.935 | -12.623 | 21.157 | 1.00 | 26.54 | L | O |
| ATOM | 4312 | C | SER | 161 | 98.811 | -14.751 | 19.556 | 1.00 | 11.36 | L | C |
| ATOM | 4313 | O | SER | 161 | 98.934 | -15.799 | 20.191 | 1.00 | 11.86 | L | O |
| ATOM | 4314 | N | VAL | 162 | 99.833 | -14.086 | 19.053 | 1.00 | 21.19 | L | N |
| ATOM | 4315 | CA | VAL | 162 | 101.170 | -14.592 | 19.215 | 1.00 | 22.81 | L | C |
| ATOM | 4316 | CB | VAL | 162 | 101.764 | -14.965 | 17.832 | 1.00 | 29.37 | L | C |
| ATOM | 4317 | CG1 | VAL | 162 | 101.449 | -13.865 | 16.834 | 1.00 | 33.68 | L | C |
| ATOM | 4318 | CG2 | VAL | 162 | 103.270 | -15.178 | 17.933 | 1.00 | 33.85 | L | C |
| ATOM | 4319 | C | VAL | 162 | 101.997 | -13.524 | 19.877 | 1.00 | 25.31 | L | C |
| ATOM | 4320 | O | VAL | 162 | 101.835 | -12.349 | 19.566 | 1.00 | 32.55 | L | O |
| ATOM | 4321 | N | THR | 163 | 102.861 | -13.928 | 20.805 | 1.00 | 22.97 | L | N |
| ATOM | 4322 | CA | THR | 163 | 103.735 | -12.975 | 21.475 | 1.00 | 21.36 | L | C |
| ATOM | 4323 | CB | THR | 163 | 104.424 | -13.567 | 22.719 | 1.00 | 4.31 | L | C |
| ATOM | 4324 | OG1 | THR | 163 | 105.214 | -14.705 | 22.342 | 1.00 | 10.67 | L | O |
| ATOM | 4325 | CG2 | THR | 163 | 103.411 | -13.966 | 23.748 | 1.00 | 4.70 | L | C |
| ATOM | 4326 | C | THR | 163 | 104.842 | -12.550 | 20.520 | 1.00 | 20.43 | L | C |
| ATOM | 4327 | O | THR | 163 | 104.880 | -12.951 | 19.350 | 1.00 | 20.01 | L | O |
| ATOM | 4328 | N | GLU | 164 | 105.741 | -11.722 | 21.022 | 1.00 | 16.64 | L | N |
| ATOM | 4329 | CA | GLU | 164 | 106.844 | -11.283 | 20.211 | 1.00 | 24.33 | L | C |
| ATOM | 4330 | CB | GLU | 164 | 107.182 | -9.828 | 20.515 | 1.00 | 53.60 | L | C |
| ATOM | 4331 | CG | GLU | 164 | 107.982 | -9.187 | 19.415 | 1.00 | 64.34 | L | C |
| ATOM | 4332 | CD | GLU | 164 | 107.202 | -9.144 | 18.126 | 1.00 | 70.19 | L | C |
| ATOM | 4333 | OE1 | GLU | 164 | 106.337 | -8.252 | 17.994 | 1.00 | 69.97 | L | O |
| ATOM | 4334 | OE2 | GLU | 164 | 107.442 | -10.011 | 17.257 | 1.00 | 73.61 | L | O |
| ATOM | 4335 | C | GLU | 164 | 107.989 | -12.190 | 20.635 | 1.00 | 22.81 | L | C |
| ATOM | 4336 | O | GLU | 164 | 107.990 | -12.697 | 21.765 | 1.00 | 25.48 | L | O |
| ATOM | 4337 | N | GLN | 165 | 108.948 | -12.407 | 19.734 | 1.00 | 26.35 | L | N |
| ATOM | 4338 | CA | GLN | 165 | 110.100 | -13.261 | 20.018 | 1.00 | 31.24 | L | C |
| ATOM | 4339 | CB | GLN | 165 | 111.181 | -13.024 | 18.967 | 1.00 | 24.53 | L | C |
| ATOM | 4340 | CG | GLN | 165 | 111.927 | -14.274 | 18.584 | 1.00 | 20.02 | L | C |
| ATOM | 4341 | CD | GLN | 165 | 112.911 | -14.054 | 17.454 | 1.00 | 22.62 | L | C |
| ATOM | 4342 | OE1 | GLN | 165 | 113.487 | -15.005 | 16.930 | 1.00 | 23.83 | L | O |
| ATOM | 4343 | NE2 | GLN | 165 | 113.118 | -12.794 | 17.080 | 1.00 | 19.11 | L | N |
| ATOM | 4344 | C | GLN | 165 | 110.633 | -12.941 | 21.412 | 1.00 | 35.11 | L | C |
| ATOM | 4345 | O | GLN | 165 | 110.857 | -11.783 | 21.739 | 1.00 | 31.98 | L | O |
| ATOM | 4346 | N | ASP | 166 | 110.826 | -13.963 | 22.236 | 1.00 | 20.85 | L | N |
| ATOM | 4347 | CA | ASP | 166 | 111.311 | -13.741 | 23.592 | 1.00 | 27.22 | L | C |
| ATOM | 4348 | CB | ASP | 166 | 111.206 | -15.030 | 24.402 | 1.00 | 40.40 | L | C |
| ATOM | 4349 | CG | ASP | 166 | 111.513 | -14.813 | 25.872 | 1.00 | 48.39 | L | C |
| ATOM | 4350 | OD1 | ASP | 166 | 112.706 | -14.808 | 26.246 | 1.00 | 51.89 | L | O |
| ATOM | 4351 | OD2 | ASP | 166 | 110.555 | -14.631 | 26.655 | 1.00 | 52.06 | L | O |
| ATOM | 4352 | C | ASP | 166 | 112.741 | -13.205 | 23.656 | 1.00 | 29.80 | L | C |
| ATOM | 4353 | O | ASP | 166 | 113.659 | -13.787 | 23.079 | 1.00 | 33.62 | L | O |
| ATOM | 4354 | N | SER | 167 | 112.923 | -12.098 | 24.371 | 1.00 | 40.62 | L | N |
| ATOM | 4355 | CA | SER | 167 | 114.238 | -11.463 | 24.521 | 1.00 | 38.35 | L | C |
| ATOM | 4356 | CB | SER | 167 | 114.089 | -10.092 | 25.191 | 1.00 | 42.38 | L | C |
| ATOM | 4357 | OG | SER | 167 | 113.564 | -10.221 | 26.499 | 1.00 | 53.10 | L | O |
| ATOM | 4358 | C | SER | 167 | 115.229 | -12.312 | 25.325 | 1.00 | 40.21 | L | C |
| ATOM | 4359 | O | SER | 167 | 116.373 | -11.913 | 25.544 | 1.00 | 45.86 | L | O |
| ATOM | 4360 | N | LYS | 168 | 114.777 | -13.475 | 25.782 | 1.00 | 39.00 | L | N |
| ATOM | 4361 | CA | LYS | 168 | 115.637 | -14.383 | 26.527 | 1.00 | 40.59 | L | C |
| ATOM | 4362 | CB | LYS | 168 | 114.968 | -14.809 | 27.837 | 1.00 | 73.78 | L | C |
| ATOM | 4363 | CG | LYS | 168 | 115.002 | -13.726 | 28.916 | 1.00 | 80.02 | L | C |
| ATOM | 4364 | CD | LYS | 168 | 114.141 | -12.523 | 28.554 | 1.00 | 89.23 | L | C |
| ATOM | 4365 | CE | LYS | 168 | 112.663 | -12.805 | 28.778 | 1.00 | 96.32 | L | C |
| ATOM | 4366 | NZ | LYS | 168 | 112.355 | -13.017 | 30.222 | 1.00 | 95.77 | L | N |
| ATOM | 4367 | C | LYS | 168 | 115.959 | -15.597 | 25.650 | 1.00 | 39.39 | L | C |
| ATOM | 4368 | O | LYS | 168 | 117.046 | -15.671 | 25.077 | 1.00 | 43.53 | L | O |
| ATOM | 4369 | N | ASP | 169 | 115.011 | -16.522 | 25.506 | 1.00 | 18.93 | L | N |
| ATOM | 4370 | CA | ASP | 169 | 115.240 | -17.716 | 24.686 | 1.00 | 15.08 | L | C |
| ATOM | 4371 | CB | ASP | 169 | 114.476 | -18.913 | 25.262 | 1.00 | 29.81 | L | C |
| ATOM | 4372 | CG | ASP | 169 | 112.992 | -18.648 | 25.407 | 1.00 | 32.60 | L | C |
| ATOM | 4373 | OD1 | ASP | 169 | 112.397 | -18.049 | 24.488 | 1.00 | 27.93 | L | O |
| ATOM | 4374 | OD2 | ASP | 169 | 112.415 | -19.054 | 26.441 | 1.00 | 29.85 | L | O |
| ATOM | 4375 | C | ASP | 169 | 114.914 | -17.596 | 23.193 | 1.00 | 15.61 | L | C |
| ATOM | 4376 | O | ASP | 169 | 115.038 | -18.571 | 22.459 | 1.00 | 9.73 | L | O |
| ATOM | 4377 | N | SER | 170 | 114.490 | -16.418 | 22.747 | 1.00 | 28.98 | L | N |
| ATOM | 4378 | CA | SER | 170 | 114.170 | -16.202 | 21.331 | 1.00 | 26.94 | L | C |
| ATOM | 4379 | CB | SER | 170 | 115.401 | -16.487 | 20.433 | 1.00 | 15.64 | L | C |
| ATOM | 4380 | OG | SER | 170 | 116.466 | -15.560 | 20.636 | 1.00 | 17.90 | L | O |

Fig. 19: A-61

```
ATOM   4381  C    SER  170    112.995  -17.042  20.825  1.00  25.42  L  C
ATOM   4382  O    SER  170    112.916  -17.345  19.636  1.00  25.18  L  O
ATOM   4383  N    THR  171    112.071  -17.411  21.702  1.00  22.07  L  N
ATOM   4384  CA   THR  171    110.946  -18.222  21.247  1.00  22.16  L  C
ATOM   4385  CB   THR  171    110.658  -19.406  22.212  1.00  16.53  L  C
ATOM   4386  OG1  THR  171    110.127  -18.911  23.452  1.00  18.93  L  O
ATOM   4387  CG2  THR  171    111.939  -20.191  22.471  1.00  18.13  L  C
ATOM   4388  C    THR  171    109.657  -17.437  21.064  1.00  26.03  L  C
ATOM   4389  O    THR  171    109.601  -16.235  21.327  1.00  31.48  L  O
ATOM   4390  N    TYR  172    108.633  -18.147  20.596  1.00   7.82  L  N
ATOM   4391  CA   TYR  172    107.297  -17.600  20.373  1.00   6.45  L  C
ATOM   4392  CB   TYR  172    106.934  -17.706  18.894  1.00  43.65  L  C
ATOM   4393  CG   TYR  172    107.809  -16.890  17.974  1.00  37.38  L  C
ATOM   4394  CD1  TYR  172    107.652  -15.507  17.865  1.00  32.97  L  C
ATOM   4395  CE1  TYR  172    108.438  -14.759  16.977  1.00  32.97  L  C
ATOM   4396  CD2  TYR  172    108.776  -17.508  17.181  1.00  37.97  L  C
ATOM   4397  CE2  TYR  172    109.565  -16.774  16.296  1.00  34.76  L  C
ATOM   4398  CZ   TYR  172    109.391  -15.405  16.194  1.00  32.97  L  C
ATOM   4399  OH   TYR  172    110.163  -14.703  15.294  1.00  32.97  L  O
ATOM   4400  C    TYR  172    106.255  -18.364  21.212  1.00   6.45  L  C
ATOM   4401  O    TYR  172    106.431  -19.539  21.528  1.00   9.78  L  O
ATOM   4402  N    SER  173    105.183  -17.687  21.600  1.00  23.67  L  N
ATOM   4403  CA   SER  173    104.123  -18.323  22.370  1.00  25.48  L  C
ATOM   4404  CB   SER  173    104.165  -17.902  23.834  1.00  31.18  L  C
ATOM   4405  OG   SER  173    105.281  -18.492  24.468  1.00  25.15  L  O
ATOM   4406  C    SER  173    102.836  -17.886  21.728  1.00  26.94  L  C
ATOM   4407  O    SER  173    102.611  -16.699  21.473  1.00  27.36  L  O
ATOM   4408  N    LEU  174    101.980  -18.857  21.474  1.00  22.39  L  N
ATOM   4409  CA   LEU  174    100.734  -18.593  20.791  1.00  25.49  L  C
ATOM   4410  CB   LEU  174    100.836  -19.238  19.399  1.00  22.33  L  C
ATOM   4411  CG   LEU  174     99.682  -19.165  18.422  1.00  13.39  L  C
ATOM   4412  CD1  LEU  174    100.207  -19.296  17.013  1.00  17.21  L  C
ATOM   4413  CD2  LEU  174     98.663  -20.257  18.769  1.00  10.23  L  C
ATOM   4414  C    LEU  174     99.510  -19.075  21.562  1.00  27.64  L  C
ATOM   4415  O    LEU  174     99.542  -20.111  22.229  1.00  30.82  L  O
ATOM   4416  N    SER  175     98.433  -18.306  21.470  1.00  22.56  L  N
ATOM   4417  CA   SER  175     97.200  -18.651  22.162  1.00  25.61  L  C
ATOM   4418  CB   SER  175     96.913  -17.644  23.292  1.00  28.99  L  C
ATOM   4419  OG   SER  175     96.487  -16.378  22.794  1.00  32.45  L  O
ATOM   4420  C    SER  175     96.009  -18.693  21.214  1.00  29.48  L  C
ATOM   4421  O    SER  175     95.733  -17.718  20.511  1.00  30.81  L  O
ATOM   4422  N    SER  176     95.316  -19.829  21.181  1.00  31.99  L  N
ATOM   4423  CA   SER  176     94.125  -19.957  20.346  1.00  32.77  L  C
ATOM   4424  CB   SER  176     94.154  -21.247  19.514  1.00  10.71  L  C
ATOM   4425  OG   SER  176     93.247  -21.176  18.421  1.00  10.34  L  O
ATOM   4426  C    SER  176     92.985  -19.991  21.352  1.00  29.41  L  C
ATOM   4427  O    SER  176     93.042  -20.712  22.350  1.00  29.56  L  O
ATOM   4428  N    THR  177     91.963  -19.183  21.118  1.00  38.41  L  N
ATOM   4429  CA   THR  177     90.846  -19.136  22.042  1.00  37.60  L  C
ATOM   4430  CB   THR  177     90.742  -17.741  22.706  1.00   7.23  L  C
ATOM   4431  OG1  THR  177     92.000  -17.399  23.318  1.00  10.12  L  O
ATOM   4432  CG2  THR  177     89.631  -17.728  23.773  1.00   2.94  L  C
ATOM   4433  C    THR  177     89.551  -19.455  21.311  1.00  35.94  L  C
ATOM   4434  O    THR  177     89.133  -18.709  20.425  1.00  37.02  L  O
ATOM   4435  N    LEU  178     88.941  -20.584  21.669  1.00  33.89  L  N
ATOM   4436  CA   LEU  178     87.682  -21.015  21.072  1.00  32.44  L  C
ATOM   4437  CB   LEU  178     87.587  -22.542  21.069  1.00  26.21  L  C
ATOM   4438  CG   LEU  178     86.291  -23.170  20.539  1.00  27.24  L  C
ATOM   4439  CD1  LEU  178     86.077  -22.824  19.070  1.00  27.77  L  C
ATOM   4440  CD2  LEU  178     86.367  -24.683  20.730  1.00  15.35  L  C
ATOM   4441  C    LEU  178     86.552  -20.412  21.901  1.00  32.70  L  C
ATOM   4442  O    LEU  178     86.476  -20.589  23.120  1.00  29.14  L  O
ATOM   4443  N    THR  179     85.669  -19.683  21.244  1.00  21.74  L  N
ATOM   4444  CA   THR  179     84.598  -19.059  21.983  1.00  27.65  L  C
ATOM   4445  CB   THR  179     84.804  -17.547  22.031  1.00  33.66  L  C
ATOM   4446  OG1  THR  179     83.651  -16.929  22.608  1.00  34.46  L  O
ATOM   4447  CG2  THR  179     85.056  -17.005  20.633  1.00  33.07  L  C
ATOM   4448  C    THR  179     83.223  -19.377  21.430  1.00  32.00  L  C
ATOM   4449  O    THR  179     82.928  -19.104  20.271  1.00  32.92  L  O
ATOM   4450  N    LEU  180     82.398  -19.981  22.278  1.00  32.07  L  N
ATOM   4451  CA   LEU  180     81.035  -20.349  21.922  1.00  33.73  L  C
ATOM   4452  CB   LEU  180     80.936  -21.831  21.528  1.00  30.85  L  C
ATOM   4453  CG   LEU  180     82.059  -22.804  21.881  1.00  33.56  L  C
```

Fig. 19: A-62

```
ATOM   4454  CD1 LEU   180      82.518 -22.589  23.309  1.00  36.03      L    C
ATOM   4455  CD2 LEU   180      81.552 -24.220  21.697  1.00  34.15      L    C
ATOM   4456  C   LEU   180      80.093 -20.062  23.084  1.00  37.58      L    C
ATOM   4457  O   LEU   180      80.526 -19.899  24.229  1.00  37.41      L    O
ATOM   4458  N   SER   181      78.801 -20.000  22.772  1.00  28.10      L    N
ATOM   4459  CA  SER   181      77.778 -19.711  23.770  1.00  31.26      L    C
ATOM   4460  CB  SER   181      76.433 -19.537  23.087  1.00  22.13      L    C
ATOM   4461  OG  SER   181      76.019 -20.764  22.513  1.00  25.39      L    O
ATOM   4462  C   SER   181      77.655 -20.802  24.815  1.00  33.74      L    C
ATOM   4463  O   SER   181      77.917 -21.978  24.533  1.00  33.98      L    O
ATOM   4464  N   LYS   182      77.247 -20.402  26.019  1.00  29.35      L    N
ATOM   4465  CA  LYS   182      77.060 -21.339  27.120  1.00  30.58      L    C
ATOM   4466  CB  LYS   182      76.375 -20.647  28.307  1.00  27.86      L    C
ATOM   4467  CG  LYS   182      76.341 -21.446  29.627  1.00  29.57      L    C
ATOM   4468  CD  LYS   182      74.912 -21.752  30.107  1.00  31.50      L    C
ATOM   4469  CE  LYS   182      74.863 -22.027  31.619  1.00  34.15      L    C
ATOM   4470  NZ  LYS   182      73.622 -22.756  32.099  1.00  38.40      L    N
ATOM   4471  C   LYS   182      76.167 -22.438  26.573  1.00  28.49      L    C
ATOM   4472  O   LYS   182      76.358 -23.618  26.878  1.00  20.36      L    O
ATOM   4473  N   ALA   183      75.206 -22.030  25.743  1.00  42.67      L    N
ATOM   4474  CA  ALA   183      74.252 -22.937  25.108  1.00  43.14      L    C
ATOM   4475  CB  ALA   183      73.319 -22.150  24.203  1.00  20.20      L    C
ATOM   4476  C   ALA   183      74.929 -24.053  24.313  1.00  42.26      L    C
ATOM   4477  O   ALA   183      74.645 -25.229  24.531  1.00  43.50      L    O
ATOM   4478  N   ASP   184      75.820 -23.691  23.395  1.00  37.65      L    N
ATOM   4479  CA  ASP   184      76.523 -24.692  22.587  1.00  39.98      L    C
ATOM   4480  CB  ASP   184      77.271 -24.023  21.434  1.00  60.24      L    C
ATOM   4481  CG  ASP   184      76.362 -23.219  20.545  1.00  66.97      L    C
ATOM   4482  OD1 ASP   184      75.360 -23.784  20.055  1.00  70.29      L    O
ATOM   4483  OD2 ASP   184      76.653 -22.023  20.335  1.00  70.50      L    O
ATOM   4484  C   ASP   184      77.519 -25.525  23.395  1.00  38.91      L    C
ATOM   4485  O   ASP   184      77.531 -26.753  23.308  1.00  36.50      L    O
ATOM   4486  N   TYR   185      78.362 -24.849  24.167  1.00  50.74      L    N
ATOM   4487  CA  TYR   185      79.352 -25.544  24.972  1.00  51.74      L    C
ATOM   4488  CB  TYR   185      80.011 -24.589  25.965  1.00  23.76      L    C
ATOM   4489  CG  TYR   185      81.104 -25.256  26.771  1.00  21.08      L    C
ATOM   4490  CD1 TYR   185      82.328 -25.552  26.192  1.00  16.43      L    C
ATOM   4491  CE1 TYR   185      83.332 -26.186  26.915  1.00  15.99      L    C
ATOM   4492  CD2 TYR   185      80.905 -25.613  28.104  1.00  17.64      L    C
ATOM   4493  CE2 TYR   185      81.902 -26.244  28.839  1.00  14.97      L    C
ATOM   4494  CZ  TYR   185      83.118 -26.526  28.235  1.00  14.93      L    C
ATOM   4495  OH  TYR   185      84.141 -27.119  28.944  1.00  16.56      L    O
ATOM   4496  C   TYR   185      78.729 -26.695  25.756  1.00  52.88      L    C
ATOM   4497  O   TYR   185      79.364 -27.728  25.978  1.00  52.42      L    O
ATOM   4498  N   GLU   186      77.484 -26.505  26.177  1.00  52.93      L    N
ATOM   4499  CA  GLU   186      76.787 -27.509  26.965  1.00  54.71      L    C
ATOM   4500  CB  GLU   186      75.643 -26.870  27.748  1.00  28.62      L    C
ATOM   4501  CG  GLU   186      76.067 -26.060  28.955  1.00  35.11      L    C
ATOM   4502  CD  GLU   186      74.876 -25.493  29.702  1.00  38.66      L    C
ATOM   4503  OE1 GLU   186      75.089 -24.850  30.746  1.00  41.21      L    O
ATOM   4504  OE2 GLU   186      73.725 -25.689  29.245  1.00  36.89      L    O
ATOM   4505  C   GLU   186      76.242 -28.694  26.190  1.00  52.40      L    C
ATOM   4506  O   GLU   186      76.029 -29.755  26.769  1.00  48.88      L    O
ATOM   4507  N   LYS   187      76.004 -28.538  24.895  1.00  35.74      L    N
ATOM   4508  CA  LYS   187      75.472 -29.662  24.147  1.00  37.64      L    C
ATOM   4509  CB  LYS   187      74.507 -29.173  23.057  1.00  53.22      L    C
ATOM   4510  CG  LYS   187      75.138 -28.512  21.849  1.00  54.27      L    C
ATOM   4511  CD  LYS   187      74.055 -27.941  20.930  1.00  53.80      L    C
ATOM   4512  CE  LYS   187      74.665 -27.203  19.740  1.00  49.76      L    C
ATOM   4513  NZ  LYS   187      73.707 -26.272  19.069  1.00  48.24      L    N
ATOM   4514  C   LYS   187      76.568 -30.553  23.549  1.00  36.73      L    C
ATOM   4515  O   LYS   187      76.287 -31.436  22.732  1.00  37.96      L    O
ATOM   4516  N   HIS   188      77.813 -30.339  23.972  1.00  23.77      L    N
ATOM   4517  CA  HIS   188      78.934 -31.124  23.468  1.00  21.36      L    C
ATOM   4518  CB  HIS   188      79.811 -30.257  22.562  1.00  41.13      L    C
ATOM   4519  CG  HIS   188      79.099 -29.774  21.338  1.00  42.53      L    C
ATOM   4520  CD2 HIS   188      78.800 -28.524  20.913  1.00  44.25      L    C
ATOM   4521  ND1 HIS   188      78.562 -30.633  20.405  1.00  41.45      L    N
ATOM   4522  CE1 HIS   188      77.961 -29.935  19.458  1.00  45.45      L    C
ATOM   4523  NE2 HIS   188      78.090 -28.652  19.743  1.00  43.75      L    N
ATOM   4524  C   HIS   188      79.743 -31.715  24.610  1.00  19.53      L    C
ATOM   4525  O   HIS   188      79.648 -31.253  25.751  1.00  19.70      L    O
ATOM   4526  N   LYS   189      80.521 -32.747  24.294  1.00  33.83      L    N
```

Fig. 19: A-63

```
ATOM   4527  CA   LYS  189      81.334 -33.445  25.281  1.00  33.86      L  C
ATOM   4528  CB   LYS  189      81.136 -34.957  25.152  1.00  43.10      L  C
ATOM   4529  CG   LYS  189      79.898 -35.516  25.815  1.00  47.03      L  C
ATOM   4530  CD   LYS  189      79.974 -37.041  25.887  1.00  53.76      L  C
ATOM   4531  CE   LYS  189      79.997 -37.680  24.505  1.00  59.30      L  C
ATOM   4532  NZ   LYS  189      78.694 -37.545  23.794  1.00  59.64      L  N
ATOM   4533  C    LYS  189      82.831 -33.155  25.201  1.00  33.18      L  C
ATOM   4534  O    LYS  189      83.435 -32.657  26.155  1.00  36.85      L  O
ATOM   4535  N    VAL  190      83.435 -33.482  24.069  1.00  39.67      L  N
ATOM   4536  CA   VAL  190      84.860 -33.260  23.916  1.00  35.33      L  C
ATOM   4537  CB   VAL  190      85.516 -34.439  23.214  1.00  33.71      L  C
ATOM   4538  CG1  VAL  190      85.356 -35.648  24.059  1.00  26.86      L  C
ATOM   4539  CG2  VAL  190      84.880 -34.657  21.855  1.00  36.79      L  C
ATOM   4540  C    VAL  190      85.249 -31.992  23.170  1.00  35.17      L  C
ATOM   4541  O    VAL  190      84.656 -31.641  22.141  1.00  36.62      L  O
ATOM   4542  N    TYR  191      86.256 -31.319  23.718  1.00  27.65      L  N
ATOM   4543  CA   TYR  191      86.811 -30.105  23.152  1.00  26.85      L  C
ATOM   4544  CB   TYR  191      86.554 -28.934  24.095  1.00  16.61      L  C
ATOM   4545  CG   TYR  191      85.109 -28.475  24.056  1.00  23.44      L  C
ATOM   4546  CD1  TYR  191      84.654 -27.650  23.030  1.00  27.57      L  C
ATOM   4547  CE1  TYR  191      83.322 -27.300  22.929  1.00  29.06      L  C
ATOM   4548  CD2  TYR  191      84.178 -28.937  24.991  1.00  24.37      L  C
ATOM   4549  CE2  TYR  191      82.838 -28.592  24.894  1.00  25.88      L  C
ATOM   4550  CZ   TYR  191      82.419 -27.773  23.859  1.00  28.22      L  C
ATOM   4551  OH   TYR  191      81.097 -27.419  23.745  1.00  30.91      L  O
ATOM   4552  C    TYR  191      88.295 -30.381  23.010  1.00  28.07      L  C
ATOM   4553  O    TYR  191      88.946 -30.821  23.960  1.00  29.13      L  O
ATOM   4554  N    ALA  192      88.837 -30.159  21.822  1.00  17.93      L  N
ATOM   4555  CA   ALA  192      90.246 -30.425  21.621  1.00  13.94      L  C
ATOM   4556  CB   ALA  192      90.424 -31.850  21.160  1.00  12.32      L  C
ATOM   4557  C    ALA  192      90.921 -29.489  20.640  1.00  14.27      L  C
ATOM   4558  O    ALA  192      90.271 -28.885  19.784  1.00  14.89      L  O
ATOM   4559  N    CYS  193      92.234 -29.362  20.787  1.00  20.91      L  N
ATOM   4560  CA   CYS  193      93.015 -28.544  19.883  1.00  19.50      L  C
ATOM   4561  C    CYS  193      94.268 -29.301  19.502  1.00  17.29      L  C
ATOM   4562  O    CYS  193      95.057 -29.729  20.352  1.00  15.43      L  O
ATOM   4563  CB   CYS  193      93.361 -27.183  20.490  1.00  44.80      L  C
ATOM   4564  SG   CYS  193      94.412 -27.194  21.962  1.00  52.58      L  S
ATOM   4565  N    GLU  194      94.411 -29.480  18.195  1.00  24.90      L  N
ATOM   4566  CA   GLU  194      95.522 -30.193  17.600  1.00  25.90      L  C
ATOM   4567  CB   GLU  194      95.004 -30.956  16.384  1.00  66.26      L  C
ATOM   4568  CG   GLU  194      95.979 -31.887  15.718  1.00  77.97      L  C
ATOM   4569  CD   GLU  194      95.392 -32.479  14.461  1.00  83.25      L  C
ATOM   4570  OE1  GLU  194      95.276 -31.738  13.462  1.00  80.00      L  O
ATOM   4571  OE2  GLU  194      95.028 -33.674  14.477  1.00  89.05      L  O
ATOM   4572  C    GLU  194      96.546 -29.158  17.175  1.00  25.27      L  C
ATOM   4573  O    GLU  194      96.204 -28.171  16.538  1.00  23.30      L  O
ATOM   4574  N    VAL  195      97.798 -29.373  17.537  1.00  38.95      L  N
ATOM   4575  CA   VAL  195      98.850 -28.443  17.168  1.00  34.83      L  C
ATOM   4576  CB   VAL  195      99.715 -28.048  18.403  1.00  15.18      L  C
ATOM   4577  CG1  VAL  195     100.911 -27.210  17.971  1.00  11.26      L  C
ATOM   4578  CG2  VAL  195      98.869 -27.268  19.395  1.00  16.15      L  C
ATOM   4579  C    VAL  195      99.730 -29.115  16.126  1.00  34.14      L  C
ATOM   4580  O    VAL  195      99.964 -30.319  16.180  1.00  32.63      L  O
ATOM   4581  N    THR  196     100.190 -28.340  15.157  1.00  43.12      L  N
ATOM   4582  CA   THR  196     101.063 -28.876  14.135  1.00  42.44      L  C
ATOM   4583  CB   THR  196     100.411 -28.867  12.764  1.00  26.65      L  C
ATOM   4584  OG1  THR  196      99.001 -28.673  12.909  1.00  36.35      L  O
ATOM   4585  CG2  THR  196     100.671 -30.180  12.067  1.00  28.65      L  C
ATOM   4586  C    THR  196     102.233 -27.927  14.121  1.00  42.04      L  C
ATOM   4587  O    THR  196     102.049 -26.710  14.053  1.00  37.83      L  O
ATOM   4588  N    HIS  197     103.437 -28.479  14.186  1.00  32.41      L  N
ATOM   4589  CA   HIS  197     104.623 -27.653  14.217  1.00  27.77      L  C
ATOM   4590  CB   HIS  197     104.867 -27.172  15.651  1.00  21.71      L  C
ATOM   4591  CG   HIS  197     105.914 -26.113  15.762  1.00  23.27      L  C
ATOM   4592  CD2  HIS  197     105.817 -24.761  15.753  1.00  17.64      L  C
ATOM   4593  ND1  HIS  197     107.257 -26.402  15.868  1.00  25.39      L  N
ATOM   4594  CE1  HIS  197     107.944 -25.274  15.923  1.00  22.67      L  C
ATOM   4595  NE2  HIS  197     107.093 -24.264  15.854  1.00  24.76      L  N
ATOM   4596  C    HIS  197     105.825 -28.417  13.708  1.00  24.98      L  C
ATOM   4597  O    HIS  197     105.932 -29.629  13.885  1.00  29.24      L  O
ATOM   4598  N    GLN  198     106.728 -27.687  13.070  1.00  28.46      L  N
ATOM   4599  CA   GLN  198     107.944 -28.252  12.515  1.00  26.49      L  C
```

Fig. 19: A-64

```
ATOM   4600  CB   GLN  198      108.840  -27.114   12.048  1.00  34.42      L    C
ATOM   4601  CG   GLN  198      110.091  -27.549   11.333  1.00  36.17      L    C
ATOM   4602  CD   GLN  198      110.868  -26.365   10.821  1.00  48.65      L    C
ATOM   4603  OE1  GLN  198      110.286  -25.414   10.299  1.00  57.22      L    O
ATOM   4604  NE2  GLN  198      112.185  -26.414   10.956  1.00  51.65      L    N
ATOM   4605  C    GLN  198      108.681  -29.107   13.541  1.00  29.43      L    C
ATOM   4606  O    GLN  198      109.331  -30.088   13.182  1.00  31.15      L    O
ATOM   4607  N    GLY  199      108.568  -28.728   14.815  1.00  31.39      L    N
ATOM   4608  CA   GLY  199      109.234  -29.452   15.887  1.00  36.65      L    C
ATOM   4609  C    GLY  199      108.465  -30.636   16.444  1.00  39.08      L    C
ATOM   4610  O    GLY  199      108.880  -31.244   17.425  1.00  43.81      L    O
ATOM   4611  N    LEU  200      107.339  -30.961   15.823  1.00  25.48      L    N
ATOM   4612  CA   LEU  200      106.510  -32.087   16.247  1.00  22.67      L    C
ATOM   4613  CB   LEU  200      105.094  -31.597   16.570  1.00  31.49      L    C
ATOM   4614  CG   LEU  200      104.868  -31.002   17.964  1.00  34.60      L    C
ATOM   4615  CD1  LEU  200      106.036  -30.149   18.361  1.00  37.97      L    C
ATOM   4616  CD2  LEU  200      103.592  -30.188   17.967  1.00  34.28      L    C
ATOM   4617  C    LEU  200      106.463  -33.152   15.144  1.00  23.29      L    C
ATOM   4618  O    LEU  200      106.089  -32.869   14.003  1.00  24.15      L    O
ATOM   4619  N    SER  201      106.860  -34.372   15.499  1.00  21.11      L    N
ATOM   4620  CA   SER  201      106.886  -35.503   14.570  1.00  24.08      L    C
ATOM   4621  CB   SER  201      107.367  -36.747   15.311  1.00  27.13      L    C
ATOM   4622  OG   SER  201      106.702  -36.875   16.561  1.00  28.99      L    O
ATOM   4623  C    SER  201      105.510  -35.761   13.957  1.00  24.14      L    C
ATOM   4624  O    SER  201      105.392  -36.267   12.835  1.00  25.49      L    O
ATOM   4625  N    SER  202      104.476  -35.405   14.717  1.00  17.09      L    N
ATOM   4626  CA   SER  202      103.086  -35.562   14.302  1.00  21.15      L    C
ATOM   4627  CB   SER  202      102.636  -37.010   14.522  1.00  43.22      L    C
ATOM   4628  OG   SER  202      103.011  -37.462   15.810  1.00  46.12      L    O
ATOM   4629  C    SER  202      102.265  -34.603   15.155  1.00  21.60      L    C
ATOM   4630  O    SER  202      102.656  -34.296   16.282  1.00  27.36      L    O
ATOM   4631  N    PRO  203      101.119  -34.121   14.636  1.00  22.94      L    N
ATOM   4632  CD   PRO  203      100.457  -34.478   13.368  1.00  32.35      L    C
ATOM   4633  CA   PRO  203      100.290  -33.187   15.407  1.00  18.89      L    C
ATOM   4634  CB   PRO  203       98.971  -33.177   14.643  1.00  26.47      L    C
ATOM   4635  CG   PRO  203       99.416  -33.370   13.223  1.00  29.48      L    C
ATOM   4636  C    PRO  203      100.128  -33.646   16.836  1.00  18.90      L    C
ATOM   4637  O    PRO  203      100.178  -34.842   17.100  1.00  21.86      L    O
ATOM   4638  N    VAL  204       99.980  -32.693   17.753  1.00  28.11      L    N
ATOM   4639  CA   VAL  204       99.794  -32.996   19.172  1.00  29.99      L    C
ATOM   4640  CB   VAL  204      100.759  -32.201   20.081  1.00  20.42      L    C
ATOM   4641  CG1  VAL  204      100.254  -32.204   21.512  1.00  20.30      L    C
ATOM   4642  CG2  VAL  204      102.141  -32.819   20.036  1.00  15.23      L    C
ATOM   4643  C    VAL  204       98.393  -32.574   19.514  1.00  33.93      L    C
ATOM   4644  O    VAL  204       97.887  -31.601   18.963  1.00  35.36      L    O
ATOM   4645  N    THR  205       97.755  -33.293   20.422  1.00  45.34      L    N
ATOM   4646  CA   THR  205       96.402  -32.933   20.787  1.00  46.97      L    C
ATOM   4647  CB   THR  205       95.386  -33.896   20.137  1.00  14.48      L    C
ATOM   4648  OG1  THR  205       95.275  -33.587   18.747  1.00  10.44      L    O
ATOM   4649  CG2  THR  205       94.013  -33.761   20.769  1.00  11.16      L    C
ATOM   4650  C    THR  205       96.169  -32.886   22.280  1.00  47.18      L    C
ATOM   4651  O    THR  205       96.596  -33.763   23.032  1.00  49.19      L    O
ATOM   4652  N    LYS  206       95.513  -31.822   22.709  1.00  22.09      L    N
ATOM   4653  CA   LYS  206       95.167  -31.681   24.108  1.00  26.52      L    C
ATOM   4654  CB   LYS  206       95.791  -30.422   24.710  1.00  41.08      L    C
ATOM   4655  CG   LYS  206       97.208  -30.641   25.215  1.00  44.88      L    C
ATOM   4656  CD   LYS  206       97.269  -31.688   26.312  1.00  47.36      L    C
ATOM   4657  CE   LYS  206       98.654  -31.760   26.957  1.00  49.27      L    C
ATOM   4658  NZ   LYS  206       99.723  -32.144   25.997  1.00  50.40      L    N
ATOM   4659  C    LYS  206       93.653  -31.602   24.100  1.00  29.29      L    C
ATOM   4660  O    LYS  206       93.063  -30.939   23.246  1.00  34.45      L    O
ATOM   4661  N    SER  207       93.026  -32.304   25.033  1.00  32.39      L    N
ATOM   4662  CA   SER  207       91.578  -32.324   25.083  1.00  29.18      L    C
ATOM   4663  CB   SER  207       91.046  -33.364   24.080  1.00  31.23      L    C
ATOM   4664  OG   SER  207       91.613  -34.655   24.294  1.00  31.62      L    O
ATOM   4665  C    SER  207       91.039  -32.624   26.476  1.00  28.78      L    C
ATOM   4666  O    SER  207       91.798  -32.938   27.397  1.00  29.47      L    O
ATOM   4667  N    PHE  208       89.719  -32.517   26.606  1.00  33.89      L    N
ATOM   4668  CA   PHE  208       89.013  -32.777   27.852  1.00  39.79      L    C
ATOM   4669  CB   PHE  208       89.217  -31.615   28.842  1.00  17.06      L    C
ATOM   4670  CG   PHE  208       88.662  -30.300   28.353  1.00  14.11      L    C
ATOM   4671  CD1  PHE  208       89.409  -29.482   27.499  1.00  18.84      L    C
ATOM   4672  CD2  PHE  208       87.376  -29.906   28.690  1.00  11.57      L    C
```

Fig. 19: A-65

```
ATOM   4673  CE1 PHE  208      88.879 -28.298  26.990  1.00   19.93      L  C
ATOM   4674  CE2 PHE  208      86.846 -28.729  28.182  1.00   14.34      L  C
ATOM   4675  CZ  PHE  208      87.602 -27.925  27.330  1.00   20.99      L  C
ATOM   4676  C   PHE  208      87.536 -32.873  27.472  1.00   45.59      L  C
ATOM   4677  O   PHE  208      87.168 -32.576  26.335  1.00   47.78      L  O
ATOM   4678  N   ASN  209      86.703 -33.293  28.420  1.00   24.67      L  N
ATOM   4679  CA  ASN  209      85.257 -33.398  28.213  1.00   28.33      L  C
ATOM   4680  CB  ASN  209      84.751 -34.785  28.623  1.00   27.05      L  C
ATOM   4681  CG  ASN  209      85.664 -35.913  28.172  1.00   33.97      L  C
ATOM   4682  OD1 ASN  209      85.777 -36.941  28.841  1.00   34.19      L  O
ATOM   4683  ND2 ASN  209      86.304 -35.732  27.031  1.00   37.01      L  N
ATOM   4684  C   ASN  209      84.630 -32.370  29.160  1.00   29.95      L  C
ATOM   4685  O   ASN  209      85.203 -32.108  30.218  1.00   31.18      L  O
ATOM   4686  N   ARG  210      83.473 -31.800  28.805  1.00   15.88      L  N
ATOM   4687  CA  ARG  210      82.810 -30.829  29.687  1.00   19.72      L  C
ATOM   4688  CB  ARG  210      81.337 -30.721  29.371  1.00   31.19      L  C
ATOM   4689  CG  ARG  210      81.027 -29.666  28.361  1.00   32.77      L  C
ATOM   4690  CD  ARG  210      79.655 -29.104  28.627  1.00   36.35      L  C
ATOM   4691  NE  ARG  210      78.656 -30.166  28.633  1.00   41.72      L  N
ATOM   4692  CZ  ARG  210      77.502 -30.095  29.282  1.00   45.49      L  C
ATOM   4693  NH1 ARG  210      77.204 -29.008  29.981  1.00   46.04      L  N
ATOM   4694  NH2 ARG  210      76.655 -31.112  29.232  1.00   47.73      L  N
ATOM   4695  C   ARG  210      82.964 -31.252  31.137  1.00   22.05      L  C
ATOM   4696  O   ARG  210      82.962 -32.440  31.428  1.00   23.93      L  O
ATOM   4697  N   GLY  211      83.096 -30.291  32.048  1.00   53.99      L  N
ATOM   4698  CA  GLY  211      83.297 -30.638  33.447  1.00   53.99      L  C
ATOM   4699  C   GLY  211      84.740 -31.088  33.630  1.00   53.99      L  C
ATOM   4700  O   GLY  211      85.665 -30.312  33.387  1.00   53.99      L  O
ATOM   4701  N   GLU  212      84.942 -32.336  34.046  1.00   80.95      L  N
ATOM   4702  CA  GLU  212      86.287 -32.890  34.236  1.00   80.95      L  C
ATOM   4703  CB  GLU  212      86.995 -33.004  32.871  1.00   34.07      L  C
ATOM   4704  CG  GLU  212      88.259 -33.888  32.849  1.00   34.07      L  C
ATOM   4705  CD  GLU  212      88.691 -34.311  31.435  1.00   34.07      L  C
ATOM   4706  OE1 GLU  212      89.803 -34.863  31.296  1.00   34.07      L  O
ATOM   4707  OE2 GLU  212      87.923 -34.113  30.468  1.00   34.07      L  O
ATOM   4708  C   GLU  212      87.134 -32.080  35.227  1.00   80.95      L  C
ATOM   4709  O   GLU  212      86.690 -31.043  35.732  1.00   80.95      L  O
ATOM   4710  N   CYS  213      88.341 -32.566  35.516  1.00   81.74      L  N
ATOM   4711  CA  CYS  213      89.243 -31.893  36.450  1.00   81.74      L  C
ATOM   4712  CB  CYS  213      88.990 -32.374  37.883  1.00   54.42      L  C
ATOM   4713  SG  CYS  213      87.479 -31.701  38.656  1.00   54.42      L  S
ATOM   4714  C   CYS  213      90.715 -32.123  36.095  1.00   81.74      L  C
ATOM   4715  O   CYS  213      90.996 -32.758  35.051  1.00   81.74      L  O
ATOM   4716  OXT CYS  213      91.581 -31.647  36.863  1.00   72.88      L  O
ATOM   4717  MN  MN   400     117.831  24.682   6.345  1.00   34.24      M
ATOM   4718  CB  THR  145     114.226  73.843  15.327  1.00   72.71      B  C
ATOM   4719  OG1 THR  145     113.673  74.174  16.611  1.00   72.71      B  O
ATOM   4720  CG2 THR  145     114.208  75.069  14.426  1.00   72.71      B  C
ATOM   4721  C   THR  145     113.665  71.399  15.485  1.00  109.74      B  C
ATOM   4722  O   THR  145     113.590  70.290  14.948  1.00  110.14      B  O
ATOM   4723  N   THR  145     111.957  72.996  14.632  1.00  108.12      B  N
ATOM   4724  CA  THR  145     113.414  72.677  14.686  1.00  107.72      B  C
ATOM   4725  N   GLN  146     113.963  71.561  16.769  1.00   79.22      B  N
ATOM   4726  CA  GLN  146     114.224  70.425  17.633  1.00   77.37      B  C
ATOM   4727  CB  GLN  146     115.554  70.620  18.378  1.00   80.28      B  C
ATOM   4728  CG  GLN  146     115.640  71.886  19.208  1.00   80.28      B  C
ATOM   4729  CD  GLN  146     116.952  72.001  19.955  1.00   80.28      B  C
ATOM   4730  OE1 GLN  146     117.150  72.929  20.742  1.00   80.28      B  O
ATOM   4731  NE2 GLN  146     117.858  71.059  19.712  1.00   80.28      B  N
ATOM   4732  C   GLN  146     113.077  70.200  18.620  1.00   77.79      B  C
ATOM   4733  O   GLN  146     112.818  71.018  19.511  1.00   79.65      B  O
ATOM   4734  N   LEU  147     112.383  69.081  18.432  1.00   43.47      B  N
ATOM   4735  CA  LEU  147     111.265  68.710  19.288  1.00   42.60      B  C
ATOM   4736  CB  LEU  147     109.936  68.755  18.525  1.00   51.95      B  C
ATOM   4737  CG  LEU  147     109.450  69.952  17.707  1.00   52.14      B  C
ATOM   4738  CD1 LEU  147     110.464  70.296  16.632  1.00   47.35      B  C
ATOM   4739  CD2 LEU  147     108.114  69.607  17.060  1.00   51.99      B  C
ATOM   4740  C   LEU  147     111.461  67.281  19.756  1.00   41.58      B  C
ATOM   4741  O   LEU  147     112.077  66.470  19.058  1.00   42.88      B  O
ATOM   4742  N   ASP  148     110.944  66.988  20.945  1.00   31.29      B  N
ATOM   4743  CA  ASP  148     110.974  65.640  21.493  1.00   28.75      B  C
ATOM   4744  CB  ASP  148     111.394  65.642  22.960  1.00   32.78      B  C
ATOM   4745  CG  ASP  148     112.897  65.718  23.133  1.00   32.40      B  C
```

Fig. 19: A-66

| | | | | | | | | | | |
|---|---|---|---|---|---|---|---|---|---|---|
| ATOM | 4746 | OD1 | ASP | 148 | 113.366 | 65.715 | 24.290 | 1.00 | 31.51 | B O |
| ATOM | 4747 | OD2 | ASP | 148 | 113.616 | 65.777 | 22.116 | 1.00 | 30.58 | B O |
| ATOM | 4748 | C | ASP | 148 | 109.526 | 65.181 | 21.358 | 1.00 | 25.13 | B C |
| ATOM | 4749 | O | ASP | 148 | 108.664 | 65.583 | 22.128 | 1.00 | 24.43 | B O |
| ATOM | 4750 | N | ILE | 149 | 109.260 | 64.368 | 20.345 | 1.00 | 21.33 | B N |
| ATOM | 4751 | CA | ILE | 149 | 107.918 | 63.885 | 20.105 | 1.00 | 20.27 | B C |
| ATOM | 4752 | CB | ILE | 149 | 107.610 | 63.880 | 18.605 | 1.00 | 13.57 | B C |
| ATOM | 4753 | CG2 | ILE | 149 | 106.140 | 63.573 | 18.378 | 1.00 | 8.58 | B C |
| ATOM | 4754 | CG1 | ILE | 149 | 107.932 | 65.234 | 17.998 | 1.00 | 9.29 | B C |
| ATOM | 4755 | CD1 | ILE | 149 | 107.697 | 65.263 | 16.508 | 1.00 | 12.04 | B C |
| ATOM | 4756 | C | ILE | 149 | 107.723 | 62.464 | 20.629 | 1.00 | 21.92 | B C |
| ATOM | 4757 | O | ILE | 149 | 108.507 | 61.563 | 20.315 | 1.00 | 22.32 | B O |
| ATOM | 4758 | N | VAL | 150 | 106.680 | 62.271 | 21.433 | 1.00 | 32.56 | B N |
| ATOM | 4759 | CA | VAL | 150 | 106.357 | 60.950 | 21.956 | 1.00 | 34.12 | B C |
| ATOM | 4760 | CB | VAL | 150 | 106.256 | 60.940 | 23.492 | 1.00 | 12.90 | B C |
| ATOM | 4761 | CG1 | VAL | 150 | 105.775 | 59.579 | 23.967 | 1.00 | 15.09 | B C |
| ATOM | 4762 | CG2 | VAL | 150 | 107.620 | 61.256 | 24.110 | 1.00 | 14.71 | B C |
| ATOM | 4763 | C | VAL | 150 | 105.001 | 60.604 | 21.381 | 1.00 | 31.68 | B C |
| ATOM | 4764 | O | VAL | 150 | 104.057 | 61.380 | 21.523 | 1.00 | 29.83 | B O |
| ATOM | 4765 | N | ILE | 151 | 104.904 | 59.459 | 20.714 | 1.00 | 36.82 | B N |
| ATOM | 4766 | CA | ILE | 151 | 103.640 | 59.037 | 20.115 | 1.00 | 35.62 | B C |
| ATOM | 4767 | CB | ILE | 151 | 103.862 | 58.436 | 18.709 | 1.00 | 31.63 | B C |
| ATOM | 4768 | CG2 | ILE | 151 | 102.537 | 58.084 | 18.081 | 1.00 | 27.99 | B C |
| ATOM | 4769 | CG1 | ILE | 151 | 104.582 | 59.454 | 17.817 | 1.00 | 30.05 | B C |
| ATOM | 4770 | CD1 | ILE | 151 | 104.981 | 58.916 | 16.457 | 1.00 | 32.03 | B C |
| ATOM | 4771 | C | ILE | 151 | 102.978 | 58.008 | 21.016 | 1.00 | 33.74 | B C |
| ATOM | 4772 | O | ILE | 151 | 103.593 | 57.013 | 21.394 | 1.00 | 33.98 | B O |
| ATOM | 4773 | N | VAL | 152 | 101.725 | 58.254 | 21.368 | 1.00 | 29.85 | B N |
| ATOM | 4774 | CA | VAL | 152 | 100.996 | 57.347 | 22.243 | 1.00 | 30.70 | B C |
| ATOM | 4775 | CB | VAL | 152 | 100.279 | 58.127 | 23.344 | 1.00 | 30.57 | B C |
| ATOM | 4776 | CG1 | VAL | 152 | 99.721 | 57.170 | 24.385 | 1.00 | 29.70 | B C |
| ATOM | 4777 | CG2 | VAL | 152 | 101.245 | 59.134 | 23.962 | 1.00 | 27.01 | B C |
| ATOM | 4778 | C | VAL | 152 | 99.966 | 56.560 | 21.451 | 1.00 | 28.60 | B C |
| ATOM | 4779 | O | VAL | 152 | 98.867 | 57.044 | 21.194 | 1.00 | 22.20 | B O |
| ATOM | 4780 | N | LEU | 153 | 100.324 | 55.336 | 21.083 | 1.00 | 26.94 | B N |
| ATOM | 4781 | CA | LEU | 153 | 99.451 | 54.479 | 20.289 | 1.00 | 27.05 | B C |
| ATOM | 4782 | CB | LEU | 153 | 100.312 | 53.600 | 19.370 | 1.00 | 31.93 | B C |
| ATOM | 4783 | CG | LEU | 153 | 100.518 | 54.010 | 17.910 | 1.00 | 33.71 | B C |
| ATOM | 4784 | CD1 | LEU | 153 | 100.287 | 55.490 | 17.732 | 1.00 | 34.22 | B C |
| ATOM | 4785 | CD2 | LEU | 153 | 101.914 | 53.616 | 17.481 | 1.00 | 36.25 | B C |
| ATOM | 4786 | C | LEU | 153 | 98.475 | 53.597 | 21.058 | 1.00 | 28.11 | B C |
| ATOM | 4787 | O | LEU | 153 | 98.837 | 52.930 | 22.035 | 1.00 | 27.11 | B O |
| ATOM | 4788 | N | ASP | 154 | 97.228 | 53.602 | 20.604 | 1.00 | 33.48 | B N |
| ATOM | 4789 | CA | ASP | 154 | 96.199 | 52.768 | 21.204 | 1.00 | 32.96 | B C |
| ATOM | 4790 | CB | ASP | 154 | 94.809 | 53.341 | 20.911 | 1.00 | 34.05 | B C |
| ATOM | 4791 | CG | ASP | 154 | 93.686 | 52.502 | 21.505 | 1.00 | 33.25 | B C |
| ATOM | 4792 | OD1 | ASP | 154 | 93.959 | 51.385 | 21.985 | 1.00 | 36.76 | B O |
| ATOM | 4793 | OD2 | ASP | 154 | 92.523 | 52.960 | 21.489 | 1.00 | 29.57 | B O |
| ATOM | 4794 | C | ASP | 154 | 96.362 | 51.412 | 20.515 | 1.00 | 36.30 | B C |
| ATOM | 4795 | O | ASP | 154 | 96.349 | 51.326 | 19.285 | 1.00 | 32.62 | B O |
| ATOM | 4796 | N | GLY | 155 | 96.539 | 50.361 | 21.303 | 1.00 | 16.68 | B N |
| ATOM | 4797 | CA | GLY | 155 | 96.700 | 49.039 | 20.732 | 1.00 | 18.75 | B C |
| ATOM | 4798 | C | GLY | 155 | 95.706 | 48.058 | 21.321 | 1.00 | 20.01 | B C |
| ATOM | 4799 | O | GLY | 155 | 95.856 | 46.845 | 21.177 | 1.00 | 22.50 | B O |
| ATOM | 4800 | N | SER | 156 | 94.692 | 48.595 | 21.992 | 1.00 | 30.46 | B N |
| ATOM | 4801 | CA | SER | 156 | 93.653 | 47.780 | 22.612 | 1.00 | 35.04 | B C |
| ATOM | 4802 | CB | SER | 156 | 92.616 | 48.670 | 23.302 | 1.00 | 22.70 | B C |
| ATOM | 4803 | OG | SER | 156 | 91.999 | 49.542 | 22.372 | 1.00 | 25.62 | B O |
| ATOM | 4804 | C | SER | 156 | 92.962 | 46.891 | 21.584 | 1.00 | 32.03 | B C |
| ATOM | 4805 | O | SER | 156 | 93.057 | 47.122 | 20.379 | 1.00 | 35.21 | B O |
| ATOM | 4806 | N | ASN | 157 | 92.257 | 45.879 | 22.074 | 1.00 | 34.08 | B N |
| ATOM | 4807 | CA | ASN | 157 | 91.565 | 44.927 | 21.216 | 1.00 | 31.16 | B C |
| ATOM | 4808 | CB | ASN | 157 | 90.632 | 44.046 | 22.047 | 1.00 | 34.61 | B C |
| ATOM | 4809 | CG | ASN | 157 | 91.378 | 42.971 | 22.811 | 1.00 | 36.10 | B C |
| ATOM | 4810 | OD1 | ASN | 157 | 90.795 | 42.270 | 23.638 | 1.00 | 33.17 | B O |
| ATOM | 4811 | ND2 | ASN | 157 | 92.672 | 42.832 | 22.536 | 1.00 | 33.38 | B N |
| ATOM | 4812 | C | ASN | 157 | 90.783 | 45.529 | 20.069 | 1.00 | 29.13 | B C |
| ATOM | 4813 | O | ASN | 157 | 90.806 | 45.003 | 18.956 | 1.00 | 27.11 | B O |
| ATOM | 4814 | N | SER | 158 | 90.094 | 46.631 | 20.339 | 1.00 | 20.01 | B N |
| ATOM | 4815 | CA | SER | 158 | 89.275 | 47.285 | 19.324 | 1.00 | 18.22 | B C |
| ATOM | 4816 | CB | SER | 158 | 88.506 | 48.464 | 19.936 | 1.00 | 15.08 | B C |
| ATOM | 4817 | OG | SER | 158 | 89.356 | 49.363 | 20.616 | 1.00 | 17.79 | B O |
| ATOM | 4818 | C | SER | 158 | 90.035 | 47.739 | 18.087 | 1.00 | 18.99 | B C |

Fig. 19: A-67

| | | | | | | | | | | |
|---|---|---|---|---|---|---|---|---|---|---|
| ATOM | 4819 | O | SER | 158 | 89.527 | 47.602 | 16.984 | 1.00 | 16.16 | B | O |
| ATOM | 4820 | N | ILE | 159 | 91.245 | 48.269 | 18.257 | 1.00 | 19.55 | B | N |
| ATOM | 4821 | CA | ILE | 159 | 92.033 | 48.722 | 17.110 | 1.00 | 24.15 | B | C |
| ATOM | 4822 | CB | ILE | 159 | 93.423 | 49.203 | 17.541 | 1.00 | 21.45 | B | C |
| ATOM | 4823 | CG2 | ILE | 159 | 94.256 | 49.546 | 16.307 | 1.00 | 21.36 | B | C |
| ATOM | 4824 | CG1 | ILE | 159 | 93.293 | 50.411 | 18.471 | 1.00 | 26.23 | B | C |
| ATOM | 4825 | CD1 | ILE | 159 | 92.779 | 51.664 | 17.787 | 1.00 | 31.39 | B | C |
| ATOM | 4826 | C | ILE | 159 | 92.204 | 47.597 | 16.089 | 1.00 | 28.46 | B | C |
| ATOM | 4827 | O | ILE | 159 | 92.638 | 46.502 | 16.434 | 1.00 | 27.87 | B | O |
| ATOM | 4828 | N | TYR | 160 | 91.863 | 47.876 | 14.832 | 1.00 | 56.09 | B | N |
| ATOM | 4829 | CA | TYR | 160 | 91.959 | 46.886 | 13.756 | 1.00 | 58.22 | B | C |
| ATOM | 4830 | CB | TYR | 160 | 90.931 | 45.768 | 13.980 | 1.00 | 40.50 | B | C |
| ATOM | 4831 | CG | TYR | 160 | 90.932 | 44.654 | 12.939 | 1.00 | 37.26 | B | C |
| ATOM | 4832 | CD1 | TYR | 160 | 91.606 | 43.449 | 13.172 | 1.00 | 39.68 | B | C |
| ATOM | 4833 | CE1 | TYR | 160 | 91.602 | 42.423 | 12.225 | 1.00 | 37.28 | B | C |
| ATOM | 4834 | CD2 | TYR | 160 | 90.254 | 44.803 | 11.722 | 1.00 | 34.91 | B | C |
| ATOM | 4835 | CE2 | TYR | 160 | 90.251 | 43.782 | 10.770 | 1.00 | 38.62 | B | C |
| ATOM | 4836 | CZ | TYR | 160 | 90.926 | 42.598 | 11.030 | 1.00 | 37.97 | B | C |
| ATOM | 4837 | OH | TYR | 160 | 90.922 | 41.597 | 10.095 | 1.00 | 42.97 | B | O |
| ATOM | 4838 | C | TYR | 160 | 91.696 | 47.533 | 12.400 | 1.00 | 59.94 | B | C |
| ATOM | 4839 | O | TYR | 160 | 90.730 | 48.276 | 12.232 | 1.00 | 65.86 | B | O |
| ATOM | 4840 | N | PRO | 161 | 92.548 | 47.241 | 11.407 | 1.00 | 26.83 | B | N |
| ATOM | 4841 | CD | PRO | 161 | 92.182 | 47.499 | 10.002 | 1.00 | 24.03 | B | C |
| ATOM | 4842 | CA | PRO | 161 | 93.721 | 46.362 | 11.479 | 1.00 | 25.11 | B | C |
| ATOM | 4843 | CB | PRO | 161 | 93.784 | 45.785 | 10.075 | 1.00 | 28.41 | B | C |
| ATOM | 4844 | CG | PRO | 161 | 93.364 | 46.960 | 9.239 | 1.00 | 31.57 | B | C |
| ATOM | 4845 | C | PRO | 161 | 95.008 | 47.109 | 11.857 | 1.00 | 23.77 | B | C |
| ATOM | 4846 | O | PRO | 161 | 95.234 | 48.238 | 11.413 | 1.00 | 23.09 | B | O |
| ATOM | 4847 | N | TRP | 162 | 95.856 | 46.463 | 12.654 | 1.00 | 23.22 | B | N |
| ATOM | 4848 | CA | TRP | 162 | 97.108 | 47.062 | 13.111 | 1.00 | 24.29 | B | C |
| ATOM | 4849 | CB | TRP | 162 | 97.922 | 46.022 | 13.878 | 1.00 | 29.42 | B | C |
| ATOM | 4850 | CG | TRP | 162 | 99.067 | 46.586 | 14.670 | 1.00 | 29.94 | B | C |
| ATOM | 4851 | CD2 | TRP | 162 | 99.004 | 47.603 | 15.676 | 1.00 | 24.78 | B | C |
| ATOM | 4852 | CE2 | TRP | 162 | 100.308 | 47.769 | 16.185 | 1.00 | 28.33 | B | C |
| ATOM | 4853 | CE3 | TRP | 162 | 97.973 | 48.389 | 16.201 | 1.00 | 24.19 | B | C |
| ATOM | 4854 | CD1 | TRP | 162 | 100.369 | 46.192 | 14.611 | 1.00 | 29.13 | B | C |
| ATOM | 4855 | NE1 | TRP | 162 | 101.123 | 46.898 | 15.516 | 1.00 | 31.00 | B | N |
| ATOM | 4856 | CZ2 | TRP | 162 | 100.607 | 48.687 | 17.195 | 1.00 | 26.87 | B | C |
| ATOM | 4857 | CZ3 | TRP | 162 | 98.274 | 49.303 | 17.208 | 1.00 | 22.52 | B | C |
| ATOM | 4858 | CH2 | TRP | 162 | 99.580 | 49.441 | 17.691 | 1.00 | 27.43 | B | C |
| ATOM | 4859 | C | TRP | 162 | 97.961 | 47.663 | 11.988 | 1.00 | 26.07 | B | C |
| ATOM | 4860 | O | TRP | 162 | 98.554 | 48.734 | 12.161 | 1.00 | 25.22 | B | O |
| ATOM | 4861 | N | GLU | 163 | 98.010 | 46.979 | 10.843 | 1.00 | 39.64 | B | N |
| ATOM | 4862 | CA | GLU | 163 | 98.797 | 47.432 | 9.693 | 1.00 | 41.42 | B | C |
| ATOM | 4863 | CB | GLU | 163 | 98.585 | 46.509 | 8.485 | 1.00 | 121.98 | B | C |
| ATOM | 4864 | CG | GLU | 163 | 97.219 | 46.612 | 7.826 | 1.00 | 128.29 | B | C |
| ATOM | 4865 | CD | GLU | 163 | 97.206 | 46.043 | 6.418 | 1.00 | 130.43 | B | C |
| ATOM | 4866 | OE1 | GLU | 163 | 97.894 | 46.611 | 5.541 | 1.00 | 132.14 | B | O |
| ATOM | 4867 | OE2 | GLU | 163 | 96.512 | 45.029 | 6.187 | 1.00 | 129.39 | B | O |
| ATOM | 4868 | C | GLU | 163 | 98.491 | 48.867 | 9.280 | 1.00 | 41.08 | B | C |
| ATOM | 4869 | O | GLU | 163 | 99.390 | 49.609 | 8.881 | 1.00 | 37.25 | B | O |
| ATOM | 4870 | N | SER | 164 | 97.225 | 49.262 | 9.368 | 1.00 | 24.58 | B | N |
| ATOM | 4871 | CA | SER | 164 | 96.850 | 50.620 | 8.989 | 1.00 | 21.77 | B | C |
| ATOM | 4872 | CB | SER | 164 | 95.320 | 50.772 | 8.984 | 1.00 | 53.34 | B | C |
| ATOM | 4873 | OG | SER | 164 | 94.722 | 49.950 | 7.992 | 1.00 | 59.23 | B | O |
| ATOM | 4874 | C | SER | 164 | 97.484 | 51.619 | 9.956 | 1.00 | 22.53 | B | C |
| ATOM | 4875 | O | SER | 164 | 97.993 | 52.661 | 9.536 | 1.00 | 25.73 | B | O |
| ATOM | 4876 | N | VAL | 165 | 97.451 | 51.286 | 11.247 | 1.00 | 28.47 | B | N |
| ATOM | 4877 | CA | VAL | 165 | 98.027 | 52.137 | 12.280 | 1.00 | 27.86 | B | C |
| ATOM | 4878 | CB | VAL | 165 | 97.841 | 51.525 | 13.680 | 1.00 | 11.01 | B | C |
| ATOM | 4879 | CG1 | VAL | 165 | 98.722 | 52.245 | 14.697 | 1.00 | 12.40 | B | C |
| ATOM | 4880 | CG2 | VAL | 165 | 96.376 | 51.622 | 14.089 | 1.00 | 14.01 | B | C |
| ATOM | 4881 | C | VAL | 165 | 99.509 | 52.334 | 12.028 | 1.00 | 29.02 | B | C |
| ATOM | 4882 | O | VAL | 165 | 100.032 | 53.444 | 12.137 | 1.00 | 30.84 | B | O |
| ATOM | 4883 | N | ILE | 166 | 100.184 | 51.248 | 11.678 | 1.00 | 20.94 | B | N |
| ATOM | 4884 | CA | ILE | 166 | 101.613 | 51.305 | 11.400 | 1.00 | 20.26 | B | C |
| ATOM | 4885 | CB | ILE | 166 | 102.211 | 49.894 | 11.330 | 1.00 | 40.92 | B | C |
| ATOM | 4886 | CG2 | ILE | 166 | 103.697 | 49.962 | 10.986 | 1.00 | 40.13 | B | C |
| ATOM | 4887 | CG1 | ILE | 166 | 102.017 | 49.214 | 12.687 | 1.00 | 40.78 | B | C |
| ATOM | 4888 | CD1 | ILE | 166 | 102.580 | 47.823 | 12.762 | 1.00 | 37.18 | B | C |
| ATOM | 4889 | C | ILE | 166 | 101.920 | 52.073 | 10.121 | 1.00 | 19.71 | B | C |
| ATOM | 4890 | O | ILE | 166 | 102.909 | 52.792 | 10.059 | 1.00 | 21.46 | B | O |
| ATOM | 4891 | N | ALA | 167 | 101.076 | 51.927 | 9.106 | 1.00 | 22.08 | B | N |

Fig. 19: A-68

| | | | | | | | | | | |
|---|---|---|---|---|---|---|---|---|---|---|
| ATOM | 4892 | CA | ALA | 167 | 101.271 | 52.670 | 7.866 | 1.00 | 22.68 | B | C |
| ATOM | 4893 | CB | ALA | 167 | 100.207 | 52.309 | 6.859 | 1.00 | 1.87 | B | C |
| ATOM | 4894 | C | ALA | 167 | 101.165 | 54.150 | 8.224 | 1.00 | 23.89 | B | C |
| ATOM | 4895 | O | ALA | 167 | 101.881 | 54.989 | 7.684 | 1.00 | 20.49 | B | O |
| ATOM | 4896 | N | PHE | 168 | 100.261 | 54.458 | 9.147 | 1.00 | 25.99 | B | N |
| ATOM | 4897 | CA | PHE | 168 | 100.083 | 55.823 | 9.583 | 1.00 | 24.51 | B | C |
| ATOM | 4898 | CB | PHE | 168 | 98.964 | 55.902 | 10.623 | 1.00 | 28.51 | B | C |
| ATOM | 4899 | CG | PHE | 168 | 98.962 | 57.185 | 11.406 | 1.00 | 27.01 | B | C |
| ATOM | 4900 | CD1 | PHE | 168 | 99.549 | 57.240 | 12.671 | 1.00 | 28.61 | B | C |
| ATOM | 4901 | CD2 | PHE | 168 | 98.409 | 58.341 | 10.872 | 1.00 | 25.32 | B | C |
| ATOM | 4902 | CE1 | PHE | 168 | 99.587 | 58.424 | 13.392 | 1.00 | 27.09 | B | C |
| ATOM | 4903 | CE2 | PHE | 168 | 98.442 | 59.529 | 11.587 | 1.00 | 27.14 | B | C |
| ATOM | 4904 | CZ | PHE | 168 | 99.034 | 59.570 | 12.853 | 1.00 | 29.63 | B | C |
| ATOM | 4905 | C | PHE | 168 | 101.397 | 56.325 | 10.178 | 1.00 | 25.37 | B | C |
| ATOM | 4906 | O | PHE | 168 | 101.832 | 57.446 | 9.908 | 1.00 | 21.81 | B | O |
| ATOM | 4907 | N | LEU | 169 | 102.030 | 55.488 | 10.990 | 1.00 | 25.37 | B | N |
| ATOM | 4908 | CA | LEU | 169 | 103.286 | 55.867 | 11.611 | 1.00 | 27.96 | B | C |
| ATOM | 4909 | CB | LEU | 169 | 103.749 | 54.790 | 12.585 | 1.00 | 24.35 | B | C |
| ATOM | 4910 | CG | LEU | 169 | 103.127 | 54.723 | 13.977 | 1.00 | 23.51 | B | C |
| ATOM | 4911 | CD1 | LEU | 169 | 103.983 | 53.810 | 14.831 | 1.00 | 19.97 | B | C |
| ATOM | 4912 | CD2 | LEU | 169 | 103.079 | 56.105 | 14.609 | 1.00 | 20.37 | B | C |
| ATOM | 4913 | C | LEU | 169 | 104.357 | 56.081 | 10.555 | 1.00 | 30.26 | B | C |
| ATOM | 4914 | O | LEU | 169 | 105.055 | 57.095 | 10.555 | 1.00 | 31.69 | B | O |
| ATOM | 4915 | N | ASN | 170 | 104.488 | 55.115 | 9.655 | 1.00 | 28.40 | B | N |
| ATOM | 4916 | CA | ASN | 170 | 105.470 | 55.208 | 8.591 | 1.00 | 25.53 | B | C |
| ATOM | 4917 | CB | ASN | 170 | 105.243 | 54.077 | 7.580 | 1.00 | 72.75 | B | C |
| ATOM | 4918 | CG | ASN | 170 | 106.484 | 53.768 | 6.747 | 1.00 | 76.17 | B | C |
| ATOM | 4919 | OD1 | ASN | 170 | 106.703 | 54.346 | 5.680 | 1.00 | 71.70 | B | O |
| ATOM | 4920 | ND2 | ASN | 170 | 107.307 | 52.854 | 7.242 | 1.00 | 74.08 | B | N |
| ATOM | 4921 | C | ASN | 170 | 105.335 | 56.578 | 7.913 | 1.00 | 25.54 | B | C |
| ATOM | 4922 | O | ASN | 170 | 106.242 | 57.408 | 7.992 | 1.00 | 25.75 | B | O |
| ATOM | 4923 | N | ASP | 171 | 104.189 | 56.819 | 7.275 | 1.00 | 35.44 | B | N |
| ATOM | 4924 | CA | ASP | 171 | 103.940 | 58.079 | 6.581 | 1.00 | 37.56 | B | C |
| ATOM | 4925 | CB | ASP | 171 | 102.467 | 58.179 | 6.168 | 1.00 | 72.00 | B | C |
| ATOM | 4926 | CG | ASP | 171 | 102.163 | 57.427 | 4.880 | 1.00 | 79.65 | B | C |
| ATOM | 4927 | OD1 | ASP | 171 | 102.448 | 56.213 | 4.805 | 1.00 | 81.87 | B | O |
| ATOM | 4928 | OD2 | ASP | 171 | 101.635 | 58.055 | 3.937 | 1.00 | 81.51 | B | O |
| ATOM | 4929 | C | ASP | 171 | 104.309 | 59.289 | 7.418 | 1.00 | 39.05 | B | C |
| ATOM | 4930 | O | ASP | 171 | 104.975 | 60.202 | 6.937 | 1.00 | 37.77 | B | O |
| ATOM | 4931 | N | LEU | 172 | 103.881 | 59.289 | 8.674 | 1.00 | 36.54 | B | N |
| ATOM | 4932 | CA | LEU | 172 | 104.152 | 60.403 | 9.570 | 1.00 | 37.22 | B | C |
| ATOM | 4933 | CB | LEU | 172 | 103.410 | 60.204 | 10.891 | 1.00 | 36.27 | B | C |
| ATOM | 4934 | CG | LEU | 172 | 102.901 | 61.423 | 11.674 | 1.00 | 35.76 | B | C |
| ATOM | 4935 | CD1 | LEU | 172 | 103.145 | 61.178 | 13.158 | 1.00 | 33.36 | B | C |
| ATOM | 4936 | CD2 | LEU | 172 | 103.593 | 62.706 | 11.237 | 1.00 | 33.93 | B | C |
| ATOM | 4937 | C | LEU | 172 | 105.642 | 60.561 | 9.849 | 1.00 | 37.56 | B | C |
| ATOM | 4938 | O | LEU | 172 | 106.212 | 61.628 | 9.627 | 1.00 | 37.55 | B | O |
| ATOM | 4939 | N | LEU | 173 | 106.269 | 59.493 | 10.337 | 1.00 | 40.49 | B | N |
| ATOM | 4940 | CA | LEU | 173 | 107.692 | 59.520 | 10.669 | 1.00 | 43.24 | B | C |
| ATOM | 4941 | CB | LEU | 173 | 108.115 | 58.215 | 11.364 | 1.00 | 18.13 | B | C |
| ATOM | 4942 | CG | LEU | 173 | 107.801 | 57.866 | 12.826 | 1.00 | 19.48 | B | C |
| ATOM | 4943 | CD1 | LEU | 173 | 108.033 | 59.060 | 13.729 | 1.00 | 23.00 | B | C |
| ATOM | 4944 | CD2 | LEU | 173 | 106.380 | 57.395 | 12.943 | 1.00 | 20.03 | B | C |
| ATOM | 4945 | C | LEU | 173 | 108.650 | 59.772 | 9.503 | 1.00 | 44.67 | B | C |
| ATOM | 4946 | O | LEU | 173 | 109.601 | 60.537 | 9.642 | 1.00 | 41.39 | B | O |
| ATOM | 4947 | N | LYS | 174 | 108.409 | 59.135 | 8.360 | 1.00 | 37.56 | B | N |
| ATOM | 4948 | CA | LYS | 174 | 109.304 | 59.291 | 7.221 | 1.00 | 37.78 | B | C |
| ATOM | 4949 | CB | LYS | 174 | 108.836 | 58.421 | 6.047 | 1.00 | 42.14 | B | C |
| ATOM | 4950 | CG | LYS | 174 | 107.739 | 58.988 | 5.169 | 1.00 | 42.47 | B | C |
| ATOM | 4951 | CD | LYS | 174 | 107.472 | 58.022 | 4.008 | 1.00 | 41.72 | B | C |
| ATOM | 4952 | CE | LYS | 174 | 106.689 | 58.660 | 2.852 | 1.00 | 36.97 | B | C |
| ATOM | 4953 | NZ | LYS | 174 | 105.297 | 59.097 | 3.187 | 1.00 | 33.44 | B | N |
| ATOM | 4954 | C | LYS | 174 | 109.511 | 60.738 | 6.774 | 1.00 | 36.14 | B | C |
| ATOM | 4955 | O | LYS | 174 | 110.571 | 61.078 | 6.245 | 1.00 | 37.01 | B | O |
| ATOM | 4956 | N | ARG | 175 | 108.514 | 61.589 | 7.004 | 1.00 | 41.42 | B | N |
| ATOM | 4957 | CA | ARG | 175 | 108.587 | 63.006 | 6.635 | 1.00 | 43.65 | B | C |
| ATOM | 4958 | CB | ARG | 175 | 107.182 | 63.634 | 6.654 | 1.00 | 108.28 | B | C |
| ATOM | 4959 | CG | ARG | 175 | 106.189 | 63.149 | 5.589 | 1.00 | 115.21 | B | C |
| ATOM | 4960 | CD | ARG | 175 | 104.762 | 63.613 | 5.939 | 1.00 | 119.49 | B | C |
| ATOM | 4961 | NE | ARG | 175 | 103.895 | 63.818 | 4.775 | 1.00 | 124.39 | B | N |
| ATOM | 4962 | CZ | ARG | 175 | 103.454 | 62.856 | 3.969 | 1.00 | 127.97 | B | C |
| ATOM | 4963 | NH1 | ARG | 175 | 103.793 | 61.593 | 4.182 | 1.00 | 128.17 | B | N |
| ATOM | 4964 | NH2 | ARG | 175 | 102.666 | 63.162 | 2.945 | 1.00 | 128.87 | B | N |

Fig. 19: A-69

| ATOM | 4965 | C | ARG | 175 | 109.471 | 63.798 | 7.611 | 1.00 | 41.18 | B | C |
|---|---|---|---|---|---|---|---|---|---|---|---|
| ATOM | 4966 | O | ARG | 175 | 109.696 | 64.986 | 7.411 | 1.00 | 41.02 | B | O |
| ATOM | 4967 | N | MET | 176 | 109.970 | 63.145 | 8.660 | 1.00 | 47.15 | B | N |
| ATOM | 4968 | CA | MET | 176 | 110.777 | 63.821 | 9.678 | 1.00 | 43.63 | B | C |
| ATOM | 4969 | CB | MET | 176 | 110.320 | 63.383 | 11.065 | 1.00 | 33.29 | B | C |
| ATOM | 4970 | CG | MET | 176 | 108.969 | 63.920 | 11.456 | 1.00 | 30.19 | B | C |
| ATOM | 4971 | SD | MET | 176 | 108.444 | 63.366 | 13.073 | 1.00 | 34.33 | B | S |
| ATOM | 4972 | CE | MET | 176 | 107.041 | 62.339 | 12.619 | 1.00 | 27.84 | B | C |
| ATOM | 4973 | C | MET | 176 | 112.284 | 63.663 | 9.611 | 1.00 | 47.14 | B | C |
| ATOM | 4974 | O | MET | 176 | 112.795 | 62.707 | 9.037 | 1.00 | 47.21 | B | O |
| ATOM | 4975 | N | ASP | 177 | 112.991 | 64.617 | 10.213 | 1.00 | 51.06 | B | N |
| ATOM | 4976 | CA | ASP | 177 | 114.451 | 64.590 | 10.276 | 1.00 | 53.55 | B | C |
| ATOM | 4977 | CB | ASP | 177 | 115.047 | 65.944 | 9.881 | 1.00 | 101.95 | B | C |
| ATOM | 4978 | CG | ASP | 177 | 115.065 | 66.158 | 8.381 | 1.00 | 104.90 | B | C |
| ATOM | 4979 | OD1 | ASP | 177 | 115.635 | 67.174 | 7.934 | 1.00 | 104.57 | B | O |
| ATOM | 4980 | OD2 | ASP | 177 | 114.511 | 65.310 | 7.647 | 1.00 | 106.55 | B | O |
| ATOM | 4981 | C | ASP | 177 | 114.851 | 64.249 | 11.706 | 1.00 | 53.47 | B | C |
| ATOM | 4982 | O | ASP | 177 | 115.107 | 65.133 | 12.519 | 1.00 | 53.19 | B | O |
| ATOM | 4983 | N | ILE | 178 | 114.888 | 62.954 | 12.003 | 1.00 | 55.91 | B | N |
| ATOM | 4984 | CA | ILE | 178 | 115.236 | 62.465 | 13.331 | 1.00 | 56.05 | B | C |
| ATOM | 4985 | CB | ILE | 178 | 114.719 | 61.004 | 13.543 | 1.00 | 33.37 | B | C |
| ATOM | 4986 | CG2 | ILE | 178 | 115.323 | 60.410 | 14.790 | 1.00 | 31.65 | B | C |
| ATOM | 4987 | CG1 | ILE | 178 | 113.191 | 60.985 | 13.665 | 1.00 | 34.43 | B | C |
| ATOM | 4988 | CD1 | ILE | 178 | 112.464 | 60.671 | 12.376 | 1.00 | 36.27 | B | C |
| ATOM | 4989 | C | ILE | 178 | 116.743 | 62.502 | 13.583 | 1.00 | 55.19 | B | C |
| ATOM | 4990 | O | ILE | 178 | 117.543 | 62.224 | 12.686 | 1.00 | 57.18 | B | O |
| ATOM | 4991 | N | GLY | 179 | 117.117 | 62.846 | 14.812 | 1.00 | 23.09 | B | N |
| ATOM | 4992 | CA | GLY | 179 | 118.521 | 62.912 | 15.178 | 1.00 | 22.81 | B | C |
| ATOM | 4993 | C | GLY | 179 | 118.736 | 63.508 | 16.560 | 1.00 | 23.57 | B | C |
| ATOM | 4994 | O | GLY | 179 | 117.931 | 64.325 | 17.012 | 1.00 | 21.72 | B | O |
| ATOM | 4995 | N | PRO | 180 | 119.815 | 63.113 | 17.265 | 1.00 | 39.73 | B | N |
| ATOM | 4996 | CD | PRO | 180 | 120.782 | 62.068 | 16.873 | 1.00 | 73.51 | B | C |
| ATOM | 4997 | CA | PRO | 180 | 120.124 | 63.620 | 18.606 | 1.00 | 40.79 | B | C |
| ATOM | 4998 | CB | PRO | 180 | 121.542 | 63.113 | 18.840 | 1.00 | 72.35 | B | C |
| ATOM | 4999 | CG | PRO | 180 | 121.502 | 61.776 | 18.184 | 1.00 | 74.74 | B | C |
| ATOM | 5000 | C | PRO | 180 | 120.019 | 65.135 | 18.697 | 1.00 | 42.57 | B | C |
| ATOM | 5001 | O | PRO | 180 | 119.718 | 65.680 | 19.761 | 1.00 | 43.21 | B | O |
| ATOM | 5002 | N | LYS | 181 | 120.268 | 65.810 | 17.578 | 1.00 | 56.97 | B | N |
| ATOM | 5003 | CA | LYS | 181 | 120.186 | 67.265 | 17.534 | 1.00 | 57.39 | B | C |
| ATOM | 5004 | CB | LYS | 181 | 121.522 | 67.867 | 17.092 | 1.00 | 83.43 | B | C |
| ATOM | 5005 | CG | LYS | 181 | 122.677 | 67.613 | 18.052 | 1.00 | 84.03 | B | C |
| ATOM | 5006 | CD | LYS | 181 | 122.430 | 68.205 | 19.442 | 1.00 | 82.89 | B | C |
| ATOM | 5007 | CE | LYS | 181 | 123.580 | 67.868 | 20.394 | 1.00 | 85.41 | B | C |
| ATOM | 5008 | NZ | LYS | 181 | 123.351 | 68.348 | 21.790 | 1.00 | 84.98 | B | N |
| ATOM | 5009 | C | LYS | 181 | 119.070 | 67.736 | 16.597 | 1.00 | 56.74 | B | C |
| ATOM | 5010 | O | LYS | 181 | 118.973 | 68.917 | 16.274 | 1.00 | 55.06 | B | O |
| ATOM | 5011 | N | GLN | 182 | 118.225 | 66.804 | 16.167 | 1.00 | 33.36 | B | N |
| ATOM | 5012 | CA | GLN | 182 | 117.112 | 67.117 | 15.279 | 1.00 | 32.02 | B | C |
| ATOM | 5013 | CB | GLN | 182 | 117.152 | 66.219 | 14.044 | 1.00 | 74.94 | B | C |
| ATOM | 5014 | CG | GLN | 182 | 118.512 | 66.050 | 13.424 | 1.00 | 76.22 | B | C |
| ATOM | 5015 | CD | GLN | 182 | 119.037 | 67.334 | 12.850 | 1.00 | 77.84 | B | C |
| ATOM | 5016 | OE1 | GLN | 182 | 119.266 | 68.305 | 13.573 | 1.00 | 78.68 | B | O |
| ATOM | 5017 | NE2 | GLN | 182 | 119.230 | 67.356 | 11.537 | 1.00 | 79.20 | B | N |
| ATOM | 5018 | C | GLN | 182 | 115.831 | 66.826 | 16.046 | 1.00 | 30.93 | B | C |
| ATOM | 5019 | O | GLN | 182 | 115.638 | 67.278 | 17.173 | 1.00 | 35.26 | B | O |
| ATOM | 5020 | N | THR | 183 | 114.961 | 66.046 | 15.419 | 1.00 | 29.87 | B | N |
| ATOM | 5021 | CA | THR | 183 | 113.706 | 65.648 | 16.025 | 1.00 | 26.79 | B | C |
| ATOM | 5022 | CB | THR | 183 | 112.612 | 65.493 | 14.962 | 1.00 | 31.40 | B | C |
| ATOM | 5023 | OG1 | THR | 183 | 112.484 | 66.721 | 14.231 | 1.00 | 27.85 | B | O |
| ATOM | 5024 | CG2 | THR | 183 | 111.285 | 65.127 | 15.610 | 1.00 | 29.08 | B | C |
| ATOM | 5025 | C | THR | 183 | 113.957 | 64.288 | 16.666 | 1.00 | 26.45 | B | C |
| ATOM | 5026 | O | THR | 183 | 114.624 | 63.428 | 16.077 | 1.00 | 24.98 | B | O |
| ATOM | 5027 | N | GLN | 184 | 113.464 | 64.102 | 17.883 | 1.00 | 44.27 | B | N |
| ATOM | 5028 | CA | GLN | 184 | 113.619 | 62.822 | 18.546 | 1.00 | 39.92 | B | C |
| ATOM | 5029 | CB | GLN | 184 | 114.254 | 62.981 | 19.920 | 1.00 | 33.99 | B | C |
| ATOM | 5030 | CG | GLN | 184 | 115.752 | 63.197 | 19.878 | 1.00 | 33.74 | B | C |
| ATOM | 5031 | CD | GLN | 184 | 116.427 | 62.766 | 21.163 | 1.00 | 33.21 | B | C |
| ATOM | 5032 | OE1 | GLN | 184 | 116.097 | 63.258 | 22.244 | 1.00 | 28.91 | B | O |
| ATOM | 5033 | NE2 | GLN | 184 | 117.375 | 61.835 | 21.053 | 1.00 | 31.51 | B | N |
| ATOM | 5034 | C | GLN | 184 | 112.227 | 62.240 | 18.670 | 1.00 | 40.30 | B | C |
| ATOM | 5035 | O | GLN | 184 | 111.249 | 62.978 | 18.834 | 1.00 | 37.69 | B | O |
| ATOM | 5036 | N | VAL | 185 | 112.131 | 60.918 | 18.574 | 1.00 | 24.17 | B | N |
| ATOM | 5037 | CA | VAL | 185 | 110.837 | 60.255 | 18.649 | 1.00 | 22.54 | B | C |

Fig. 19: A-70

```
ATOM   5038  CB   VAL  185   110.345  59.858  17.235  1.00  12.44  B  C
ATOM   5039  CG1  VAL  185   109.105  58.990  17.335  1.00  12.43  B  C
ATOM   5040  CG2  VAL  185   110.052  61.103  16.425  1.00   1.87  B  C
ATOM   5041  C    VAL  185   110.840  59.025  19.536  1.00  23.13  B  C
ATOM   5042  O    VAL  185   111.756  58.206  19.510  1.00  20.28  B  O
ATOM   5043  N    GLY  186   109.789  58.914  20.328  1.00  27.91  B  N
ATOM   5044  CA   GLY  186   109.630  57.782  21.213  1.00  29.54  B  C
ATOM   5045  C    GLY  186   108.200  57.319  21.045  1.00  27.52  B  C
ATOM   5046  O    GLY  186   107.308  58.138  20.839  1.00  32.88  B  O
ATOM   5047  N    ILE  187   107.970  56.017  21.105  1.00  20.77  B  N
ATOM   5048  CA   ILE  187   106.617  55.519  20.958  1.00  19.36  B  C
ATOM   5049  CB   ILE  187   106.460  54.729  19.642  1.00  17.70  B  C
ATOM   5050  CG2  ILE  187   105.081  54.079  19.577  1.00  15.03  B  C
ATOM   5051  CG1  ILE  187   106.639  55.676  18.454  1.00  18.22  B  C
ATOM   5052  CD1  ILE  187   106.437  55.033  17.100  1.00  19.27  B  C
ATOM   5053  C    ILE  187   106.160  54.674  22.143  1.00  18.65  B  C
ATOM   5054  O    ILE  187   106.852  53.763  22.590  1.00  17.55  B  O
ATOM   5055  N    VAL  188   104.984  55.015  22.649  1.00  23.72  B  N
ATOM   5056  CA   VAL  188   104.370  54.332  23.774  1.00  23.39  B  C
ATOM   5057  CB   VAL  188   104.053  55.333  24.911  1.00  24.28  B  C
ATOM   5058  CG1  VAL  188   103.055  54.728  25.896  1.00  19.55  B  C
ATOM   5059  CG2  VAL  188   105.320  55.715  25.625  1.00  24.70  B  C
ATOM   5060  C    VAL  188   103.055  53.702  23.303  1.00  21.93  B  C
ATOM   5061  O    VAL  188   102.274  54.341  22.591  1.00  21.34  B  O
ATOM   5062  N    GLN  189   102.815  52.453  23.686  1.00  21.90  B  N
ATOM   5063  CA   GLN  189   101.580  51.785  23.312  1.00  21.58  B  C
ATOM   5064  CB   GLN  189   101.857  50.545  22.463  1.00  19.75  B  C
ATOM   5065  CG   GLN  189   100.577  49.784  22.128  1.00  17.26  B  C
ATOM   5066  CD   GLN  189   100.819  48.495  21.377  1.00  17.97  B  C
ATOM   5067  OE1  GLN  189    99.930  47.647  21.283  1.00  19.19  B  O
ATOM   5068  NE2  GLN  189   102.022  48.340  20.831  1.00  19.01  B  N
ATOM   5069  C    GLN  189   100.820  51.386  24.572  1.00  18.57  B  C
ATOM   5070  O    GLN  189   101.423  50.980  25.567  1.00  16.93  B  O
ATOM   5071  N    TYR  190    99.494  51.500  24.524  1.00  20.56  B  N
ATOM   5072  CA   TYR  190    98.671  51.159  25.680  1.00  24.08  B  C
ATOM   5073  CB   TYR  190    98.255  52.432  26.418  1.00  22.72  B  C
ATOM   5074  CG   TYR  190    97.213  53.255  25.687  1.00  17.37  B  C
ATOM   5075  CD1  TYR  190    95.849  53.072  25.929  1.00  15.48  B  C
ATOM   5076  CE1  TYR  190    94.882  53.820  25.244  1.00  17.37  B  C
ATOM   5077  CD2  TYR  190    97.586  54.207  24.739  1.00  13.48  B  C
ATOM   5078  CE2  TYR  190    96.624  54.957  24.051  1.00  14.90  B  C
ATOM   5079  CZ   TYR  190    95.279  54.760  24.311  1.00  15.79  B  C
ATOM   5080  OH   TYR  190    94.340  55.527  23.663  1.00  14.38  B  O
ATOM   5081  C    TYR  190    97.428  50.342  25.344  1.00  25.93  B  C
ATOM   5082  O    TYR  190    97.000  50.260  24.195  1.00  26.01  B  O
ATOM   5083  N    GLY  191    96.860  49.746  26.385  1.00  24.69  B  N
ATOM   5084  CA   GLY  191    95.675  48.920  26.270  1.00  22.44  B  C
ATOM   5085  C    GLY  191    95.277  48.649  27.701  1.00  23.88  B  C
ATOM   5086  O    GLY  191    94.720  49.532  28.348  1.00  27.26  B  O
ATOM   5087  N    GLU  192    95.572  47.446  28.197  1.00  23.59  B  N
ATOM   5088  CA   GLU  192    95.284  47.084  29.584  1.00  25.60  B  C
ATOM   5089  CB   GLU  192    95.232  45.574  29.758  1.00  40.14  B  C
ATOM   5090  CG   GLU  192    94.135  44.871  29.002  1.00  40.52  B  C
ATOM   5091  CD   GLU  192    94.134  43.382  29.273  1.00  40.71  B  C
ATOM   5092  OE1  GLU  192    93.230  42.690  28.759  1.00  43.60  B  O
ATOM   5093  OE2  GLU  192    95.038  42.906  29.999  1.00  38.58  B  O
ATOM   5094  C    GLU  192    96.465  47.608  30.390  1.00  25.41  B  C
ATOM   5095  O    GLU  192    96.325  48.027  31.536  1.00  26.78  B  O
ATOM   5096  N    ASN  193    97.637  47.569  29.770  1.00  17.36  B  N
ATOM   5097  CA   ASN  193    98.862  48.041  30.395  1.00  18.57  B  C
ATOM   5098  CB   ASN  193    99.814  46.877  30.653  1.00  57.60  B  C
ATOM   5099  CG   ASN  193    99.159  45.755  31.418  1.00  60.77  B  C
ATOM   5100  OD1  ASN  193    98.225  45.115  30.933  1.00  64.88  B  O
ATOM   5101  ND2  ASN  193    99.644  45.509  32.626  1.00  62.88  B  N
ATOM   5102  C    ASN  193    99.510  49.007  29.425  1.00  16.75  B  C
ATOM   5103  O    ASN  193    98.917  49.360  28.413  1.00  17.75  B  O
ATOM   5104  N    VAL  194   100.735  49.418  29.728  1.00  23.63  B  N
ATOM   5105  CA   VAL  194   101.454  50.346  28.866  1.00  25.97  B  C
ATOM   5106  CB   VAL  194   101.516  51.750  29.490  1.00  24.85  B  C
ATOM   5107  CG1  VAL  194   102.014  52.745  28.459  1.00  25.88  B  C
ATOM   5108  CG2  VAL  194   100.153  52.147  30.032  1.00  22.12  B  C
ATOM   5109  C    VAL  194   102.887  49.864  28.661  1.00  23.74  B  C
ATOM   5110  O    VAL  194   103.535  49.384  29.597  1.00  21.86  B  O
```

Fig. 19: A-71

| | | | | | | | | | | | |
|---|---|---|---|---|---|---|---|---|---|---|---|
| ATOM | 5111 | N | THR | 195 | 103.397 | 49.986 | 27.444 | 1.00 | 25.03 | B | N |
| ATOM | 5112 | CA | THR | 195 | 104.758 | 49.552 | 27.197 | 1.00 | 26.21 | B | C |
| ATOM | 5113 | CB | THR | 195 | 104.797 | 48.182 | 26.450 | 1.00 | 38.61 | B | C |
| ATOM | 5114 | OG1 | THR | 195 | 104.420 | 48.360 | 25.081 | 1.00 | 42.62 | B | O |
| ATOM | 5115 | CG2 | THR | 195 | 103.828 | 47.195 | 27.087 | 1.00 | 40.24 | B | C |
| ATOM | 5116 | C | THR | 195 | 105.511 | 50.599 | 26.391 | 1.00 | 27.05 | B | C |
| ATOM | 5117 | O | THR | 195 | 104.944 | 51.254 | 25.514 | 1.00 | 29.64 | B | O |
| ATOM | 5118 | N | HIS | 196 | 106.791 | 50.765 | 26.716 | 1.00 | 33.64 | B | N |
| ATOM | 5119 | CA | HIS | 196 | 107.656 | 51.713 | 26.029 | 1.00 | 33.74 | B | C |
| ATOM | 5120 | CB | HIS | 196 | 108.815 | 52.119 | 26.942 | 1.00 | 34.91 | B | C |
| ATOM | 5121 | CG | HIS | 196 | 108.417 | 53.011 | 28.079 | 1.00 | 31.41 | B | C |
| ATOM | 5122 | CD2 | HIS | 196 | 108.084 | 52.725 | 29.360 | 1.00 | 32.04 | B | C |
| ATOM | 5123 | ND1 | HIS | 196 | 108.322 | 54.382 | 27.955 | 1.00 | 30.06 | B | N |
| ATOM | 5124 | CE1 | HIS | 196 | 107.949 | 54.901 | 29.111 | 1.00 | 26.78 | B | C |
| ATOM | 5125 | NE2 | HIS | 196 | 107.797 | 53.918 | 29.979 | 1.00 | 24.99 | B | N |
| ATOM | 5126 | C | HIS | 196 | 108.219 | 51.017 | 24.806 | 1.00 | 33.60 | B | C |
| ATOM | 5127 | O | HIS | 196 | 109.201 | 50.289 | 24.932 | 1.00 | 32.26 | B | O |
| ATOM | 5128 | N | GLU | 197 | 107.609 | 51.216 | 23.636 | 1.00 | 34.73 | B | N |
| ATOM | 5129 | CA | GLU | 197 | 108.123 | 50.583 | 22.417 | 1.00 | 32.06 | B | C |
| ATOM | 5130 | CB | GLU | 197 | 107.313 | 50.999 | 21.193 | 1.00 | 45.57 | B | C |
| ATOM | 5131 | CG | GLU | 197 | 105.913 | 50.386 | 21.130 | 1.00 | 45.91 | B | C |
| ATOM | 5132 | CD | GLU | 197 | 105.911 | 48.876 | 21.303 | 1.00 | 44.98 | B | C |
| ATOM | 5133 | OE1 | GLU | 197 | 106.869 | 48.228 | 20.834 | 1.00 | 43.56 | B | O |
| ATOM | 5134 | OE2 | GLU | 197 | 104.949 | 48.331 | 21.892 | 1.00 | 46.64 | B | O |
| ATOM | 5135 | C | GLU | 197 | 109.595 | 50.958 | 22.245 | 1.00 | 29.53 | B | C |
| ATOM | 5136 | O | GLU | 197 | 110.447 | 50.081 | 22.151 | 1.00 | 34.73 | B | O |
| ATOM | 5137 | N | PHE | 198 | 109.898 | 52.254 | 22.203 | 1.00 | 32.40 | B | N |
| ATOM | 5138 | CA | PHE | 198 | 111.293 | 52.691 | 22.126 | 1.00 | 34.20 | B | C |
| ATOM | 5139 | CB | PHE | 198 | 111.881 | 52.501 | 20.714 | 1.00 | 23.77 | B | C |
| ATOM | 5140 | CG | PHE | 198 | 111.239 | 53.331 | 19.636 | 1.00 | 22.02 | B | C |
| ATOM | 5141 | CD1 | PHE | 198 | 111.379 | 54.711 | 19.614 | 1.00 | 28.16 | B | C |
| ATOM | 5142 | CD2 | PHE | 198 | 110.539 | 52.715 | 18.597 | 1.00 | 16.76 | B | C |
| ATOM | 5143 | CE1 | PHE | 198 | 110.837 | 55.468 | 18.571 | 1.00 | 24.19 | B | C |
| ATOM | 5144 | CE2 | PHE | 198 | 109.990 | 53.460 | 17.548 | 1.00 | 22.67 | B | C |
| ATOM | 5145 | CZ | PHE | 198 | 110.140 | 54.838 | 17.536 | 1.00 | 26.47 | B | C |
| ATOM | 5146 | C | PHE | 198 | 111.471 | 54.120 | 22.642 | 1.00 | 36.88 | B | C |
| ATOM | 5147 | O | PHE | 198 | 110.631 | 54.973 | 22.398 | 1.00 | 38.17 | B | O |
| ATOM | 5148 | N | ASN | 199 | 112.552 | 54.366 | 23.386 | 1.00 | 21.75 | B | N |
| ATOM | 5149 | CA | ASN | 199 | 112.810 | 55.686 | 23.971 | 1.00 | 22.04 | B | C |
| ATOM | 5150 | CB | ASN | 199 | 113.924 | 55.613 | 25.007 | 1.00 | 33.57 | B | C |
| ATOM | 5151 | CG | ASN | 199 | 113.636 | 54.633 | 26.105 | 1.00 | 34.83 | B | C |
| ATOM | 5152 | OD1 | ASN | 199 | 112.614 | 54.717 | 26.785 | 1.00 | 36.36 | B | O |
| ATOM | 5153 | ND2 | ASN | 199 | 114.549 | 53.688 | 26.295 | 1.00 | 33.71 | B | N |
| ATOM | 5154 | C | ASN | 199 | 113.159 | 56.792 | 22.996 | 1.00 | 24.50 | B | C |
| ATOM | 5155 | O | ASN | 199 | 113.569 | 56.546 | 21.862 | 1.00 | 22.31 | B | O |
| ATOM | 5156 | N | LEU | 200 | 113.004 | 58.023 | 23.473 | 1.00 | 27.41 | B | N |
| ATOM | 5157 | CA | LEU | 200 | 113.286 | 59.215 | 22.685 | 1.00 | 29.37 | B | C |
| ATOM | 5158 | CB | LEU | 200 | 113.094 | 60.467 | 23.542 | 1.00 | 22.93 | B | C |
| ATOM | 5159 | CG | LEU | 200 | 111.694 | 61.088 | 23.545 | 1.00 | 20.78 | B | C |
| ATOM | 5160 | CD1 | LEU | 200 | 111.613 | 62.208 | 24.578 | 1.00 | 25.90 | B | C |
| ATOM | 5161 | CD2 | LEU | 200 | 111.375 | 61.607 | 22.140 | 1.00 | 21.95 | B | C |
| ATOM | 5162 | C | LEU | 200 | 114.685 | 59.223 | 22.104 | 1.00 | 29.77 | B | C |
| ATOM | 5163 | O | LEU | 200 | 114.899 | 59.698 | 20.992 | 1.00 | 30.79 | B | O |
| ATOM | 5164 | N | ASN | 201 | 115.635 | 58.685 | 22.856 | 1.00 | 32.06 | B | N |
| ATOM | 5165 | CA | ASN | 201 | 117.027 | 58.660 | 22.426 | 1.00 | 33.91 | B | C |
| ATOM | 5166 | CB | ASN | 201 | 117.920 | 59.105 | 23.578 | 1.00 | 34.75 | B | C |
| ATOM | 5167 | CG | ASN | 201 | 117.838 | 58.168 | 24.769 | 1.00 | 37.03 | B | C |
| ATOM | 5168 | OD1 | ASN | 201 | 118.389 | 58.443 | 25.832 | 1.00 | 37.17 | B | O |
| ATOM | 5169 | ND2 | ASN | 201 | 117.147 | 57.052 | 24.592 | 1.00 | 34.87 | B | N |
| ATOM | 5170 | C | ASN | 201 | 117.517 | 57.309 | 21.936 | 1.00 | 33.96 | B | C |
| ATOM | 5171 | O | ASN | 201 | 118.723 | 57.111 | 21.825 | 1.00 | 29.86 | B | O |
| ATOM | 5172 | N | LYS | 202 | 116.603 | 56.382 | 21.653 | 1.00 | 35.80 | B | N |
| ATOM | 5173 | CA | LYS | 202 | 116.990 | 55.051 | 21.183 | 1.00 | 35.92 | B | C |
| ATOM | 5174 | CB | LYS | 202 | 115.786 | 54.107 | 21.160 | 1.00 | 34.30 | B | C |
| ATOM | 5175 | CG | LYS | 202 | 116.107 | 52.652 | 20.788 | 1.00 | 35.84 | B | C |
| ATOM | 5176 | CD | LYS | 202 | 116.841 | 51.929 | 21.898 | 1.00 | 37.75 | B | C |
| ATOM | 5177 | CE | LYS | 202 | 116.185 | 52.179 | 23.273 | 1.00 | 43.50 | B | C |
| ATOM | 5178 | NZ | LYS | 202 | 114.729 | 51.801 | 23.388 | 1.00 | 42.52 | B | N |
| ATOM | 5179 | C | LYS | 202 | 117.617 | 55.071 | 19.800 | 1.00 | 34.79 | B | C |
| ATOM | 5180 | O | LYS | 202 | 118.667 | 54.472 | 19.589 | 1.00 | 32.07 | B | O |
| ATOM | 5181 | N | TYR | 203 | 116.977 | 55.747 | 18.852 | 1.00 | 23.81 | B | N |
| ATOM | 5182 | CA | TYR | 203 | 117.509 | 55.815 | 17.491 | 1.00 | 23.49 | B | C |
| ATOM | 5183 | CB | TYR | 203 | 116.466 | 55.300 | 16.499 | 1.00 | 32.41 | B | C |

Fig. 19: A-72

| | | | | | | | | | | | |
|---|---|---|---|---|---|---|---|---|---|---|---|
| ATOM | 5184 | CG | TYR | 203 | 115.907 | 53.951 | 16.886 | 1.00 | 31.08 | B | C |
| ATOM | 5185 | CD1 | TYR | 203 | 114.665 | 53.844 | 17.509 | 1.00 | 31.69 | B | C |
| ATOM | 5186 | CE1 | TYR | 203 | 114.179 | 52.613 | 17.930 | 1.00 | 28.16 | B | C |
| ATOM | 5187 | CD2 | TYR | 203 | 116.649 | 52.784 | 16.689 | 1.00 | 33.97 | B | C |
| ATOM | 5188 | CE2 | TYR | 203 | 116.173 | 51.550 | 17.109 | 1.00 | 36.72 | B | C |
| ATOM | 5189 | CZ | TYR | 203 | 114.940 | 51.474 | 17.730 | 1.00 | 36.34 | B | C |
| ATOM | 5190 | OH | TYR | 203 | 114.466 | 50.262 | 18.169 | 1.00 | 41.34 | B | O |
| ATOM | 5191 | C | TYR | 203 | 117.957 | 57.230 | 17.114 | 1.00 | 24.13 | B | C |
| ATOM | 5192 | O | TYR | 203 | 117.268 | 58.211 | 17.387 | 1.00 | 22.30 | B | O |
| ATOM | 5193 | N | SER | 204 | 119.122 | 57.323 | 16.484 | 1.00 | 32.64 | B | N |
| ATOM | 5194 | CA | SER | 204 | 119.693 | 58.608 | 16.089 | 1.00 | 34.49 | B | C |
| ATOM | 5195 | CB | SER | 204 | 121.199 | 58.588 | 16.320 | 1.00 | 50.27 | B | C |
| ATOM | 5196 | OG | SER | 204 | 121.780 | 57.499 | 15.621 | 1.00 | 52.10 | B | O |
| ATOM | 5197 | C | SER | 204 | 119.432 | 58.924 | 14.632 | 1.00 | 37.07 | B | C |
| ATOM | 5198 | O | SER | 204 | 119.922 | 59.919 | 14.118 | 1.00 | 37.58 | B | O |
| ATOM | 5199 | N | SER | 205 | 118.657 | 58.082 | 13.966 | 1.00 | 56.25 | B | N |
| ATOM | 5200 | CA | SER | 205 | 118.379 | 58.289 | 12.558 | 1.00 | 55.91 | B | C |
| ATOM | 5201 | CB | SER | 205 | 119.256 | 57.357 | 11.734 | 1.00 | 30.45 | B | C |
| ATOM | 5202 | OG | SER | 205 | 118.818 | 57.302 | 10.393 | 1.00 | 35.94 | B | O |
| ATOM | 5203 | C | SER | 205 | 116.918 | 58.067 | 12.195 | 1.00 | 54.04 | B | C |
| ATOM | 5204 | O | SER | 205 | 116.208 | 57.320 | 12.866 | 1.00 | 50.30 | B | O |
| ATOM | 5205 | N | THR | 206 | 116.477 | 58.718 | 11.122 | 1.00 | 22.26 | B | N |
| ATOM | 5206 | CA | THR | 206 | 115.105 | 58.589 | 10.661 | 1.00 | 23.61 | B | C |
| ATOM | 5207 | CB | THR | 206 | 114.799 | 59.611 | 9.560 | 1.00 | 36.04 | B | C |
| ATOM | 5208 | OG1 | THR | 206 | 114.968 | 60.935 | 10.086 | 1.00 | 34.85 | B | O |
| ATOM | 5209 | CG2 | THR | 206 | 113.364 | 59.438 | 9.047 | 1.00 | 34.41 | B | C |
| ATOM | 5210 | C | THR | 206 | 114.780 | 57.188 | 10.144 | 1.00 | 24.20 | B | C |
| ATOM | 5211 | O | THR | 206 | 113.676 | 56.683 | 10.363 | 1.00 | 26.99 | B | O |
| ATOM | 5212 | N | GLU | 207 | 115.719 | 56.554 | 9.447 | 1.00 | 31.43 | B | N |
| ATOM | 5213 | CA | GLU | 207 | 115.444 | 55.210 | 8.964 | 1.00 | 30.59 | B | C |
| ATOM | 5214 | CB | GLU | 207 | 116.448 | 54.791 | 7.893 | 1.00 | 74.76 | B | C |
| ATOM | 5215 | CG | GLU | 207 | 117.897 | 54.985 | 8.248 | 1.00 | 75.48 | B | C |
| ATOM | 5216 | CD | GLU | 207 | 118.817 | 54.402 | 7.189 | 1.00 | 76.89 | B | C |
| ATOM | 5217 | OE1 | GLU | 207 | 118.595 | 54.668 | 5.982 | 1.00 | 76.12 | B | O |
| ATOM | 5218 | OE2 | GLU | 207 | 119.765 | 53.679 | 7.565 | 1.00 | 75.79 | B | O |
| ATOM | 5219 | C | GLU | 207 | 115.462 | 54.237 | 10.141 | 1.00 | 31.09 | B | C |
| ATOM | 5220 | O | GLU | 207 | 114.647 | 53.315 | 10.194 | 1.00 | 31.04 | B | O |
| ATOM | 5221 | N | GLU | 208 | 116.373 | 54.449 | 11.093 | 1.00 | 40.73 | B | N |
| ATOM | 5222 | CA | GLU | 208 | 116.441 | 53.584 | 12.267 | 1.00 | 42.46 | B | C |
| ATOM | 5223 | CB | GLU | 208 | 117.542 | 54.038 | 13.230 | 1.00 | 57.02 | B | C |
| ATOM | 5224 | CG | GLU | 208 | 118.951 | 53.899 | 12.682 | 1.00 | 54.49 | B | C |
| ATOM | 5225 | CD | GLU | 208 | 120.022 | 54.254 | 13.703 | 1.00 | 54.01 | B | C |
| ATOM | 5226 | OE1 | GLU | 208 | 121.217 | 54.253 | 13.333 | 1.00 | 59.78 | B | O |
| ATOM | 5227 | OE2 | GLU | 208 | 119.669 | 54.533 | 14.873 | 1.00 | 52.73 | B | O |
| ATOM | 5228 | C | GLU | 208 | 115.100 | 53.611 | 12.991 | 1.00 | 43.16 | B | C |
| ATOM | 5229 | O | GLU | 208 | 114.637 | 52.584 | 13.489 | 1.00 | 44.16 | B | O |
| ATOM | 5230 | N | VAL | 209 | 114.478 | 54.787 | 13.046 | 1.00 | 30.06 | B | N |
| ATOM | 5231 | CA | VAL | 209 | 113.190 | 54.922 | 13.709 | 1.00 | 28.98 | B | C |
| ATOM | 5232 | CB | VAL | 209 | 112.879 | 56.399 | 14.058 | 1.00 | 17.77 | B | C |
| ATOM | 5233 | CG1 | VAL | 209 | 111.379 | 56.612 | 14.232 | 1.00 | 18.10 | B | C |
| ATOM | 5234 | CG2 | VAL | 209 | 113.575 | 56.762 | 15.349 | 1.00 | 18.79 | B | C |
| ATOM | 5235 | C | VAL | 209 | 112.098 | 54.359 | 12.820 | 1.00 | 27.00 | B | C |
| ATOM | 5236 | O | VAL | 209 | 111.198 | 53.660 | 13.296 | 1.00 | 25.96 | B | O |
| ATOM | 5237 | N | LEU | 210 | 112.187 | 54.655 | 11.529 | 1.00 | 33.19 | B | N |
| ATOM | 5238 | CA | LEU | 210 | 111.207 | 54.164 | 10.570 | 1.00 | 33.52 | B | C |
| ATOM | 5239 | CB | LEU | 210 | 111.557 | 54.643 | 9.168 | 1.00 | 15.67 | B | C |
| ATOM | 5240 | CG | LEU | 210 | 110.629 | 55.672 | 8.535 | 1.00 | 15.91 | B | C |
| ATOM | 5241 | CD1 | LEU | 210 | 111.182 | 55.981 | 7.171 | 1.00 | 12.46 | B | C |
| ATOM | 5242 | CD2 | LEU | 210 | 109.191 | 55.157 | 8.437 | 1.00 | 9.36 | B | C |
| ATOM | 5243 | C | LEU | 210 | 111.152 | 52.639 | 10.571 | 1.00 | 31.78 | B | C |
| ATOM | 5244 | O | LEU | 210 | 110.090 | 52.042 | 10.382 | 1.00 | 32.55 | B | O |
| ATOM | 5245 | N | VAL | 211 | 112.307 | 52.017 | 10.779 | 1.00 | 24.37 | B | N |
| ATOM | 5246 | CA | VAL | 211 | 112.404 | 50.569 | 10.809 | 1.00 | 24.13 | B | C |
| ATOM | 5247 | CB | VAL | 211 | 113.852 | 50.123 | 10.575 | 1.00 | 20.01 | B | C |
| ATOM | 5248 | CG1 | VAL | 211 | 114.002 | 48.647 | 10.897 | 1.00 | 22.19 | B | C |
| ATOM | 5249 | CG2 | VAL | 211 | 114.239 | 50.405 | 9.118 | 1.00 | 20.62 | B | C |
| ATOM | 5250 | C | VAL | 211 | 111.913 | 49.997 | 12.129 | 1.00 | 23.38 | B | C |
| ATOM | 5251 | O | VAL | 211 | 111.260 | 48.958 | 12.164 | 1.00 | 24.06 | B | O |
| ATOM | 5252 | N | ALA | 212 | 112.230 | 50.674 | 13.221 | 1.00 | 40.83 | B | N |
| ATOM | 5253 | CA | ALA | 212 | 111.803 | 50.203 | 14.526 | 1.00 | 39.81 | B | C |
| ATOM | 5254 | CB | ALA | 212 | 112.489 | 51.000 | 15.612 | 1.00 | 28.52 | B | C |
| ATOM | 5255 | C | ALA | 212 | 110.295 | 50.339 | 14.650 | 1.00 | 37.62 | B | C |
| ATOM | 5256 | O | ALA | 212 | 109.626 | 49.493 | 15.256 | 1.00 | 37.56 | B | O |

Fig. 19: A-73

| ATOM | 5257 | N | ALA | 213 | 109.759 | 51.408 | 14.069 | 1.00 | 31.97 | B | N |
| --- | --- | --- | --- | --- | --- | --- | --- | --- | --- | --- | --- |
| ATOM | 5258 | CA | ALA | 213 | 108.324 | 51.658 | 14.122 | 1.00 | 33.14 | B | C |
| ATOM | 5259 | CB | ALA | 213 | 107.999 | 52.998 | 13.459 | 1.00 | 19.99 | B | C |
| ATOM | 5260 | C | ALA | 213 | 107.530 | 50.535 | 13.458 | 1.00 | 31.94 | B | C |
| ATOM | 5261 | O | ALA | 213 | 106.556 | 50.029 | 14.025 | 1.00 | 29.57 | B | O |
| ATOM | 5262 | N | ASN | 214 | 107.954 | 50.142 | 12.258 | 1.00 | 35.89 | B | N |
| ATOM | 5263 | CA | ASN | 214 | 107.264 | 49.091 | 11.524 | 1.00 | 39.76 | B | C |
| ATOM | 5264 | CB | ASN | 214 | 107.804 | 48.970 | 10.100 | 1.00 | 79.46 | B | C |
| ATOM | 5265 | CG | ASN | 214 | 107.278 | 50.049 | 9.190 | 1.00 | 81.19 | B | C |
| ATOM | 5266 | OD1 | ASN | 214 | 107.668 | 51.210 | 9.296 | 1.00 | 83.12 | B | O |
| ATOM | 5267 | ND2 | ASN | 214 | 106.379 | 49.676 | 8.289 | 1.00 | 81.61 | B | N |
| ATOM | 5268 | C | ASN | 214 | 107.348 | 47.738 | 12.207 | 1.00 | 42.15 | B | C |
| ATOM | 5269 | O | ASN | 214 | 106.583 | 46.829 | 11.891 | 1.00 | 42.87 | B | O |
| ATOM | 5270 | N | LYS | 215 | 108.271 | 47.596 | 13.148 | 1.00 | 30.37 | B | N |
| ATOM | 5271 | CA | LYS | 215 | 108.418 | 46.326 | 13.856 | 1.00 | 30.81 | B | C |
| ATOM | 5272 | CB | LYS | 215 | 109.852 | 46.059 | 14.209 | 1.00 | 46.54 | B | C |
| ATOM | 5273 | CG | LYS | 215 | 110.791 | 45.922 | 12.978 | 1.00 | 54.12 | B | C |
| ATOM | 5274 | CD | LYS | 215 | 112.062 | 45.124 | 13.256 | 1.00 | 57.66 | B | C |
| ATOM | 5275 | CE | LYS | 215 | 112.950 | 45.778 | 14.311 | 1.00 | 61.12 | B | C |
| ATOM | 5276 | NZ | LYS | 215 | 114.249 | 45.057 | 14.483 | 1.00 | 62.11 | B | N |
| ATOM | 5277 | C | LYS | 215 | 107.560 | 46.274 | 15.113 | 1.00 | 28.94 | B | C |
| ATOM | 5278 | O | LYS | 215 | 107.568 | 45.277 | 15.832 | 1.00 | 30.16 | B | O |
| ATOM | 5279 | N | ILE | 216 | 106.809 | 47.341 | 15.377 | 1.00 | 44.32 | B | N |
| ATOM | 5280 | CA | ILE | 216 | 105.945 | 47.362 | 16.553 | 1.00 | 41.14 | B | C |
| ATOM | 5281 | CB | ILE | 216 | 105.443 | 48.776 | 16.874 | 1.00 | 15.33 | B | C |
| ATOM | 5282 | CG2 | ILE | 216 | 104.492 | 48.730 | 18.038 | 1.00 | 12.11 | B | C |
| ATOM | 5283 | CG1 | ILE | 216 | 106.616 | 49.674 | 17.243 | 1.00 | 12.01 | B | C |
| ATOM | 5284 | CD1 | ILE | 216 | 106.191 | 51.073 | 17.602 | 1.00 | 10.70 | B | C |
| ATOM | 5285 | C | ILE | 216 | 104.740 | 46.447 | 16.369 | 1.00 | 39.58 | B | C |
| ATOM | 5286 | O | ILE | 216 | 104.035 | 46.498 | 15.361 | 1.00 | 40.28 | B | O |
| ATOM | 5287 | N | VAL | 217 | 104.524 | 45.611 | 17.372 | 1.00 | 36.13 | B | N |
| ATOM | 5288 | CA | VAL | 217 | 103.436 | 44.647 | 17.392 | 1.00 | 37.90 | B | C |
| ATOM | 5289 | CB | VAL | 217 | 103.949 | 43.284 | 17.887 | 1.00 | 59.95 | B | C |
| ATOM | 5290 | CG1 | VAL | 217 | 102.793 | 42.367 | 18.217 | 1.00 | 59.95 | B | C |
| ATOM | 5291 | CG2 | VAL | 217 | 104.837 | 42.666 | 16.829 | 1.00 | 59.95 | B | C |
| ATOM | 5292 | C | VAL | 217 | 102.316 | 45.111 | 18.311 | 1.00 | 39.06 | B | C |
| ATOM | 5293 | O | VAL | 217 | 102.565 | 45.725 | 19.352 | 1.00 | 38.52 | B | O |
| ATOM | 5294 | N | GLN | 218 | 101.084 | 44.809 | 17.914 | 1.00 | 32.14 | B | N |
| ATOM | 5295 | CA | GLN | 218 | 99.907 | 45.181 | 18.687 | 1.00 | 32.80 | B | C |
| ATOM | 5296 | CB | GLN | 218 | 98.646 | 44.976 | 17.850 | 1.00 | 28.44 | B | C |
| ATOM | 5297 | CG | GLN | 218 | 97.378 | 45.433 | 18.528 | 1.00 | 28.44 | B | C |
| ATOM | 5298 | CD | GLN | 218 | 96.153 | 45.273 | 17.644 | 1.00 | 28.44 | B | C |
| ATOM | 5299 | OE1 | GLN | 218 | 95.096 | 45.843 | 17.928 | 1.00 | 28.44 | B | O |
| ATOM | 5300 | NE2 | GLN | 218 | 96.283 | 44.490 | 16.571 | 1.00 | 28.44 | B | N |
| ATOM | 5301 | C | GLN | 218 | 99.856 | 44.288 | 19.913 | 1.00 | 32.25 | B | C |
| ATOM | 5302 | O | GLN | 218 | 99.948 | 43.079 | 19.792 | 1.00 | 36.00 | B | O |
| ATOM | 5303 | N | ARG | 219 | 99.709 | 44.883 | 21.091 | 1.00 | 14.17 | B | N |
| ATOM | 5304 | CA | ARG | 219 | 99.664 | 44.114 | 22.330 | 1.00 | 13.82 | B | C |
| ATOM | 5305 | CB | ARG | 219 | 100.490 | 44.828 | 23.394 | 1.00 | 43.11 | B | C |
| ATOM | 5306 | CG | ARG | 219 | 101.627 | 45.640 | 22.823 | 1.00 | 43.11 | B | C |
| ATOM | 5307 | CD | ARG | 219 | 102.594 | 46.039 | 23.901 | 1.00 | 43.11 | B | C |
| ATOM | 5308 | NE | ARG | 219 | 103.597 | 45.007 | 24.124 | 1.00 | 43.11 | B | N |
| ATOM | 5309 | CZ | ARG | 219 | 104.694 | 44.867 | 23.384 | 1.00 | 43.11 | B | C |
| ATOM | 5310 | NH1 | ARG | 219 | 104.921 | 45.705 | 22.369 | 1.00 | 43.11 | B | N |
| ATOM | 5311 | NH2 | ARG | 219 | 105.566 | 43.900 | 23.661 | 1.00 | 43.11 | B | N |
| ATOM | 5312 | C | ARG | 219 | 98.221 | 43.910 | 22.821 | 1.00 | 15.03 | B | C |
| ATOM | 5313 | O | ARG | 219 | 97.976 | 43.309 | 23.871 | 1.00 | 15.04 | B | O |
| ATOM | 5314 | N | GLY | 220 | 97.269 | 44.423 | 22.048 | 1.00 | 30.91 | B | N |
| ATOM | 5315 | CA | GLY | 220 | 95.868 | 44.283 | 22.402 | 1.00 | 30.52 | B | C |
| ATOM | 5316 | C | GLY | 220 | 95.495 | 44.884 | 23.742 | 1.00 | 30.19 | B | C |
| ATOM | 5317 | O | GLY | 220 | 96.246 | 45.674 | 24.327 | 1.00 | 28.53 | B | O |
| ATOM | 5318 | N | GLY | 221 | 94.316 | 44.511 | 24.222 | 1.00 | 22.15 | B | N |
| ATOM | 5319 | CA | GLY | 221 | 93.852 | 45.009 | 25.500 | 1.00 | 20.72 | B | C |
| ATOM | 5320 | C | GLY | 221 | 92.348 | 44.902 | 25.652 | 1.00 | 21.14 | B | C |
| ATOM | 5321 | O | GLY | 221 | 91.598 | 45.328 | 24.776 | 1.00 | 17.94 | B | O |
| ATOM | 5322 | N | ARG | 222 | 91.897 | 44.327 | 26.760 | 1.00 | 28.36 | B | N |
| ATOM | 5323 | CA | ARG | 222 | 90.467 | 44.199 | 27.011 | 1.00 | 29.07 | B | C |
| ATOM | 5324 | CB | ARG | 222 | 90.204 | 43.114 | 28.053 | 1.00 | 26.86 | B | C |
| ATOM | 5325 | CG | ARG | 222 | 90.365 | 41.713 | 27.491 | 1.00 | 26.86 | B | C |
| ATOM | 5326 | CD | ARG | 222 | 90.427 | 40.663 | 28.578 | 1.00 | 26.86 | B | C |
| ATOM | 5327 | NE | ARG | 222 | 91.679 | 40.734 | 29.316 | 1.00 | 26.86 | B | N |
| ATOM | 5328 | CZ | ARG | 222 | 92.021 | 39.885 | 30.274 | 1.00 | 26.86 | B | C |
| ATOM | 5329 | NH1 | ARG | 222 | 91.201 | 38.895 | 30.612 | 1.00 | 26.86 | B | N |

Fig. 19: A-74

| | | | | | | | | | | |
|---|---|---|---|---|---|---|---|---|---|---|
| ATOM | 5330 | NH2 | ARG | 222 | 93.184 | 40.027 | 30.893 | 1.00 | 26.86 | B N |
| ATOM | 5331 | C | ARG | 222 | 89.899 | 45.529 | 27.482 | 1.00 | 29.12 | B C |
| ATOM | 5332 | O | ARG | 222 | 88.686 | 45.686 | 27.599 | 1.00 | 29.89 | B O |
| ATOM | 5333 | N | GLN | 223 | 90.792 | 46.477 | 27.756 | 1.00 | 34.74 | B N |
| ATOM | 5334 | CA | GLN | 223 | 90.423 | 47.826 | 28.182 | 1.00 | 33.03 | B C |
| ATOM | 5335 | CB | GLN | 223 | 90.700 | 48.050 | 29.677 | 1.00 | 36.16 | B C |
| ATOM | 5336 | CG | GLN | 223 | 89.723 | 47.394 | 30.641 | 1.00 | 37.60 | B C |
| ATOM | 5337 | CD | GLN | 223 | 90.065 | 45.957 | 30.915 | 1.00 | 38.01 | B C |
| ATOM | 5338 | OE1 | GLN | 223 | 91.209 | 45.635 | 31.230 | 1.00 | 38.41 | B O |
| ATOM | 5339 | NE2 | GLN | 223 | 89.075 | 45.080 | 30.811 | 1.00 | 38.45 | B N |
| ATOM | 5340 | C | GLN | 223 | 91.221 | 48.849 | 27.372 | 1.00 | 33.77 | B C |
| ATOM | 5341 | O | GLN | 223 | 92.122 | 48.487 | 26.619 | 1.00 | 33.25 | B O |
| ATOM | 5342 | N | THR | 224 | 90.893 | 50.126 | 27.535 | 1.00 | 56.95 | B N |
| ATOM | 5343 | CA | THR | 224 | 91.572 | 51.197 | 26.820 | 1.00 | 54.83 | B C |
| ATOM | 5344 | CB | THR | 224 | 90.628 | 51.834 | 25.793 | 1.00 | 7.14 | B C |
| ATOM | 5345 | OG1 | THR | 224 | 90.118 | 50.811 | 24.930 | 1.00 | 7.13 | B O |
| ATOM | 5346 | CG2 | THR | 224 | 91.357 | 52.895 | 24.965 | 1.00 | 4.73 | B C |
| ATOM | 5347 | C | THR | 224 | 92.002 | 52.252 | 27.829 | 1.00 | 51.84 | B C |
| ATOM | 5348 | O | THR | 224 | 91.290 | 53.221 | 28.067 | 1.00 | 48.33 | B O |
| ATOM | 5349 | N | MET | 225 | 93.175 | 52.061 | 28.419 | 1.00 | 27.08 | B N |
| ATOM | 5350 | CA | MET | 225 | 93.679 | 52.980 | 29.426 | 1.00 | 27.97 | B C |
| ATOM | 5351 | CB | MET | 225 | 94.712 | 52.269 | 30.301 | 1.00 | 32.79 | B C |
| ATOM | 5352 | CG | MET | 225 | 94.280 | 50.904 | 30.804 | 1.00 | 30.22 | B C |
| ATOM | 5353 | SD | MET | 225 | 92.971 | 50.963 | 31.995 | 1.00 | 37.96 | B S |
| ATOM | 5354 | CE | MET | 225 | 93.153 | 49.343 | 32.760 | 1.00 | 34.54 | B C |
| ATOM | 5355 | C | MET | 225 | 94.304 | 54.237 | 28.846 | 1.00 | 29.00 | B C |
| ATOM | 5356 | O | MET | 225 | 95.442 | 54.561 | 29.180 | 1.00 | 30.46 | B O |
| ATOM | 5357 | N | THR | 226 | 93.571 | 54.953 | 27.997 | 1.00 | 32.08 | B N |
| ATOM | 5358 | CA | THR | 226 | 94.102 | 56.178 | 27.393 | 1.00 | 31.55 | B C |
| ATOM | 5359 | CB | THR | 226 | 93.013 | 56.963 | 26.655 | 1.00 | 28.80 | B C |
| ATOM | 5360 | OG1 | THR | 226 | 92.395 | 56.132 | 25.665 | 1.00 | 30.82 | B O |
| ATOM | 5361 | CG2 | THR | 226 | 93.620 | 58.170 | 25.976 | 1.00 | 26.52 | B C |
| ATOM | 5362 | C | THR | 226 | 94.735 | 57.104 | 28.438 | 1.00 | 30.15 | B C |
| ATOM | 5363 | O | THR | 226 | 95.804 | 57.672 | 28.216 | 1.00 | 24.84 | B O |
| ATOM | 5364 | N | ALA | 227 | 94.075 | 57.249 | 29.581 | 1.00 | 17.95 | B N |
| ATOM | 5365 | CA | ALA | 227 | 94.594 | 58.094 | 30.645 | 1.00 | 16.89 | B C |
| ATOM | 5366 | CB | ALA | 227 | 93.655 | 58.069 | 31.829 | 1.00 | 18.36 | B C |
| ATOM | 5367 | C | ALA | 227 | 95.975 | 57.633 | 31.076 | 1.00 | 17.55 | B C |
| ATOM | 5368 | O | ALA | 227 | 96.898 | 58.439 | 31.199 | 1.00 | 18.35 | B O |
| ATOM | 5369 | N | LEU | 228 | 96.111 | 56.331 | 31.307 | 1.00 | 19.16 | B N |
| ATOM | 5370 | CA | LEU | 228 | 97.384 | 55.752 | 31.728 | 1.00 | 17.60 | B C |
| ATOM | 5371 | CB | LEU | 228 | 97.206 | 54.252 | 32.017 | 1.00 | 6.84 | B C |
| ATOM | 5372 | CG | LEU | 228 | 98.453 | 53.498 | 32.483 | 1.00 | 14.73 | B C |
| ATOM | 5373 | CD1 | LEU | 228 | 99.020 | 54.157 | 33.734 | 1.00 | 12.32 | B C |
| ATOM | 5374 | CD2 | LEU | 228 | 98.097 | 52.064 | 32.732 | 1.00 | 11.78 | B C |
| ATOM | 5375 | C | LEU | 228 | 98.463 | 55.955 | 30.662 | 1.00 | 16.78 | B C |
| ATOM | 5376 | O | LEU | 228 | 99.605 | 56.321 | 30.971 | 1.00 | 19.76 | B O |
| ATOM | 5377 | N | GLY | 229 | 98.094 | 55.713 | 29.408 | 1.00 | 21.79 | B N |
| ATOM | 5378 | CA | GLY | 229 | 99.033 | 55.877 | 28.318 | 1.00 | 24.15 | B C |
| ATOM | 5379 | C | GLY | 229 | 99.620 | 57.267 | 28.293 | 1.00 | 26.71 | B C |
| ATOM | 5380 | O | GLY | 229 | 100.843 | 57.422 | 28.296 | 1.00 | 27.30 | B O |
| ATOM | 5381 | N | ILE | 230 | 98.756 | 58.281 | 28.280 | 1.00 | 20.54 | B N |
| ATOM | 5382 | CA | ILE | 230 | 99.216 | 59.666 | 28.259 | 1.00 | 21.87 | B C |
| ATOM | 5383 | CB | ILE | 230 | 98.039 | 60.677 | 28.160 | 1.00 | 18.79 | B C |
| ATOM | 5384 | CG2 | ILE | 230 | 98.595 | 62.090 | 28.034 | 1.00 | 18.79 | B C |
| ATOM | 5385 | CG1 | ILE | 230 | 97.174 | 60.370 | 26.933 | 1.00 | 18.79 | B C |
| ATOM | 5386 | CD1 | ILE | 230 | 95.945 | 61.225 | 26.807 | 1.00 | 18.79 | B C |
| ATOM | 5387 | C | ILE | 230 | 100.042 | 60.007 | 29.505 | 1.00 | 22.13 | B C |
| ATOM | 5388 | O | ILE | 230 | 101.101 | 60.634 | 29.402 | 1.00 | 20.06 | B O |
| ATOM | 5389 | N | ASP | 231 | 99.566 | 59.595 | 30.677 | 1.00 | 30.92 | B N |
| ATOM | 5390 | CA | ASP | 231 | 100.286 | 59.876 | 31.916 | 1.00 | 29.32 | B C |
| ATOM | 5391 | CB | ASP | 231 | 99.494 | 59.354 | 33.116 | 1.00 | 27.91 | B C |
| ATOM | 5392 | CG | ASP | 231 | 99.993 | 59.917 | 34.442 | 1.00 | 34.91 | B C |
| ATOM | 5393 | OD1 | ASP | 231 | 99.939 | 61.155 | 34.644 | 1.00 | 33.67 | B O |
| ATOM | 5394 | OD2 | ASP | 231 | 100.432 | 59.112 | 35.288 | 1.00 | 38.45 | B O |
| ATOM | 5395 | C | ASP | 231 | 101.676 | 59.231 | 31.884 | 1.00 | 30.30 | B C |
| ATOM | 5396 | O | ASP | 231 | 102.669 | 59.838 | 32.318 | 1.00 | 27.52 | B O |
| ATOM | 5397 | N | THR | 232 | 101.741 | 58.007 | 31.361 | 1.00 | 43.37 | B N |
| ATOM | 5398 | CA | THR | 232 | 102.998 | 57.276 | 31.260 | 1.00 | 42.16 | B C |
| ATOM | 5399 | CB | THR | 232 | 102.768 | 55.830 | 30.801 | 1.00 | 59.43 | B C |
| ATOM | 5400 | OG1 | THR | 232 | 101.963 | 55.148 | 31.771 | 1.00 | 57.94 | B O |
| ATOM | 5401 | CG2 | THR | 232 | 104.097 | 55.098 | 30.645 | 1.00 | 52.97 | B C |
| ATOM | 5402 | C | THR | 232 | 103.939 | 57.959 | 30.274 | 1.00 | 42.79 | B C |

Fig. 19: A-75

| ATOM | 5403 | O | THR | 232 | 105.153 | 58.050 | 30.509 | 1.00 | 42.96 | B | O |
|---|---|---|---|---|---|---|---|---|---|---|---|
| ATOM | 5404 | N | ALA | 233 | 103.383 | 58.427 | 29.161 | 1.00 | 22.02 | B | N |
| ATOM | 5405 | CA | ALA | 233 | 104.202 | 59.116 | 28.179 | 1.00 | 24.67 | B | C |
| ATOM | 5406 | CB | ALA | 233 | 103.373 | 59.472 | 26.961 | 1.00 | 49.88 | B | C |
| ATOM | 5407 | C | ALA | 233 | 104.752 | 60.385 | 28.836 | 1.00 | 26.98 | B | C |
| ATOM | 5408 | O | ALA | 233 | 105.862 | 60.834 | 28.532 | 1.00 | 28.89 | B | O |
| ATOM | 5409 | N | ARG | 234 | 103.967 | 60.947 | 29.751 | 1.00 | 50.27 | B | N |
| ATOM | 5410 | CA | ARG | 234 | 104.361 | 62.165 | 30.431 | 1.00 | 53.37 | B | C |
| ATOM | 5411 | CB | ARG | 234 | 103.146 | 62.842 | 31.077 | 1.00 | 50.29 | B | C |
| ATOM | 5412 | CG | ARG | 234 | 103.377 | 64.312 | 31.390 | 1.00 | 50.29 | B | C |
| ATOM | 5413 | CD | ARG | 234 | 102.536 | 64.816 | 32.561 | 1.00 | 50.29 | B | C |
| ATOM | 5414 | NE | ARG | 234 | 103.103 | 64.432 | 33.852 | 1.00 | 50.29 | B | N |
| ATOM | 5415 | CZ | ARG | 234 | 102.668 | 63.418 | 34.592 | 1.00 | 50.29 | B | C |
| ATOM | 5416 | NH1 | ARG | 234 | 101.650 | 62.682 | 34.172 | 1.00 | 50.29 | B | N |
| ATOM | 5417 | NH2 | ARG | 234 | 103.258 | 63.135 | 35.744 | 1.00 | 50.29 | B | N |
| ATOM | 5418 | C | ARG | 234 | 105.406 | 61.904 | 31.498 | 1.00 | 55.50 | B | C |
| ATOM | 5419 | O | ARG | 234 | 106.556 | 62.316 | 31.368 | 1.00 | 55.55 | B | O |
| ATOM | 5420 | N | LYS | 235 | 105.009 | 61.196 | 32.547 | 1.00 | 27.28 | B | N |
| ATOM | 5421 | CA | LYS | 235 | 105.914 | 60.939 | 33.660 | 1.00 | 27.23 | B | C |
| ATOM | 5422 | CB | LYS | 235 | 105.129 | 60.356 | 34.848 | 1.00 | 39.45 | B | C |
| ATOM | 5423 | CG | LYS | 235 | 104.888 | 58.857 | 34.831 | 1.00 | 40.60 | B | C |
| ATOM | 5424 | CD | LYS | 235 | 104.027 | 58.450 | 36.030 | 1.00 | 40.42 | B | C |
| ATOM | 5425 | CE | LYS | 235 | 104.119 | 56.955 | 36.346 | 1.00 | 41.22 | B | C |
| ATOM | 5426 | NZ | LYS | 235 | 103.715 | 56.073 | 35.205 | 1.00 | 41.98 | B | N |
| ATOM | 5427 | C | LYS | 235 | 107.149 | 60.078 | 33.375 | 1.00 | 27.37 | B | C |
| ATOM | 5428 | O | LYS | 235 | 108.112 | 60.118 | 34.130 | 1.00 | 27.71 | B | O |
| ATOM | 5429 | N | GLU | 236 | 107.133 | 59.313 | 32.290 | 1.00 | 28.33 | B | N |
| ATOM | 5430 | CA | GLU | 236 | 108.264 | 58.454 | 31.964 | 1.00 | 29.95 | B | C |
| ATOM | 5431 | CB | GLU | 236 | 107.803 | 56.992 | 31.884 | 1.00 | 47.54 | B | C |
| ATOM | 5432 | CG | GLU | 236 | 107.861 | 56.249 | 33.216 | 1.00 | 50.31 | B | C |
| ATOM | 5433 | CD | GLU | 236 | 107.031 | 54.965 | 33.245 | 1.00 | 52.79 | B | C |
| ATOM | 5434 | OE1 | GLU | 236 | 107.194 | 54.118 | 32.342 | 1.00 | 52.88 | B | O |
| ATOM | 5435 | OE2 | GLU | 236 | 106.219 | 54.797 | 34.184 | 1.00 | 52.63 | B | O |
| ATOM | 5436 | C | GLU | 236 | 108.966 | 58.840 | 30.670 | 1.00 | 28.50 | B | C |
| ATOM | 5437 | O | GLU | 236 | 110.092 | 59.336 | 30.684 | 1.00 | 29.93 | B | O |
| ATOM | 5438 | N | ALA | 237 | 108.287 | 58.617 | 29.552 | 1.00 | 22.73 | B | N |
| ATOM | 5439 | CA | ALA | 237 | 108.860 | 58.901 | 28.248 | 1.00 | 20.20 | B | C |
| ATOM | 5440 | CB | ALA | 237 | 107.783 | 58.831 | 27.180 | 1.00 | 41.37 | B | C |
| ATOM | 5441 | C | ALA | 237 | 109.562 | 60.233 | 28.187 | 1.00 | 19.04 | B | C |
| ATOM | 5442 | O | ALA | 237 | 110.636 | 60.344 | 27.589 | 1.00 | 17.46 | B | O |
| ATOM | 5443 | N | PHE | 238 | 108.962 | 61.242 | 28.810 | 1.00 | 29.57 | B | N |
| ATOM | 5444 | CA | PHE | 238 | 109.530 | 62.580 | 28.795 | 1.00 | 29.00 | B | C |
| ATOM | 5445 | CB | PHE | 238 | 108.419 | 63.620 | 28.752 | 1.00 | 35.30 | B | C |
| ATOM | 5446 | CG | PHE | 238 | 107.856 | 63.854 | 27.381 | 1.00 | 34.33 | B | C |
| ATOM | 5447 | CD1 | PHE | 238 | 106.531 | 63.532 | 27.101 | 1.00 | 35.56 | B | C |
| ATOM | 5448 | CD2 | PHE | 238 | 108.635 | 64.429 | 26.380 | 1.00 | 31.93 | B | C |
| ATOM | 5449 | CE1 | PHE | 238 | 105.985 | 63.780 | 25.841 | 1.00 | 33.36 | B | C |
| ATOM | 5450 | CE2 | PHE | 238 | 108.106 | 64.682 | 25.124 | 1.00 | 38.24 | B | C |
| ATOM | 5451 | CZ | PHE | 238 | 106.778 | 64.359 | 24.850 | 1.00 | 39.66 | B | C |
| ATOM | 5452 | C | PHE | 238 | 110.468 | 62.908 | 29.943 | 1.00 | 30.85 | B | C |
| ATOM | 5453 | O | PHE | 238 | 110.433 | 64.012 | 30.479 | 1.00 | 30.95 | B | O |
| ATOM | 5454 | N | THR | 239 | 111.303 | 61.951 | 30.325 | 1.00 | 29.27 | B | N |
| ATOM | 5455 | CA | THR | 239 | 112.266 | 62.182 | 31.391 | 1.00 | 33.21 | B | C |
| ATOM | 5456 | CB | THR | 239 | 112.113 | 61.150 | 32.520 | 1.00 | 23.55 | B | C |
| ATOM | 5457 | OG1 | THR | 239 | 112.276 | 59.840 | 31.989 | 1.00 | 21.51 | B | O |
| ATOM | 5458 | CG2 | THR | 239 | 110.745 | 61.242 | 33.153 | 1.00 | 26.46 | B | C |
| ATOM | 5459 | C | THR | 239 | 113.660 | 62.084 | 30.770 | 1.00 | 33.47 | B | C |
| ATOM | 5460 | O | THR | 239 | 113.930 | 61.177 | 29.980 | 1.00 | 33.97 | B | O |
| ATOM | 5461 | N | GLU | 240 | 114.531 | 63.030 | 31.117 | 1.00 | 17.24 | B | N |
| ATOM | 5462 | CA | GLU | 240 | 115.890 | 63.085 | 30.580 | 1.00 | 17.49 | B | C |
| ATOM | 5463 | CB | GLU | 240 | 116.748 | 64.003 | 31.444 | 1.00 | 74.12 | B | C |
| ATOM | 5464 | CG | GLU | 240 | 118.007 | 64.483 | 30.758 | 1.00 | 78.76 | B | C |
| ATOM | 5465 | CD | GLU | 240 | 118.634 | 65.654 | 31.479 | 1.00 | 81.67 | B | C |
| ATOM | 5466 | OE1 | GLU | 240 | 117.904 | 66.627 | 31.774 | 1.00 | 81.77 | B | O |
| ATOM | 5467 | OE2 | GLU | 240 | 119.853 | 65.605 | 31.746 | 1.00 | 81.74 | B | O |
| ATOM | 5468 | C | GLU | 240 | 116.555 | 61.712 | 30.465 | 1.00 | 18.84 | B | C |
| ATOM | 5469 | O | GLU | 240 | 117.323 | 61.444 | 29.530 | 1.00 | 20.05 | B | O |
| ATOM | 5470 | N | ALA | 241 | 116.234 | 60.839 | 31.415 | 1.00 | 54.75 | B | N |
| ATOM | 5471 | CA | ALA | 241 | 116.784 | 59.491 | 31.446 | 1.00 | 55.60 | B | C |
| ATOM | 5472 | CB | ALA | 241 | 116.331 | 58.783 | 32.723 | 1.00 | 26.00 | B | C |
| ATOM | 5473 | C | ALA | 241 | 116.387 | 58.678 | 30.212 | 1.00 | 55.07 | B | C |
| ATOM | 5474 | O | ALA | 241 | 117.093 | 57.751 | 29.823 | 1.00 | 56.53 | B | O |
| ATOM | 5475 | N | ARG | 242 | 115.259 | 59.024 | 29.598 | 1.00 | 25.17 | B | N |

Fig. 19: A-76

| ATOM | 5476 | CA | ARG | 242 | 114.805 | 58.305 | 28.417 | 1.00 | 24.91 | B | C |
|------|------|------|-----|-----|---------|--------|--------|------|-------|---|---|
| ATOM | 5477 | CB | ARG | 242 | 113.337 | 57.917 | 28.570 | 1.00 | 45.62 | B | C |
| ATOM | 5478 | CG | ARG | 242 | 113.136 | 56.644 | 29.392 | 1.00 | 45.82 | B | C |
| ATOM | 5479 | CD | ARG | 242 | 111.684 | 56.188 | 29.334 | 1.00 | 46.68 | B | C |
| ATOM | 5480 | NE | ARG | 242 | 111.525 | 54.733 | 29.424 | 1.00 | 47.88 | B | N |
| ATOM | 5481 | CZ | ARG | 242 | 111.348 | 54.055 | 30.557 | 1.00 | 47.08 | B | C |
| ATOM | 5482 | NH1 | ARG | 242 | 111.307 | 54.695 | 31.721 | 1.00 | 46.13 | B | N |
| ATOM | 5483 | NH2 | ARG | 242 | 111.187 | 52.738 | 30.526 | 1.00 | 49.10 | B | N |
| ATOM | 5484 | C | ARG | 242 | 115.039 | 59.088 | 27.120 | 1.00 | 26.11 | B | C |
| ATOM | 5485 | O | ARG | 242 | 114.450 | 58.796 | 26.076 | 1.00 | 29.12 | B | O |
| ATOM | 5486 | N | GLY | 243 | 115.919 | 60.079 | 27.194 | 1.00 | 41.48 | B | N |
| ATOM | 5487 | CA | GLY | 243 | 116.226 | 60.863 | 26.014 | 1.00 | 39.63 | B | C |
| ATOM | 5488 | C | GLY | 243 | 115.497 | 62.187 | 25.893 | 1.00 | 37.91 | B | C |
| ATOM | 5489 | O | GLY | 243 | 115.454 | 62.774 | 24.810 | 1.00 | 37.53 | B | O |
| ATOM | 5490 | N | ALA | 244 | 114.913 | 62.665 | 26.986 | 1.00 | 32.61 | B | N |
| ATOM | 5491 | CA | ALA | 244 | 114.209 | 63.941 | 26.939 | 1.00 | 30.61 | B | C |
| ATOM | 5492 | CB | ALA | 244 | 113.253 | 64.074 | 28.124 | 1.00 | 2.29 | B | C |
| ATOM | 5493 | C | ALA | 244 | 115.262 | 65.033 | 26.984 | 1.00 | 32.49 | B | C |
| ATOM | 5494 | O | ALA | 244 | 115.867 | 65.266 | 28.021 | 1.00 | 31.95 | B | O |
| ATOM | 5495 | N | ARG | 245 | 115.491 | 65.690 | 25.854 | 1.00 | 46.10 | B | N |
| ATOM | 5496 | CA | ARG | 245 | 116.482 | 66.760 | 25.768 | 1.00 | 46.93 | B | C |
| ATOM | 5497 | CB | ARG | 245 | 116.690 | 67.163 | 24.309 | 1.00 | 24.44 | B | C |
| ATOM | 5498 | CG | ARG | 245 | 117.460 | 66.126 | 23.503 | 1.00 | 26.91 | B | C |
| ATOM | 5499 | CD | ARG | 245 | 117.553 | 66.517 | 22.054 | 1.00 | 27.12 | B | C |
| ATOM | 5500 | NE | ARG | 245 | 116.229 | 66.560 | 21.457 | 1.00 | 21.54 | B | N |
| ATOM | 5501 | CZ | ARG | 245 | 115.999 | 66.826 | 20.179 | 1.00 | 21.36 | B | C |
| ATOM | 5502 | NH1 | ARG | 245 | 117.016 | 67.074 | 19.370 | 1.00 | 20.56 | B | N |
| ATOM | 5503 | NH2 | ARG | 245 | 114.756 | 66.834 | 19.708 | 1.00 | 18.65 | B | N |
| ATOM | 5504 | C | ARG | 245 | 116.101 | 67.986 | 26.585 | 1.00 | 45.30 | B | C |
| ATOM | 5505 | O | ARG | 245 | 114.975 | 68.480 | 26.496 | 1.00 | 41.41 | B | O |
| ATOM | 5506 | N | ARG | 246 | 117.051 | 68.476 | 27.376 | 1.00 | 48.54 | B | N |
| ATOM | 5507 | CA | ARG | 246 | 116.830 | 69.640 | 28.229 | 1.00 | 51.33 | B | C |
| ATOM | 5508 | CB | ARG | 246 | 118.096 | 69.982 | 29.012 | 1.00 | 83.48 | B | C |
| ATOM | 5509 | CG | ARG | 246 | 117.975 | 71.269 | 29.811 | 1.00 | 88.84 | B | C |
| ATOM | 5510 | CD | ARG | 246 | 119.295 | 71.647 | 30.449 | 1.00 | 94.76 | B | C |
| ATOM | 5511 | NE | ARG | 246 | 119.896 | 70.525 | 31.165 | 1.00 | 97.67 | B | N |
| ATOM | 5512 | CZ | ARG | 246 | 119.288 | 69.828 | 32.123 | 1.00 | 100.78 | B | C |
| ATOM | 5513 | NH1 | ARG | 246 | 118.047 | 70.132 | 32.491 | 1.00 | 100.47 | B | N |
| ATOM | 5514 | NH2 | ARG | 246 | 119.923 | 68.825 | 32.717 | 1.00 | 101.56 | B | N |
| ATOM | 5515 | C | ARG | 246 | 116.415 | 70.871 | 27.448 | 1.00 | 49.15 | B | C |
| ATOM | 5516 | O | ARG | 246 | 117.082 | 71.246 | 26.489 | 1.00 | 51.78 | B | O |
| ATOM | 5517 | N | GLY | 247 | 115.311 | 71.489 | 27.868 | 1.00 | 46.59 | B | N |
| ATOM | 5518 | CA | GLY | 247 | 114.825 | 72.705 | 27.233 | 1.00 | 49.17 | B | C |
| ATOM | 5519 | C | GLY | 247 | 114.381 | 72.609 | 25.787 | 1.00 | 49.24 | B | C |
| ATOM | 5520 | O | GLY | 247 | 114.531 | 73.560 | 25.019 | 1.00 | 52.20 | B | O |
| ATOM | 5521 | N | VAL | 248 | 113.836 | 71.462 | 25.407 | 1.00 | 57.57 | B | N |
| ATOM | 5522 | CA | VAL | 248 | 113.357 | 71.266 | 24.049 | 1.00 | 55.58 | B | C |
| ATOM | 5523 | CB | VAL | 248 | 114.012 | 70.043 | 23.407 | 1.00 | 22.85 | B | C |
| ATOM | 5524 | CG1 | VAL | 248 | 113.384 | 69.765 | 22.056 | 1.00 | 20.50 | B | C |
| ATOM | 5525 | CG2 | VAL | 248 | 115.499 | 70.287 | 23.266 | 1.00 | 14.62 | B | C |
| ATOM | 5526 | C | VAL | 248 | 111.855 | 71.056 | 24.094 | 1.00 | 58.60 | B | C |
| ATOM | 5527 | O | VAL | 248 | 111.343 | 70.403 | 25.005 | 1.00 | 62.65 | B | O |
| ATOM | 5528 | N | LYS | 249 | 111.147 | 71.607 | 23.115 | 1.00 | 37.34 | B | N |
| ATOM | 5529 | CA | LYS | 249 | 109.698 | 71.464 | 23.086 | 1.00 | 38.25 | B | C |
| ATOM | 5530 | CB | LYS | 249 | 109.115 | 72.122 | 21.832 | 1.00 | 57.29 | B | C |
| ATOM | 5531 | CG | LYS | 249 | 107.594 | 72.204 | 21.869 | 1.00 | 62.81 | B | C |
| ATOM | 5532 | CD | LYS | 249 | 107.103 | 72.892 | 23.155 | 1.00 | 63.88 | B | C |
| ATOM | 5533 | CE | LYS | 249 | 105.634 | 72.579 | 23.450 | 1.00 | 66.24 | B | C |
| ATOM | 5534 | NZ | LYS | 249 | 105.067 | 73.292 | 24.636 | 1.00 | 69.06 | B | N |
| ATOM | 5535 | C | LYS | 249 | 109.244 | 69.998 | 23.173 | 1.00 | 36.91 | B | C |
| ATOM | 5536 | O | LYS | 249 | 109.790 | 69.112 | 22.505 | 1.00 | 36.73 | B | O |
| ATOM | 5537 | N | LYS | 250 | 108.238 | 69.755 | 24.009 | 1.00 | 33.42 | B | N |
| ATOM | 5538 | CA | LYS | 250 | 107.706 | 68.419 | 24.208 | 1.00 | 33.07 | B | C |
| ATOM | 5539 | CB | LYS | 250 | 107.603 | 68.147 | 25.710 | 1.00 | 46.37 | B | C |
| ATOM | 5540 | CG | LYS | 250 | 108.970 | 68.151 | 26.374 | 1.00 | 44.97 | B | C |
| ATOM | 5541 | CD | LYS | 250 | 108.918 | 68.429 | 27.872 | 1.00 | 46.52 | B | C |
| ATOM | 5542 | CE | LYS | 250 | 108.389 | 67.256 | 28.686 | 1.00 | 45.68 | B | C |
| ATOM | 5543 | NZ | LYS | 250 | 108.578 | 67.474 | 30.157 | 1.00 | 47.50 | B | N |
| ATOM | 5544 | C | LYS | 250 | 106.355 | 68.263 | 23.506 | 1.00 | 32.42 | B | C |
| ATOM | 5545 | O | LYS | 250 | 105.380 | 68.931 | 23.842 | 1.00 | 32.10 | B | O |
| ATOM | 5546 | N | VAL | 251 | 106.320 | 67.372 | 22.519 | 1.00 | 37.83 | B | N |
| ATOM | 5547 | CA | VAL | 251 | 105.121 | 67.115 | 21.730 | 1.00 | 37.74 | B | C |
| ATOM | 5548 | CB | VAL | 251 | 105.403 | 67.373 | 20.248 | 1.00 | 28.71 | B | C |

Fig. 19: A-77

| | | | | | | | | | | |
|---|---|---|---|---|---|---|---|---|---|---|
| ATOM | 5549 | CG1 | VAL | 251 | 104.180 | 67.017 | 19.410 | 1.00 | 26.86 | B C |
| ATOM | 5550 | CG2 | VAL | 251 | 105.819 | 68.822 | 20.057 | 1.00 | 29.92 | B C |
| ATOM | 5551 | C | VAL | 251 | 104.591 | 65.689 | 21.866 | 1.00 | 36.22 | B C |
| ATOM | 5552 | O | VAL | 251 | 105.339 | 64.715 | 21.714 | 1.00 | 32.22 | B O |
| ATOM | 5553 | N | MET | 252 | 103.289 | 65.572 | 22.122 | 1.00 | 42.57 | B N |
| ATOM | 5554 | CA | MET | 252 | 102.651 | 64.269 | 22.275 | 1.00 | 43.55 | B C |
| ATOM | 5555 | CB | MET | 252 | 102.013 | 64.160 | 23.660 | 1.00 | 27.32 | B C |
| ATOM | 5556 | CG | MET | 252 | 101.440 | 62.787 | 23.998 | 1.00 | 26.01 | B C |
| ATOM | 5557 | SD | MET | 252 | 100.740 | 62.725 | 25.675 | 1.00 | 30.06 | B S |
| ATOM | 5558 | CE | MET | 252 | 102.222 | 63.011 | 26.691 | 1.00 | 21.37 | B C |
| ATOM | 5559 | C | MET | 252 | 101.583 | 64.060 | 21.217 | 1.00 | 42.57 | B C |
| ATOM | 5560 | O | MET | 252 | 100.761 | 64.937 | 20.982 | 1.00 | 44.94 | B O |
| ATOM | 5561 | N | VAL | 253 | 101.604 | 62.900 | 20.573 | 1.00 | 21.89 | B N |
| ATOM | 5562 | CA | VAL | 253 | 100.607 | 62.580 | 19.558 | 1.00 | 23.04 | B C |
| ATOM | 5563 | CB | VAL | 253 | 101.267 | 62.281 | 18.187 | 1.00 | 9.79 | B C |
| ATOM | 5564 | CG1 | VAL | 253 | 100.191 | 61.900 | 17.168 | 1.00 | 11.21 | B C |
| ATOM | 5565 | CG2 | VAL | 253 | 102.044 | 63.490 | 17.701 | 1.00 | 9.43 | B C |
| ATOM | 5566 | C | VAL | 253 | 99.819 | 61.353 | 20.015 | 1.00 | 22.61 | B C |
| ATOM | 5567 | O | VAL | 253 | 100.383 | 60.276 | 20.161 | 1.00 | 21.05 | B O |
| ATOM | 5568 | N | ILE | 254 | 98.522 | 61.516 | 20.252 | 1.00 | 29.50 | B N |
| ATOM | 5569 | CA | ILE | 254 | 97.692 | 60.403 | 20.701 | 1.00 | 26.40 | B C |
| ATOM | 5570 | CB | ILE | 254 | 96.820 | 60.777 | 21.925 | 1.00 | 25.01 | B C |
| ATOM | 5571 | CG2 | ILE | 254 | 96.017 | 59.564 | 22.369 | 1.00 | 21.48 | B C |
| ATOM | 5572 | CG1 | ILE | 254 | 97.697 | 61.256 | 23.089 | 1.00 | 23.59 | B C |
| ATOM | 5573 | CD1 | ILE | 254 | 98.231 | 62.661 | 22.921 | 1.00 | 23.22 | B C |
| ATOM | 5574 | C | ILE | 254 | 96.757 | 59.905 | 19.611 | 1.00 | 24.49 | B C |
| ATOM | 5575 | O | ILE | 254 | 96.163 | 60.692 | 18.876 | 1.00 | 26.36 | B O |
| ATOM | 5576 | N | VAL | 255 | 96.628 | 58.587 | 19.516 | 1.00 | 26.63 | B N |
| ATOM | 5577 | CA | VAL | 255 | 95.758 | 57.981 | 18.521 | 1.00 | 25.37 | B C |
| ATOM | 5578 | CB | VAL | 255 | 96.553 | 57.259 | 17.428 | 1.00 | 15.78 | B C |
| ATOM | 5579 | CG1 | VAL | 255 | 95.672 | 57.064 | 16.198 | 1.00 | 14.23 | B C |
| ATOM | 5580 | CG2 | VAL | 255 | 97.805 | 58.036 | 17.089 | 1.00 | 16.42 | B C |
| ATOM | 5581 | C | VAL | 255 | 94.907 | 56.947 | 19.221 | 1.00 | 23.12 | B C |
| ATOM | 5582 | O | VAL | 255 | 95.444 | 56.089 | 19.916 | 1.00 | 25.12 | B O |
| ATOM | 5583 | N | THR | 256 | 93.591 | 57.012 | 19.036 | 1.00 | 8.41 | B N |
| ATOM | 5584 | CA | THR | 256 | 92.709 | 56.052 | 19.689 | 1.00 | 8.83 | B C |
| ATOM | 5585 | CB | THR | 256 | 92.529 | 56.416 | 21.189 | 1.00 | 19.33 | B C |
| ATOM | 5586 | OG1 | THR | 256 | 91.459 | 55.645 | 21.755 | 1.00 | 15.37 | B O |
| ATOM | 5587 | CG2 | THR | 256 | 92.255 | 57.908 | 21.344 | 1.00 | 18.18 | B C |
| ATOM | 5588 | C | THR | 256 | 91.353 | 55.955 | 18.992 | 1.00 | 12.31 | B C |
| ATOM | 5589 | O | THR | 256 | 90.941 | 56.881 | 18.308 | 1.00 | 8.47 | B O |
| ATOM | 5590 | N | ASP | 257 | 90.673 | 54.824 | 19.162 | 1.00 | 17.26 | B N |
| ATOM | 5591 | CA | ASP | 257 | 89.375 | 54.601 | 18.530 | 1.00 | 17.64 | B C |
| ATOM | 5592 | CB | ASP | 257 | 89.491 | 53.474 | 17.491 | 1.00 | 29.20 | B C |
| ATOM | 5593 | CG | ASP | 257 | 89.534 | 52.074 | 18.122 | 1.00 | 34.56 | B C |
| ATOM | 5594 | OD1 | ASP | 257 | 89.894 | 51.957 | 19.313 | 1.00 | 35.03 | B O |
| ATOM | 5595 | OD2 | ASP | 257 | 89.220 | 51.084 | 17.421 | 1.00 | 39.83 | B O |
| ATOM | 5596 | C | ASP | 257 | 88.267 | 54.259 | 19.535 | 1.00 | 14.23 | B C |
| ATOM | 5597 | O | ASP | 257 | 87.243 | 53.660 | 19.169 | 1.00 | 13.47 | B O |
| ATOM | 5598 | N | GLY | 258 | 88.462 | 54.634 | 20.798 | 1.00 | 26.33 | B N |
| ATOM | 5599 | CA | GLY | 258 | 87.450 | 54.331 | 21.793 | 1.00 | 28.75 | B C |
| ATOM | 5600 | C | GLY | 258 | 87.546 | 55.109 | 23.088 | 1.00 | 32.57 | B C |
| ATOM | 5601 | O | GLY | 258 | 88.615 | 55.601 | 23.476 | 1.00 | 28.29 | B O |
| ATOM | 5602 | N | GLU | 259 | 86.404 | 55.231 | 23.755 | 1.00 | 39.52 | B N |
| ATOM | 5603 | CA | GLU | 259 | 86.335 | 55.931 | 25.025 | 1.00 | 41.40 | B C |
| ATOM | 5604 | CB | GLU | 259 | 84.905 | 55.925 | 25.555 | 1.00 | 36.52 | B C |
| ATOM | 5605 | CG | GLU | 259 | 83.950 | 56.783 | 24.749 | 1.00 | 44.30 | B C |
| ATOM | 5606 | CD | GLU | 259 | 82.509 | 56.415 | 24.994 | 1.00 | 48.11 | B C |
| ATOM | 5607 | OE1 | GLU | 259 | 81.625 | 57.175 | 24.546 | 1.00 | 54.86 | B O |
| ATOM | 5608 | OE2 | GLU | 259 | 82.262 | 55.360 | 25.626 | 1.00 | 48.13 | B O |
| ATOM | 5609 | C | GLU | 259 | 87.240 | 55.210 | 26.003 | 1.00 | 40.26 | B C |
| ATOM | 5610 | O | GLU | 259 | 87.125 | 53.999 | 26.194 | 1.00 | 37.43 | B O |
| ATOM | 5611 | N | SER | 260 | 88.155 | 55.953 | 26.610 | 1.00 | 34.06 | B N |
| ATOM | 5612 | CA | SER | 260 | 89.067 | 55.369 | 27.576 | 1.00 | 37.22 | B C |
| ATOM | 5613 | CB | SER | 260 | 90.041 | 56.432 | 28.083 | 1.00 | 50.00 | B C |
| ATOM | 5614 | OG | SER | 260 | 89.341 | 57.516 | 28.666 | 1.00 | 50.51 | B O |
| ATOM | 5615 | C | SER | 260 | 88.261 | 54.814 | 28.740 | 1.00 | 37.12 | B C |
| ATOM | 5616 | O | SER | 260 | 87.177 | 55.300 | 29.043 | 1.00 | 33.15 | B O |
| ATOM | 5617 | N | HIS | 261 | 88.781 | 53.787 | 29.392 | 1.00 | 36.47 | B N |
| ATOM | 5618 | CA | HIS | 261 | 88.084 | 53.212 | 30.527 | 1.00 | 40.82 | B C |
| ATOM | 5619 | CB | HIS | 261 | 88.509 | 51.755 | 30.728 | 1.00 | 21.13 | B C |
| ATOM | 5620 | CG | HIS | 261 | 87.908 | 50.809 | 29.732 | 1.00 | 24.33 | B C |
| ATOM | 5621 | CD2 | HIS | 261 | 88.345 | 50.398 | 28.519 | 1.00 | 23.44 | B C |

Fig. 19: A-78

```
ATOM   5622  ND1 HIS   261      86.688  50.197  29.925  1.00   25.81      B  N
ATOM   5623  CE1 HIS   261      86.400  49.448  28.876  1.00   25.88      B  C
ATOM   5624  NE2 HIS   261      87.390  49.554  28.009  1.00   23.15      B  N
ATOM   5625  C   HIS   261      88.394  54.045  31.761  1.00   41.88      B  C
ATOM   5626  O   HIS   261      87.711  53.940  32.779  1.00   39.10      B  O
ATOM   5627  N   ASP   262      89.425  54.880  31.657  1.00   49.36      B  N
ATOM   5628  CA  ASP   262      89.825  55.758  32.753  1.00   54.33      B  C
ATOM   5629  CB  ASP   262      91.343  55.676  32.985  1.00   33.92      B  C
ATOM   5630  CG  ASP   262      92.124  55.281  31.733  1.00   33.92      B  C
ATOM   5631  OD1 ASP   262      91.724  55.659  30.611  1.00   33.92      B  O
ATOM   5632  OD2 ASP   262      93.162  54.600  31.875  1.00   33.92      B  O
ATOM   5633  C   ASP   262      89.418  57.218  32.507  1.00   54.38      B  C
ATOM   5634  O   ASP   262      90.221  58.134  32.700  1.00   54.24      B  O
ATOM   5635  N   ASN   263      88.171  57.424  32.085  1.00   68.10      B  N
ATOM   5636  CA  ASN   263      87.646  58.765  31.813  1.00   69.27      B  C
ATOM   5637  CB  ASN   263      86.123  58.734  31.630  1.00   82.52      B  C
ATOM   5638  CG  ASN   263      85.660  57.631  30.707  1.00   86.89      B  C
ATOM   5639  OD1 ASN   263      85.981  57.626  29.519  1.00   88.39      B  O
ATOM   5640  ND2 ASN   263      84.893  56.686  31.249  1.00   81.39      B  N
ATOM   5641  C   ASN   263      87.948  59.670  32.998  1.00   69.91      B  C
ATOM   5642  O   ASN   263      88.360  60.822  32.841  1.00   68.81      B  O
ATOM   5643  N   TYR   264      87.732  59.122  34.187  1.00   59.82      B  N
ATOM   5644  CA  TYR   264      87.925  59.837  35.432  1.00   57.67      B  C
ATOM   5645  CB  TYR   264      87.914  58.853  36.590  1.00  108.49      B  C
ATOM   5646  CG  TYR   264      86.626  58.083  36.660  1.00  108.49      B  C
ATOM   5647  CD1 TYR   264      86.284  57.171  35.663  1.00  108.49      B  C
ATOM   5648  CE1 TYR   264      85.074  56.490  35.698  1.00  108.49      B  C
ATOM   5649  CD2 TYR   264      85.723  58.292  37.699  1.00  108.49      B  C
ATOM   5650  CE2 TYR   264      84.509  57.615  37.744  1.00  108.49      B  C
ATOM   5651  CZ  TYR   264      84.190  56.717  36.741  1.00  108.49      B  C
ATOM   5652  OH  TYR   264      82.987  56.052  36.783  1.00  108.49      B  O
ATOM   5653  C   TYR   264      89.156  60.710  35.512  1.00   56.32      B  C
ATOM   5654  O   TYR   264      89.047  61.935  35.549  1.00   53.45      B  O
ATOM   5655  N   ARG   265      90.331  60.098  35.527  1.00   41.74      B  N
ATOM   5656  CA  ARG   265      91.544  60.892  35.641  1.00   40.64      B  C
ATOM   5657  CB  ARG   265      92.610  60.127  36.427  1.00   58.89      B  C
ATOM   5658  CG  ARG   265      93.152  58.875  35.779  1.00   59.34      B  C
ATOM   5659  CD  ARG   265      94.501  58.614  36.400  1.00   61.17      B  C
ATOM   5660  NE  ARG   265      95.183  57.456  35.851  1.00   66.56      B  N
ATOM   5661  CZ  ARG   265      96.506  57.349  35.784  1.00   66.73      B  C
ATOM   5662  NH1 ARG   265      97.281  58.334  36.227  1.00   71.36      B  N
ATOM   5663  NH2 ARG   265      97.059  56.256  35.280  1.00   70.70      B  N
ATOM   5664  C   ARG   265      92.147  61.423  34.347  1.00   39.89      B  C
ATOM   5665  O   ARG   265      93.311  61.833  34.319  1.00   41.20      B  O
ATOM   5666  N   LEU   266      91.360  61.433  33.278  1.00   45.12      B  N
ATOM   5667  CA  LEU   266      91.855  61.947  32.007  1.00   46.69      B  C
ATOM   5668  CB  LEU   266      90.885  61.580  30.886  1.00   30.69      B  C
ATOM   5669  CG  LEU   266      91.357  61.919  29.480  1.00   29.90      B  C
ATOM   5670  CD1 LEU   266      92.760  61.369  29.232  1.00   32.24      B  C
ATOM   5671  CD2 LEU   266      90.347  61.344  28.500  1.00   26.36      B  C
ATOM   5672  C   LEU   266      91.989  63.466  32.139  1.00   49.51      B  C
ATOM   5673  O   LEU   266      92.861  64.093  31.541  1.00   49.39      B  O
ATOM   5674  N   LYS   267      91.107  64.041  32.945  1.00   50.12      B  N
ATOM   5675  CA  LYS   267      91.097  65.473  33.206  1.00   52.43      B  C
ATOM   5676  CB  LYS   267      89.927  65.807  34.136  1.00   99.33      B  C
ATOM   5677  CG  LYS   267      89.719  67.279  34.431  1.00   99.33      B  C
ATOM   5678  CD  LYS   267      88.623  67.863  33.558  1.00   99.33      B  C
ATOM   5679  CE  LYS   267      88.211  69.242  34.049  1.00   99.33      B  C
ATOM   5680  NZ  LYS   267      87.044  69.788  33.293  1.00   99.33      B  N
ATOM   5681  C   LYS   267      92.417  65.835  33.882  1.00   51.92      B  C
ATOM   5682  O   LYS   267      93.126  66.738  33.440  1.00   51.44      B  O
ATOM   5683  N   GLN   268      92.736  65.115  34.956  1.00   36.69      B  N
ATOM   5684  CA  GLN   268      93.968  65.338  35.709  1.00   35.66      B  C
ATOM   5685  CB  GLN   268      94.098  64.324  36.841  1.00  127.61      B  C
ATOM   5686  CG  GLN   268      93.032  64.387  37.906  1.00  127.61      B  C
ATOM   5687  CD  GLN   268      93.203  63.286  38.941  1.00  127.61      B  C
ATOM   5688  OE1 GLN   268      92.487  63.236  39.939  1.00  127.61      B  O
ATOM   5689  NE2 GLN   268      94.158  62.392  38.702  1.00  127.61      B  N
ATOM   5690  C   GLN   268      95.203  65.210  34.824  1.00   31.41      B  C
ATOM   5691  O   GLN   268      96.044  66.108  34.788  1.00   32.59      B  O
ATOM   5692  N   VAL   269      95.308  64.085  34.114  1.00   29.89      B  N
ATOM   5693  CA  VAL   269      96.457  63.831  33.256  1.00   27.64      B  C
ATOM   5694  CB  VAL   269      96.321  62.467  32.516  1.00   26.10      B  C
```

Fig. 19: A-79

| ATOM | 5695 | CG1 | VAL | 269 | 97.551 | 62.215 | 31.663 | 1.00 | 21.75 | B | C |
| --- | --- | --- | --- | --- | --- | --- | --- | --- | --- | --- | --- |
| ATOM | 5696 | CG2 | VAL | 269 | 96.161 | 61.338 | 33.520 | 1.00 | 23.96 | B | C |
| ATOM | 5697 | C | VAL | 269 | 96.683 | 64.956 | 32.246 | 1.00 | 27.23 | B | C |
| ATOM | 5698 | O | VAL | 269 | 97.784 | 65.502 | 32.174 | 1.00 | 30.07 | B | O |
| ATOM | 5699 | N | ILE | 270 | 95.658 | 65.306 | 31.471 | 1.00 | 16.50 | B | N |
| ATOM | 5700 | CA | ILE | 270 | 95.797 | 66.379 | 30.487 | 1.00 | 17.12 | B | C |
| ATOM | 5701 | CB | ILE | 270 | 94.459 | 66.696 | 29.777 | 1.00 | 35.19 | B | C |
| ATOM | 5702 | CG2 | ILE | 270 | 94.594 | 67.973 | 28.937 | 1.00 | 29.81 | B | C |
| ATOM | 5703 | CG1 | ILE | 270 | 94.060 | 65.520 | 28.885 | 1.00 | 32.75 | B | C |
| ATOM | 5704 | CD1 | ILE | 270 | 95.062 | 65.231 | 27.778 | 1.00 | 33.87 | B | C |
| ATOM | 5705 | C | ILE | 270 | 96.275 | 67.631 | 31.210 | 1.00 | 20.99 | B | C |
| ATOM | 5706 | O | ILE | 270 | 97.060 | 68.413 | 30.670 | 1.00 | 19.77 | B | O |
| ATOM | 5707 | N | GLN | 271 | 95.802 | 67.796 | 32.444 | 1.00 | 57.05 | B | N |
| ATOM | 5708 | CA | GLN | 271 | 96.169 | 68.935 | 33.269 | 1.00 | 59.11 | B | C |
| ATOM | 5709 | CB | GLN | 271 | 95.440 | 68.865 | 34.610 | 1.00 | 85.78 | B | C |
| ATOM | 5710 | CG | GLN | 271 | 95.525 | 70.134 | 35.439 | 1.00 | 87.68 | B | C |
| ATOM | 5711 | CD | GLN | 271 | 94.967 | 71.338 | 34.708 | 1.00 | 90.18 | B | C |
| ATOM | 5712 | OE1 | GLN | 271 | 95.614 | 71.898 | 33.822 | 1.00 | 90.51 | B | O |
| ATOM | 5713 | NE2 | GLN | 271 | 93.752 | 71.735 | 35.065 | 1.00 | 91.75 | B | N |
| ATOM | 5714 | C | GLN | 271 | 97.673 | 68.932 | 33.495 | 1.00 | 61.57 | B | C |
| ATOM | 5715 | O | GLN | 271 | 98.359 | 69.896 | 33.172 | 1.00 | 64.26 | B | O |
| ATOM | 5716 | N | ASP | 272 | 98.184 | 67.837 | 34.042 | 1.00 | 39.03 | B | N |
| ATOM | 5717 | CA | ASP | 272 | 99.612 | 67.716 | 34.304 | 1.00 | 40.31 | B | C |
| ATOM | 5718 | CB | ASP | 272 | 99.922 | 66.338 | 34.890 | 1.00 | 54.12 | B | C |
| ATOM | 5719 | CG | ASP | 272 | 99.275 | 66.122 | 36.255 | 1.00 | 55.74 | B | C |
| ATOM | 5720 | OD1 | ASP | 272 | 99.087 | 64.949 | 36.647 | 1.00 | 57.81 | B | O |
| ATOM | 5721 | OD2 | ASP | 272 | 98.961 | 67.123 | 36.939 | 1.00 | 62.00 | B | O |
| ATOM | 5722 | C | ASP | 272 | 100.420 | 67.937 | 33.033 | 1.00 | 41.11 | B | C |
| ATOM | 5723 | O | ASP | 272 | 101.550 | 68.418 | 33.083 | 1.00 | 38.56 | B | O |
| ATOM | 5724 | N | CYS | 273 | 99.843 | 67.587 | 31.891 | 1.00 | 49.56 | B | N |
| ATOM | 5725 | CA | CYS | 273 | 100.538 | 67.776 | 30.629 | 1.00 | 47.99 | B | C |
| ATOM | 5726 | CB | CYS | 273 | 99.824 | 67.028 | 29.503 | 1.00 | 39.07 | B | C |
| ATOM | 5727 | SG | CYS | 273 | 100.050 | 65.235 | 29.538 | 1.00 | 37.17 | B | S |
| ATOM | 5728 | C | CYS | 273 | 100.628 | 69.257 | 30.291 | 1.00 | 48.36 | B | C |
| ATOM | 5729 | O | CYS | 273 | 101.602 | 69.695 | 29.686 | 1.00 | 42.67 | B | O |
| ATOM | 5730 | N | GLU | 274 | 99.609 | 70.022 | 30.682 | 1.00 | 40.12 | B | N |
| ATOM | 5731 | CA | GLU | 274 | 99.584 | 71.467 | 30.425 | 1.00 | 42.92 | B | C |
| ATOM | 5732 | CB | GLU | 274 | 98.187 | 72.055 | 30.703 | 1.00 | 40.77 | B | C |
| ATOM | 5733 | CG | GLU | 274 | 97.285 | 72.151 | 29.470 | 1.00 | 45.89 | B | C |
| ATOM | 5734 | CD | GLU | 274 | 97.830 | 73.108 | 28.405 | 1.00 | 51.00 | B | C |
| ATOM | 5735 | OE1 | GLU | 274 | 97.269 | 73.155 | 27.284 | 1.00 | 52.87 | B | O |
| ATOM | 5736 | OE2 | GLU | 274 | 98.816 | 73.818 | 28.691 | 1.00 | 55.56 | B | O |
| ATOM | 5737 | C | GLU | 274 | 100.615 | 72.172 | 31.293 | 1.00 | 45.34 | B | C |
| ATOM | 5738 | O | GLU | 274 | 101.309 | 73.081 | 30.842 | 1.00 | 47.54 | B | O |
| ATOM | 5739 | N | ASP | 275 | 100.711 | 71.735 | 32.542 | 1.00 | 77.40 | B | N |
| ATOM | 5740 | CA | ASP | 275 | 101.656 | 72.302 | 33.495 | 1.00 | 76.14 | B | C |
| ATOM | 5741 | CB | ASP | 275 | 101.456 | 71.665 | 34.871 | 1.00 | 72.98 | B | C |
| ATOM | 5742 | CG | ASP | 275 | 100.070 | 71.900 | 35.432 | 1.00 | 74.25 | B | C |
| ATOM | 5743 | OD1 | ASP | 275 | 99.160 | 72.258 | 34.656 | 1.00 | 77.95 | B | O |
| ATOM | 5744 | OD2 | ASP | 275 | 99.887 | 71.712 | 36.652 | 1.00 | 75.91 | B | O |
| ATOM | 5745 | C | ASP | 275 | 103.093 | 72.050 | 33.046 | 1.00 | 75.13 | B | C |
| ATOM | 5746 | O | ASP | 275 | 104.021 | 72.707 | 33.512 | 1.00 | 70.68 | B | O |
| ATOM | 5747 | N | GLU | 276 | 103.275 | 71.091 | 32.146 | 1.00 | 44.46 | B | N |
| ATOM | 5748 | CA | GLU | 276 | 104.606 | 70.757 | 31.668 | 1.00 | 44.11 | B | C |
| ATOM | 5749 | CB | GLU | 276 | 104.846 | 69.258 | 31.847 | 1.00 | 54.99 | B | C |
| ATOM | 5750 | CG | GLU | 276 | 104.556 | 68.799 | 33.266 | 1.00 | 54.86 | B | C |
| ATOM | 5751 | CD | GLU | 276 | 105.018 | 67.383 | 33.547 | 1.00 | 55.96 | B | C |
| ATOM | 5752 | OE1 | GLU | 276 | 104.861 | 66.934 | 34.705 | 1.00 | 56.67 | B | O |
| ATOM | 5753 | OE2 | GLU | 276 | 105.538 | 66.724 | 32.616 | 1.00 | 52.90 | B | O |
| ATOM | 5754 | C | GLU | 276 | 104.843 | 71.175 | 30.222 | 1.00 | 42.94 | B | C |
| ATOM | 5755 | O | GLU | 276 | 105.823 | 70.759 | 29.597 | 1.00 | 44.05 | B | O |
| ATOM | 5756 | N | ASN | 277 | 103.938 | 71.997 | 29.700 | 1.00 | 43.81 | B | N |
| ATOM | 5757 | CA | ASN | 277 | 104.043 | 72.505 | 28.338 | 1.00 | 43.78 | B | C |
| ATOM | 5758 | CB | ASN | 277 | 105.229 | 73.464 | 28.233 | 1.00 | 55.27 | B | C |
| ATOM | 5759 | CG | ASN | 277 | 105.219 | 74.514 | 29.311 | 1.00 | 60.19 | B | C |
| ATOM | 5760 | OD1 | ASN | 277 | 104.288 | 75.315 | 29.403 | 1.00 | 60.01 | B | O |
| ATOM | 5761 | ND2 | ASN | 277 | 106.256 | 74.518 | 30.145 | 1.00 | 59.15 | B | N |
| ATOM | 5762 | C | ASN | 277 | 104.188 | 71.428 | 27.261 | 1.00 | 40.13 | B | C |
| ATOM | 5763 | O | ASN | 277 | 105.083 | 71.515 | 26.416 | 1.00 | 41.11 | B | O |
| ATOM | 5764 | N | ILE | 278 | 103.309 | 70.427 | 27.278 | 1.00 | 17.87 | B | N |
| ATOM | 5765 | CA | ILE | 278 | 103.366 | 69.361 | 26.289 | 1.00 | 18.32 | B | C |
| ATOM | 5766 | CB | ILE | 278 | 103.110 | 67.975 | 26.928 | 1.00 | 22.06 | B | C |
| ATOM | 5767 | CG2 | ILE | 278 | 103.120 | 66.897 | 25.854 | 1.00 | 23.45 | B | C |

Fig. 19: A-80

| ATOM | 5768 | CG1 | ILE | 278 | 104.172 | 67.675 | 27.987 | 1.00 | 19.51 | B | C |
|---|---|---|---|---|---|---|---|---|---|---|---|
| ATOM | 5769 | CD1 | ILE | 278 | 103.941 | 66.373 | 28.707 | 1.00 | 21.79 | B | C |
| ATOM | 5770 | C | ILE | 278 | 102.316 | 69.579 | 25.213 | 1.00 | 18.92 | B | C |
| ATOM | 5771 | O | ILE | 278 | 101.132 | 69.378 | 25.463 | 1.00 | 19.26 | B | O |
| ATOM | 5772 | N | GLN | 279 | 102.749 | 69.994 | 24.024 | 1.00 | 49.21 | B | N |
| ATOM | 5773 | CA | GLN | 279 | 101.831 | 70.198 | 22.908 | 1.00 | 48.81 | B | C |
| ATOM | 5774 | CB | GLN | 279 | 102.579 | 70.633 | 21.652 | 1.00 | 63.04 | B | C |
| ATOM | 5775 | CG | GLN | 279 | 103.187 | 71.998 | 21.752 | 1.00 | 68.82 | B | C |
| ATOM | 5776 | CD | GLN | 279 | 102.173 | 73.043 | 22.155 | 1.00 | 72.74 | B | C |
| ATOM | 5777 | OE1 | GLN | 279 | 101.233 | 73.328 | 21.410 | 1.00 | 66.98 | B | O |
| ATOM | 5778 | NE2 | GLN | 279 | 102.352 | 73.618 | 23.345 | 1.00 | 72.33 | B | N |
| ATOM | 5779 | C | GLN | 279 | 101.175 | 68.864 | 22.640 | 1.00 | 46.68 | B | C |
| ATOM | 5780 | O | GLN | 279 | 101.861 | 67.859 | 22.467 | 1.00 | 43.60 | B | O |
| ATOM | 5781 | N | ARG | 280 | 99.851 | 68.848 | 22.595 | 1.00 | 28.30 | B | N |
| ATOM | 5782 | CA | ARG | 280 | 99.138 | 67.605 | 22.363 | 1.00 | 29.82 | B | C |
| ATOM | 5783 | CB | ARG | 280 | 98.276 | 67.277 | 23.575 | 1.00 | 38.67 | B | C |
| ATOM | 5784 | CG | ARG | 280 | 99.036 | 67.225 | 24.874 | 1.00 | 37.30 | B | C |
| ATOM | 5785 | CD | ARG | 280 | 98.068 | 67.012 | 26.018 | 1.00 | 36.97 | B | C |
| ATOM | 5786 | NE | ARG | 280 | 97.070 | 68.075 | 26.073 | 1.00 | 34.02 | B | N |
| ATOM | 5787 | CZ | ARG | 280 | 97.288 | 69.298 | 26.557 | 1.00 | 37.93 | B | C |
| ATOM | 5788 | NH1 | ARG | 280 | 98.483 | 69.627 | 27.041 | 1.00 | 40.85 | B | N |
| ATOM | 5789 | NH2 | ARG | 280 | 96.307 | 70.192 | 26.554 | 1.00 | 42.87 | B | N |
| ATOM | 5790 | C | ARG | 280 | 98.264 | 67.579 | 21.111 | 1.00 | 29.48 | B | C |
| ATOM | 5791 | O | ARG | 280 | 97.406 | 68.437 | 20.912 | 1.00 | 29.21 | B | O |
| ATOM | 5792 | N | PHE | 281 | 98.501 | 66.582 | 20.266 | 1.00 | 31.71 | B | N |
| ATOM | 5793 | CA | PHE | 281 | 97.713 | 66.392 | 19.066 | 1.00 | 33.70 | B | C |
| ATOM | 5794 | CB | PHE | 281 | 98.594 | 66.335 | 17.826 | 1.00 | 18.70 | B | C |
| ATOM | 5795 | CG | PHE | 281 | 99.324 | 67.604 | 17.555 | 1.00 | 21.73 | B | C |
| ATOM | 5796 | CD1 | PHE | 281 | 100.438 | 67.950 | 18.308 | 1.00 | 25.58 | B | C |
| ATOM | 5797 | CD2 | PHE | 281 | 98.887 | 68.469 | 16.551 | 1.00 | 23.46 | B | C |
| ATOM | 5798 | CE1 | PHE | 281 | 101.111 | 69.136 | 18.070 | 1.00 | 25.64 | B | C |
| ATOM | 5799 | CE2 | PHE | 281 | 99.554 | 69.665 | 16.301 | 1.00 | 21.19 | B | C |
| ATOM | 5800 | CZ | PHE | 281 | 100.669 | 69.999 | 17.064 | 1.00 | 22.62 | B | C |
| ATOM | 5801 | C | PHE | 281 | 97.025 | 65.060 | 19.266 | 1.00 | 34.41 | B | C |
| ATOM | 5802 | O | PHE | 281 | 97.677 | 64.053 | 19.509 | 1.00 | 36.78 | B | O |
| ATOM | 5803 | N | SER | 282 | 95.704 | 65.061 | 19.202 | 1.00 | 16.00 | B | N |
| ATOM | 5804 | CA | SER | 282 | 94.962 | 63.835 | 19.374 | 1.00 | 17.85 | B | C |
| ATOM | 5805 | CB | SER | 282 | 93.973 | 63.973 | 20.528 | 1.00 | 14.79 | B | C |
| ATOM | 5806 | OG | SER | 282 | 93.036 | 64.997 | 20.286 | 1.00 | 11.34 | B | O |
| ATOM | 5807 | C | SER | 282 | 94.231 | 63.507 | 18.093 | 1.00 | 19.73 | B | C |
| ATOM | 5808 | O | SER | 282 | 93.909 | 64.389 | 17.306 | 1.00 | 23.59 | B | O |
| ATOM | 5809 | N | ILE | 283 | 93.986 | 62.224 | 17.881 | 1.00 | 19.27 | B | N |
| ATOM | 5810 | CA | ILE | 283 | 93.288 | 61.779 | 16.693 | 1.00 | 17.19 | B | C |
| ATOM | 5811 | CB | ILE | 283 | 94.245 | 61.146 | 15.697 | 1.00 | 9.92 | B | C |
| ATOM | 5812 | CG2 | ILE | 283 | 93.501 | 60.806 | 14.425 | 1.00 | 10.73 | B | C |
| ATOM | 5813 | CG1 | ILE | 283 | 95.377 | 62.118 | 15.383 | 1.00 | 6.39 | B | C |
| ATOM | 5814 | CD1 | ILE | 283 | 96.630 | 61.446 | 14.894 | 1.00 | 9.95 | B | C |
| ATOM | 5815 | C | ILE | 283 | 92.278 | 60.748 | 17.127 | 1.00 | 16.26 | B | C |
| ATOM | 5816 | O | ILE | 283 | 92.574 | 59.886 | 17.947 | 1.00 | 16.12 | B | O |
| ATOM | 5817 | N | ALA | 284 | 91.078 | 60.836 | 16.584 | 1.00 | 18.66 | B | N |
| ATOM | 5818 | CA | ALA | 284 | 90.050 | 59.896 | 16.955 | 1.00 | 18.68 | B | C |
| ATOM | 5819 | CB | ALA | 284 | 88.903 | 60.627 | 17.622 | 1.00 | 45.12 | B | C |
| ATOM | 5820 | C | ALA | 284 | 89.542 | 59.107 | 15.759 | 1.00 | 16.81 | B | C |
| ATOM | 5821 | O | ALA | 284 | 89.045 | 59.681 | 14.792 | 1.00 | 15.47 | B | O |
| ATOM | 5822 | N | ILE | 285 | 89.691 | 57.788 | 15.826 | 1.00 | 23.61 | B | N |
| ATOM | 5823 | CA | ILE | 285 | 89.205 | 56.922 | 14.772 | 1.00 | 17.81 | B | C |
| ATOM | 5824 | CB | ILE | 285 | 89.960 | 55.564 | 14.741 | 1.00 | 12.20 | B | C |
| ATOM | 5825 | CG2 | ILE | 285 | 89.210 | 54.576 | 13.862 | 1.00 | 7.02 | B | C |
| ATOM | 5826 | CG1 | ILE | 285 | 91.380 | 55.738 | 14.204 | 1.00 | 7.53 | B | C |
| ATOM | 5827 | CD1 | ILE | 285 | 92.342 | 56.334 | 15.179 | 1.00 | 8.67 | B | C |
| ATOM | 5828 | C | ILE | 285 | 87.745 | 56.678 | 15.148 | 1.00 | 21.13 | B | C |
| ATOM | 5829 | O | ILE | 285 | 87.466 | 56.108 | 16.201 | 1.00 | 22.87 | B | O |
| ATOM | 5830 | N | LEU | 286 | 86.820 | 57.112 | 14.297 | 1.00 | 18.22 | B | N |
| ATOM | 5831 | CA | LEU | 286 | 85.399 | 56.937 | 14.581 | 1.00 | 18.70 | B | C |
| ATOM | 5832 | CB | LEU | 286 | 84.615 | 58.129 | 14.039 | 1.00 | 27.86 | B | C |
| ATOM | 5833 | CG | LEU | 286 | 85.105 | 59.512 | 14.456 | 1.00 | 30.68 | B | C |
| ATOM | 5834 | CD1 | LEU | 286 | 84.112 | 60.536 | 13.961 | 1.00 | 33.24 | B | C |
| ATOM | 5835 | CD2 | LEU | 286 | 85.249 | 59.599 | 15.963 | 1.00 | 32.35 | B | C |
| ATOM | 5836 | C | LEU | 286 | 84.774 | 55.645 | 14.044 | 1.00 | 19.15 | B | C |
| ATOM | 5837 | O | LEU | 286 | 83.552 | 55.458 | 14.122 | 1.00 | 19.99 | B | O |
| ATOM | 5838 | N | GLY | 287 | 85.609 | 54.752 | 13.520 | 1.00 | 37.37 | B | N |
| ATOM | 5839 | CA | GLY | 287 | 85.115 | 53.501 | 12.967 | 1.00 | 36.15 | B | C |
| ATOM | 5840 | C | GLY | 287 | 84.059 | 52.745 | 13.760 | 1.00 | 33.73 | B | C |

Fig. 19: A-81

| | | | | | | | | | | |
|---|---|---|---|---|---|---|---|---|---|---|
| ATOM | 5841 | O | GLY | 287 | 82.899 | 52.681 | 13.367 | 1.00 | 37.83 | B O |
| ATOM | 5842 | N | HIS | 288 | 84.464 | 52.162 | 14.878 | 1.00 | 34.79 | B N |
| ATOM | 5843 | CA | HIS | 288 | 83.563 | 51.376 | 15.700 | 1.00 | 32.75 | B C |
| ATOM | 5844 | CB | HIS | 288 | 84.272 | 51.016 | 16.996 | 1.00 | 68.63 | B C |
| ATOM | 5845 | CG | HIS | 288 | 85.486 | 50.181 | 16.763 | 1.00 | 70.54 | B C |
| ATOM | 5846 | CD2 | HIS | 288 | 85.781 | 48.912 | 17.123 | 1.00 | 66.91 | B C |
| ATOM | 5847 | ND1 | HIS | 288 | 86.520 | 50.600 | 15.955 | 1.00 | 65.20 | B N |
| ATOM | 5848 | CE1 | HIS | 288 | 87.397 | 49.623 | 15.821 | 1.00 | 65.56 | B C |
| ATOM | 5849 | NE2 | HIS | 288 | 86.972 | 48.586 | 16.519 | 1.00 | 64.05 | B N |
| ATOM | 5850 | C | HIS | 288 | 82.214 | 52.006 | 15.968 | 1.00 | 30.23 | B C |
| ATOM | 5851 | O | HIS | 288 | 81.180 | 51.398 | 15.711 | 1.00 | 29.80 | B O |
| ATOM | 5852 | N | TYR | 289 | 82.219 | 53.233 | 16.461 | 1.00 | 26.68 | B N |
| ATOM | 5853 | CA | TYR | 289 | 80.982 | 53.912 | 16.754 | 1.00 | 27.59 | B C |
| ATOM | 5854 | CB | TYR | 289 | 81.287 | 55.288 | 17.309 | 1.00 | 20.91 | B C |
| ATOM | 5855 | CG | TYR | 289 | 81.803 | 55.203 | 18.717 | 1.00 | 23.71 | B C |
| ATOM | 5856 | CD1 | TYR | 289 | 83.163 | 55.293 | 18.997 | 1.00 | 24.30 | B C |
| ATOM | 5857 | CE1 | TYR | 289 | 83.633 | 55.127 | 20.281 | 1.00 | 27.49 | B C |
| ATOM | 5858 | CD2 | TYR | 289 | 80.928 | 54.947 | 19.764 | 1.00 | 26.60 | B C |
| ATOM | 5859 | CE2 | TYR | 289 | 81.381 | 54.776 | 21.047 | 1.00 | 21.41 | B C |
| ATOM | 5860 | CZ | TYR | 289 | 82.733 | 54.866 | 21.303 | 1.00 | 23.14 | B C |
| ATOM | 5861 | OH | TYR | 289 | 83.166 | 54.686 | 22.597 | 1.00 | 27.79 | B O |
| ATOM | 5862 | C | TYR | 289 | 80.039 | 54.015 | 15.572 | 1.00 | 29.36 | B C |
| ATOM | 5863 | O | TYR | 289 | 78.849 | 53.720 | 15.692 | 1.00 | 28.55 | B O |
| ATOM | 5864 | N | ASN | 290 | 80.551 | 54.414 | 14.419 | 1.00 | 30.33 | B N |
| ATOM | 5865 | CA | ASN | 290 | 79.681 | 54.538 | 13.264 | 1.00 | 29.82 | B C |
| ATOM | 5866 | CB | ASN | 290 | 80.390 | 55.290 | 12.141 | 1.00 | 19.88 | B C |
| ATOM | 5867 | CG | ASN | 290 | 80.582 | 56.750 | 12.466 | 1.00 | 23.09 | B C |
| ATOM | 5868 | OD1 | ASN | 290 | 79.681 | 57.395 | 13.005 | 1.00 | 24.51 | B O |
| ATOM | 5869 | ND2 | ASN | 290 | 81.748 | 57.286 | 12.133 | 1.00 | 26.61 | B N |
| ATOM | 5870 | C | ASN | 290 | 79.142 | 53.214 | 12.746 | 1.00 | 28.65 | B C |
| ATOM | 5871 | O | ASN | 290 | 78.008 | 53.153 | 12.264 | 1.00 | 35.25 | B O |
| ATOM | 5872 | N | ARG | 291 | 79.944 | 52.155 | 12.842 | 1.00 | 46.80 | B N |
| ATOM | 5873 | CA | ARG | 291 | 79.513 | 50.850 | 12.362 | 1.00 | 46.11 | B C |
| ATOM | 5874 | CB | ARG | 291 | 80.694 | 49.867 | 12.337 | 1.00 | 45.84 | B C |
| ATOM | 5875 | CG | ARG | 291 | 81.661 | 50.063 | 11.152 | 1.00 | 50.80 | B C |
| ATOM | 5876 | CD | ARG | 291 | 82.722 | 48.943 | 11.054 | 1.00 | 54.88 | B C |
| ATOM | 5877 | NE | ARG | 291 | 83.916 | 49.157 | 11.883 | 1.00 | 47.06 | B N |
| ATOM | 5878 | CZ | ARG | 291 | 84.884 | 50.030 | 11.603 | 1.00 | 56.55 | B C |
| ATOM | 5879 | NH1 | ARG | 291 | 84.813 | 50.787 | 10.515 | 1.00 | 55.39 | B N |
| ATOM | 5880 | NH2 | ARG | 291 | 85.936 | 50.131 | 12.401 | 1.00 | 53.31 | B N |
| ATOM | 5881 | C | ARG | 291 | 78.367 | 50.296 | 13.207 | 1.00 | 43.91 | B C |
| ATOM | 5882 | O | ARG | 291 | 77.338 | 49.876 | 12.676 | 1.00 | 47.17 | B O |
| ATOM | 5883 | N | GLY | 292 | 78.531 | 50.306 | 14.523 | 1.00 | 18.83 | B N |
| ATOM | 5884 | CA | GLY | 292 | 77.476 | 49.795 | 15.374 | 1.00 | 19.08 | B C |
| ATOM | 5885 | C | GLY | 292 | 76.427 | 50.857 | 15.628 | 1.00 | 26.45 | B C |
| ATOM | 5886 | O | GLY | 292 | 75.874 | 50.947 | 16.722 | 1.00 | 32.58 | B O |
| ATOM | 5887 | N | ASN | 293 | 76.151 | 51.664 | 14.610 | 1.00 | 32.56 | B N |
| ATOM | 5888 | CA | ASN | 293 | 75.177 | 52.740 | 14.724 | 1.00 | 34.89 | B C |
| ATOM | 5889 | CB | ASN | 293 | 73.785 | 52.239 | 14.339 | 1.00 | 18.98 | B C |
| ATOM | 5890 | CG | ASN | 293 | 73.623 | 52.066 | 12.846 | 1.00 | 25.56 | B C |
| ATOM | 5891 | OD1 | ASN | 293 | 74.249 | 52.776 | 12.063 | 1.00 | 27.19 | B O |
| ATOM | 5892 | ND2 | ASN | 293 | 72.767 | 51.132 | 12.440 | 1.00 | 26.33 | B N |
| ATOM | 5893 | C | ASN | 293 | 75.116 | 53.389 | 16.111 | 1.00 | 36.22 | B C |
| ATOM | 5894 | O | ASN | 293 | 74.054 | 53.448 | 16.722 | 1.00 | 31.70 | B O |
| ATOM | 5895 | N | LEU | 294 | 76.247 | 53.875 | 16.614 | 1.00 | 40.17 | B N |
| ATOM | 5896 | CA | LEU | 294 | 76.260 | 54.525 | 17.921 | 1.00 | 39.32 | B C |
| ATOM | 5897 | CB | LEU | 294 | 77.141 | 53.737 | 18.901 | 1.00 | 27.66 | B C |
| ATOM | 5898 | CG | LEU | 294 | 76.633 | 52.343 | 19.291 | 1.00 | 26.48 | B C |
| ATOM | 5899 | CD1 | LEU | 294 | 77.463 | 51.781 | 20.440 | 1.00 | 27.02 | B C |
| ATOM | 5900 | CD2 | LEU | 294 | 75.175 | 52.437 | 19.714 | 1.00 | 27.39 | B C |
| ATOM | 5901 | C | LEU | 294 | 76.730 | 55.985 | 17.823 | 1.00 | 41.69 | B C |
| ATOM | 5902 | O | LEU | 294 | 77.579 | 56.314 | 16.984 | 1.00 | 40.35 | B O |
| ATOM | 5903 | N | SER | 295 | 76.158 | 56.860 | 18.656 | 1.00 | 29.47 | B N |
| ATOM | 5904 | CA | SER | 295 | 76.534 | 58.272 | 18.644 | 1.00 | 29.33 | B C |
| ATOM | 5905 | CB | SER | 295 | 75.802 | 59.063 | 19.740 | 1.00 | 35.11 | B C |
| ATOM | 5906 | OG | SER | 295 | 76.336 | 60.371 | 19.894 | 1.00 | 41.79 | B O |
| ATOM | 5907 | C | SER | 295 | 78.022 | 58.329 | 18.890 | 1.00 | 25.45 | B C |
| ATOM | 5908 | O | SER | 295 | 78.583 | 57.444 | 19.533 | 1.00 | 22.32 | B O |
| ATOM | 5909 | N | THR | 296 | 78.661 | 59.379 | 18.401 | 1.00 | 28.05 | B N |
| ATOM | 5910 | CA | THR | 296 | 80.096 | 59.500 | 18.559 | 1.00 | 28.09 | B C |
| ATOM | 5911 | CB | THR | 296 | 80.786 | 59.452 | 17.191 | 1.00 | 44.94 | B C |
| ATOM | 5912 | OG1 | THR | 296 | 80.305 | 60.534 | 16.383 | 1.00 | 50.00 | B O |
| ATOM | 5913 | CG2 | THR | 296 | 80.485 | 58.150 | 16.487 | 1.00 | 44.81 | B C |

Fig. 19: A-82

| ATOM | 5914 | C | THR | 296 | 80.519 | 60.792 | 19.227 | 1.00 | 29.07 | B | C |
|---|---|---|---|---|---|---|---|---|---|---|---|
| ATOM | 5915 | O | THR | 296 | 81.695 | 60.971 | 19.535 | 1.00 | 27.88 | B | O |
| ATOM | 5916 | N | GLU | 297 | 79.581 | 61.705 | 19.451 | 1.00 | 50.64 | B | N |
| ATOM | 5917 | CA | GLU | 297 | 79.970 | 62.978 | 20.038 | 1.00 | 54.10 | B | C |
| ATOM | 5918 | CB | GLU | 297 | 78.781 | 63.943 | 20.111 | 1.00 | 93.12 | B | C |
| ATOM | 5919 | CG | GLU | 297 | 77.787 | 63.695 | 21.213 | 1.00 | 100.15 | B | C |
| ATOM | 5920 | CD | GLU | 297 | 77.036 | 64.960 | 21.569 | 1.00 | 101.40 | B | C |
| ATOM | 5921 | OE1 | GLU | 297 | 76.160 | 64.911 | 22.455 | 1.00 | 104.84 | B | O |
| ATOM | 5922 | OE2 | GLU | 297 | 77.333 | 66.010 | 20.964 | 1.00 | 102.89 | B | O |
| ATOM | 5923 | C | GLU | 297 | 80.639 | 62.849 | 21.399 | 1.00 | 52.14 | B | C |
| ATOM | 5924 | O | GLU | 297 | 81.715 | 63.406 | 21.612 | 1.00 | 51.64 | B | O |
| ATOM | 5925 | N | LYS | 298 | 80.029 | 62.104 | 22.315 | 1.00 | 35.40 | B | N |
| ATOM | 5926 | CA | LYS | 298 | 80.622 | 61.942 | 23.636 | 1.00 | 35.40 | B | C |
| ATOM | 5927 | CB | LYS | 298 | 79.837 | 60.916 | 24.443 | 1.00 | 37.32 | B | C |
| ATOM | 5928 | CG | LYS | 298 | 80.199 | 60.902 | 25.910 | 1.00 | 46.03 | B | C |
| ATOM | 5929 | CD | LYS | 298 | 79.201 | 60.085 | 26.727 | 1.00 | 47.75 | B | C |
| ATOM | 5930 | CE | LYS | 298 | 77.777 | 60.625 | 26.578 | 1.00 | 51.57 | B | C |
| ATOM | 5931 | NZ | LYS | 298 | 77.676 | 62.075 | 26.908 | 1.00 | 55.89 | B | N |
| ATOM | 5932 | C | LYS | 298 | 82.087 | 61.518 | 23.514 | 1.00 | 33.00 | B | C |
| ATOM | 5933 | O | LYS | 298 | 82.939 | 61.933 | 24.310 | 1.00 | 33.88 | B | O |
| ATOM | 5934 | N | PHE | 299 | 82.371 | 60.699 | 22.505 | 1.00 | 29.00 | B | N |
| ATOM | 5935 | CA | PHE | 299 | 83.729 | 60.226 | 22.244 | 1.00 | 27.24 | B | C |
| ATOM | 5936 | CB | PHE | 299 | 83.701 | 59.054 | 21.263 | 1.00 | 39.15 | B | C |
| ATOM | 5937 | CG | PHE | 299 | 85.065 | 58.571 | 20.851 | 1.00 | 31.59 | B | C |
| ATOM | 5938 | CD1 | PHE | 299 | 86.020 | 58.237 | 21.806 | 1.00 | 28.04 | B | C |
| ATOM | 5939 | CD2 | PHE | 299 | 85.396 | 58.435 | 19.505 | 1.00 | 29.32 | B | C |
| ATOM | 5940 | CE1 | PHE | 299 | 87.284 | 57.776 | 21.422 | 1.00 | 27.45 | B | C |
| ATOM | 5941 | CE2 | PHE | 299 | 86.667 | 57.970 | 19.119 | 1.00 | 23.73 | B | C |
| ATOM | 5942 | CZ | PHE | 299 | 87.603 | 57.643 | 20.078 | 1.00 | 22.24 | B | C |
| ATOM | 5943 | C | PHE | 299 | 84.562 | 61.361 | 21.662 | 1.00 | 27.59 | B | C |
| ATOM | 5944 | O | PHE | 299 | 85.625 | 61.702 | 22.183 | 1.00 | 23.40 | B | O |
| ATOM | 5945 | N | VAL | 300 | 84.077 | 61.946 | 20.576 | 1.00 | 13.78 | B | N |
| ATOM | 5946 | CA | VAL | 300 | 84.791 | 63.050 | 19.944 | 1.00 | 18.73 | B | C |
| ATOM | 5947 | CB | VAL | 300 | 83.954 | 63.701 | 18.822 | 1.00 | 24.12 | B | C |
| ATOM | 5948 | CG1 | VAL | 300 | 84.616 | 64.979 | 18.363 | 1.00 | 27.69 | B | C |
| ATOM | 5949 | CG2 | VAL | 300 | 83.814 | 62.731 | 17.646 | 1.00 | 28.13 | B | C |
| ATOM | 5950 | C | VAL | 300 | 85.142 | 64.119 | 20.966 | 1.00 | 17.37 | B | C |
| ATOM | 5951 | O | VAL | 300 | 86.209 | 64.715 | 20.906 | 1.00 | 17.87 | B | O |
| ATOM | 5952 | N | GLU | 301 | 84.248 | 64.359 | 21.914 | 1.00 | 33.19 | B | N |
| ATOM | 5953 | CA | GLU | 301 | 84.520 | 65.377 | 22.915 | 1.00 | 33.85 | B | C |
| ATOM | 5954 | CB | GLU | 301 | 83.255 | 65.707 | 23.706 | 1.00 | 133.49 | B | C |
| ATOM | 5955 | CG | GLU | 301 | 83.426 | 66.851 | 24.703 | 1.00 | 135.76 | B | C |
| ATOM | 5956 | CD | GLU | 301 | 84.115 | 68.077 | 24.108 | 1.00 | 141.57 | B | C |
| ATOM | 5957 | OE1 | GLU | 301 | 83.669 | 68.566 | 23.046 | 1.00 | 141.12 | B | O |
| ATOM | 5958 | OE2 | GLU | 301 | 85.102 | 68.555 | 24.713 | 1.00 | 143.84 | B | O |
| ATOM | 5959 | C | GLU | 301 | 85.634 | 64.925 | 23.847 | 1.00 | 32.42 | B | C |
| ATOM | 5960 | O | GLU | 301 | 86.495 | 65.723 | 24.239 | 1.00 | 30.50 | B | O |
| ATOM | 5961 | N | GLU | 302 | 85.628 | 63.642 | 24.190 | 1.00 | 18.71 | B | N |
| ATOM | 5962 | CA | GLU | 302 | 86.663 | 63.091 | 25.060 | 1.00 | 18.52 | B | C |
| ATOM | 5963 | CB | GLU | 302 | 86.420 | 61.596 | 25.293 | 1.00 | 49.27 | B | C |
| ATOM | 5964 | CG | GLU | 302 | 87.438 | 60.934 | 26.207 | 1.00 | 49.02 | B | C |
| ATOM | 5965 | CD | GLU | 302 | 87.100 | 59.486 | 26.491 | 1.00 | 45.95 | B | C |
| ATOM | 5966 | OE1 | GLU | 302 | 86.051 | 59.237 | 27.118 | 1.00 | 45.93 | B | O |
| ATOM | 5967 | OE2 | GLU | 302 | 87.875 | 58.594 | 26.084 | 1.00 | 50.37 | B | O |
| ATOM | 5968 | C | GLU | 302 | 88.046 | 63.301 | 24.456 | 1.00 | 21.59 | B | C |
| ATOM | 5969 | O | GLU | 302 | 88.964 | 63.720 | 25.150 | 1.00 | 20.85 | B | O |
| ATOM | 5970 | N | ILE | 303 | 88.188 | 63.031 | 23.159 | 1.00 | 30.73 | B | N |
| ATOM | 5971 | CA | ILE | 303 | 89.479 | 63.175 | 22.472 | 1.00 | 30.78 | B | C |
| ATOM | 5972 | CB | ILE | 303 | 89.470 | 62.431 | 21.112 | 1.00 | 21.11 | B | C |
| ATOM | 5973 | CG2 | ILE | 303 | 90.865 | 62.406 | 20.518 | 1.00 | 16.29 | B | C |
| ATOM | 5974 | CG1 | ILE | 303 | 88.932 | 61.003 | 21.306 | 1.00 | 18.71 | B | C |
| ATOM | 5975 | CD1 | ILE | 303 | 89.501 | 60.262 | 22.515 | 1.00 | 15.17 | B | C |
| ATOM | 5976 | C | ILE | 303 | 89.922 | 64.625 | 22.242 | 1.00 | 32.81 | B | C |
| ATOM | 5977 | O | ILE | 303 | 91.097 | 64.955 | 22.415 | 1.00 | 35.30 | B | O |
| ATOM | 5978 | N | LYS | 304 | 88.989 | 65.485 | 21.847 | 1.00 | 41.13 | B | N |
| ATOM | 5979 | CA | LYS | 304 | 89.321 | 66.881 | 21.624 | 1.00 | 41.93 | B | C |
| ATOM | 5980 | CB | LYS | 304 | 88.087 | 67.695 | 21.239 | 1.00 | 34.23 | B | C |
| ATOM | 5981 | CG | LYS | 304 | 87.578 | 67.484 | 19.837 | 1.00 | 40.90 | B | C |
| ATOM | 5982 | CD | LYS | 304 | 86.491 | 68.498 | 19.526 | 1.00 | 42.43 | B | C |
| ATOM | 5983 | CE | LYS | 304 | 85.937 | 68.312 | 18.122 | 1.00 | 45.16 | B | C |
| ATOM | 5984 | NZ | LYS | 304 | 84.893 | 69.323 | 17.799 | 1.00 | 47.34 | B | N |
| ATOM | 5985 | C | LYS | 304 | 89.892 | 67.455 | 22.906 | 1.00 | 38.02 | B | C |
| ATOM | 5986 | O | LYS | 304 | 90.833 | 68.240 | 22.871 | 1.00 | 42.10 | B | O |

Fig. 19: A-83

| ATOM | 5987 | N | SER | 305 | 89.322 | 67.066 | 24.043 | 1.00 | 21.53 | B | N |
|---|---|---|---|---|---|---|---|---|---|---|---|
| ATOM | 5988 | CA | SER | 305 | 89.788 | 67.571 | 25.335 | 1.00 | 18.69 | B | C |
| ATOM | 5989 | CB | SER | 305 | 88.872 | 67.096 | 26.460 | 1.00 | 39.18 | B | C |
| ATOM | 5990 | OG | SER | 305 | 89.039 | 65.715 | 26.696 | 1.00 | 35.86 | B | O |
| ATOM | 5991 | C | SER | 305 | 91.223 | 67.134 | 25.622 | 1.00 | 19.21 | B | C |
| ATOM | 5992 | O | SER | 305 | 91.935 | 67.754 | 26.418 | 1.00 | 21.78 | B | O |
| ATOM | 5993 | N | ILE | 306 | 91.652 | 66.063 | 24.969 | 1.00 | 47.39 | B | N |
| ATOM | 5994 | CA | ILE | 306 | 93.005 | 65.582 | 25.158 | 1.00 | 44.14 | B | C |
| ATOM | 5995 | CB | ILE | 306 | 93.129 | 64.131 | 24.682 | 1.00 | 20.56 | B | C |
| ATOM | 5996 | CG2 | ILE | 306 | 94.584 | 63.769 | 24.454 | 1.00 | 21.29 | B | C |
| ATOM | 5997 | CG1 | ILE | 306 | 92.479 | 63.210 | 25.713 | 1.00 | 23.19 | B | C |
| ATOM | 5998 | CD1 | ILE | 306 | 92.459 | 61.762 | 25.302 | 1.00 | 20.90 | B | C |
| ATOM | 5999 | C | ILE | 306 | 93.966 | 66.469 | 24.378 | 1.00 | 41.90 | B | C |
| ATOM | 6000 | O | ILE | 306 | 95.146 | 66.583 | 24.717 | 1.00 | 42.43 | B | O |
| ATOM | 6001 | N | ALA | 307 | 93.445 | 67.103 | 23.334 | 1.00 | 47.34 | B | N |
| ATOM | 6002 | CA | ALA | 307 | 94.247 | 67.979 | 22.497 | 1.00 | 49.53 | B | C |
| ATOM | 6003 | CB | ALA | 307 | 93.538 | 68.236 | 21.181 | 1.00 | 34.34 | B | C |
| ATOM | 6004 | C | ALA | 307 | 94.526 | 69.296 | 23.200 | 1.00 | 49.19 | B | C |
| ATOM | 6005 | O | ALA | 307 | 93.952 | 69.595 | 24.253 | 1.00 | 48.18 | B | O |
| ATOM | 6006 | N | SER | 308 | 95.415 | 70.078 | 22.604 | 1.00 | 31.36 | B | N |
| ATOM | 6007 | CA | SER | 308 | 95.801 | 71.367 | 23.141 | 1.00 | 34.29 | B | C |
| ATOM | 6008 | CB | SER | 308 | 97.299 | 71.580 | 22.943 | 1.00 | 9.08 | B | C |
| ATOM | 6009 | OG | SER | 308 | 98.040 | 70.819 | 23.867 | 1.00 | 12.47 | B | O |
| ATOM | 6010 | C | SER | 308 | 95.054 | 72.489 | 22.446 | 1.00 | 37.94 | B | C |
| ATOM | 6011 | O | SER | 308 | 94.703 | 72.373 | 21.272 | 1.00 | 35.28 | B | O |
| ATOM | 6012 | N | GLU | 309 | 94.813 | 73.575 | 23.178 | 1.00 | 31.30 | B | N |
| ATOM | 6013 | CA | GLU | 309 | 94.137 | 74.735 | 22.614 | 1.00 | 34.79 | B | C |
| ATOM | 6014 | CB | GLU | 309 | 93.786 | 75.736 | 23.721 | 1.00 | 74.37 | B | C |
| ATOM | 6015 | CG | GLU | 309 | 92.834 | 75.203 | 24.787 | 1.00 | 79.74 | B | C |
| ATOM | 6016 | CD | GLU | 309 | 91.461 | 74.845 | 24.234 | 1.00 | 82.50 | B | C |
| ATOM | 6017 | OE1 | GLU | 309 | 90.533 | 74.618 | 25.043 | 1.00 | 84.83 | B | O |
| ATOM | 6018 | OE2 | GLU | 309 | 91.307 | 74.784 | 22.995 | 1.00 | 86.65 | B | O |
| ATOM | 6019 | C | GLU | 309 | 95.138 | 75.359 | 21.642 | 1.00 | 35.54 | B | C |
| ATOM | 6020 | O | GLU | 309 | 96.321 | 75.480 | 21.971 | 1.00 | 37.19 | B | O |
| ATOM | 6021 | N | PRO | 310 | 94.685 | 75.762 | 20.435 | 1.00 | 19.46 | B | N |
| ATOM | 6022 | CD | PRO | 310 | 95.588 | 76.399 | 19.457 | 1.00 | 19.32 | B | C |
| ATOM | 6023 | CA | PRO | 310 | 93.324 | 75.694 | 19.890 | 1.00 | 19.65 | B | C |
| ATOM | 6024 | CB | PRO | 310 | 93.362 | 76.729 | 18.770 | 1.00 | 21.15 | B | C |
| ATOM | 6025 | CG | PRO | 310 | 94.715 | 76.515 | 18.203 | 1.00 | 20.71 | B | C |
| ATOM | 6026 | C | PRO | 310 | 92.884 | 74.312 | 19.384 | 1.00 | 20.14 | B | C |
| ATOM | 6027 | O | PRO | 310 | 93.368 | 73.816 | 18.374 | 1.00 | 16.93 | B | O |
| ATOM | 6028 | N | THR | 311 | 91.945 | 73.714 | 20.101 | 1.00 | 34.98 | B | N |
| ATOM | 6029 | CA | THR | 311 | 91.410 | 72.410 | 19.764 | 1.00 | 35.85 | B | C |
| ATOM | 6030 | CB | THR | 311 | 89.985 | 72.276 | 20.321 | 1.00 | 54.06 | B | C |
| ATOM | 6031 | OG1 | THR | 311 | 89.327 | 71.159 | 19.711 | 1.00 | 58.22 | B | O |
| ATOM | 6032 | CG2 | THR | 311 | 89.195 | 73.556 | 20.052 | 1.00 | 57.14 | B | C |
| ATOM | 6033 | C | THR | 311 | 91.390 | 72.103 | 18.265 | 1.00 | 37.72 | B | C |
| ATOM | 6034 | O | THR | 311 | 91.801 | 71.022 | 17.847 | 1.00 | 38.89 | B | O |
| ATOM | 6035 | N | GLU | 312 | 90.929 | 73.049 | 17.451 | 1.00 | 45.13 | B | N |
| ATOM | 6036 | CA | GLU | 312 | 90.842 | 72.825 | 16.004 | 1.00 | 43.75 | B | C |
| ATOM | 6037 | CB | GLU | 312 | 90.160 | 74.008 | 15.309 | 1.00 | 94.13 | B | C |
| ATOM | 6038 | CG | GLU | 312 | 90.848 | 75.342 | 15.528 | 1.00 | 95.89 | B | C |
| ATOM | 6039 | CD | GLU | 312 | 90.633 | 76.309 | 14.376 | 1.00 | 95.00 | B | C |
| ATOM | 6040 | OE1 | GLU | 312 | 90.998 | 77.496 | 14.516 | 1.00 | 98.35 | B | O |
| ATOM | 6041 | OE2 | GLU | 312 | 90.109 | 75.880 | 13.327 | 1.00 | 95.87 | B | O |
| ATOM | 6042 | C | GLU | 312 | 92.168 | 72.547 | 15.310 | 1.00 | 42.37 | B | C |
| ATOM | 6043 | O | GLU | 312 | 92.219 | 71.771 | 14.367 | 1.00 | 42.33 | B | O |
| ATOM | 6044 | N | LYS | 313 | 93.240 | 73.180 | 15.763 | 1.00 | 62.67 | B | N |
| ATOM | 6045 | CA | LYS | 313 | 94.537 | 72.966 | 15.141 | 1.00 | 61.87 | B | C |
| ATOM | 6046 | CB | LYS | 313 | 95.368 | 74.255 | 15.192 | 1.00 | 80.35 | B | C |
| ATOM | 6047 | CG | LYS | 313 | 94.954 | 75.308 | 14.167 | 1.00 | 80.23 | B | C |
| ATOM | 6048 | CD | LYS | 313 | 95.351 | 74.917 | 12.745 | 1.00 | 76.53 | B | C |
| ATOM | 6049 | CE | LYS | 313 | 96.790 | 75.307 | 12.430 | 1.00 | 78.57 | B | C |
| ATOM | 6050 | NZ | LYS | 313 | 97.781 | 74.730 | 13.383 | 1.00 | 83.05 | B | N |
| ATOM | 6051 | C | LYS | 313 | 95.308 | 71.832 | 15.800 | 1.00 | 63.02 | B | C |
| ATOM | 6052 | O | LYS | 313 | 96.473 | 71.610 | 15.491 | 1.00 | 65.34 | B | O |
| ATOM | 6053 | N | HIS | 314 | 94.656 | 71.103 | 16.697 | 1.00 | 42.28 | B | N |
| ATOM | 6054 | CA | HIS | 314 | 95.326 | 70.011 | 17.391 | 1.00 | 43.13 | B | C |
| ATOM | 6055 | CB | HIS | 314 | 95.631 | 70.426 | 18.828 | 1.00 | 51.27 | B | C |
| ATOM | 6056 | CG | HIS | 314 | 96.611 | 71.551 | 18.938 | 1.00 | 48.13 | B | C |
| ATOM | 6057 | CD2 | HIS | 314 | 96.423 | 72.880 | 19.111 | 1.00 | 47.60 | B | C |
| ATOM | 6058 | ND1 | HIS | 314 | 97.973 | 71.364 | 18.847 | 1.00 | 47.71 | B | N |
| ATOM | 6059 | CE1 | HIS | 314 | 98.582 | 72.530 | 18.960 | 1.00 | 47.00 | B | C |

Fig. 19: A-84

| | | | | | | | | | | |
|---|---|---|---|---|---|---|---|---|---|---|
| ATOM | 6060 | NE2 | HIS | 314 | 97.664 | 73.466 | 19.121 | 1.00 | 47.39 | B N |
| ATOM | 6061 | C | HIS | 314 | 94.540 | 68.706 | 17.405 | 1.00 | 43.26 | B C |
| ATOM | 6062 | O | HIS | 314 | 95.034 | 67.690 | 17.896 | 1.00 | 46.66 | B O |
| ATOM | 6063 | N | PHE | 315 | 93.324 | 68.732 | 16.868 | 1.00 | 55.79 | B N |
| ATOM | 6064 | CA | PHE | 315 | 92.475 | 67.546 | 16.835 | 1.00 | 55.59 | B C |
| ATOM | 6065 | CB | PHE | 315 | 91.175 | 67.834 | 17.578 | 1.00 | 29.85 | B C |
| ATOM | 6066 | CG | PHE | 315 | 90.175 | 66.731 | 17.499 | 1.00 | 24.83 | B C |
| ATOM | 6067 | CD1 | PHE | 315 | 90.445 | 65.490 | 18.057 | 1.00 | 26.67 | B C |
| ATOM | 6068 | CD2 | PHE | 315 | 88.944 | 66.942 | 16.890 | 1.00 | 22.91 | B C |
| ATOM | 6069 | CE1 | PHE | 315 | 89.503 | 64.473 | 18.016 | 1.00 | 21.62 | B C |
| ATOM | 6070 | CE2 | PHE | 315 | 87.989 | 65.939 | 16.838 | 1.00 | 23.61 | B C |
| ATOM | 6071 | CZ | PHE | 315 | 88.268 | 64.700 | 17.404 | 1.00 | 25.28 | B C |
| ATOM | 6072 | C | PHE | 315 | 92.172 | 67.086 | 15.412 | 1.00 | 56.31 | B C |
| ATOM | 6073 | O | PHE | 315 | 91.948 | 67.903 | 14.516 | 1.00 | 57.71 | B O |
| ATOM | 6074 | N | PHE | 316 | 92.170 | 65.772 | 15.212 | 1.00 | 44.89 | B N |
| ATOM | 6075 | CA | PHE | 316 | 91.898 | 65.200 | 13.899 | 1.00 | 41.94 | B C |
| ATOM | 6076 | CB | PHE | 316 | 93.175 | 64.621 | 13.282 | 1.00 | 20.23 | B C |
| ATOM | 6077 | CG | PHE | 316 | 94.195 | 65.652 | 12.900 | 1.00 | 23.85 | B C |
| ATOM | 6078 | CD1 | PHE | 316 | 95.118 | 66.114 | 13.828 | 1.00 | 19.44 | B C |
| ATOM | 6079 | CD2 | PHE | 316 | 94.229 | 66.165 | 11.605 | 1.00 | 20.70 | B C |
| ATOM | 6080 | CE1 | PHE | 316 | 96.066 | 67.074 | 13.475 | 1.00 | 22.01 | B C |
| ATOM | 6081 | CE2 | PHE | 316 | 95.171 | 67.125 | 11.242 | 1.00 | 23.81 | B C |
| ATOM | 6082 | CZ | PHE | 316 | 96.092 | 67.580 | 12.180 | 1.00 | 24.04 | B C |
| ATOM | 6083 | C | PHE | 316 | 90.841 | 64.107 | 13.990 | 1.00 | 39.87 | B C |
| ATOM | 6084 | O | PHE | 316 | 90.845 | 63.302 | 14.910 | 1.00 | 39.11 | B O |
| ATOM | 6085 | N | ASN | 317 | 89.938 | 64.088 | 13.020 | 1.00 | 36.72 | B N |
| ATOM | 6086 | CA | ASN | 317 | 88.863 | 63.110 | 12.978 | 1.00 | 37.94 | B C |
| ATOM | 6087 | CB | ASN | 317 | 87.538 | 63.826 | 12.746 | 1.00 | 58.19 | B C |
| ATOM | 6088 | CG | ASN | 317 | 86.496 | 63.443 | 13.752 | 1.00 | 61.18 | B C |
| ATOM | 6089 | OD1 | ASN | 317 | 86.408 | 62.284 | 14.144 | 1.00 | 63.11 | B O |
| ATOM | 6090 | ND2 | ASN | 317 | 85.688 | 64.411 | 14.176 | 1.00 | 59.44 | B N |
| ATOM | 6091 | C | ASN | 317 | 89.102 | 62.140 | 11.831 | 1.00 | 38.90 | B C |
| ATOM | 6092 | O | ASN | 317 | 89.519 | 62.549 | 10.757 | 1.00 | 39.76 | B O |
| ATOM | 6093 | N | VAL | 318 | 88.840 | 60.858 | 12.045 | 1.00 | 40.86 | B N |
| ATOM | 6094 | CA | VAL | 318 | 89.027 | 59.872 | 10.981 | 1.00 | 39.49 | B C |
| ATOM | 6095 | CB | VAL | 318 | 90.348 | 59.096 | 11.156 | 1.00 | 59.32 | B C |
| ATOM | 6096 | CG1 | VAL | 318 | 90.497 | 58.075 | 10.065 | 1.00 | 59.45 | B C |
| ATOM | 6097 | CG2 | VAL | 318 | 91.519 | 60.052 | 11.111 | 1.00 | 59.30 | B C |
| ATOM | 6098 | C | VAL | 318 | 87.861 | 58.894 | 10.987 | 1.00 | 34.64 | B C |
| ATOM | 6099 | O | VAL | 318 | 87.363 | 58.523 | 12.050 | 1.00 | 35.31 | B O |
| ATOM | 6100 | N | SER | 319 | 87.417 | 58.482 | 9.803 | 1.00 | 25.74 | B N |
| ATOM | 6101 | CA | SER | 319 | 86.300 | 57.557 | 9.711 | 1.00 | 25.00 | B C |
| ATOM | 6102 | CB | SER | 319 | 85.769 | 57.502 | 8.275 | 1.00 | 46.83 | B C |
| ATOM | 6103 | OG | SER | 319 | 86.801 | 57.222 | 7.348 | 1.00 | 58.78 | B O |
| ATOM | 6104 | C | SER | 319 | 86.672 | 56.161 | 10.195 | 1.00 | 23.60 | B C |
| ATOM | 6105 | O | SER | 319 | 85.877 | 55.513 | 10.876 | 1.00 | 21.67 | B O |
| ATOM | 6106 | N | ASP | 320 | 87.875 | 55.702 | 9.855 | 1.00 | 29.04 | B N |
| ATOM | 6107 | CA | ASP | 320 | 88.342 | 54.377 | 10.272 | 1.00 | 29.02 | B C |
| ATOM | 6108 | CB | ASP | 320 | 87.700 | 53.292 | 9.391 | 1.00 | 54.50 | B C |
| ATOM | 6109 | CG | ASP | 320 | 88.036 | 53.455 | 7.907 | 1.00 | 52.95 | B C |
| ATOM | 6110 | OD1 | ASP | 320 | 87.708 | 54.505 | 7.318 | 1.00 | 51.63 | B O |
| ATOM | 6111 | OD2 | ASP | 320 | 88.628 | 52.525 | 7.324 | 1.00 | 53.50 | B O |
| ATOM | 6112 | C | ASP | 320 | 89.878 | 54.249 | 10.227 | 1.00 | 27.39 | B C |
| ATOM | 6113 | O | ASP | 320 | 90.574 | 55.142 | 9.734 | 1.00 | 27.17 | B O |
| ATOM | 6114 | N | GLU | 321 | 90.403 | 53.140 | 10.745 | 1.00 | 32.71 | B N |
| ATOM | 6115 | CA | GLU | 321 | 91.845 | 52.909 | 10.748 | 1.00 | 33.69 | B C |
| ATOM | 6116 | CB | GLU | 321 | 92.152 | 51.430 | 11.018 | 1.00 | 76.40 | B C |
| ATOM | 6117 | CG | GLU | 321 | 92.439 | 51.066 | 12.469 | 1.00 | 70.24 | B C |
| ATOM | 6118 | CD | GLU | 321 | 91.229 | 51.194 | 13.373 | 1.00 | 69.99 | B C |
| ATOM | 6119 | OE1 | GLU | 321 | 90.159 | 50.621 | 13.053 | 1.00 | 71.42 | B O |
| ATOM | 6120 | OE2 | GLU | 321 | 91.357 | 51.862 | 14.418 | 1.00 | 74.03 | B O |
| ATOM | 6121 | C | GLU | 321 | 92.476 | 53.300 | 9.412 | 1.00 | 37.68 | B C |
| ATOM | 6122 | O | GLU | 321 | 93.529 | 53.943 | 9.369 | 1.00 | 34.44 | B O |
| ATOM | 6123 | N | LEU | 322 | 91.820 | 52.905 | 8.323 | 1.00 | 34.24 | B N |
| ATOM | 6124 | CA | LEU | 322 | 92.310 | 53.175 | 6.971 | 1.00 | 36.93 | B C |
| ATOM | 6125 | CB | LEU | 322 | 91.345 | 52.598 | 5.937 | 1.00 | 67.00 | B C |
| ATOM | 6126 | CG | LEU | 322 | 91.361 | 51.081 | 5.743 | 1.00 | 65.63 | B C |
| ATOM | 6127 | CD1 | LEU | 322 | 92.716 | 50.681 | 5.198 | 1.00 | 67.37 | B C |
| ATOM | 6128 | CD2 | LEU | 322 | 91.058 | 50.353 | 7.063 | 1.00 | 70.68 | B C |
| ATOM | 6129 | C | LEU | 322 | 92.566 | 54.632 | 6.643 | 1.00 | 38.52 | B C |
| ATOM | 6130 | O | LEU | 322 | 93.607 | 54.971 | 6.097 | 1.00 | 41.87 | B O |
| ATOM | 6131 | N | ALA | 323 | 91.617 | 55.492 | 6.974 | 1.00 | 34.22 | B N |
| ATOM | 6132 | CA | ALA | 323 | 91.759 | 56.908 | 6.687 | 1.00 | 34.65 | B C |

Fig. 19: A-85

| | | | | | | | | | | |
|---|---|---|---|---|---|---|---|---|---|---|
| ATOM | 6133 | CB | ALA | 323 | 90.420 | 57.600 | 6.897 | 1.00 | 1.87 | B C |
| ATOM | 6134 | C | ALA | 323 | 92.859 | 57.644 | 7.476 | 1.00 | 35.06 | B C |
| ATOM | 6135 | O | ALA | 323 | 93.171 | 58.804 | 7.181 | 1.00 | 35.08 | B O |
| ATOM | 6136 | N | LEU | 324 | 93.447 | 56.995 | 8.476 | 1.00 | 26.80 | B N |
| ATOM | 6137 | CA | LEU | 324 | 94.492 | 57.652 | 9.256 | 1.00 | 25.28 | B C |
| ATOM | 6138 | CB | LEU | 324 | 95.221 | 56.640 | 10.146 | 1.00 | 29.36 | B C |
| ATOM | 6139 | CG | LEU | 324 | 94.590 | 56.344 | 11.516 | 1.00 | 28.09 | B C |
| ATOM | 6140 | CD1 | LEU | 324 | 95.288 | 55.158 | 12.170 | 1.00 | 27.23 | B C |
| ATOM | 6141 | CD2 | LEU | 324 | 94.676 | 57.580 | 12.406 | 1.00 | 26.02 | B C |
| ATOM | 6142 | C | LEU | 324 | 95.495 | 58.366 | 8.354 | 1.00 | 28.81 | B C |
| ATOM | 6143 | O | LEU | 324 | 95.822 | 59.521 | 8.588 | 1.00 | 25.35 | B O |
| ATOM | 6144 | N | VAL | 325 | 95.966 | 57.679 | 7.317 | 1.00 | 52.77 | B N |
| ATOM | 6145 | CA | VAL | 325 | 96.934 | 58.246 | 6.378 | 1.00 | 56.30 | B C |
| ATOM | 6146 | CB | VAL | 325 | 97.153 | 57.321 | 5.185 | 1.00 | 36.74 | B C |
| ATOM | 6147 | CG1 | VAL | 325 | 97.936 | 56.099 | 5.614 | 1.00 | 36.85 | B C |
| ATOM | 6148 | CG2 | VAL | 325 | 95.810 | 56.923 | 4.599 | 1.00 | 40.13 | B C |
| ATOM | 6149 | C | VAL | 325 | 96.524 | 59.598 | 5.818 | 1.00 | 59.12 | B C |
| ATOM | 6150 | O | VAL | 325 | 97.324 | 60.529 | 5.761 | 1.00 | 61.18 | B O |
| ATOM | 6151 | N | THR | 326 | 95.277 | 59.694 | 5.384 | 1.00 | 40.34 | B N |
| ATOM | 6152 | CA | THR | 326 | 94.743 | 60.925 | 4.818 | 1.00 | 41.75 | B C |
| ATOM | 6153 | CB | THR | 326 | 93.298 | 60.706 | 4.344 | 1.00 | 81.94 | B C |
| ATOM | 6154 | OG1 | THR | 326 | 92.430 | 60.600 | 5.481 | 1.00 | 83.85 | B O |
| ATOM | 6155 | CG2 | THR | 326 | 93.206 | 59.417 | 3.534 | 1.00 | 84.31 | B C |
| ATOM | 6156 | C | THR | 326 | 94.744 | 62.070 | 5.836 | 1.00 | 41.76 | B C |
| ATOM | 6157 | O | THR | 326 | 93.885 | 62.952 | 5.785 | 1.00 | 40.58 | B O |
| ATOM | 6158 | N | ILE | 327 | 95.705 | 62.052 | 6.755 | 1.00 | 36.65 | B N |
| ATOM | 6159 | CA | ILE | 327 | 95.812 | 63.075 | 7.792 | 1.00 | 36.84 | B C |
| ATOM | 6160 | CB | ILE | 327 | 95.078 | 62.604 | 9.085 | 1.00 | 16.25 | B C |
| ATOM | 6161 | CG2 | ILE | 327 | 95.934 | 62.757 | 10.328 | 1.00 | 17.02 | B C |
| ATOM | 6162 | CG1 | ILE | 327 | 93.807 | 63.408 | 9.260 | 1.00 | 16.61 | B C |
| ATOM | 6163 | CD1 | ILE | 327 | 92.943 | 62.878 | 10.372 | 1.00 | 16.28 | B C |
| ATOM | 6164 | C | ILE | 327 | 97.272 | 63.402 | 8.093 | 1.00 | 37.35 | B C |
| ATOM | 6165 | O | ILE | 327 | 97.590 | 64.494 | 8.559 | 1.00 | 37.60 | B O |
| ATOM | 6166 | N | VAL | 328 | 98.158 | 62.455 | 7.804 | 1.00 | 43.89 | B N |
| ATOM | 6167 | CA | VAL | 328 | 99.575 | 62.643 | 8.060 | 1.00 | 46.03 | B C |
| ATOM | 6168 | CB | VAL | 328 | 100.407 | 61.469 | 7.510 | 1.00 | 54.81 | B C |
| ATOM | 6169 | CG1 | VAL | 328 | 99.871 | 60.157 | 8.061 | 1.00 | 56.76 | B C |
| ATOM | 6170 | CG2 | VAL | 328 | 100.381 | 61.480 | 5.997 | 1.00 | 56.08 | B C |
| ATOM | 6171 | C | VAL | 328 | 100.121 | 63.943 | 7.481 | 1.00 | 45.95 | B C |
| ATOM | 6172 | O | VAL | 328 | 100.998 | 64.563 | 8.075 | 1.00 | 45.23 | B O |
| ATOM | 6173 | N | LYS | 329 | 99.611 | 64.366 | 6.331 | 1.00 | 44.51 | B N |
| ATOM | 6174 | CA | LYS | 329 | 100.097 | 65.609 | 5.732 | 1.00 | 43.72 | B C |
| ATOM | 6175 | CB | LYS | 329 | 99.471 | 65.824 | 4.356 | 1.00 | 45.34 | B C |
| ATOM | 6176 | CG | LYS | 329 | 100.174 | 66.880 | 3.520 | 1.00 | 46.89 | B C |
| ATOM | 6177 | CD | LYS | 329 | 99.423 | 67.129 | 2.220 | 1.00 | 49.21 | B C |
| ATOM | 6178 | CE | LYS | 329 | 100.179 | 68.074 | 1.298 | 1.00 | 52.25 | B C |
| ATOM | 6179 | NZ | LYS | 329 | 101.450 | 67.466 | 0.831 | 1.00 | 55.93 | B N |
| ATOM | 6180 | C | LYS | 329 | 99.762 | 66.797 | 6.640 | 1.00 | 41.89 | B C |
| ATOM | 6181 | O | LYS | 329 | 100.640 | 67.552 | 7.056 | 1.00 | 43.10 | B O |
| ATOM | 6182 | N | ALA | 330 | 98.483 | 66.957 | 6.952 | 1.00 | 14.46 | B N |
| ATOM | 6183 | CA | ALA | 330 | 98.053 | 68.043 | 7.814 | 1.00 | 14.49 | B C |
| ATOM | 6184 | CB | ALA | 330 | 96.538 | 68.052 | 7.906 | 1.00 | 26.19 | B C |
| ATOM | 6185 | C | ALA | 330 | 98.657 | 67.910 | 9.210 | 1.00 | 15.64 | B C |
| ATOM | 6186 | O | ALA | 330 | 99.090 | 68.896 | 9.796 | 1.00 | 15.54 | B O |
| ATOM | 6187 | N | LEU | 331 | 98.666 | 66.688 | 9.745 | 1.00 | 29.61 | B N |
| ATOM | 6188 | CA | LEU | 331 | 99.200 | 66.447 | 11.078 | 1.00 | 27.25 | B C |
| ATOM | 6189 | CB | LEU | 331 | 99.108 | 64.969 | 11.454 | 1.00 | 20.84 | B C |
| ATOM | 6190 | CG | LEU | 331 | 99.086 | 64.642 | 12.958 | 1.00 | 17.26 | B C |
| ATOM | 6191 | CD1 | LEU | 331 | 99.332 | 63.152 | 13.131 | 1.00 | 18.89 | B C |
| ATOM | 6192 | CD2 | LEU | 331 | 100.130 | 65.436 | 13.722 | 1.00 | 12.95 | B C |
| ATOM | 6193 | C | LEU | 331 | 100.647 | 66.860 | 11.070 | 1.00 | 27.28 | B C |
| ATOM | 6194 | O | LEU | 331 | 101.090 | 67.613 | 11.931 | 1.00 | 26.63 | B O |
| ATOM | 6195 | N | GLY | 332 | 101.374 | 66.358 | 10.079 | 1.00 | 36.12 | B N |
| ATOM | 6196 | CA | GLY | 332 | 102.784 | 66.666 | 9.949 | 1.00 | 37.22 | B C |
| ATOM | 6197 | C | GLY | 332 | 103.089 | 68.150 | 9.917 | 1.00 | 37.48 | B C |
| ATOM | 6198 | O | GLY | 332 | 103.940 | 68.628 | 10.670 | 1.00 | 41.35 | B O |
| ATOM | 6199 | N | GLU | 333 | 102.398 | 68.892 | 9.058 | 1.00 | 41.72 | B N |
| ATOM | 6200 | CA | GLU | 333 | 102.653 | 70.317 | 8.967 | 1.00 | 39.78 | B C |
| ATOM | 6201 | CB | GLU | 333 | 102.052 | 70.889 | 7.683 | 1.00 | 98.89 | B C |
| ATOM | 6202 | CG | GLU | 333 | 100.546 | 70.988 | 7.678 | 1.00 | 97.26 | B C |
| ATOM | 6203 | CD | GLU | 333 | 100.018 | 71.598 | 6.400 | 1.00 | 97.28 | B C |
| ATOM | 6204 | OE1 | GLU | 333 | 98.795 | 71.849 | 6.322 | 1.00 | 99.33 | B O |
| ATOM | 6205 | OE2 | GLU | 333 | 100.824 | 71.823 | 5.472 | 1.00 | 91.40 | B O |

Fig. 19: A-86

| | | | | | | | | | | |
|---|---|---|---|---|---|---|---|---|---|---|
| ATOM | 6206 | C | GLU | 333 | 102.120 | 71.069 | 10.179 | 1.00 | 38.76 | B C |
| ATOM | 6207 | O | GLU | 333 | 102.747 | 72.010 | 10.650 | 1.00 | 38.38 | B O |
| ATOM | 6208 | N | ARG | 334 | 100.969 | 70.659 | 10.695 | 1.00 | 43.09 | B N |
| ATOM | 6209 | CA | ARG | 334 | 100.398 | 71.340 | 11.847 | 1.00 | 46.47 | B C |
| ATOM | 6210 | CB | ARG | 334 | 99.089 | 70.667 | 12.265 | 1.00 | 41.05 | B C |
| ATOM | 6211 | CG | ARG | 334 | 98.167 | 71.568 | 13.056 | 1.00 | 40.34 | B C |
| ATOM | 6212 | CD | ARG | 334 | 96.722 | 71.432 | 12.592 | 1.00 | 39.10 | B C |
| ATOM | 6213 | NE | ARG | 334 | 96.544 | 71.911 | 11.222 | 1.00 | 34.65 | B N |
| ATOM | 6214 | CZ | ARG | 334 | 95.446 | 71.721 | 10.488 | 1.00 | 38.74 | B C |
| ATOM | 6215 | NH1 | ARG | 334 | 94.407 | 71.052 | 10.987 | 1.00 | 35.48 | B N |
| ATOM | 6216 | NH2 | ARG | 334 | 95.388 | 72.197 | 9.246 | 1.00 | 44.88 | B N |
| ATOM | 6217 | C | ARG | 334 | 101.419 | 71.321 | 12.980 | 1.00 | 47.77 | B C |
| ATOM | 6218 | O | ARG | 334 | 101.633 | 72.329 | 13.643 | 1.00 | 44.69 | B O |
| ATOM | 6219 | N | ILE | 335 | 102.060 | 70.177 | 13.192 | 1.00 | 95.68 | B N |
| ATOM | 6220 | CA | ILE | 335 | 103.084 | 70.066 | 14.227 | 1.00 | 95.61 | B C |
| ATOM | 6221 | CB | ILE | 335 | 103.349 | 68.565 | 14.599 | 1.00 | 69.44 | B C |
| ATOM | 6222 | CG2 | ILE | 335 | 103.371 | 67.701 | 13.359 | 1.00 | 72.22 | B C |
| ATOM | 6223 | CG1 | ILE | 335 | 104.671 | 68.420 | 15.350 | 1.00 | 70.66 | B C |
| ATOM | 6224 | CD1 | ILE | 335 | 105.043 | 66.983 | 15.628 | 1.00 | 73.45 | B C |
| ATOM | 6225 | C | ILE | 335 | 104.346 | 70.716 | 13.653 | 1.00 | 93.90 | B C |
| ATOM | 6226 | O | ILE | 335 | 105.317 | 70.979 | 14.364 | 1.00 | 96.50 | B O |
| ATOM | 6227 | N | PHE | 336 | 104.273 | 71.011 | 12.356 | 1.00 | 144.26 | B N |
| ATOM | 6228 | CA | PHE | 336 | 105.347 | 71.604 | 11.560 | 1.00 | 143.89 | B C |
| ATOM | 6229 | CB | PHE | 336 | 105.336 | 73.156 | 11.625 | 1.00 | 83.50 | B C |
| ATOM | 6230 | CG | PHE | 336 | 105.600 | 73.748 | 12.992 | 1.00 | 79.82 | B C |
| ATOM | 6231 | CD1 | PHE | 336 | 106.696 | 73.355 | 13.760 | 1.00 | 79.24 | B C |
| ATOM | 6232 | CD2 | PHE | 336 | 104.783 | 74.762 | 13.479 | 1.00 | 77.77 | B C |
| ATOM | 6233 | CE1 | PHE | 336 | 106.973 | 73.966 | 14.988 | 1.00 | 69.57 | B C |
| ATOM | 6234 | CE2 | PHE | 336 | 105.053 | 75.377 | 14.702 | 1.00 | 72.13 | B C |
| ATOM | 6235 | CZ | PHE | 336 | 106.152 | 74.977 | 15.457 | 1.00 | 72.59 | B C |
| ATOM | 6236 | C | PHE | 336 | 106.737 | 71.068 | 11.853 | 1.00 | 143.92 | B C |
| ATOM | 6237 | O | PHE | 336 | 106.889 | 70.255 | 12.788 | 1.00 | 123.54 | B O |
| ATOM | 6238 | OXT | PHE | 336 | 107.658 | 71.461 | 11.111 | 1.00 | 66.99 | B O |
| ATOM | 6239 | CB | GLU | 1 | 68.990 | 38.972 | 10.337 | 1.00 | 143.47 | X C |
| ATOM | 6240 | CG | GLU | 1 | 68.785 | 37.653 | 11.053 | 1.00 | 143.47 | X C |
| ATOM | 6241 | CD | GLU | 1 | 68.300 | 36.572 | 10.118 | 1.00 | 143.47 | X C |
| ATOM | 6242 | OE1 | GLU | 1 | 69.012 | 36.278 | 9.134 | 1.00 | 143.47 | X O |
| ATOM | 6243 | OE2 | GLU | 1 | 67.209 | 36.019 | 10.363 | 1.00 | 143.47 | X O |
| ATOM | 6244 | C | GLU | 1 | 71.024 | 39.462 | 11.710 | 1.00 | 74.19 | X C |
| ATOM | 6245 | O | GLU | 1 | 71.492 | 38.415 | 11.265 | 1.00 | 74.19 | X O |
| ATOM | 6246 | N | GLU | 1 | 69.921 | 41.257 | 10.328 | 1.00 | 74.19 | X N |
| ATOM | 6247 | CA | GLU | 1 | 69.711 | 40.037 | 11.162 | 1.00 | 74.19 | X C |
| ATOM | 6248 | N | VAL | 2 | 71.613 | 40.151 | 12.681 | 1.00 | 55.61 | X N |
| ATOM | 6249 | CA | VAL | 2 | 72.858 | 39.694 | 13.284 | 1.00 | 55.61 | X C |
| ATOM | 6250 | CB | VAL | 2 | 73.533 | 40.812 | 14.089 | 1.00 | 66.95 | X C |
| ATOM | 6251 | CG1 | VAL | 2 | 74.850 | 40.323 | 14.647 | 1.00 | 66.95 | X C |
| ATOM | 6252 | CG2 | VAL | 2 | 73.752 | 42.021 | 13.210 | 1.00 | 66.95 | X C |
| ATOM | 6253 | C | VAL | 2 | 72.566 | 38.543 | 14.232 | 1.00 | 55.61 | X C |
| ATOM | 6254 | O | VAL | 2 | 71.728 | 38.673 | 15.127 | 1.00 | 55.61 | X O |
| ATOM | 6255 | N | GLN | 3 | 73.258 | 37.421 | 14.045 | 1.00 | 39.72 | X N |
| ATOM | 6256 | CA | GLN | 3 | 73.044 | 36.261 | 14.908 | 1.00 | 39.72 | X C |
| ATOM | 6257 | CB | GLN | 3 | 71.807 | 35.502 | 14.455 | 1.00 | 102.66 | X C |
| ATOM | 6258 | CG | GLN | 3 | 71.852 | 35.144 | 13.002 | 1.00 | 102.66 | X C |
| ATOM | 6259 | CD | GLN | 3 | 70.688 | 34.291 | 12.604 | 1.00 | 102.66 | X C |
| ATOM | 6260 | OE1 | GLN | 3 | 69.537 | 34.635 | 12.873 | 1.00 | 102.66 | X O |
| ATOM | 6261 | NE2 | GLN | 3 | 70.972 | 33.168 | 11.955 | 1.00 | 102.66 | X N |
| ATOM | 6262 | C | GLN | 3 | 74.213 | 35.288 | 15.002 | 1.00 | 39.72 | X C |
| ATOM | 6263 | O | GLN | 3 | 75.064 | 35.207 | 14.108 | 1.00 | 39.72 | X O |
| ATOM | 6264 | N | LEU | 4 | 74.231 | 34.553 | 16.109 | 1.00 | 34.59 | X N |
| ATOM | 6265 | CA | LEU | 4 | 75.260 | 33.555 | 16.389 | 1.00 | 34.59 | X C |
| ATOM | 6266 | CB | LEU | 4 | 76.043 | 33.931 | 17.653 | 1.00 | 34.08 | X C |
| ATOM | 6267 | CG | LEU | 4 | 77.107 | 35.040 | 17.665 | 1.00 | 34.08 | X C |
| ATOM | 6268 | CD1 | LEU | 4 | 77.119 | 35.820 | 16.353 | 1.00 | 34.08 | X C |
| ATOM | 6269 | CD2 | LEU | 4 | 76.844 | 35.950 | 18.863 | 1.00 | 34.08 | X C |
| ATOM | 6270 | C | LEU | 4 | 74.581 | 32.212 | 16.615 | 1.00 | 34.59 | X C |
| ATOM | 6271 | O | LEU | 4 | 73.737 | 32.080 | 17.503 | 1.00 | 34.59 | X O |
| ATOM | 6272 | N | VAL | 5 | 74.933 | 31.218 | 15.806 | 1.00 | 36.99 | X N |
| ATOM | 6273 | CA | VAL | 5 | 74.350 | 29.889 | 15.961 | 1.00 | 36.99 | X C |
| ATOM | 6274 | CB | VAL | 5 | 73.536 | 29.456 | 14.698 | 1.00 | 37.13 | X C |
| ATOM | 6275 | CG1 | VAL | 5 | 74.285 | 29.815 | 13.430 | 1.00 | 37.13 | X C |
| ATOM | 6276 | CG2 | VAL | 5 | 73.264 | 27.963 | 14.744 | 1.00 | 37.13 | X C |
| ATOM | 6277 | C | VAL | 5 | 75.429 | 28.861 | 16.277 | 1.00 | 36.99 | X C |
| ATOM | 6278 | O | VAL | 5 | 76.163 | 28.404 | 15.398 | 1.00 | 36.99 | X O |

Fig. 19: A-87

| | | | | | | | | | | |
|---|---|---|---|---|---|---|---|---|---|---|
| ATOM | 6279 | N | GLU | 6 | 75.519 | 28.517 | 17.555 | 1.00 | 44.32 | X N |
| ATOM | 6280 | CA | GLU | 6 | 76.499 | 27.550 | 18.020 | 1.00 | 44.32 | X C |
| ATOM | 6281 | CB | GLU | 6 | 76.924 | 27.884 | 19.457 | 1.00 | 53.96 | X C |
| ATOM | 6282 | CG | GLU | 6 | 75.844 | 28.531 | 20.292 | 1.00 | 53.96 | X C |
| ATOM | 6283 | CD | GLU | 6 | 76.340 | 28.943 | 21.659 | 1.00 | 53.96 | X C |
| ATOM | 6284 | OE1 | GLU | 6 | 75.590 | 29.646 | 22.368 | 1.00 | 53.96 | X O |
| ATOM | 6285 | OE2 | GLU | 6 | 77.472 | 28.561 | 22.028 | 1.00 | 53.96 | X O |
| ATOM | 6286 | C | GLU | 6 | 76.029 | 26.095 | 17.930 | 1.00 | 44.32 | X C |
| ATOM | 6287 | O | GLU | 6 | 74.856 | 25.813 | 17.668 | 1.00 | 44.32 | X O |
| ATOM | 6288 | N | SER | 7 | 76.980 | 25.185 | 18.135 | 1.00 | 42.31 | X N |
| ATOM | 6289 | CA | SER | 7 | 76.758 | 23.745 | 18.091 | 1.00 | 42.31 | X C |
| ATOM | 6290 | CB | SER | 7 | 76.762 | 23.261 | 16.642 | 1.00 | 44.31 | X C |
| ATOM | 6291 | OG | SER | 7 | 77.832 | 23.845 | 15.922 | 1.00 | 44.31 | X O |
| ATOM | 6292 | C | SER | 7 | 77.919 | 23.123 | 18.848 | 1.00 | 42.31 | X C |
| ATOM | 6293 | O | SER | 7 | 78.889 | 23.813 | 19.138 | 1.00 | 42.31 | X O |
| ATOM | 6294 | N | GLY | 8 | 77.822 | 21.838 | 19.178 | 1.00 | 39.85 | X N |
| ATOM | 6295 | CA | GLY | 8 | 78.908 | 21.177 | 19.893 | 1.00 | 39.85 | X C |
| ATOM | 6296 | C | GLY | 8 | 78.569 | 20.747 | 21.313 | 1.00 | 39.85 | X C |
| ATOM | 6297 | O | GLY | 8 | 79.330 | 20.016 | 21.962 | 1.00 | 39.85 | X O |
| ATOM | 6298 | N | GLY | 9 | 77.417 | 21.199 | 21.795 | 1.00 | 54.13 | X N |
| ATOM | 6299 | CA | GLY | 9 | 76.998 | 20.852 | 23.138 | 1.00 | 54.13 | X C |
| ATOM | 6300 | C | GLY | 9 | 76.467 | 19.439 | 23.283 | 1.00 | 54.13 | X C |
| ATOM | 6301 | O | GLY | 9 | 75.390 | 19.102 | 22.783 | 1.00 | 54.13 | X O |
| ATOM | 6302 | N | GLY | 10 | 77.235 | 18.606 | 23.972 | 1.00 | 51.55 | X N |
| ATOM | 6303 | CA | GLY | 10 | 76.825 | 17.236 | 24.195 | 1.00 | 51.55 | X C |
| ATOM | 6304 | C | GLY | 10 | 77.359 | 16.807 | 25.544 | 1.00 | 51.55 | X C |
| ATOM | 6305 | O | GLY | 10 | 77.723 | 17.651 | 26.370 | 1.00 | 51.55 | X O |
| ATOM | 6306 | N | LEU | 11 | 77.409 | 15.500 | 25.776 | 1.00 | 54.73 | X N |
| ATOM | 6307 | CA | LEU | 11 | 77.930 | 14.981 | 27.032 | 1.00 | 54.73 | X C |
| ATOM | 6308 | CB | LEU | 11 | 76.994 | 13.903 | 27.583 | 1.00 | 40.69 | X C |
| ATOM | 6309 | CG | LEU | 11 | 77.583 | 13.086 | 28.735 | 1.00 | 40.69 | X C |
| ATOM | 6310 | CD1 | LEU | 11 | 78.170 | 14.011 | 29.795 | 1.00 | 40.69 | X C |
| ATOM | 6311 | CD2 | LEU | 11 | 76.508 | 12.198 | 29.317 | 1.00 | 40.69 | X C |
| ATOM | 6312 | C | LEU | 11 | 79.341 | 14.412 | 26.852 | 1.00 | 54.73 | X C |
| ATOM | 6313 | O | LEU | 11 | 79.664 | 13.853 | 25.806 | 1.00 | 54.73 | X O |
| ATOM | 6314 | N | VAL | 12 | 80.177 | 14.576 | 27.872 | 1.00 | 43.40 | X N |
| ATOM | 6315 | CA | VAL | 12 | 81.552 | 14.079 | 27.848 | 1.00 | 43.40 | X C |
| ATOM | 6316 | CB | VAL | 12 | 82.538 | 15.118 | 27.273 | 1.00 | 57.73 | X C |
| ATOM | 6317 | CG1 | VAL | 12 | 82.222 | 15.388 | 25.812 | 1.00 | 57.73 | X C |
| ATOM | 6318 | CG2 | VAL | 12 | 82.473 | 16.404 | 28.086 | 1.00 | 57.73 | X C |
| ATOM | 6319 | C | VAL | 12 | 81.991 | 13.753 | 29.269 | 1.00 | 43.40 | X C |
| ATOM | 6320 | O | VAL | 12 | 81.490 | 14.344 | 30.230 | 1.00 | 43.40 | X O |
| ATOM | 6321 | N | GLN | 13 | 82.931 | 12.821 | 29.403 | 1.00 | 46.11 | X N |
| ATOM | 6322 | CA | GLN | 13 | 83.404 | 12.420 | 30.720 | 1.00 | 46.11 | X C |
| ATOM | 6323 | CB | GLN | 13 | 83.873 | 10.965 | 30.676 | 1.00 | 148.60 | X C |
| ATOM | 6324 | CG | GLN | 13 | 82.843 | 10.015 | 30.094 | 1.00 | 148.60 | X C |
| ATOM | 6325 | CD | GLN | 13 | 83.232 | 8.560 | 30.263 | 1.00 | 148.60 | X C |
| ATOM | 6326 | OE1 | GLN | 13 | 84.322 | 8.145 | 29.868 | 1.00 | 148.60 | X O |
| ATOM | 6327 | NE2 | GLN | 13 | 82.337 | 7.774 | 30.852 | 1.00 | 148.60 | X N |
| ATOM | 6328 | C | GLN | 13 | 84.532 | 13.311 | 31.234 | 1.00 | 46.11 | X C |
| ATOM | 6329 | O | GLN | 13 | 85.186 | 14.002 | 30.454 | 1.00 | 46.11 | X O |
| ATOM | 6330 | N | PRO | 14 | 84.763 | 13.319 | 32.563 | 1.00 | 39.23 | X N |
| ATOM | 6331 | CD | PRO | 14 | 83.989 | 12.657 | 33.630 | 1.00 | 55.62 | X C |
| ATOM | 6332 | CA | PRO | 14 | 85.831 | 14.141 | 33.141 | 1.00 | 39.23 | X C |
| ATOM | 6333 | CB | PRO | 14 | 85.902 | 13.648 | 34.581 | 1.00 | 55.62 | X C |
| ATOM | 6334 | CG | PRO | 14 | 84.474 | 13.374 | 34.887 | 1.00 | 55.62 | X C |
| ATOM | 6335 | C | PRO | 14 | 87.122 | 13.905 | 32.392 | 1.00 | 39.23 | X C |
| ATOM | 6336 | O | PRO | 14 | 87.357 | 12.810 | 31.885 | 1.00 | 39.23 | X O |
| ATOM | 6337 | N | GLY | 15 | 87.954 | 14.935 | 32.320 | 1.00 | 28.04 | X N |
| ATOM | 6338 | CA | GLY | 15 | 89.220 | 14.816 | 31.616 | 1.00 | 28.04 | X C |
| ATOM | 6339 | C | GLY | 15 | 89.037 | 14.807 | 30.109 | 1.00 | 28.04 | X C |
| ATOM | 6340 | O | GLY | 15 | 89.990 | 14.979 | 29.352 | 1.00 | 28.04 | X O |
| ATOM | 6341 | N | GLY | 16 | 87.801 | 14.613 | 29.672 | 1.00 | 22.75 | X N |
| ATOM | 6342 | CA | GLY | 16 | 87.529 | 14.583 | 28.250 | 1.00 | 22.75 | X C |
| ATOM | 6343 | C | GLY | 16 | 87.705 | 15.912 | 27.539 | 1.00 | 22.75 | X C |
| ATOM | 6344 | O | GLY | 16 | 87.887 | 16.969 | 28.155 | 1.00 | 22.75 | X O |
| ATOM | 6345 | N | SER | 17 | 87.633 | 15.845 | 26.217 | 1.00 | 36.95 | X N |
| ATOM | 6346 | CA | SER | 17 | 87.789 | 17.014 | 25.371 | 1.00 | 36.95 | X C |
| ATOM | 6347 | CB | SER | 17 | 88.962 | 16.795 | 24.417 | 1.00 | 47.78 | X C |
| ATOM | 6348 | OG | SER | 17 | 89.203 | 17.952 | 23.645 | 1.00 | 47.78 | X O |
| ATOM | 6349 | C | SER | 17 | 86.509 | 17.311 | 24.581 | 1.00 | 36.95 | X C |
| ATOM | 6350 | O | SER | 17 | 85.817 | 16.402 | 24.106 | 1.00 | 36.95 | X O |
| ATOM | 6351 | N | LEU | 18 | 86.199 | 18.593 | 24.429 | 1.00 | 50.75 | X N |

Fig. 19: A-88

| | | | | | | | | | | | |
|---|---|---|---|---|---|---|---|---|---|---|---|
| ATOM | 6352 | CA | LEU | 18 | 84.995 | 18.978 | 23.719 | 1.00 | 50.75 | X | C |
| ATOM | 6353 | CB | LEU | 18 | 83.833 | 18.944 | 24.701 | 1.00 | 37.38 | X | C |
| ATOM | 6354 | CG | LEU | 18 | 82.463 | 19.285 | 24.146 | 1.00 | 37.38 | X | C |
| ATOM | 6355 | CD1 | LEU | 18 | 82.177 | 18.476 | 22.874 | 1.00 | 37.38 | X | C |
| ATOM | 6356 | CD2 | LEU | 18 | 81.442 | 19.012 | 25.239 | 1.00 | 37.38 | X | C |
| ATOM | 6357 | C | LEU | 18 | 85.107 | 20.355 | 23.069 | 1.00 | 50.75 | X | C |
| ATOM | 6358 | O | LEU | 18 | 85.530 | 21.313 | 23.714 | 1.00 | 50.75 | X | O |
| ATOM | 6359 | N | ARG | 19 | 84.737 | 20.454 | 21.792 | 1.00 | 27.07 | X | N |
| ATOM | 6360 | CA | ARG | 19 | 84.805 | 21.739 | 21.097 | 1.00 | 27.07 | X | C |
| ATOM | 6361 | CB | ARG | 19 | 85.774 | 21.708 | 19.924 | 1.00 | 43.18 | X | C |
| ATOM | 6362 | CG | ARG | 19 | 85.825 | 23.068 | 19.238 | 1.00 | 43.18 | X | C |
| ATOM | 6363 | CD | ARG | 19 | 86.689 | 23.075 | 18.015 | 1.00 | 43.18 | X | C |
| ATOM | 6364 | NE | ARG | 19 | 86.060 | 22.389 | 16.896 | 1.00 | 43.18 | X | N |
| ATOM | 6365 | CZ | ARG | 19 | 86.564 | 22.371 | 15.666 | 1.00 | 43.18 | X | C |
| ATOM | 6366 | NH1 | ARG | 19 | 87.708 | 23.006 | 15.407 | 1.00 | 43.18 | X | N |
| ATOM | 6367 | NH2 | ARG | 19 | 85.924 | 21.725 | 14.696 | 1.00 | 43.18 | X | N |
| ATOM | 6368 | C | ARG | 19 | 83.501 | 22.302 | 20.558 | 1.00 | 27.07 | X | C |
| ATOM | 6369 | O | ARG | 19 | 82.895 | 21.745 | 19.625 | 1.00 | 27.07 | X | O |
| ATOM | 6370 | N | LEU | 20 | 83.109 | 23.438 | 21.135 | 1.00 | 30.57 | X | N |
| ATOM | 6371 | CA | LEU | 20 | 81.908 | 24.150 | 20.731 | 1.00 | 30.57 | X | C |
| ATOM | 6372 | CB | LEU | 20 | 81.354 | 24.965 | 21.896 | 1.00 | 36.53 | X | C |
| ATOM | 6373 | CG | LEU | 20 | 80.981 | 24.196 | 23.159 | 1.00 | 36.53 | X | C |
| ATOM | 6374 | CD1 | LEU | 20 | 80.415 | 25.142 | 24.218 | 1.00 | 36.53 | X | C |
| ATOM | 6375 | CD2 | LEU | 20 | 79.964 | 23.135 | 22.802 | 1.00 | 36.53 | X | C |
| ATOM | 6376 | C | LEU | 20 | 82.304 | 25.098 | 19.618 | 1.00 | 30.57 | X | C |
| ATOM | 6377 | O | LEU | 20 | 83.313 | 25.784 | 19.723 | 1.00 | 30.57 | X | O |
| ATOM | 6378 | N | SER | 21 | 81.527 | 25.122 | 18.544 | 1.00 | 31.77 | X | N |
| ATOM | 6379 | CA | SER | 21 | 81.789 | 26.024 | 17.426 | 1.00 | 31.77 | X | C |
| ATOM | 6380 | CB | SER | 21 | 81.876 | 25.252 | 16.117 | 1.00 | 32.65 | X | C |
| ATOM | 6381 | OG | SER | 21 | 80.580 | 24.896 | 15.682 | 1.00 | 32.65 | X | O |
| ATOM | 6382 | C | SER | 21 | 80.593 | 26.971 | 17.383 | 1.00 | 31.77 | X | C |
| ATOM | 6383 | O | SER | 21 | 79.591 | 26.738 | 18.057 | 1.00 | 31.77 | X | O |
| ATOM | 6384 | N | CYS | 22 | 80.673 | 28.024 | 16.585 | 1.00 | 49.03 | X | N |
| ATOM | 6385 | CA | CYS | 22 | 79.580 | 28.981 | 16.526 | 1.00 | 49.03 | X | C |
| ATOM | 6386 | C | CYS | 22 | 79.725 | 29.812 | 15.272 | 1.00 | 49.03 | X | C |
| ATOM | 6387 | O | CYS | 22 | 80.743 | 30.484 | 15.096 | 1.00 | 49.03 | X | O |
| ATOM | 6388 | CB | CYS | 22 | 79.643 | 29.849 | 17.788 | 1.00 | 49.62 | X | C |
| ATOM | 6389 | SG | CYS | 22 | 78.993 | 31.555 | 17.774 | 1.00 | 49.62 | X | S |
| ATOM | 6390 | N | ALA | 23 | 78.724 | 29.744 | 14.389 | 1.00 | 43.82 | X | N |
| ATOM | 6391 | CA | ALA | 23 | 78.742 | 30.509 | 13.136 | 1.00 | 43.82 | X | C |
| ATOM | 6392 | CB | ALA | 23 | 78.022 | 29.768 | 12.021 | 1.00 | 1.87 | X | C |
| ATOM | 6393 | C | ALA | 23 | 78.093 | 31.854 | 13.329 | 1.00 | 43.82 | X | C |
| ATOM | 6394 | O | ALA | 23 | 77.118 | 31.999 | 14.070 | 1.00 | 43.82 | X | O |
| ATOM | 6395 | N | ALA | 24 | 78.644 | 32.843 | 12.645 | 1.00 | 28.70 | X | N |
| ATOM | 6396 | CA | ALA | 24 | 78.129 | 34.190 | 12.735 | 1.00 | 28.70 | X | C |
| ATOM | 6397 | CB | ALA | 24 | 79.199 | 35.129 | 13.323 | 1.00 | 18.49 | X | C |
| ATOM | 6398 | C | ALA | 24 | 77.725 | 34.659 | 11.356 | 1.00 | 28.70 | X | C |
| ATOM | 6399 | O | ALA | 24 | 78.213 | 34.160 | 10.345 | 1.00 | 28.70 | X | O |
| ATOM | 6400 | N | SER | 25 | 76.816 | 35.620 | 11.338 | 1.00 | 39.45 | X | N |
| ATOM | 6401 | CA | SER | 25 | 76.338 | 36.218 | 10.108 | 1.00 | 39.45 | X | C |
| ATOM | 6402 | CB | SER | 25 | 75.279 | 35.322 | 9.443 | 1.00 | 48.28 | X | C |
| ATOM | 6403 | OG | SER | 25 | 74.163 | 35.090 | 10.287 | 1.00 | 48.28 | X | O |
| ATOM | 6404 | C | SER | 25 | 75.751 | 37.575 | 10.486 | 1.00 | 39.45 | X | C |
| ATOM | 6405 | O | SER | 25 | 75.425 | 37.819 | 11.656 | 1.00 | 39.45 | X | O |
| ATOM | 6406 | N | GLY | 26 | 75.651 | 38.464 | 9.506 | 1.00 | 15.13 | X | N |
| ATOM | 6407 | CA | GLY | 26 | 75.093 | 39.773 | 9.767 | 1.00 | 15.13 | X | C |
| ATOM | 6408 | C | GLY | 26 | 76.061 | 40.808 | 10.313 | 1.00 | 15.13 | X | C |
| ATOM | 6409 | O | GLY | 26 | 75.650 | 41.692 | 11.070 | 1.00 | 15.13 | X | O |
| ATOM | 6410 | N | PHE | 27 | 77.336 | 40.697 | 9.941 | 1.00 | 51.25 | X | N |
| ATOM | 6411 | CA | PHE | 27 | 78.375 | 41.638 | 10.358 | 1.00 | 51.25 | X | C |
| ATOM | 6412 | CB | PHE | 27 | 78.322 | 41.921 | 11.860 | 1.00 | 33.43 | X | C |
| ATOM | 6413 | CG | PHE | 27 | 78.647 | 40.736 | 12.720 | 1.00 | 33.43 | X | C |
| ATOM | 6414 | CD1 | PHE | 27 | 77.696 | 39.749 | 12.958 | 1.00 | 33.43 | X | C |
| ATOM | 6415 | CD2 | PHE | 27 | 79.891 | 40.629 | 13.337 | 1.00 | 33.43 | X | C |
| ATOM | 6416 | CE1 | PHE | 27 | 77.978 | 38.673 | 13.810 | 1.00 | 33.43 | X | C |
| ATOM | 6417 | CE2 | PHE | 27 | 80.186 | 39.558 | 14.190 | 1.00 | 33.43 | X | C |
| ATOM | 6418 | CZ | PHE | 27 | 79.227 | 38.581 | 14.428 | 1.00 | 33.43 | X | C |
| ATOM | 6419 | C | PHE | 27 | 79.748 | 41.100 | 10.012 | 1.00 | 51.25 | X | C |
| ATOM | 6420 | O | PHE | 27 | 79.966 | 39.894 | 10.027 | 1.00 | 51.25 | X | O |
| ATOM | 6421 | N | THR | 28 | 80.671 | 42.006 | 9.707 | 1.00 | 31.93 | X | N |
| ATOM | 6422 | CA | THR | 28 | 82.031 | 41.637 | 9.348 | 1.00 | 31.93 | X | C |
| ATOM | 6423 | CB | THR | 28 | 82.821 | 42.872 | 8.910 | 1.00 | 48.89 | X | C |
| ATOM | 6424 | OG1 | THR | 28 | 82.126 | 43.520 | 7.836 | 1.00 | 48.89 | X | O |

Fig. 19: A-89

| ATOM | 6425 | CG2 | THR | 28 | 84.212 | 42.474 | 8.454 | 1.00 | 48.89 | X | C |
|---|---|---|---|---|---|---|---|---|---|---|---|
| ATOM | 6426 | C | THR | 28 | 82.744 | 40.981 | 10.519 | 1.00 | 31.93 | X | C |
| ATOM | 6427 | O | THR | 28 | 83.431 | 41.640 | 11.286 | 1.00 | 31.93 | X | O |
| ATOM | 6428 | N | PHE | 29 | 82.576 | 39.671 | 10.636 | 1.00 | 37.68 | X | N |
| ATOM | 6429 | CA | PHE | 29 | 83.166 | 38.876 | 11.712 | 1.00 | 37.68 | X | C |
| ATOM | 6430 | CB | PHE | 29 | 83.068 | 37.386 | 11.352 | 1.00 | 38.41 | X | C |
| ATOM | 6431 | CG | PHE | 29 | 83.484 | 36.454 | 12.462 | 1.00 | 38.41 | X | C |
| ATOM | 6432 | CD1 | PHE | 29 | 82.795 | 36.440 | 13.676 | 1.00 | 38.41 | X | C |
| ATOM | 6433 | CD2 | PHE | 29 | 84.570 | 35.587 | 12.296 | 1.00 | 38.41 | X | C |
| ATOM | 6434 | CE1 | PHE | 29 | 83.183 | 35.577 | 14.709 | 1.00 | 38.41 | X | C |
| ATOM | 6435 | CE2 | PHE | 29 | 84.967 | 34.718 | 13.324 | 1.00 | 38.41 | X | C |
| ATOM | 6436 | CZ | PHE | 29 | 84.272 | 34.715 | 14.530 | 1.00 | 38.41 | X | C |
| ATOM | 6437 | C | PHE | 29 | 84.616 | 39.225 | 12.021 | 1.00 | 37.68 | X | C |
| ATOM | 6438 | O | PHE | 29 | 84.958 | 39.552 | 13.160 | 1.00 | 37.68 | X | O |
| ATOM | 6439 | N | SER | 30 | 85.462 | 39.160 | 10.998 | 1.00 | 22.05 | X | N |
| ATOM | 6440 | CA | SER | 30 | 86.890 | 39.421 | 11.157 | 1.00 | 22.05 | X | C |
| ATOM | 6441 | CB | SER | 30 | 87.553 | 39.545 | 9.783 | 1.00 | 37.79 | X | C |
| ATOM | 6442 | OG | SER | 30 | 86.886 | 40.481 | 8.959 | 1.00 | 37.79 | X | O |
| ATOM | 6443 | C | SER | 30 | 87.270 | 40.622 | 12.014 | 1.00 | 22.05 | X | C |
| ATOM | 6444 | O | SER | 30 | 88.326 | 40.634 | 12.639 | 1.00 | 22.05 | X | O |
| ATOM | 6445 | N | ARG | 31 | 86.395 | 41.615 | 12.063 | 1.00 | 29.69 | X | N |
| ATOM | 6446 | CA | ARG | 31 | 86.651 | 42.846 | 12.801 | 1.00 | 29.69 | X | C |
| ATOM | 6447 | CB | ARG | 31 | 85.819 | 43.956 | 12.162 | 1.00 | 51.15 | X | C |
| ATOM | 6448 | CG | ARG | 31 | 86.068 | 45.323 | 12.719 | 1.00 | 51.15 | X | C |
| ATOM | 6449 | CD | ARG | 31 | 84.999 | 46.281 | 12.231 | 1.00 | 51.15 | X | C |
| ATOM | 6450 | NE | ARG | 31 | 84.964 | 46.383 | 10.772 | 1.00 | 51.15 | X | N |
| ATOM | 6451 | CZ | ARG | 31 | 85.899 | 46.974 | 10.038 | 1.00 | 51.15 | X | C |
| ATOM | 6452 | NH1 | ARG | 31 | 86.959 | 47.523 | 10.621 | 1.00 | 51.15 | X | N |
| ATOM | 6453 | NH2 | ARG | 31 | 85.764 | 47.027 | 8.722 | 1.00 | 51.15 | X | N |
| ATOM | 6454 | C | ARG | 31 | 86.425 | 42.833 | 14.329 | 1.00 | 29.69 | X | C |
| ATOM | 6455 | O | ARG | 31 | 87.226 | 43.399 | 15.080 | 1.00 | 29.69 | X | O |
| ATOM | 6456 | N | TYR | 32 | 85.352 | 42.185 | 14.785 | 1.00 | 39.46 | X | N |
| ATOM | 6457 | CA | TYR | 32 | 85.009 | 42.144 | 16.217 | 1.00 | 39.46 | X | C |
| ATOM | 6458 | CB | TYR | 32 | 83.506 | 41.880 | 16.409 | 1.00 | 51.56 | X | C |
| ATOM | 6459 | CG | TYR | 32 | 82.601 | 42.689 | 15.516 | 1.00 | 51.56 | X | C |
| ATOM | 6460 | CD1 | TYR | 32 | 82.540 | 42.437 | 14.148 | 1.00 | 51.56 | X | C |
| ATOM | 6461 | CE1 | TYR | 32 | 81.721 | 43.181 | 13.316 | 1.00 | 51.56 | X | C |
| ATOM | 6462 | CD2 | TYR | 32 | 81.811 | 43.714 | 16.034 | 1.00 | 51.56 | X | C |
| ATOM | 6463 | CE2 | TYR | 32 | 80.985 | 44.467 | 15.209 | 1.00 | 51.56 | X | C |
| ATOM | 6464 | CZ | TYR | 32 | 80.946 | 44.193 | 13.851 | 1.00 | 51.56 | X | C |
| ATOM | 6465 | OH | TYR | 32 | 80.135 | 44.929 | 13.015 | 1.00 | 51.56 | X | O |
| ATOM | 6466 | C | TYR | 32 | 85.761 | 41.108 | 17.037 | 1.00 | 39.46 | X | C |
| ATOM | 6467 | O | TYR | 32 | 86.159 | 40.072 | 16.515 | 1.00 | 39.46 | X | O |
| ATOM | 6468 | N | THR | 33 | 85.943 | 41.386 | 18.328 | 1.00 | 29.44 | X | N |
| ATOM | 6469 | CA | THR | 33 | 86.611 | 40.421 | 19.191 | 1.00 | 29.44 | X | C |
| ATOM | 6470 | CB | THR | 33 | 87.510 | 41.080 | 20.315 | 1.00 | 20.65 | X | C |
| ATOM | 6471 | OG1 | THR | 33 | 86.749 | 41.242 | 21.514 | 1.00 | 20.65 | X | O |
| ATOM | 6472 | CG2 | THR | 33 | 88.072 | 42.437 | 19.866 | 1.00 | 20.65 | X | C |
| ATOM | 6473 | C | THR | 33 | 85.483 | 39.614 | 19.835 | 1.00 | 29.44 | X | C |
| ATOM | 6474 | O | THR | 33 | 84.632 | 40.167 | 20.536 | 1.00 | 29.44 | X | O |
| ATOM | 6475 | N | MET | 34 | 85.484 | 38.307 | 19.568 | 1.00 | 30.35 | X | N |
| ATOM | 6476 | CA | MET | 34 | 84.474 | 37.391 | 20.084 | 1.00 | 30.35 | X | C |
| ATOM | 6477 | CB | MET | 34 | 84.235 | 36.284 | 19.067 | 1.00 | 43.39 | X | C |
| ATOM | 6478 | CG | MET | 34 | 84.070 | 36.798 | 17.652 | 1.00 | 43.39 | X | C |
| ATOM | 6479 | SD | MET | 34 | 82.775 | 38.029 | 17.525 | 1.00 | 43.39 | X | S |
| ATOM | 6480 | CE | MET | 34 | 81.376 | 37.024 | 17.198 | 1.00 | 43.39 | X | C |
| ATOM | 6481 | C | MET | 34 | 84.867 | 36.785 | 21.430 | 1.00 | 30.35 | X | C |
| ATOM | 6482 | O | MET | 34 | 86.049 | 36.761 | 21.790 | 1.00 | 30.35 | X | O |
| ATOM | 6483 | N | SER | 35 | 83.866 | 36.293 | 22.164 | 1.00 | 35.95 | X | N |
| ATOM | 6484 | CA | SER | 35 | 84.073 | 35.701 | 23.487 | 1.00 | 35.95 | X | C |
| ATOM | 6485 | CB | SER | 35 | 83.875 | 36.765 | 24.580 | 1.00 | 34.42 | X | C |
| ATOM | 6486 | OG | SER | 35 | 84.740 | 37.878 | 24.420 | 1.00 | 34.42 | X | O |
| ATOM | 6487 | C | SER | 35 | 83.105 | 34.548 | 23.761 | 1.00 | 35.95 | X | C |
| ATOM | 6488 | O | SER | 35 | 82.191 | 34.290 | 22.978 | 1.00 | 35.95 | X | O |
| ATOM | 6489 | N | TRP | 36 | 83.323 | 33.856 | 24.879 | 1.00 | 43.17 | X | N |
| ATOM | 6490 | CA | TRP | 36 | 82.457 | 32.758 | 25.309 | 1.00 | 43.17 | X | C |
| ATOM | 6491 | CB | TRP | 36 | 83.159 | 31.383 | 25.200 | 1.00 | 32.84 | X | C |
| ATOM | 6492 | CG | TRP | 36 | 83.355 | 30.875 | 23.782 | 1.00 | 32.84 | X | C |
| ATOM | 6493 | CD2 | TRP | 36 | 82.419 | 30.118 | 22.998 | 1.00 | 32.84 | X | C |
| ATOM | 6494 | CE2 | TRP | 36 | 82.982 | 29.957 | 21.711 | 1.00 | 32.84 | X | C |
| ATOM | 6495 | CE3 | TRP | 36 | 81.153 | 29.564 | 23.257 | 1.00 | 32.84 | X | C |
| ATOM | 6496 | CD1 | TRP | 36 | 84.419 | 31.124 | 22.962 | 1.00 | 32.84 | X | C |
| ATOM | 6497 | NE1 | TRP | 36 | 84.201 | 30.579 | 21.716 | 1.00 | 32.84 | X | N |

Fig. 19: A-90

| ATOM | 6498 | CZ2 | TRP | 36 | 82.324 | 29.267 | 20.681 | 1.00 | 32.84 | X | C |
|------|------|-----|-----|----|--------|--------|--------|------|-------|---|---|
| ATOM | 6499 | CZ3 | TRP | 36 | 80.495 | 28.877 | 22.228 | 1.00 | 32.84 | X | C |
| ATOM | 6500 | CH2 | TRP | 36 | 81.086 | 28.738 | 20.957 | 1.00 | 32.84 | X | C |
| ATOM | 6501 | C | TRP | 36 | 82.056 | 33.022 | 26.764 | 1.00 | 43.17 | X | C |
| ATOM | 6502 | O | TRP | 36 | 82.908 | 33.298 | 27.615 | 1.00 | 43.17 | X | O |
| ATOM | 6503 | N | VAL | 37 | 80.751 | 32.958 | 27.026 | 1.00 | 29.19 | X | N |
| ATOM | 6504 | CA | VAL | 37 | 80.177 | 33.175 | 28.360 | 1.00 | 29.19 | X | C |
| ATOM | 6505 | CB | VAL | 37 | 79.213 | 34.419 | 28.353 | 1.00 | 8.00 | X | C |
| ATOM | 6506 | CG1 | VAL | 37 | 78.350 | 34.467 | 29.621 | 1.00 | 8.00 | X | C |
| ATOM | 6507 | CG2 | VAL | 37 | 80.026 | 35.689 | 28.240 | 1.00 | 8.00 | X | C |
| ATOM | 6508 | C | VAL | 37 | 79.412 | 31.907 | 28.760 | 1.00 | 29.19 | X | C |
| ATOM | 6509 | O | VAL | 37 | 78.629 | 31.381 | 27.971 | 1.00 | 29.19 | X | O |
| ATOM | 6510 | N | ARG | 38 | 79.651 | 31.415 | 29.974 | 1.00 | 61.80 | X | N |
| ATOM | 6511 | CA | ARG | 38 | 78.992 | 30.198 | 30.454 | 1.00 | 61.80 | X | C |
| ATOM | 6512 | CB | ARG | 38 | 80.036 | 29.167 | 30.899 | 1.00 | 27.50 | X | C |
| ATOM | 6513 | CG | ARG | 38 | 80.926 | 29.688 | 32.011 | 1.00 | 27.50 | X | C |
| ATOM | 6514 | CD | ARG | 38 | 81.370 | 28.603 | 32.965 | 1.00 | 27.50 | X | C |
| ATOM | 6515 | NE | ARG | 38 | 82.222 | 27.579 | 32.364 | 1.00 | 27.50 | X | N |
| ATOM | 6516 | CZ | ARG | 38 | 83.391 | 27.181 | 32.874 | 1.00 | 27.50 | X | C |
| ATOM | 6517 | NH1 | ARG | 38 | 83.862 | 27.725 | 33.992 | 1.00 | 27.50 | X | N |
| ATOM | 6518 | NH2 | ARG | 38 | 84.087 | 26.217 | 32.281 | 1.00 | 27.50 | X | N |
| ATOM | 6519 | C | ARG | 38 | 78.053 | 30.468 | 31.628 | 1.00 | 61.80 | X | C |
| ATOM | 6520 | O | ARG | 38 | 78.104 | 31.528 | 32.245 | 1.00 | 61.80 | X | O |
| ATOM | 6521 | N | GLN | 39 | 77.204 | 29.491 | 31.934 | 1.00 | 39.46 | X | N |
| ATOM | 6522 | CA | GLN | 39 | 76.269 | 29.597 | 33.049 | 1.00 | 39.46 | X | C |
| ATOM | 6523 | CB | GLN | 39 | 74.982 | 30.269 | 32.588 | 1.00 | 44.48 | X | C |
| ATOM | 6524 | CG | GLN | 39 | 73.997 | 30.530 | 33.708 | 1.00 | 44.48 | X | C |
| ATOM | 6525 | CD | GLN | 39 | 72.916 | 31.497 | 33.294 | 1.00 | 44.48 | X | C |
| ATOM | 6526 | OE1 | GLN | 39 | 72.269 | 31.320 | 32.252 | 1.00 | 44.48 | X | O |
| ATOM | 6527 | NE2 | GLN | 39 | 72.709 | 32.532 | 34.106 | 1.00 | 44.48 | X | N |
| ATOM | 6528 | C | GLN | 39 | 75.955 | 28.224 | 33.663 | 1.00 | 39.46 | X | C |
| ATOM | 6529 | O | GLN | 39 | 75.233 | 27.404 | 33.076 | 1.00 | 39.46 | X | O |
| ATOM | 6530 | N | ALA | 40 | 76.514 | 27.984 | 34.846 | 1.00 | 47.11 | X | N |
| ATOM | 6531 | CA | ALA | 40 | 76.324 | 26.727 | 35.558 | 1.00 | 47.11 | X | C |
| ATOM | 6532 | CB | ALA | 40 | 77.241 | 26.678 | 36.773 | 1.00 | 19.87 | X | C |
| ATOM | 6533 | C | ALA | 40 | 74.875 | 26.592 | 35.995 | 1.00 | 47.11 | X | C |
| ATOM | 6534 | O | ALA | 40 | 74.296 | 27.542 | 36.512 | 1.00 | 47.11 | X | O |
| ATOM | 6535 | N | PRO | 41 | 74.271 | 25.403 | 35.802 | 1.00 | 63.91 | X | N |
| ATOM | 6536 | CD | PRO | 41 | 74.879 | 24.157 | 35.299 | 1.00 | 66.56 | X | C |
| ATOM | 6537 | CA | PRO | 41 | 72.875 | 25.168 | 36.187 | 1.00 | 63.91 | X | C |
| ATOM | 6538 | CB | PRO | 41 | 72.793 | 23.649 | 36.244 | 1.00 | 66.56 | X | C |
| ATOM | 6539 | CG | PRO | 41 | 73.667 | 23.254 | 35.115 | 1.00 | 66.56 | X | C |
| ATOM | 6540 | C | PRO | 41 | 72.507 | 25.826 | 37.508 | 1.00 | 63.91 | X | C |
| ATOM | 6541 | O | PRO | 41 | 73.186 | 25.637 | 38.522 | 1.00 | 63.91 | X | O |
| ATOM | 6542 | N | GLY | 42 | 71.432 | 26.608 | 37.478 | 1.00 | 63.56 | X | N |
| ATOM | 6543 | CA | GLY | 42 | 70.979 | 27.297 | 38.671 | 1.00 | 63.56 | X | C |
| ATOM | 6544 | C | GLY | 42 | 71.963 | 28.342 | 39.165 | 1.00 | 63.56 | X | C |
| ATOM | 6545 | O | GLY | 42 | 71.920 | 28.732 | 40.334 | 1.00 | 63.56 | X | O |
| ATOM | 6546 | N | LYS | 43 | 72.846 | 28.793 | 38.276 | 1.00 | 103.79 | X | N |
| ATOM | 6547 | CA | LYS | 43 | 73.852 | 29.802 | 38.607 | 1.00 | 103.79 | X | C |
| ATOM | 6548 | CB | LYS | 43 | 75.248 | 29.168 | 38.641 | 1.00 | 95.84 | X | C |
| ATOM | 6549 | CG | LYS | 43 | 75.752 | 28.830 | 40.037 | 1.00 | 95.84 | X | C |
| ATOM | 6550 | CD | LYS | 43 | 74.840 | 27.853 | 40.755 | 1.00 | 95.84 | X | C |
| ATOM | 6551 | CE | LYS | 43 | 75.225 | 27.734 | 42.222 | 1.00 | 95.84 | X | C |
| ATOM | 6552 | NZ | LYS | 43 | 75.138 | 29.048 | 42.920 | 1.00 | 95.84 | X | N |
| ATOM | 6553 | C | LYS | 43 | 73.848 | 30.984 | 37.634 | 1.00 | 103.79 | X | C |
| ATOM | 6554 | O | LYS | 43 | 73.085 | 31.013 | 36.668 | 1.00 | 103.79 | X | O |
| ATOM | 6555 | N | GLY | 44 | 74.714 | 31.956 | 37.899 | 1.00 | 36.05 | X | N |
| ATOM | 6556 | CA | GLY | 44 | 74.796 | 33.131 | 37.055 | 1.00 | 36.05 | X | C |
| ATOM | 6557 | C | GLY | 44 | 75.710 | 33.025 | 35.845 | 1.00 | 36.05 | X | C |
| ATOM | 6558 | O | GLY | 44 | 76.150 | 31.931 | 35.477 | 1.00 | 36.05 | X | O |
| ATOM | 6559 | N | LEU | 45 | 76.003 | 34.186 | 35.249 | 1.00 | 24.14 | X | N |
| ATOM | 6560 | CA | LEU | 45 | 76.832 | 34.316 | 34.046 | 1.00 | 24.14 | X | C |
| ATOM | 6561 | CB | LEU | 45 | 76.343 | 35.504 | 33.214 | 1.00 | 15.59 | X | C |
| ATOM | 6562 | CG | LEU | 45 | 74.932 | 35.346 | 32.638 | 1.00 | 15.59 | X | C |
| ATOM | 6563 | CD1 | LEU | 45 | 74.470 | 36.606 | 31.917 | 1.00 | 15.59 | X | C |
| ATOM | 6564 | CD2 | LEU | 45 | 74.942 | 34.179 | 31.677 | 1.00 | 15.59 | X | C |
| ATOM | 6565 | C | LEU | 45 | 78.316 | 34.474 | 34.311 | 1.00 | 24.14 | X | C |
| ATOM | 6566 | O | LEU | 45 | 78.732 | 35.324 | 35.095 | 1.00 | 24.14 | X | O |
| ATOM | 6567 | N | GLU | 46 | 79.110 | 33.661 | 33.624 | 1.00 | 56.59 | X | N |
| ATOM | 6568 | CA | GLU | 46 | 80.557 | 33.686 | 33.774 | 1.00 | 56.59 | X | C |
| ATOM | 6569 | CB | GLU | 46 | 81.034 | 32.373 | 34.412 | 1.00 | 46.99 | X | C |
| ATOM | 6570 | CG | GLU | 46 | 82.536 | 32.308 | 34.666 | 1.00 | 46.99 | X | C |

Fig. 19: A-91

```
ATOM   6571  CD   GLU  46      82.953  31.066  35.438  1.00  46.99      X  C
ATOM   6572  OE1  GLU  46      82.642  29.952  34.970  1.00  46.99      X  O
ATOM   6573  OE2  GLU  46      83.594  31.201  36.508  1.00  46.99      X  O
ATOM   6574  C    GLU  46      81.272  33.904  32.439  1.00  56.59      X  C
ATOM   6575  O    GLU  46      80.821  33.433  31.393  1.00  56.59      X  O
ATOM   6576  N    TRP  47      82.385  34.632  32.489  1.00  30.60      X  N
ATOM   6577  CA   TRP  47      83.188  34.910  31.300  1.00  30.60      X  C
ATOM   6578  CB   TRP  47      83.889  36.273  31.426  1.00  23.41      X  C
ATOM   6579  CG   TRP  47      84.944  36.481  30.385  1.00  23.41      X  C
ATOM   6580  CD2  TRP  47      86.358  36.500  30.601  1.00  23.41      X  C
ATOM   6581  CE2  TRP  47      86.971  36.591  29.328  1.00  23.41      X  C
ATOM   6582  CE3  TRP  47      87.170  36.441  31.746  1.00  23.41      X  C
ATOM   6583  CD1  TRP  47      84.759  36.570  29.031  1.00  23.41      X  C
ATOM   6584  NE1  TRP  47      85.969  36.633  28.392  1.00  23.41      X  N
ATOM   6585  CZ2  TRP  47      88.365  36.622  29.165  1.00  23.41      X  C
ATOM   6586  CZ3  TRP  47      88.553  36.470  31.587  1.00  23.41      X  C
ATOM   6587  CH2  TRP  47      89.137  36.560  30.304  1.00  23.41      X  C
ATOM   6588  C    TRP  47      84.231  33.810  31.153  1.00  30.60      X  C
ATOM   6589  O    TRP  47      84.965  33.516  32.097  1.00  30.60      X  O
ATOM   6590  N    VAL  48      84.317  33.219  29.967  1.00  24.17      X  N
ATOM   6591  CA   VAL  48      85.270  32.128  29.755  1.00  24.17      X  C
ATOM   6592  CB   VAL  48      84.589  30.924  29.011  1.00  22.03      X  C
ATOM   6593  CG1  VAL  48      85.589  29.786  28.790  1.00  22.03      X  C
ATOM   6594  CG2  VAL  48      83.408  30.436  29.805  1.00  22.03      X  C
ATOM   6595  C    VAL  48      86.550  32.490  29.006  1.00  24.17      X  C
ATOM   6596  O    VAL  48      87.640  32.477  29.579  1.00  24.17      X  O
ATOM   6597  N    ALA  49      86.407  32.800  27.724  1.00  21.43      X  N
ATOM   6598  CA   ALA  49      87.550  33.118  26.885  1.00  21.43      X  C
ATOM   6599  CB   ALA  49      87.953  31.884  26.094  1.00  38.48      X  C
ATOM   6600  C    ALA  49      87.228  34.257  25.934  1.00  21.43      X  C
ATOM   6601  O    ALA  49      86.066  34.661  25.825  1.00  21.43      X  O
ATOM   6602  N    THR  50      88.257  34.745  25.235  1.00  24.70      X  N
ATOM   6603  CA   THR  50      88.115  35.856  24.286  1.00  24.70      X  C
ATOM   6604  CB   THR  50      87.952  37.202  25.048  1.00  38.80      X  C
ATOM   6605  OG1  THR  50      86.711  37.215  25.763  1.00  38.80      X  O
ATOM   6606  CG2  THR  50      87.981  38.369  24.087  1.00  38.80      X  C
ATOM   6607  C    THR  50      89.298  36.039  23.324  1.00  24.70      X  C
ATOM   6608  O    THR  50      90.456  35.935  23.738  1.00  24.70      X  O
ATOM   6609  N    ILE  51      89.010  36.300  22.047  1.00  32.54      X  N
ATOM   6610  CA   ILE  51      90.075  36.599  21.074  1.00  32.54      X  C
ATOM   6611  CB   ILE  51      90.333  35.495  19.998  1.00  54.98      X  C
ATOM   6612  CG2  ILE  51      90.567  34.178  20.661  1.00  54.98      X  C
ATOM   6613  CG1  ILE  51      89.180  35.415  18.997  1.00  54.98      X  C
ATOM   6614  CD1  ILE  51      87.893  34.921  19.582  1.00  54.98      X  C
ATOM   6615  C    ILE  51      89.674  37.865  20.335  1.00  32.54      X  C
ATOM   6616  O    ILE  51      88.516  38.024  19.937  1.00  32.54      X  O
ATOM   6617  N    SER  52      90.628  38.774  20.167  1.00  43.61      X  N
ATOM   6618  CA   SER  52      90.361  40.024  19.477  1.00  43.61      X  C
ATOM   6619  CB   SER  52      91.374  41.081  19.910  1.00  24.33      X  C
ATOM   6620  OG   SER  52      92.684  40.702  19.528  1.00  24.33      X  O
ATOM   6621  C    SER  52      90.450  39.789  17.973  1.00  43.61      X  C
ATOM   6622  O    SER  52      90.677  38.663  17.533  1.00  43.61      X  O
ATOM   6623  N    GLY  53      90.243  40.843  17.187  1.00  34.59      X  N
ATOM   6624  CA   GLY  53      90.336  40.707  15.747  1.00  34.59      X  C
ATOM   6625  C    GLY  53      91.800  40.559  15.381  1.00  34.59      X  C
ATOM   6626  O    GLY  53      92.152  40.020  14.332  1.00  34.59      X  O
ATOM   6627  N    GLY  54      92.658  41.047  16.266  1.00  29.30      X  N
ATOM   6628  CA   GLY  54      94.079  40.949  16.033  1.00  29.30      X  C
ATOM   6629  C    GLY  54      94.555  39.550  16.359  1.00  29.30      X  C
ATOM   6630  O    GLY  54      95.642  39.135  15.954  1.00  29.30      X  O
ATOM   6631  N    GLY  55      93.747  38.811  17.103  1.00  15.27      X  N
ATOM   6632  CA   GLY  55      94.139  37.465  17.437  1.00  15.27      X  C
ATOM   6633  C    GLY  55      94.596  37.254  18.867  1.00  15.27      X  C
ATOM   6634  O    GLY  55      94.878  36.105  19.231  1.00  15.27      X  O
ATOM   6635  N    HIS  56      94.676  38.319  19.675  1.00  13.76      X  N
ATOM   6636  CA   HIS  56      95.101  38.181  21.076  1.00  13.76      X  C
ATOM   6637  CB   HIS  56      95.268  39.543  21.741  1.00  60.58      X  C
ATOM   6638  CG   HIS  56      96.115  40.490  20.957  1.00  60.58      X  C
ATOM   6639  CD2  HIS  56      97.417  40.838  21.087  1.00  60.58      X  C
ATOM   6640  ND1  HIS  56      95.638  41.180  19.862  1.00  60.58      X  N
ATOM   6641  CE1  HIS  56      96.611  41.913  19.351  1.00  60.58      X  C
ATOM   6642  NE2  HIS  56      97.701  41.724  20.075  1.00  60.58      X  N
ATOM   6643  C    HIS  56      94.071  37.383  21.857  1.00  13.76      X  C
```

Fig. 19: A-92

| | | | | | | | | | | | |
|---|---|---|---|---|---|---|---|---|---|---|---|
| ATOM | 6644 | O | HIS | 56 | 92.864 | 37.621 | 21.736 | 1.00 | 13.76 | X | O |
| ATOM | 6645 | N | THR | 57 | 94.529 | 36.438 | 22.671 | 1.00 | 20.05 | X | N |
| ATOM | 6646 | CA | THR | 57 | 93.583 | 35.632 | 23.436 | 1.00 | 20.05 | X | C |
| ATOM | 6647 | CB | THR | 57 | 93.759 | 34.123 | 23.096 | 1.00 | 15.53 | X | C |
| ATOM | 6648 | OG1 | THR | 57 | 95.015 | 33.651 | 23.587 | 1.00 | 15.53 | X | O |
| ATOM | 6649 | CG2 | THR | 57 | 93.734 | 33.929 | 21.593 | 1.00 | 15.53 | X | C |
| ATOM | 6650 | C | THR | 57 | 93.655 | 35.876 | 24.952 | 1.00 | 20.05 | X | C |
| ATOM | 6651 | O | THR | 57 | 94.716 | 36.142 | 25.512 | 1.00 | 20.05 | X | O |
| ATOM | 6652 | N | TYR | 58 | 92.500 | 35.808 | 25.603 | 1.00 | 19.06 | X | N |
| ATOM | 6653 | CA | TYR | 58 | 92.410 | 36.037 | 27.040 | 1.00 | 19.06 | X | C |
| ATOM | 6654 | CB | TYR | 58 | 91.829 | 37.428 | 27.304 | 1.00 | 22.48 | X | C |
| ATOM | 6655 | CG | TYR | 58 | 92.614 | 38.542 | 26.661 | 1.00 | 22.48 | X | C |
| ATOM | 6656 | CD1 | TYR | 58 | 93.565 | 39.252 | 27.384 | 1.00 | 22.48 | X | C |
| ATOM | 6657 | CE1 | TYR | 58 | 94.308 | 40.265 | 26.788 | 1.00 | 22.48 | X | C |
| ATOM | 6658 | CD2 | TYR | 58 | 92.423 | 38.871 | 25.316 | 1.00 | 22.48 | X | C |
| ATOM | 6659 | CE2 | TYR | 58 | 93.167 | 39.886 | 24.703 | 1.00 | 22.48 | X | C |
| ATOM | 6660 | CZ | TYR | 58 | 94.105 | 40.580 | 25.447 | 1.00 | 22.48 | X | C |
| ATOM | 6661 | OH | TYR | 58 | 94.828 | 41.611 | 24.876 | 1.00 | 22.48 | X | O |
| ATOM | 6662 | C | TYR | 58 | 91.513 | 34.973 | 27.656 | 1.00 | 19.06 | X | C |
| ATOM | 6663 | O | TYR | 58 | 90.442 | 34.660 | 27.123 | 1.00 | 19.06 | X | O |
| ATOM | 6664 | N | TYR | 59 | 91.945 | 34.437 | 28.792 | 1.00 | 29.06 | X | N |
| ATOM | 6665 | CA | TYR | 59 | 91.199 | 33.378 | 29.456 | 1.00 | 29.06 | X | C |
| ATOM | 6666 | CB | TYR | 59 | 91.988 | 32.080 | 29.371 | 1.00 | 21.37 | X | C |
| ATOM | 6667 | CG | TYR | 59 | 92.252 | 31.641 | 27.969 | 1.00 | 21.37 | X | C |
| ATOM | 6668 | CD1 | TYR | 59 | 91.352 | 30.813 | 27.303 | 1.00 | 21.37 | X | C |
| ATOM | 6669 | CE1 | TYR | 59 | 91.573 | 30.428 | 25.988 | 1.00 | 21.37 | X | C |
| ATOM | 6670 | CD2 | TYR | 59 | 93.382 | 32.076 | 27.286 | 1.00 | 21.37 | X | C |
| ATOM | 6671 | CE2 | TYR | 59 | 93.608 | 31.698 | 25.968 | 1.00 | 21.37 | X | C |
| ATOM | 6672 | CZ | TYR | 59 | 92.697 | 30.874 | 25.330 | 1.00 | 21.37 | X | C |
| ATOM | 6673 | OH | TYR | 59 | 92.897 | 30.495 | 24.027 | 1.00 | 21.37 | X | O |
| ATOM | 6674 | C | TYR | 59 | 90.857 | 33.605 | 30.910 | 1.00 | 29.06 | X | C |
| ATOM | 6675 | O | TYR | 59 | 91.575 | 34.287 | 31.648 | 1.00 | 29.06 | X | O |
| ATOM | 6676 | N | LEU | 60 | 89.745 | 33.002 | 31.308 | 1.00 | 26.45 | X | N |
| ATOM | 6677 | CA | LEU | 60 | 89.309 | 33.048 | 32.689 | 1.00 | 26.45 | X | C |
| ATOM | 6678 | CB | LEU | 60 | 87.927 | 32.397 | 32.826 | 1.00 | 24.21 | X | C |
| ATOM | 6679 | CG | LEU | 60 | 87.411 | 32.193 | 34.252 | 1.00 | 24.21 | X | C |
| ATOM | 6680 | CD1 | LEU | 60 | 87.173 | 33.538 | 34.911 | 1.00 | 24.21 | X | C |
| ATOM | 6681 | CD2 | LEU | 60 | 86.135 | 31.380 | 34.223 | 1.00 | 24.21 | X | C |
| ATOM | 6682 | C | LEU | 60 | 90.382 | 32.189 | 33.360 | 1.00 | 26.45 | X | C |
| ATOM | 6683 | O | LEU | 60 | 90.822 | 31.191 | 32.781 | 1.00 | 26.45 | X | O |
| ATOM | 6684 | N | ASP | 61 | 90.822 | 32.570 | 34.553 | 1.00 | 64.06 | X | N |
| ATOM | 6685 | CA | ASP | 61 | 91.865 | 31.810 | 35.240 | 1.00 | 64.06 | X | C |
| ATOM | 6686 | CB | ASP | 61 | 92.297 | 32.556 | 36.502 | 1.00 | 60.41 | X | C |
| ATOM | 6687 | CG | ASP | 61 | 92.984 | 33.865 | 36.183 | 1.00 | 60.41 | X | C |
| ATOM | 6688 | OD1 | ASP | 61 | 93.262 | 34.650 | 37.114 | 1.00 | 60.41 | X | O |
| ATOM | 6689 | OD2 | ASP | 61 | 93.250 | 34.106 | 34.986 | 1.00 | 60.41 | X | O |
| ATOM | 6690 | C | ASP | 61 | 91.477 | 30.371 | 35.576 | 1.00 | 64.06 | X | C |
| ATOM | 6691 | O | ASP | 61 | 92.337 | 29.503 | 35.701 | 1.00 | 64.06 | X | O |
| ATOM | 6692 | N | SER | 62 | 90.181 | 30.122 | 35.707 | 1.00 | 57.78 | X | N |
| ATOM | 6693 | CA | SER | 62 | 89.681 | 28.791 | 36.028 | 1.00 | 57.78 | X | C |
| ATOM | 6694 | CB | SER | 62 | 88.196 | 28.868 | 36.386 | 1.00 | 42.55 | X | C |
| ATOM | 6695 | OG | SER | 62 | 87.643 | 27.575 | 36.556 | 1.00 | 42.55 | X | O |
| ATOM | 6696 | C | SER | 62 | 89.872 | 27.787 | 34.894 | 1.00 | 57.78 | X | C |
| ATOM | 6697 | O | SER | 62 | 90.000 | 26.590 | 35.142 | 1.00 | 57.78 | X | O |
| ATOM | 6698 | N | VAL | 63 | 89.890 | 28.269 | 33.655 | 1.00 | 47.11 | X | N |
| ATOM | 6699 | CA | VAL | 63 | 90.047 | 27.383 | 32.504 | 1.00 | 47.11 | X | C |
| ATOM | 6700 | CB | VAL | 63 | 88.796 | 27.464 | 31.555 | 1.00 | 39.29 | X | C |
| ATOM | 6701 | CG1 | VAL | 63 | 87.513 | 27.472 | 32.375 | 1.00 | 39.29 | X | C |
| ATOM | 6702 | CG2 | VAL | 63 | 88.863 | 28.700 | 30.679 | 1.00 | 39.29 | X | C |
| ATOM | 6703 | C | VAL | 63 | 91.318 | 27.660 | 31.686 | 1.00 | 47.11 | X | C |
| ATOM | 6704 | O | VAL | 63 | 91.504 | 27.093 | 30.603 | 1.00 | 47.11 | X | O |
| ATOM | 6705 | N | LYS | 64 | 92.200 | 28.511 | 32.208 | 1.00 | 47.01 | X | N |
| ATOM | 6706 | CA | LYS | 64 | 93.424 | 28.843 | 31.483 | 1.00 | 47.01 | X | C |
| ATOM | 6707 | CB | LYS | 64 | 94.116 | 30.063 | 32.107 | 1.00 | 84.46 | X | C |
| ATOM | 6708 | CG | LYS | 64 | 95.038 | 30.797 | 31.135 | 1.00 | 84.46 | X | C |
| ATOM | 6709 | CD | LYS | 64 | 95.670 | 32.025 | 31.766 | 1.00 | 84.46 | X | C |
| ATOM | 6710 | CE | LYS | 64 | 96.370 | 32.907 | 30.725 | 1.00 | 84.46 | X | C |
| ATOM | 6711 | NZ | LYS | 64 | 95.419 | 33.654 | 29.833 | 1.00 | 84.46 | X | N |
| ATOM | 6712 | C | LYS | 64 | 94.388 | 27.666 | 31.441 | 1.00 | 47.01 | X | C |
| ATOM | 6713 | O | LYS | 64 | 94.757 | 27.113 | 32.479 | 1.00 | 47.01 | X | O |
| ATOM | 6714 | N | GLY | 65 | 94.795 | 27.289 | 30.231 | 1.00 | 35.35 | X | N |
| ATOM | 6715 | CA | GLY | 65 | 95.704 | 26.167 | 30.073 | 1.00 | 35.35 | X | C |
| ATOM | 6716 | C | GLY | 65 | 94.953 | 24.919 | 29.652 | 1.00 | 35.35 | X | C |

Fig. 19: A-93

| | | | | | | | | | | |
|---|---|---|---|---|---|---|---|---|---|---|
| ATOM | 6717 | O | GLY | 65 | 95.547 | 23.945 | 29.195 | 1.00 | 35.35 | X | O |
| ATOM | 6718 | N | ARG | 66 | 93.634 | 24.956 | 29.809 | 1.00 | 33.32 | X | N |
| ATOM | 6719 | CA | ARG | 66 | 92.791 | 23.833 | 29.450 | 1.00 | 33.32 | X | C |
| ATOM | 6720 | CB | ARG | 66 | 91.881 | 23.470 | 30.616 | 1.00 | 43.17 | X | C |
| ATOM | 6721 | CG | ARG | 66 | 92.594 | 23.386 | 31.958 | 1.00 | 43.17 | X | C |
| ATOM | 6722 | CD | ARG | 66 | 91.684 | 22.813 | 33.050 | 1.00 | 43.17 | X | C |
| ATOM | 6723 | NE | ARG | 66 | 90.548 | 23.679 | 33.367 | 1.00 | 43.17 | X | N |
| ATOM | 6724 | CZ | ARG | 66 | 89.277 | 23.296 | 33.305 | 1.00 | 43.17 | X | C |
| ATOM | 6725 | NH1 | ARG | 66 | 88.973 | 22.061 | 32.932 | 1.00 | 43.17 | X | N |
| ATOM | 6726 | NH2 | ARG | 66 | 88.309 | 24.144 | 33.630 | 1.00 | 43.17 | X | N |
| ATOM | 6727 | C | ARG | 66 | 91.945 | 24.169 | 28.232 | 1.00 | 33.32 | X | C |
| ATOM | 6728 | O | ARG | 66 | 91.775 | 23.336 | 27.346 | 1.00 | 33.32 | X | O |
| ATOM | 6729 | N | PHE | 67 | 91.411 | 25.389 | 28.191 | 1.00 | 33.69 | X | N |
| ATOM | 6730 | CA | PHE | 67 | 90.567 | 25.834 | 27.074 | 1.00 | 33.69 | X | C |
| ATOM | 6731 | CB | PHE | 67 | 89.444 | 26.750 | 27.587 | 1.00 | 42.44 | X | C |
| ATOM | 6732 | CG | PHE | 67 | 88.346 | 26.030 | 28.330 | 1.00 | 42.44 | X | C |
| ATOM | 6733 | CD1 | PHE | 67 | 88.573 | 24.802 | 28.943 | 1.00 | 42.44 | X | C |
| ATOM | 6734 | CD2 | PHE | 67 | 87.074 | 26.594 | 28.426 | 1.00 | 42.44 | X | C |
| ATOM | 6735 | CE1 | PHE | 67 | 87.547 | 24.145 | 29.637 | 1.00 | 42.44 | X | C |
| ATOM | 6736 | CE2 | PHE | 67 | 86.038 | 25.940 | 29.122 | 1.00 | 42.44 | X | C |
| ATOM | 6737 | CZ | PHE | 67 | 86.278 | 24.717 | 29.724 | 1.00 | 42.44 | X | C |
| ATOM | 6738 | C | PHE | 67 | 91.393 | 26.578 | 26.027 | 1.00 | 33.69 | X | C |
| ATOM | 6739 | O | PHE | 67 | 92.405 | 27.194 | 26.344 | 1.00 | 33.69 | X | O |
| ATOM | 6740 | N | THR | 68 | 90.949 | 26.526 | 24.779 | 1.00 | 56.59 | X | N |
| ATOM | 6741 | CA | THR | 68 | 91.646 | 27.201 | 23.689 | 1.00 | 56.59 | X | C |
| ATOM | 6742 | CB | THR | 68 | 92.454 | 26.193 | 22.846 | 1.00 | 46.98 | X | C |
| ATOM | 6743 | OG1 | THR | 68 | 93.611 | 25.781 | 23.578 | 1.00 | 46.98 | X | O |
| ATOM | 6744 | CG2 | THR | 68 | 92.870 | 26.808 | 21.512 | 1.00 | 46.98 | X | C |
| ATOM | 6745 | C | THR | 68 | 90.661 | 27.913 | 22.768 | 1.00 | 56.59 | X | C |
| ATOM | 6746 | O | THR | 68 | 89.899 | 27.270 | 22.047 | 1.00 | 56.59 | X | O |
| ATOM | 6747 | N | ILE | 69 | 90.672 | 29.239 | 22.781 | 1.00 | 20.15 | X | N |
| ATOM | 6748 | CA | ILE | 69 | 89.760 | 29.975 | 21.918 | 1.00 | 20.15 | X | C |
| ATOM | 6749 | CB | ILE | 69 | 89.287 | 31.289 | 22.607 | 1.00 | 31.46 | X | C |
| ATOM | 6750 | CG2 | ILE | 69 | 90.480 | 32.153 | 22.953 | 1.00 | 31.46 | X | C |
| ATOM | 6751 | CG1 | ILE | 69 | 88.283 | 32.028 | 21.722 | 1.00 | 31.46 | X | C |
| ATOM | 6752 | CD1 | ILE | 69 | 87.574 | 33.159 | 22.446 | 1.00 | 31.46 | X | C |
| ATOM | 6753 | C | ILE | 69 | 90.464 | 30.262 | 20.591 | 1.00 | 20.15 | X | C |
| ATOM | 6754 | O | ILE | 69 | 91.672 | 30.481 | 20.559 | 1.00 | 20.15 | X | O |
| ATOM | 6755 | N | SER | 70 | 89.724 | 30.223 | 19.489 | 1.00 | 21.14 | X | N |
| ATOM | 6756 | CA | SER | 70 | 90.319 | 30.482 | 18.182 | 1.00 | 21.14 | X | C |
| ATOM | 6757 | CB | SER | 70 | 91.105 | 29.263 | 17.693 | 1.00 | 37.41 | X | C |
| ATOM | 6758 | OG | SER | 70 | 90.228 | 28.236 | 17.253 | 1.00 | 37.41 | X | O |
| ATOM | 6759 | C | SER | 70 | 89.242 | 30.824 | 17.163 | 1.00 | 21.14 | X | C |
| ATOM | 6760 | O | SER | 70 | 88.045 | 30.637 | 17.413 | 1.00 | 21.14 | X | O |
| ATOM | 6761 | N | ARG | 71 | 89.673 | 31.322 | 16.009 | 1.00 | 30.73 | X | N |
| ATOM | 6762 | CA | ARG | 71 | 88.734 | 31.687 | 14.966 | 1.00 | 30.73 | X | C |
| ATOM | 6763 | CB | ARG | 71 | 88.369 | 33.178 | 15.073 | 1.00 | 24.51 | X | C |
| ATOM | 6764 | CG | ARG | 71 | 89.546 | 34.139 | 14.901 | 1.00 | 24.51 | X | C |
| ATOM | 6765 | CD | ARG | 71 | 89.071 | 35.503 | 14.453 | 1.00 | 24.51 | X | C |
| ATOM | 6766 | NE | ARG | 71 | 88.464 | 36.278 | 15.534 | 1.00 | 24.51 | X | N |
| ATOM | 6767 | CZ | ARG | 71 | 87.604 | 37.283 | 15.351 | 1.00 | 24.51 | X | C |
| ATOM | 6768 | NH1 | ARG | 71 | 87.229 | 37.643 | 14.131 | 1.00 | 24.51 | X | N |
| ATOM | 6769 | NH2 | ARG | 71 | 87.132 | 37.948 | 16.391 | 1.00 | 24.51 | X | N |
| ATOM | 6770 | C | ARG | 71 | 89.259 | 31.393 | 13.560 | 1.00 | 30.73 | X | C |
| ATOM | 6771 | O | ARG | 71 | 90.464 | 31.415 | 13.301 | 1.00 | 30.73 | X | O |
| ATOM | 6772 | N | ASP | 72 | 88.326 | 31.106 | 12.663 | 1.00 | 55.72 | X | N |
| ATOM | 6773 | CA | ASP | 72 | 88.619 | 30.836 | 11.268 | 1.00 | 55.72 | X | C |
| ATOM | 6774 | CB | ASP | 72 | 88.219 | 29.405 | 10.902 | 1.00 | 83.09 | X | C |
| ATOM | 6775 | CG | ASP | 72 | 88.255 | 29.153 | 9.409 | 1.00 | 83.09 | X | C |
| ATOM | 6776 | OD1 | ASP | 72 | 89.282 | 29.466 | 8.773 | 1.00 | 83.09 | X | O |
| ATOM | 6777 | OD2 | ASP | 72 | 87.256 | 28.637 | 8.870 | 1.00 | 83.09 | X | O |
| ATOM | 6778 | C | ASP | 72 | 87.749 | 31.837 | 10.528 | 1.00 | 55.72 | X | C |
| ATOM | 6779 | O | ASP | 72 | 86.613 | 31.539 | 10.162 | 1.00 | 55.72 | X | O |
| ATOM | 6780 | N | ASN | 73 | 88.284 | 33.036 | 10.340 | 1.00 | 57.89 | X | N |
| ATOM | 6781 | CA | ASN | 73 | 87.552 | 34.098 | 9.673 | 1.00 | 57.89 | X | C |
| ATOM | 6782 | CB | ASN | 73 | 88.426 | 35.345 | 9.558 | 1.00 | 43.96 | X | C |
| ATOM | 6783 | CG | ASN | 73 | 88.777 | 35.928 | 10.912 | 1.00 | 43.96 | X | C |
| ATOM | 6784 | OD1 | ASN | 73 | 88.021 | 35.794 | 11.879 | 1.00 | 43.96 | X | O |
| ATOM | 6785 | ND2 | ASN | 73 | 89.919 | 36.593 | 10.986 | 1.00 | 43.96 | X | N |
| ATOM | 6786 | C | ASN | 73 | 87.020 | 33.715 | 8.306 | 1.00 | 57.89 | X | C |
| ATOM | 6787 | O | ASN | 73 | 85.949 | 34.173 | 7.903 | 1.00 | 57.89 | X | O |
| ATOM | 6788 | N | SER | 74 | 87.756 | 32.870 | 7.594 | 1.00 | 50.09 | X | N |
| ATOM | 6789 | CA | SER | 74 | 87.324 | 32.451 | 6.268 | 1.00 | 50.09 | X | C |

Fig. 19: A-94

```
ATOM   6790  CB   SER  74      88.277  31.398   5.705  1.00  34.87      X    C
ATOM   6791  OG   SER  74      88.179  30.197   6.441  1.00  34.87      X    O
ATOM   6792  C    SER  74      85.910  31.880   6.303  1.00  50.09      X    C
ATOM   6793  O    SER  74      85.141  32.050   5.356  1.00  50.09      X    O
ATOM   6794  N    LYS  75      85.572  31.209   7.400  1.00  50.16      X    N
ATOM   6795  CA   LYS  75      84.257  30.597   7.551  1.00  50.16      X    C
ATOM   6796  CB   LYS  75      84.418  29.097   7.814  1.00  60.89      X    C
ATOM   6797  CG   LYS  75      85.206  28.372   6.729  1.00  60.89      X    C
ATOM   6798  CD   LYS  75      85.356  26.884   7.009  1.00  60.89      X    C
ATOM   6799  CE   LYS  75      86.046  26.195   5.840  1.00  60.89      X    C
ATOM   6800  NZ   LYS  75      85.341  26.459   4.551  1.00  60.89      X    N
ATOM   6801  C    LYS  75      83.423  31.226   8.663  1.00  50.16      X    C
ATOM   6802  O    LYS  75      82.470  30.618   9.142  1.00  50.16      X    O
ATOM   6803  N    ASN  76      83.786  32.441   9.066  1.00  54.49      X    N
ATOM   6804  CA   ASN  76      83.075  33.165  10.117  1.00  54.49      X    C
ATOM   6805  CB   ASN  76      81.812  33.818   9.559  1.00  41.29      X    C
ATOM   6806  CG   ASN  76      82.116  34.956   8.620  1.00  41.29      X    C
ATOM   6807  OD1  ASN  76      81.399  35.956   8.592  1.00  41.29      X    O
ATOM   6808  ND2  ASN  76      83.181  34.812   7.839  1.00  41.29      X    N
ATOM   6809  C    ASN  76      82.684  32.285  11.286  1.00  54.49      X    C
ATOM   6810  O    ASN  76      81.523  32.278  11.706  1.00  54.49      X    O
ATOM   6811  N    THR  77      83.645  31.550  11.827  1.00  48.88      X    N
ATOM   6812  CA   THR  77      83.325  30.675  12.938  1.00  48.88      X    C
ATOM   6813  CB   THR  77      83.321  29.215  12.481  1.00  67.62      X    C
ATOM   6814  OG1  THR  77      82.318  29.048  11.469  1.00  67.62      X    O
ATOM   6815  CG2  THR  77      83.028  28.284  13.653  1.00  67.62      X    C
ATOM   6816  C    THR  77      84.245  30.817  14.132  1.00  48.88      X    C
ATOM   6817  O    THR  77      85.463  30.858  13.990  1.00  48.88      X    O
ATOM   6818  N    LEU  78      83.641  30.900  15.313  1.00  25.08      X    N
ATOM   6819  CA   LEU  78      84.387  31.014  16.562  1.00  25.08      X    C
ATOM   6820  CB   LEU  78      83.739  32.047  17.488  1.00  24.57      X    C
ATOM   6821  CG   LEU  78      84.362  32.022  18.881  1.00  24.57      X    C
ATOM   6822  CD1  LEU  78      85.757  32.625  18.789  1.00  24.57      X    C
ATOM   6823  CD2  LEU  78      83.507  32.770  19.868  1.00  24.57      X    C
ATOM   6824  C    LEU  78      84.370  29.653  17.250  1.00  25.08      X    C
ATOM   6825  O    LEU  78      83.312  29.041  17.389  1.00  25.08      X    O
ATOM   6826  N    TYR  79      85.530  29.179  17.687  1.00  41.94      X    N
ATOM   6827  CA   TYR  79      85.595  27.880  18.344  1.00  41.94      X    C
ATOM   6828  CB   TYR  79      86.608  26.963  17.657  1.00  47.62      X    C
ATOM   6829  CG   TYR  79      86.328  26.619  16.226  1.00  47.62      X    C
ATOM   6830  CD1  TYR  79      85.264  25.794  15.887  1.00  47.62      X    C
ATOM   6831  CE1  TYR  79      85.008  25.460  14.559  1.00  47.62      X    C
ATOM   6832  CD2  TYR  79      87.139  27.108  15.207  1.00  47.62      X    C
ATOM   6833  CE2  TYR  79      86.896  26.784  13.878  1.00  47.62      X    C
ATOM   6834  CZ   TYR  79      85.826  25.959  13.559  1.00  47.62      X    C
ATOM   6835  OH   TYR  79      85.564  25.640  12.245  1.00  47.62      X    O
ATOM   6836  C    TYR  79      86.043  27.991  19.779  1.00  41.94      X    C
ATOM   6837  O    TYR  79      86.890  28.824  20.100  1.00  41.94      X    O
ATOM   6838  N    LEU  80      85.470  27.160  20.642  1.00  19.15      X    N
ATOM   6839  CA   LEU  80      85.917  27.110  22.022  1.00  19.15      X    C
ATOM   6840  CB   LEU  80      84.809  27.382  23.047  1.00  21.08      X    C
ATOM   6841  CG   LEU  80      85.271  27.127  24.510  1.00  21.08      X    C
ATOM   6842  CD1  LEU  80      86.500  27.981  24.840  1.00  21.08      X    C
ATOM   6843  CD2  LEU  80      84.142  27.412  25.503  1.00  21.08      X    C
ATOM   6844  C    LEU  80      86.342  25.671  22.129  1.00  19.15      X    C
ATOM   6845  O    LEU  80      85.517  24.769  21.941  1.00  19.15      X    O
ATOM   6846  N    GLN  81      87.631  25.455  22.395  1.00  31.28      X    N
ATOM   6847  CA   GLN  81      88.193  24.111  22.530  1.00  31.28      X    C
ATOM   6848  CB   GLN  81      89.497  24.015  21.738  1.00  68.87      X    C
ATOM   6849  CG   GLN  81      90.141  22.647  21.783  1.00  68.87      X    C
ATOM   6850  CD   GLN  81      89.318  21.580  21.075  1.00  68.87      X    C
ATOM   6851  OE1  GLN  81      89.101  21.648  19.864  1.00  68.87      X    O
ATOM   6852  NE2  GLN  81      88.857  20.588  21.831  1.00  68.87      X    N
ATOM   6853  C    GLN  81      88.448  23.775  24.001  1.00  31.28      X    C
ATOM   6854  O    GLN  81      89.402  24.260  24.604  1.00  31.28      X    O
ATOM   6855  N    MET  82      87.589  22.935  24.569  1.00  32.50      X    N
ATOM   6856  CA   MET  82      87.701  22.541  25.975  1.00  32.50      X    C
ATOM   6857  CB   MET  82      86.297  22.429  26.589  1.00  41.50      X    C
ATOM   6858  CG   MET  82      85.537  23.752  26.653  1.00  41.50      X    C
ATOM   6859  SD   MET  82      83.790  23.594  27.062  1.00  41.50      X    S
ATOM   6860  CE   MET  82      83.088  23.391  25.452  1.00  41.50      X    C
ATOM   6861  C    MET  82      88.463  21.230  26.188  1.00  32.50      X    C
ATOM   6862  O    MET  82      88.239  20.250  25.487  1.00  32.50      X    O
```

Fig. 19: A-95

| | | | | | | | | | | | |
|---|---|---|---|---|---|---|---|---|---|---|---|
| ATOM | 6863 | N | ASN | 83 | 89.369 | 21.224 | 27.160 | 1.00 | 43.69 | X | N |
| ATOM | 6864 | CA | ASN | 83 | 90.155 | 20.032 | 27.459 | 1.00 | 43.69 | X | C |
| ATOM | 6865 | CB | ASN | 83 | 91.574 | 20.157 | 26.883 | 1.00 | 34.50 | X | C |
| ATOM | 6866 | CG | ASN | 83 | 91.574 | 20.391 | 25.383 | 1.00 | 34.50 | X | C |
| ATOM | 6867 | OD1 | ASN | 83 | 90.920 | 19.670 | 24.636 | 1.00 | 34.50 | X | O |
| ATOM | 6868 | ND2 | ASN | 83 | 92.313 | 21.401 | 24.937 | 1.00 | 34.50 | X | N |
| ATOM | 6869 | C | ASN | 83 | 90.225 | 19.855 | 28.967 | 1.00 | 43.69 | X | C |
| ATOM | 6870 | O | ASN | 83 | 90.054 | 20.822 | 29.705 | 1.00 | 43.69 | X | O |
| ATOM | 6871 | N | SER | 84 | 90.480 | 18.625 | 29.416 | 1.00 | 47.01 | X | N |
| ATOM | 6872 | CA | SER | 84 | 90.560 | 18.322 | 30.843 | 1.00 | 47.01 | X | C |
| ATOM | 6873 | CB | SER | 84 | 91.748 | 19.045 | 31.482 | 1.00 | 36.84 | X | C |
| ATOM | 6874 | OG | SER | 84 | 92.963 | 18.623 | 30.892 | 1.00 | 36.84 | X | O |
| ATOM | 6875 | C | SER | 84 | 89.270 | 18.757 | 31.516 | 1.00 | 47.01 | X | C |
| ATOM | 6876 | O | SER | 84 | 89.272 | 19.261 | 32.644 | 1.00 | 47.01 | X | O |
| ATOM | 6877 | N | LEU | 85 | 88.170 | 18.548 | 30.804 | 1.00 | 35.88 | X | N |
| ATOM | 6878 | CA | LEU | 85 | 86.842 | 18.920 | 31.273 | 1.00 | 35.88 | X | C |
| ATOM | 6879 | CB | LEU | 85 | 85.800 | 18.466 | 30.250 | 1.00 | 45.16 | X | C |
| ATOM | 6880 | CG | LEU | 85 | 85.854 | 19.211 | 28.921 | 1.00 | 45.16 | X | C |
| ATOM | 6881 | CD1 | LEU | 85 | 84.875 | 18.608 | 27.936 | 1.00 | 45.16 | X | C |
| ATOM | 6882 | CD2 | LEU | 85 | 85.536 | 20.672 | 29.178 | 1.00 | 45.16 | X | C |
| ATOM | 6883 | C | LEU | 85 | 86.450 | 18.396 | 32.652 | 1.00 | 35.88 | X | C |
| ATOM | 6884 | O | LEU | 85 | 86.175 | 17.208 | 32.818 | 1.00 | 35.88 | X | O |
| ATOM | 6885 | N | ARG | 86 | 86.415 | 19.290 | 33.636 | 1.00 | 55.90 | X | N |
| ATOM | 6886 | CA | ARG | 86 | 86.022 | 18.907 | 34.985 | 1.00 | 55.90 | X | C |
| ATOM | 6887 | CB | ARG | 86 | 86.606 | 19.864 | 36.023 | 1.00 | 50.18 | X | C |
| ATOM | 6888 | CG | ARG | 86 | 88.108 | 20.015 | 35.994 | 1.00 | 50.18 | X | C |
| ATOM | 6889 | CD | ARG | 86 | 88.620 | 20.357 | 37.385 | 1.00 | 50.18 | X | C |
| ATOM | 6890 | NE | ARG | 86 | 89.970 | 20.904 | 37.355 | 1.00 | 50.18 | X | N |
| ATOM | 6891 | CZ | ARG | 86 | 90.256 | 22.185 | 37.133 | 1.00 | 50.18 | X | C |
| ATOM | 6892 | NH1 | ARG | 86 | 89.280 | 23.066 | 36.926 | 1.00 | 50.18 | X | N |
| ATOM | 6893 | NH2 | ARG | 86 | 91.524 | 22.587 | 37.109 | 1.00 | 50.18 | X | N |
| ATOM | 6894 | C | ARG | 86 | 84.501 | 18.954 | 35.069 | 1.00 | 55.90 | X | C |
| ATOM | 6895 | O | ARG | 86 | 83.818 | 19.086 | 34.055 | 1.00 | 55.90 | X | O |
| ATOM | 6896 | N | ALA | 87 | 83.974 | 18.856 | 36.282 | 1.00 | 39.09 | X | N |
| ATOM | 6897 | CA | ALA | 87 | 82.533 | 18.893 | 36.485 | 1.00 | 39.09 | X | C |
| ATOM | 6898 | CB | ALA | 87 | 82.164 | 18.133 | 37.750 | 1.00 | 69.79 | X | C |
| ATOM | 6899 | C | ALA | 87 | 82.028 | 20.325 | 36.578 | 1.00 | 39.09 | X | C |
| ATOM | 6900 | O | ALA | 87 | 80.885 | 20.607 | 36.219 | 1.00 | 39.09 | X | O |
| ATOM | 6901 | N | GLU | 88 | 82.876 | 21.228 | 37.066 | 1.00 | 49.44 | X | N |
| ATOM | 6902 | CA | GLU | 88 | 82.492 | 22.628 | 37.197 | 1.00 | 49.44 | X | C |
| ATOM | 6903 | CB | GLU | 88 | 83.586 | 23.435 | 37.899 | 1.00 | 57.40 | X | C |
| ATOM | 6904 | CG | GLU | 88 | 84.189 | 22.765 | 39.107 | 1.00 | 57.40 | X | C |
| ATOM | 6905 | CD | GLU | 88 | 85.178 | 21.691 | 38.724 | 1.00 | 57.40 | X | C |
| ATOM | 6906 | OE1 | GLU | 88 | 86.227 | 22.035 | 38.146 | 1.00 | 57.40 | X | O |
| ATOM | 6907 | OE2 | GLU | 88 | 84.906 | 20.504 | 38.993 | 1.00 | 57.40 | X | O |
| ATOM | 6908 | C | GLU | 88 | 82.242 | 23.242 | 35.824 | 1.00 | 49.44 | X | C |
| ATOM | 6909 | O | GLU | 88 | 81.474 | 24.195 | 35.687 | 1.00 | 49.44 | X | O |
| ATOM | 6910 | N | ASP | 89 | 82.892 | 22.698 | 34.803 | 1.00 | 49.12 | X | N |
| ATOM | 6911 | CA | ASP | 89 | 82.720 | 23.229 | 33.464 | 1.00 | 49.12 | X | C |
| ATOM | 6912 | CB | ASP | 89 | 83.818 | 22.698 | 32.549 | 1.00 | 52.75 | X | C |
| ATOM | 6913 | CG | ASP | 89 | 85.194 | 22.903 | 33.124 | 1.00 | 52.75 | X | C |
| ATOM | 6914 | OD1 | ASP | 89 | 85.430 | 23.960 | 33.752 | 1.00 | 52.75 | X | O |
| ATOM | 6915 | OD2 | ASP | 89 | 86.043 | 22.011 | 32.936 | 1.00 | 52.75 | X | O |
| ATOM | 6916 | C | ASP | 89 | 81.348 | 22.914 | 32.871 | 1.00 | 49.12 | X | C |
| ATOM | 6917 | O | ASP | 89 | 80.981 | 23.459 | 31.834 | 1.00 | 49.12 | X | O |
| ATOM | 6918 | N | THR | 90 | 80.590 | 22.034 | 33.517 | 1.00 | 33.14 | X | N |
| ATOM | 6919 | CA | THR | 90 | 79.265 | 21.686 | 33.012 | 1.00 | 33.14 | X | C |
| ATOM | 6920 | CB | THR | 90 | 78.652 | 20.480 | 33.766 | 1.00 | 40.77 | X | C |
| ATOM | 6921 | OG1 | THR | 90 | 78.585 | 20.770 | 35.162 | 1.00 | 40.77 | X | O |
| ATOM | 6922 | CG2 | THR | 90 | 79.498 | 19.257 | 33.590 | 1.00 | 40.77 | X | C |
| ATOM | 6923 | C | THR | 90 | 78.361 | 22.899 | 33.174 | 1.00 | 33.14 | X | C |
| ATOM | 6924 | O | THR | 90 | 78.260 | 23.486 | 34.263 | 1.00 | 33.14 | X | O |
| ATOM | 6925 | N | ALA | 91 | 77.718 | 23.276 | 32.076 | 1.00 | 55.37 | X | N |
| ATOM | 6926 | CA | ALA | 91 | 76.832 | 24.428 | 32.058 | 1.00 | 55.37 | X | C |
| ATOM | 6927 | CB | ALA | 91 | 77.527 | 25.625 | 32.692 | 1.00 | 7.95 | X | C |
| ATOM | 6928 | C | ALA | 91 | 76.504 | 24.732 | 30.609 | 1.00 | 55.37 | X | C |
| ATOM | 6929 | O | ALA | 91 | 77.073 | 24.128 | 29.698 | 1.00 | 55.37 | X | O |
| ATOM | 6930 | N | VAL | 92 | 75.579 | 25.656 | 30.387 | 1.00 | 44.83 | X | N |
| ATOM | 6931 | CA | VAL | 92 | 75.243 | 26.017 | 29.021 | 1.00 | 44.83 | X | C |
| ATOM | 6932 | CB | VAL | 92 | 73.747 | 26.429 | 28.878 | 1.00 | 41.51 | X | C |
| ATOM | 6933 | CG1 | VAL | 92 | 73.210 | 26.967 | 30.198 | 1.00 | 41.51 | X | C |
| ATOM | 6934 | CG2 | VAL | 92 | 73.596 | 27.460 | 27.769 | 1.00 | 41.51 | X | C |
| ATOM | 6935 | C | VAL | 92 | 76.182 | 27.145 | 28.591 | 1.00 | 44.83 | X | C |

Fig. 19: A-96

| | | | | | | | | | | | |
|---|---|---|---|---|---|---|---|---|---|---|---|
| ATOM | 6936 | O | VAL | 92 | 76.446 | 28.085 | 29.354 | 1.00 | 44.83 | X | O |
| ATOM | 6937 | N | TYR | 93 | 76.701 | 27.019 | 27.371 | 1.00 | 51.76 | X | N |
| ATOM | 6938 | CA | TYR | 93 | 77.642 | 27.978 | 26.811 | 1.00 | 51.76 | X | C |
| ATOM | 6939 | CB | TYR | 93 | 78.838 | 27.241 | 26.227 | 1.00 | 15.58 | X | C |
| ATOM | 6940 | CG | TYR | 93 | 79.743 | 26.693 | 27.287 | 1.00 | 15.58 | X | C |
| ATOM | 6941 | CD1 | TYR | 93 | 79.520 | 25.443 | 27.841 | 1.00 | 15.58 | X | C |
| ATOM | 6942 | CE1 | TYR | 93 | 80.339 | 24.959 | 28.860 | 1.00 | 15.58 | X | C |
| ATOM | 6943 | CD2 | TYR | 93 | 80.802 | 27.454 | 27.777 | 1.00 | 15.58 | X | C |
| ATOM | 6944 | CE2 | TYR | 93 | 81.618 | 26.983 | 28.797 | 1.00 | 15.58 | X | C |
| ATOM | 6945 | CZ | TYR | 93 | 81.384 | 25.735 | 29.328 | 1.00 | 15.58 | X | C |
| ATOM | 6946 | OH | TYR | 93 | 82.223 | 25.253 | 30.297 | 1.00 | 15.58 | X | O |
| ATOM | 6947 | C | TYR | 93 | 77.091 | 28.908 | 25.757 | 1.00 | 51.76 | X | C |
| ATOM | 6948 | O | TYR | 93 | 76.223 | 28.534 | 24.972 | 1.00 | 51.76 | X | O |
| ATOM | 6949 | N | TYR | 94 | 77.633 | 30.121 | 25.729 | 1.00 | 29.82 | X | N |
| ATOM | 6950 | CA | TYR | 94 | 77.210 | 31.143 | 24.774 | 1.00 | 29.82 | X | C |
| ATOM | 6951 | CB | TYR | 94 | 76.448 | 32.267 | 25.489 | 1.00 | 45.66 | X | C |
| ATOM | 6952 | CG | TYR | 94 | 75.282 | 31.829 | 26.343 | 1.00 | 45.66 | X | C |
| ATOM | 6953 | CD1 | TYR | 94 | 74.053 | 31.494 | 25.771 | 1.00 | 45.66 | X | C |
| ATOM | 6954 | CE1 | TYR | 94 | 72.979 | 31.108 | 26.564 | 1.00 | 45.66 | X | C |
| ATOM | 6955 | CD2 | TYR | 94 | 75.405 | 31.763 | 27.733 | 1.00 | 45.66 | X | C |
| ATOM | 6956 | CE2 | TYR | 94 | 74.342 | 31.376 | 28.532 | 1.00 | 45.66 | X | C |
| ATOM | 6957 | CZ | TYR | 94 | 73.132 | 31.051 | 27.943 | 1.00 | 45.66 | X | C |
| ATOM | 6958 | OH | TYR | 94 | 72.082 | 30.665 | 28.743 | 1.00 | 45.66 | X | O |
| ATOM | 6959 | C | TYR | 94 | 78.389 | 31.799 | 24.074 | 1.00 | 29.82 | X | C |
| ATOM | 6960 | O | TYR | 94 | 79.360 | 32.174 | 24.727 | 1.00 | 29.82 | X | O |
| ATOM | 6961 | N | CYS | 95 | 78.332 | 31.923 | 22.752 | 1.00 | 22.64 | X | N |
| ATOM | 6962 | CA | CYS | 95 | 79.394 | 32.659 | 22.091 | 1.00 | 22.64 | X | C |
| ATOM | 6963 | C | CYS | 95 | 78.871 | 34.094 | 22.103 | 1.00 | 22.64 | X | C |
| ATOM | 6964 | O | CYS | 95 | 77.656 | 34.337 | 22.170 | 1.00 | 22.64 | X | O |
| ATOM | 6965 | CB | CYS | 95 | 79.660 | 32.185 | 20.660 | 1.00 | 55.79 | X | C |
| ATOM | 6966 | SG | CYS | 95 | 78.222 | 31.748 | 19.650 | 1.00 | 55.79 | X | S |
| ATOM | 6967 | N | THR | 96 | 79.778 | 35.057 | 22.067 | 1.00 | 43.77 | X | N |
| ATOM | 6968 | CA | THR | 96 | 79.337 | 36.435 | 22.107 | 1.00 | 43.77 | X | C |
| ATOM | 6969 | CB | THR | 96 | 79.387 | 36.985 | 23.556 | 1.00 | 38.47 | X | C |
| ATOM | 6970 | OG1 | THR | 96 | 80.723 | 36.865 | 24.069 | 1.00 | 38.47 | X | O |
| ATOM | 6971 | CG2 | THR | 96 | 78.421 | 36.220 | 24.453 | 1.00 | 38.47 | X | C |
| ATOM | 6972 | C | THR | 96 | 80.130 | 37.370 | 21.220 | 1.00 | 43.77 | X | C |
| ATOM | 6973 | O | THR | 96 | 81.328 | 37.174 | 20.987 | 1.00 | 43.77 | X | O |
| ATOM | 6974 | N | ARG | 97 | 79.432 | 38.379 | 20.709 | 1.00 | 52.60 | X | N |
| ATOM | 6975 | CA | ARG | 97 | 80.068 | 39.400 | 19.899 | 1.00 | 52.60 | X | C |
| ATOM | 6976 | CB | ARG | 97 | 79.237 | 39.799 | 18.689 | 1.00 | 26.06 | X | C |
| ATOM | 6977 | CG | ARG | 97 | 80.052 | 40.645 | 17.733 | 1.00 | 26.06 | X | C |
| ATOM | 6978 | CD | ARG | 97 | 79.235 | 41.249 | 16.624 | 1.00 | 26.06 | X | C |
| ATOM | 6979 | NE | ARG | 97 | 78.494 | 42.412 | 17.074 | 1.00 | 26.06 | X | N |
| ATOM | 6980 | CZ | ARG | 97 | 77.853 | 43.231 | 16.255 | 1.00 | 26.06 | X | C |
| ATOM | 6981 | NH1 | ARG | 97 | 77.873 | 43.004 | 14.948 | 1.00 | 26.06 | X | N |
| ATOM | 6982 | NH2 | ARG | 97 | 77.187 | 44.271 | 16.742 | 1.00 | 26.06 | X | N |
| ATOM | 6983 | C | ARG | 97 | 80.142 | 40.590 | 20.820 | 1.00 | 52.60 | X | C |
| ATOM | 6984 | O | ARG | 97 | 79.116 | 41.100 | 21.260 | 1.00 | 52.60 | X | O |
| ATOM | 6985 | N | GLY | 98 | 81.353 | 41.020 | 21.129 | 1.00 | 31.82 | X | N |
| ATOM | 6986 | CA | GLY | 98 | 81.505 | 42.162 | 22.004 | 1.00 | 31.82 | X | C |
| ATOM | 6987 | C | GLY | 98 | 81.635 | 43.450 | 21.225 | 1.00 | 31.82 | X | C |
| ATOM | 6988 | O | GLY | 98 | 81.903 | 43.452 | 20.020 | 1.00 | 31.82 | X | O |
| ATOM | 6989 | N | PHE | 99 | 81.416 | 44.558 | 21.913 | 1.00 | 20.36 | X | N |
| ATOM | 6990 | CA | PHE | 99 | 81.554 | 45.859 | 21.289 | 1.00 | 20.36 | X | C |
| ATOM | 6991 | CB | PHE | 99 | 80.358 | 46.753 | 21.621 | 1.00 | 37.93 | X | C |
| ATOM | 6992 | CG | PHE | 99 | 80.633 | 48.214 | 21.431 | 1.00 | 37.93 | X | C |
| ATOM | 6993 | CD1 | PHE | 99 | 80.968 | 49.015 | 22.517 | 1.00 | 37.93 | X | C |
| ATOM | 6994 | CD2 | PHE | 99 | 80.606 | 48.783 | 20.158 | 1.00 | 37.93 | X | C |
| ATOM | 6995 | CE1 | PHE | 99 | 81.276 | 50.355 | 22.339 | 1.00 | 37.93 | X | C |
| ATOM | 6996 | CE2 | PHE | 99 | 80.913 | 50.127 | 19.967 | 1.00 | 37.93 | X | C |
| ATOM | 6997 | CZ | PHE | 99 | 81.250 | 50.914 | 21.058 | 1.00 | 37.93 | X | C |
| ATOM | 6998 | C | PHE | 99 | 82.836 | 46.468 | 21.835 | 1.00 | 20.36 | X | C |
| ATOM | 6999 | O | PHE | 99 | 83.239 | 46.164 | 22.969 | 1.00 | 20.36 | X | O |
| ATOM | 7000 | N | GLY | 100 | 83.480 | 47.309 | 21.030 | 1.00 | 25.28 | X | N |
| ATOM | 7001 | CA | GLY | 100 | 84.704 | 47.954 | 21.469 | 1.00 | 25.28 | X | C |
| ATOM | 7002 | C | GLY | 100 | 85.850 | 46.983 | 21.672 | 1.00 | 25.28 | X | C |
| ATOM | 7003 | O | GLY | 100 | 86.390 | 46.466 | 20.700 | 1.00 | 25.28 | X | O |
| ATOM | 7004 | N | ASP | 101 | 86.231 | 46.744 | 22.926 | 1.00 | 27.39 | X | N |
| ATOM | 7005 | CA | ASP | 101 | 87.315 | 45.814 | 23.233 | 1.00 | 27.39 | X | C |
| ATOM | 7006 | CB | ASP | 101 | 88.175 | 46.338 | 24.396 | 1.00 | 32.17 | X | C |
| ATOM | 7007 | CG | ASP | 101 | 89.037 | 47.540 | 24.013 | 1.00 | 32.17 | X | C |
| ATOM | 7008 | OD1 | ASP | 101 | 89.287 | 47.744 | 22.812 | 1.00 | 32.17 | X | O |

Fig. 19: A-97

| | | | | | | | | | | | |
|---|---|---|---|---|---|---|---|---|---|---|---|
| ATOM | 7009 | OD2 | ASP | 101 | 89.483 | 48.274 | 24.920 | 1.00 | 32.17 | X | O |
| ATOM | 7010 | C | ASP | 101 | 86.773 | 44.418 | 23.596 | 1.00 | 27.39 | X | C |
| ATOM | 7011 | O | ASP | 101 | 87.549 | 43.518 | 23.929 | 1.00 | 27.39 | X | O |
| ATOM | 7012 | N | GLY | 102 | 85.449 | 44.250 | 23.538 | 1.00 | 18.22 | X | N |
| ATOM | 7013 | CA | GLY | 102 | 84.822 | 42.973 | 23.861 | 1.00 | 18.22 | X | C |
| ATOM | 7014 | C | GLY | 102 | 83.925 | 42.948 | 25.100 | 1.00 | 18.22 | X | C |
| ATOM | 7015 | O | GLY | 102 | 83.031 | 42.113 | 25.198 | 1.00 | 18.22 | X | O |
| ATOM | 7016 | N | GLY | 103 | 84.147 | 43.870 | 26.034 | 1.00 | 34.16 | X | N |
| ATOM | 7017 | CA | GLY | 103 | 83.370 | 43.915 | 27.268 | 1.00 | 34.16 | X | C |
| ATOM | 7018 | C | GLY | 103 | 81.850 | 43.964 | 27.216 | 1.00 | 34.16 | X | C |
| ATOM | 7019 | O | GLY | 103 | 81.182 | 43.416 | 28.087 | 1.00 | 34.16 | X | O |
| ATOM | 7020 | N | TYR | 104 | 81.290 | 44.649 | 26.230 | 1.00 | 25.31 | X | N |
| ATOM | 7021 | CA | TYR | 104 | 79.839 | 44.732 | 26.096 | 1.00 | 25.31 | X | C |
| ATOM | 7022 | CB | TYR | 104 | 79.433 | 46.131 | 25.639 | 1.00 | 26.21 | X | C |
| ATOM | 7023 | CG | TYR | 104 | 77.989 | 46.260 | 25.234 | 1.00 | 26.21 | X | C |
| ATOM | 7024 | CD1 | TYR | 104 | 77.635 | 46.980 | 24.087 | 1.00 | 26.21 | X | C |
| ATOM | 7025 | CE1 | TYR | 104 | 76.309 | 47.079 | 23.677 | 1.00 | 26.21 | X | C |
| ATOM | 7026 | CD2 | TYR | 104 | 76.972 | 45.646 | 25.972 | 1.00 | 26.21 | X | C |
| ATOM | 7027 | CE2 | TYR | 104 | 75.639 | 45.742 | 25.573 | 1.00 | 26.21 | X | C |
| ATOM | 7028 | CZ | TYR | 104 | 75.323 | 46.456 | 24.422 | 1.00 | 26.21 | X | C |
| ATOM | 7029 | OH | TYR | 104 | 74.025 | 46.523 | 23.995 | 1.00 | 26.21 | X | O |
| ATOM | 7030 | C | TYR | 104 | 79.484 | 43.700 | 25.037 | 1.00 | 25.31 | X | C |
| ATOM | 7031 | O | TYR | 104 | 79.905 | 43.810 | 23.886 | 1.00 | 25.31 | X | O |
| ATOM | 7032 | N | PHE | 105 | 78.728 | 42.686 | 25.432 | 1.00 | 17.54 | X | N |
| ATOM | 7033 | CA | PHE | 105 | 78.354 | 41.616 | 24.518 | 1.00 | 17.54 | X | C |
| ATOM | 7034 | CB | PHE | 105 | 78.088 | 40.337 | 25.309 | 1.00 | 20.12 | X | C |
| ATOM | 7035 | CG | PHE | 105 | 79.154 | 40.010 | 26.312 | 1.00 | 20.12 | X | C |
| ATOM | 7036 | CD1 | PHE | 105 | 80.478 | 39.817 | 25.908 | 1.00 | 20.12 | X | C |
| ATOM | 7037 | CD2 | PHE | 105 | 78.832 | 39.891 | 27.661 | 1.00 | 20.12 | X | C |
| ATOM | 7038 | CE1 | PHE | 105 | 81.472 | 39.511 | 26.836 | 1.00 | 20.12 | X | C |
| ATOM | 7039 | CE2 | PHE | 105 | 79.808 | 39.586 | 28.594 | 1.00 | 20.12 | X | C |
| ATOM | 7040 | CZ | PHE | 105 | 81.136 | 39.395 | 28.183 | 1.00 | 20.12 | X | C |
| ATOM | 7041 | C | PHE | 105 | 77.127 | 41.938 | 23.669 | 1.00 | 17.54 | X | C |
| ATOM | 7042 | O | PHE | 105 | 75.989 | 41.689 | 24.080 | 1.00 | 17.54 | X | O |
| ATOM | 7043 | N | ASP | 106 | 77.376 | 42.488 | 22.482 | 1.00 | 46.21 | X | N |
| ATOM | 7044 | CA | ASP | 106 | 76.327 | 42.840 | 21.532 | 1.00 | 46.21 | X | C |
| ATOM | 7045 | CB | ASP | 106 | 76.908 | 43.074 | 20.143 | 1.00 | 54.80 | X | C |
| ATOM | 7046 | CG | ASP | 106 | 77.456 | 44.442 | 19.976 | 1.00 | 54.80 | X | C |
| ATOM | 7047 | OD1 | ASP | 106 | 76.774 | 45.384 | 20.429 | 1.00 | 54.80 | X | O |
| ATOM | 7048 | OD2 | ASP | 106 | 78.552 | 44.576 | 19.387 | 1.00 | 54.80 | X | O |
| ATOM | 7049 | C | ASP | 106 | 75.355 | 41.705 | 21.399 | 1.00 | 46.21 | X | C |
| ATOM | 7050 | O | ASP | 106 | 74.281 | 41.707 | 21.974 | 1.00 | 46.21 | X | O |
| ATOM | 7051 | N | VAL | 107 | 75.769 | 40.732 | 20.603 | 1.00 | 33.04 | X | N |
| ATOM | 7052 | CA | VAL | 107 | 74.979 | 39.559 | 20.312 | 1.00 | 33.04 | X | C |
| ATOM | 7053 | CB | VAL | 107 | 75.180 | 39.152 | 18.858 | 1.00 | 31.62 | X | C |
| ATOM | 7054 | CG1 | VAL | 107 | 74.156 | 38.100 | 18.457 | 1.00 | 31.62 | X | C |
| ATOM | 7055 | CG2 | VAL | 107 | 75.092 | 40.388 | 17.980 | 1.00 | 31.62 | X | C |
| ATOM | 7056 | C | VAL | 107 | 75.322 | 38.379 | 21.197 | 1.00 | 33.04 | X | C |
| ATOM | 7057 | O | VAL | 107 | 76.413 | 38.296 | 21.763 | 1.00 | 33.04 | X | O |
| ATOM | 7058 | N | TRP | 108 | 74.359 | 37.474 | 21.306 | 1.00 | 37.95 | X | N |
| ATOM | 7059 | CA | TRP | 108 | 74.501 | 36.266 | 22.092 | 1.00 | 37.95 | X | C |
| ATOM | 7060 | CB | TRP | 108 | 73.674 | 36.351 | 23.372 | 1.00 | 32.89 | X | C |
| ATOM | 7061 | CG | TRP | 108 | 74.212 | 37.315 | 24.368 | 1.00 | 32.89 | X | C |
| ATOM | 7062 | CD2 | TRP | 108 | 74.712 | 37.004 | 25.668 | 1.00 | 32.89 | X | C |
| ATOM | 7063 | CE2 | TRP | 108 | 75.114 | 38.216 | 26.261 | 1.00 | 32.89 | X | C |
| ATOM | 7064 | CE3 | TRP | 108 | 74.861 | 35.816 | 26.390 | 1.00 | 32.89 | X | C |
| ATOM | 7065 | CD1 | TRP | 108 | 74.327 | 38.664 | 24.225 | 1.00 | 32.89 | X | C |
| ATOM | 7066 | NE1 | TRP | 108 | 74.867 | 39.216 | 25.358 | 1.00 | 32.89 | X | N |
| ATOM | 7067 | CZ2 | TRP | 108 | 75.655 | 38.278 | 27.543 | 1.00 | 32.89 | X | C |
| ATOM | 7068 | CZ3 | TRP | 108 | 75.402 | 35.878 | 27.670 | 1.00 | 32.89 | X | C |
| ATOM | 7069 | CH2 | TRP | 108 | 75.792 | 37.103 | 28.231 | 1.00 | 32.89 | X | C |
| ATOM | 7070 | C | TRP | 108 | 73.984 | 35.119 | 21.260 | 1.00 | 37.95 | X | C |
| ATOM | 7071 | O | TRP | 108 | 73.067 | 35.296 | 20.451 | 1.00 | 37.95 | X | O |
| ATOM | 7072 | N | GLY | 109 | 74.568 | 33.942 | 21.460 | 1.00 | 75.91 | X | N |
| ATOM | 7073 | CA | GLY | 109 | 74.124 | 32.770 | 20.732 | 1.00 | 75.91 | X | C |
| ATOM | 7074 | C | GLY | 109 | 72.791 | 32.307 | 21.288 | 1.00 | 75.91 | X | C |
| ATOM | 7075 | O | GLY | 109 | 71.997 | 33.114 | 21.780 | 1.00 | 75.91 | X | O |
| ATOM | 7076 | N | GLN | 110 | 72.537 | 31.007 | 21.207 | 1.00 | 35.37 | X | N |
| ATOM | 7077 | CA | GLN | 110 | 71.291 | 30.457 | 21.724 | 1.00 | 35.37 | X | C |
| ATOM | 7078 | CB | GLN | 110 | 70.652 | 29.498 | 20.714 | 1.00 | 98.79 | X | C |
| ATOM | 7079 | CG | GLN | 110 | 71.443 | 28.228 | 20.442 | 1.00 | 98.79 | X | C |
| ATOM | 7080 | CD | GLN | 110 | 72.597 | 28.441 | 19.485 | 1.00 | 98.79 | X | C |
| ATOM | 7081 | OE1 | GLN | 110 | 73.318 | 27.502 | 19.152 | 1.00 | 98.79 | X | O |

Fig. 19: A-98

```
ATOM   7082  NE2 GLN  110      72.775  29.675  19.031  1.00  98.79   X  N
ATOM   7083  C   GLN  110      71.610  29.708  23.004  1.00  35.37   X  C
ATOM   7084  O   GLN  110      70.793  29.626  23.918  1.00  35.37   X  O
ATOM   7085  N   GLY  111      72.831  29.194  23.067  1.00  45.85   X  N
ATOM   7086  CA  GLY  111      73.257  28.430  24.219  1.00  45.85   X  C
ATOM   7087  C   GLY  111      73.349  26.981  23.781  1.00  45.85   X  C
ATOM   7088  O   GLY  111      72.596  26.540  22.913  1.00  45.85   X  O
ATOM   7089  N   THR  112      74.281  26.243  24.369  1.00  30.06   X  N
ATOM   7090  CA  THR  112      74.480  24.840  24.040  1.00  30.06   X  C
ATOM   7091  CB  THR  112      75.550  24.696  22.962  1.00  24.67   X  C
ATOM   7092  OG1 THR  112      75.636  23.327  22.562  1.00  24.67   X  O
ATOM   7093  CG2 THR  112      76.903  25.177  23.487  1.00  24.67   X  C
ATOM   7094  C   THR  112      74.944  24.184  25.328  1.00  30.06   X  C
ATOM   7095  O   THR  112      75.883  24.658  25.960  1.00  30.06   X  O
ATOM   7096  N   LEU  113      74.292  23.102  25.725  1.00  42.99   X  N
ATOM   7097  CA  LEU  113      74.646  22.449  26.981  1.00  42.99   X  C
ATOM   7098  CB  LEU  113      73.434  21.652  27.499  1.00  32.90   X  C
ATOM   7099  CG  LEU  113      73.366  21.006  28.896  1.00  32.90   X  C
ATOM   7100  CD1 LEU  113      73.914  19.580  28.860  1.00  32.90   X  C
ATOM   7101  CD2 LEU  113      74.109  21.884  29.889  1.00  32.90   X  C
ATOM   7102  C   LEU  113      75.890  21.560  26.932  1.00  42.99   X  C
ATOM   7103  O   LEU  113      76.190  20.899  25.929  1.00  42.99   X  O
ATOM   7104  N   VAL  114      76.621  21.561  28.037  1.00  35.21   X  N
ATOM   7105  CA  VAL  114      77.815  20.754  28.141  1.00  35.21   X  C
ATOM   7106  CB  VAL  114      79.070  21.592  27.837  1.00  43.74   X  C
ATOM   7107  CG1 VAL  114      80.324  20.909  28.384  1.00  43.74   X  C
ATOM   7108  CG2 VAL  114      79.189  21.774  26.331  1.00  43.74   X  C
ATOM   7109  C   VAL  114      77.906  20.141  29.529  1.00  35.21   X  C
ATOM   7110  O   VAL  114      78.064  20.845  30.529  1.00  35.21   X  O
ATOM   7111  N   THR  115      77.788  18.819  29.575  1.00  58.81   X  N
ATOM   7112  CA  THR  115      77.855  18.099  30.829  1.00  58.81   X  C
ATOM   7113  CB  THR  115      76.717  17.098  30.956  1.00  63.66   X  C
ATOM   7114  OG1 THR  115      75.549  17.620  30.311  1.00  63.66   X  O
ATOM   7115  CG2 THR  115      76.412  16.849  32.422  1.00  63.66   X  C
ATOM   7116  C   THR  115      79.161  17.337  30.903  1.00  58.81   X  C
ATOM   7117  O   THR  115      79.831  17.121  29.893  1.00  58.81   X  O
ATOM   7118  N   VAL  116      79.516  16.933  32.114  1.00  73.79   X  N
ATOM   7119  CA  VAL  116      80.741  16.191  32.352  1.00  73.79   X  C
ATOM   7120  CB  VAL  116      81.899  17.135  32.747  1.00  46.90   X  C
ATOM   7121  CG1 VAL  116      83.172  16.339  32.941  1.00  46.90   X  C
ATOM   7122  CG2 VAL  116      82.101  18.194  31.667  1.00  46.90   X  C
ATOM   7123  C   VAL  116      80.478  15.202  33.482  1.00  73.79   X  C
ATOM   7124  O   VAL  116      80.382  15.584  34.649  1.00  73.79   X  O
ATOM   7125  N   SER  117      80.349  13.931  33.114  1.00  65.98   X  N
ATOM   7126  CA  SER  117      80.088  12.858  34.066  1.00  65.98   X  C
ATOM   7127  CB  SER  117      78.608  12.861  34.458  1.00  62.16   X  C
ATOM   7128  OG  SER  117      77.776  12.825  33.308  1.00  62.16   X  O
ATOM   7129  C   SER  117      80.454  11.521  33.427  1.00  65.98   X  C
ATOM   7130  O   SER  117      81.498  11.396  32.789  1.00  65.98   X  O
ATOM   7131  N   SER  118      79.587  10.524  33.594  1.00  80.64   X  N
ATOM   7132  CA  SER  118      79.828   9.208  33.014  1.00  80.64   X  C
ATOM   7133  CB  SER  118      80.556   8.329  34.031  1.00  66.12   X  C
ATOM   7134  OG  SER  118      81.771   8.944  34.438  1.00  66.12   X  O
ATOM   7135  C   SER  118      78.524   8.543  32.563  1.00  80.64   X  C
ATOM   7136  O   SER  118      77.445   9.021  32.973  1.00  79.69   X  O
ATOM   7137  OXT SER  118      78.594   7.553  31.804  1.00  65.17   X  O
ATOM   7138  CB  ILE    2      85.629  44.767  39.417  1.00  24.34   Y  C
ATOM   7139  CG2 ILE    2      84.329  45.456  39.830  1.00  24.34   Y  C
ATOM   7140  CG1 ILE    2      86.754  45.793  39.275  1.00  24.34   Y  C
ATOM   7141  CD1 ILE    2      86.473  46.861  38.237  1.00  24.34   Y  C
ATOM   7142  C   ILE    2      84.812  42.776  40.634  1.00  29.24   Y  C
ATOM   7143  O   ILE    2      84.508  41.962  39.756  1.00  29.24   Y  O
ATOM   7144  N   ILE    2      87.254  42.972  40.068  1.00  29.24   Y  N
ATOM   7145  CA  ILE    2      86.011  43.705  40.462  1.00  29.24   Y  C
ATOM   7146  N   GLN    3      84.122  42.926  41.761  1.00  42.94   Y  N
ATOM   7147  CA  GLN    3      82.960  42.107  42.070  1.00  42.94   Y  C
ATOM   7148  CB  GLN    3      83.156  41.435  43.434  1.00  85.86   Y  C
ATOM   7149  CG  GLN    3      82.045  40.492  43.850  1.00  85.86   Y  C
ATOM   7150  CD  GLN    3      82.371  39.747  45.131  1.00  85.86   Y  C
ATOM   7151  OE1 GLN    3      81.534  39.028  45.670  1.00  85.86   Y  O
ATOM   7152  NE2 GLN    3      83.597  39.911  45.621  1.00  85.86   Y  N
ATOM   7153  C   GLN    3      81.684  42.943  42.059  1.00  42.94   Y  C
ATOM   7154  O   GLN    3      81.626  44.026  42.645  1.00  42.94   Y  O
```

Fig. 19: A-99

| ATOM | 7155 | N | LEU | 4 | 80.666 | 42.426 | 41.380 | 1.00 | 33.35 | Y | N |
|---|---|---|---|---|---|---|---|---|---|---|---|
| ATOM | 7156 | CA | LEU | 4 | 79.378 | 43.098 | 41.269 | 1.00 | 33.35 | Y | C |
| ATOM | 7157 | CB | LEU | 4 | 78.954 | 43.160 | 39.800 | 1.00 | 47.12 | Y | C |
| ATOM | 7158 | CG | LEU | 4 | 79.344 | 44.389 | 38.979 | 1.00 | 47.12 | Y | C |
| ATOM | 7159 | CD1 | LEU | 4 | 80.683 | 44.945 | 39.443 | 1.00 | 47.12 | Y | C |
| ATOM | 7160 | CD2 | LEU | 4 | 79.370 | 44.008 | 37.512 | 1.00 | 47.12 | Y | C |
| ATOM | 7161 | C | LEU | 4 | 78.296 | 42.395 | 42.073 | 1.00 | 33.35 | Y | C |
| ATOM | 7162 | O | LEU | 4 | 78.012 | 41.215 | 41.852 | 1.00 | 33.35 | Y | O |
| ATOM | 7163 | N | THR | 5 | 77.691 | 43.129 | 43.001 | 1.00 | 42.53 | Y | N |
| ATOM | 7164 | CA | THR | 5 | 76.628 | 42.586 | 43.833 | 1.00 | 42.53 | Y | C |
| ATOM | 7165 | CB | THR | 5 | 77.100 | 42.482 | 45.315 | 1.00 | 37.95 | Y | C |
| ATOM | 7166 | OG1 | THR | 5 | 75.992 | 42.697 | 46.196 | 1.00 | 37.95 | Y | O |
| ATOM | 7167 | CG2 | THR | 5 | 78.209 | 43.479 | 45.604 | 1.00 | 37.95 | Y | C |
| ATOM | 7168 | C | THR | 5 | 75.348 | 43.426 | 43.699 | 1.00 | 42.53 | Y | C |
| ATOM | 7169 | O | THR | 5 | 75.306 | 44.593 | 44.089 | 1.00 | 42.53 | Y | O |
| ATOM | 7170 | N | GLN | 6 | 74.318 | 42.806 | 43.119 | 1.00 | 44.79 | Y | N |
| ATOM | 7171 | CA | GLN | 6 | 73.009 | 43.423 | 42.877 | 1.00 | 44.79 | Y | C |
| ATOM | 7172 | CB | GLN | 6 | 72.340 | 42.791 | 41.641 | 1.00 | 23.30 | Y | C |
| ATOM | 7173 | CG | GLN | 6 | 73.239 | 42.643 | 40.421 | 1.00 | 23.30 | Y | C |
| ATOM | 7174 | CD | GLN | 6 | 72.520 | 42.055 | 39.195 | 1.00 | 23.30 | Y | C |
| ATOM | 7175 | OE1 | GLN | 6 | 73.163 | 41.628 | 38.231 | 1.00 | 23.30 | Y | O |
| ATOM | 7176 | NE2 | GLN | 6 | 71.193 | 42.046 | 39.226 | 1.00 | 23.30 | Y | N |
| ATOM | 7177 | C | GLN | 6 | 72.050 | 43.274 | 44.061 | 1.00 | 44.79 | Y | C |
| ATOM | 7178 | O | GLN | 6 | 72.195 | 42.370 | 44.883 | 1.00 | 44.79 | Y | O |
| ATOM | 7179 | N | SER | 7 | 71.057 | 44.156 | 44.128 | 1.00 | 78.31 | Y | N |
| ATOM | 7180 | CA | SER | 7 | 70.069 | 44.113 | 45.201 | 1.00 | 78.31 | Y | C |
| ATOM | 7181 | CB | SER | 7 | 70.640 | 44.715 | 46.480 | 1.00 | 85.46 | Y | C |
| ATOM | 7182 | OG | SER | 7 | 71.028 | 46.058 | 46.262 | 1.00 | 85.46 | Y | O |
| ATOM | 7183 | C | SER | 7 | 68.797 | 44.855 | 44.824 | 1.00 | 78.31 | Y | C |
| ATOM | 7184 | O | SER | 7 | 68.847 | 45.923 | 44.220 | 1.00 | 78.31 | Y | O |
| ATOM | 7185 | N | PRO | 8 | 67.633 | 44.283 | 45.165 | 1.00 | 83.70 | Y | N |
| ATOM | 7186 | CD | PRO | 8 | 66.277 | 44.777 | 44.863 | 1.00 | 54.81 | Y | C |
| ATOM | 7187 | CA | PRO | 8 | 67.571 | 43.000 | 45.865 | 1.00 | 83.70 | Y | C |
| ATOM | 7188 | CB | PRO | 8 | 66.097 | 42.880 | 46.226 | 1.00 | 54.81 | Y | C |
| ATOM | 7189 | CG | PRO | 8 | 65.427 | 43.534 | 45.054 | 1.00 | 54.81 | Y | C |
| ATOM | 7190 | C | PRO | 8 | 68.015 | 41.895 | 44.925 | 1.00 | 83.70 | Y | C |
| ATOM | 7191 | O | PRO | 8 | 68.274 | 42.136 | 43.745 | 1.00 | 83.70 | Y | O |
| ATOM | 7192 | N | SER | 9 | 68.111 | 40.685 | 45.455 | 1.00 | 47.38 | Y | N |
| ATOM | 7193 | CA | SER | 9 | 68.504 | 39.541 | 44.651 | 1.00 | 47.38 | Y | C |
| ATOM | 7194 | CB | SER | 9 | 69.145 | 38.481 | 45.543 | 1.00 | 74.91 | Y | C |
| ATOM | 7195 | OG | SER | 9 | 70.214 | 39.045 | 46.283 | 1.00 | 74.91 | Y | O |
| ATOM | 7196 | C | SER | 9 | 67.232 | 39.002 | 44.025 | 1.00 | 47.38 | Y | C |
| ATOM | 7197 | O | SER | 9 | 67.237 | 38.434 | 42.936 | 1.00 | 47.38 | Y | O |
| ATOM | 7198 | N | SER | 10 | 66.134 | 39.214 | 44.736 | 1.00 | 60.45 | Y | N |
| ATOM | 7199 | CA | SER | 10 | 64.819 | 38.770 | 44.305 | 1.00 | 60.45 | Y | C |
| ATOM | 7200 | CB | SER | 10 | 64.476 | 37.449 | 44.991 | 1.00 | 51.82 | Y | C |
| ATOM | 7201 | OG | SER | 10 | 63.252 | 36.935 | 44.504 | 1.00 | 51.82 | Y | O |
| ATOM | 7202 | C | SER | 10 | 63.797 | 39.840 | 44.691 | 1.00 | 60.45 | Y | C |
| ATOM | 7203 | O | SER | 10 | 63.976 | 40.552 | 45.683 | 1.00 | 60.45 | Y | O |
| ATOM | 7204 | N | LEU | 11 | 62.730 | 39.964 | 43.910 | 1.00 | 65.48 | Y | N |
| ATOM | 7205 | CA | LEU | 11 | 61.710 | 40.964 | 44.206 | 1.00 | 65.48 | Y | C |
| ATOM | 7206 | CB | LEU | 11 | 62.206 | 42.366 | 43.830 | 1.00 | 51.28 | Y | C |
| ATOM | 7207 | CG | LEU | 11 | 62.310 | 42.727 | 42.342 | 1.00 | 51.28 | Y | C |
| ATOM | 7208 | CD1 | LEU | 11 | 60.949 | 43.139 | 41.803 | 1.00 | 51.28 | Y | C |
| ATOM | 7209 | CD2 | LEU | 11 | 63.294 | 43.877 | 42.168 | 1.00 | 51.28 | Y | C |
| ATOM | 7210 | C | LEU | 11 | 60.413 | 40.680 | 43.473 | 1.00 | 65.48 | Y | C |
| ATOM | 7211 | O | LEU | 11 | 60.412 | 40.363 | 42.282 | 1.00 | 65.48 | Y | O |
| ATOM | 7212 | N | SER | 12 | 59.305 | 40.803 | 44.189 | 1.00 | 84.56 | Y | N |
| ATOM | 7213 | CA | SER | 12 | 58.004 | 40.567 | 43.595 | 1.00 | 84.56 | Y | C |
| ATOM | 7214 | CB | SER | 12 | 57.209 | 39.578 | 44.445 | 1.00 | 71.89 | Y | C |
| ATOM | 7215 | OG | SER | 12 | 56.137 | 39.026 | 43.705 | 1.00 | 71.89 | Y | O |
| ATOM | 7216 | C | SER | 12 | 57.273 | 41.902 | 43.507 | 1.00 | 84.56 | Y | C |
| ATOM | 7217 | O | SER | 12 | 57.232 | 42.666 | 44.471 | 1.00 | 84.56 | Y | O |
| ATOM | 7218 | N | ALA | 13 | 56.713 | 42.192 | 42.341 | 1.00 | 109.71 | Y | N |
| ATOM | 7219 | CA | ALA | 13 | 55.997 | 43.442 | 42.152 | 1.00 | 109.71 | Y | C |
| ATOM | 7220 | CB | ALA | 13 | 56.947 | 44.509 | 41.632 | 1.00 | 88.46 | Y | C |
| ATOM | 7221 | C | ALA | 13 | 54.838 | 43.244 | 41.186 | 1.00 | 109.71 | Y | C |
| ATOM | 7222 | O | ALA | 13 | 54.869 | 42.347 | 40.341 | 1.00 | 109.71 | Y | O |
| ATOM | 7223 | N | SER | 14 | 53.816 | 44.084 | 41.315 | 1.00 | 66.55 | Y | N |
| ATOM | 7224 | CA | SER | 14 | 52.632 | 44.000 | 40.461 | 1.00 | 66.55 | Y | C |
| ATOM | 7225 | CB | SER | 14 | 51.370 | 44.265 | 41.290 | 1.00 | 62.23 | Y | C |
| ATOM | 7226 | OG | SER | 14 | 51.506 | 45.449 | 42.059 | 1.00 | 62.23 | Y | O |
| ATOM | 7227 | C | SER | 14 | 52.699 | 44.984 | 39.299 | 1.00 | 66.55 | Y | C |

Fig. 19: A-100

| | | | | | | | | | | |
|---|---|---|---|---|---|---|---|---|---|---|
| ATOM | 7228 | O | SER | 14 | 53.362 | 46.015 | 39.394 | 1.00 | 66.55 | Y | O |
| ATOM | 7229 | N | VAL | 15 | 52.018 | 44.660 | 38.202 | 1.00 | 56.27 | Y | N |
| ATOM | 7230 | CA | VAL | 15 | 52.017 | 45.540 | 37.037 | 1.00 | 56.27 | Y | C |
| ATOM | 7231 | CB | VAL | 15 | 50.922 | 45.156 | 36.016 | 1.00 | 42.35 | Y | C |
| ATOM | 7232 | CG1 | VAL | 15 | 51.449 | 44.089 | 35.066 | 1.00 | 42.35 | Y | C |
| ATOM | 7233 | CG2 | VAL | 15 | 49.679 | 44.644 | 36.750 | 1.00 | 42.35 | Y | C |
| ATOM | 7234 | C | VAL | 15 | 51.773 | 46.964 | 37.492 | 1.00 | 56.27 | Y | C |
| ATOM | 7235 | O | VAL | 15 | 50.948 | 47.208 | 38.369 | 1.00 | 56.27 | Y | O |
| ATOM | 7236 | N | GLY | 16 | 52.509 | 47.903 | 36.911 | 1.00 | 54.44 | Y | N |
| ATOM | 7237 | CA | GLY | 16 | 52.343 | 49.296 | 37.280 | 1.00 | 54.44 | Y | C |
| ATOM | 7238 | C | GLY | 16 | 53.284 | 49.795 | 38.359 | 1.00 | 54.44 | Y | C |
| ATOM | 7239 | O | GLY | 16 | 53.419 | 51.000 | 38.542 | 1.00 | 54.44 | Y | O |
| ATOM | 7240 | N | ASP | 17 | 53.931 | 48.885 | 39.082 | 1.00 | 75.77 | Y | N |
| ATOM | 7241 | CA | ASP | 17 | 54.863 | 49.283 | 40.134 | 1.00 | 75.77 | Y | C |
| ATOM | 7242 | CB | ASP | 17 | 55.212 | 48.091 | 41.034 | 1.00 | 114.73 | Y | C |
| ATOM | 7243 | CG | ASP | 17 | 54.035 | 47.608 | 41.849 | 1.00 | 114.73 | Y | C |
| ATOM | 7244 | OD1 | ASP | 17 | 54.208 | 46.639 | 42.623 | 1.00 | 114.73 | Y | O |
| ATOM | 7245 | OD2 | ASP | 17 | 52.942 | 48.198 | 41.716 | 1.00 | 114.73 | Y | O |
| ATOM | 7246 | C | ASP | 17 | 56.149 | 49.824 | 39.525 | 1.00 | 75.77 | Y | C |
| ATOM | 7247 | O | ASP | 17 | 56.476 | 49.533 | 38.373 | 1.00 | 75.77 | Y | O |
| ATOM | 7248 | N | ARG | 18 | 56.873 | 50.616 | 40.304 | 1.00 | 69.15 | Y | N |
| ATOM | 7249 | CA | ARG | 18 | 58.139 | 51.161 | 39.844 | 1.00 | 69.15 | Y | C |
| ATOM | 7250 | CB | ARG | 18 | 58.263 | 52.634 | 40.225 | 1.00 | 52.23 | Y | C |
| ATOM | 7251 | CG | ARG | 18 | 59.557 | 53.291 | 39.779 | 1.00 | 52.23 | Y | C |
| ATOM | 7252 | CD | ARG | 18 | 59.365 | 54.788 | 39.625 | 1.00 | 52.23 | Y | C |
| ATOM | 7253 | NE | ARG | 18 | 60.622 | 55.478 | 39.370 | 1.00 | 52.23 | Y | N |
| ATOM | 7254 | CZ | ARG | 18 | 61.621 | 55.550 | 40.246 | 1.00 | 52.23 | Y | C |
| ATOM | 7255 | NH1 | ARG | 18 | 61.506 | 54.968 | 41.436 | 1.00 | 52.23 | Y | N |
| ATOM | 7256 | NH2 | ARG | 18 | 62.733 | 56.209 | 39.933 | 1.00 | 52.23 | Y | N |
| ATOM | 7257 | C | ARG | 18 | 59.232 | 50.346 | 40.514 | 1.00 | 69.15 | Y | C |
| ATOM | 7258 | O | ARG | 18 | 59.318 | 50.293 | 41.744 | 1.00 | 69.15 | Y | O |
| ATOM | 7259 | N | VAL | 19 | 60.064 | 49.706 | 39.701 | 1.00 | 58.62 | Y | N |
| ATOM | 7260 | CA | VAL | 19 | 61.132 | 48.871 | 40.221 | 1.00 | 58.62 | Y | C |
| ATOM | 7261 | CB | VAL | 19 | 61.068 | 47.477 | 39.567 | 1.00 | 74.00 | Y | C |
| ATOM | 7262 | CG1 | VAL | 19 | 62.050 | 46.531 | 40.235 | 1.00 | 74.00 | Y | C |
| ATOM | 7263 | CG2 | VAL | 19 | 59.651 | 46.938 | 39.664 | 1.00 | 74.00 | Y | C |
| ATOM | 7264 | C | VAL | 19 | 62.518 | 49.477 | 40.003 | 1.00 | 58.62 | Y | C |
| ATOM | 7265 | O | VAL | 19 | 62.782 | 50.096 | 38.975 | 1.00 | 58.62 | Y | O |
| ATOM | 7266 | N | THR | 20 | 63.399 | 49.297 | 40.978 | 1.00 | 54.75 | Y | N |
| ATOM | 7267 | CA | THR | 20 | 64.753 | 49.815 | 40.878 | 1.00 | 54.75 | Y | C |
| ATOM | 7268 | CB | THR | 20 | 64.883 | 51.148 | 41.639 | 1.00 | 56.43 | Y | C |
| ATOM | 7269 | OG1 | THR | 20 | 64.132 | 52.154 | 40.955 | 1.00 | 56.43 | Y | O |
| ATOM | 7270 | CG2 | THR | 20 | 66.337 | 51.586 | 41.726 | 1.00 | 56.43 | Y | C |
| ATOM | 7271 | C | THR | 20 | 65.806 | 48.834 | 41.401 | 1.00 | 54.75 | Y | C |
| ATOM | 7272 | O | THR | 20 | 65.963 | 48.663 | 42.611 | 1.00 | 54.75 | Y | O |
| ATOM | 7273 | N | ILE | 21 | 66.526 | 48.194 | 40.484 | 1.00 | 38.23 | Y | N |
| ATOM | 7274 | CA | ILE | 21 | 67.572 | 47.250 | 40.855 | 1.00 | 38.23 | Y | C |
| ATOM | 7275 | CB | ILE | 21 | 67.775 | 46.182 | 39.765 | 1.00 | 34.57 | Y | C |
| ATOM | 7276 | CG2 | ILE | 21 | 68.753 | 45.112 | 40.252 | 1.00 | 34.57 | Y | C |
| ATOM | 7277 | CG1 | ILE | 21 | 66.427 | 45.547 | 39.426 | 1.00 | 34.57 | Y | C |
| ATOM | 7278 | CD1 | ILE | 21 | 66.496 | 44.426 | 38.415 | 1.00 | 34.57 | Y | C |
| ATOM | 7279 | C | ILE | 21 | 68.877 | 48.006 | 41.047 | 1.00 | 38.23 | Y | C |
| ATOM | 7280 | O | ILE | 21 | 69.215 | 48.885 | 40.256 | 1.00 | 38.23 | Y | O |
| ATOM | 7281 | N | THR | 22 | 69.610 | 47.660 | 42.100 | 1.00 | 41.70 | Y | N |
| ATOM | 7282 | CA | THR | 22 | 70.880 | 48.312 | 42.396 | 1.00 | 41.70 | Y | C |
| ATOM | 7283 | CB | THR | 22 | 70.919 | 48.826 | 43.856 | 1.00 | 62.77 | Y | C |
| ATOM | 7284 | OG1 | THR | 22 | 69.986 | 49.903 | 44.017 | 1.00 | 62.77 | Y | O |
| ATOM | 7285 | CG2 | THR | 22 | 72.322 | 49.303 | 44.222 | 1.00 | 62.77 | Y | C |
| ATOM | 7286 | C | THR | 22 | 72.052 | 47.370 | 42.199 | 1.00 | 41.70 | Y | C |
| ATOM | 7287 | O | THR | 22 | 72.028 | 46.237 | 42.674 | 1.00 | 41.70 | Y | O |
| ATOM | 7288 | N | CYS | 23 | 73.077 | 47.852 | 41.500 | 1.00 | 52.46 | Y | N |
| ATOM | 7289 | CA | CYS | 23 | 74.289 | 47.076 | 41.247 | 1.00 | 52.46 | Y | C |
| ATOM | 7290 | C | CYS | 23 | 75.446 | 47.833 | 41.875 | 1.00 | 52.46 | Y | C |
| ATOM | 7291 | O | CYS | 23 | 75.749 | 48.957 | 41.476 | 1.00 | 52.46 | Y | O |
| ATOM | 7292 | CB | CYS | 23 | 74.522 | 46.938 | 39.744 | 1.00 | 61.15 | Y | C |
| ATOM | 7293 | SG | CYS | 23 | 75.983 | 45.982 | 39.184 | 1.00 | 61.15 | Y | S |
| ATOM | 7294 | N | SER | 24 | 76.079 | 47.219 | 42.866 | 1.00 | 43.95 | Y | N |
| ATOM | 7295 | CA | SER | 24 | 77.200 | 47.837 | 43.556 | 1.00 | 43.95 | Y | C |
| ATOM | 7296 | CB | SER | 24 | 76.992 | 47.751 | 45.072 | 1.00 | 58.07 | Y | C |
| ATOM | 7297 | OG | SER | 24 | 75.782 | 48.379 | 45.462 | 1.00 | 58.07 | Y | O |
| ATOM | 7298 | C | SER | 24 | 78.495 | 47.138 | 43.177 | 1.00 | 43.95 | Y | C |
| ATOM | 7299 | O | SER | 24 | 78.582 | 45.912 | 43.222 | 1.00 | 43.95 | Y | O |
| ATOM | 7300 | N | ALA | 25 | 79.503 | 47.924 | 42.814 | 1.00 | 35.63 | Y | N |

Fig. 19: A-101

| | | | | | | | | | | | |
|---|---|---|---|---|---|---|---|---|---|---|---|
| ATOM | 7301 | CA | ALA | 25 | 80.796 | 47.373 | 42.427 | 1.00 | 35.63 | Y | C |
| ATOM | 7302 | CB | ALA | 25 | 81.214 | 47.920 | 41.068 | 1.00 | 50.18 | Y | C |
| ATOM | 7303 | C | ALA | 25 | 81.894 | 47.635 | 43.454 | 1.00 | 35.63 | Y | C |
| ATOM | 7304 | O | ALA | 25 | 82.050 | 48.754 | 43.959 | 1.00 | 35.63 | Y | O |
| ATOM | 7305 | N | SER | 26 | 82.650 | 46.579 | 43.742 | 1.00 | 37.44 | Y | N |
| ATOM | 7306 | CA | SER | 26 | 83.746 | 46.616 | 44.697 | 1.00 | 37.44 | Y | C |
| ATOM | 7307 | CB | SER | 26 | 84.492 | 45.280 | 44.672 | 1.00 | 31.41 | Y | C |
| ATOM | 7308 | OG | SER | 26 | 85.018 | 45.005 | 43.381 | 1.00 | 31.41 | Y | O |
| ATOM | 7309 | C | SER | 26 | 84.718 | 47.745 | 44.393 | 1.00 | 37.44 | Y | C |
| ATOM | 7310 | O | SER | 26 | 85.358 | 48.286 | 45.297 | 1.00 | 37.44 | Y | O |
| ATOM | 7311 | N | SER | 27 | 84.835 | 48.088 | 43.116 | 1.00 | 70.39 | Y | N |
| ATOM | 7312 | CA | SER | 27 | 85.726 | 49.157 | 42.687 | 1.00 | 70.39 | Y | C |
| ATOM | 7313 | CB | SER | 27 | 86.941 | 48.581 | 41.954 | 1.00 | 53.81 | Y | C |
| ATOM | 7314 | OG | SER | 27 | 87.574 | 47.567 | 42.716 | 1.00 | 53.81 | Y | O |
| ATOM | 7315 | C | SER | 27 | 84.922 | 50.023 | 41.736 | 1.00 | 70.39 | Y | C |
| ATOM | 7316 | O | SER | 27 | 83.960 | 49.545 | 41.139 | 1.00 | 70.39 | Y | O |
| ATOM | 7317 | N | SER | 28 | 85.306 | 51.290 | 41.595 | 1.00 | 30.73 | Y | N |
| ATOM | 7318 | CA | SER | 28 | 84.598 | 52.194 | 40.695 | 1.00 | 30.73 | Y | C |
| ATOM | 7319 | CB | SER | 28 | 85.060 | 53.628 | 40.920 | 1.00 | 55.81 | Y | C |
| ATOM | 7320 | OG | SER | 28 | 86.448 | 53.723 | 40.688 | 1.00 | 55.81 | Y | O |
| ATOM | 7321 | C | SER | 28 | 84.824 | 51.813 | 39.230 | 1.00 | 30.73 | Y | C |
| ATOM | 7322 | O | SER | 28 | 85.873 | 51.287 | 38.863 | 1.00 | 30.73 | Y | O |
| ATOM | 7323 | N | VAL | 29 | 83.832 | 52.092 | 38.398 | 1.00 | 34.83 | Y | N |
| ATOM | 7324 | CA | VAL | 29 | 83.909 | 51.780 | 36.983 | 1.00 | 34.83 | Y | C |
| ATOM | 7325 | CB | VAL | 29 | 83.173 | 50.443 | 36.682 | 1.00 | 24.96 | Y | C |
| ATOM | 7326 | CG1 | VAL | 29 | 83.891 | 49.286 | 37.382 | 1.00 | 24.96 | Y | C |
| ATOM | 7327 | CG2 | VAL | 29 | 81.717 | 50.518 | 37.153 | 1.00 | 24.96 | Y | C |
| ATOM | 7328 | C | VAL | 29 | 83.267 | 52.929 | 36.208 | 1.00 | 34.83 | Y | C |
| ATOM | 7329 | O | VAL | 29 | 82.397 | 53.621 | 36.738 | 1.00 | 34.83 | Y | O |
| ATOM | 7330 | N | ASN | 30 | 83.689 | 53.134 | 34.963 | 1.00 | 19.83 | Y | N |
| ATOM | 7331 | CA | ASN | 30 | 83.152 | 54.225 | 34.145 | 1.00 | 19.83 | Y | C |
| ATOM | 7332 | CB | ASN | 30 | 84.086 | 54.517 | 32.963 | 1.00 | 44.92 | Y | C |
| ATOM | 7333 | CG | ASN | 30 | 84.524 | 53.261 | 32.254 | 1.00 | 44.92 | Y | C |
| ATOM | 7334 | OD1 | ASN | 30 | 85.235 | 52.431 | 32.832 | 1.00 | 44.92 | Y | O |
| ATOM | 7335 | ND2 | ASN | 30 | 84.097 | 53.099 | 31.001 | 1.00 | 44.92 | Y | N |
| ATOM | 7336 | C | ASN | 30 | 81.740 | 53.976 | 33.634 | 1.00 | 19.83 | Y | C |
| ATOM | 7337 | O | ASN | 30 | 80.998 | 54.926 | 33.381 | 1.00 | 19.83 | Y | O |
| ATOM | 7338 | N | HIS | 31 | 81.367 | 52.708 | 33.475 | 1.00 | 24.55 | Y | N |
| ATOM | 7339 | CA | HIS | 31 | 80.031 | 52.373 | 32.991 | 1.00 | 24.55 | Y | C |
| ATOM | 7340 | CB | HIS | 31 | 80.003 | 52.259 | 31.459 | 1.00 | 41.70 | Y | C |
| ATOM | 7341 | CG | HIS | 31 | 80.061 | 53.572 | 30.737 | 1.00 | 41.70 | Y | C |
| ATOM | 7342 | CD2 | HIS | 31 | 79.124 | 54.233 | 30.016 | 1.00 | 41.70 | Y | C |
| ATOM | 7343 | ND1 | HIS | 31 | 81.196 | 54.351 | 30.692 | 1.00 | 41.70 | Y | N |
| ATOM | 7344 | CE1 | HIS | 31 | 80.958 | 55.435 | 29.973 | 1.00 | 41.70 | Y | C |
| ATOM | 7345 | NE2 | HIS | 31 | 79.708 | 55.387 | 29.551 | 1.00 | 41.70 | Y | N |
| ATOM | 7346 | C | HIS | 31 | 79.548 | 51.058 | 33.567 | 1.00 | 24.55 | Y | C |
| ATOM | 7347 | O | HIS | 31 | 80.274 | 50.392 | 34.305 | 1.00 | 24.55 | Y | O |
| ATOM | 7348 | N | MET | 32 | 78.312 | 50.698 | 33.227 | 1.00 | 16.59 | Y | N |
| ATOM | 7349 | CA | MET | 32 | 77.719 | 49.440 | 33.664 | 1.00 | 16.59 | Y | C |
| ATOM | 7350 | CB | MET | 32 | 76.944 | 49.624 | 34.971 | 1.00 | 29.77 | Y | C |
| ATOM | 7351 | CG | MET | 32 | 76.606 | 48.310 | 35.684 | 1.00 | 29.77 | Y | C |
| ATOM | 7352 | SD | MET | 32 | 78.097 | 47.369 | 36.143 | 1.00 | 29.77 | Y | S |
| ATOM | 7353 | CE | MET | 32 | 78.855 | 48.463 | 37.337 | 1.00 | 29.77 | Y | C |
| ATOM | 7354 | C | MET | 32 | 76.779 | 48.941 | 32.563 | 1.00 | 16.59 | Y | C |
| ATOM | 7355 | O | MET | 32 | 76.138 | 49.734 | 31.871 | 1.00 | 16.59 | Y | O |
| ATOM | 7356 | N | PHE | 33 | 76.706 | 47.629 | 32.383 | 1.00 | 41.04 | Y | N |
| ATOM | 7357 | CA | PHE | 33 | 75.830 | 47.089 | 31.358 | 1.00 | 41.04 | Y | C |
| ATOM | 7358 | CB | PHE | 33 | 76.639 | 46.329 | 30.315 | 1.00 | 16.08 | Y | C |
| ATOM | 7359 | CG | PHE | 33 | 77.695 | 47.161 | 29.657 | 1.00 | 16.08 | Y | C |
| ATOM | 7360 | CD1 | PHE | 33 | 78.846 | 47.528 | 30.354 | 1.00 | 16.08 | Y | C |
| ATOM | 7361 | CD2 | PHE | 33 | 77.524 | 47.609 | 28.350 | 1.00 | 16.08 | Y | C |
| ATOM | 7362 | CE1 | PHE | 33 | 79.810 | 48.328 | 29.763 | 1.00 | 16.08 | Y | C |
| ATOM | 7363 | CE2 | PHE | 33 | 78.484 | 48.414 | 27.745 | 1.00 | 16.08 | Y | C |
| ATOM | 7364 | CZ | PHE | 33 | 79.634 | 48.776 | 28.456 | 1.00 | 16.08 | Y | C |
| ATOM | 7365 | C | PHE | 33 | 74.803 | 46.175 | 31.985 | 1.00 | 41.04 | Y | C |
| ATOM | 7366 | O | PHE | 33 | 75.036 | 45.622 | 33.057 | 1.00 | 41.04 | Y | O |
| ATOM | 7367 | N | TRP | 34 | 73.664 | 46.020 | 31.322 | 1.00 | 26.10 | Y | N |
| ATOM | 7368 | CA | TRP | 34 | 72.604 | 45.168 | 31.843 | 1.00 | 26.10 | Y | C |
| ATOM | 7369 | CB | TRP | 34 | 71.438 | 46.009 | 32.364 | 1.00 | 47.27 | Y | C |
| ATOM | 7370 | CG | TRP | 34 | 71.807 | 46.935 | 33.466 | 1.00 | 47.27 | Y | C |
| ATOM | 7371 | CD2 | TRP | 34 | 71.660 | 46.692 | 34.868 | 1.00 | 47.27 | Y | C |
| ATOM | 7372 | CE2 | TRP | 34 | 72.145 | 47.836 | 35.542 | 1.00 | 47.27 | Y | C |
| ATOM | 7373 | CE3 | TRP | 34 | 71.167 | 45.621 | 35.622 | 1.00 | 47.27 | Y | C |

Fig. 19: A-102

| ATOM | 7374 | CD1 | TRP | 34 | 72.360 | 48.175 | 33.346 | 1.00 | 47.27 | Y | C |
|---|---|---|---|---|---|---|---|---|---|---|---|
| ATOM | 7375 | NE1 | TRP | 34 | 72.567 | 48.725 | 34.589 | 1.00 | 47.27 | Y | N |
| ATOM | 7376 | CZ2 | TRP | 34 | 72.150 | 47.939 | 36.940 | 1.00 | 47.27 | Y | C |
| ATOM | 7377 | CZ3 | TRP | 34 | 71.172 | 45.725 | 37.013 | 1.00 | 47.27 | Y | C |
| ATOM | 7378 | CH2 | TRP | 34 | 71.661 | 46.879 | 37.655 | 1.00 | 47.27 | Y | C |
| ATOM | 7379 | C | TRP | 34 | 72.067 | 44.187 | 30.812 | 1.00 | 26.10 | Y | C |
| ATOM | 7380 | O | TRP | 34 | 71.904 | 44.513 | 29.630 | 1.00 | 26.10 | Y | O |
| ATOM | 7381 | N | TYR | 35 | 71.793 | 42.972 | 31.267 | 1.00 | 43.42 | Y | N |
| ATOM | 7382 | CA | TYR | 35 | 71.248 | 41.964 | 30.381 | 1.00 | 43.42 | Y | C |
| ATOM | 7383 | CB | TYR | 35 | 72.230 | 40.808 | 30.189 | 1.00 | 22.29 | Y | C |
| ATOM | 7384 | CG | TYR | 35 | 73.549 | 41.240 | 29.596 | 1.00 | 22.29 | Y | C |
| ATOM | 7385 | CD1 | TYR | 35 | 74.645 | 41.535 | 30.417 | 1.00 | 22.29 | Y | C |
| ATOM | 7386 | CE1 | TYR | 35 | 75.841 | 41.962 | 29.881 | 1.00 | 22.29 | Y | C |
| ATOM | 7387 | CD2 | TYR | 35 | 73.697 | 41.385 | 28.216 | 1.00 | 22.29 | Y | C |
| ATOM | 7388 | CE2 | TYR | 35 | 74.898 | 41.808 | 27.670 | 1.00 | 22.29 | Y | C |
| ATOM | 7389 | CZ | TYR | 35 | 75.960 | 42.094 | 28.510 | 1.00 | 22.29 | Y | C |
| ATOM | 7390 | OH | TYR | 35 | 77.148 | 42.516 | 27.972 | 1.00 | 22.29 | Y | O |
| ATOM | 7391 | C | TYR | 35 | 69.966 | 41.449 | 30.991 | 1.00 | 43.42 | Y | C |
| ATOM | 7392 | O | TYR | 35 | 69.826 | 41.393 | 32.214 | 1.00 | 43.42 | Y | O |
| ATOM | 7393 | N | GLN | 36 | 69.015 | 41.107 | 30.136 | 1.00 | 45.64 | Y | N |
| ATOM | 7394 | CA | GLN | 36 | 67.760 | 40.567 | 30.607 | 1.00 | 45.64 | Y | C |
| ATOM | 7395 | CB | GLN | 36 | 66.574 | 41.346 | 30.054 | 1.00 | 37.71 | Y | C |
| ATOM | 7396 | CG | GLN | 36 | 65.259 | 40.610 | 30.277 | 1.00 | 37.71 | Y | C |
| ATOM | 7397 | CD | GLN | 36 | 64.189 | 41.002 | 29.287 | 1.00 | 37.71 | Y | C |
| ATOM | 7398 | OE1 | GLN | 36 | 63.601 | 42.072 | 29.391 | 1.00 | 37.71 | Y | O |
| ATOM | 7399 | NE2 | GLN | 36 | 63.936 | 40.137 | 28.314 | 1.00 | 37.71 | Y | N |
| ATOM | 7400 | C | GLN | 36 | 67.664 | 39.138 | 30.118 | 1.00 | 45.64 | Y | C |
| ATOM | 7401 | O | GLN | 36 | 67.725 | 38.881 | 28.910 | 1.00 | 45.64 | Y | O |
| ATOM | 7402 | N | GLN | 37 | 67.522 | 38.205 | 31.050 | 1.00 | 50.28 | Y | N |
| ATOM | 7403 | CA | GLN | 37 | 67.390 | 36.809 | 30.670 | 1.00 | 50.28 | Y | C |
| ATOM | 7404 | CB | GLN | 37 | 68.522 | 35.961 | 31.265 | 1.00 | 34.85 | Y | C |
| ATOM | 7405 | CG | GLN | 37 | 68.392 | 34.487 | 30.904 | 1.00 | 34.85 | Y | C |
| ATOM | 7406 | CD | GLN | 37 | 69.543 | 33.645 | 31.388 | 1.00 | 34.85 | Y | C |
| ATOM | 7407 | OE1 | GLN | 37 | 69.925 | 33.699 | 32.565 | 1.00 | 34.85 | Y | O |
| ATOM | 7408 | NE2 | GLN | 37 | 70.098 | 32.842 | 30.484 | 1.00 | 34.85 | Y | N |
| ATOM | 7409 | C | GLN | 37 | 66.042 | 36.248 | 31.108 | 1.00 | 50.28 | Y | C |
| ATOM | 7410 | O | GLN | 37 | 65.690 | 36.272 | 32.293 | 1.00 | 50.28 | Y | O |
| ATOM | 7411 | N | LYS | 38 | 65.284 | 35.763 | 30.133 | 1.00 | 68.24 | Y | N |
| ATOM | 7412 | CA | LYS | 38 | 63.983 | 35.175 | 30.403 | 1.00 | 68.24 | Y | C |
| ATOM | 7413 | CB | LYS | 38 | 62.991 | 35.530 | 29.291 | 1.00 | 55.54 | Y | C |
| ATOM | 7414 | CG | LYS | 38 | 62.893 | 37.031 | 29.023 | 1.00 | 55.54 | Y | C |
| ATOM | 7415 | CD | LYS | 38 | 61.764 | 37.382 | 28.056 | 1.00 | 55.54 | Y | C |
| ATOM | 7416 | CE | LYS | 38 | 60.394 | 37.298 | 28.726 | 1.00 | 55.54 | Y | C |
| ATOM | 7417 | NZ | LYS | 38 | 60.290 | 38.166 | 29.943 | 1.00 | 55.54 | Y | N |
| ATOM | 7418 | C | LYS | 38 | 64.198 | 33.667 | 30.473 | 1.00 | 68.24 | Y | C |
| ATOM | 7419 | O | LYS | 38 | 64.971 | 33.104 | 29.696 | 1.00 | 68.24 | Y | O |
| ATOM | 7420 | N | PRO | 39 | 63.520 | 32.994 | 31.412 | 1.00 | 67.87 | Y | N |
| ATOM | 7421 | CD | PRO | 39 | 62.478 | 33.563 | 32.282 | 1.00 | 58.47 | Y | C |
| ATOM | 7422 | CA | PRO | 39 | 63.621 | 31.546 | 31.614 | 1.00 | 67.87 | Y | C |
| ATOM | 7423 | CB | PRO | 39 | 62.368 | 31.234 | 32.417 | 1.00 | 58.47 | Y | C |
| ATOM | 7424 | CG | PRO | 39 | 62.247 | 32.446 | 33.271 | 1.00 | 58.47 | Y | C |
| ATOM | 7425 | C | PRO | 39 | 63.717 | 30.714 | 30.338 | 1.00 | 67.87 | Y | C |
| ATOM | 7426 | O | PRO | 39 | 62.898 | 30.859 | 29.425 | 1.00 | 67.87 | Y | O |
| ATOM | 7427 | N | GLY | 40 | 64.730 | 29.847 | 30.288 | 1.00 | 54.98 | Y | N |
| ATOM | 7428 | CA | GLY | 40 | 64.925 | 28.977 | 29.137 | 1.00 | 54.98 | Y | C |
| ATOM | 7429 | C | GLY | 40 | 65.488 | 29.625 | 27.882 | 1.00 | 54.98 | Y | C |
| ATOM | 7430 | O | GLY | 40 | 65.625 | 28.957 | 26.855 | 1.00 | 54.98 | Y | O |
| ATOM | 7431 | N | LYS | 41 | 65.801 | 30.918 | 27.955 | 1.00 | 83.28 | Y | N |
| ATOM | 7432 | CA | LYS | 41 | 66.364 | 31.641 | 26.816 | 1.00 | 83.28 | Y | C |
| ATOM | 7433 | CB | LYS | 41 | 65.414 | 32.754 | 26.354 | 1.00 | 72.06 | Y | C |
| ATOM | 7434 | CG | LYS | 41 | 64.045 | 32.271 | 25.882 | 1.00 | 72.06 | Y | C |
| ATOM | 7435 | CD | LYS | 41 | 63.316 | 33.311 | 25.008 | 1.00 | 72.06 | Y | C |
| ATOM | 7436 | CE | LYS | 41 | 63.035 | 34.642 | 25.726 | 1.00 | 72.06 | Y | C |
| ATOM | 7437 | NZ | LYS | 41 | 64.229 | 35.536 | 25.855 | 1.00 | 72.06 | Y | N |
| ATOM | 7438 | C | LYS | 41 | 67.727 | 32.245 | 27.160 | 1.00 | 83.28 | Y | C |
| ATOM | 7439 | O | LYS | 41 | 68.110 | 32.327 | 28.331 | 1.00 | 83.28 | Y | O |
| ATOM | 7440 | N | ALA | 42 | 68.458 | 32.666 | 26.133 | 1.00 | 55.60 | Y | N |
| ATOM | 7441 | CA | ALA | 42 | 69.776 | 33.261 | 26.326 | 1.00 | 55.60 | Y | C |
| ATOM | 7442 | CB | ALA | 42 | 70.561 | 33.194 | 25.041 | 1.00 | 1.87 | Y | C |
| ATOM | 7443 | C | ALA | 42 | 69.623 | 34.707 | 26.754 | 1.00 | 55.60 | Y | C |
| ATOM | 7444 | O | ALA | 42 | 68.607 | 35.337 | 26.462 | 1.00 | 55.60 | Y | O |
| ATOM | 7445 | N | PRO | 43 | 70.628 | 35.259 | 27.455 | 1.00 | 54.21 | Y | N |
| ATOM | 7446 | CD | PRO | 43 | 71.849 | 34.627 | 27.983 | 1.00 | 18.24 | Y | C |

Fig. 19: A-103

```
ATOM   7447  CA   PRO  43     70.537  36.656  27.889  1.00  54.21  Y  C
ATOM   7448  CB   PRO  43     71.875  36.890  28.594  1.00  18.24  Y  C
ATOM   7449  CG   PRO  43     72.202  35.544  29.149  1.00  18.24  Y  C
ATOM   7450  C    PRO  43     70.349  37.584  26.689  1.00  54.21  Y  C
ATOM   7451  O    PRO  43     70.660  37.219  25.555  1.00  54.21  Y  O
ATOM   7452  N    LYS  44     69.837  38.782  26.946  1.00  55.44  Y  N
ATOM   7453  CA   LYS  44     69.618  39.764  25.892  1.00  55.44  Y  C
ATOM   7454  CB   LYS  44     68.120  39.894  25.601  1.00  46.11  Y  C
ATOM   7455  CG   LYS  44     67.705  39.473  24.199  1.00  46.11  Y  C
ATOM   7456  CD   LYS  44     66.189  39.520  24.018  1.00  46.11  Y  C
ATOM   7457  CE   LYS  44     65.457  38.464  24.865  1.00  46.11  Y  C
ATOM   7458  NZ   LYS  44     65.564  38.665  26.354  1.00  46.11  Y  N
ATOM   7459  C    LYS  44     70.172  41.117  26.328  1.00  55.44  Y  C
ATOM   7460  O    LYS  44     69.930  41.554  27.454  1.00  55.44  Y  O
ATOM   7461  N    PRO  45     70.946  41.785  25.451  1.00  21.39  Y  N
ATOM   7462  CD   PRO  45     71.303  41.365  24.085  1.00  11.37  Y  C
ATOM   7463  CA   PRO  45     71.523  43.103  25.772  1.00  21.39  Y  C
ATOM   7464  CB   PRO  45     72.159  43.539  24.457  1.00  11.37  Y  C
ATOM   7465  CG   PRO  45     72.485  42.234  23.795  1.00  11.37  Y  C
ATOM   7466  C    PRO  45     70.361  44.010  26.138  1.00  21.39  Y  C
ATOM   7467  O    PRO  45     69.407  44.103  25.383  1.00  21.39  Y  O
ATOM   7468  N    TRP  46     70.434  44.676  27.281  1.00  48.64  Y  N
ATOM   7469  CA   TRP  46     69.333  45.532  27.704  1.00  48.64  Y  C
ATOM   7470  CB   TRP  46     68.783  45.038  29.043  1.00  23.18  Y  C
ATOM   7471  CG   TRP  46     67.316  45.220  29.143  1.00  23.18  Y  C
ATOM   7472  CD2  TRP  46     66.330  44.620  28.299  1.00  23.18  Y  C
ATOM   7473  CE2  TRP  46     65.070  45.075  28.739  1.00  23.18  Y  C
ATOM   7474  CE3  TRP  46     66.391  43.736  27.206  1.00  23.18  Y  C
ATOM   7475  CD1  TRP  46     66.637  45.997  30.038  1.00  23.18  Y  C
ATOM   7476  NE1  TRP  46     65.282  45.914  29.803  1.00  23.18  Y  N
ATOM   7477  CZ2  TRP  46     63.881  44.679  28.126  1.00  23.18  Y  C
ATOM   7478  CZ3  TRP  46     65.212  43.342  26.599  1.00  23.18  Y  C
ATOM   7479  CH2  TRP  46     63.973  43.814  27.059  1.00  23.18  Y  C
ATOM   7480  C    TRP  46     69.694  47.007  27.826  1.00  48.64  Y  C
ATOM   7481  O    TRP  46     68.986  47.877  27.324  1.00  48.64  Y  O
ATOM   7482  N    ILE  47     70.785  47.283  28.523  1.00  42.06  Y  N
ATOM   7483  CA   ILE  47     71.238  48.644  28.717  1.00  42.06  Y  C
ATOM   7484  CB   ILE  47     70.801  49.172  30.099  1.00  37.03  Y  C
ATOM   7485  CG2  ILE  47     71.345  50.580  30.325  1.00  37.03  Y  C
ATOM   7486  CG1  ILE  47     69.275  49.168  30.198  1.00  37.03  Y  C
ATOM   7487  CD1  ILE  47     68.749  49.670  31.538  1.00  37.03  Y  C
ATOM   7488  C    ILE  47     72.758  48.641  28.638  1.00  42.06  Y  C
ATOM   7489  O    ILE  47     73.417  47.951  29.414  1.00  42.06  Y  O
ATOM   7490  N    TYR  48     73.310  49.387  27.684  1.00  17.47  Y  N
ATOM   7491  CA   TYR  48     74.753  49.467  27.532  1.00  17.47  Y  C
ATOM   7492  CB   TYR  48     75.189  49.145  26.106  1.00  20.64  Y  C
ATOM   7493  CG   TYR  48     74.613  50.048  25.046  1.00  20.64  Y  C
ATOM   7494  CD1  TYR  48     73.267  49.988  24.710  1.00  20.64  Y  C
ATOM   7495  CE1  TYR  48     72.743  50.792  23.704  1.00  20.64  Y  C
ATOM   7496  CD2  TYR  48     75.425  50.940  24.353  1.00  20.64  Y  C
ATOM   7497  CE2  TYR  48     74.916  51.750  23.347  1.00  20.64  Y  C
ATOM   7498  CZ   TYR  48     73.573  51.671  23.028  1.00  20.64  Y  C
ATOM   7499  OH   TYR  48     73.051  52.476  22.045  1.00  20.64  Y  O
ATOM   7500  C    TYR  48     75.193  50.861  27.892  1.00  17.47  Y  C
ATOM   7501  O    TYR  48     74.365  51.754  28.021  1.00  17.47  Y  O
ATOM   7502  N    LEU  49     76.497  51.044  28.054  1.00  31.07  Y  N
ATOM   7503  CA   LEU  49     77.042  52.337  28.429  1.00  31.07  Y  C
ATOM   7504  CB   LEU  49     77.200  53.247  27.205  1.00  20.44  Y  C
ATOM   7505  CG   LEU  49     78.368  53.044  26.236  1.00  20.44  Y  C
ATOM   7506  CD1  LEU  49     79.662  52.870  27.019  1.00  20.44  Y  C
ATOM   7507  CD2  LEU  49     78.121  51.836  25.385  1.00  20.44  Y  C
ATOM   7508  C    LEU  49     76.173  53.037  29.475  1.00  31.07  Y  C
ATOM   7509  O    LEU  49     75.769  54.178  29.293  1.00  31.07  Y  O
ATOM   7510  N    THR  50     75.861  52.329  30.555  1.00  28.24  Y  N
ATOM   7511  CA   THR  50     75.083  52.870  31.670  1.00  28.24  Y  C
ATOM   7512  CB   THR  50     75.754  54.128  32.230  1.00  41.62  Y  C
ATOM   7513  OG1  THR  50     77.134  53.847  32.495  1.00  41.62  Y  O
ATOM   7514  CG2  THR  50     75.066  54.568  33.522  1.00  41.62  Y  C
ATOM   7515  C    THR  50     73.605  53.187  31.485  1.00  28.24  Y  C
ATOM   7516  O    THR  50     72.761  52.603  32.158  1.00  28.24  Y  O
ATOM   7517  N    SER  51     73.283  54.114  30.595  1.00  28.33  Y  N
ATOM   7518  CA   SER  51     71.889  54.496  30.402  1.00  28.33  Y  C
ATOM   7519  CB   SER  51     71.729  55.981  30.714  1.00  81.44  Y  C
```

Fig. 19: A-104

| | | | | | | | | | | | |
|---|---|---|---|---|---|---|---|---|---|---|---|
| ATOM | 7520 | OG | SER | 51 | 72.714 | 56.738 | 30.034 | 1.00 | 81.44 | Y | O |
| ATOM | 7521 | C | SER | 51 | 71.312 | 54.190 | 29.019 | 1.00 | 28.33 | Y | C |
| ATOM | 7522 | O | SER | 51 | 70.092 | 54.174 | 28.831 | 1.00 | 28.33 | Y | O |
| ATOM | 7523 | N | ASN | 52 | 72.184 | 53.941 | 28.053 | 1.00 | 27.44 | Y | N |
| ATOM | 7524 | CA | ASN | 52 | 71.736 | 53.648 | 26.704 | 1.00 | 27.44 | Y | C |
| ATOM | 7525 | CB | ASN | 52 | 72.942 | 53.523 | 25.779 | 1.00 | 42.81 | Y | C |
| ATOM | 7526 | CG | ASN | 52 | 73.623 | 54.849 | 25.546 | 1.00 | 42.81 | Y | C |
| ATOM | 7527 | OD1 | ASN | 52 | 73.059 | 55.733 | 24.907 | 1.00 | 42.81 | Y | O |
| ATOM | 7528 | ND2 | ASN | 52 | 74.829 | 55.006 | 26.076 | 1.00 | 42.81 | Y | N |
| ATOM | 7529 | C | ASN | 52 | 70.896 | 52.390 | 26.623 | 1.00 | 27.44 | Y | C |
| ATOM | 7530 | O | ASN | 52 | 71.336 | 51.320 | 27.027 | 1.00 | 27.44 | Y | O |
| ATOM | 7531 | N | LEU | 53 | 69.682 | 52.519 | 26.100 | 1.00 | 46.42 | Y | N |
| ATOM | 7532 | CA | LEU | 53 | 68.805 | 51.367 | 25.954 | 1.00 | 46.42 | Y | C |
| ATOM | 7533 | CB | LEU | 53 | 67.349 | 51.803 | 25.887 | 1.00 | 19.90 | Y | C |
| ATOM | 7534 | CG | LEU | 53 | 66.763 | 52.595 | 27.051 | 1.00 | 19.90 | Y | C |
| ATOM | 7535 | CD1 | LEU | 53 | 65.255 | 52.685 | 26.846 | 1.00 | 19.90 | Y | C |
| ATOM | 7536 | CD2 | LEU | 53 | 67.071 | 51.918 | 28.382 | 1.00 | 19.90 | Y | C |
| ATOM | 7537 | C | LEU | 53 | 69.136 | 50.610 | 24.676 | 1.00 | 46.42 | Y | C |
| ATOM | 7538 | O | LEU | 53 | 69.414 | 51.220 | 23.644 | 1.00 | 46.42 | Y | O |
| ATOM | 7539 | N | ALA | 54 | 69.101 | 49.281 | 24.744 | 1.00 | 35.05 | Y | N |
| ATOM | 7540 | CA | ALA | 54 | 69.378 | 48.447 | 23.583 | 1.00 | 35.05 | Y | C |
| ATOM | 7541 | CB | ALA | 54 | 69.220 | 46.994 | 23.930 | 1.00 | 27.54 | Y | C |
| ATOM | 7542 | C | ALA | 54 | 68.373 | 48.829 | 22.530 | 1.00 | 35.05 | Y | C |
| ATOM | 7543 | O | ALA | 54 | 67.680 | 49.834 | 22.666 | 1.00 | 35.05 | Y | O |
| ATOM | 7544 | N | SER | 55 | 68.259 | 48.026 | 21.486 | 1.00 | 47.40 | Y | N |
| ATOM | 7545 | CA | SER | 55 | 67.319 | 48.376 | 20.443 | 1.00 | 47.40 | Y | C |
| ATOM | 7546 | CB | SER | 55 | 67.689 | 47.681 | 19.140 | 1.00 | 36.06 | Y | C |
| ATOM | 7547 | OG | SER | 55 | 67.083 | 48.359 | 18.051 | 1.00 | 36.06 | Y | O |
| ATOM | 7548 | C | SER | 55 | 65.866 | 48.073 | 20.801 | 1.00 | 47.40 | Y | C |
| ATOM | 7549 | O | SER | 55 | 64.993 | 48.921 | 20.631 | 1.00 | 47.40 | Y | O |
| ATOM | 7550 | N | GLY | 56 | 65.599 | 46.878 | 21.312 | 1.00 | 54.09 | Y | N |
| ATOM | 7551 | CA | GLY | 56 | 64.225 | 46.531 | 21.647 | 1.00 | 54.09 | Y | C |
| ATOM | 7552 | C | GLY | 56 | 63.650 | 47.071 | 22.948 | 1.00 | 54.09 | Y | C |
| ATOM | 7553 | O | GLY | 56 | 62.457 | 47.370 | 23.025 | 1.00 | 54.09 | Y | O |
| ATOM | 7554 | N | VAL | 57 | 64.497 | 47.197 | 23.965 | 1.00 | 63.10 | Y | N |
| ATOM | 7555 | CA | VAL | 57 | 64.082 | 47.667 | 25.282 | 1.00 | 63.10 | Y | C |
| ATOM | 7556 | CB | VAL | 57 | 65.311 | 48.113 | 26.120 | 1.00 | 46.15 | Y | C |
| ATOM | 7557 | CG1 | VAL | 57 | 64.923 | 48.248 | 27.588 | 1.00 | 46.15 | Y | C |
| ATOM | 7558 | CG2 | VAL | 57 | 66.446 | 47.118 | 25.961 | 1.00 | 46.15 | Y | C |
| ATOM | 7559 | C | VAL | 57 | 63.071 | 48.817 | 25.251 | 1.00 | 63.10 | Y | C |
| ATOM | 7560 | O | VAL | 57 | 63.363 | 49.898 | 24.747 | 1.00 | 63.10 | Y | O |
| ATOM | 7561 | N | PRO | 58 | 61.862 | 48.594 | 25.791 | 1.00 | 51.01 | Y | N |
| ATOM | 7562 | CD | PRO | 58 | 61.362 | 47.365 | 26.426 | 1.00 | 31.12 | Y | C |
| ATOM | 7563 | CA | PRO | 58 | 60.834 | 49.639 | 25.815 | 1.00 | 51.01 | Y | C |
| ATOM | 7564 | CB | PRO | 58 | 59.634 | 48.929 | 26.433 | 1.00 | 31.12 | Y | C |
| ATOM | 7565 | CG | PRO | 58 | 60.258 | 47.899 | 27.300 | 1.00 | 31.12 | Y | C |
| ATOM | 7566 | C | PRO | 58 | 61.305 | 50.829 | 26.643 | 1.00 | 51.01 | Y | C |
| ATOM | 7567 | O | PRO | 58 | 61.992 | 50.660 | 27.653 | 1.00 | 51.01 | Y | O |
| ATOM | 7568 | N | SER | 59 | 60.918 | 52.027 | 26.216 | 1.00 | 33.61 | Y | N |
| ATOM | 7569 | CA | SER | 59 | 61.330 | 53.267 | 26.874 | 1.00 | 33.61 | Y | C |
| ATOM | 7570 | CB | SER | 59 | 60.780 | 54.482 | 26.113 | 1.00 | 61.12 | Y | C |
| ATOM | 7571 | OG | SER | 59 | 59.368 | 54.481 | 26.096 | 1.00 | 61.12 | Y | O |
| ATOM | 7572 | C | SER | 59 | 61.023 | 53.411 | 28.359 | 1.00 | 33.61 | Y | C |
| ATOM | 7573 | O | SER | 59 | 61.495 | 54.353 | 28.990 | 1.00 | 33.61 | Y | O |
| ATOM | 7574 | N | ARG | 60 | 60.244 | 52.500 | 28.928 | 1.00 | 39.70 | Y | N |
| ATOM | 7575 | CA | ARG | 60 | 59.963 | 52.599 | 30.359 | 1.00 | 39.70 | Y | C |
| ATOM | 7576 | CB | ARG | 60 | 58.764 | 51.731 | 30.751 | 1.00 | 42.51 | Y | C |
| ATOM | 7577 | CG | ARG | 60 | 58.846 | 50.293 | 30.287 | 1.00 | 42.51 | Y | C |
| ATOM | 7578 | CD | ARG | 60 | 57.798 | 49.425 | 30.971 | 1.00 | 42.51 | Y | C |
| ATOM | 7579 | NE | ARG | 60 | 57.683 | 48.120 | 30.333 | 1.00 | 42.51 | Y | N |
| ATOM | 7580 | CZ | ARG | 60 | 57.277 | 47.939 | 29.079 | 1.00 | 42.51 | Y | C |
| ATOM | 7581 | NH1 | ARG | 60 | 56.943 | 48.979 | 28.324 | 1.00 | 42.51 | Y | N |
| ATOM | 7582 | NH2 | ARG | 60 | 57.210 | 46.718 | 28.569 | 1.00 | 42.51 | Y | N |
| ATOM | 7583 | C | ARG | 60 | 61.202 | 52.180 | 31.158 | 1.00 | 39.70 | Y | C |
| ATOM | 7584 | O | ARG | 60 | 61.311 | 52.451 | 32.357 | 1.00 | 39.70 | Y | O |
| ATOM | 7585 | N | PHE | 61 | 62.136 | 51.522 | 30.480 | 1.00 | 40.60 | Y | N |
| ATOM | 7586 | CA | PHE | 61 | 63.372 | 51.086 | 31.109 | 1.00 | 40.60 | Y | C |
| ATOM | 7587 | CB | PHE | 61 | 63.965 | 49.886 | 30.370 | 1.00 | 38.42 | Y | C |
| ATOM | 7588 | CG | PHE | 61 | 63.416 | 48.563 | 30.811 | 1.00 | 38.42 | Y | C |
| ATOM | 7589 | CD1 | PHE | 61 | 62.493 | 47.881 | 30.028 | 1.00 | 38.42 | Y | C |
| ATOM | 7590 | CD2 | PHE | 61 | 63.830 | 47.997 | 32.010 | 1.00 | 38.42 | Y | C |
| ATOM | 7591 | CE1 | PHE | 61 | 61.990 | 46.652 | 30.434 | 1.00 | 38.42 | Y | C |
| ATOM | 7592 | CE2 | PHE | 61 | 63.332 | 46.770 | 32.423 | 1.00 | 38.42 | Y | C |

Fig. 19: A-105

| ATOM | 7593 | CZ | PHE | 61 | 62.410 | 46.096 | 31.634 | 1.00 | 38.42 | Y | C |
|---|---|---|---|---|---|---|---|---|---|---|---|
| ATOM | 7594 | C | PHE | 61 | 64.399 | 52.209 | 31.097 | 1.00 | 40.60 | Y | C |
| ATOM | 7595 | O | PHE | 61 | 64.470 | 52.989 | 30.144 | 1.00 | 40.60 | Y | O |
| ATOM | 7596 | N | SER | 62 | 65.202 | 52.284 | 32.152 | 1.00 | 26.58 | Y | N |
| ATOM | 7597 | CA | SER | 62 | 66.238 | 53.306 | 32.247 | 1.00 | 26.58 | Y | C |
| ATOM | 7598 | CB | SER | 62 | 65.658 | 54.604 | 32.802 | 1.00 | 47.08 | Y | C |
| ATOM | 7599 | OG | SER | 62 | 65.071 | 54.395 | 34.076 | 1.00 | 47.08 | Y | O |
| ATOM | 7600 | C | SER | 62 | 67.376 | 52.828 | 33.145 | 1.00 | 26.58 | Y | C |
| ATOM | 7601 | O | SER | 62 | 67.160 | 52.123 | 34.125 | 1.00 | 26.58 | Y | O |
| ATOM | 7602 | N | GLY | 63 | 68.595 | 53.208 | 32.797 | 1.00 | 30.78 | Y | N |
| ATOM | 7603 | CA | GLY | 63 | 69.738 | 52.810 | 33.591 | 1.00 | 30.78 | Y | C |
| ATOM | 7604 | C | GLY | 63 | 70.426 | 54.067 | 34.056 | 1.00 | 30.78 | Y | C |
| ATOM | 7605 | O | GLY | 63 | 70.266 | 55.122 | 33.442 | 1.00 | 30.78 | Y | O |
| ATOM | 7606 | N | SER | 64 | 71.195 | 53.964 | 35.130 | 1.00 | 54.48 | Y | N |
| ATOM | 7607 | CA | SER | 64 | 71.884 | 55.130 | 35.652 | 1.00 | 54.48 | Y | C |
| ATOM | 7608 | CB | SER | 64 | 70.869 | 56.075 | 36.290 | 1.00 | 25.06 | Y | C |
| ATOM | 7609 | OG | SER | 64 | 71.519 | 57.204 | 36.839 | 1.00 | 25.06 | Y | O |
| ATOM | 7610 | C | SER | 64 | 72.947 | 54.763 | 36.675 | 1.00 | 54.48 | Y | C |
| ATOM | 7611 | O | SER | 64 | 73.000 | 53.632 | 37.154 | 1.00 | 54.48 | Y | O |
| ATOM | 7612 | N | GLY | 65 | 73.793 | 55.732 | 37.007 | 1.00 | 43.76 | Y | N |
| ATOM | 7613 | CA | GLY | 65 | 74.836 | 55.494 | 37.984 | 1.00 | 43.76 | Y | C |
| ATOM | 7614 | C | GLY | 65 | 76.218 | 56.023 | 37.637 | 1.00 | 43.76 | Y | C |
| ATOM | 7615 | O | GLY | 65 | 76.431 | 56.698 | 36.622 | 1.00 | 43.76 | Y | O |
| ATOM | 7616 | N | SER | 66 | 77.167 | 55.703 | 38.508 | 1.00 | 27.01 | Y | N |
| ATOM | 7617 | CA | SER | 66 | 78.546 | 56.110 | 38.339 | 1.00 | 27.01 | Y | C |
| ATOM | 7618 | CB | SER | 66 | 78.641 | 57.635 | 38.286 | 1.00 | 58.01 | Y | C |
| ATOM | 7619 | OG | SER | 66 | 77.927 | 58.229 | 39.355 | 1.00 | 58.01 | Y | O |
| ATOM | 7620 | C | SER | 66 | 79.367 | 55.563 | 39.498 | 1.00 | 27.01 | Y | C |
| ATOM | 7621 | O | SER | 66 | 78.817 | 55.039 | 40.464 | 1.00 | 27.01 | Y | O |
| ATOM | 7622 | N | GLY | 67 | 80.685 | 55.668 | 39.385 | 1.00 | 73.15 | Y | N |
| ATOM | 7623 | CA | GLY | 67 | 81.555 | 55.179 | 40.436 | 1.00 | 73.15 | Y | C |
| ATOM | 7624 | C | GLY | 67 | 81.312 | 53.733 | 40.822 | 1.00 | 73.15 | Y | C |
| ATOM | 7625 | O | GLY | 67 | 81.609 | 52.814 | 40.056 | 1.00 | 73.15 | Y | O |
| ATOM | 7626 | N | THR | 68 | 80.758 | 53.530 | 42.011 | 1.00 | 44.05 | Y | N |
| ATOM | 7627 | CA | THR | 68 | 80.506 | 52.186 | 42.506 | 1.00 | 44.05 | Y | C |
| ATOM | 7628 | CB | THR | 68 | 81.118 | 52.003 | 43.894 | 1.00 | 42.61 | Y | C |
| ATOM | 7629 | OG1 | THR | 68 | 80.524 | 52.945 | 44.793 | 1.00 | 42.61 | Y | O |
| ATOM | 7630 | CG2 | THR | 68 | 82.627 | 52.225 | 43.845 | 1.00 | 42.61 | Y | C |
| ATOM | 7631 | C | THR | 68 | 79.042 | 51.786 | 42.592 | 1.00 | 44.05 | Y | C |
| ATOM | 7632 | O | THR | 68 | 78.743 | 50.632 | 42.879 | 1.00 | 44.05 | Y | O |
| ATOM | 7633 | N | ASP | 69 | 78.128 | 52.720 | 42.352 | 1.00 | 35.15 | Y | N |
| ATOM | 7634 | CA | ASP | 69 | 76.708 | 52.392 | 42.424 | 1.00 | 35.15 | Y | C |
| ATOM | 7635 | CB | ASP | 69 | 76.066 | 53.103 | 43.617 | 1.00 | 108.02 | Y | C |
| ATOM | 7636 | CG | ASP | 69 | 76.592 | 52.591 | 44.946 | 1.00 | 108.02 | Y | C |
| ATOM | 7637 | OD1 | ASP | 69 | 76.357 | 51.406 | 45.268 | 1.00 | 108.02 | Y | O |
| ATOM | 7638 | OD2 | ASP | 69 | 77.249 | 53.370 | 45.667 | 1.00 | 108.02 | Y | O |
| ATOM | 7639 | C | ASP | 69 | 75.942 | 52.705 | 41.139 | 1.00 | 35.15 | Y | C |
| ATOM | 7640 | O | ASP | 69 | 75.884 | 53.850 | 40.693 | 1.00 | 35.15 | Y | O |
| ATOM | 7641 | N | TYR | 70 | 75.359 | 51.664 | 40.551 | 1.00 | 27.55 | Y | N |
| ATOM | 7642 | CA | TYR | 70 | 74.599 | 51.787 | 39.317 | 1.00 | 27.55 | Y | C |
| ATOM | 7643 | CB | TYR | 70 | 75.315 | 51.016 | 38.191 | 1.00 | 25.09 | Y | C |
| ATOM | 7644 | CG | TYR | 70 | 76.543 | 51.737 | 37.662 | 1.00 | 25.09 | Y | C |
| ATOM | 7645 | CD1 | TYR | 70 | 76.447 | 52.637 | 36.596 | 1.00 | 25.09 | Y | C |
| ATOM | 7646 | CE1 | TYR | 70 | 77.562 | 53.365 | 36.158 | 1.00 | 25.09 | Y | C |
| ATOM | 7647 | CD2 | TYR | 70 | 77.787 | 51.577 | 38.275 | 1.00 | 25.09 | Y | C |
| ATOM | 7648 | CE2 | TYR | 70 | 78.906 | 52.299 | 37.848 | 1.00 | 25.09 | Y | C |
| ATOM | 7649 | CZ | TYR | 70 | 78.785 | 53.194 | 36.790 | 1.00 | 25.09 | Y | C |
| ATOM | 7650 | OH | TYR | 70 | 79.873 | 53.933 | 36.382 | 1.00 | 25.09 | Y | O |
| ATOM | 7651 | C | TYR | 70 | 73.184 | 51.267 | 39.523 | 1.00 | 27.55 | Y | C |
| ATOM | 7652 | O | TYR | 70 | 72.920 | 50.545 | 40.488 | 1.00 | 27.55 | Y | O |
| ATOM | 7653 | N | THR | 71 | 72.270 | 51.635 | 38.627 | 1.00 | 38.36 | Y | N |
| ATOM | 7654 | CA | THR | 71 | 70.893 | 51.184 | 38.767 | 1.00 | 38.36 | Y | C |
| ATOM | 7655 | CB | THR | 71 | 70.074 | 52.152 | 39.657 | 1.00 | 44.65 | Y | C |
| ATOM | 7656 | OG1 | THR | 71 | 69.921 | 53.403 | 38.978 | 1.00 | 44.65 | Y | O |
| ATOM | 7657 | CG2 | THR | 71 | 70.770 | 52.394 | 40.989 | 1.00 | 44.65 | Y | C |
| ATOM | 7658 | C | THR | 71 | 70.099 | 50.991 | 37.473 | 1.00 | 38.36 | Y | C |
| ATOM | 7659 | O | THR | 71 | 70.281 | 51.707 | 36.485 | 1.00 | 38.36 | Y | O |
| ATOM | 7660 | N | LEU | 72 | 69.216 | 50.001 | 37.499 | 1.00 | 32.67 | Y | N |
| ATOM | 7661 | CA | LEU | 72 | 68.324 | 49.718 | 36.385 | 1.00 | 32.67 | Y | C |
| ATOM | 7662 | CB | LEU | 72 | 68.392 | 48.238 | 35.985 | 1.00 | 53.11 | Y | C |
| ATOM | 7663 | CG | LEU | 72 | 67.283 | 47.694 | 35.073 | 1.00 | 53.11 | Y | C |
| ATOM | 7664 | CD1 | LEU | 72 | 66.871 | 48.731 | 34.059 | 1.00 | 53.11 | Y | C |
| ATOM | 7665 | CD2 | LEU | 72 | 67.769 | 46.444 | 34.372 | 1.00 | 53.11 | Y | C |

Fig. 19: A-106

| | | | | | | | | | | |
|---|---|---|---|---|---|---|---|---|---|---|
| ATOM | 7666 | C | LEU | 72 | 66.958 | 50.056 | 36.972 | 1.00 | 32.67 | Y C |
| ATOM | 7667 | O | LEU | 72 | 66.688 | 49.738 | 38.129 | 1.00 | 32.67 | Y O |
| ATOM | 7668 | N | THR | 73 | 66.106 | 50.715 | 36.195 | 1.00 | 42.60 | Y N |
| ATOM | 7669 | CA | THR | 73 | 64.795 | 51.100 | 36.700 | 1.00 | 42.60 | Y C |
| ATOM | 7670 | CB | THR | 73 | 64.780 | 52.597 | 37.094 | 1.00 | 57.15 | Y C |
| ATOM | 7671 | OG1 | THR | 73 | 66.018 | 52.943 | 37.730 | 1.00 | 57.15 | Y O |
| ATOM | 7672 | CG2 | THR | 73 | 63.639 | 52.879 | 38.058 | 1.00 | 57.15 | Y C |
| ATOM | 7673 | C | THR | 73 | 63.665 | 50.854 | 35.708 | 1.00 | 42.60 | Y C |
| ATOM | 7674 | O | THR | 73 | 63.791 | 51.132 | 34.516 | 1.00 | 42.60 | Y O |
| ATOM | 7675 | N | ILE | 74 | 62.564 | 50.316 | 36.212 | 1.00 | 51.99 | Y N |
| ATOM | 7676 | CA | ILE | 74 | 61.396 | 50.068 | 35.386 | 1.00 | 51.99 | Y C |
| ATOM | 7677 | CB | ILE | 74 | 60.934 | 48.597 | 35.455 | 1.00 | 52.44 | Y C |
| ATOM | 7678 | CG2 | ILE | 74 | 60.081 | 48.271 | 34.231 | 1.00 | 52.44 | Y C |
| ATOM | 7679 | CG1 | ILE | 74 | 62.138 | 47.656 | 35.471 | 1.00 | 52.44 | Y C |
| ATOM | 7680 | CD1 | ILE | 74 | 61.757 | 46.182 | 35.513 | 1.00 | 52.44 | Y C |
| ATOM | 7681 | C | ILE | 74 | 60.314 | 50.963 | 35.988 | 1.00 | 51.99 | Y C |
| ATOM | 7682 | O | ILE | 74 | 59.739 | 50.639 | 37.030 | 1.00 | 51.99 | Y O |
| ATOM | 7683 | N | SER | 75 | 60.058 | 52.094 | 35.335 | 1.00 | 41.67 | Y N |
| ATOM | 7684 | CA | SER | 75 | 59.069 | 53.066 | 35.801 | 1.00 | 41.67 | Y C |
| ATOM | 7685 | CB | SER | 75 | 59.090 | 54.291 | 34.889 | 1.00 | 51.63 | Y C |
| ATOM | 7686 | OG | SER | 75 | 58.934 | 53.909 | 33.535 | 1.00 | 51.63 | Y O |
| ATOM | 7687 | C | SER | 75 | 57.644 | 52.524 | 35.901 | 1.00 | 41.67 | Y C |
| ATOM | 7688 | O | SER | 75 | 56.885 | 52.924 | 36.777 | 1.00 | 41.67 | Y O |
| ATOM | 7689 | N | SER | 76 | 57.280 | 51.627 | 34.993 | 1.00 | 62.86 | Y N |
| ATOM | 7690 | CA | SER | 76 | 55.950 | 51.032 | 34.996 | 1.00 | 62.86 | Y C |
| ATOM | 7691 | CB | SER | 76 | 55.045 | 51.724 | 33.980 | 1.00 | 71.45 | Y C |
| ATOM | 7692 | OG | SER | 76 | 53.779 | 51.086 | 33.932 | 1.00 | 71.45 | Y O |
| ATOM | 7693 | C | SER | 76 | 56.056 | 49.558 | 34.649 | 1.00 | 62.86 | Y C |
| ATOM | 7694 | O | SER | 76 | 55.970 | 49.176 | 33.480 | 1.00 | 62.86 | Y O |
| ATOM | 7695 | N | LEU | 77 | 56.237 | 48.734 | 35.675 | 1.00 | 53.25 | Y N |
| ATOM | 7696 | CA | LEU | 77 | 56.380 | 47.298 | 35.490 | 1.00 | 53.25 | Y C |
| ATOM | 7697 | CB | LEU | 77 | 56.342 | 46.596 | 36.841 | 1.00 | 41.03 | Y C |
| ATOM | 7698 | CG | LEU | 77 | 57.317 | 45.433 | 37.008 | 1.00 | 41.03 | Y C |
| ATOM | 7699 | CD1 | LEU | 77 | 56.911 | 44.632 | 38.239 | 1.00 | 41.03 | Y C |
| ATOM | 7700 | CD2 | LEU | 77 | 57.310 | 44.548 | 35.766 | 1.00 | 41.03 | Y C |
| ATOM | 7701 | C | LEU | 77 | 55.303 | 46.703 | 34.590 | 1.00 | 53.25 | Y C |
| ATOM | 7702 | O | LEU | 77 | 54.114 | 46.944 | 34.787 | 1.00 | 53.25 | Y O |
| ATOM | 7703 | N | GLN | 78 | 55.723 | 45.921 | 33.602 | 1.00 | 82.27 | Y N |
| ATOM | 7704 | CA | GLN | 78 | 54.781 | 45.285 | 32.691 | 1.00 | 82.27 | Y C |
| ATOM | 7705 | CB | GLN | 78 | 55.094 | 45.667 | 31.243 | 1.00 | 41.92 | Y C |
| ATOM | 7706 | CG | GLN | 78 | 54.907 | 47.148 | 30.956 | 1.00 | 41.92 | Y C |
| ATOM | 7707 | CD | GLN | 78 | 53.508 | 47.627 | 31.288 | 1.00 | 41.92 | Y C |
| ATOM | 7708 | OE1 | GLN | 78 | 52.520 | 47.033 | 30.852 | 1.00 | 41.92 | Y O |
| ATOM | 7709 | NE2 | GLN | 78 | 53.416 | 48.711 | 32.056 | 1.00 | 41.92 | Y N |
| ATOM | 7710 | C | GLN | 78 | 54.830 | 43.774 | 32.852 | 1.00 | 82.27 | Y C |
| ATOM | 7711 | O | GLN | 78 | 55.851 | 43.213 | 33.244 | 1.00 | 82.27 | Y O |
| ATOM | 7712 | N | PRO | 79 | 53.718 | 43.093 | 32.549 | 1.00 | 81.12 | Y N |
| ATOM | 7713 | CD | PRO | 79 | 52.505 | 43.636 | 31.915 | 1.00 | 80.96 | Y C |
| ATOM | 7714 | CA | PRO | 79 | 53.632 | 41.636 | 32.660 | 1.00 | 81.12 | Y C |
| ATOM | 7715 | CB | PRO | 79 | 52.198 | 41.351 | 32.225 | 1.00 | 80.96 | Y C |
| ATOM | 7716 | CG | PRO | 79 | 51.949 | 42.426 | 31.213 | 1.00 | 80.96 | Y C |
| ATOM | 7717 | C | PRO | 79 | 54.663 | 40.914 | 31.792 | 1.00 | 81.12 | Y C |
| ATOM | 7718 | O | PRO | 79 | 54.865 | 39.708 | 31.914 | 1.00 | 81.12 | Y O |
| ATOM | 7719 | N | GLU | 80 | 55.316 | 41.670 | 30.921 | 1.00 | 44.20 | Y N |
| ATOM | 7720 | CA | GLU | 80 | 56.316 | 41.120 | 30.021 | 1.00 | 44.20 | Y C |
| ATOM | 7721 | CB | GLU | 80 | 56.117 | 41.729 | 28.636 | 1.00 | 102.65 | Y C |
| ATOM | 7722 | CG | GLU | 80 | 55.853 | 43.217 | 28.678 | 1.00 | 102.65 | Y C |
| ATOM | 7723 | CD | GLU | 80 | 55.814 | 43.833 | 27.301 | 1.00 | 102.65 | Y C |
| ATOM | 7724 | OE1 | GLU | 80 | 56.717 | 43.528 | 26.494 | 1.00 | 102.65 | Y O |
| ATOM | 7725 | OE2 | GLU | 80 | 54.891 | 44.629 | 27.026 | 1.00 | 102.65 | Y O |
| ATOM | 7726 | C | GLU | 80 | 57.742 | 41.368 | 30.520 | 1.00 | 44.20 | Y C |
| ATOM | 7727 | O | GLU | 80 | 58.672 | 40.652 | 30.145 | 1.00 | 44.20 | Y O |
| ATOM | 7728 | N | ASP | 81 | 57.902 | 42.380 | 31.371 | 1.00 | 52.34 | Y N |
| ATOM | 7729 | CA | ASP | 81 | 59.206 | 42.733 | 31.931 | 1.00 | 52.34 | Y C |
| ATOM | 7730 | CB | ASP | 81 | 59.167 | 44.111 | 32.593 | 1.00 | 55.47 | Y C |
| ATOM | 7731 | CG | ASP | 81 | 58.700 | 45.195 | 31.663 | 1.00 | 55.47 | Y C |
| ATOM | 7732 | OD1 | ASP | 81 | 58.950 | 45.085 | 30.446 | 1.00 | 55.47 | Y O |
| ATOM | 7733 | OD2 | ASP | 81 | 58.099 | 46.171 | 32.156 | 1.00 | 55.47 | Y O |
| ATOM | 7734 | C | ASP | 81 | 59.641 | 41.740 | 32.991 | 1.00 | 52.34 | Y C |
| ATOM | 7735 | O | ASP | 81 | 60.649 | 41.946 | 33.673 | 1.00 | 52.34 | Y O |
| ATOM | 7736 | N | PHE | 82 | 58.884 | 40.664 | 33.138 | 1.00 | 63.15 | Y N |
| ATOM | 7737 | CA | PHE | 82 | 59.207 | 39.685 | 34.158 | 1.00 | 63.15 | Y C |
| ATOM | 7738 | CB | PHE | 82 | 57.917 | 39.041 | 34.647 | 1.00 | 168.46 | Y C |

Fig. 19: A-107

| | | | | | | | | | | | |
|---|---|---|---|---|---|---|---|---|---|---|---|
| ATOM | 7739 | CG | PHE | 82 | 57.024 | 40.004 | 35.381 | 1.00 | 168.46 | Y | C |
| ATOM | 7740 | CD1 | PHE | 82 | 57.371 | 40.454 | 36.650 | 1.00 | 168.46 | Y | C |
| ATOM | 7741 | CD2 | PHE | 82 | 55.866 | 40.498 | 34.791 | 1.00 | 168.46 | Y | C |
| ATOM | 7742 | CE1 | PHE | 82 | 56.579 | 41.384 | 37.321 | 1.00 | 168.46 | Y | C |
| ATOM | 7743 | CE2 | PHE | 82 | 55.067 | 41.430 | 35.458 | 1.00 | 168.46 | Y | C |
| ATOM | 7744 | CZ | PHE | 82 | 55.425 | 41.872 | 36.724 | 1.00 | 168.46 | Y | C |
| ATOM | 7745 | C | PHE | 82 | 60.238 | 38.657 | 33.742 | 1.00 | 63.15 | Y | C |
| ATOM | 7746 | O | PHE | 82 | 59.960 | 37.733 | 32.979 | 1.00 | 63.15 | Y | O |
| ATOM | 7747 | N | ALA | 83 | 61.447 | 38.867 | 34.256 | 1.00 | 34.42 | Y | N |
| ATOM | 7748 | CA | ALA | 83 | 62.601 | 38.015 | 34.000 | 1.00 | 34.42 | Y | C |
| ATOM | 7749 | CB | ALA | 83 | 63.138 | 38.260 | 32.595 | 1.00 | 53.93 | Y | C |
| ATOM | 7750 | C | ALA | 83 | 63.669 | 38.353 | 35.036 | 1.00 | 34.42 | Y | C |
| ATOM | 7751 | O | ALA | 83 | 63.389 | 39.033 | 36.025 | 1.00 | 34.42 | Y | O |
| ATOM | 7752 | N | THR | 84 | 64.890 | 37.877 | 34.821 | 1.00 | 50.51 | Y | N |
| ATOM | 7753 | CA | THR | 84 | 65.968 | 38.161 | 35.758 | 1.00 | 50.51 | Y | C |
| ATOM | 7754 | CB | THR | 84 | 66.566 | 36.849 | 36.323 | 1.00 | 63.35 | Y | C |
| ATOM | 7755 | OG1 | THR | 84 | 67.888 | 37.096 | 36.819 | 1.00 | 63.35 | Y | O |
| ATOM | 7756 | CG2 | THR | 84 | 66.584 | 35.766 | 35.260 | 1.00 | 63.35 | Y | C |
| ATOM | 7757 | C | THR | 84 | 67.028 | 39.021 | 35.065 | 1.00 | 50.51 | Y | C |
| ATOM | 7758 | O | THR | 84 | 67.474 | 38.708 | 33.959 | 1.00 | 50.51 | Y | O |
| ATOM | 7759 | N | TYR | 85 | 67.401 | 40.119 | 35.723 | 1.00 | 40.66 | Y | N |
| ATOM | 7760 | CA | TYR | 85 | 68.364 | 41.076 | 35.187 | 1.00 | 40.66 | Y | C |
| ATOM | 7761 | CB | TYR | 85 | 67.819 | 42.503 | 35.330 | 1.00 | 42.00 | Y | C |
| ATOM | 7762 | CG | TYR | 85 | 66.476 | 42.693 | 34.668 | 1.00 | 42.00 | Y | C |
| ATOM | 7763 | CD1 | TYR | 85 | 65.330 | 42.084 | 35.185 | 1.00 | 42.00 | Y | C |
| ATOM | 7764 | CE1 | TYR | 85 | 64.110 | 42.163 | 34.521 | 1.00 | 42.00 | Y | C |
| ATOM | 7765 | CD2 | TYR | 85 | 66.363 | 43.401 | 33.472 | 1.00 | 42.00 | Y | C |
| ATOM | 7766 | CE2 | TYR | 85 | 65.148 | 43.486 | 32.800 | 1.00 | 42.00 | Y | C |
| ATOM | 7767 | CZ | TYR | 85 | 64.028 | 42.860 | 33.327 | 1.00 | 42.00 | Y | C |
| ATOM | 7768 | OH | TYR | 85 | 62.841 | 42.889 | 32.633 | 1.00 | 42.00 | Y | O |
| ATOM | 7769 | C | TYR | 85 | 69.746 | 41.012 | 35.816 | 1.00 | 40.66 | Y | C |
| ATOM | 7770 | O | TYR | 85 | 69.891 | 40.982 | 37.042 | 1.00 | 40.66 | Y | O |
| ATOM | 7771 | N | TYR | 86 | 70.756 | 41.016 | 34.949 | 1.00 | 43.34 | Y | N |
| ATOM | 7772 | CA | TYR | 86 | 72.159 | 40.970 | 35.349 | 1.00 | 43.34 | Y | C |
| ATOM | 7773 | CB | TYR | 86 | 72.890 | 39.833 | 34.633 | 1.00 | 34.52 | Y | C |
| ATOM | 7774 | CG | TYR | 86 | 72.406 | 38.441 | 34.941 | 1.00 | 34.52 | Y | C |
| ATOM | 7775 | CD1 | TYR | 86 | 72.902 | 37.731 | 36.040 | 1.00 | 34.52 | Y | C |
| ATOM | 7776 | CE1 | TYR | 86 | 72.472 | 36.433 | 36.303 | 1.00 | 34.52 | Y | C |
| ATOM | 7777 | CD2 | TYR | 86 | 71.466 | 37.820 | 34.118 | 1.00 | 34.52 | Y | C |
| ATOM | 7778 | CE2 | TYR | 86 | 71.031 | 36.530 | 34.375 | 1.00 | 34.52 | Y | C |
| ATOM | 7779 | CZ | TYR | 86 | 71.538 | 35.841 | 35.462 | 1.00 | 34.52 | Y | C |
| ATOM | 7780 | OH | TYR | 86 | 71.124 | 34.549 | 35.683 | 1.00 | 34.52 | Y | O |
| ATOM | 7781 | C | TYR | 86 | 72.873 | 42.259 | 34.957 | 1.00 | 43.34 | Y | C |
| ATOM | 7782 | O | TYR | 86 | 72.662 | 42.780 | 33.851 | 1.00 | 43.34 | Y | O |
| ATOM | 7783 | N | CYS | 87 | 73.706 | 42.773 | 35.862 | 1.00 | 31.05 | Y | N |
| ATOM | 7784 | CA | CYS | 87 | 74.499 | 43.945 | 35.548 | 1.00 | 31.05 | Y | C |
| ATOM | 7785 | C | CYS | 87 | 75.857 | 43.346 | 35.237 | 1.00 | 31.05 | Y | C |
| ATOM | 7786 | O | CYS | 87 | 76.171 | 42.248 | 35.707 | 1.00 | 31.05 | Y | O |
| ATOM | 7787 | CB | CYS | 87 | 74.587 | 44.922 | 36.721 | 1.00 | 63.19 | Y | C |
| ATOM | 7788 | SG | CYS | 87 | 75.151 | 44.318 | 38.354 | 1.00 | 63.19 | Y | S |
| ATOM | 7789 | N | GLN | 88 | 76.653 | 44.040 | 34.431 | 1.00 | 35.54 | Y | N |
| ATOM | 7790 | CA | GLN | 88 | 77.964 | 43.536 | 34.058 | 1.00 | 35.54 | Y | C |
| ATOM | 7791 | CB | GLN | 88 | 77.834 | 42.232 | 32.769 | 1.00 | 42.46 | Y | C |
| ATOM | 7792 | CG | GLN | 88 | 79.114 | 42.125 | 32.259 | 1.00 | 42.46 | Y | C |
| ATOM | 7793 | CD | GLN | 88 | 79.594 | 42.783 | 30.983 | 1.00 | 42.46 | Y | C |
| ATOM | 7794 | OE1 | GLN | 88 | 78.834 | 42.928 | 30.019 | 1.00 | 42.46 | Y | O |
| ATOM | 7795 | NE2 | GLN | 88 | 80.863 | 43.183 | 30.965 | 1.00 | 42.46 | Y | N |
| ATOM | 7796 | C | GLN | 88 | 78.930 | 44.691 | 33.873 | 1.00 | 35.54 | Y | C |
| ATOM | 7797 | O | GLN | 88 | 78.530 | 45.774 | 33.436 | 1.00 | 35.54 | Y | O |
| ATOM | 7798 | N | GLN | 89 | 80.195 | 44.465 | 34.216 | 1.00 | 24.85 | Y | N |
| ATOM | 7799 | CA | GLN | 89 | 81.208 | 45.502 | 34.082 | 1.00 | 24.85 | Y | C |
| ATOM | 7800 | CB | GLN | 89 | 81.794 | 45.851 | 35.458 | 1.00 | 29.69 | Y | C |
| ATOM | 7801 | CG | GLN | 89 | 82.481 | 44.722 | 36.182 | 1.00 | 29.69 | Y | C |
| ATOM | 7802 | CD | GLN | 89 | 83.903 | 44.496 | 35.696 | 1.00 | 29.69 | Y | C |
| ATOM | 7803 | OE1 | GLN | 89 | 84.676 | 45.442 | 35.535 | 1.00 | 29.69 | Y | O |
| ATOM | 7804 | NE2 | GLN | 89 | 84.261 | 43.238 | 35.476 | 1.00 | 29.69 | Y | N |
| ATOM | 7805 | C | GLN | 89 | 82.294 | 45.043 | 33.128 | 1.00 | 24.85 | Y | C |
| ATOM | 7806 | O | GLN | 89 | 82.527 | 43.853 | 32.990 | 1.00 | 24.85 | Y | O |
| ATOM | 7807 | N | TRP | 90 | 82.943 | 45.993 | 32.460 | 1.00 | 39.13 | Y | N |
| ATOM | 7808 | CA | TRP | 90 | 84.008 | 45.672 | 31.510 | 1.00 | 39.13 | Y | C |
| ATOM | 7809 | CB | TRP | 90 | 83.529 | 45.955 | 30.069 | 1.00 | 30.35 | Y | C |
| ATOM | 7810 | CG | TRP | 90 | 83.422 | 47.437 | 29.678 | 1.00 | 30.35 | Y | C |
| ATOM | 7811 | CD2 | TRP | 90 | 83.088 | 47.967 | 28.385 | 1.00 | 30.35 | Y | C |

Fig. 19: A-108

| ATOM | 7812 | CE2 | TRP | 90 | 83.122 | 49.375 | 28.486 | 1.00 | 30.35 | Y | C |
| --- | --- | --- | --- | --- | --- | --- | --- | --- | --- | --- | --- |
| ATOM | 7813 | CE3 | TRP | 90 | 82.762 | 47.389 | 27.152 | 1.00 | 30.35 | Y | C |
| ATOM | 7814 | CD1 | TRP | 90 | 83.635 | 48.523 | 30.484 | 1.00 | 30.35 | Y | C |
| ATOM | 7815 | NE1 | TRP | 90 | 83.460 | 49.686 | 29.776 | 1.00 | 30.35 | Y | N |
| ATOM | 7816 | CZ2 | TRP | 90 | 82.840 | 50.217 | 27.398 | 1.00 | 30.35 | Y | C |
| ATOM | 7817 | CZ3 | TRP | 90 | 82.480 | 48.232 | 26.063 | 1.00 | 30.35 | Y | C |
| ATOM | 7818 | CH2 | TRP | 90 | 82.522 | 49.627 | 26.199 | 1.00 | 30.35 | Y | C |
| ATOM | 7819 | C | TRP | 90 | 85.290 | 46.457 | 31.816 | 1.00 | 39.13 | Y | C |
| ATOM | 7820 | O | TRP | 90 | 86.293 | 46.339 | 31.115 | 1.00 | 39.13 | Y | O |
| ATOM | 7821 | N | SER | 91 | 85.251 | 47.254 | 32.876 | 1.00 | 18.51 | Y | N |
| ATOM | 7822 | CA | SER | 91 | 86.395 | 48.067 | 33.257 | 1.00 | 18.51 | Y | C |
| ATOM | 7823 | CB | SER | 91 | 85.948 | 49.152 | 34.237 | 1.00 | 45.24 | Y | C |
| ATOM | 7824 | OG | SER | 91 | 84.909 | 49.937 | 33.686 | 1.00 | 45.24 | Y | O |
| ATOM | 7825 | C | SER | 91 | 87.555 | 47.267 | 33.866 | 1.00 | 18.51 | Y | C |
| ATOM | 7826 | O | SER | 91 | 88.717 | 47.649 | 33.739 | 1.00 | 18.51 | Y | O |
| ATOM | 7827 | N | GLY | 92 | 87.241 | 46.166 | 34.534 | 1.00 | 40.34 | Y | N |
| ATOM | 7828 | CA | GLY | 92 | 88.282 | 45.360 | 35.146 | 1.00 | 40.34 | Y | C |
| ATOM | 7829 | C | GLY | 92 | 88.273 | 43.910 | 34.687 | 1.00 | 40.34 | Y | C |
| ATOM | 7830 | O | GLY | 92 | 87.248 | 43.386 | 34.244 | 1.00 | 40.34 | Y | O |
| ATOM | 7831 | N | ASN | 93 | 89.420 | 43.249 | 34.801 | 1.00 | 37.36 | Y | N |
| ATOM | 7832 | CA | ASN | 93 | 89.544 | 41.863 | 34.380 | 1.00 | 37.36 | Y | C |
| ATOM | 7833 | CB | ASN | 93 | 90.765 | 41.702 | 33.492 | 1.00 | 14.59 | Y | C |
| ATOM | 7834 | CG | ASN | 93 | 90.634 | 42.451 | 32.208 | 1.00 | 14.59 | Y | C |
| ATOM | 7835 | OD1 | ASN | 93 | 91.556 | 43.159 | 31.796 | 1.00 | 14.59 | Y | O |
| ATOM | 7836 | ND2 | ASN | 93 | 89.482 | 42.305 | 31.552 | 1.00 | 14.59 | Y | N |
| ATOM | 7837 | C | ASN | 93 | 89.668 | 40.944 | 35.574 | 1.00 | 37.36 | Y | C |
| ATOM | 7838 | O | ASN | 93 | 90.346 | 41.265 | 36.539 | 1.00 | 37.36 | Y | O |
| ATOM | 7839 | N | PRO | 94 | 89.005 | 39.783 | 35.525 | 1.00 | 28.71 | Y | N |
| ATOM | 7840 | CD | PRO | 94 | 88.990 | 38.808 | 36.629 | 1.00 | 9.29 | Y | C |
| ATOM | 7841 | CA | PRO | 94 | 88.167 | 39.322 | 34.412 | 1.00 | 28.71 | Y | C |
| ATOM | 7842 | CB | PRO | 94 | 87.940 | 37.858 | 34.745 | 1.00 | 9.29 | Y | C |
| ATOM | 7843 | CG | PRO | 94 | 87.823 | 37.904 | 36.251 | 1.00 | 9.29 | Y | C |
| ATOM | 7844 | C | PRO | 94 | 86.845 | 40.076 | 34.372 | 1.00 | 28.71 | Y | C |
| ATOM | 7845 | O | PRO | 94 | 86.418 | 40.640 | 35.384 | 1.00 | 28.71 | Y | O |
| ATOM | 7846 | N | TRP | 95 | 86.200 | 40.084 | 33.206 | 1.00 | 37.86 | Y | N |
| ATOM | 7847 | CA | TRP | 95 | 84.910 | 40.743 | 33.082 | 1.00 | 37.86 | Y | C |
| ATOM | 7848 | CB | TRP | 95 | 84.428 | 40.762 | 31.629 | 1.00 | 24.14 | Y | C |
| ATOM | 7849 | CG | TRP | 95 | 85.220 | 41.665 | 30.744 | 1.00 | 24.14 | Y | C |
| ATOM | 7850 | CD2 | TRP | 95 | 85.537 | 41.458 | 29.359 | 1.00 | 24.14 | Y | C |
| ATOM | 7851 | CE2 | TRP | 95 | 86.285 | 42.575 | 28.929 | 1.00 | 24.14 | Y | C |
| ATOM | 7852 | CE3 | TRP | 95 | 85.264 | 40.437 | 28.440 | 1.00 | 24.14 | Y | C |
| ATOM | 7853 | CD1 | TRP | 95 | 85.770 | 42.867 | 31.085 | 1.00 | 24.14 | Y | C |
| ATOM | 7854 | NE1 | TRP | 95 | 86.411 | 43.419 | 30.000 | 1.00 | 24.14 | Y | N |
| ATOM | 7855 | CZ2 | TRP | 95 | 86.765 | 42.697 | 27.624 | 1.00 | 24.14 | Y | C |
| ATOM | 7856 | CZ3 | TRP | 95 | 85.748 | 40.566 | 27.133 | 1.00 | 24.14 | Y | C |
| ATOM | 7857 | CH2 | TRP | 95 | 86.487 | 41.685 | 26.744 | 1.00 | 24.14 | Y | C |
| ATOM | 7858 | C | TRP | 95 | 83.959 | 39.922 | 33.941 | 1.00 | 37.86 | Y | C |
| ATOM | 7859 | O | TRP | 95 | 83.997 | 38.688 | 33.920 | 1.00 | 37.86 | Y | O |
| ATOM | 7860 | N | THR | 96 | 83.105 | 40.605 | 34.695 | 1.00 | 19.88 | Y | N |
| ATOM | 7861 | CA | THR | 96 | 82.192 | 39.913 | 35.582 | 1.00 | 19.88 | Y | C |
| ATOM | 7862 | CB | THR | 96 | 82.692 | 40.028 | 37.038 | 1.00 | 22.31 | Y | C |
| ATOM | 7863 | OG1 | THR | 96 | 82.747 | 41.408 | 37.404 | 1.00 | 22.31 | Y | O |
| ATOM | 7864 | CG2 | THR | 96 | 84.091 | 39.443 | 37.186 | 1.00 | 22.31 | Y | C |
| ATOM | 7865 | C | THR | 96 | 80.759 | 40.413 | 35.508 | 1.00 | 19.88 | Y | C |
| ATOM | 7866 | O | THR | 96 | 80.500 | 41.491 | 34.998 | 1.00 | 19.88 | Y | O |
| ATOM | 7867 | N | PHE | 97 | 79.839 | 39.596 | 36.015 | 1.00 | 20.15 | Y | N |
| ATOM | 7868 | CA | PHE | 97 | 78.420 | 39.912 | 36.073 | 1.00 | 20.15 | Y | C |
| ATOM | 7869 | CB | PHE | 97 | 77.580 | 38.827 | 35.397 | 1.00 | 25.28 | Y | C |
| ATOM | 7870 | CG | PHE | 97 | 77.890 | 38.613 | 33.946 | 1.00 | 25.28 | Y | C |
| ATOM | 7871 | CD1 | PHE | 97 | 79.062 | 37.994 | 33.554 | 1.00 | 25.28 | Y | C |
| ATOM | 7872 | CD2 | PHE | 97 | 76.979 | 38.990 | 32.969 | 1.00 | 25.28 | Y | C |
| ATOM | 7873 | CE1 | PHE | 97 | 79.322 | 37.750 | 32.204 | 1.00 | 25.28 | Y | C |
| ATOM | 7874 | CE2 | PHE | 97 | 77.234 | 38.748 | 31.611 | 1.00 | 25.28 | Y | C |
| ATOM | 7875 | CZ | PHE | 97 | 78.404 | 38.128 | 31.233 | 1.00 | 25.28 | Y | C |
| ATOM | 7876 | C | PHE | 97 | 78.054 | 39.931 | 37.557 | 1.00 | 20.15 | Y | C |
| ATOM | 7877 | O | PHE | 97 | 78.841 | 39.487 | 38.394 | 1.00 | 20.15 | Y | O |
| ATOM | 7878 | N | GLY | 98 | 76.875 | 40.460 | 37.879 | 1.00 | 30.22 | Y | N |
| ATOM | 7879 | CA | GLY | 98 | 76.412 | 40.488 | 39.256 | 1.00 | 30.22 | Y | C |
| ATOM | 7880 | C | GLY | 98 | 75.676 | 39.178 | 39.406 | 1.00 | 30.22 | Y | C |
| ATOM | 7881 | O | GLY | 98 | 75.506 | 38.478 | 38.405 | 1.00 | 30.22 | Y | O |
| ATOM | 7882 | N | GLN | 99 | 75.235 | 38.819 | 40.608 | 1.00 | 24.51 | Y | N |
| ATOM | 7883 | CA | GLN | 99 | 74.537 | 37.541 | 40.755 | 1.00 | 24.51 | Y | C |
| ATOM | 7884 | CB | GLN | 99 | 74.350 | 37.163 | 42.231 | 1.00 | 60.71 | Y | C |

Fig. 19: A-109

```
ATOM   7885  CG   GLN   99    74.599  38.274  43.209  1.00   60.71  Y  C
ATOM   7886  CD   GLN   99    73.728  39.464  42.945  1.00   60.71  Y  C
ATOM   7887  OE1  GLN   99    72.510  39.411  43.113  1.00   60.71  Y  O
ATOM   7888  NE2  GLN   99    74.346  40.551  42.515  1.00   60.71  Y  N
ATOM   7889  C    GLN   99    73.189  37.507  40.043  1.00   24.51  Y  C
ATOM   7890  O    GLN   99    72.587  36.443  39.894  1.00   24.51  Y  O
ATOM   7891  N    GLY   100   72.730  38.666  39.586  1.00   42.40  Y  N
ATOM   7892  CA   GLY   100   71.455  38.725  38.900  1.00   42.40  Y  C
ATOM   7893  C    GLY   100   70.355  39.043  39.886  1.00   42.40  Y  C
ATOM   7894  O    GLY   100   70.483  38.749  41.074  1.00   42.40  Y  O
ATOM   7895  N    THR   101   69.283  39.662  39.399  1.00   27.30  Y  N
ATOM   7896  CA   THR   101   68.144  40.021  40.236  1.00   27.30  Y  C
ATOM   7897  CB   THR   101   68.024  41.538  40.401  1.00   28.79  Y  C
ATOM   7898  OG1  THR   101   69.008  41.995  41.336  1.00   28.79  Y  O
ATOM   7899  CG2  THR   101   66.646  41.907  40.892  1.00   28.79  Y  C
ATOM   7900  C    THR   101   66.903  39.492  39.551  1.00   27.30  Y  C
ATOM   7901  O    THR   101   66.619  39.845  38.408  1.00   27.30  Y  O
ATOM   7902  N    LYS   102   66.166  38.635  40.240  1.00   67.88  Y  N
ATOM   7903  CA   LYS   102   64.978  38.064  39.642  1.00   67.88  Y  C
ATOM   7904  CB   LYS   102   64.806  36.618  40.106  1.00  117.75  Y  C
ATOM   7905  CG   LYS   102   63.920  35.785  39.198  1.00  117.75  Y  C
ATOM   7906  CD   LYS   102   63.925  34.321  39.608  1.00  117.75  Y  C
ATOM   7907  CE   LYS   102   63.094  33.485  38.651  1.00  117.75  Y  C
ATOM   7908  NZ   LYS   102   63.586  33.621  37.250  1.00  117.75  Y  N
ATOM   7909  C    LYS   102   63.749  38.885  39.996  1.00   67.88  Y  C
ATOM   7910  O    LYS   102   63.560  39.262  41.155  1.00   67.88  Y  O
ATOM   7911  N    VAL   103   62.926  39.176  38.989  1.00   55.50  Y  N
ATOM   7912  CA   VAL   103   61.706  39.941  39.208  1.00   55.50  Y  C
ATOM   7913  CB   VAL   103   61.779  41.349  38.510  1.00   68.46  Y  C
ATOM   7914  CG1  VAL   103   63.207  41.865  38.530  1.00   68.46  Y  C
ATOM   7915  CG2  VAL   103   61.258  41.290  37.084  1.00   68.46  Y  C
ATOM   7916  C    VAL   103   60.489  39.141  38.709  1.00   55.50  Y  C
ATOM   7917  O    VAL   103   60.378  38.828  37.517  1.00   55.50  Y  O
ATOM   7918  N    GLU   104   59.597  38.779  39.633  1.00   70.95  Y  N
ATOM   7919  CA   GLU   104   58.395  38.025  39.281  1.00   70.95  Y  C
ATOM   7920  CB   GLU   104   58.243  36.764  40.145  1.00  145.77  Y  C
ATOM   7921  CG   GLU   104   57.957  37.019  41.616  1.00  145.77  Y  C
ATOM   7922  CD   GLU   104   59.215  37.263  42.418  1.00  145.77  Y  C
ATOM   7923  OE1  GLU   104   59.106  37.542  43.631  1.00  145.77  Y  O
ATOM   7924  OE2  GLU   104   60.315  37.167  41.839  1.00  145.77  Y  O
ATOM   7925  C    GLU   104   57.157  38.897  39.443  1.00   70.95  Y  C
ATOM   7926  O    GLU   104   57.197  39.939  40.108  1.00   70.95  Y  O
ATOM   7927  N    ILE   105   56.058  38.459  38.834  1.00  139.77  Y  N
ATOM   7928  CA   ILE   105   54.791  39.184  38.876  1.00  139.77  Y  C
ATOM   7929  CB   ILE   105   53.838  38.730  37.757  1.00  105.35  Y  C
ATOM   7930  CG2  ILE   105   52.923  39.875  37.373  1.00  105.35  Y  C
ATOM   7931  CG1  ILE   105   54.633  38.232  36.553  1.00  105.35  Y  C
ATOM   7932  CD1  ILE   105   53.775  37.746  35.397  1.00  105.35  Y  C
ATOM   7933  C    ILE   105   54.047  38.952  40.180  1.00  139.77  Y  C
ATOM   7934  O    ILE   105   53.763  37.810  40.533  1.00  139.77  Y  O
ATOM   7935  N    LYS   106   53.706  40.031  40.880  1.00  101.75  Y  N
ATOM   7936  CA   LYS   106   52.969  39.916  42.135  1.00  101.75  Y  C
ATOM   7937  CB   LYS   106   53.545  40.870  43.189  1.00   95.13  Y  C
ATOM   7938  CG   LYS   106   52.954  40.690  44.584  1.00   95.13  Y  C
ATOM   7939  CD   LYS   106   53.556  41.665  45.586  1.00   95.13  Y  C
ATOM   7940  CE   LYS   106   52.939  41.482  46.965  1.00   95.13  Y  C
ATOM   7941  NZ   LYS   106   53.446  42.478  47.948  1.00   95.13  Y  N
ATOM   7942  C    LYS   106   51.492  40.235  41.897  1.00  101.75  Y  C
ATOM   7943  O    LYS   106   51.148  40.637  40.765  1.00  100.80  Y  O
ATOM   7944  OXT  LYS   106   50.694  40.080  42.844  1.00   94.18  Y  O
ATOM   7945  MN   MN    400   89.864  50.249  22.621  1.00   34.24  N
END
```

SEQUENCE LISTING

<160> NUMBER OF SEQ ID NOS: 70

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Ile Val Leu Thr Gln Phe Pro Ala Leu Met Ser Ala Ser Pro Gly
 1               5                  10                  15

Glu Lys Val Thr Met Thr Cys Ser Ala Ser Ser Ser Val Asn His Met
            20                  25                  30

Phe Trp Tyr Gln Gln Lys Pro Lys Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Lys Val Val Glu Ser Gly Gly Gly Leu Val Lys Pro Gly Gly
 1               5                  10                  15

Ser Leu Lys Leu Ala Cys Ala Ala Ser Gly Phe Ser Phe Ser Arg Tyr
            20                  25                  30

Thr Met Ser Trp Val Arg Gln Ile Pro Glu Lys Arg Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
            100                 105                 110

Thr Val Thr Val Ser Ser
        115

<210> SEQ ID NO 3
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Ile Gln Leu Thr Gln Ser Pro Ser Ser Leu Ser Ala Ser Val Gly
  1               5                  10                  15
Asp Arg Val Thr Ile Thr Cys Ser Ala Ser Ser Val Asn His Met
             20                  25                  30
Phe Trp Tyr Gln Gln Lys Pro Gly Lys Ala Pro Lys Pro Trp Ile Tyr
             35                  40                  45
Leu Thr Ser Asn Leu Ala Ser Gly Val Pro Ser Arg Phe Ser Gly Ser
 50                  55                  60
Gly Ser Gly Thr Asp Tyr Thr Leu Thr Ile Ser Ser Leu Gln Pro Glu
 65                  70                  75                  80
Asp Phe Ala Thr Tyr Tyr Cys Gln Gln Trp Ser Gly Asn Pro Trp Thr
             85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
            165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn Arg Gly Glu Cys
        210
```

<210> SEQ ID NO 4
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Arg Tyr
             20                  25                  30
Thr Met Ser Trp Val Arg Gln Ala Pro Gly Lys Gly Leu Glu Trp Val
             35                  40                  45
Ala Thr Ile Ser Gly Gly His Thr Tyr Tyr Leu Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Thr
             85                  90                  95
Arg Gly Phe Gly Asp Gly Gly Tyr Phe Asp Val Trp Gly Gln Gly Thr
            100                 105                 110
Leu Val Thr Val Ser Ser Ala Ser Thr Lys Gly Pro Ser Val Phe Pro
            115                 120                 125
```

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 5
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
```

-continued

```
                35                  40                  45
Ala Thr Ile Ser Gly Gly His Thr Tyr Tyr Leu Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Thr
                 85                  90                  95
Arg Gly Phe Gly Asp Gly Gly Tyr Phe Asp Val Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
                210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Gln Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
                435                 440                 445
```

<210> SEQ ID NO 6

<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Thr Met Ser Trp Val Arg Gln Ala Pro Gly Lys Gly Leu Glu Trp Val
         35                  40                  45

Ala Thr Ile Ser Gly Gly His Thr Tyr Tyr Leu Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
             85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
```

```
                370             375             380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
                435                 440                 445

<210> SEQ ID NO 7
<211> LENGTH: 26
<212> TYPE: DNA
<213> ORGANISM: Homo sapiens

<400> SEQUENCE: 7
caggatccgt cagccccaca tttcaa                                        26

<210> SEQ ID NO 8
<211> LENGTH: 26
<212> TYPE: DNA
<213> ORGANISM: Homo sapiens

<400> SEQUENCE: 8
tcctcgaggg cttgcagggc aaatat                                        26

<210> SEQ ID NO 9
<211> LENGTH: 26
<212> TYPE: DNA
<213> ORGANISM: Rattus sp.

<400> SEQUENCE: 9
caggatccgt cagtcctaca tttcaa                                        26

<210> SEQ ID NO 10
<211> LENGTH: 26
<212> TYPE: DNA
<213> ORGANISM: Rattus sp.

<400> SEQUENCE: 10
tcctcgagcg cttccaaagc gaatat                                        26

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaggagacg gtgaccgtgg cccttggccc c                                  31

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aggtsmarct gcagsagtcw gg                                            22
```

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
actagtcgac atggatttwc aggtgcagat twtcagcttc                             40

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
actggatggt gggaagatgg a                                                 21

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Val Lys Val Val Glu Ser Gly Gly
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Val Lys Val Val Glu
 1               5

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaccaggtg cccactccga cgtcaaggtg gtggagtcag ggggaggctt agtg             54

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
ggaggcacca agctggagat ctaacgggct gatgctgc                              38
```

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
cataatgtcc aggggagaaa ttgttctcac ccag                                  34
```

<210> SEQ ID NO 20
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
ggtgcccact ccgacgtcca gctggtcgag tcaggggag gcttagtcca gcctggaggg       60
tccctgagac tctcctgtgc agcctctgga ttc                                   93
```

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
atgtcttggg ttcgccaggc tccggggaag gggctggagt gggtcgcaac c              51
```

<210> SEQ ID NO 22
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
ttcaccatct ccagagacaa ttccaagaac accctgtacc tgcagatgaa cagtctgagg      60
gccgaggaca cagccgtgta ttactgtaca aga                                   93
```

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
tggggccaag gtaccctggt caccgtctcc tcaggtgag                             39
```

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcctgtgcag cctctggatt caccttcagt aggtatacta tgtcttgggt t    51

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcaccaggtg cgcactccga ggtccagctg gtcgagtca    39

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gagtcagggg gaggcttaat ccagcctgga gggtccctg    39

<210> SEQ ID NO 27
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caaattgttc tcacccagtc tccatcctcc ctgtctgcgt ctgtagggga cagagtcacc    60
atcacatgca gtgccagctc a    81

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttctggtatc agcagaagcc cgggaaagcc cccaaaccct ggatt    45

<210> SEQ ID NO 29
<211> LENGTH: 105
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcttctggag tcccttcacg cttcagtggc agtgggtctg ggacagatta cactctcaca    60
atcagcagcc tgcaacctga agattttgcc acttattact gccag    105

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 30
ggtggaggca ctaaggtgga gatctaacgg gct                                33

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 31
cccgggaaag cgcccaaact cctgatttat ctcacatcc                          39

<210> SEQ ID NO 32
<211> LENGTH: 51
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 32
gcctcagtca taatgtcccg gggacaaatt cagctcaccc agtctccatc c             51

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 33
ggtaacccgt ggacgttcgg tcagggcact aaggtggaga tctaacgggc t             51

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 34
gcctcagtca taatgtcccg gggacaaatt cagctcaccc agtctccatc c             51

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 35
ggtaacccgt ggacgttcgg tcagggcact aaggtggaga tctaacgggc t             51

<210> SEQ ID NO 36
<211> LENGTH: 39
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 36
gggaaagcac ccaaactctg gatctatctc acatccaac                          39

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aagcccggga aggcgcccaa acccctgatt tatctcacat ccaac                   45

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcataatgt cccggggaga tatccagctc acccagtct                          39

<210> SEQ ID NO 39
<211> LENGTH: 354
<212> TYPE: DNA
<213> ORGANISM: Artificial Sequence
<220> FEATURE:
<221> NAME/KEY: CDS
<222> LOCATION: (1)..(354)
<220> FEATURE:
<223> OTHER INFORMATION: Description of Artificial Sequence: Synthetic
      oligonucleotide

<400> SEQUENCE: 39

```
gac gtc aag gtg gtg gag tca ggg gga ggc tta gtg aag cct gga ggg        48
Asp Val Lys Val Val Glu Ser Gly Gly Gly Leu Val Lys Pro Gly Gly
 1               5                  10                  15 tcc ctg aaa ctc gcc tgt gca gcc tct gga ttc agt ttc agt aga tat        96
Ser Leu Lys Leu Ala Cys Ala Ala Ser Gly Phe Ser Phe Ser Arg Tyr
             20                  25                  30 act atg tct tgg gtt cgc cag att ccg gag aag agg ctg gag tgg gtc       144
Thr Met Ser Trp Val Arg Gln Ile Pro Glu Lys Arg Leu Glu Trp Val
         35                  40                  45 gca acc att agt ggt ggt ggt cac acc tac tat cta gac agt gtg aag       192
Ala Thr Ile Ser Gly Gly Gly His Thr Tyr Tyr Leu Asp Ser Val Lys
     50                  55                  60 ggc cga ttc acc atc tcc aga gac aat gcc aag aac acc ctg tac ctg       240
Gly Arg Phe Thr Ile Ser Arg Asp Asn Ala Lys Asn Thr Leu Tyr Leu
 65                  70                  75                  80 caa atg agc agt ctg agg tct gag gac aca gcc atg tat tac tgt aca       288
Gln Met Ser Ser Leu Arg Ser Glu Asp Thr Ala Met Tyr Tyr Cys Thr
                 85                  90                  95 aga ggt ttt gga gac ggg ggg tac ttc gat gtc tgg ggc caa ggg acc       336
Arg Gly Phe Gly Asp Gly Gly Tyr Phe Asp Val Trp Gly Gln Gly Thr
            100                 105                 110 acg gtc acc gtc tcc tca                                               354
Thr Val Thr Val Ser Ser
            115
```

<210> SEQ ID NO 40
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Val Lys Val Val Glu Ser Gly Gly Gly Leu Val Lys Pro Gly Gly
 1               5                  10                  15

Ser Leu Lys Leu Ala Cys Ala Ala Ser Gly Phe Ser Phe Ser Arg Tyr
            20                  25                  30

Thr Met Ser Trp Val Arg Gln Ile Pro Glu Lys Arg Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
           100                  105                 110

Thr Val Thr Val Ser Ser
       115

<210> SEQ ID NO 41
<211> LENGTH: 354
<212> TYPE: DNA
<213> ORGANISM: Artificial Sequence
<220> FEATURE:
<221> NAME/KEY: CDS
<222> LOCATION: (1)..(354)
<220> FEATURE:
<223> OTHER INFORMATION: Description of Artificial Sequence: Synthetic
      oligonucleotide

<400> SEQUENCE: 41 gac gtc cag ctg gtc gag tca ggg gga ggc tta gtc cag cct gga ggg      48
Asp Val Gln Leu Val Glu Ser Gly Gly Gly Leu Val Gln Pro Gly Gly
 1               5                  10                  15 tcc ctg aga ctc tcc tgt gca gcc tct gga ttc agt ttc agt aga tat     96
Ser Leu Arg Leu Ser Cys Ala Ala Ser Gly Phe Ser Phe Ser Arg Tyr
            20                  25                  30 act atg tct tgg gtt cgc cag gct ccg ggg aag ggg ctg gag tgg gtc    144
Thr Met Ser Trp Val Arg Gln Ala Pro Gly Lys Gly Leu Glu Trp Val
        35                  40                  45 gca acc att agt ggt ggt ggt cac acc tac tat cta gac agt gtg aag    192
Ala Thr Ile Ser Gly Gly Gly His Thr Tyr Tyr Leu Asp Ser Val Lys
    50                  55                  60 ggc cga ttc acc atc tcc aga gac aat tcc aag aac acc ctg tac ctg    240
Gly Arg Phe Thr Ile Ser Arg Asp Asn Ser Lys Asn Thr Leu Tyr Leu
65                  70                  75                  80 cag atg aac agt ctg agg gcc gag gac aca gcc gtg tat tac tgt aca    288
Gln Met Asn Ser Leu Arg Ala Glu Asp Thr Ala Val Tyr Tyr Cys Thr
                85                  90                  95 aga ggt ttt gga gac ggg ggg tac ttc gat gtc tgg ggc caa ggt acc    336
Arg Gly Phe Gly Asp Gly Gly Tyr Phe Asp Val Trp Gly Gln Gly Thr
           100                  105                 110 ctg gtc acc gtc tcc tca                                            354
Leu Val Thr Val Ser Ser <210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Asp Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115
```

<210> SEQ ID NO 43
<211> LENGTH: 356
<212> TYPE: DNA
<213> ORGANISM: Artificial Sequence
<220> FEATURE:
<221> NAME/KEY: CDS
<222> LOCATION: (1)..(354)
<220> FEATURE:
<223> OTHER INFORMATION: Description of Artificial Sequence: Synthetic oligonucleotide

<400> SEQUENCE: 43

```
gag gtc cag ctg gtc gag tca ggg gga ggc tta atc cag cct gga ggg      48
Glu Val Gln Leu Val Glu Ser Gly Gly Gly Leu Ile Gln Pro Gly Gly
 1               5                  10                  15 tcc ctg aga ctc tcc tgt gca gcc tct gga ttc acc ttc agt agg tat      96
Ser Leu Arg Leu Ser Cys Ala Ala Ser Gly Phe Thr Phe Ser Arg Tyr
            20                  25                  30 act atg tct tgg gtt cgc cag gct ccg ggg aag ggg ctg gag tgg gtc     144
Thr Met Ser Trp Val Arg Gln Ala Pro Gly Lys Gly Leu Glu Trp Val
        35                  40                  45 gca acc att agt ggt ggt ggt cac acc tac tat cta gac agt gtg aag     192
Ala Thr Ile Ser Gly Gly Gly His Thr Tyr Tyr Leu Asp Ser Val Lys
    50                  55                  60 ggc cga ttc acc atc tcc aga gac aat tcc aag aac acc ctg tac ctg     240
Gly Arg Phe Thr Ile Ser Arg Asp Asn Ser Lys Asn Thr Leu Tyr Leu
65                  70                  75                  80 cag atg aac agt ctg agg gcc gag gac aca gcc gtg tat tac tgt aca     288
Gln Met Asn Ser Leu Arg Ala Glu Asp Thr Ala Val Tyr Tyr Cys Thr
                85                  90                  95 aga ggt ttt gga gac ggg ggg tac ttc gat gtc tgg ggc caa ggt acc     336
Arg Gly Phe Gly Asp Gly Gly Tyr Phe Asp Val Trp Gly Gln Gly Thr
            100                 105                 110
```

```
ctg gtc acc gtc tcc tca gg                                              356
Leu Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 45
<211> LENGTH: 356
<212> TYPE: DNA
<213> ORGANISM: Artificial Sequence
<220> FEATURE:
<221> NAME/KEY: CDS
<222> LOCATION: (1)..(354)
<220> FEATURE:
<223> OTHER INFORMATION: Description of Artificial Sequence: Synthetic
      oligonucleotide

<400> SEQUENCE: 45 gag gtc cag ctg gtc gag tca ggg gga ggc tta gtc cag cct gga ggg        48
Glu Val Gln Leu Val Glu Ser Gly Gly Gly Leu Val Gln Pro Gly Gly
 1               5                  10                  15 tcc ctg aga ctc tcc tgt gca gcc tct gga ttc acc ttc agt agg tat        96
Ser Leu Arg Leu Ser Cys Ala Ala Ser Gly Phe Thr Phe Ser Arg Tyr
            20                  25                  30 act atg tct tgg gtt cgc cag gct ccg ggg aag ggg ctg gag tgg gtc       144
Thr Met Ser Trp Val Arg Gln Ala Pro Gly Lys Gly Leu Glu Trp Val
        35                  40                  45 gca acc att agt ggt ggt ggt cac acc tac tat cta gac agt gtg aag       192
Ala Thr Ile Ser Gly Gly Gly His Thr Tyr Tyr Leu Asp Ser Val Lys
    50                  55                  60 ggc cga ttc acc atc tcc aga gac aat tcc aag aac acc ctg tac ctg       240
Gly Arg Phe Thr Ile Ser Arg Asp Asn Ser Lys Asn Thr Leu Tyr Leu
65                  70                  75                  80 cag atg aac agt ctg agg gcc gag gac aca gcc gtg tat tac tgt aca       288
Gln Met Asn Ser Leu Arg Ala Glu Asp Thr Ala Val Tyr Tyr Cys Thr
                85                  90                  95 aga ggt ttt gga gac ggg ggg tac ttc gat gtc tgg ggc caa ggt acc       336
Arg Gly Phe Gly Asp Gly Gly Tyr Phe Asp Val Trp Gly Gln Gly Thr
```

```
                   100                 105                 110
ctg gtc acc gtc tcc tca gg                                              356
Leu Val Thr Val Ser Ser
        115

<210> SEQ ID NO 46
<211> LENGTH: 318
<212> TYPE: DNA
<213> ORGANISM: Artificial Sequence
<220> FEATURE:
<221> NAME/KEY: CDS
<222> LOCATION: (1)..(318)
<220> FEATURE:
<223> OTHER INFORMATION: Description of Artificial Sequence: Synthetic
      oligonucleotide

<400> SEQUENCE: 46 caa att gtt ctc acc cag ttt cca gca ctc atg tct gcg tct cca ggg         48
Gln Ile Val Leu Thr Gln Phe Pro Ala Leu Met Ser Ala Ser Pro Gly
  1               5                  10                  15 gag aag gtc acc atg acc tgc agt gcc agc tca agt gta aat cac atg         96
Glu Lys Val Thr Met Thr Cys Ser Ala Ser Ser Ser Val Asn His Met
             20                  25                  30 ttc tgg tat cag cag aag cca aaa tcc tcc ccc aaa ccc tgg att tat        144
Phe Trp Tyr Gln Gln Lys Pro Lys Ser Ser Pro Lys Pro Trp Ile Tyr
         35                  40                  45 ctc aca tcc aac ctg gct tct gga gtc cct gct cgc ttc agt ggc agt        192
Leu Thr Ser Asn Leu Ala Ser Gly Val Pro Ala Arg Phe Ser Gly Ser
     50                  55                  60 ggg tct ggg acc tct tac tct ctc aca atc agc agc atg gag gct gaa        240
Gly Ser Gly Thr Ser Tyr Ser Leu Thr Ile Ser Ser Met Glu Ala Glu
 65                  70                  75                  80 gat gct gcc act tat tac tgc cag cag tgg agt ggt aac ccg tgg acg        288
Asp Ala Ala Thr Tyr Tyr Cys Gln Gln Trp Ser Gly Asn Pro Trp Thr
                 85                  90                  95 ttc ggt gga ggc acc aag ctg gag atc aaa                                318
Phe Gly Gly Gly Thr Lys Leu Glu Ile Lys
            100                 105

<210> SEQ ID NO 47
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ile Val Leu Thr Gln Phe Pro Ala Leu Met Ser Ala Ser Pro Gly
  1               5                  10                  15

Glu Lys Val Thr Met Thr Cys Ser Ala Ser Ser Ser Val Asn His Met
             20                  25                  30

Phe Trp Tyr Gln Gln Lys Pro Lys Ser Ser Pro Lys Pro Trp Ile Tyr
         35                  40                  45

Leu Thr Ser Asn Leu Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Gly Asn Pro Trp Thr
                 85                  90                  95

Phe Gly Gly Gly Thr Lys Leu Glu Ile Lys
            100                 105
```

<210> SEQ ID NO 48
<211> LENGTH: 318
<212> TYPE: DNA
<213> ORGANISM: Artificial Sequence
<220> FEATURE:
<221> NAME/KEY: CDS
<222> LOCATION: (1)..(318)
<220> FEATURE:
<223> OTHER INFORMATION: Description of Artificial Sequence: Synthetic oligonucleotide

<400> SEQUENCE: 48

```
caa att gtt ctc acc cag tct cca tcc tcc ctg tct gcg tct gta ggg      48
Gln Ile Val Leu Thr Gln Ser Pro Ser Ser Leu Ser Ala Ser Val Gly
  1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
             20                  25                  30 ttc tgg tat cag cag aag ccc ggg aaa gcc ccc aaa ccc tgg att tat     144
Phe Trp Tyr Gln Gln Lys Pro Gly Lys Ala Pro Lys Pro Trp Ile Tyr
         35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
     50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                 85                  90                  95 ttc ggt gga ggc act aag gtg gag atc aaa                             318
Phe Gly Gly Gly Thr Lys Val Glu Ile Lys
            100                 105
```

<210> SEQ ID NO 49
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Gln Ile Val Leu Thr Gln Ser Pro Ser Ser Leu Ser Ala Ser Val Gly
  1               5                  10                  15

Asp Arg Val Thr Ile Thr Cys Ser Ala Ser Ser Ser Val Asn His Met
             20                  25                  30

Phe Trp Tyr Gln Gln Lys Pro Gly Lys Ala Pro Lys Pro Trp Ile Tyr
         35                  40                  45

Leu Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gly Gly Thr Lys Val Glu Ile Lys
            100                 105
```

<210> SEQ ID NO 50
<211> LENGTH: 318
<212> TYPE: DNA

<213> ORGANISM: Artificial Sequence
<220> FEATURE:
<221> NAME/KEY: CDS
<222> LOCATION: (1)..(318)
<220> FEATURE:
<223> OTHER INFORMATION: Description of Artificial Sequence: Synthetic oligonucleotide

<400> SEQUENCE: 50

```
caa att gtt ctc acc cag tct cca tcc tcc ctg tct gcg tct gta ggg      48
Gln Ile Val Leu Thr Gln Ser Pro Ser Ser Leu Ser Ala Ser Val Gly
  1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
             20                  25                  30 ttc tgg tat cag cag aag ccc ggg aaa gcg ccc aaa ctc ctg att tat     144
Phe Trp Tyr Gln Gln Lys Pro Gly Lys Ala Pro Lys Leu Leu Ile Tyr
         35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
     50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                 85                  90                  95 ttc ggt gga ggc act aag gtg gag atc aaa                             318
Phe Gly Gly Gly Thr Lys Val Glu Ile Lys
            100                 105
```

<210> SEQ ID NO 51
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Gln Ile Val Leu Thr Gln Ser Pro Ser Ser Leu Ser Ala Ser Val Gly
  1               5                  10                  15

Asp Arg Val Thr Ile Thr Cys Ser Ala Ser Ser Ser Val Asn His Met
             20                  25                  30

Phe Trp Tyr Gln Gln Lys Pro Gly Lys Ala Pro Lys Leu Leu Ile Tyr
         35                  40                  45

Leu Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gly Gly Thr Lys Val Glu Ile Lys
            100                 105
```

<210> SEQ ID NO 52
<211> LENGTH: 318
<212> TYPE: DNA
<213> ORGANISM: Artificial Sequence
<220> FEATURE:
<221> NAME/KEY: CDS
<222> LOCATION: (1)..(318)
<220> FEATURE:

<223> OTHER INFORMATION: Description of Artificial Sequence: Synthetic
      oligonucleotide

<400> SEQUENCE: 52

```
caa att cag ctc acc cag tct cca tcc tcc ctg tct gcg tct gta ggg      48
Gln Ile Gln Leu Thr Gln Ser Pro Ser Ser Leu Ser Ala Ser Val Gly
 1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
                20                  25                  30 ttc tgg tat cag cag aag ccc ggg aaa gcc ccc aaa ccc tgg att tat     144
Phe Trp Tyr Gln Gln Lys Pro Gly Lys Ala Pro Lys Pro Trp Ile Tyr
            35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
        50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                 85                  90                  95 ttc ggt cag ggc act aag gtg gag atc aaa                             318
Phe Gly Gln Gly Thr Lys Val Glu Ile Lys
            100                 105
```

<210> SEQ ID NO 53
<211> LENGTH: 318
<212> TYPE: DNA
<213> ORGANISM: Artificial Sequence
<220> FEATURE:
<221> NAME/KEY: CDS
<222> LOCATION: (1)..(318)
<220> FEATURE:
<223> OTHER INFORMATION: Description of Artificial Sequence: Synthetic
      oligonucleotide

<400> SEQUENCE: 53

```
caa att cag ctc acc cag tct cca tcc tcc ctg tct gcg tct gta ggg      48
Gln Ile Gln Leu Thr Gln Ser Pro Ser Ser Leu Ser Ala Ser Val Gly
 1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
                20                  25                  30 ttc tgg tat cag cag aag ccc ggg aaa gcg ccc aaa ctc ctg att tat     144
Phe Trp Tyr Gln Gln Lys Pro Gly Lys Ala Pro Lys Leu Leu Ile Tyr
            35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
        50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                 85                  90                  95 ttc ggt cag ggc act aag gtg gag atc aaa                             318
Phe Gly Gln Gly Thr Lys Val Glu Ile Lys
            100                 105
```

<210> SEQ ID NO 54
<211> LENGTH: 106
<212> TYPE: PRT

<213> ORGANISM: Artificial Sequence
<220> FEATURE:
<223> OTHER INFORMATION: Description of Artificial Sequence: Synthetic
   polypeptide

<400> SEQUENCE: 54

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Asn His Met
            20                  25                  30

Phe Trp Tyr Gln Gln Lys Pro Gly Lys Ala Pro Lys Leu Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 55
<211> LENGTH: 318
<212> TYPE: DNA
<213> ORGANISM: Artificial Sequence
<220> FEATURE:
<221> NAME/KEY: CDS
<222> LOCATION: (1)..(318)
<220> FEATURE:
<223> OTHER INFORMATION: Description of Artificial Sequence: Synthetic
   oligonucleotide

<400> SEQUENCE: 55 gaa att gtt ctc acc cag ttt cca gca ctc atg tct gcg tct cca ggg     48
Glu Ile Val Leu Thr Gln Phe Pro Ala Leu Met Ser Ala Ser Pro Gly
1               5                   10                  15 gag aag gtc acc atg acc tgc agt gcc agc tca agt gta aat cac atg     96
Glu Lys Val Thr Met Thr Cys Ser Ala Ser Ser Ser Val Asn His Met
            20                  25                  30 ttc tgg tat cag cag aag cca aaa tcc tcc ccc aaa ccc tgg att tat    144
Phe Trp Tyr Gln Gln Lys Pro Lys Ser Ser Pro Lys Pro Trp Ile Tyr
        35                  40                  45 ctc aca tcc aac ctg gct tct gga gtc cct gct cgc ttc agt ggc agt    192
Leu Thr Ser Asn Leu Ala Ser Gly Val Pro Ala Arg Phe Ser Gly Ser
    50                  55                  60 ggg tct ggg acc tct tac tct ctc aca atc agc agc atg gag gct gaa    240
Gly Ser Gly Thr Ser Tyr Ser Leu Thr Ile Ser Ser Met Glu Ala Glu
65                  70                  75                  80 gat gct gcc act tat tac tgc cag cag tgg agt ggt aac ccg tgg acg    288
Asp Ala Ala Thr Tyr Tyr Cys Gln Gln Trp Ser Gly Asn Pro Trp Thr
                85                  90                  95 ttc ggt gga ggc acc aag ctg gag atc aaa                            318
Phe Gly Gly Gly Thr Lys Leu Glu Ile Lys
            100                 105

<210> SEQ ID NO 56
<211> LENGTH: 106
<212> TYPE: PRT
<213> ORGANISM: Artificial Sequence
<220> FEATURE:
<223> OTHER INFORMATION: Description of Artificial Sequence: Synthetic
   polypeptide -continued

```
<400> SEQUENCE: 56

Glu Ile Val Leu Thr Gln Phe Pro Ala Leu Met Ser Ala Ser Pro Gly
 1               5                  10                  15

Glu Lys Val Thr Met Thr Cys Ser Ala Ser Ser Ser Val Asn His Met
            20                  25                  30

Phe Trp Tyr Gln Gln Lys Pro Lys Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105

<210> SEQ ID NO 57
<211> LENGTH: 318
<212> TYPE: DNA
<213> ORGANISM: Artificial Sequence
<220> FEATURE:
<221> NAME/KEY: CDS
<222> LOCATION: (1)..(318)
<220> FEATURE:
<223> OTHER INFORMATION: Description of Artificial Sequence: Synthetic
      oligonucleotide

<400> SEQUENCE: 57 gat atc cag ctc acc cag tct cca tcc tcc ctg tct gcg tct gta ggg      48
Asp Ile Gln Leu Thr Gln Ser Pro Ser Ser Leu Ser Ala Ser Val Gly
 1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat     144
Phe Trp Tyr Gln Gln Lys Pro Gly Lys Ala Pro Lys Pro Trp Ile Tyr
        35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                85                  90                  95 ttc ggt cag ggc act aag gtg gag atc aaa                             318
Phe Gly Gln Gly Thr Lys Val Glu Ile Lys
            100                 105

<210> SEQ ID NO 58
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Leu Thr Gln Ser Pro Ser Ser Leu Ser Ala Ser Val Gly
 1               5                  10                  15
```

-continued

Asp Arg Val Thr Ile Thr Cys Ser Ala Ser Ser Val Asn His Met
            20                  25                  30

Phe Trp Tyr Gln Gln Lys Pro Gly Lys Ala Pro Lys Pro Trp Ile Tyr
                35                  40                  45

Leu Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 59
<211> LENGTH: 192
<212> TYPE: PRT
<213> ORGANISM: Artificial Sequence
<220> FEATURE:
<223> OTHER INFORMATION: Description of Artificial Sequence: Rat/human
      chimeric I domain construct

<400> SEQUENCE: 59

Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Met
                20                  25                  30

Asp Ile Gly Pro Lys Gln Thr Gln Val Gly Ile Val Gln Tyr Gly Glu
            35                  40                  45

Asn Val Thr His Glu Phe Asn Leu Asn Lys Tyr Ser Ser Thr Glu Glu
        50                  55                  60

Val Leu Val Ala Ala Asn Lys Ile Val Gln Arg Gly Gly Arg Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
        115                 120                 125

Cys Glu Asp Glu Asn Ile Gln Arg Phe Ser Ile Ala Ile Leu Gly His
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Ile Val Lys Ala Leu Gly Glu Arg Ile Phe
            180                 185                 190

<210> SEQ ID NO 60
<211> LENGTH: 192
<212> TYPE: PRT
<213> ORGANISM: Rattus sp.

<400> SEQUENCE: 60

Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Met
                20                  25                  30

```
Asp Ile Gly Pro Lys Gln Thr Gln Val Gly Ile Val Gln Tyr Gly Glu
            35                  40                  45

Asn Val Thr His Glu Phe Asn Leu Asn Lys Tyr Ser Ser Thr Glu Glu
 50                  55                  60

Val Leu Val Ala Ala Asn Lys Ile Gly Arg Gln Gly Gly Leu Gln Thr
 65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
            115                 120                 125

Cys Glu Asp Glu Asn Ile Gln Arg Phe Ser Ile Ala Ile Leu Gly His
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Ile Val Lys Ala Leu Gly Glu Arg Ile Phe
                180                 185                 190

<210> SEQ ID NO 61
<211> LENGTH: 192
<212> TYPE: PRT
<213> ORGANISM: Homo sapiens

<400> SEQUENCE: 61

Thr Gln Leu Asp Ile Val Ile Val Leu Asp Gly Ser Asn Ser Ile Tyr
 1               5                   10                  15

Pro Trp Asp Ser Val Thr Ala Phe Leu Asn Asp Leu Leu Lys Arg Met
                20                  25                  30

Asp Ile Gly Pro Lys Gln Thr Gln Val Gly Ile Val Gln Tyr Gly Glu
            35                  40                  45

Asn Val Thr His Glu Phe Asn Leu Asn Lys Tyr Ser Ser Thr Glu Glu
 50                  55                  60

Val Leu Val Ala Ala Lys Lys Ile Val Gln Arg Gly Gly Arg Gln Thr
 65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn His Arg Leu Lys Lys Val Ile Gln Asp
            115                 120                 125

Cys Glu Asp Glu Asn Ile Gln Arg Phe Ser Ile Ala Ile Leu Gly Ser
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Ile Ala Leu Val Thr Ile Val Lys Thr Leu Gly Glu Arg Ile Phe
                180                 185                 190

<210> SEQ ID NO 62
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 62

Gly Phe Gly Asp Gly Gly Tyr
  1               5

<210> SEQ ID NO 63
<211> LENGTH: 214
<212> TYPE: PRT
<213> ORGANISM: Rattus sp.

<400> SEQUENCE: 63

Val Ser Pro Thr Phe Gln Val Val Asn Ser Phe Ala Pro Val Gln Glu
  1               5                  10                  15

Cys Ser Thr Gln Leu Asp Ile Val Ile Val Leu Asp Gly Ser Asn Ser
                 20                  25                  30

Ile Tyr Pro Trp Glu Ser Val Ile Ala Phe Leu Asn Asp Leu Leu Lys
             35                  40                  45

Arg Met Asp Ile Gly Pro Lys Gln Thr Gln Val Gly Ile Val Gln Tyr
 50                  55                  60

Gly Glu Asn Val Thr His Glu Phe Asn Leu Asn Lys Tyr Ser Ser Thr
 65                  70                  75                  80

Glu Glu Val Leu Val Ala Ala Lys Lys Ile Gly Arg Gln Gly Gly Leu
                 85                  90                  95

Gln Thr Met Thr Ala Leu Gly Ile Asp Thr Ala Arg Lys Glu Ala Phe
            100                 105                 110

Thr Glu Ala Arg Gly Ala Arg Arg Gly Val Lys Lys Val Met Val Ile
            115                 120                 125

Val Thr Asp Gly Glu Ser His Asp Asn Tyr Arg Leu Lys Gln Val Ile
130                 135                 140

Gln Asp Cys Glu Asp Glu Asn Ile Gln Arg Phe Ser Ile Ala Ile Leu
145                 150                 155                 160

Gly His Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Ala Leu Gly Glu Arg
            195                 200                 205

Ile Phe Ala Leu Glu Ala
            210

<210> SEQ ID NO 64
<211> LENGTH: 214
<212> TYPE: PRT
<213> ORGANISM: Homo sapiens

<400> SEQUENCE: 64

Val Ser Pro Thr Phe Gln Val Val Asn Ser Ile Ala Pro Val Gln Glu
  1               5                  10                  15

Cys Ser Thr Gln Leu Asp Ile Val Ile Val Leu Asp Gly Ser Asn Ser
                 20                  25                  30

Ile Tyr Pro Trp Asp Ser Val Thr Ala Phe Leu Asn Asp Leu Leu Lys
             35                  40                  45

Arg Met Asp Ile Gly Pro Lys Gln Thr Gln Val Gly Ile Val Gln Tyr
 50                  55                  60
```

```
Gly Glu Asn Val Thr His Glu Phe Asn Leu Asn Lys Tyr Ser Ser Thr
 65                  70                  75                  80

Glu Glu Val Leu Val Ala Ala Lys Lys Ile Val Gln Arg Gly Gly Arg
                 85                  90                  95

Gln Thr Met Thr Ala Leu Gly Thr Asp Thr Ala Arg Lys Glu Ala Phe
            100                 105                 110

Thr Glu Ala Arg Gly Ala Arg Arg Gly Val Lys Lys Val Met Val Ile
        115                 120                 125

Val Thr Asp Gly Glu Ser His Asp Asn His Arg Leu Lys Lys Val Ile
130                 135                 140

Gln Asp Cys Glu Asp Glu Asn Ile Gln Arg Phe Ser Ile Ala Ile Leu
145                 150                 155                 160

Gly Ser Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Thr Leu Gly Glu Arg
        195                 200                 205

Ile Phe Ala Leu Glu Ala
    210

<210> SEQ ID NO 65
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Val Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Tyr Leu
             20                  25                  30

Asn Trp Tyr Gln Gln Lys Pro Gly Lys Ala Pro Lys Leu Leu Ile Tyr
         35                  40                  45

Ala Ala Ser Ser Leu Gln Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Leu Thr
                 85                  90                  95

Phe Gly Gly Gly Thr Lys Val Glu Ile Lys
            100                 105

<210> SEQ ID NO 66
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Ile Gln Leu Thr Gln Ser Pro Ser Ser Leu Ser Ala Ser Val Gly
  1               5                  10                  15

Asp Arg Val Thr Ile Thr Cys Ser Ala Ser Ser Ser Val Asn His Met
             20                  25                  30
```

```
Phe Trp Tyr Gln Gln Lys Pro Gly Lys Ala Pro Lys Pro Trp Ile Tyr
                35                  40                  45

Leu Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gln Gly Thr Lys Val Glu Ile Lys
            100                 105
```

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Ser Ile Arg Phe Leu Glu Trp Ser Phe Asp Tyr Trp Gly Gln Gly Thr
            100                 105                 110

Leu Val Thr Val Ser Ser
        115
```

<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95
```

```
Arg Gly Phe Gly Asp Gly Gly Tyr Phe Asp Val Trp Gly Gln Gly Thr
            100                 105                 110

Leu Val Thr Val Ser Ser
        115
```

<210> SEQ ID NO 69
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Thr Met Ser Trp Val Arg Gln Ala Pro Gly Lys Gly Leu Glu Trp Val
         35                  40                  45

Ala Thr Ile Ser Gly Gly His Thr Tyr Tyr Leu Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
             85                  90                  95

Arg Gly Phe Gly Asp Gly Gly Tyr Phe Asp Val Trp Gly Gln Gly Thr
            100                 105                 110

Leu Val Thr Val Ser Ser
        115
```

<210> SEQ ID NO 70
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gln Ile Gln Leu Thr Gln Ser Pro Ser Ser Leu Ser Ala Ser Val Gly
  1               5                  10                  15

Asp Arg Val Thr Ile Thr Cys Ser Ala Ser Ser Ser Val Asn His Met
             20                  25                  30

Phe Trp Tyr Gln Gln Lys Pro Gly Lys Ala Pro Lys Pro Trp Ile Tyr
         35                  40                  45

Leu Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
             85                  90                  95

Phe Gly Gln Gly Thr Lys Val Glu Ile Lys
            100                 105
```

US 7,358,054 B2

ANTIBODIES TO VLA-1

CROSS-REFERENCE TO RELATED APPLICATIONS

This application is a National Stage filing under 35 U.S.C. §371 of International Application No. PCT/US02/11521, filed Apr. 12, 2002, which claims benefit under 35 U.S.C. §119(e) of U.S. provisional application Nos. 60/283,794, filed Apr. 13, 2001 and 60/303,689, filed Jul. 6, 2001. The disclosures of PCT application No. PCT/US02/11521 and U.S. provisional application Nos. 60/283,794 and 60/303,689 are incorporated by reference herein in their entirety.

FIELD OF THE INVENTION

This invention relates to antibodies to VLA-1 integrin and the use of these antibodies in treating inflammatory diseases and other immunological disorders.

This invention also relates to the crystal structure of the complex between one such antibody and the α1-I domain of VLA-1, and to the use of this structural information for computational drug design.

BACKGROUND OF THE INVENTION

Integrins are a superfamily of cell surface receptors that mediate cell-cell and cell-matrix adhesion. These proteins are known to provide anchorage as well as signals for cellular growth, migration and differentiation during development and tissue repair. They have been implicated in immune and inflammatory processes.

Integrins are heterodimeric proteins composed of two noncovalently linked polypeptide chains, α and β. The amino terminus of each chain forms a globular head that contributes to interchain linking and to ligand binding. The globular heads are connected to the transmembrane segments by stalks. The cytoplasmic tails are usually less than 50 amino acid residues long. Integrin subfamilies were originally defined on the basis of which β subunit was used to form the heterodimers. The β1-containing integrins are also called VLA molecules, referring to "very late activation" antigens. VLA-1 to VLA-6 refer to β1 subfamily members containing α1 to α6 (i.e., CD49a to CD49f), respectively. For general review, see *Cellular and Molecular Immunology*, eds. Abul K. Abbas et al., W. B. Saunders Company, Philadelphia, Pa., 2000.

Collagen (both types I and IV) and laminin are known ligands of α1β1 integrin (i.e., VLA-1). VLA-1 has been implicated in cell adhesion and migration on collagen (Keely et al., 1995, *J. Cell Sci.* 108:595-607; and Gotwals et al., 1996, *J. Clin. Invest.* 97:2469-2477); in promoting contraction and reorganization of collagen matrices, a critical component of wound healing (Gotwals et al., supra; and Chiro, 1991, *Cell* 67:403-410); and in regulating the expression of genes involved in extracellular matrix remodeling (Riikonen et al., 1995, *J. Biol. Chem.* 270:1-5; and Langholz et al., 1995, *J. Cell Biol.* 131:1903-1915). Thus, improper regulation of VLA-1 may result in certain pathological conditions such as fibrosis.

Moreover, it has been suggested that VLA-1 may play a role in T cell/monocyte-driven diseases. Anti-VLA-1 antibodies block T-cell dependent cytokine expression (Miyake et al., 1993, *J. Exp. Med.* 177:863-868). Expression of VLA-1 is increased in persistently activated, 2 to 4 week old cultured T cells (Hemler et al., 1985, *Eur. J. Immunol.* 15:502-508). VLA-1 is also expressed on a high percentage of T cells isolated from the synovium of patients with rheumatoid arthritis (Hemler et al., 1986, *J. Clin. Invest.* 78:692-702).

Several crystal structures of integrin α subunits have been determined, including the structures of the α2-I domain of α2β1 (PDB accession code 1aox; Emsley et al., 1997, *J. Biol. Chem.* 272:28512-28517); the α1-I domain of rat α1β1 (PDB accession number 1ck4; Nolte et al., 1999, *FEBS Lett.* 452:379-385; WO 00/20459); the α1 subunit of human α1β1 (PDB accession code 1qc5; Rich et al., 1999, *J. Biol. Chem.* 274:24906-24913); the αL-I and αM-I domains; and vWF-A3 (Lee et al., 1995, *Cell* 80:631-635; Lee et al., 1995, *Structure* 3:1333-1340; Qu et al., 1995, *Proc. Natl. Acad. Sci. USA* 92:10277-10281; Qu et al., 1996, *Structure* 4:931-942). The α2β1 structure revealed a helix (i.e., the C-helix) that created a trench or groove on one face of the protein at the metal-ion binding site (Emsley et al., supra). The crystal structure of the α2-I domain complexed to a short collagen-based triple helical peptide revealed that the collagen-based peptide was bound to that trench, where the α2-I amino acids that made intermolecular or metal contacts included Asp151, Asn154, Tyr157, Gln215, Asp219, Leu220, Thr221, Asp254, Glu256, His258, Tyr285, Leu286, Asn289, Leu291, Asn295, and Lys298 (PDB accession code 1dzi; Emsley et al., 2000, *Cell* 101:47-56; WO 01/73444). The amino acid numbering immediately above is based on PDB accession code 1 dzi and herein referred to as "crystal numbering." The crystal structures of the rat and human α1-I domains revealed a similar trench.

SUMMARY OF THE INVENTION

The present invention provides anti-VLA-1 antibodies and methods of using these antibodies to treat a variety of inflammatory and immunological disorders.

Specifically, the invention embraces an antibody that specifically binds to VLA-1 (e.g., human VLA-1). This antibody contains light chain complementarity determining regions ("CDR"s) defined by amino acid residues 24 to 33, 49 to 55, and 88 to 96 of SEQ ID NO:1, and/or heavy chain complementarity determining regions defined by amino acid residues 31 to 35, 50 to 65, and 98 to 107 of SEQ ID NO:2. These CDRs may contain mutations (e.g., deletions, insertions and/or substitutions) in the non-antigen-contacting portions, as determined from the crystal structure disclosed herein, without affecting the VLA-1-binding activity of the antibody. Exemplary mutations are S24N, G92S and D101A in the light chain CDRs, and G55S in the heavy chain CDR2. In one embodiment, the antibody of this invention contains a light chain variable domain sequence of SEQ ID NO:1 and/or a heavy chain variable domain sequence of SEQ ID NO:2.

In a related embodiment, the antibody of this invention contains the same heavy and light chain polypeptide sequences as an antibody produced by hybridoma mAQC2, deposited on Apr. 18, 2001 at the American Type Culture Collection ("ATCC"), 10801 University Boulevard, Manassas, Va. 20110-2209 and having ATCC accession number PTA3273. (All ATCC deposits recited herein were made under the Budapest Treaty). This antibody can be produced by, for example, hybridoma mAQC2, or cells containing nucleic acid sequences isolated from that hybridoma that encode the heavy and light chains of the mAQC2 monoclonal antibody.

In another embodiment, the antibody is a humanized antibody comprising at least one (e.g., 2, 3, 4, or 5) of the following residues in its light chain: Q1, L4, P46, W47 and Y71; or at least one (e.g., 2, 3, 4, 5, 6 or 7) of the following residues in its heavy chain: D1, V12, S28, F29, A49, T93, R94 (Kabat numbering convention). For instance, the antibody comprises Q1, L4 and Y71 in the light chain; and/or (i) F29, A49, T93 and R94, or (ii) A49 and T93, in the heavy chain.

The humanized antibody of this invention may contain a light chain variable domain sequence defined by amino acid residues 1 to 106 of SEQ ID NO:3, and/or a heavy chain variable domain sequence defined by amino acid residues 1 to 118 of SEQ ID NO:4. The humanized antibody may comprise the same heavy and/or light chain polypeptide sequences as an antibody produced by cell line hAQC2 (ATCC accession number PTA3275; deposited on Apr. 18, 2001).

In another embodiment, the humanized antibody of this invention may contain a mutation (e.g., deletion, substitution or addition) at one or more (e.g., 2, 3, 4, 5, 6, 7 or 8) of certain positions in the heavy chain such that an effector function of the antibody (e.g., the ability of the antibody to bind to a Fc receptor or a complement factor) is altered without affecting the antibody's ability to bind to VLA-1 (U.S. Pat. No. 5,648,260). These heavy chain positions include, without limitation, residues 234, 235, 236, 237, 297, 318, 320 and 322 (EU numbering system). The humanized antibody can, for instance, contain the mutations L234A (i.e., replacing leucine at position 234 of an unmodified antibody with alanine) and L235A (EU numbering system) in its heavy chain. In one related embodiment, the antibody comprises the same heavy chain polypeptide sequence as an antibody produced by cell line hsAQC2 (ATCC accession number PTA3356; deposited on May 4, 2001).

In yet another embodiment, the humanized antibody of this invention may contain a mutation (e.g., deletion or substitution) at an amino acid residue that is a site for glycosylation, such that the glycosylation site is eliminated. Such an antibody may be clinically beneficial for having reduced effector functions or other undesired functions while retaining its VLA-1 binding affinity. Mutations of glycosylation sites can also be beneficial for process development (e.g., protein expression and purification). For instance, the heavy chain of the antibody may contain the mutation N297Q (EU numbering system) such that the heavy chain can no longer be glycosylated at this site. In one related embodiment, the humanized antibody may comprise the same heavy chain polypeptide sequence as an antibody produced by cell line haAQC2 (ATCC accession number PTA3274; deposited on Apr. 18, 2001).

In still other embodiments, the heavy and/or light chains of the antibody of this invention contain mutations that increase affinity for binding to VLA-1 and thereby increase potency for treating VLA-1-mediated disorders.

Embraced in this invention are also a composition containing an antibody of the invention and a pharmaceutically acceptable carrier; an isolated nucleic acid containing a coding sequence for SEQ ID NO:1; an isolated nucleic acid containing a coding sequence for SEQ ID NO:2; an isolated nucleic acid containing a coding sequence for the light chain of an antibody produced by hybridoma mAQC2; an isolated nucleic acid containing a coding sequence for the heavy chain of an antibody produced by hybridoma mAQC2; an isolated nucleic acid containing a coding sequence for the light chain of an antibody produced by cell line hAQC2; an isolated nucleic acid containing a coding sequence for the heavy chain of an antibody produced by cell line hAQC2; an isolated nucleic acid containing a coding sequence for the heavy chain of an antibody produced by cell line haAQC2; an isolated nucleic acid containing a coding sequence for the heavy chain of an antibody produced by cell line hsAQC2; an isolated nucleic acid containing a coding sequence for residues I to 106 of SEQ ID NO:3; an isolated nucleic acid containing a coding sequence for residues 1 to 118 of SEQ ID NO:4; cells of hybridoma mAQC2; cells from cell line hAQC2; cells from cell line haAQC2; and cells from cell line hsAQC2.

The present invention also provides a method of treating a subject with an immunological disorder mediated by VLA-1, including administering to the subject an effective amount of an antibody of this invention. For instance, this method is used to treat a human subject to palliate, ameliorate, stabilize, reverse, prevent, slow or delay progression of the disorder. Alternatively, this method is used prophylactically to treat a human subject at risk for developing this immunological disorder so as to prevent or delay the onset of the disorder. An "effective amount" of the composition can be administered in one or more dosages.

VLA-1 mediated immunological disorders include, but are not limited to, disorders in which the VLA-1 activity level is elevated in one or more tissues as compared to a normal subject. Examples of such disorders are skin related conditions (e.g., psoriasis, eczema, burns, dermatitis, and abnormal proliferation of hair follicle cells), fibrosis (e.g., kidney or lung fibrosis), allergic rhinitis, respiratory distress syndrome, asthma, bronchitis, tendinitis, bursitis, fever, migraine headaches, gastrointestinal conditions (e.g., inflammatory bowel disease, Crohn's disease, gastritis, irritable bowel syndrome, colitis and colorectal cancer), vascular diseases (e.g., atherosclerosis), periarteritis nodosa, thyroiditis, aplastic anemia, Hodgkin's Disease, rheumatic fever, osteoarthritis, autoimmune diseases (e.g., type I diabetes, myasthenia gravis, rheumatoid arthritis, systemic lupus erythematosus, and multiple sclerosis), sarcoidosis, nephrotic syndrome, renal failure, Bechet's Syndrome, polymyositis, gingivitis, hypersensitivity (e.g., delayed type hypersentivity or immediate hypersensitivity), graft and transplant rejections, graft versus host disease (GVHD), conjunctivitis, swelling occurring after injury, myocardial ischemia, and endotoxin shock syndrome.

The present invention also provides a method of determining the level of VLA-1 in a tissue (e.g., tissue specimen and body fluid) comprising contacting the tissue (e.g., in vivo or in vitro) with the antibody of the invention, and then detecting the binding of the antibody to the tissue, thereby determining the level of VLA-1 in the tissue.

As used herein, the antibody of this invention can be, for instance, a murine antibody, a humanized antibody, or a chimeric antibody. It can be a whole antibody (i.e., with two full length light chains and two full length heavy chains) of any isotype and subtypes (e.g., IgM, IgD, $IgG_1$, $IgG_2$, $IgG_3$, $IgG_4$, IgE, $IgA_1$, and $IgA_2$; with either kappa or lambda light chain). Alternatively, the antibody of this invention refers to an antigen-binding fragment (e.g., Fab, $F(ab')_2$, and single chain Fv) of a whole antibody.

The present invention further provides crystallizable compositions and crystals of complexes formed by a rat-human chimeric α1-I domain (mutant RΔH) and a hAQC2 Fab fragment, and methods for using such compositions and crystals. This invention also provides the structure coordinates and binding sites of the chimeric domain and the hAQC2 Fab fragment. The atomic coordinates derived from the crystal structure described herein provide a structural basis for the biological activities of hAQC2 as well as a basis for rational design of VLA-1 agonists or antagonists with predicted biological activities (e.g., small molecule compounds or antibodies such as hAQC2 variants).

The crystal structure disclosed herein is the first crystal structure of an α1-I domain of an α1β1 integrin/Fab complex. This structure shows the residues critical for Fab binding by α1-I domain. In addition, the Fab binds in the putative collagen-binding site and inhibits collagen binding. Amino acid residues found in the binding site on the α1-I domain include Asp154, Ser156, Asn157, Ser158, Tyr160, Glu192, Glu218, Arg219, Gly220, Gly221, Arg222, Gln223, Thr224, Asp257, His261, Asn263, Arg291, and Leu294 (crystal numbering). Residues on the Fab fragment found to bind to the α1-I domain include light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering).

This invention also provides a computer for producing a three-dimensional representation of a molecular complex, where the molecular complex is defined by the set of structure coordinates of a complex of a chimeric I domain of an α1β1 integrin RΔH and humanized antibody hAQC2, according to FIG. 19; or a homologue of the-molecular complex, the homologue having a root mean square deviation from the backbone atoms of the amino acids of not more than 0.65 Å. The computer includes a machine-readable data storage medium including a data storage material encoded with machine-readable data, where the data contains at least a portion of the structure coordinates of the complex according to FIG. 19; a working memory for storing instructions for processing the machine-readable data; a central-processing unit coupled to the working memory and to the machine-readable data storage medium for processing the machine readable data into the three-dimensional representations; and a display coupled to the central-processing unit for displaying the three-dimensional representation.

This invention further provides a computer for producing a three-dimensional representation of a molecule or molecular complex including a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19; or a homologue of the molecule or molecular complex, where the homologue includes a binding site that has a root mean square deviation from the backbone atoms of the hAQC2 amino acids of not more than 1.10 Å. This invention also provides a computer for producing a three-dimensional representation of: a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19; a binding site of a homologue that has a root mean square deviation from the backbone atoms of the hAQC2 amino acids of not more than 1.10 Å.

This invention also provides a method for identifying an inhibitor of an I domain of an integrin including the steps of using structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19 or ± a root mean square deviation from the backbone atoms of the hAQC2 amino acids not more than 1.10 Å, to generate a three-dimensional structure of a binding site; employing the three-dimensional structure to design or select a potential antagonist; synthesizing the potential antagonist; and contacting the potential antagonist with hAQC2 to determine the ability of the potential antagonist to interact with hAQC2, where the ability of the potential antagonist to interact with hAQC2 indicates that the potential antagonist is an inhibitor of the I domain. This invention further provides an inhibitor of I domain of integrin identified by this method.

This invention also provides a computer for producing a three-dimensional representation of a molecule or molecular complex including: a binding site defined by structure coordinates of I domain amino acid residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a homologue of the molecule or molecular complex, where the homologue includes a second binding site that has a root mean square deviation from the backbone atoms of the I domain amino acids not more than 0.65 Å. This invention also provides a computer for producing a three-dimensional representation of: a first binding site defined by structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a binding site of a homologue that has a root mean square deviation from the backbone atoms of the I domain amino acids not more than 0.65 Å.

This invention also provides a computer for producing a three-dimensional representation of a molecule or molecular complex including: a binding site defined by structure coordinates of I domain amino acids including at least three of residues Glu192, Gln218, Arg219, Gly220, and Gly221 (crystal numbering), according to FIG. 19; or a homologue of the molecule or molecular complex, where the homologue includes a second binding site that has a root mean square deviation from the backbone atoms of the I domain amino acids not more than 1.0 Å. The invention further provides a computer for producing a three-dimensional representation of a binding site defined by structure coordinates of I domain amino acids including at least three of residues Glu192, Gln218, Arg219, Gly220, and Gly221 (crystal numbering), according to FIG. 19; or a binding site of a homologue that has a root mean square deviation from the backbone atoms of the I domain amino acids not more than 1.0 Å.

This invention further provides methods for using these three-dimensional representations to design chemical entities that associate with the chimeric domain or the hAQC2 Fab fragment, or portions thereof; and act as potential inhibitors of the chimeric domain or the hAQC2 Fab fragment, or portions thereof. This invention also relates to compositions including chemical entities, such as inhibitors and variants of the chimeric domain or variants of the hAQC2 Fab fragment, where such chemical entities and variants are rationally designed by means of the structure coordinates of the chimeric domain or the hAQC2 Fab fragment, or binding sites. The invention further relates to use of the above-identified chemical entities to treat or prevent conditions associated with inappropriate or abnormal α1β1 activity in a subject.

This invention further provides a method for identifying an inhibitor of an I domain of an integrin including the steps of using the structure coordinates of I domain amino acids residues Asp154, Ser156, Asn157, Ser158, Tyr160, Glu192, Gln218, Arg219, Gly220, Arg221, Gly222, Gln223, Thr224, Asp257, His261, Asn263, Arg291, and Leu294 (crystal numbering), according to FIG. 19, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain, where the ability of the potential antagonist to interact with the I domain indicates that the potential antagonist is an inhibitor of the I domain.

This invention also provides a method for identifying an inhibitor of an I domain of an integrin including the steps of using the structure coordinates of at least three of I domain amino acids including residues Glu192, Gln218, Arg129, Gly220, and Gly221 (crystal numbering), according to FIG. 19, or ± a root mean square deviation from the backbone atoms of the I domain amino acids not more than 0.65 Å, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain of integrin, where the ability of the potential antagonist to interact with the I domain indicates that the potential antagonist is an inhibitor of the I domain. This invention also provides an inhibitor of I domain of integrin identified by this method.

Other features and advantages of the invention will be apparent from the following detailed description, and from the claims.

BRIEF DESCRIPTION OF THE DRAWINGS

FIG. 12. Amino acid sequence of the human α1-I domain (SEQ ID NO:64).

FIG. 14. Species Cross-reactivity of the blocking mAbs analyzed by fluorescence activated cell sorter (FACS). Rabbit vascular smooth muscle cells were incubated with either mAb AJH10 (bottom) or murine IgG control (top) and analyzed by fluorescence activated cell sorter (FACS).

FIG. 16. Characterization of Humanized AQC2 Forms. mAQC2 (triangles), chAQC2 (circles), hAQC2 (inverted triangles) and hAQC2' (squares) were evaluated.
  A. Inhibition of VLA-1 binding to type IV collagen.
  B. Inhibition of α1-I domain binding to type IV collagen.
  C. Binding to immobilized α1-I domain.
  D. Competition with biotinylated mAQC2 for binding to immobilized α1-I domain.

FIG. 19. Atomic structure coordinates for the α1-I domain/Fab complex, as derived by X-ray crystallography from crystals of that complex in Protein Data Bank (PDB) format. The coordinates of the two complexes in the asymmetric unit are listed as follows.
  Complex 1: molecule A=I domain of integrin
    molecule H=heavy chain of hAQC2 Fab
    molecule L=light chain of hAQC2 Fab
    molecule M=Mn$^{+2}$
  Complex 2: molecule B=I domain of integrin
    molecule X=heavy chain of hAQC2 Fab
    molecule Y=light chain of hAQC2 Fab
    molecule M=Mn$^{+2}$ FIG. 20. I domain-Fab complex. A. Ribbon diagram of the I domain-Fab complex. The I domain and the antibody heavy and light chain are labeled. The Mn$^{+2}$ ion is shown as a sphere. B. Close-up of the MIDAS (Metal-Ion-Dependent-Adhesion-Site) site showing the coordination of the metal ion (sphere) by Asp101 (crystal numbering). The protein backbones are shown as ribbons and the side chains in the ball-and-stick representation. The cylinders represent interactions between the metal ion and protein atoms. The thin lines represent H-bonds.

DETAILED DESCRIPTION OF THE INVENTION

Figure 1A:
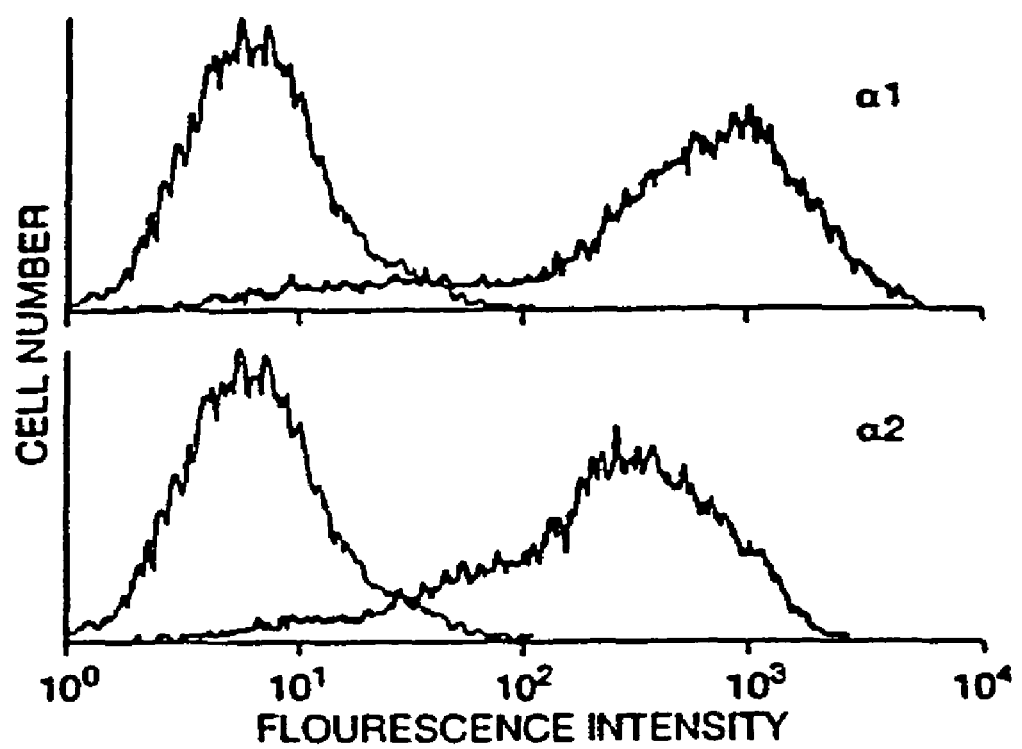
FIG. 1. Collagen-binding integrins α1β1 and α2β1 on activated leukocytes. (A). Flow cytometric analysis of α1 and α2β1 integrin expression on IL-2-activated splenocytes (d 11). Cells were labeled with either anti-α1 mAb, anti-α2 mAb, or non-binding control mAb (grey lines), and followed by FITC-anti-hamster immunoglobulin. (B) Effect of anti-α1 and anti-α2 mAbs on leukocyte adhesion to collagen. $10^5$ IL-2 activated splenocytes were treated with indicated mAbs for 15 min before plating onto either type IV or type I collagen-coated wells for 1 h at 37° C. Adhesion was calculated as illustrated in Example 1, and expressed as % adhesion relative to control mAb-treated cells. Adhesion assays were done in triplicate, and at least three independent experiments were performed. One representative experiment is shown.

It is a discovery of the present invention that an antibody to an integrin (e.g., VLA-1) and fragment thereof, particularly, an α1-integrin subunit, can block the interaction of pro-inflammatory leukocytes with components of the extracellular matrix including, but not limited to collagens, laminin and fibronectin. This discovery illustrates the importance of adhesion molecules of the integrin family, particularly α1β1, in the peripheral tissue environment during conditions related to inflammation. It also extends the role of integrins family and fragments thereof in inflammation beyond leukocyte attachment and extravasation at the endothelial interface by highlighting the importance of the matrix-rich peripheral tissue environment to immune responses and it reveals peripheral tissues as a new point of intervention for adhesion based therapies.

I. Anti-Integrin Antibodies

The methods of the present invention contemplate the use of antibodies to integrins where the integrins contemplated include molecules which comprise a β chain, including but not limited to β1, β2, β3, β4, β5, β6, β7, β8, non-covalently bound to an a: chain, including but not limited to α1, α2, α3, α4, α5, α6, α7, α8, α9, α10, αV, αL, αM, αX, αD, αE, αIIb. Examples of the various integrins contemplated for use in the invention include, but are not limited to:

α1β1, α2β1, α3β1, α4β1, α5β1, α6β1, α7β1, α8β1, α9β1, α10β1, αVβ1, αLβ1, αMβ1, αXβ1, αDβ1, αIIbβ1, αEβ1;

α1β2, α2β2, α3β2, α4β2, α5β2, α6β2, α7β2, α8β2, α9β2, α10β2, αVβ2, αLβ2, αMβ2, αXβ2, αDβ2, αIIbβ2, αEβ2;

α1β3, α2β3, α3β3, α4β3, α5β3, α6β3, α7β3, α8β3, α9β3, α10β3, αVβ3, αLβ3, αMβ3, αXβ3, αDβ3, αIIbβ3, αEβ3;

α1β4, α2β4, α3β4, α4β4, α5β4, α6β4, α7β4, α8β4, α9β4, α10β4, αVβ4, αLβ4, αMβ4, αXβ4 αDβ4, αIIbβ4, αEβ4;

α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5;

α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6;

α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7;

α1β7, α2β8, α3β8, α4β8, α5β8, α6β8, α7β8, α8β8, α9β8, α10β8, αVβ8, αLβ8, αMβ8, αXβ8, αDβ8, αIIbβ8, αEβ8;

The methods of the present invention also contemplate the use of antibodies to integrin fragments including for example antibodies to a β chain alone, including but not limited to β1, β2, β3, β4, β5, β6, β7, β8, as well as an α chain alone, including but not limited to α1, α2, α3, α4, α5, α6, α7, α8, α9, α10, αV, αL, αM, αX, αD, αE, αIIb. In addition, the methods of the present invention further contemplate the use of antibodies to integrin fragments including for example antibodies to the I domain of the α chain, including but not limited to the I domain from α1 β2 (Briesewitz et al., 1993, *J. Biol. Chem.* 268:2989); α2 β1 (Takada and Hemler, 1989, *J. Cell Biol* 109:397), αL β2 (Larson et al., 1989, *J. Cell Biol* 108:703), αM β2 (Corbi et al., 1988, *J Biol Chem* 263:12403), αX β2 (Corbi et al., 1987, *EMBO J* 6:4023), αDβ2 (Grayson et al., 1988, *J Exp Med* 188:2187), αE β7 (Shaw et al., 1994, *J Biol Chem* 269:6016). In one embodiment, the α1-I domain antigenic determinant includes an amino acid sequence of at least 6 contiguous amino acids, wherein the contiguous sequence is found within the sequence of FIG. 12. In a related embodiment, the contiguous sequence is Val-Gln-Arg-Gly-Gly-Arg (residues 91-96 of SEQ ID NO:64).

Methods for producing integrins for use in the present invention are known to those of skill in the art (see, e.g., Springer et al., 1990, *Nature* 346:425-434).

Embodiments of the present invention farther include anti-integrin polyclonal and monoclonal antibodies. Embodiments of the present invention include a monoclonal antibody such an anti-α1monoclonal antibody. Antibodies for treatment, in particular for human treatment, include human antibodies, humanized antibodies, chimeric antibodies, and antigen-binding fragments of whole antibodies such as Fab, Fab', F(ab')2 and F(v) antibody fragments. Some antibodies of this invention may also include proteins containing one or more immunoglobulin light chains and/or heavy chains, such as monomers and homo-or hetero-multimers (e.g., dimers or trimers) of these chains, where these chains are optionally disulfide-bonded or otherwise cross-linked. These antibodies may be capable of binding to one or more antigens (e.g., α1, α2, α6 or alpha-I domain containing integrin subunits).

Figure 12:
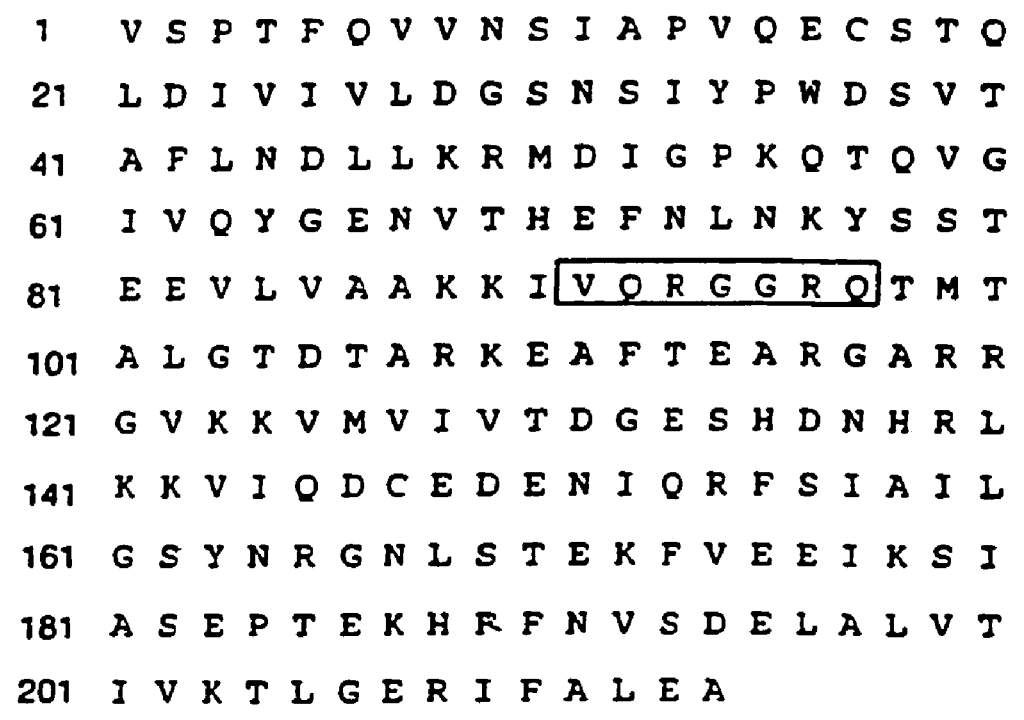

An α1β1 function blocking antibody as used herein refers to an antibody that binds to the α1-I domain, for example, residues 91-97 of FIG. 12, and blocks α1β1 function as tested, for example, by their ability to inhibit K562-1 dependent adhesion to Collagen IV (see Example 15).

The following describes the various methods of making the antibodies of this invention. Methods that are known in the art but not specifically described herein are also within the scope of this invention. For instance, antibodies of this invention can also be identified using phage-displayed antibody libraries, such as those described in Smith, 1985, *Science* 228:1315-7; U.S. Pat. Nos. 5,565,332, 5,733,743, 6,291,650, and 6,303,313. Additional antibodies of this invention can be made by coupling the heavy chains identified herein with a noncognate light chain, e.g., a light chain identified by phage display technology.

II. Non-Human Hybridoma Antibodies

The monoclonal antibodies of this invention can be generated by well known hybridoma technology. For instance, β$_1$ −/− animals (e.g., mice, rats or rabbits) can be immunized with purified or crude α$_1$β$_1$ preparations, cells transfected with cDNA constructs encoding α$_1$, β$_1$ or both antigens, cells that constitutively express α$_1$β$_1$, and the like. The antigen can be delivered as purified protein, protein expressed on cells, protein fragment or peptide thereof, or as naked DNA or viral vectors encoding the protein, protein fragment, or peptide. Sera of the immunized animals are then tested for the presence of anti-α$_1$β$_1$ antibodies. B cells are isolated from animals that test positive, and hybridomas are made with these B cells.

Antibodies secreted by the hybridomas are screened for their ability to bind specifically to VLA-1 (e.g., binding to α$_1$-transfected cells and not to untransfected parent cells) and for any other desired features, e.g., having the desired CDR consensus sequences, inhibiting (or not inhibiting in the case of nonblockers) the binding between collagen and VLA-1.

Hybridoma cells that test positive in the screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e.g., CHO or NSO cells) with the cDNAs, culturing the transfected host cells, and recovering the antibody from the culture medium.

III. Chimeric Antibodies

The monoclonal antibodies of this invention can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain-identical or substantially so to the variable domains of the cognate antibody. Such-an engineered antibody is called a chimeric antibody and is less antigenic than the cognate antibody when administered to an individual of the species from which the hinge and/or constant region is derived (e.g., a human). Methods of making chimeric antibodies are well known in the art. Human constant regions include those derived from IgG1 and IgG4.

IV. Fully Human Antibodies

The monoclonal antibodies of this invention also include fully human antibodies. They may be prepared using in vitro-primed human splenocytes, as described by Boemer et al., 1991, *J. Immunol.* 147:86-95, or using phage-displayed antibody libraries, as described in, e.g., U.S. Pat. No. 6,300,064.

Alternatively, fully human antibodies may be prepared by repertoire cloning as described by Persson et al., 1991, *Proc. Nat. Acad. Sci. USA* 88: 2432-2436; and Huang and Stollar, 1991, *J. Immunol. Methods* 141: 227-236. In addition, U.S. Pat. No. 5,798,230 (Aug. 25, 1998) describes preparation of human monoclonal antibodies from human B cells, wherein human antibody-producing B cells are immortalized by infection with an Epstein-Barr virus, or a derivative thereof, that expresses Epstein-Barr virus nuclear antigen 2 (EBNA2), a protein required for immortalization. The EBNA2 function is subsequently shut off, resulting in an increase in antibody production.

Some other methods for producing fully human antibodies involve the use of non-human animals that have inactivated endogenous Ig loci and are transgenic for un-rearranged human antibody heavy chain and light chain genes. Such transgenic animals can be immunized with $\alpha_1\beta_1$ and hybridomas are then made from B cells derived therefrom. These methods are described in, e.g., the various GenPharm/Medarex (Palo Alto, Calif.) publications/patents concerning transgenic mice containing human Ig miniloci (e.g., Lonberg U.S. Pat. No. 5,789,650); the various Abgenix (Fremont, Calif.) publications/patents with respect to XENOMICE (e.g., Kucherlapati U.S. Pat. Nos. 6,075,181, 6,150,584 and 6,162,963; Green et al., 1994, *Nature Genetics* 7:13-21; and Mendez et al., 1997, *Nature Genetics* 15(2):146-56); and the various Kirin (Japan) publications/patents concerning "transomic" mice (e.g., EP 843 961, and Tomizuka et al., 1997, *Nature Genetics* 16:133-1443).

V. Humanized Antibodies

The monoclonal antibodies of this invention also include humanized versions of cognate anti-$\alpha_1\beta_1$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer non-human components.

The methods for making humanized antibodies are described in, e.g., Winter EP 239 400; Jones et al., 1986, *Nature* 321:522-525; Riechmann et al., 1988, *Nature* 332: 323-327 (1988); Verhoeyen et al., 1988, *Science* 239:1534-1536; Queen et al., 1989, *Proc. Nat. Acad. Sci. USA* 86:10029; U.S. Pat. No. 6,180,370; and Orlandi et al., 1989, *Proc. Natl. Acad. Sci. USA* 86:3833. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs encoding the CDRs are transferred to the corresponding regions of a human antibody heavy or light chain variable domain coding sequence by site directed mutagenesis. Then human constant region gene segments of a desired isotype (e.g, $\gamma 1$ for CH and k for CL) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" (supra) in the framework regions of the acceptor antibody in order to retain the antigen-binding activity of the cognate antibody.

The general approach of making back mutations is known in the art. For instance, Queen et al. (supra), Co et al., 1991, *Proc. Nat. Acad. Sci. USA* 88:2869-2873, and-WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the non-human donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, 1991, *Biotechnology* 9: 266-271. Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

VI. Other Moieties

The monoclonal antibodies of this invention may further include other moieties to effect the desired functions. For instance, the antibodies may include a toxin moiety (e.g., tetanus toxoid or ricin) or a radionuclide (e.g., $^{111}$In or $^{90}$Y) for killing of cells targeted by the antibodies (see, e.g., U.S. Pat. No. 6,307,026). The antibodies may include a moiety (e.g., biotin, fluorescent moieties, radioactive moieties, histidine tag or other peptide tags) for easy isolation or detection. The antibodies may also include a moiety that can prolong their serum half life, for example, a polyethylene glycol (PEG) moiety, and a member of the immunoglobulin super family or fragment thereof (e.g., a portion of human IgG1 heavy chain constant region such as the hinge, CH2 and CH3 regions).

VII. Crystallizable Compositions and Crystals

Figure 20:
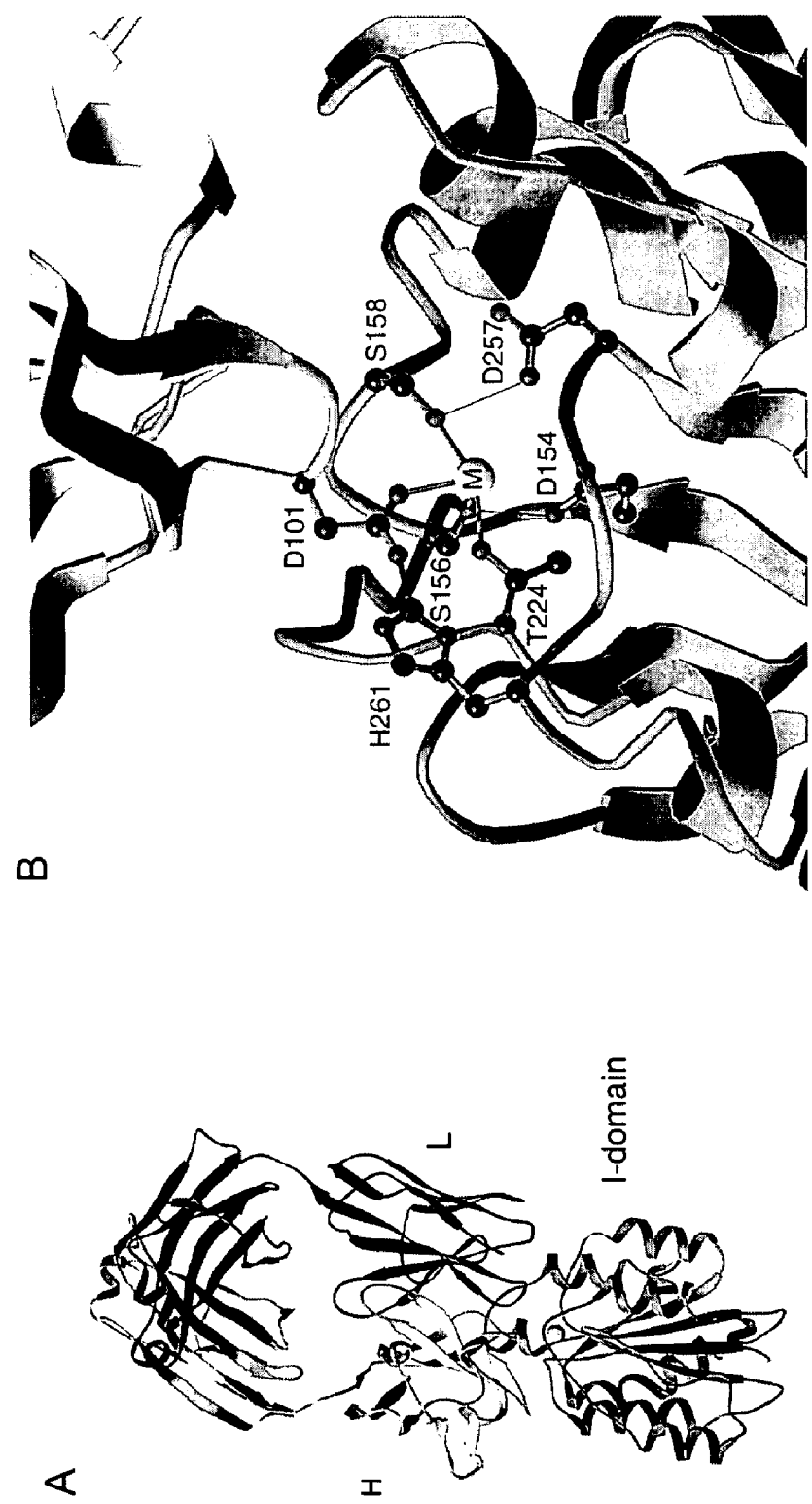
FIG. 20 was made with the software program RIBBONS (Carson, 1991, *J. Appl. Cryst.* 24:958-961).

This invention also provides a crystallizable composition containing a complex of: (1) a rat-human chimeric α1-I domain (e.g., mutant RΔH), or a portion thereof (e.g., a polypeptide including 135 to 336 amino acids of the rat-human chimeric α1-I domain); and (2) a Fab fragment of hAQC2, or a portion thereof (e.g., a polypeptide including 3 to 213 amino acids of the light chain and/or a polypeptide including 3 to 219 amino acids of the heavy chain). An exemplary complex is shown in FIG. 20. The RΔH α1-I domain can include, e.g., amino acid residues 145 to 336 (crystal numbering) (SEQ ID NO:59, infra) of the rat α1 subunit. The hAQC2 Fab fragments may include light chain amino acid residues 1 to 106 (e.g., 1-213) of SEQ ID NO:3 and heavy chain amino acid residues 1 to 118 (e.g., 1-219) of SEQ ID NO:4. The hAQC2 Fab fragments may be obtained by papain digestion of the whole antibody or made by recombinant methods. The Fab fragments include at least an antigen-binding portion of the variable domains of the light chain and/or the heavy chains of hAQC2.

```
                                                    (SEQ ID NO:59)
145    TQLDIV

151    IVLDGSNSIY PWESVIAFLN DLLKRNDIGP KQTQVGIVQY

191    GENVTHEFNL NKYSSTEEVL VAANKIVQRG GRQTMTALGI

231    DTARKEAFTE ARGARRGVKK VMVIVTDGES HDNYRLKQVI

271    QDCEDENIQR FSIAILGHYN RGNLSTEKFV EEIKSIASEP

311    TEKHFFNVSD ELALVTTVKA LGERIF
```

Some crystallizable compositions and crystals of this invention may contain a molecule or molecular complex that is homologous to the α1-I domain and/or the hAQC2 Fab fragment by amino acid sequence or by three-dimensional structure. Examples of homologues include, but are not limited to: the α1-I domain and/or the hAQC2 Fab fragment with mutations, such as conservative substitutions, additions, deletions or a combination thereof. "Conservative substitutions" refer to replacement residues that are physically similar in size, shape, hydrophobicity, charge, and/or chemical properties to the corresponding reference residues. Methods for identifying a "corresponding" amino acid are known in the art and are based upon sequence, structural alignment, its functional position or a combination thereof as compared to the crystal structure solved in the present invention. For example, corresponding amino acids may be identified by superimposing the backbone atoms of the amino acids in the α1-I domain/hAQC2 complex and a α1-I domain and/or hAQC2 homologue using well known software applications, such as QUANTA (Molecular Simulations, Inc., San Diego, Calif. © 1998,2000). The corresponding amino acids may also be identified using sequence alignment programs such as the "bestfit" program available from the Genetics Computer Group, which uses the local homology algorithm described by Smith and Waterman in *Adv. Appl. Math.* 2:482 (1981).

Crystallizable compositions of this invention may further include one or more components that promote crystallization and/or is compatible with crystallization conditions. Such components may include, but are not limited to, buffer, salts, precipitating agents and other reagents. One component can be 30% weight/volume Polyethylene Glycol 1500 (PEG1500).

The instant invention also provides methods of making crystals from crystallizable compositions including a complex of α1-I domain and an antigen-binding portion of hAQC2 (e.g., Fab, Fab' or other fragments, supra). Various techniques of crystallization can be used in the claimed invention, including, but not limited to, vapor-diffusion, dialysis, microbatch, batch, and liquid-liquid diffusion. Vapor diffusion methods include, but are not limited too, sitting-drop, hanging-drop and sandwich-drop techniques. Vapor-diffusion methods can use techniques to control the rate of crystallization, such as the addition of oils on the drops or reservoir solution. Crystallization methods can include mixing a reservoir solution containing precipitating agent with an aqueous solution of a complex of α1-I domain and an antigen-binding portion of hAQC2 to produce a crystallizable composition. The mixture or crystallizable composition may then be crystallized using the various above-listed techniques. The crystallizable composition of this invention may be an aqueous solution of a complex of α1-I domain and an antigen-binding portion of hAQC2 containing the complex at a concentration of about 1 to 50 mg per mL, such as a concentration of about 5 to 15 mg per mL (e.g., 11 mg per mL).

VIII. Crystal Structures and Structure Coordinates

This invention further provides the three-dimensional structure of a crystal including a complex of mutant RΔH, and a hAQC2 Fab fragment at 2.8 Å resolution (Example 24, infra). The three-dimensional structures of other related crystals may also be determined using techniques described herein and those known in the art. The three-dimensional structure of this complex is defined by a set of structure coordinates set forth in FIG. 19. These structure coordinates are Cartesian atomic coordinates derived from mathematical equations related to the patterns obtained from diffraction of a monochromatic beam of X-rays by the atoms or scattering centers of the crystalline complex of the α1-I domain and the hAQC2 Fab fragment. Diffraction data are first used to calculate an electron density map of the repeating unit of the crystal. The electron density map is then used to establish the positions of individual atoms of the complex.

This invention provides a molecule or a molecular complex defined by all or part of the structure coordinates of all amino acids set forth in FIG. 19, as well as a homologue of the molecule or molecular complex, where the homologue has a root mean square deviation from the backbone atoms of these amino acids between 0.00 Å and 0.65 Å, such as between 0.00 Å and 0.60 Å (e.g., between 0.00 Å and 0.50 Å). The term "root mean square deviation" or "r.m.s. deviation" means the square root of the arithmetic mean of the squares of the deviations from the mean. It is a way to express the deviation or variation from a trend or object. For purposes of this invention, the "root mean square deviation" or "r.m.s. positional deviation" defines the variation in the backbone of a protein from the relevant portion of the backbone of the polypeptide as defined by the structure coordinates described herein.

A molecule or a molecular complex of this invention may also include a binding site defined by structure coordinates of at least seven amino acids of the hAQC2 Fab fragment selected from the group including of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19; or a homologue of the molecule or molecular complex, where the homologue includes a binding site that has a root mean square deviation from the backbone atoms of one or more of these amino acids between 0.00 Å and 1.10 Å, such as between 0.00 Å and 1.00 Å (e.g., between 0.00 Å and 0.50 Å). The term "binding site" as used herein, refers to a region of a molecule or molecular complex that, as a result of its shape and charge, favorably associates with another chemical entity. The term "site" includes, but is not limited to, trench, cleft, channel or pocket. For instance, binding sites on the α1-I domain may include a collagen-binding site (Emsley et al., 1997, supra), an antibody-binding site, and an allosteric (or IDAS) binding site (Huth et al., 2000, *Proc. Natl. Acad. Sci. U.S.A.* 97:5231-5236). The term "chemical entity" includes, but is not limited to, any molecule, molecular complex, compound or fragment thereof. The term "associate with" refers to an association or binding in a condition of proximity between a chemical entity, or portions thereof, and a binding pocket or binding site on a protein. The association may be non-covalent—where the juxtaposition is energetically favored by hydrogen bonding or van der Waals or electrostatic interaction—or it may be covalent.

A molecule or molecular complex of this invention can include a binding site defined by structure coordinates of α1-I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19, or a homologue of the molecule or molecular complex, where the homologue includes a binding site that has a root mean square deviation from the backbone atoms of the α1-I domain amino acids between 0.00 Å and 0.92 Å.

A molecule or molecular complex of this invention also may include a binding site defined by structure coordinates of α1-I domain amino acids selected from the group consisting of residues Glu192, Gln218, Arg219, Gly220, and Gly221 (crystal numbering), according to FIG. 19; or a homologue of the molecule or molecular complex, where the homologue includes a binding site that has a root mean square deviation from the backbone atoms of the α1-I domain amino acids between 0.00 Å and 0.30 Å.

Those of skill in the art will understand that a set of structure coordinates for a polypeptide is a relative set of points that define a shape in three dimensions. Thus, it is possible that an entirely different set of coordinates that define a similar or identical shape could be generated using mathematical manipulations of the structure coordinates in FIG. 19. For example, the structure coordinates could be manipulated by crystallographic permutations of the structure coordinates, fractionalization of the structure coordinates, integer additions or subtractions to sets of the structure coordinates, inversion of the structure coordinates, or any combination thereof. Moreover, slight variations in the individual coordinates will have little effect on overall shape.

Alternatively, modification in the crystal structure due to mutations, such as additions, substitutions, and/or deletions of amino acids, or other changes in any of the polypeptide components (e.g., a hAQC2 Fab fragment or a α1-I domain) that make up the crystal can also account for variations in structure coordinates. If such variations are within an acceptable standard error as compared to the original coordinates, the resulting three-dimensional shape is considered to be the same as that of the unmodified crystal.

It is therefore necessary to determine whether an entity is sufficiently similar to all or parts of the structure described herein as to be considered the same. Such analyses may be carried out using current software applications, such as QUANTA (Accelrys, Inc. and Molecular Simulations, Inc., San Diego, Calif. © 1998,2000) and O (Jones et al., 1991, *Acta Cryst.* A47:110-119), and accompanying User Guides. The Molecular Similarity application of QUANTA and the LSQ application of O permit comparisons between different structures, different conformations of the same structure, and different parts of the same structure. The general procedure used in both applications is to input the structures to be compared, define the equivalent atomic positions in these structures, perform a fitting operation, and analyze the results.

When each structure is input into the application, it is given a name. and identified as the fixed structure or a moving structures. Atom equivalency is usually defined by equivalent atoms such as protein backbone atoms (N, Cα, C and O) for all conserved residues between the two structures being compared. The moving structure is translated and rotated to obtain an optimum or least-squares fit with the fixed structure. The root mean square difference of the fit over the specified pairs of equivalent atom is reported by both programs in angstroms.

For the purpose of this invention, any molecular complex that has a root mean square deviation of conserved residue backbone atoms (N, Cα, C, 0) between 0.00 Å and 1.50 Å, such as between 0.00 Å and 1.00 Å (e.g., between 0.00 Å and 0.50 Å), when superimposed on the relevant backbone atoms described by structure coordinates listed in FIG. 19 are considered identical.

IX. Determining Other Crystal Structures

The structure coordinates set forth in FIG. 19 can also be used to aid in obtaining structural information about another crystallized molecular entity, such as another hAQC2 containing amino acid substitutions in one of its CDRs. This may be achieved by any well-known techniques, including molecular replacement, an especially useful method for determining the structures of mutants and homologues of α1-I domain/Fab.

The structure coordinates set forth in FIG. 19 can also be used for determining at least a portion of the three-dimensional structure of molecular entities that contain at least some structural features similar to at least a portion of the α1-I domain or the hAQC2 Fab. Therefore, another embodiment of this invention provides a method of utilizing molecular replacement to obtain structural information about a crystallized molecule or molecular complex with unknown structure including the steps of: (a) generating an X-ray diffraction pattern from the crystallized molecule or molecular complex; and (b) applying at least a portion of the structure coordinates set forth in FIG. 19 to the X-ray diffraction pattern to generate a three-dimensional electron density map of the molecule or molecular complex with unknown structure.

By using molecular replacement, all or part of the structure coordinates set forth in FIG. 19 can be used to determine the unknown structure of a crystallized molecular entity more rapidly and efficiently than attempting to determine such information ab initio. Molecular replacement provides an accurate estimation of the phases for an unknown structure. Phases are a factor in equations used to solve crystal structures that cannot be determined directly. Obtaining accurate values for the phases, by methods other than molecular replacement, can often be a time-consuming process that involves iterative cycles of approximations and refinements and greatly hinders the solution of crystal structures. However, when the crystal structure of a protein containing at least a homologous portion has been solved, the phases from the known structure can often provide a satisfactory estimate of the phases for the unknown structure.

Thus, molecular replacement involves generating a preliminary model of a molecule or molecular complex whose structure coordinates are unknown, by orienting and positioning the relevant portion of the complex according to FIG. 19 within the unit cell of the crystal of the unknown molecule or molecular complex, so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, 1985, *Meth. Enzymol.* 115:55-77; Rossmann, ed., "The Molecular Replacement Method", Int. Sci. Rev. Ser., No. 13, Gordon & Breach, New York, 1972). The structure of any portion of any crystallized molecule or molecular complex that is sufficiently homologous to any portion of the α1-I domain and/or the hAQC2 Fab fragment (according to FIG. 19) can be solved by this method.

X. Computer and Storage Medium

To use the structure coordinates of this invention, e.g., those set forth in FIG. 19, it is usually necessary to convert the coordinates into a three-dimensional representation or shape. Commercially available graphical software programs including, but not limited to, O (Jones et al., 1991, *Acta Cryst. A*47:110-119) and INSIGHTII (© Accelrys, Inc. and Molecular Simulations, Inc., San Diego, Calif.) are capable of generating three-dimensional representations of molecules or molecular complexes, or portions thereof, from a set of structure coordinates.

In accordance with the present invention, the structure coordinates of the molecular entities of this invention are stored in a storage medium readable by machine (e.g., a computer). Using a computer and appropriate software, such data may be used for a variety of purposes, such as drug discovery and X-ray crystallographic analysis of other protein crystals.

Accordingly, a machine-readable data storage medium may include a data storage material encoded with machine-readable data including at least a portion of the structure coordinates set forth in FIG. 19. The computer may further include instructions to produce three-dimensional representations of the molecular complexes of α1-I domain and the hAQC2 Fab fragment by processing the machine-readable data of this invention. The computer of this invention may also include a display, a graphical interface for displaying, or an input device for moving and manipulating the three-dimensional graphical representation of the structure coordinates.

This invention also provides a computer for determining at least a portion of the structure coordinates corresponding to X-ray diffraction data obtained from a molecular complex of α1β1 integrin and the Fab fragment of hAQC2 antibody, where the computer includes a machine-readable data storage medium including a data storage material encoded with machine-readable data, where the data includes at least a portion of the structure coordinates of the molecular complex of α1-I domain and the hAQC2 Fab fragment according to FIG. 19, or X-ray diffraction data obtained from the crystalline molecular complex. The computer further includes instructions for performing a Fourier transform of the machine readable coordinate data, and instructions for processing this machine readable diffraction data into structure coordinates. This computer may further include: a working memory for storing instructions for processing the machine-readable data; a central-processing unit coupled to the working memory and to the machine-readable data; and optionally a graphical interface or display coupled to the central-processing unit for displaying the three-dimensional graphical representation of the structure coordinates of the molecule or molecular complex.

This invention further provides a computer for producing a three-dimensional representation of: a molecule or a molecular complex defined by at least a portion or all of the structure coordinates of all the α1-I domain and the hAQC2 Fab fragment amino acids set forth in FIG. 19, or a homologue of the molecule or molecular complex, where the homologue has a root mean square deviation from the backbone atoms of the amino acids of between 0.00 Å than 1.50 Å, such as between 0.00 Å and 1.00 Å, (e.g., between 0.00 Å and 0.50 Å). Further in this invention the computer includes: a machine-readable data storage medium including a data storage material encoded with machine-readable data, where the data includes at least a portion or all of the structure coordinates of all of the α1-I domain and the Fab hAQC2 fragment amino acids set forth in FIG. 19.

A computer of this invention may also produce a three-dimensional representation of a molecule or molecular complex including a binding site. The binding site may be defined by structure coordinates of at least seven amino acids of: the hAQC2 Fab fragment selected from the group including light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19; or a homologue of the molecule or molecular complex, where the homologue includes a binding site that has a root mean square deviation from the backbone atoms of the at least one amino acid of the hAQC2 Fab fragment of between 0.00 Å and 1.10 Å, such as between 0.00 Å and 1.00 Å, (e.g., between 0.00 Å and 0.50 Å). Further, the computer of this invention includes: a machine-readable data storage medium including a data storage material encoded with machine-readable data, where the data includes the structure coordinates of at least seven amino acids of the hAQC2 Fab fragment selected from the group consisting of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19.

This invention also provides a computer for producing a three-dimensional representation of: a molecule or molecular complex including a binding site defined by structure coordinates I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19; or a homologue of the molecule or molecular complex, where the homologue includes a binding site that has a root mean square deviation from the backbone atoms of the I domain amino acids between 0.00 Å and 0.92 Å. Further in this invention, the computer includes: a machine-readable data storage medium including a data storage material encoded with machine-readable data, where the data includes the structure coordinates of I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19.

This invention also provides a computer for producing a three-dimensional representation of a molecule or molecular complex including a binding site defined by structure coordinates of I domain amino acids selected from the group consisting of residues Glu192, Gln218, Arg219, Gly220, and Gly221 (crystal numbering), according to FIG. 19; or a homologue of the molecule or molecular complex, where the homologue includes a binding site that has a root mean square deviation from the backbone atoms of I domain amino acids between 0.00 Å and 0.30 Å. Further in this invention the computer includes: a machine-readable data storage medium including a data storage material encoded with machine-readable data, where the data includes the structure coordinates I domain amino acids selected from the group consisting of residues Glu192, Gln218, Arg219, Gly220, and Gly221 (crystal numbering), according to FIG. 19.

Figure 21:
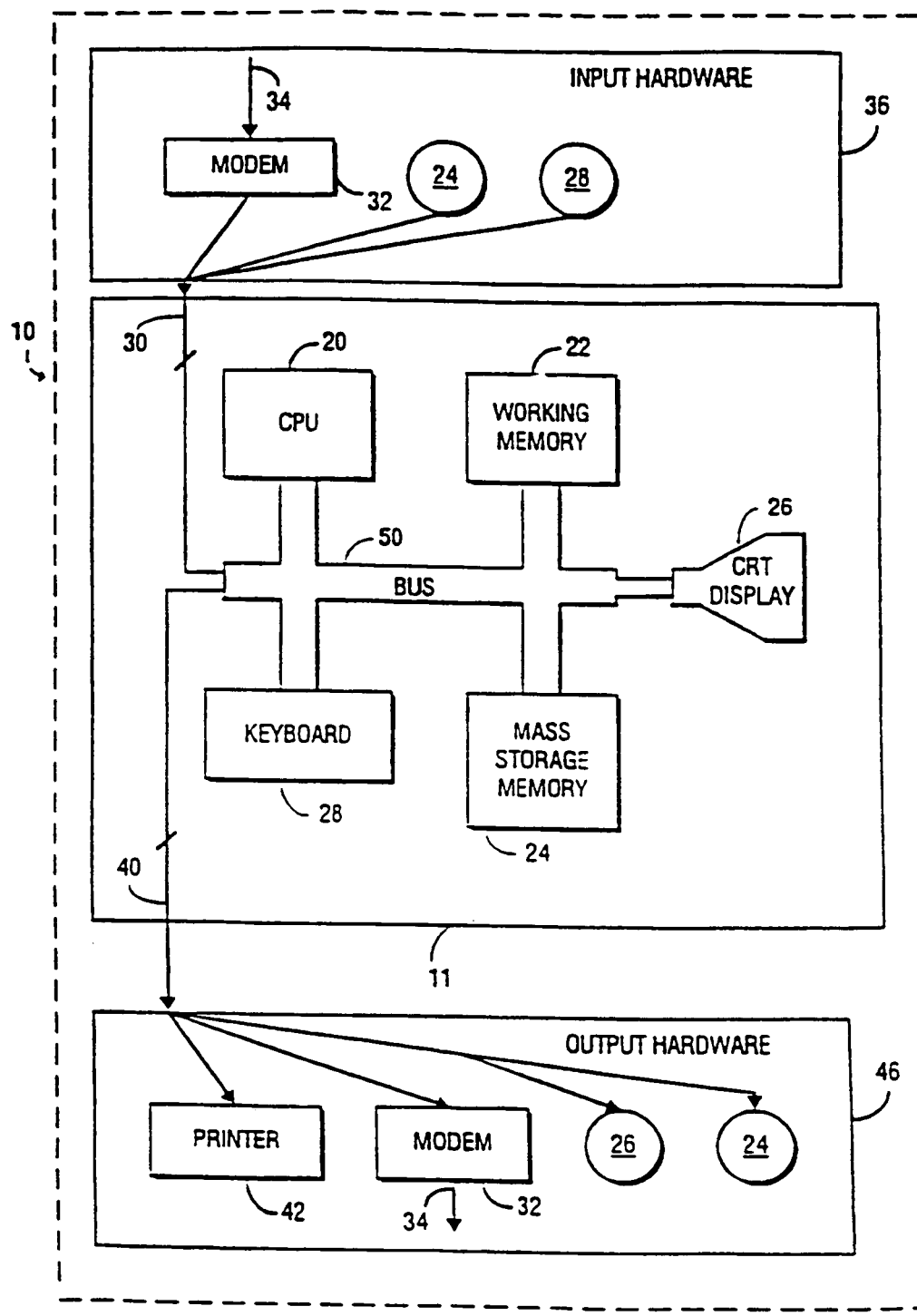
FIG. 21. A diagram of a system used to carry out the instructions encoded by the storage medium of FIGS. 22 and 23.

FIG. 21 demonstrates one such embodiment. System 10 includes a computer 11 including a central-processing unit ("CPU") 20, a working memory 22 which may be, e.g., RAM (random-access memory) or "core" memory, mass storage memory 24 (such as one or more disk or tape drives or CD-ROM or DVD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may include CD-ROM or DVD-ROM drives or tape or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding site of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

Figure 22:
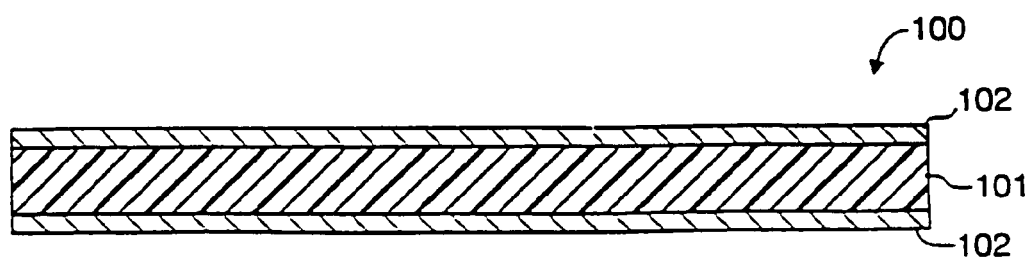
FIG. 22. A cross section of a magnetic storage medium.

FIG. 22 shows a cross-section of a magnetic data storage medium 100 which can be encoded with machine-readable data that can be carried out by a system such as system 10 of FIG. 21. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 10 of FIG. 21.

Figure 23:
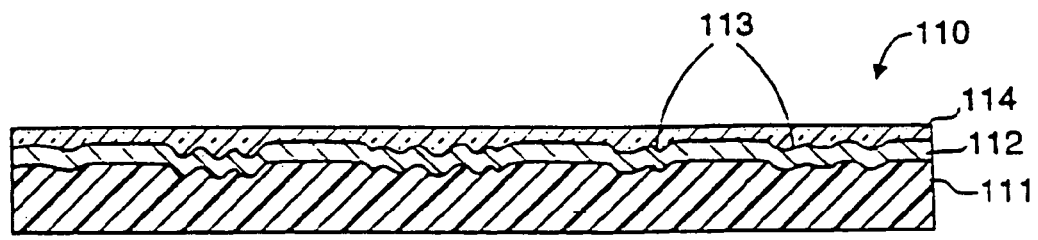
FIG. 23. A cross section of an optically-readable data storage medium.

FIG. 23 shows a cross-section of an optically-readable data storage medium 110 which also can be encoded with such machine-readable data, or a set of instructions, which can be carried out by a system such as system 10 of FIG. 21. Medium 110 can be a conventional compact disk or DVD disk read only memory (CD-ROM or DVD-ROM) or a rewritable medium, such as a magneto-optical disk which is optically readable and magneto-optically writable. Medium 100 has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

XI. Rational Drug Design

The present invention permits the use of structure-based and rational drug design techniques to design, select, and synthesize or isolate chemical entities, such as inhibitors of the α1-I domain and to improve known inhibitors of this domain. These inhibitors may be capable of blocking the collagen-binding site of VLA-1. This invention also permits the use of structure-based and rational drug design techniques to design variants that may act as inhibitors of collagen binding.

The three-dimensional representation of this invention can be used experimentally or computationally to design potential inhibitors, other chemical entities, variants of the Fab fragment or combinations of chemical entities that may bind to and effect the biological functions of the hAQC2 Fab fragment or the chimeric α1-I domain of the current invention.

One skilled in the art can use one of several methods to screen chemical entities for their ability to associate with the complex of the hAQC2 Fab fragment or the chimeric α1-I domain of the current invention and more particularly with a binding site of either the I domain or the Fab fragment. This process may begin by visual inspection of, for example, the binding site for either the I domain or the Fab fragment on the computer screen, based on the coordinates of the complex in FIG. 19. Selected chemical entities may then be positioned in a variety of orientations, or docked, within an individual binding site of either the I domain or the Fab fragment. Docking may be accomplished using software such as QUANTA, followed by energy minimization and molecular dynamics with standard molecular mechanics forcefields, such as CHARMM (Molecular Simulations, Inc., Burlington, Mass. © 1994) and AMBER (P. A. Kollman, University of California at San Francisco, © 1994).

Specialized computer programs may also assist in the process of selecting chemical entities. These include, inter alia:

1. GRID (Goodford, P. J., 1985, *J. Med. Chem.* 28:849-857). GRID is available from Oxford University, Oxford, UK.
2. MCSS (Miranker, A. and M. Karplus, 1991, *Proteins: Structure, Function and Genetics* 11:29-34). MCSS is available from Molecular Simulations, Burlington, Mass.
3. AUTODOCK (Goodsell, D. S. and A. J. Olsen, 1990, *Proteins: Structure, Function, and Genetics* 8:195-202). AUTODOCK is available from Scripps Research Institute, La Jolla, Calif.
4. DOCK (Kuntz, I. D. et al., 1982, *J. Mol. Biol.* 161:269-288). DOCK is available from University of California, San Francisco, Calif.

Once suitable chemical entities have been selected, they can be assembled into a single compound. Assembly may proceed by visual inspection of the relationship of the entities to each other on the three-dimensional image displayed on a computer screen in relation to the structure coordinates of the complex of hAQC2 Fab fragment and the chimeric α1-I domain. This is followed by manual model building using software such as Quanta or Sybyl.

The above-described evaluation process for chemical entities may be performed in a similar fashion for compounds or for variants that may bind the α1-I domain.

Useful programs to aid one of skill in the art in connecting the individual chemical entities include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., 1989, Royal Chem. Soc., 78:182-196). CAVEAT is available from the University of California, Berkeley, Calif.
2. 3D Database systems such as MACCS-3D (MDL Information Systems, San Leandro, Calif.). This area is reviewed in Martin, Y. C., 1992, *J. Med. Chem.* 35:2145-2154.
3. HOOK (available from Molecular Simulations, Burlington, Mass.).

Instead of proceeding to build an inhibitor or binding compound in a step-wise fashion one chemical entity at a time, as described above, binding compounds may be designed as a whole or "de novo" using either an empty binding site (such as a binding site of the α1-I domain or the hAQC2 Fab fragment) or optionally including some portion(s) of a known α1-I domain or the hAQC2 Fab fragment binding compound. These methods include:

1. LUDI (Bohm, H.-J., 1992, *J. Comp. Aid. Molec. Design* 6:61-78). LUDI is available from Biosym Technologies, San Diego, Calif.
2. LEGEND (Nishibata, Y. and A. Itai, 1991, *Tetrahedron* 47:8985). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., 1990, *J Med. Chem.* 33:883-894. See also Navia, M. A. and M. A. Murcko, 1992, *Curr. Opin. Struct. Biol.* 2:202-210.

Once an entity has been designed or selected by the above methods, the efficiency with which that entity may bind to the α1-I domain or the hAQC2 Fab fragment can be tested and optimized by computational evaluation. For example, a compound that has been designed or selected to function as a α1-I domain binding compound can traverse a volume not overlapping that occupied by the binding site when it is bound to the chimeric α1-I domain. An effective α1-I domain binding compound can demonstrate a relatively small difference in energy between its bound and free states (i.e., a small deformation energy of binding). Thus, the most efficient α1-I domain binding compound should be designed with a deformation energy of binding of not greater than about 10 kcal/mole, e.g., not greater than 7 kcal/mole. α1-I domain binding compounds may interact with the α1-I domain in more than one conformation that is similar in overall binding energy. In those cases, the deformation energy of binding is taken to be the difference between the energy of the free compound and the average energy of the conformations observed when the compound binds to the protein.

A compound designed or selected as binding to α1-I domain may be further computationally optimized so that in its bound state it would lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the compound and the protein when the compound is bound to α1-I domain, should make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa. © 1992); AMBER, version 4.0 (P. A. Kollman; University of California at San Francisco, © 1994); QUANTA/CHARMM (Molecular Simulations, Inc., Burlington, Mass. © 1994); and Insight II/Discover (Biosysm Technologies Inc., San Diego, Calif. © 1994). These programs may be implemented, for instance, using a Silicon Graphics workstation. Other hardware systems and software packages will be known to those skilled in the art.

One other useful drug design technique enabled by this invention is iterative drug design. Iterative drug design is a method for optimizing associations between a protein and a compound (that compound includes an antibody) by determining and evaluating the three-dimensional structures of successive sets of protein/compound complexes. In iterative drug design, a series of crystals of a protein complexed with entities that bind the protein are obtained and then the three-dimensional structure of each molecular complex is solved. Such an approach provides insight into the associations between the proteins and other entities of each complex. This is accomplished by selecting chemical entities with inhibitory activity, obtaining crystals of these new complexes, solving the three-dimensional structure of the complexes, and comparing the associations between the new complexes and the previously solved complex. Associations within a complex can be optimized by observing how changes in the components of the complex affect associations.

In some cases, iterative drug design is carried out by forming successive complexes and then crystallizing each new complex. Alternatively, a pre-formed protein crystal is soaked in the presence of another chemical entity, thereby forming a complex and obviating the need to crystallize each individual complex.

XII. Pharmaceutical Compositions

The pharmaceutical compositions of this invention contains one or more VLA-1 antagonists of the present invention (e.g., anti-VLA-1 antibodies and the small molecular VLA-1 antagonists identified by the above-described rational drug design methods), or pharmaceutically acceptable derivatives thereof. The compositions may further contain a pharmaceutically acceptable carrier, such as an adjuvant, a vehicle, a buffer, and a stabilizer.

The pharmaceutical compositions of this invention may be given orally, topically, intravenously, subcutaneously, intraperitoneally, intramuscularly, intramedullarily, intraarterially, intra-articularly, intra-synovially, intrasternally, intrathecally, intrahepatically, intraspinally, intracranially as desired, or just locally at sites of inflammation or tumor growth. The pharmaceutical compositions of this invention may also be administered by inhalation through the use of, e.g., a nebulizer, a dry powder inhaler or a metered dose inhaler, or by implantation of an infusion pump or a biocompatible sustained release implant into the subject.

The pharmaceutical compositions may be in the form of a sterile injectable preparation, for example a sterile injectable aqueous or oleaginous suspension. This suspension may be formulated according to techniques known in the art using suitable dispersing, wetting, and suspending agents. If given orally, the pharmaceutical compositions can be administered in form of capsules, tablets, aqueous suspensions or solutions. For topical applications, the pharmaceutical compositions may be formulated in a suitable ointment.

The dosage and dose rate of the VLA-1 antagonists of this invention effective to produce the desired effects will depend on a variety of factors, such as the nature of the disease to be treated, the size of the subject, the goal of the treatment, the specific pharmaceutical composition used, and the judgment of the treating physician. Dosage levels of between about 0.001 and about 100 mg/kg body weight per day, for example between about 0.1 and about 50 mg/kg body weight per day, of the active ingredient compound are useful. For instance, an antibody of the invention will be administered at a dose ranging between about 0.01 mg/kg body weight/day and about 20 mg/kg body weight/day, e.g., ranging between about 0.1 mg/kg body weight/day and about 10 mg/kg body weight/day, and at intervals of every one to fourteen days. In another embodiment, the antibody is administered at a dose of about 0.3 to 1 mg/kg body weight when administered intraperitoneally. In yet another embodiment, the antibody is administered at a dose of about 5 to 12.5 mg/kg body weight when administered intravenously. In one embodiment, an antibody composition is administered in an amount effective to provide a plasma level of antibody of at least 1 mg/ml.

XIII. Diseased Conditions And Animal Models

The VLA-1 antagonists of the invention are useful in the treatment, including prevention, of $\alpha_1\beta_1$-mediated diseases such as those enumerated above. The treatments of this invention are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

The efficacy of the VLA-1 antagonists of the invention can be tested in various animal models. For instance, useful psoriasis and arthritis models include those described in WO 00/72881. Kidney fibrosis models include those described in WO 99/61040, the Alport's syndrome kidney model described in Cosgrove et al., 2000, Am. J. Path. 157:1649-1659, and the SNF1 mouse model of lupus nephritis described in Kalled et al., 2001, Lupus 10:9-22. Vascular fibrosis models for restenosis include a rat carotid balloon injury model described in Smith et al., 1999, Circ. Res. 84:1212-1222. Lung fibrosis models for idiopathic pulmonary fibrosis and scleroderma-associated pulmonary fibrosis include a bleomycin-induced pulmonary fibrosis model described in Wang et al., 1999, Thorax 54:805-812. Liver cirrhosis models for hepatitis C- or alcohol-induced cirrhosis include the bile duct ligation model described in George et al., 1999, Proc. Natl. Acad. Sci. USA 96:12719-12724 and the CCL4-induced liver fibrosis model described in Shi et al., 1997, Proc. Natl. Acad. Sci. USA 94:10663-10668.

The efficacy of the treatments of this invention may be measured by a number of available diagnostic tools, including physical examination, blood tests, proteinuria measurements, creatinine levels and creatinine clearance, pulmonary function tests, chest X-rays, bronchoscopy, bronchoalveolar lavage, lung biopsy, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

XIV. Diagnostic Methods

The antibodies of this invention can be used to diagnose diseased conditions associated with altered $\alpha_1\beta_1$ expression levels. A tissue sample from a subject, such as a tissue biopsy, body fluid sample or lavage (e.g., alveolar lavage), can be tested in an antigen capture assay, ELISA, immunohistochemistry assay, and the like using the antibodies. A tissue sample from a normal individual is used as control.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, *Molecular Cloning: A Laboratory Manual*, 2nd edition (Sambrook et al., Eds.), 1989; *Oligonucleotide Synthesis*, (M. J. Gait, Ed.), 1984; U.S. Pat. No. 4,683,195 to Mullis et al.; *Nucleic Acid Hybridization*, (B. D. Hames and S. J. Higgins), 1984; *Transcription and Translation*, (B. D. Hames and S. J. Higgins), 1984; *Culture of Animal Cells* (R. I. Freshney, Ed.), 1987; *Immobilized Cells and Enzymes*, IRL Press, 1986; *A Practical Guide to Molecular Cloning* (B. Perbal), 1984; *Methods in Enzymology*, Volumes 154 and 155 (Wu et al., Eds.), Academic Press, New York; *Gene Transfer Vectors for Mammalian Cells* (J. H. Miller and M. P. Calos, Eds.), 1987; *Immunochemical Methods in Cell and Molecular Biology* (Mayer and Walker, Eds.), 1987; *Handbook of Experiment Immunology*, Volumes I-IV (D. M. Weir and C. C. Blackwell, Eds.), 1986; *Manipulating the Mouse Embryo*, 1986.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

The following Examples are provided to illustrate the present invention, and should not be construed as limiting thereof.

EXAMPLES

Chemical Reagents

Fluorescein isothiocyanate (FITC) was purchased from Sigma Chemical Co. (St. Louis, Mo.). Croton oil was purchased from ICN Biochemicals (Aurora, Ohio). Whole sheep blood in Alsevers solution was obtained from East Acres Biologicals (Southbridge, Mass.). Type I rat tail collagen and type IV mouse collagen were purchased from Collaborative Research Inc. (Bedford, Mass.) and Gibco (Gaithersburg, Md.), respectively.

Balb/c female mice of 6-8 weeks of age were purchased from Taconic (Germantown, N.Y.) and the $\alpha1\beta1$ integrin-deficient mice on a Balb/c background were as previously described (3).

Example 1

Monoclonal Antibodies. Function-blocking mAbs to murine antigens were prepared in an azide-free and low endotoxin format: Ha31/8 (hamster anti-CD49a; integrin $\alpha1$) (Mendrick et al. 1995. *Lab. Invest.* 72:367-375), Ha1/29 (hamster anti-CD49b; integrin $\alpha2)(\beta1$) (Mendrick et al. 1995. *Lab. Invest.* 72:367-375; Mendrick, D. L. and D. M. Kelly 1993 *Lab. Invest.* 69:690-702), hamster group II control mAb Ha4/8 (hamster anti-KLH)(Mendrick, D. L. and D. M. Kelly 1993 *Lab. Invest.* 69:690-702), and PS/2 (rat anti-CD49d; integrin $\alpha4\beta$chain) (Miyake et al. 1991 *J.*

*Exp. Med.* 173:599-607). In addition, the following function-blocking mAbs to murine antigens were purchased as no-azide/low endotoxin preparations from Pharmingen (San Diego, Calif.): HM$\beta$1-1 (hamster anti-CD29; integrin $\beta1$ chain) (Noto et al. 1995 *Int. Immunol.* 7:835-842), Ha2/5 (hamster anti-CD29; integrin $\beta1$ chain)(Mendrick, D. L. and D. M. Kelly 1993 *Lab. Invest.* 69:690-702), 3E2 (hamster anti-CD54, ICAM-1)(Scheynius et al. 1993 *J. Immunol.* 150:655-663), 5H10-27 (rat anti-CD49e; integrin $\alpha5$)(Kinashi, T., and T. A. Springer. 1994. *Blood Cells.* 20:25-44), GoH3 (rat anti-CD49f; integrin $\alpha6$)(Sonnenberg et al. 1987 *J Biol. Chem.* 262:10376-10383), and the rat isotype control mAbs R35-95 (rat IgG2a) and R35-38 (rat IgG2b).

Adhesion Assay. Splenocytes from Balb/c mice were cultured with 20 ng/ml IL-2 for 7-12 d. Adhesion of cells to type I and type IV collagen was as previously described (Gotwals et al. 1996 *J. Clin. Invest.* 97:2469-2477). Briefly, 96-well Maxisorp plates (Nunc, Napierville, Ill.) were coated with either 10 µg/ml type IV or 5 µg/ml type I collagen and non-specific sites blocked with 1% BSA. IL-2 activated splenocytes were labeled with 2 µM BCECF [2',7'-bis(carboxyethyl)-5(6) carboxyl fluorescein penta acetoxymethylester](Molecular Probes, Eugene, Oreg.) and incubated with 10 µg/ml of indicated mAbs for 15 min. $10^5$ cells in 0.25% BSA in RPMI were then added to coated wells and incubated for 60 min at 37° C. Unbound cells were removed by washing three times with 0.25% BSA in RPMI. Adhesion was quantified using a CytoFluor 2350 fluorescent plate reader (Millipore, Bedford, Mass.). The ratio of bound cells to input cells was measured and percent adhesion relative to control mAb-treated cells (normalized to 100%) calculated. Background values due to cell adhesion on wells coated with BSA alone were subtracted.

Figure 1B:
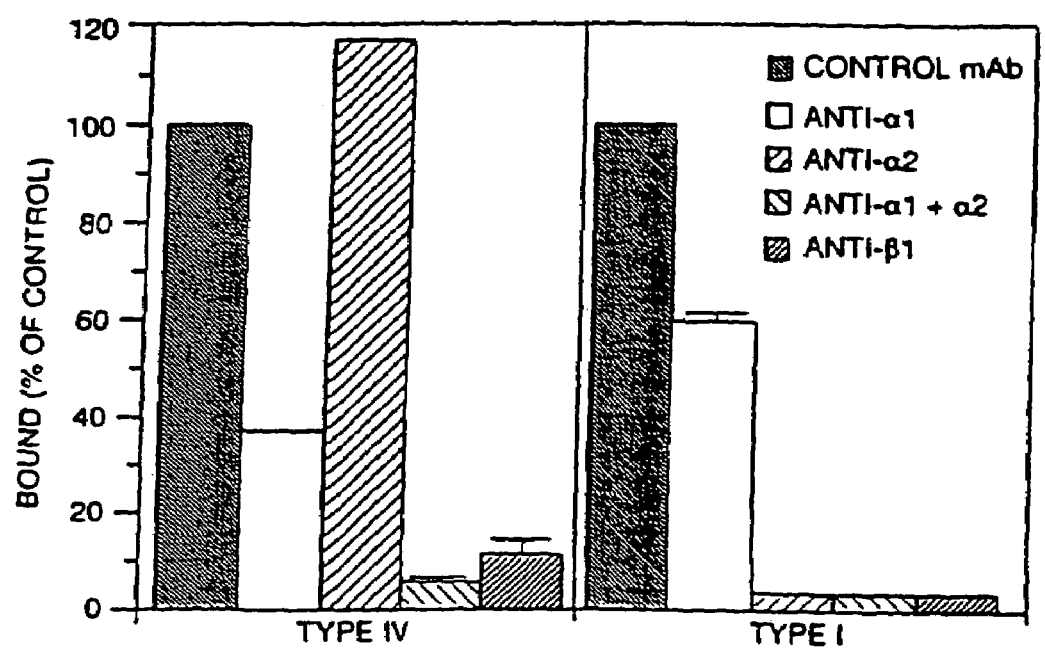

Expression and functional blockade of $\alpha1\beta1$ and $\alpha2\beta1$ on activated leukocytes. Given the key role leukocytes play in inflammation, we decided to test whether anti-$\alpha1$ and anti-$\alpha2$ mAbs were capable of blocking leukocyte adhesion to collagens. In order to obtain leukocytes expressing high levels of both $\alpha1$ and $\alpha2$, murine T cells were stimulated in vitro with IL-2 for 7-12 d. These cells expressed high levels of both $\alpha1$ and $\alpha2$ (FIG. 1A), and bound well to both collagen type IV and type I-coated surfaces (FIG. 1B). Adhesion to type IV collagen was partially inhibited by anti-$\alpha1$ mAb alone and was not inhibited by anti-$\alpha2$ mAb alone. In contrast, adhesion to type I collagen was completely inhibited by anti-$\alpha2$ mAb and anti-$\alpha1$ mAb alone showed only partial inhibition. Both anti-$\beta1$ mAb and the combination of anti-$\alpha1$ and anti-$\alpha2$ mAbs completely inhibited adhesion to types I and IV collagen. Having demonstrated that the $\alpha1\beta1$ and $\alpha2\beta1$ integrins are expressed on activated T cells and that anti-$\alpha1$ and $\alpha2$ mAbs are able to functionally block leukocyte adhesion to collagens, we used these mAbs to investigate the in vivo role of these integrins in animal models of inflammatory disorders.

Example 2

Inhibition of DTH responses by anti-integrin mAbs. SRBC-induced delayed type hypersensitivity (DTH) responses were adapted from a previously published protocol (Hurtrel et al., 1992, *Cell. Immunol.* 142:252-263). Briefly, mice were immunized s.c. in the back with $2\times10^7$ SRBC in 100 ul PBS on d 0. The mice were challenged on d 5 by injecting $1\times10^8$ SRBC in 25 ul PBS s.c into the right hind footpad. Footpad thickness was measured with an engineer's caliper (Mitutoyo/MTI, Paramus, N.J.) 20 h after antigen challenge, and the degree of footpad swelling calculated. Results are reported as the mean percent increase footpad thickness ±SEM and calculated as % increase=[1−(Right footpad thickness 20 h after antigen challenge/Uninjected left footpad thickness 20 h after antigen challenge)]×100. To block the effector phase of the SRBC-induced DTH response, therapeutic or control mAb (100 ug), which were prepared according to the methods described in Example 1, was given i.p. 1 h prior to antigen challenge on d 5.

Figure 2:
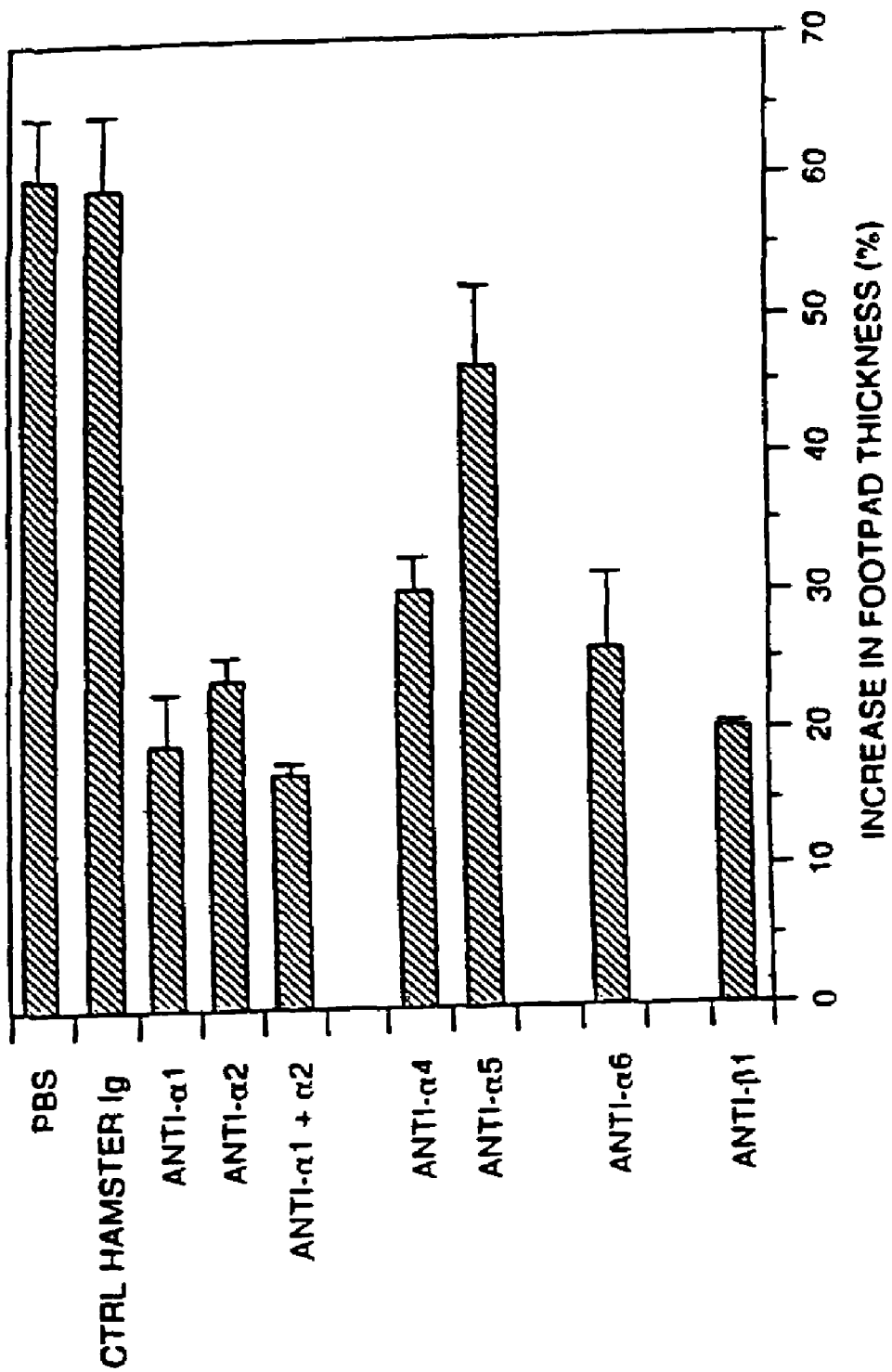
FIG. 2. Effect of anti-integrin mAbs on the effector phase of delayed-type hypersensitivity. SRBC-sensitized mice were injected i.p. with the indicated mAbs 1 h prior to SRBC challenge. Footpad thickness was measured 20 h after antigen challenge, and results shown as % increase in footpad thickness ±SEM as illustrated in Example 2. These data represent a summary of eight experiments with n=79 (PBS), 68 (control hamster Ig), 68 (anti-α1), 29 (anti-α2), 18 (anti-α1+anti-α2), 45 (anti-α4), 18 (anti-α5), 20 (anti-α6), and 10 (anti-β1). The mAbs used were: Ha4/8 (control hamster Ig group 2), Ha31/8 (anti-α1), Ha1/29 (anti-α2), PS/2 (anti-α4), 5H10-27 (anti-α5), GoH3 (anti-α6), and HMβ1-1 (anti-β1).

SRBC-induced DTH is a well characterized in vivo model of inflammation, and in particular psoriasis, that has been used to demonstrate the importance of a variety of cytokines and adhesion molecules in inflammation (Tedder et al., 1995, *J. Exp. Med.* 181:2259-2264, Terashita et al., 1996, *J. Immunol.* 156:4638-4643). SRBC-sensitized mice received anti-integrin mAbs 1 h prior to footpad antigen challenge and inflammation was assessed 20 h later as measured by increased footpad thickness. PBS and control hamster Ig-treated mice showed a 60-70% increase in footpad thickness 20 h after antigen challenge (FIG. 2). Compared to control hamster Ig treatment, anti-α1 or anti-α2 mAbs resulted in a 68% and 60% inhibition in footpad thickness, respectively. The combination of anti-α1 and α2 mAbs resulted in 71% inhibition, demonstrating little additive effect over anti-α1 or anti-α2 mAbs alone. Treatment with other anti-integrin mAbs was also effective at inhibiting DTH effector response. The degree of inhibition seen with the various mAb treatments was 49% (anti-α4), 23% (anti-α5), and 57% (anti-α6). Lastly, mAb blockade of the common β1 integrin subunit (mAb HMBI-1) inhibited the effector DTH response by 67%.

Example 3

Inhibition of CHS effector responses by anti-integrin mAbs. Contact hypersensitivity (CHS) to FITC was assayed as previously described (Gaspari et al., 1991, In Current Protocols in Immunology. J. E. Coligan, A. M. Kruisbeek, D. H. Margulies, E. M. Shevach, and W. Strober, editors. John Wiley & Sons, New York. Section 4.2:1). Briefly, mice were sensitized by painting 100 ul 0.5% FITC in 1:1 acetone/dibutylphthalate onto the shaved back on d 0. 10 d later, animals were challenged by applying 5 ul 0.5% FITC onto both sides of each ear. Ear swelling response was determined by ear thickness measured with an engineer's caliper (Mitutoyo/MTI, Paramus, N.J.) at the time of antigen challenge (d 10) and 24 h later, and the results reported as mean percent increase in baseline ear thickness ±SEM. Increase in ear thickness was calculated as % increase=[1−(Ear thickness 24 h after antigen challenge/Ear thickness at the time of antigen challenge)]×100. To block the effector phase of the CHS response, therapeutic or control mAb (250 ug) was given i.p. 4 h prior to antigen challenge on d 10. Mice that were antigen-sensitized and ear challenged with vehicle only (vehicle control) or mice that were ear challenged without prior sensitization (irritant control) served as negative controls (never exceeded 2% increase in ear thickness).

Figure 3:
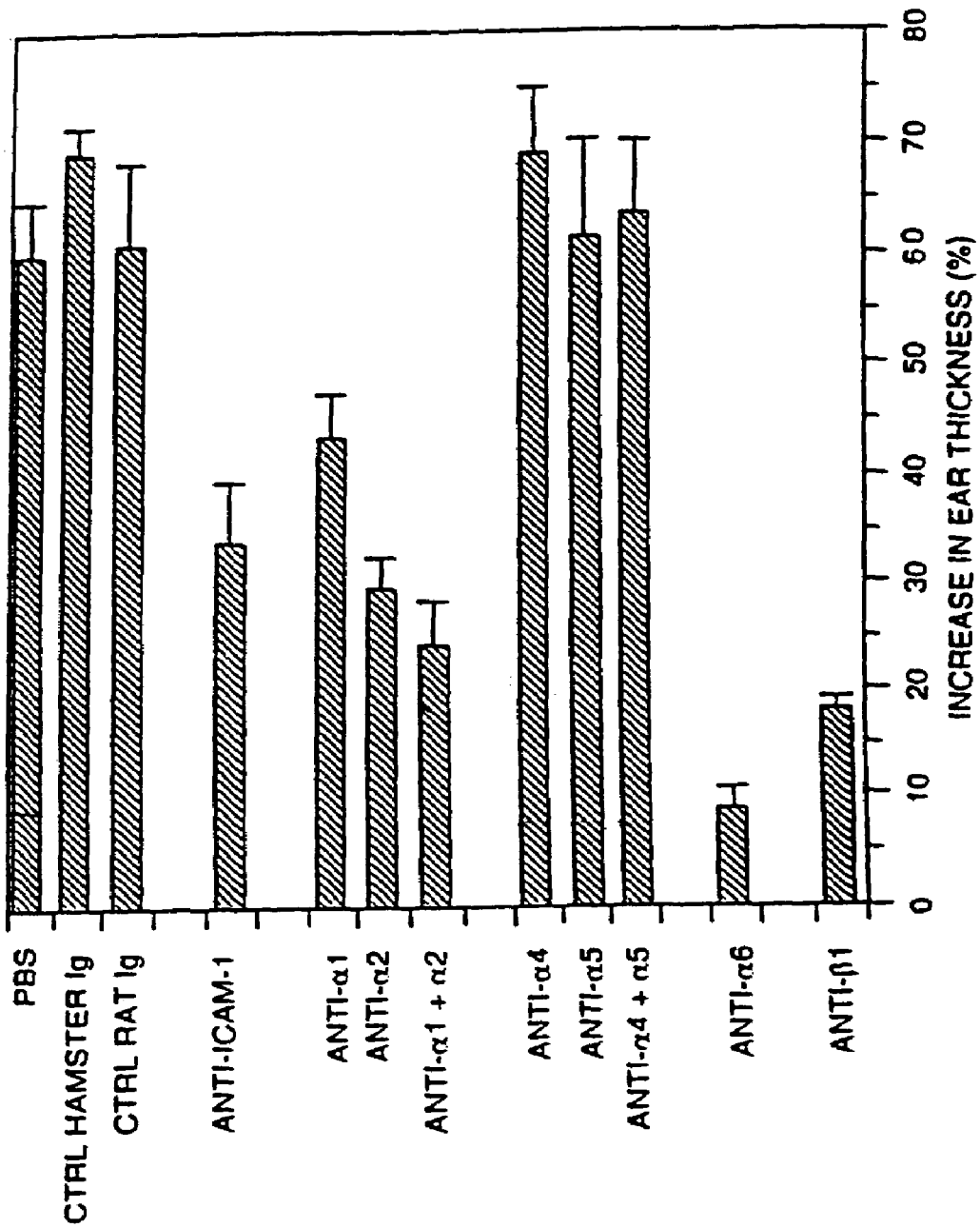
FIG. 3. Effect of anti-integrin mAbs on the effector phase of contact hypersensitivity. FITC-sensitized mice were injected i.p. with the indicated mAbs 4 h prior to FITC challenge. Ear thickness was measured at baseline and 24 h later, and results shown as % increase in ear thickness ±SEM as illustrated in Example 3. These data represent a summary of nine experiments with n=74 (PBS), 60 (control hamster Ig), 26 (anti-ICAM-1), 44 (anti-α1), 44 (anti-α2), 38 (anti-α1+anti-α2), 36 (anti-α4), 16 (anti-α5), 26 (anti-α4+anti-α5), 24 (anti-α6), and 22 (anti-β1). The hamster mAbs used were: Ha4/8 (control hamster Ig group 2), Ha31/8 (anti-α1), Ha1/29 (anti-α2), HMβ1-1 (anti-β1), 3E2 (anti-ICAM-1); the rat mAbs used were: R35-95 and R35-38 (control rat IgG2a and rat IgG2b, respectively), PS/2 (anti-α4), 5H10-27 (anti-α5), GoH3 (anti-α6).

Given that CHS is mechanistically distinct from DTH and involves different effector cells, we investigated what effect anti-integrin mAbs had on the effector phase of the CHS response. Mice were hapten-sensitized using FITC applied to their shaved backs, followed 10 d later with FITC challenge to the ear resulting in an inflammatory response the next day. FITC-sensitized mice demonstrated a 60-70% increase in thickness 24 h after antigen challenge (FIG. 3). Consistent with published results (Scheynius et al., *J. Immunol.* 150:655-663), anti-ICAM-1 mAb treatment resulted in 51% inhibition of ear swelling. Compared to control hamster mAb, treatment of mice with anti-α1 or anti-α2 mAb 4 h prior to antigen challenge resulted in 37% and 57% inhibition in ear swelling, respectively (FIG. 3). The combination of anti-α1 and anti-α2 mAbs resulted in slightly greater inhibition of ear swelling (65%). Treatment with other mAbs to β1 integrins revealed that while anti-α4 and anti-α5 mAbs resulted in no inhibition of FITC-induced CHS effector response when compared to control rat mAb, treatment with anti-α6 mAb resulted in an 86% inhibition of effector responses. Lastly, mAb blockade of the common β1 integrin subunit inhibited CHS effector responses by 74%. Similar CHS results were obtained using different strains of mice (C57/BL6, 129/Sv) and a different sensitizing agent (oxazolone) (data not shown). Similar to the results seen in the SRBC-induced DTH model, histologic analysis of inflamed ears revealed that both edema formation and leukocytic infiltration were inhibited by anti-α1 and anti-α2 mAb treatment.

Consistent with the finding that α1β1 and α2β1 can be expressed on EL-2-activated splenocytes, analysis of lymph nodes from antigen-sensitized mice (FITC or oxazolone) revealed α1β1 and α2β1 to be expressed exclusively on $CD44^{hi}$ $LFA-1^{hi}$ activated CD4+ and CD8+ T cells (data not shown). Treatment of mice with anti-α1 and anti-α2 mAbs did not result in deletion of these cells, as the numbers of activated T cells in both spleen and lymph nodes seen in response to antigen sensitization in the CHS model was unaffected. In addition, effector cells were hot functionally deleted as prolonged treatment of antigen-sensitized mice with anti-α1 and anti-α2 mAbs (d 10-16) did not affect the inflammatory response of mice challenged with antigen at d 20 (data not shown).

Example 4

Figure 4:
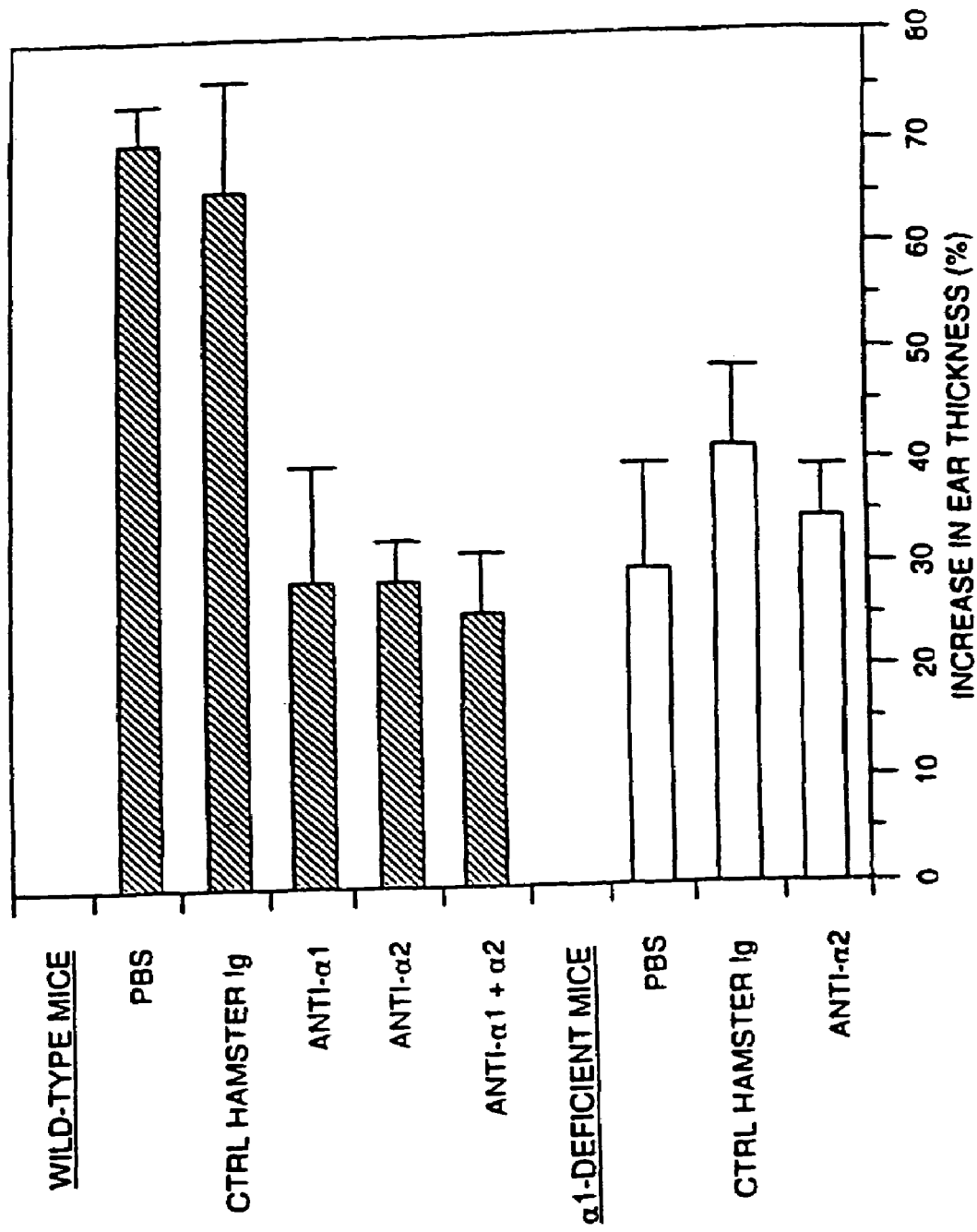
FIG. 4. Contact hypersensitivity responses in α1-deficient mice compared to wild-type mice. FITC-sensitized mice were injected i.p. with indicated mAbs 4 h prior to FITC challenge. Ear thickness was measured at baseline and 24 h later, and results shown as % increase in ear thickness ±SEM as illustrated in Example 4. Groups of four to five mice per condition were used, and all experiments were performed a minimum of three times. One representative experiment is shown.

CHS effector responses are decreased in α1β1-deficient mice. To exclude the possibility that the inhibitory role of α1β1 in the effector response of FITC-mediated CHS was mAb-mediated, experiments were carried out in wild-type and α1β1-integrin deficient mice (FIG. 4). MAb inhibition of the effector phase in wild-type mice was consistent with previous results, with 56% inhibition in ear thickness seen with anti-α1, 56% with anti-α2, and 62% with a combination of anti-α1 and anti-α2. The effector phase of CHS was significantly reduced in untreated α1β1-deficient mice as compared to untreated wild-type mice (30% vs 71% increase in ear thickness, respectively). As expected, the level of ear swelling in untreated α1β1-deficient mice was equivalent to the level of ear swelling seen in anti-α1 mAb-treated wild-type mice. Lastly, mAb blockade of α2β1 in the α1β1-deficient mice resulted in only slightly increased inhibition of ear swelling, consistent with the results seen in wild-type mice treated with a combination of anti-α1 and anti-α2 mAbs.

Example 5

To further exclude the possibility that the inhibitory effect of the anti-integrin mAbs seen in both the DTH and CHS models of inflammation is caused by a general anti-inflammatory effect mediated by the anti-α1 and anti-α2 mAbs, the effect of these mAbs on irritant dermatitis was studied.

To assess irritant dermatitis, mice were painted with 5 ul of 0.8% croton oil in acetone on both sides of each ear.

Therapeutic or control antibodies were given 4 h prior to the application of the irritant. Ear swelling was measured 24 h later as described above and compared to ear thickness prior to croton oil application. Results are reported as mean percent increase in baseline ear thickness ±SEM as described above. Mice painted with acetone only (vehicle control) served as a negative control.

Figure 5:
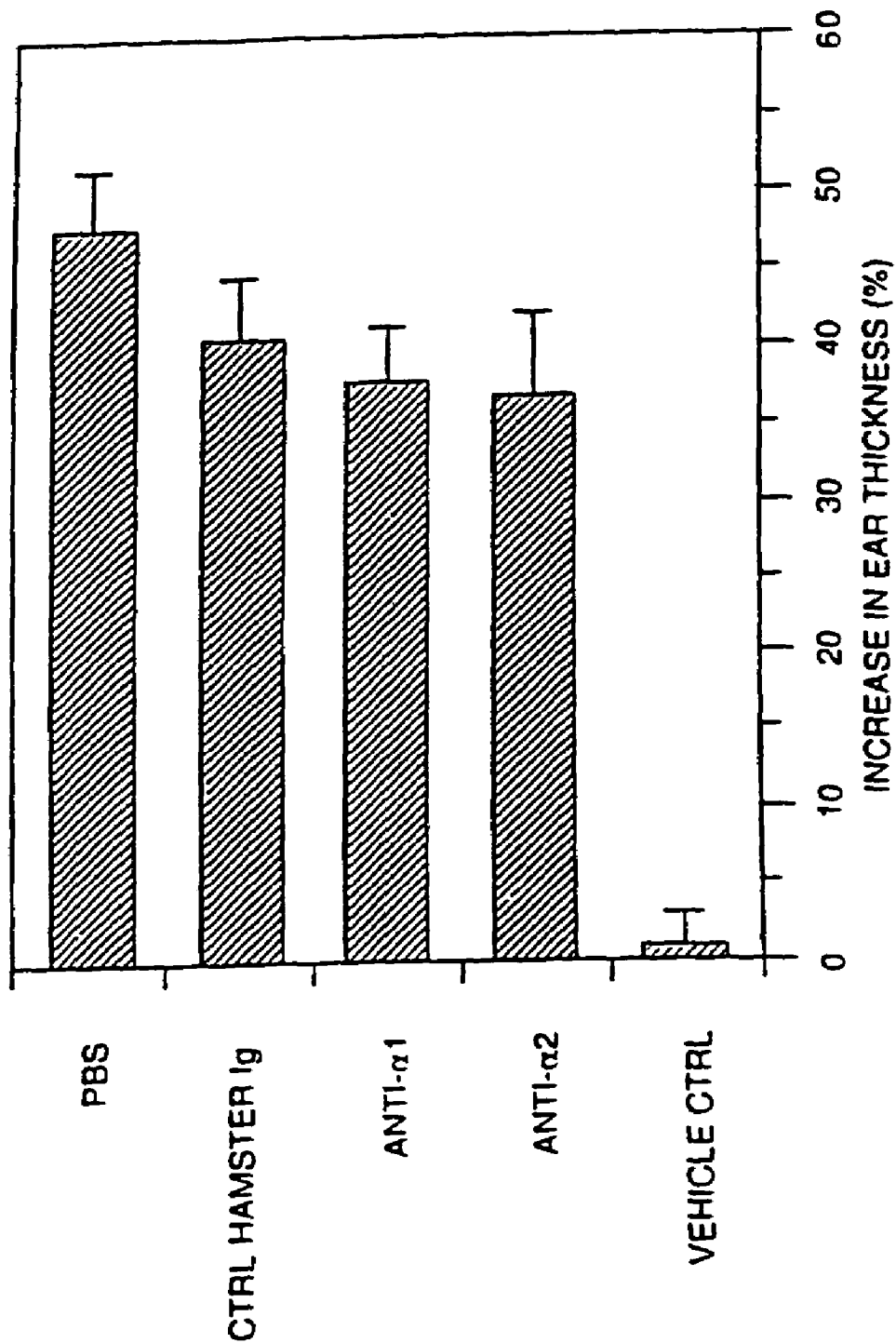
FIG. 5. Effect of anti-α1 and anti-α2 mAbs on croton oil-induced non-specific inflammation. Mice were injected i.p. with indicated mAbs 4 h prior to ear painting with croton oil. Ear thickness was measured at baseline and 24 h later, and results shown as % increase in ear thickness ±SEM as illustrated in Example 5. Groups of four to five mice per condition were used, and all experiments were performed a minimum of three times. One representative experiment is shown.

24 h later, ears of mice treated with croton oil showed a significant increase in ear thickness (48%), when compared to mice receiving vehicle only (acetone). Toxic ear swelling caused by croton oil was not significantly affected in mice pretreated with anti-α1 or anti-α2 mAbs when compared to either PBS or control mAb-treated animals (FIG. 5). Histologic examination of the croton oil-treated ears revealed no differences in numbers or types of infiltrating cells or edema formation in mice treated with anti-α1 or anti-α2 mAbs, as compared to control mAb-treated mice or PBS-treated mice (data not shown).

Example 6

Inhibition of arthritis by α1β1 and α2β1. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, *J. Immunol.* 148:2103-2108; Terato et al., 1995, *Autoimmunity* 22:137-147).

Arthrogen-CIA Antibody kits were purchased from Stratagene (La Jolla, Calif.) and arthritis induced using a well established protocol (Terato et al., 1992, *J. Immunol.* 148: 2103-2108; Terato et al., 1995, *Autoimmunity* 22:137-147). Briefly, arthritis was induced through i.p. injection of a cocktail of 4 anti-collagen type II mAbs (1 mg each) on d 0, followed by i.p. injection of 50 ug LPS on d 3. Over the course of the next 3-4 d, the mice developed swollen wrists, ankles and digits. Therapeutic or control mAb (250 ug) was administered i.p. 4 h prior to injection of the anti-collagen mAbs on d 0, and again 4 h prior to LPS administration on d 3, and then continuing every $3^{rd}$ day for the length of the experiment. Beginning on d 3, mice were evaluated for the development of arthritis. Severity of arthritis in each limb was scored using a four point system. 0=normal; 1=mild redness, slight swelling of ankle or wrist; 2=moderate swelling of ankle or wrist; 3=severe swelling including some digits, ankle, and foot; 4=maximally inflamed.

Figure 6:
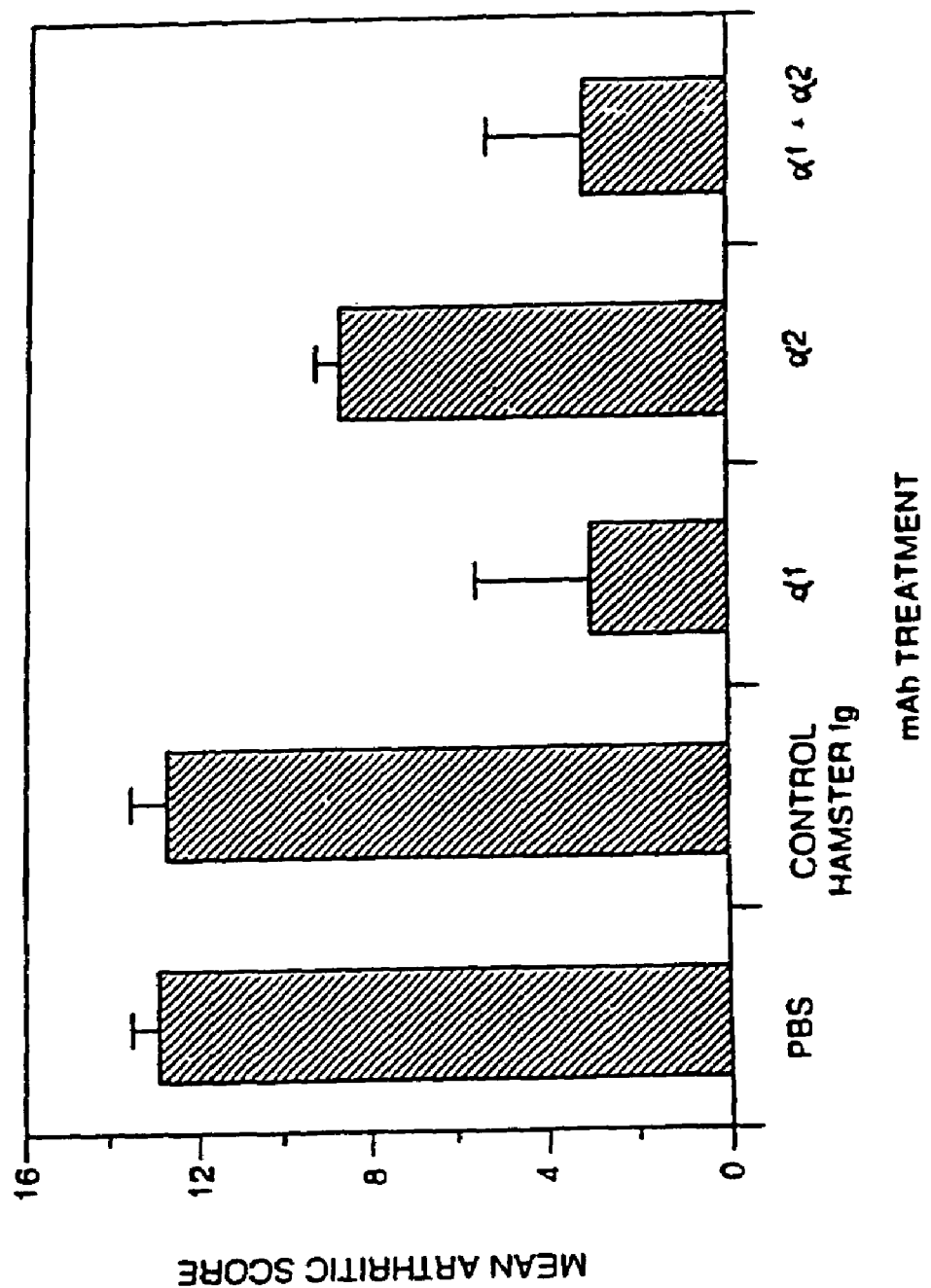
FIG. 6. Effect of anti-α1 and α2 mAbs in collagen mAb-induced arthritis. Mice were injected i.p. with anti-collagen mAbs at d 0, followed by LPS on day 3. Mice were injected i.p. with indicated mAbs-every $3^{rd}$ day starting on d 0. Clinical arthritis was apparent 2-3 d following LPS injection and continued for several weeks. Each limb was evaluated on a 0 to 4 scale every $3^{rd}$ day as illustrated in Example 6 and results are expressed as the mean arthritic score between d 9 and d 15 (±SEM) of all four limbs. These data represent a summary of four experiments with each experiment consisting of groups of three to four mice per condition.

Severe arthritis in Balb/c mice developed within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 6). In contrast, treatment with anti-α1 mAb alone resulted in a marked reduction (78%) in arthritis, lasting the duration of the experiment. Treatment with anti-α2 mAb alone also had a beneficial effect, resulting in a 32% decrease in the arthritic score as compared to control mAb-treated mice. The combination of anti-α1 and anti-α2 mAbs resulted in a similar degree of inhibition as seen with anti-α1 mAb alone.

Example 7

Histological analysis of effect of anti-α1 and anti-α2 mAb treatment on the inflammatory cellular infiltrate. Further histological analysis of the SRBC-induced DTH response confirmed the ability of anti-α1 and anti-α2 mAb treatment to modulate the elicited inflammatory response. An unchallenged footpad from an SRBC-sensitized mouse showed virtually no inflammatory cellular infiltrate when compared to an SRBC-challenged footpad from the same mouse. Treatment of SRBC-sensitized mice with anti-α1 and anti-α2 mAbs either alone or combined greatly reduced the number of these infiltrating cells found in SRBC-challenged footpads when compared to control mAb-treated mice. Closer examination of the infiltrating cells revealed most cells to be composed of neutrophils, with some monocytes and lymphocytes present, and confirmed that anti-α1 and anti-α2 mAb treatment greatly decreased the numbers of these cells.

Example 8

Immunohistochemical demonstration of α1-expressing cells in the inflammatory cellular infiltrate. Immunohistochemistry was performed to more precisely determine the nature of the infiltrating cells and whether they express collagen-binding integrins. Infiltrating cells from an inflamed footpad of an untreated mouse were examined for expression of α1β1 integrin and cell lineage markers. α1β1 integrin was found to be expressed on many infiltrating leukocytes. Dual immunohistochemistry was utilized to identify the nature of the infiltrating cells and the distribution of α1β1 expression. Using cell lineage markers, the infiltrate was found to be composed largely of granulocyte/monocytes (Mac-1+), with many of these cells being neutrophils (Gr1+), along with a smaller number of T lymphocytes (CD3+). Expression of α1 β1 integrin was found among all three subsets of cells, with α1 expressed on a subset of Mac-1+ granulocyte/monocytes, a subset of Gr1+ neutrophils, and on the majority of infiltrating CD3+ T lymphocytes. Detailed immunohistochemical analysis revealed that although anti-α1 and anti-α2 mAb treatment reduced the numbers of infiltrating cells, no change in the cellular composition of the infiltrate was seen (data not shown). Immunohistochemistry staining with a FITC anti-hamster mAb confirmed the ability of the anti-α1 and anti-α2 mAb to localize to the inflamed footpad (data not shown).

Example 9

Figure 7:
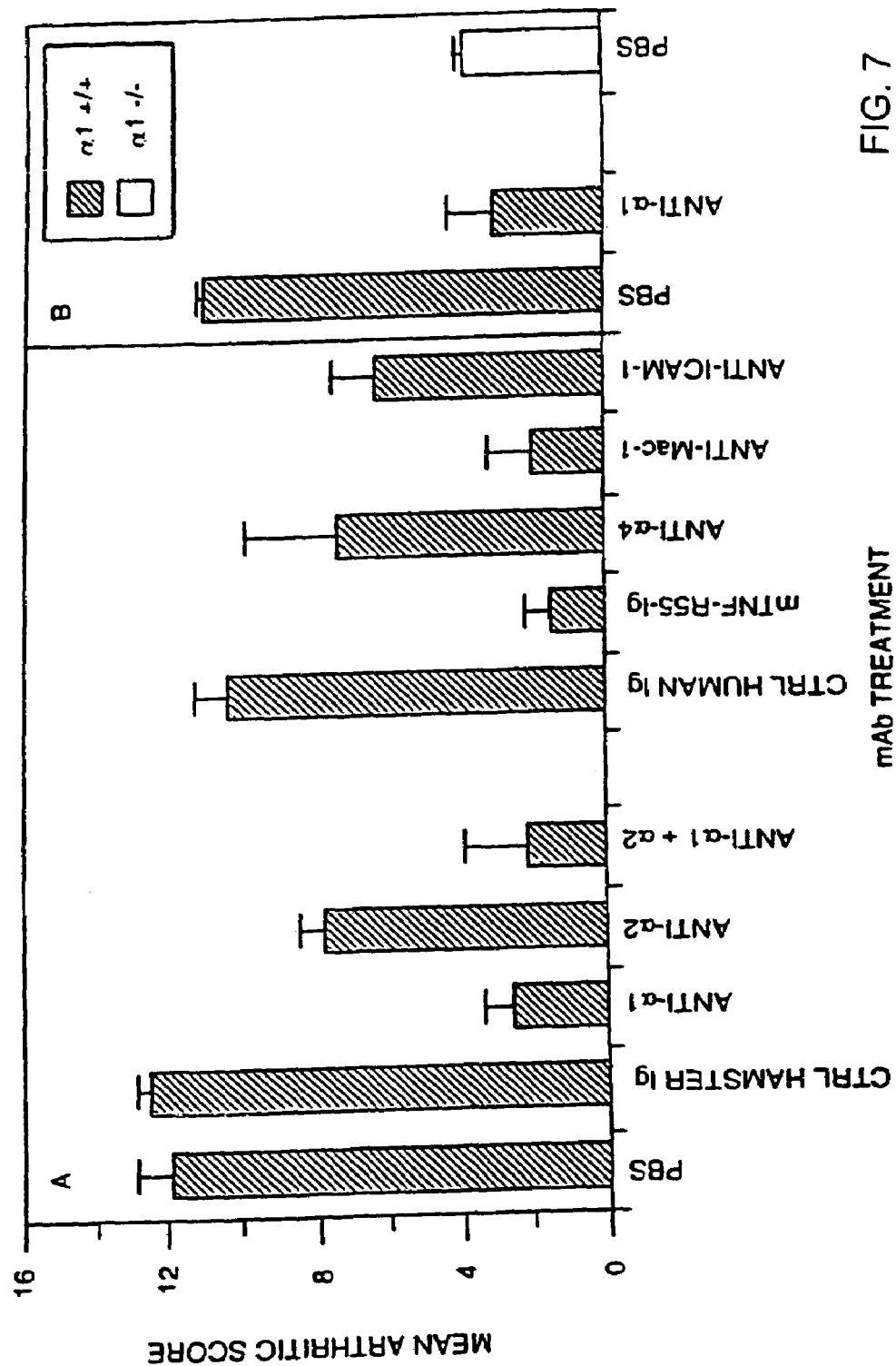
FIG. 7. Effect of anti-α1 and α2 mAbs in collagen mAb-induced arthritis. A. Preventative treatment of mice with either anti-α1 or anti-α2 mAb decreases arthritic score. Mice were treated with anti-collagen mAbs at d 0, followed by LPS on d 3. Arthritis was apparent by d 6 and continued for several weeks. Mice were treated with the indicated mAbs every $3^{rd}$ day starting on d 0. Each limb was evaluated and scored on a 0 to 4 scale every $3^{rd}$ day. Results are expressed as the mean arthritic score between d 9 and d 15 (±SEM) of all four limbs (maximum score of 16). Groups of 4 mice per condition were used; the average of 12 experiments is shown. B. α1-deficient mice have a reduced arthritic score comparable to anti-α1 mAb-treated wild-type mice. Experimental details and scoring are as outlined above. Groups of 4 mice per condition were used; the average of 2 experiments is shown.

Inhibition of arthritis by mAbs to α1β1 and α2β1 and in α1-deficient mice. As α1β1 well expressed on infiltrating cells in the synovium of arthritis patients, we decided to examine whether anti-α1 or anti-α2 mAbs would be inhibitory in an accelerated model of arthritis previously described (Terato et al., 1992, *J. Immunol* 148:2103-2108; Terato et al., 1995, *Autoimmunity* 22:137-147). This model involves injection of a cocktail of anti-collagen type II mAbs into mice, followed later by LPS administration, resulting in the development of arthritis over the next 3-7 d. Mice were given mAb every $3^{rd}$ day starting at d 0, and scored for the development of arthritis every $3^{rd}$ day. Severe arthritis developed in all mice within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 7). In contrast, treatment with anti-α1 mAb alone resulted in a marked reduction (79% and higher) in arthritis, lasting the duration of the experiment. Treatment with anti-α2 mAb alone also had a beneficial effect, resulting in a 37% decrease in the arthritic score as compared to control mAb-treated mice. The combination of anti-α1 and anti-α2 mAbs resulted in a similar degree of inhibition as seen with anti-α1 mAb alone. Reduction of arthritic score with anti-α1 mAb treatment was seen in all mice and compares favorably with several other mAb-based treatments for arthritis such as soluble TNF receptor Ig fusion protein (Mori et al., 1996, *J. Immunol.* 157:3178-3182), anti-Mac-1 (Taylor et al., 1996, *Immunology.* 88:315-321), anti-α4 (Seiffge, 1996, *J. Rheumatol.* 23:2086-2091), and anti-ICAM-1 (Kakimoto et al., 1992, *Cell Immunol.* 142:326-337). In agreement with mAb-based data showing an important role for α1β1 in arthritis, untreated α1-deficient mice showed significant reduction in arthritic score when compared to wild-type mice.

Example 10

Effect of anti-α1 mAb treatment on the immunopathology of arthritic joints. Joints from wild-type arthritic mice (day 8) receiving either control mAb or anti-α1 mAb-treatment were compared visually and histologically to joints from a normal untreated mouse. Visually, joints from control mAb-treated mice demonstrated redness and swelling of the entire foot including digits, while anti-α1 mAb-treated mice showed little if any signs of inflammation in either joints or digits. Histologic examination showed severe changes in control mAb-treated arthritic joints, with extensive infiltration of the subsynovial tissue with inflammatory cells, adherence of cells to the joint surface, and marked cartilage destruction as evidenced by proteoglycan loss. Consistent with previous reports (Terato et al., 1992, *J. Immunol* 148:2103-2108; Terato et al., 1995, *Autoimmunity* 22:137-147), the majority of the infiltrating cells in this model are neutrophils. Anti-α1 mAb treatment of mice dramatically reduced the amount of inflammatory infiltrate and the degree of cartilage destruction.

Example 11

Figure 8:
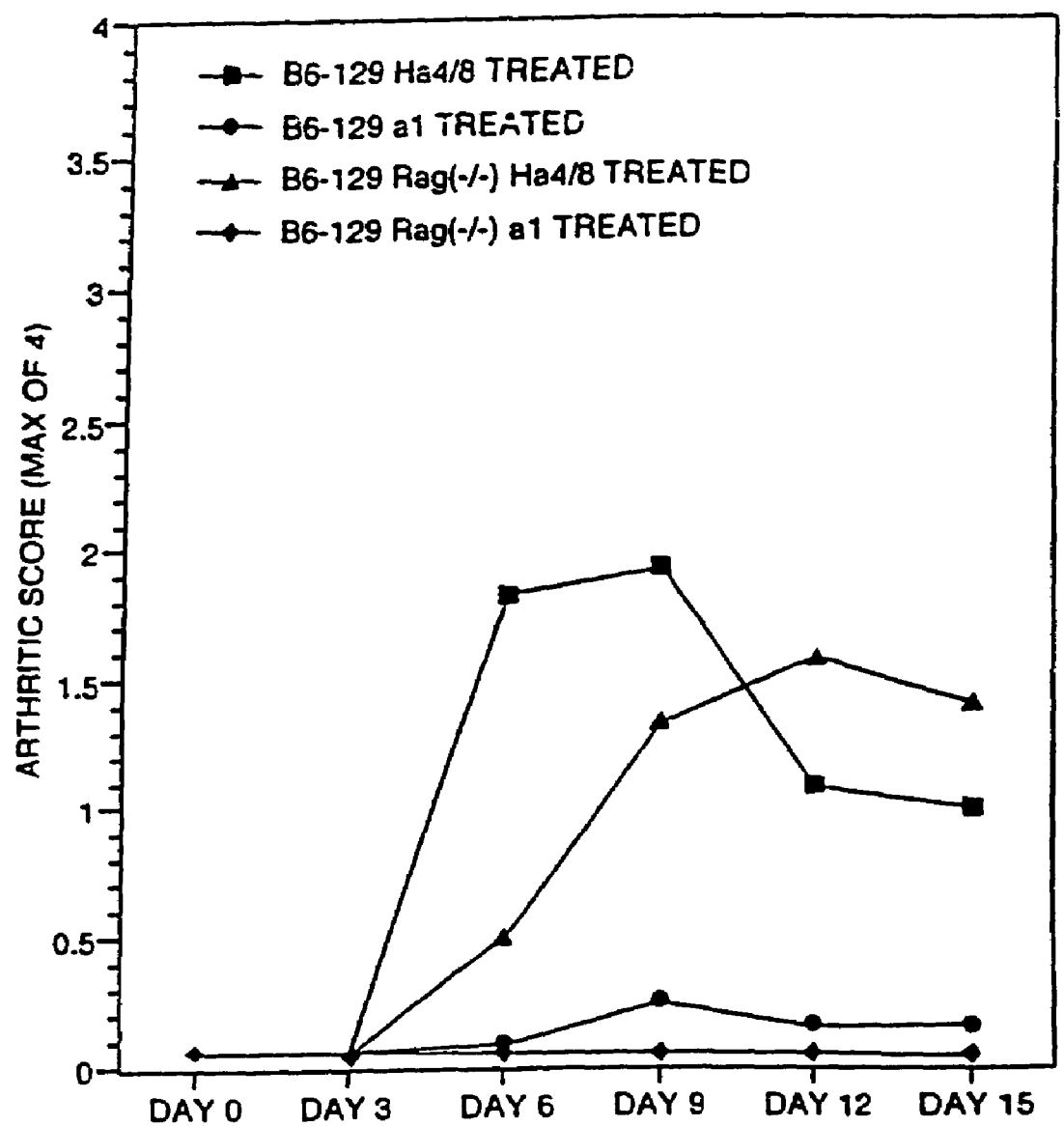
FIG. 8. Development of arthritis is delayed in the absence of lymphocytes and inhibition of arthritis by anti-α1 mAb occurs in the absence of lymphocytes. Wild-type B6,129 or RAG-1-deficient B6,129 mice were treated with anti-collagen mAbs at day 0, followed by LPS on day 3. Arthritis was apparent by day 6 and continued for several weeks. Mice were treated with the indicated mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Development of arthritis is delayed in the absence of lymphocytes and inhibition of arthritis by anti-α1 mAb occurs in the absence of lymphocytes. To determine what cell types might be important in the collagen mAb-induced arthritis model we compared the ability of wild-type B6-129 mice and RAG-1-deficient B6-129 mice to develop arthritis (FIG. 8). Genetic deletion of the RAG-1 (recombination activating gene-1) gene results in a complete loss of mature T and B lymphocytes (Mombaerts et al., 1992, *Cell* 68:869-877). Both the wild-type and RAG-1-deficient mice developed arthritis, though the kinetics of induction in the RAG-1-deficient mice is significantly slower (FIG. 8). These results suggest that while lymphocytes are involved in this model of arthritis, they are not required for the development and progression of the disease. Published reports examining the effect of the RAG-1-deficient mice in other models of arthritis also found that loss of T and B lymphocytes delayed the onset of arthritis (Plows et al., 1999, *J. Immunol.* 162:1018-1023). Treatment of either wild-type or RAG-1-deficient mice with anti-α1 mAb completely inhibited arthritis (FIG. 8). These results demonstrate that the effectiveness of anti-α1 mAb in this model is not dependent on the presence of lymphocytes, and that as suggested by previous experiments (FIG. 7), the efficacy of anti-α1 mAb in preventing disease may be through its action on other α1-expressing cells, such as macrophages and neutrophils.

Example 12

Figure 9:
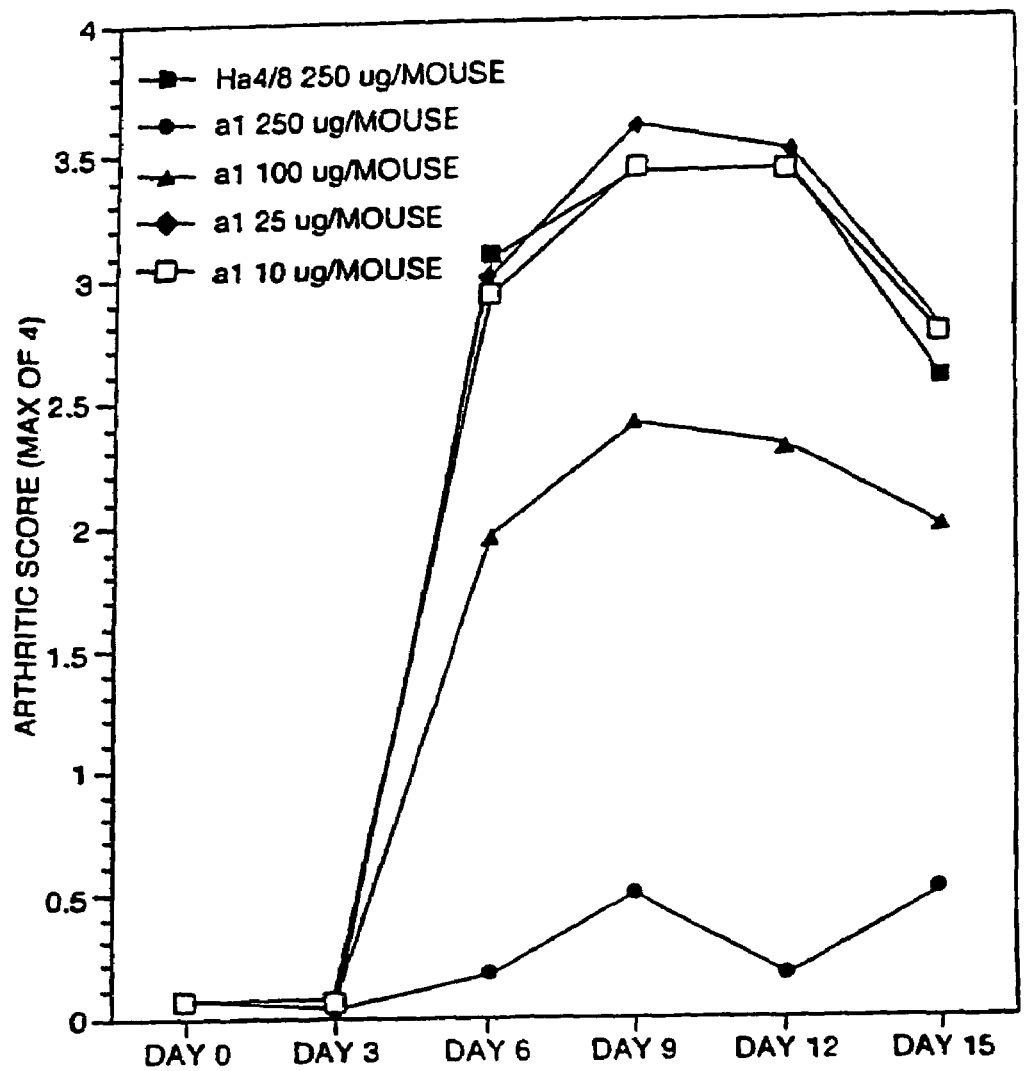
FIG. 9. Dose response of anti-α1 mAb inhibition of arthritis. Wild-type Balb/c mice were treated with anti-collagen mAbs at day 0, followed by LPS on day 3. Arthritis was apparent by day 6 and continued for several weeks. Mice were treated i.p. with the indicated dose of either Ha4/8 (isotype control) or Ha31/8 (anti-α1) mAbs every 3$^{rd}$ day starting on day 0. Each limb was evaluated and scored on a 0 to 4 scale every 3$^{rd}$ day. Results are expressed as the mean arthritic score per limb (maximum score of 4). Groups of 4 mice per condition were used.

Dose response of anti-α1 mAb inhibition of arthritis. Given the striking effects of anti-α1 mAb treatment on preventing arthritis, we extended these studies to include a dose response analysis (FIG. 9). Different doses of mAb were admininstered i.p. every $3^{rd}$ day starting at day 0. In agreement with earlier data, a 250 ug dose of anti-α1 mAb resulted in near complete prevention of arthritis. A lower dose of 100 ug of anti-α1 mAb was partially effective at preventing arthritis in this model, while lower doses did not have any discernable effect on arthritic score (FIG. 9).

Example 13

Figure 10:
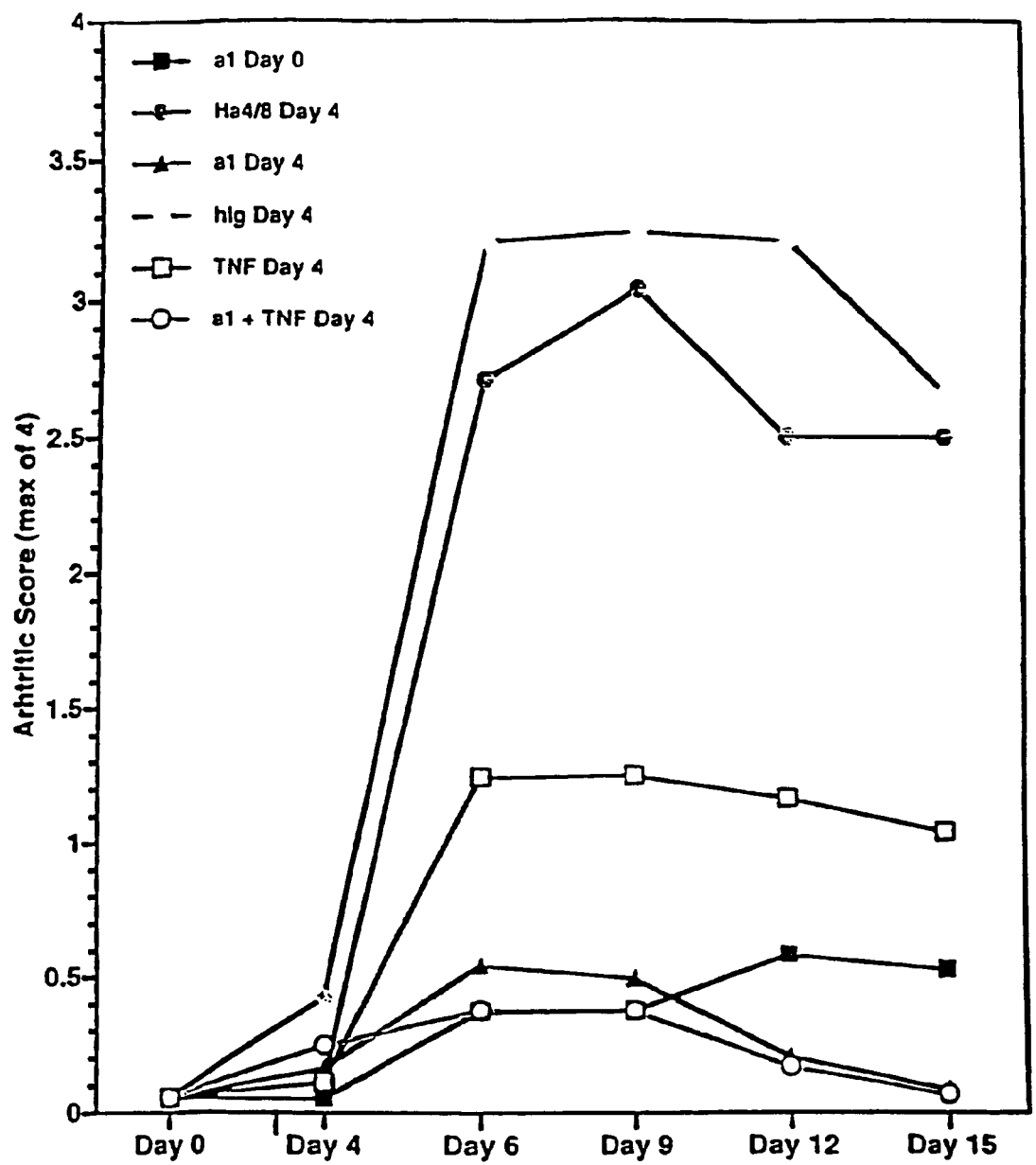
FIG. 10. Therapeutic treatment with anti-α1 mAb can decrease arthritic score. Wild-type Balb/c mice were treated with anti-collagen mAbs at day 0, followed by LPS on day 3. Arthritis was apparent by day 6 and continued for several weeks. Mice were treated i.p. with mAbs (250 μg) or Ig fusion protein (200 μg) every 3$^{rd}$ day starting on day 4. Mice received either mAb (Ha4/8 isotype control or Ha31/8 anti-α1), Ig fusion protein (Isotype control Ig or TNF-R55-Ig) or a combination of both (250 ug Ha31/8 and 200 ug TNF-R55-Ig). Each limb was evaluated and scored on a 0 to 4 scale every 3$^{rd}$ day. Results are expressed as the mean arthritic score per limb (maximum score of 4). Groups of 4 mice per condition were used.

Therapeutic treatment with anti-α1 mAb can decrease arthritic score. Given the effectiveness of anti-α1 mAb in preventing arthritis, we attempted to treat mice that are on their way to develop disease. Arthritis was induced in mice by injection of a cocktail of anti-collagen type II mAbs on day 0, followed by LPS administration on day 3. Mice were then treated with either anti-α1 mAb or a soluble TNF receptor Ig fusion protein starting on day 4. Progression of arthritis was completely blocked in mice receiving anti-α1 mAb starting at day 4, when compared to mice receiving control hamster mAb starting at day 4 (FIG. 10). The degree of inhibition seen with therapeutic administration of anti-α1 mAb was complete and was equal to that seen with preventative treatment of anti-α1 mAb (started at day 0) (FIG. 10). In comparison, treatment with TNF receptor Ig fusion protein from day 4 onwards resulted in only a 60-70% inhibition in arthritic score when compared to control Ig fusion protein (FIG. 10). Combined treatment of anti-α1 mAb and TNF receptor Ig fusion together was effective at completely inhibiting arthritic score, which is not surprising given the complete effectiveness of anti-α1 mAb treatment alone in suppressing arthritis. In summary, these results indicate that therapeutic treatment with anti-α1 mAb is effective at inhibiting arthritic score, and compares favorably to therapeutic treatment with a TNF antagonist.

Example 14

Cloning and mutagenesis of the α1-I domain. Human and rat α1β1 integrin I domain sequences were amplified from full length cDNAs (Kern, et al., 1994, *J. Biol. Chem.* 269, 22811-22816; Ignatius et al., 1990, *J. Cell Biol.* 111, 709-720) by the polymerase chain reaction (PCR) (PCR CORE Kit; Boehringer Mannheim, GmbH Germany), using either human specific primers, 5'-CAGGATCCGTCAGCCCCACATTTCAA-3' [forward] (SEQ ID NO:7), and
5'-TCCTCGAGGGCTTGCAGGGCAAATAT-3' [reverse] (SEQ ID NO:8), or rat specific primers,
5'-CAGGATCCGTCAGTCCTACATTTCAA-3' [forward] (SEQ ID NO:9), and
5'-TCCTCGAGCGCTTCCAAAGCGAATAT-3' [reverse] (SEQ ID NO:10).

The resulting PCR amplified products were purified, ligated into pGEX4t-i (Pharmacia), and transformed into competent DH5α cells (Life Technologies). Ampicillin resistant colonies were screened for the expression of the ~45 kDa glutathione S-transferase-I domain fusion protein. The sequences from inserts of plasmid DNA of clones that were selected for further characterization were confirmed by DNA sequencing.

A rat/human chimeric 1-I domain (RΔH) was generated (MORPH Mutagenesis kit; 5 prime—3 prime), exchanging the rat residues G91, R92, Q93, and L96 (FIG. 11) for the corresponding human residues, V, Q, R, and R, respectively. Clones harboring the RΔH I domain were identified by the loss of a diagnostic Stu 1 restriction enzyme site, and the inserts confirmed by DNA sequencing. The amino acid sequence of the human α1-I domain is shown in FIG. 12.

Example 15

Generation of mAbs specific to the α1-I domain. Monoclonal antibodies have proved to be very useful probes in studying the relationship between structure and function of integrin subunits. For example, mAbs were used extensively to study regions of the β1 subunit associated with an activated conformation (Qu, A., and Leahy, D. J. (1996) *Structure* 4, 931-942). Thus, to identify potential probes for conformational changes of the α1-I domain, we generated a panel of mAbs to the human α1-I domain.

Generation of anti-α1 I domain Monoclonal Antibodies. Female Robertsonian mice (Jackson Labs) were immunized intraperitoneally (i.p.) with 25 µg of purified human α1β1 (Edwards et al., 1995, *J. Biol. Chem.* 270, 12635-12640; Gotwals et al., 1999, *Biochemistry* 38:8280-8) emulsified with complete Fruend's adjuvant (LifeTechnologies). They were boosted three times i.p. with 25 µg of α1β1 emulsified with incomplete Freunds's adjuvant (LifeTechnologies). The mouse with the highest anti-α1-I domain titer was boosted i.p. with 100 µg of α1β1 three days prior to fusion, and intravenously with 50 µg of α1β1 one day prior to fusion. Spleen cells were fused with FL653 myeloma cells at a 1:6 ratio and were plated at 100,000 and 33,000 per well into 96 well tissue culture plates.

Supernatants were assessed for binding to the α1β1 integrin by single color FACS. Prior to FACS analysis, supernatants were incubated with untransfected K562 cells to eliminate IgG that bound solely to the β subunit. Subsequently, 3-5 X $10^4$ K562 cells transfected with the α1 integrin subunit (K562-α1) suspended in FACS buffer (1% fetal calf serum (FCS) in PBS containing 0.5% $NaN_3$) were incubated with supernatant for 45 minutes at 4° C., washed and incubated with anti-mouse IgG conjugated to phycoerythrin. After washing twice with FACS buffer, cells were analyzed in a Becton Dickinson Flow Cytometer.

Supemantants from the resulting hybridomas were screened for binding to the α1-I domain. Briefly, 50 µl of 30 µg/ml human α1-I domain-GST fusion in PBS was coated onto wells of a 96-well plate (Nunc) overnight at 4° C. The plates were washed with PBS, blocked with 1% BSA in PBS and the hybridoma supernatant was incubated with the I domain at room temperature for 1 hour. After extensive washing with PBS containing 0.03% Tween 20, alkaline phosphatase linked anti-mouse IgG (Jackson ImmunoResearch) was added for an additional hour. After a final wash, 1 mg/ml p-nitrophenylphosphate (pNPP) in 0.1 M glycine, 1 mM $ZnCl_2$, and 1 mM $MgCl_2$ was added for 30 minutes at room temperature, and the plates were read at O.D. 405.

Selected supernatants were tested for their ability to inhibit K562-α1 dependent adhesion to Collagen IV. K562-α1 cells were labeled with 2 mM 2',7' (bis-2-carboxyethyl-5 and 6) carboxyfluorescein penta acetoxymethylester (BCECF; Molecular Probes) in DMEM containing 0.25% BSA at 37° C. for 30 minutes. Labeled cells were washed with binding buffer (10 mM Hepes, pH 7.4; 0.9% NaCl; and 2% glucose) and resuspended in binding buffer plus 5 mM $MgCl_2$ at a final concentration of $1\times10^6$ cells/mL 50 µl of supernatant was incubated with an equal volume of $2\times10^5$ K562-α1 cells in wells of a 96 well plate. The plate was then centrifuged and the supernatants removed. Cells were resuspended in binding buffer and transferred to wells of a collagen-coated plate and incubated for 1 hour at 37° C. Following incubation, the non-adherent cells were removed by washing three times with binding buffer. Attached cells were analyzed on a Cytofluor (Millipore).

Figure 13A:
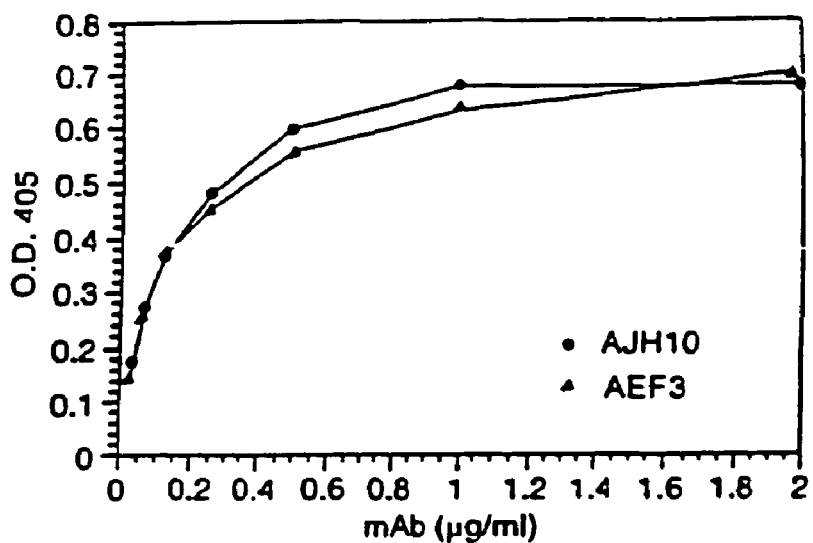
FIG. 13. Identification of a blocking mAb to the α1-I domain. A. Increasing concentration of mAbs AEF3 (triangles) or AJH10 (circles) were bound to plates coated with 30 μg/ml α1-I domain. B. The α1-I domain was treated with increasing concentrations of mAb AJH10 (diamonds) or mAb BGC5 (squares) and bound collagen IV (2 μg/ml) coated plates. C. K562-α1 cell were treated with increasing concentration of mAbs AEF3(triangles) or AJH10 (circles) and bound to collagen IV (5 μg/ml) coated plates. 45-50% of cells added to each well adhered to collagen IV. Data shown is representative of three independent experiments.
Figure 13B:
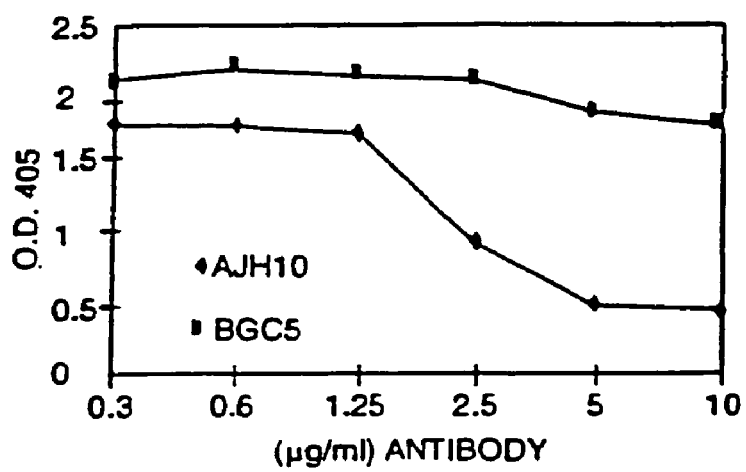
Figure 13C:
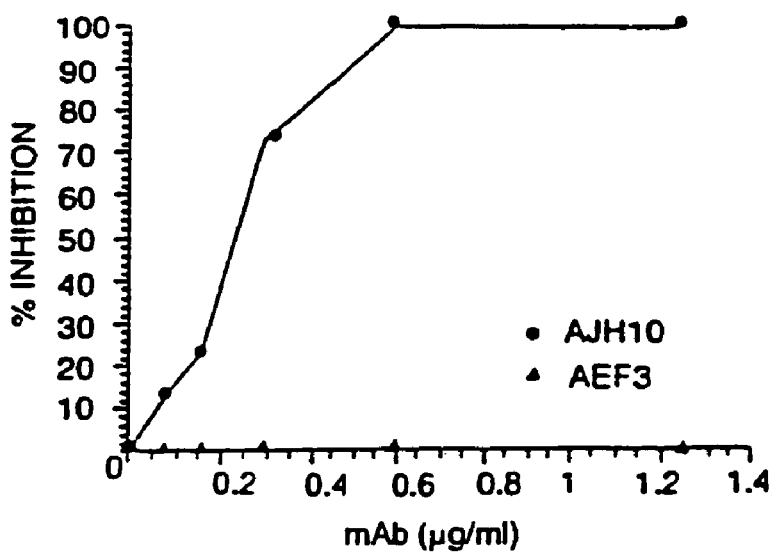

We initially identified 19 hybridomas, the supernatants of which bound to human leukemia K562 cells expressing the α1β1 integrin (K562-α1) and to the α1-I domain. The immunoglobulins were purified from each of these hybridomas and tested for the ability to block either K562-α1 or α1-I domain binding to collagen IV. The mAbs fall into two classes: those that block and those that do not block α1β1 function. For example, while the mAbs produced by clones AEF3, BGC5, AQC2 and AJH10 bind the α1-I domain (FIG. 13A, data not shown for BGC5), only mAbs AJH10 and AQC2 inhibit α1-I domain-dependent (FIG. 13B; FIG. 16B) or K562-α1 (FIG. 13C; FIG. 16C) adhesion to collagen IV.

Sequencing of the Complementarity Determining Regions. To establish the clonal origin of this panel of mAbs, we amplified by PCR and sequenced the CDRs from 12 of the 19 antibodies (data not shown).

2 µg of mRNA, isolated from $10^7$ hybridomas (FastTrack mRNA isolation kit, Invitrogen), was reverse transcribed (Ready-To-Go You Prime First Strand Kit, Pharmacia Biotech) using 25 pM each of the following primers: heavy chain VH1FOR-2 (Michishita et al., 1993, *Cell* 72:857-867); light chain, VK4FOR, which defines four separate oligos (Kern et al., 1994, *J. Biol. Chem.* 269:22811-22816). For each hybridoma, heavy and light chains were amplified in four separate PCR reactions using various combination of the following oligos: 1) Heavy chain: VH1FR1K (Kamata et al., 1995, *J. of Biol. Chem.* 270:12531-12535), VH1BACK, VH1BACK (Baldwin et al. (1998) *Structure* 6, 923-935), $V_H$fr1a, $V_H$fr1b, $V_H$fr1e, $V_H$fr1f, $V_H$fr1g (Ignatius et al. (1990) *J. Cell Biol.* 111, 709-720), or VH1FOR-2 (Michishita, M., Videm, V., and Arnaout, M. A. (1993) *Cell* 72, 857-867); 2) Light chain: VK1BACK (Baldwin et al. (1998) *Structure* 6, 923-935), VK4FOR, VK2BACK oligos (Kern et al. (1994) *J. Biol. Chem.* 269, 22811-22816), or $V_K$fr1a, $V_H$fr1c, $V_H$fr1e, $V_H$fr1f (Ignatius et al. (1990) *J. Cell Biol.* 111, 709-720). Products were amplified (5 min at 95° C., 50 cycles of 1 min at 94° C., 2 min at 55° C., 2 min at 72° C., and a final cycle of 10 min at 72° C.), gel purified (QIAquick, Qiagen), and sequenced directly using various of the listed oligos on an ABI 377 Sequencer.

Sequences from clones producing function-blocking mAbs were nearly identical across all the complementarity-determining regions (CDRs) and the intervening framework regions suggesting that these hybridomas are clonally related.

Example 16

Immunoblotting and FACS Analysis. Sequences of the variable regions of the non-blocking antibodies were markedly different from the clonally related family of sequences found for the blocking antibodies. As the blocking antibodies appear to originate from a single clone, we chose two (AJH10 and AQC2) to characterize further.

Immunoblotting The smooth muscle cell layer dissected from sheep aorta, and K562-α1 cells were extracted with 1% Triton X-100 in 50 mM Hepes, pH 7.5, 150 mM NaCl, 10 mM phenylmethylsulfonyl flouride (PMSF), 20 µg/ml aprotinin, 10 µg/ml leupeptin, 10 mM ethylenediaminetetraacetic acid (EDTA). Samples were subjected to 4-20% gradient SDS-PAGE, and electroblotted onto nitrocellulose membranes. The blots were blocked with 5% dry milk in TBS; washed in TBS containing 0.03% Tween-20, and incubated with antibodies in blocking buffer containing 0.05% $NaN_3$ for 2 hours. Blots were then washed as before, incubated with horseradish peroxidase conjugated anti-mouse IgG for one hour, washed again and then treated with ECL reagent (Amersham). Blots were then exposed to film (Kodak) for 30 to 60 seconds, and developed.

Immunoblotting and FACS analysis (FIG. 14) demonstrate that AJH10 reacts with human, rabbit, and sheep, but not rat α1β1 integrin suggesting that the blocking mAbs bind to an evolutionarily conserved, linear epitope. The non-blocking mAbs were neither efficient at immunoblotting nor did they react with species other than human.

Example 17

Binding of the α1-I Domain to Collagen is Divalent Cation-dependent

A. Purification of the α1-I Domains.

The α1-I domains were expressed in *E. coli* as GST (glutathione-S-transferase) fusion proteins containing a thrombin cleavage site at the junction of the sequences. The clarified supernatant from cells lysed in PBS was loaded onto a glutathione Sepharose 4B column (Pharmacia) which was washed extensively with PBS. The α1-I domain-GST fusion protein was eluted with 50 mM Tris-HCl, pH 8.0, 5 mM glutathione (reduced). For denaturation studies, the I domain was cleaved with thrombin in 50 mM Tris, pH 7.5, and purified from the GST fusion partner. DTT was added to 2 mM and the sample was loaded on a glutathione Sepharose 4B column. The flow-through and wash fractions were pooled and loaded onto a Q Sepharose FF column (Pharmacia). The α1-I domain was eluted with 50 mM Tris HCl, pH 7.5, 10 mM 2-mercaptoethanol, 75 mM NaCl. The purified I domain displayed its predicted mass (Lee et al. (1995) *Structure* 3, 1333-1340, 871 Da) by electrospray ionization-mass spectrometry (ESI-MS), migrated as a single band by SDS-PAGE, and the protein eluted as a single peak of appropriate size by size exclusion chromotography on a Superose 6 FPLC column (Pharmacia).

B. Functional Analysis 96 well plates were coated overnight at 4° C. with 1 µg/ml collagen IV (Sigma) or collagen Type I (Collaborative Biomedical), washed with Triton buffer (0.1% Triton X-100; 1 mM $MnCl_2$; 25 mM Tris-HCl; 150 mM NaCl), and blocked with 3% bovine serum albumin (BSA) in 25 mM Tris-HCl; 150 mM NaCl (TBS). Serial dilutions of the α1-I domain-GST fusion protein in TBS containing 1 mM $MnCl_2$ and 3% BSA were incubated on the coated plates at room temperature for 1 hour, and washed in Triton buffer. Bound α1-I domain was detected with serial additions of 10 µg/ml biotinylated anti-GST polyclonal antibody (Pharmacia); ExtrAvidin-horseradish peroxidase (Sigma) diluted 1:3000 in TBS containing 1 mM $MnCl_2$ and 3% BSA, and 1-Step ABTS (2,2'-Azine-di[3-ethylbenzthiazoline sulfonate]; Pierce). Plates were read at O.D. 405 on a microplate reader (Molecular Devices).

Results

Figure 15A:
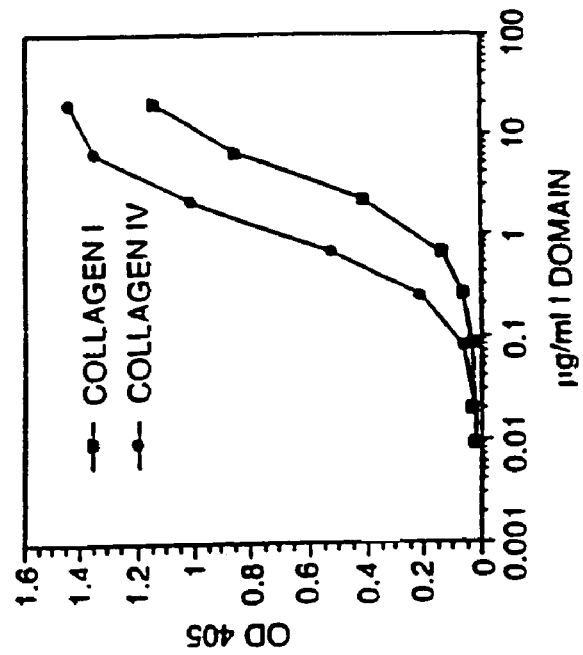
FIG. 15. The α1-I domain binds collagen. A. Increasing concentrations of the human α1-I domain were bound to plates previously coated with 1 μg/ml collagen I (squares) or collagen IV (circles). Values shown have been corrected for background binding to BSA. B. 2 μg/ml human α1-I domain was mixed with increasing concentration of an anti-human α1 integrin antibody 5E8D9 (squares) or an anti-human α2-integrin antibody A2IIE10 (circles), and then bound to plates previously coated with 1 μg/ml collagen IV. C. Plates were coated with 1 μg/ml collagen IV or 3% BSA. α1-I domain (2 μg/ml) was subsequenctly bound to coated plates in the presence of 1 mM Mn$^{2+}$, 1 mM Mg$^{2+}$, or 5 mM EDTA. Data shown is representative of three independent experiments.
Figure 15B:
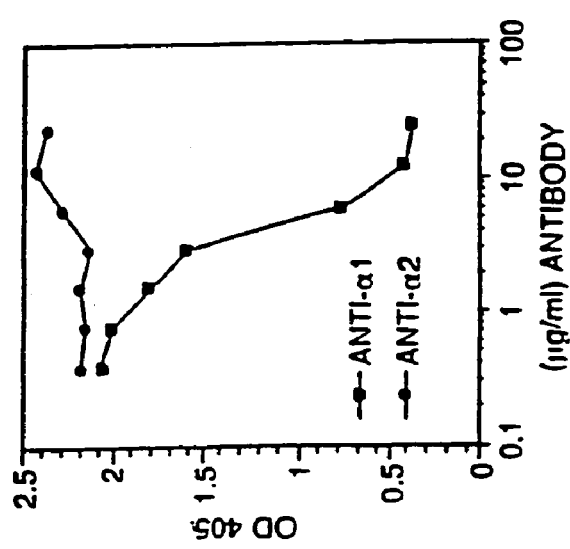
Figure 15C:
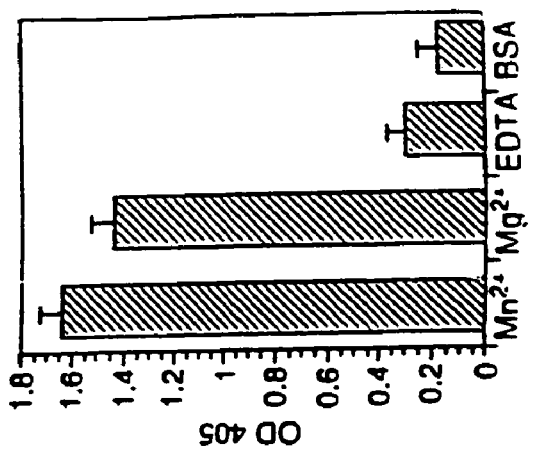

The human and rat (95% identity to human) α1-I domains were expressed in *E. coli* as GST-fusion proteins and purified over glutathione sepharose. Both proteins were examined for binding to collagen I and IV using a variation of an ELISA-based assay previously described (Qu, A., and Leahy, D. J. (1995) *Proc. Natl.; Acad. Sci. USA* 92, 10277-10281). The human α1-I domain binds collagen IV with better efficiency than collagen I (FIG. 15A). An antibody specific to the α1-I domain, but not an antibody specific to the α2-I domain (FIG. 15B) abrogated binding to both ligands (data for collagen I is not shown). Both $Mn^{2+}$ and $Mg^{2+}$ stimulated binding, and EDTA reduced binding to background levels (FIG. 15C). No measurable differences in ligand binding were detected between the human and rat α1-I domains suggesting that the sequence differences between species are not functionally relevant (data not shown). Thus, the α1-I domain, specifically, require cation for efficient ligand binding.

Example 18

Figures 11A, 11B:
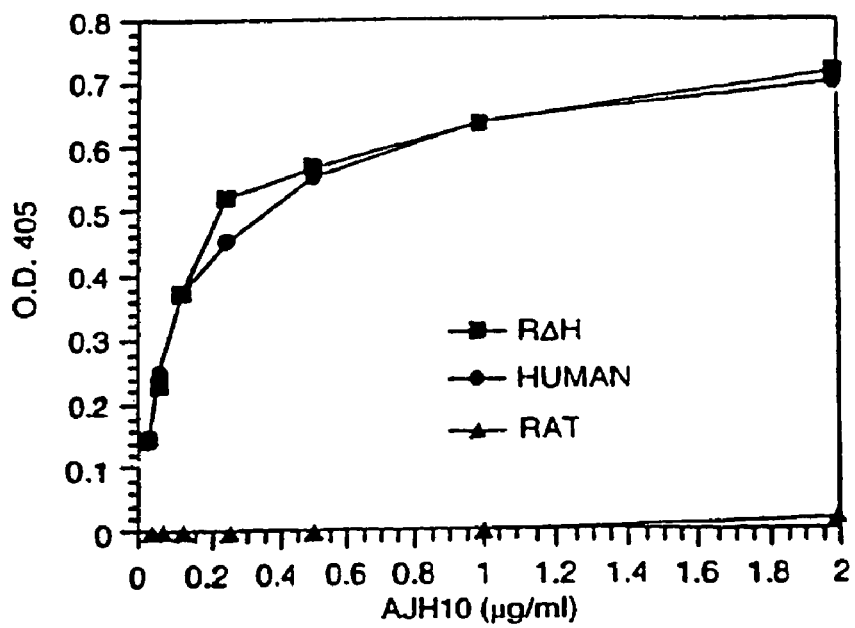
FIG. 11. Location of the Epitope for the anti-α1 I domain Blocking mAbs. A. Amino acid sequence of the rat (top; SEQ ID NO:63) and human (below; residues of SEQ ID NO:64, which are different from rat are shown) α1-I domain. The residues that comprise the MIDAS (metal ion dependent adhesion site) motif are shown in bold. The human amino acids that replaced the corresponding rat residues (RΔH) are shown below the rat sequence in the boxed region. For clarity, residue numbering in the text refers to this figure, unless otherwise designated, e.g., as crystal numbering. B. Increasing concentrations of mAb AJH10 (ATCC No. PTA-3580; deposited under the Budapest Treaty with the American Type Culture Collection, Manassas, Va., USA on Aug. 2, 2001) were bound to plates coated with 30 μg/ml human (circles), rat (triangles) or RΔH (squares) α1-I domain. Data shown is representative of three experiments.

A Cation-Dependent Epitope Resides near the MIDAS motif. We exploited the observation that AJH10 recognizes the human, but not the rat α1-I domain sequences to map the epitope for the α1β1 function-blocking mAbs. The human and rat sequences differ by only 12 amino acids, 4 of which lie in a stretch of 6 amino acids (aa 91-96, FIG. 11A) adjacent to the critical threonine (FIG. 11A, aa 98) within the MIDAS motif. To test the hypothesis that the 6 amino acid residues, Val-Gln-Arg-Gly-Gly-Arg (residues 91-96 of SEQ ID NO:64), comprise the epitope for the blocking mAbs, we constructed a chimeric I domain (RΔH), exchanging the rat residues G91, R92, Q93, and L96 for the corresponding human residues, V, Q, R, and R, respectively. AJH10, along with all the function-blocking mAbs, recognizes the chimeric I domain (RΔH; FIG. 11B).

To orient these residues with respect to the MIDAS domain in the tertiary structure of the α1-I domain, we modeled the α1-I domain using the coordinates of the crystal structure of the α2 I domain.

A homology model of the human α1 I-domain was built using the X-ray crystal structure of the human α2 I-domain (Ward et al. (1989) *Nature* 341, 544-546). The model was built using the homology modeling module of Insight II (version 2.3.5; Biosym Technologies). The program CHARMM (Clackson et al. (1991) *Nature* 352, 624-628) was used with the all-hydrogen parameter set 22 with a distant dependent dielectric constant of two times the atom separation distance. We first did 1000 steps of steepest descent minimization with mass-weighted harmonic positional constraints of 1 kcal/(mol Å$^2$) on all atoms of the α1-I domain. This minimization was followed by another 1000 steps of steepest descent and 5000 steps of Adopted-Basis Newton Raphson with constraints of 0.1 kcal/(mol Å$^2$) on the C-α atoms of the α1-I domain to avoid significant deviations from the α2-I domain X-ray crystal structure.

The α1β1 and α2β1 integrin sequences exhibit 51% identity with no insertions or deletions, suggesting that the overall structure of the two I domains will be similar. The metal coordination site is predicted to be the same in the α1-I domain as in the α2-I domain, and the residues that comprise the epitope for the blocking mAbs lie on a loop between helix α3 and helix α4 which contains the threonine within the MIDAS motif critical for cation binding. The α1-I domain model predicts that the amide nitrogen of Q92 (FIG. 11A) hydrogen bonds with the carbonyl group of I33, the residue adjacent to S32. Thus, the loop that contains the epitope may play a functional role in stabilizing the MIDAS region.

Example 19

Monoclonal antibody AQC2 (i.e., mAQC2; "m" for murine) (Example 15, supra) is an IgG$_1$, kappa antibody. To identify the nucleotide sequences encoding the heavy and light chains of this antibody, total cellular RNA from AQC2 murine hybridoma cells was obtained by using a QIAGEN RNEASY midi kit in accordance with the manufacturer's instructions. Then cDNAs encoding the variable regions of the heavy and light chains were cloned by RT-PCR from total cellular RNA using a GIBCO BRL SUPERSCRIPT Preamplification System for First Strand cDNA Synthesis following the manufacturer's recommended protocol. Random hexamers were used for priming.

The heavy chain variable domain of mAQC2 was amplified by PCR from the first strand cDNA-with the primers: 5' TGA GGA GAC GGT GAC CGT GGC CCT TGG CCC C 3' (SEQ ID NO:11) and 5' AGG TSM ARC TGC AGS AGT CWG G 3' (S=C/G, M=A/C, R=A/G, and W=A/T) (SEQ ID NO:12). The PCR was subjected to 30 cycles using Clontech's Advantage Taq polymerase: denature 30 sec at 94° C., anneal 1 min at 50° C., and elongate 1.5 min at 68° C. The mAQC2 light chain with its signal sequence was amplified by PCR using the primers: 5' ACT AGT CGA CAT GGA TTT WCA GGT GCA GAT TWT CAG CTT C 3' (W=A/T) (SEQ ID NO:13) and 5' ACT GGA TGG TGG GAA GAT GGA 3' (SEQ ID NO:14). The PCR was subjected to 30 cycles using Stratagene's cloned Pfu polymerase: denature 1 min at 94° C., anneal 1 min at 50° C., and elongate 2 min at 72° C. The PCR products for the heavy and light chains were gel-purified using a QIAGEN QIAQUICK gel extraction kit following the manufacturer's recommended protocol.

Purified heavy chain product was subdloned into Invitrogen's pCR2.1-TOPO TA vector using its TOPO TA cloning kit. Purified light chain was subcloned into Invitrogen's pCRbluntIITOPO vector using its Zero blunt TOPO cloning kit following the manufacturer's recommended protocol. Inserts from multiple independent subclones were sequenced. With the exception of degenerate positions within the PCR primers, the insert sequences of the independent subclones were identical.

The polypeptide sequences of mAQC2 were deduced from their coding sequences. The N-terminal amino acid sequence for the mature light chain predicted by the cDNA sequence from the PCR product amplified with a signal sequence exactly matched the N-terminal sequence of purified mAQC2 light chain derived from Edman degradation (DVKVVESGG; SEQ ID NO:15). BLAST analyses of the variable domain sequences confirmed their immunoglobulin identity.

The polypeptide sequence of the light chain variable domain of mAQC2 is shown below:

```
                                            (SEQ ID NO:1)
  1 QIVLTQFPAL MSASPGEKVT MTCSASSSVN HMFWYQQKPK

41 SSPKPWIYLT SNLASGVPAR FSGSGSGTSY SLTISSMEAE

81 DAATYYCQQW SGNPWTFGGG TKLEIK 106
```

The CDRs are shown in boldface. The CDRs are defined according to Kabat et al., Sequences of Proteins of Immunological Interest, 5th Edition, The United States Department of Health and Human Services, The United States Government Printing Office, 1991. Using the Kabat numbering system, SEQ ID NO:1 is represented as follows, where a dash denotes the absence of an amino acid:

```
  1 QIVLTQFPAL MSASPGEKVT MTCSASS-SV NHMFWYQQKP

41 KSSPKPWIYL TSNLASGVPA RFSGSGSGTS YSLTISSMEA

81 EDAATYYCQQ WSGNPWTFGG GTKLEIK 107
```

The polypeptide sequence of the heavy chain variable domain of mAQC2 is:

```
                                            (SEQ ID NO:2)
  1 DVKVVESGGG LVKPGGSLKL ACAASGFSFS RYTMSWVRQI

41 PEKRLEWVAT ISGGGHTYYL DSVKGRFTIS RDNAKNTLYL

81 QMSSLRSEDT AMYYCTRGFG DGGYFDVWGQ GTTVTVSS
```

The CDRs are shown in boldface. Using the Kabat numbering system, SEQ ID NO:2 is represented as follows, where positions numbers are consecutive numerals unless otherwise indicated:

```
  1      DVKVVESGGG LVKPGGSLKL ACAASGFSFS RYTMSWVRQI

41      PEKRLEWVAT ISGGGHTYYL DSVKGRFTIS RDNAKNTLYL

81      QM 82a-c   SSL

83      RSEDTAMY YCTRGFGDGG 100a-b   YF

101      DVWGQGTTVT VSS 113
```

As used herein, residue position numbers of variable domains are designated in accordance with the Kabat numbering system unless otherwise indicated.

Example 20

This example describes the generation of a murine-human chimeric antibody, chAQC2.

The cDNAs encoding the variable regions of the mAQC2 heavy and light chains were used to construct chAQC2 expression vectors, in which the mAQC2 variable regions were linked to human IgG$_1$ and kappa constant regions.

The heavy chain chimera was constructed as follows. A 0.33 kb PstI-BstEII fragment from the mAQC2 heavy chain plasmid pAND083 was subcloned into the phosphatased 2.82 kb PstI-BstEII vector fragment from the 5a8 heavy chain plasmid pLCB7, so as to add a murine heavy chain signal-encoding sequence and a murine splice donor site to the cDNA of the mAQC2 heavy chain variable region. 5a8 is a molecularly cloned CD4-specific mAb (see, e.g., Boon et al., 2002, *Toxicology* 172:191-203). In th e mature heavy chain encoded by the resultant plasmid (pAND092), the N-terminus differed by five residues from the N-terminus (DVKVVE; SEQ ID NO:16) of the cognate mAQC2 heavy chain.

To correct the heavy chain N-terminus, pAND092 was subjected to unique site elimination (USE) mutagenesis using an USE mutagenesis kit (Amersham Pharmacia Biotech) following the manufacturer's recommended protocol. The Q1D, Q3K, L4V, Q5V, Q6E substitutions were encoded by the mutagenic primer 5' GCA CCA GGT GCC CAC TCC GAC GTC AAG GTG GTG GAG TCA GGG GGA GGC TTA GTG 3' (SEQ ID NO:17). Mutated plasmid clones were identified by their new AatII and HinfI sites and eliminated PstI site. The heavy chain coding sequence was then confirmed by DNA sequencing. The correctly mutated plasmid was called pAND094. The 0.43 kb NotI-HindIII fragment from pAND094 and the 1.21 kb HindIII-NotI fragment from the plasmid pEAG964 (containing a coding sequence for a human IgG$_1$ constant region) were subcloned into the NotI site of pCH269, a plasmid derived from the pCEP4 EBV expression vector (Invitrogen). The resultant plasmid was named pAND099.

The light chain chimera was generated as follows. A 0.46 kb EcoRI fragment from the mAQC2 light chain variable domain plasmid pAND081 was subcloned into the phosphatased 2.7 kb vector fragment of the pUC-derived pNNO9 cloning vector, to add a 5' NotI site. The resulting plasmid, pAND091, was subjected to mutagenesis using the Amersham USE kit (supra) to introduce a BglII site at the 3' end of the coding sequence. The mutagenic primer had the sequence 5' GGA GGC ACC AAG CTG GAG ATC TAA CGG GCT GAT GCT GC 3' (SEQ ID NO:18). The correctly mutated plasmid was identified by its BglII and BstYI site changes. The light chain coding sequence in the resultant plasmid pAND093 was confirmed by DNA sequencing. Then the 0.44 kb NotI-BglII light chain variable domain fragment from pAND093 and the 0.68 kb BclI-NotI fragment from the plasmid pEAG963 (containing a coding sequence for a human kappa light chain constant domain) were subcloned into the NotI site of pCH269 (supra), producing plasmid pAND102. To create an unblocked kappa light chain (Q1E), pAND093 was subjected to USE mutagenesis with the mutagenic primer 5' CAT AAT GTC CAG GGG AGA AAT TGT TCT CAC CCA G 3' (SEQ ID NO:19), to introduce an XmnI site. The mutated plasmid was identified by screening for an XmnI site change. The light chain sequence in-the resultant plasmid pAND097 was confirmed by DNA sequencing. The 0.44 kb NotI-BglII light chain variable domain fragment from pAND097 and the 0.68 kb BclI-NotI fragment from the plasmid pEAG963 (containing a human kappa light chain constant domain) were subcloned into the NotI site of pCH269, producing plasmid pAND098.

To generate chAQC2 antibodies, expression vectors (chAQC2 heavy chain vector pAND099+chAQC2 light chain vector pAND102, and chAQC2 heavy chain vector pAND099+chAQC2 unblocked light chain vector pAND098) were co-transfected into 293-EBNA cells. The transfectants were tested for antibody secretion and specificity. The controls were cells transfected with the corresponding vectors without an insert or with DNA constructs encoding ch5c8 (a molecularly cloned CD154-specific mAb described in, e.g., Elster et al., 2001, *Transplantation* 72:1473-1478) or chCBE11 (a molecularly cloned LTβP-specific mAb described in, e.g., Browning et al., 1996, *J. Biol. Chem.* 271:24934-24938).

Then transfectants with the desired antibody secretion were lysed, and protein A immunoprecipitation was performed on the lysates and conditioned medium. Western blot analysis of the precipitates performed with anti-human heavy and light chain antibodies indicated that chAQC2-transfected cells synthesized and efficiently secreted heavy and light chains at levels similar to ch5c8-transfected and chCBE11-transfected cells. Further, huVLA-1-expressing K562α1 cells were stained with the conditioned medium from the transfected cells, and FACS analysis was performed on the stained cells. The results indicated that the chAQC2 antibody produced staining patterns similar to those of mAQC2, while conditioned media from mock-transfected and ch5c8-transfected cells failed to stain K562α1 cells. Chimeric AQC2 produced from scaled-up transient transfection was purified and shown to bind to VLA-1 by FACS titration. Chimeric AQC2 with either a wildtype or a genetically unblocked light chain bound to VLA-1. See also FIGS. 16A-D (discussed below).

Example 21

This example describes a method of humanizing the mAQC2 monoclonal antibody.

Analysis of the mAQC2 variable domains. The variable domains in the light and heavy chains of mAQC2 were compared with the consensus sequences for mouse and human subgroups (Kabat et al, supra) using the software program FASTA. The light chain variable domain was found to be a member of mouse subgroup VI with 89% identity in a 109 amino acid overlap. This domain also corresponded to human subgroup I with 72% identity in a 113 amino acid overlap. The heavy chain variable domain was found to be a member of mouse subgroup IIId with 86% identity in a 129 amino acid overlap. This heavy chain variable domain also corresponded to human subgroup III with 79% identity in a 130 amino acid overlap.

The CDRs were categorized into canonical classes according to Chothia et al., *Nature* 342, pp. 877-883 (1989). The key residues defining each canonical class determine to a large extent the structural conformation of the CDR loop, and-thus should be retained in the reshaped antibody. The L1 loop of n-tAQC2 fell into canonical class 1 (10 residue loop), L2 into class 1 (7 residue loop) and L3 into class 1 (9 residue loop). The H1 loop fell into class 1 (5 residue loop) and the H2 loop into class 1 (16 residue loop) residues. The H3 loop did not seem to belong to any canonical class. The canonical residues important for these classes were all included in the humanized antibodies.

Unusual framework residues in mAQC2 were determined by analyzing all mouse and human variable chain sequences in the September 1999 version of the Kabat database. It was believed that mAQC2-specific differences might indicate somatic mutations that enhance binding affinity if these differences were close to the binding site. Unusual mAQC2 residues further away from the binding site and unusual human framework residues were removed in case they would create immunogenic epitopes in the humanized antibody. Unusual framework residues found in mAQC2 were 7(F), 10(L), and 41(K) in the light chain; and 4(V), 21(A), and 40(I) in the heavy chain. None of these unusual mouse framework residues were retained the humanized antibodies.

Modeling the structure of the variable regions. The light and heavy chains of mAQC2 were aligned against a nonredundant database to determine which structural frames to use to construct three-dimensional models of the mAQC2 light and heavy chains. Using FASTA, the light chain was found to have 82% sequence identity to monoclonal murine antibody ab57 (1CLOL), whereas the heavy chain was found to have 76% sequence identity to murine 6d9 Fab fragment (1HYY). Using the molecular modeling software package SYBYL (Tripos Inc.), the approximate three-dimensional structures of the mAQC2 light and heavy chains were built using the light chain of ab57 and the heavy chain of 6d9, respectively. The structural integrity of the models was assessed at the console and was found to be reasonable.

Design of the reshaped variable regions. Two approaches were used to choose human acceptor frameworks to "accept" mAQC2's CDRs. The first approach was by homology matching and the other by using consensus human Ig sequences. Under the homology approach, the Kabat database, the nonredundant database from NCBI, ENTREZ (The National Institutes of Health), and the Incyte database were searched using the software programs FASTA and BLAST. The choice of human acceptor frameworks was made based on sequence identity between mAQC2 frameworks and human frameworks (excluding frameworks from previously humanized antibodies) and the source of the antibody.

The frameworks from an immunoglobulin variable region gene having a GENBANK accession number of gi:587330 (human kappa subgroup I Vκ-1c47) were eventually chosen for the light chain of the humanized antibody (Welschof et al., *J. Immunol. Meth.* 179:203-14 (1995)). The frameworks from Amulc11 (Kabat ID 044469; human subgroup III) were chosen for the heavy chain of the humanized antibody (Huang et al., *J. Immunol.* 151:5290-300 (1993)).

Back mutations of the human frameworks. Strategies for determining which back mutations to make are available on the Humanization bY Design web sites under mirrored urls: http://world wide web. mathbio.nimr.mrc.ac.uk/jsaldan and http://world wide web. cryst.bbk.ac.uk/~ubcg07s. Previous experiments have shown that it is important to retain canonical residues, interface packing residues and unusual murine residues that are close to the binding site. In addition, residues in the "Vernier Zone," which forms a platform on which the CDRs rest (Foote et al., *J. Mol. Biol.* 224, p. 487 (1992)) and those close to CDR H3 should be considered.

Four reshaped versions were designed for each of the variable light and heavy chains, as shown in Table 1. Two of the four versions for each chain were designed by homology matching (designated huAQC2-h1 and -h2) and the other two versions by consensus matching (huAQC2-c1 and -c2). It should be noted that the sequences for huAQC-h1 heavy chain and huAQC-c1 heavy chain are identical.

TABLE 1

Sequences of mAQC2, huAQC2, and human frameworks

LIGHT CHAIN

| | FR1 |
|---|---|
| Vk-1c147 | D--M--S-SSL---V-DR--I--* |
| huAQC2-h2 | ------S-SSL---V-DR--I-- |
| huAQC2-h1 | ------S-SSL---V-DR--I-- |
| mAQC2 | QIVLTQFPALMSASPGEKVTMTC |
| huAQC2-c1 | --Q---S-SSL---V-DR--I-- |
| huAQC2-c2 | --Q---S-SSL---V-DR--I-- |

| | CDR1 | FR2 |
|---|---|---|
| Vk-1c147 | R--Q-ISYLN | ------GKA--LL-- |
| huAQC2-h2 | ---------- | ------GKA--LL-- |
| huAQC2-h1 | ---------- | ------GKA------ |
| mAQC2 | SASSSVNHMF | WYQQKPKSSPKPWIY |
| huAQC2-c1 | ---------- | ------GKA------ |
| huAQC2-c2 | ---------- | ------GKA--LL-- |

| | CDR2 | FR3 |
|---|---|---|
| Vk-1c147 | AA-S-Q- | ---S---------DFT-----LQP--F----- |
| huAQC2-h2 | ------- | ---S---------D-T-----LQP--F----- |
| huAQC2-h1 | ------- | ---S---------D-T-----LQP--F----- |
| mAQC2 | LTSNLAS | GVPARFSGSGSGTSYSLTISSMEAEDAATYYC |
| huAQC2-c1 | ------- | ---S---------D-T-----LQP--F----- |
| huAQC2-c2 | ------- | ---S---------D-T-----LQP--F----- |

| | CDR3 | FR4 | Framework changes |
|---|---|---|---|
| Vk-1c147 | --SYST-L- | ------V--- | 25 |
| huAQC2-h2 | --------- | ------V--- | 21 |
| huAQC2-h1 | --------- | ------V--- | 19 |
| mAQC2 | QQWSGNPWT | FGGGTKLEIK** | 0 |
| huAQC2-c1 | --------- | --Q---V--- | 21 |
| huAQC2-c2 | --------- | --Q---V--- | 23 |

HEAVY CHAIN:

| | FR1 | CDR1 |
|---|---|---|
| AMU1C11 | E-QL-------IQ-----R-S------TV- | SNY-- |
| huAQC2-h2 | E-QL-------IQ-----R-S------T-- | ----- |
| hUAQC2-h1 | --QL--------Q-----R-S--------- | ----- |
| mAQC2 | DVKVVESGGGLVKPGGSLKLACAASGFSFS | RYTMS |
| huAQC2-c1 | --QL--------Q-----R-S--------- | ----- |
| huAQC2-c2 | E-QL--------Q-----R-S------T-- | ----- |

| | FR2 | CDR2 |
|---|---|---|
| AMU1C11 | ----A-G-G----S | V-YS--S---A----- |
| huAQC2-h2 | ----A-G-G----- | ---------------- |
| huAQC2-h1 | ----A-G-G----- | ---------------- |

TABLE 1-continued

Sequences of mAQC2, huAQC2, and human frameworks

| mAQC2    | WVRQIPEKRLEWVA | TISGGGHTYYLDSVKG |
|----------|----------------|------------------|
| huAQC2-c1 | ----A-G-G----- | ---------------- |
| huAQC2-c2 | ----A-G-G----- | ---------------- |

| | FR3 | CDR3 |
|---|---|---|
| AMU1C11 | --------S---------N---A----V---AS | IRFLEWS--Y |
| huAQC2-h2 | --------S---------N---A----V----- | ---------- |
| huAQC2-h1 | --------S---------N---A----V----- | ---------- |
| mAQC2 | RFTISRDNAKNTLYLQMSSLRSEDTAMYYCTR | GFGDGGYFDV |
| huAQC2-c1 | --------S---------N---A----V----- | ---------- |
| huAQC2-c2 | --------S---------N---A----V----- | ---------- |

| | FR4 | Framework changes |
|---|---|---|
| AMU1C11 | -----L----- | 20 |
| huAQC2-h2 | -----L----- | 16 |
| huAQC2-h1 | -----L----- | 13 |
| mAQC2 | WGQGTTVTVSS*** | 0 |
| huAQC2-c1 | -----L----- | 13 |
| huAQC2-c2 | -----L----- | 15 |

*Dashes indicate identity with the mAQC2 amino acid sequence.
**Part of SEQ ID NO:1.
***Part of SEQ ID NO:2.

Some of the back mutations are discussed below.
(1) light chain:
1 D->Q This mutation was made in all versions since previous reshaping experiments (e.g. Kolbinger et al, *Protein Eng.* 6, p. 971(1993)) suggested its importance for antigen binding.
4 M->L This is a vernier residue and was retained in all versions.
46 L->P This residue is both an interfacial and vernier residue and was retained only in h1 and c1.
47 L->W This is a vernier residue and was retained only in h1 and c1.
71 F->Y This residue is in an important canonical position and was retained in all versions.
(2) heavy chain:
1 E->D This back mutation was made in h1 (i.e., c1) only.
12 I->V The residue I is unusual in human and was retained in the h2 only.
28 T->S This is a vernier residue and was retained in h1 only.
29 V->F This is a canonical residue and was retained in all versions.
49 S->A This is a vernier residue and was retained in all versions.
93 A->T This is a vernier residue and interfacial and was retained in all versions.
94 S->R This is a canonical residue and was retained in both versions.

The huAQC2 variable regions were made by USE mutagenesis as described above, using the chAQC2 variable domain plasmids as starting templates. The human acceptor framework ("FR") cDNA sequences were Kabat #Z37334 for the light chain and Kabat #U00490 for the heavy chain. To facilitate identification of mutated plasmids, silent mutations were introduced to change restriction sites. Mutated plasmids were identified by the restriction site changes. The variable region cDNA sequences in the resultant plasmids were confirmed by DNA sequencing.

The h1 and c1 versions of heavy chain (which were identical) were made by using plasmid pAND094 as template. The mutagenic primers were: FR1 primer 5' GGT GCC CAC TCC GAC GTC CAG CTG GTC GAG TCA GGG GGA GGC TTA GTC CAG CCT GGA GGG TCC CTG AGA CTC TCC TGT GCA GCC TCT GGA TTC 3' (SEQ ID NO:20), which introduced TaqI and PvuII sites, and eliminated a DdeI site; FR2 primer 5' ATG TCT TGG GTT CGC CAG GCT CCG GGG AAG GGG CTG GAG TGG GTC GCA ACC 3' (SEQ ID NO:21), which introduced a NciI site, and eliminated BspEI and EarI sites; FR3 primer 5' TTC ACC ATC TCC AGA GAC AAT TCC AAG AAC ACC CTG TAC CTG CAG ATG AAC AGT CTG AGG GCC GAG GAC ACA GCC GTG TAT TAC TGT ACA AGA 3' (SEQ ID NO:22), which introduced PstI and DdeI sites; and FR4 primer 5' TGG GGC CAA GGT ACC CTG GTC ACC GTC TCC TCA GGT GAG 3' (SEQ ID NO:23), which introduced KpnI and Eco0109I sites. The resultant h1 (i.e., c1) heavy chain plasmid was designated pAND104.

The c2 version of heavy chain were made by using pAND104 as template with the following mutagenic primers: FR1 primer 5' TCC TGT GCA GCC TCT GGA TTC ACC TTC AGT AGG TAT ACT ATG TCT TGG GTT 3' (SEQ ID NO:24), which introduced an AccI site; and FR1 primer 5' GCA CCA GGT GCG CAC TCC GAG GTC CAG CTG GTC GAG TCA 3' (SEQ ID NO:25), which introduced an FspI site and eliminated an AatII site. The resultant c2 heavy chain plasmid was designated pAND115.

The h2 version of heavy chain were made by using pAND115 as template with the following primer: FR1 primer 5' GAG TCA GGG GGA GGC TTA ATC CAG CCT GGA GGG TCC CTG 3' (SEQ ID NO:26), which eliminated a DdeI site. The resultant h2 heavy chain plasmid was designated pAND113.

To generate expression vectors for the huAQC2 heavy chains, the 0.43 kb NotI-HindIII heavy chain variable domain fragment from pAND104, pAND115, or pAND113, and the 1.21 kb HindIII-NotI fragment from pEAG964 (supra) were subcloned into the NotI site of pCH269 (supra). The resultant heavy chain expression plasmids were designated pAND114 (h1), pAND121 (c2), and pAND124 (h2), respectively.

The h1 version of light chain were made by using plasmid pAND093 as template. The mutagenic primers were: FR1 primer 5' CAA ATT GTT CTC ACC CAG TCT CCA TCC TCC CTG TCT GCG TCT GTA GGG GAC AGA GTC ACC ATC ACA TGC AGT GCC AGC TCA 3' (SEQ ID NO:27), which removed BstEII and PstI sites; FR2 primer 5' TTC TGG TAT CAG CAG AAG CCC GGG AAA GCC CCC AAA CCC TGG ATT 3' (SEQ ID NO:28), which introduced an NciI site; FR3 primer 5' GCT TCT GGA GTC CCT TCA CGC TTC AGT GGC AGT GGG TCT GGG ACA GAT TAC ACT CTC ACA ATC AGC AGC CTG CAA CCT GAA GAT TTT GCC ACT TAT TAC TGC CAG 3' (SEQ ID NO:29), which introduced a DdeI site and eliminated EcoO109I and AvaII sites; and FR4 primer 5' GGT GGA GGC ACT AAG GTG GAG ATC TAA CGG GCT 3' (SEQ ID NO:30), which introduced DdeI and StyI sites. The resultant h1 light chain plasmid was designated pAND103.

The h2 version of light chain were made by using pAND103 as template with the following primer: FR2 primer 5' CCC GGG AAA GCG CCC AAA CTC CTG ATT TAT CTC ACA TCC 3' (SEQ ID NO:31), which introduced HhaI and HaeII sites. The resultant h2 light chain plasmid was designated pAND116.

The c1 version of light chain used plasmid pAND103 template with the following primers: FR1 primer 5' GCC TCA GTC ATA ATG TCC CGG GGA CAA ATT CAG CTC ACC CAG TCT CCA TCC 3' (SEQ ID NO:32), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:33), which introduced a Bsp1286I site. The resultant c1 light chain plasmid was designated pAND118.

The c2 version of light chain were made by using plasmid pAND116 template with the following primers: FR1 primer 5' GCC TCA GTC ATA ATG TCC CGG GGA CAA ATT CAG CTC ACC CAG TCT CCA TCC 3' (SEQ ID NO:34), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:35), which introduced a Bsp1286I site. The resultant c2 light chain plasmid was designated pAND119.

To generate expression vectors for the huAQC2 light chains, the 0.44 kb NotI-BglII light chain variable domain fragment from pAND103, pAND116, pAND118, or pAND119, and the 0.68 kb BclI-NotI fragment from pEAG963 (supra) were subcloned into the NotI site of pCH269 (supra). The resultant light chain expression vectors were designated pAND117 (h1), pAND120 (h2), pAND122 (c1), and pAND123 (c2), respectively.

The expression vectors were co-transfected into 293-EBNA cells, and transfected cells were tested for antibody secretion and specificity. Cells transfected with an empty vector served as negative control. The whole cell lysates and the conditioned medium were immuno-precipitated with protein A. Western blot analysis of the precipitates (developed with anti-human heavy and light chain antibodies) indicated that huAQC2-transfected cells synthesized and efficiently secreted heavy and light chains at levels similar to chAQC2-transfected cells.

FACS analysis of VLA-1-expressing K562α1 cells stained with conditioned medium from the transfected cells was then performed. To do so, the K562α1 cells were incubated with the conditioned medium on ice for 120 min. The cells were then washed three times with a FACS buffer (PBS with 5% FBS and 0.05% sodium azide). The washed cells were resuspended in the buffer and incubated with PE-conjugated anti-human IgG (H+L) (Jackson ImmunoResearch Laboratories, Inc.) on ice for 30 min on ice. After the incubation, the cells were washed three times with the FACS buffer, and resuspended in the FACS buffer for analysis. The data are shown in Table 2, in which HuAQC2-h1 refers to an mAb consisting of the h1 version of the huAQC2 heavy chain (HC) and the h1 version of the huAQC2 light chain (LC) (see Table 1). Likewise, huAQC-h2 is an mAb consisting of the h2 versions of the heavy and light chains, huAQC2-c1 the c1 versions, and huAQC2-c2 the c2 versions. In the table, relative MFI refers to mean MFI normalized to that observed for chAQC2 blocked. Data shown represents the average from two independent transfections. These data indicated that the huAQC2-h2 and -c2 mAbs bound less well than huAQC2-h1 and -c1 relative to chAQC2.

TABLE 2

FACS staining of K562α1 cells by chAQC2 and huAQC2

| | Light chain | Heavy chain | Relative MFI |
|---|---|---|---|
| chAQC2 | pAND102 | pAND099 | 1.00 |
| huAQC2-h1 | pAND117 | pAND114 | 1.50 |
| huAQC2-h2 | pAND120 | pAND124 | 0.64 |
| huAQC2-c1 | pAND122 | pAND114 | 1.50 |
| huAQC2-c2 | pAND123 | pAND121 | 0.68 |
| huAQC2 LC c1/HC c2 | pAND122 | pAND121 | 2.21 |
| huAQC2 LC c2/HC c1 | pAND123 | pAND114 | 0.76 |
| huAQC2 LC unblocked c1/HC c2 | pAND150* | pAND121 | 0.75 |
| huAQC2 LC L46P c2/HC c2 | pAND133** | pAND121 | 1.50 |
| huAQC2 LC L47W c2/HC c2 | pAND132*** | pAND121 | 1.00 |

*It encodes huAQC2 LC c1 with an unblocked N-terminus Q1D.
**It encodes huAQC2 LC c2 with L46P.
***It encodes huAQC2 LC c2 with L47W.

Co-transfections of 293-EBNA cells with chAQC2 and huAQC2-h1, -h2, -c1 and -c2 were scaled up. Antibodies in the conditioned media were purified with Protein A-Sepharose. Purified mAbs were assayed by FACS for activity. The protocol as follows.

1. Count cells from flask that was split 1:4 on the day prior to the assay.
2. Pellet cells and resuspend at 2.5e5 cells/ml in FACS buffer (5% FBS in PBS—with 0.02% NaAzide).
3. Pipette 100 μl of cells into the wells of a 96 well V bottom plate.
4. Prepare 1:3 serial dilutions of AQC2 starting at 3 μg/ml in FACS buffer.
5. Pellet the cells for 5 minutes at 800×g and flick plate to remove buffer.
6. Resuspend the cells in 100 μl of the diluted antibody series.
7. Incubate for 2 hours on ice.
8. Wash plate. Pellet the cells for 3 minutes at 800×g and flick plate to remove buffer.
9. Resuspend the cells in 100 μl of secondary antibody (diluted 1:100 in FACS buffer).
10. Incubate for 30 minutes on ice.
11. Wash plate (see above).
12. Resuspend cells in 25 μl of FACS buffer.
13. Centrifuge the FACS tubes briefly to ensure that the 50 μl is in the bottom of the tubes.
14. Vortex each tube vigorously and collect 5000 events.

Figure 17:
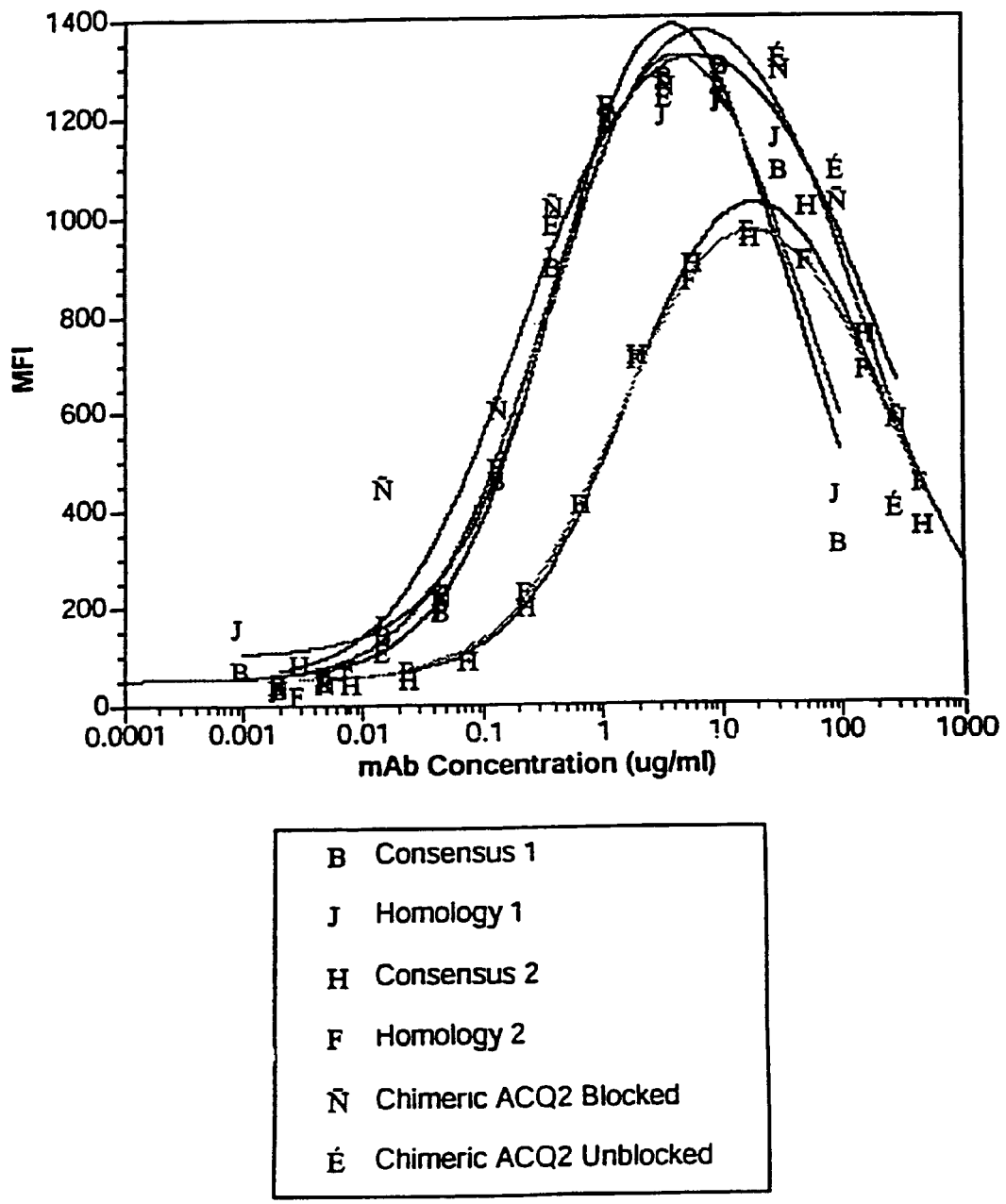
FIG. 17. Characterization of Humanized AQC2 Forms by FACS.

The data are shown in FIG. 17. These data confirmed that huAQC2-h2 and -c2 bound less well than huAQC2-h1 and -c1 relative to chAQC2.

The consensus versions of huAQC2 were studied further because they would be less immunogenic when used to treat patients with chronic indications. Mix-and-match cotransfections were performed to identify whether a single chain was responsible for the apparent decrease in binding seen with huAQC2-c2. The co-transfections suggested that the reduction could be attributed to the c2 light chain (encoded by pAND123), which differed from the c1 light chain (encoded by pAND122) at only two residues in the FR2 region: P46L and W47L.

To examine the individual contributions of each of these two changes, new c2 light chain expression vectors were constructed. Plasmid pAND125, the L47W variant of the c2 light chain was made using pAND119 as a template with the following mutagenic primer: FR2 primer 5' GGG AAA GCA CCC AAA CTC TGG ATC TAT CTC ACA TCC AAC 3' (SEQ ID NO:36), which introduced HhaI and HaeII sites. Plasmid pAND126, the L46P variant of the c2 light chain, was made by using pAND119 as a template with the following mutagenic primer: FR2 primer 5' AAG CCC GGG AAG GCG CCC AAA CCC CTG ATT TAT CTC ACA TCC AAC 3' (SEQ ID NO:37), which introduced BsaHI, BanI, and NarI sites. Expression vectors for these new huAQC2 light chains were made by subcloning the 0.44 kb NotI-BglII light chain variable domain fragment from pAND125 or pAND126, and the 0.68 kb BclI-NotI fragment from pEAG963 (supra) into the NotI site of pCH269 (supra). The resultant plasmids were designated pAND132 (c2 with L47W) (SEQ ID NO:47), and pAND133 (c2 with L46P) (SEQ ID NO:70), respectively.

Co-transfections of the new light chain plasmids with each of the huAQC2 heavy chain plasmids were performed. VLA-1 binding was examined by FACS. The data demonstrate that the L47W back mutation failed to improve binding. The L46P mutation improved the peak of the binding curve, but the EC50 was still right-shifted relative to the behavior of huAQC2 version 1 (Table 2, supra). These results suggested that both back mutations were needed for full binding activity.

A genetically unblocked c1 light chain was also made, since the Q1D variant would be one residue more "humanized." The Q1D mutant, designated pAND148, was made with the template pAND118 with the following mutagenic primer: FR1 primer 5' GTC ATA ATG TCC CGG GGA GAT ATC CAG CTC ACC CAG TCT 3' (SEQ ID NO:38), which introduced a new EcoRI site and removed an ApoI site. An expression vector for this last variant of the huAQC2 light chain was made by subcloning the 0.44 kb NotI-BglII light chain variable domain fragment from pAND148 and the 0.68 kb BclI-NotI fragment from pEAG963 into the NotI site of pCH269, producing the light chain expression vector pAND150 (c1 with unblocked N-terminus Q1D). Co-expression of the genetically unblocked light chain with the c2 heavy chain (i.e., "huAQC2 LC c1 unblocked/HC c2"; designated huAQC2-c4) was equivalent to that of "huAQC2 LC c1/HC c2" (designated as huAQC2-c3). VLA-1 binding was confirmed by FACS on VLA1-expressing K562α1 cells (Table 2).

Figure 18:
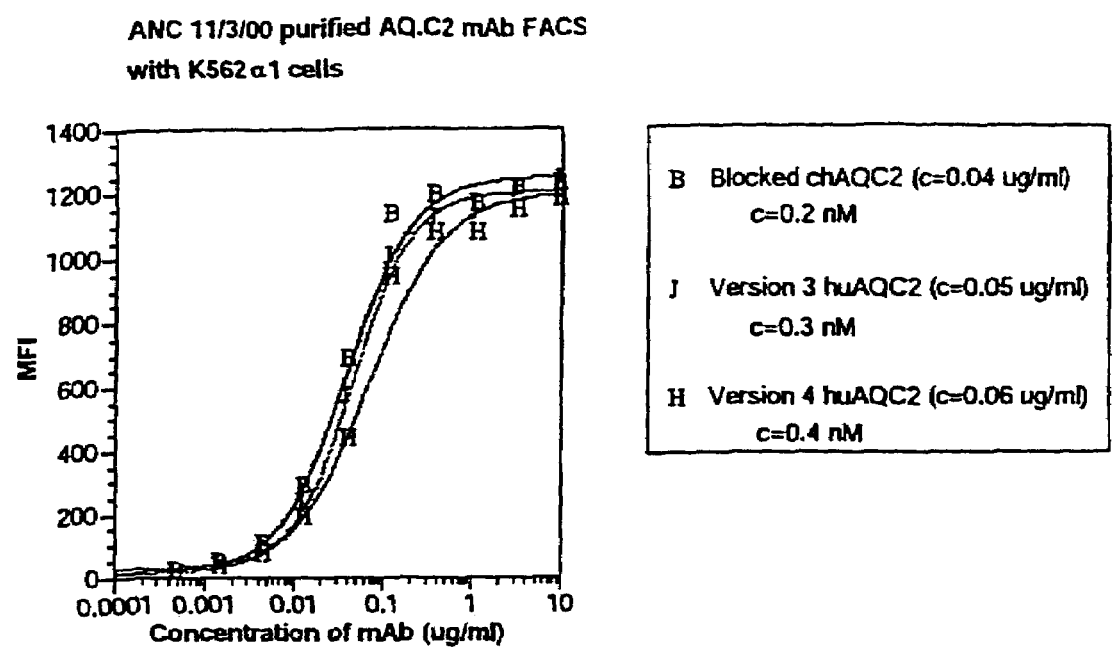
FIG. 18. Characterization of Humanized AQC2 Forms by FACS.

Co-transfections of 293-EBNA cells with chAQC2 and huAQC2-h1, -h2, -c1, -c2, -c3, and -c4. Antibodies in the conditioned media were purified on Protein A-Sepharose. The purified mAbs were assayed for activity (FIGS. 17 and 18). HuAQC2-c3 was chosen as the drug candidate, since its properties were more similar to chAQC2. Vectors were then designed for stable expression of huAQC2-c3 in CHO cells. The vectors contained a cDNA for the huAQC2 c1 LC or c2 HC, with the 5' and 3' UTRs eliminated and the heavy chain C-terminal lysine genetically deleted to ensure product homogeneity. The final vectors were pAND162 (light chain), pAND160 (heavy chain). As used herein, huAQC2-c3 is also called hAQC2.

The full polypeptide sequences of hAQC2 are as follows.

Light Chain (Plasmid: pAND162)

```
                                                 (SEQ ID NO:3)
  1  QIQLTQSPSS LSASVGDRVT ITCSASSSVN HMFWYQQKPG
     KAPKPWIYLT

51  SNLASGVPSR FSGSGSGTDY TLTISSLQPE DFATYYCQQW
     SGNPWTFGQG

101  TKVEIKRTVA APSVFIFPPS DEQLKSGTAS VVCLLNNFYP
     REAKVQWKVD

151  NALQSGNSQE SVTEQDSKDS TYSLSSTLTL SKADYEKHKV
     YACEVTHQGL

201  SSPVTKSFNR GEC
```

Heavy Chain (Plasmid: pAND160)

```
  1  EVQLVESGGG LVQPGGSLRL SCAASGFTFS RYTMSWVRQA  PGKGLEWVAT  (SEQ ID NO:4)

51  ISGGGHTYYL DSVKGRFTIS RDNSKNTLYL QMNSLRAEDT  AVYYCTRGFG

101  DGGYFDVWGQ GTLVTVSSAS TKGPSVFPLA PSSKSTSGGT  AALGCLVKDY

151  FPEPVTVSWN SGALTSGVHT FPAVLQSSGL YSLSSVVTVP  SSSLGTQTYI

201  CNVNHKPSNT KVDKKVEPKS CDKTHTCPPC PAPELLGGPS  VFLFPPKPKD

251  TLMISRTPEV TCVVVDVSHE DPEVKFNWYV DGVEVHNAKT  KPREEQYNST

301  YRVVSVLTVL HQDWLNGKEY KCKVSNKALP APIEKTISKA  KGQPREPQVY

351  TLPPSRDELT KNQVSLTCLV KGFYPSDIAV EWESNGQPEN  NYKTTPPVLD

401  SDGSFFLYSK LTVDKSRWQQ GNVFSCSVMH EALRNHYTQK  SLSLSPG
```

Other heavy and light chain polypeptide and nucleotide sequences are shown below.

A. chAQC2 heavy chain (Pand099) (SEQ ID NOs:39 and 40. The former No refers to the nucleotide sequence and the latter to the polypeptide sequence. The same order is used in the following numbering.)

```
1
GAGGTCCAGCTGGTCGAGTCAGGGGGAGGCTTAGTCCAGCCTGGAGGGTCCCTGAGACTC

E  V  Q  L  V  E  S  G  G  G  L  V  Q  P  G  G  S  L  R  L

61
TCCTGTGCAGCCTCTGGATTCACCTTCAGTAGGTATACTATGTCTTGGGTTCGCCAGGCT

S  C  A  A  S  G  F  T  F  S  R  Y  T  M  S  W  V  R  Q  A

121
CCGGGGAAGGGGCTGGAGTGGGTCGCAACCATTAGTGGTGGTGGTCACACCTACTAT

P  G  K  G  L  E  W  V  A  T  I  S  G  G  G  H  T  Y  Y  L

181
GACAGTGTGAAGGGCCGATTCACCATCTCCAGAGACAATTCCAAGAACACCCTGTACCTG

D  S  V  K  G  R  F  T  I  S  R  D  N  S  K  N  T  L  Y  L

241
CAGATGAACAGTCTGAGGGCCGAGGACACAGCCGTGTATTACTGTACAAGAGGTTTTGGA

Q  M  N  S  L  R  A  E  D  T  A  V  Y  Y  C  T  R  G  F  G

301
GACGGGGGGTACTTCGATGTCTGGGGCCAAGGTACCCTGGTCACCGTCTCCTCAGG

D  G  G  Y  F  D  V  W  G  Q  G  T  L  V  T  V  S  S

B. hAQC2 HC h1 and c1 (pAND114)
1
GACGTCCAGCTGGTCGAGTCAGGGGGAGGCTTAGTCCAGCCTGGAGGGTCCCTGAGACTC    (SEQ ID NOs:41 and 42)

D  V  Q  L  V  E  S  G  G  G  L  V  Q  P  G  G  S  L  R  L

61
TCCTGTGCAGCCTCTGGATTCAGTTTCAGTAGATATACTATGTCTTGGGTTCGCCAGGCT

S  C  A  A  S  G  F  S  F  S  R  Y  T  M  S  W  V  R  Q  A

121
CCGGGGAAGGGGCTGGAGTGGGTCGCAACCATTAGTGGTGGTGGTCACACCTACTATCTA

P  G  K  G  L  E  W  V  A  T  I  S  G  G  G  N  T  Y  Y  L

181
GACAGTGTGAAGGGCCGATTCACCATCTCCAGAGACAATTCCAAGAACACCCTGTACCTG

D  S  V  K  G  R  F  T  I  S  R  D  N  S  K  N  T  L  Y  L

241
CAGATGAACAGTCTGAGGGCCGAGGACACAGCCGTGTATTACTGTACAAGAGGTTTTGGA

Q  M  N  S  L  R  A  E  D  T  A  V  Y  Y  C  T  R  G  F  G

301
GACGGGGGGTACTTCGATGTCTGGGGCCAAGGTACCCTGGTCACCGTCTCCTCA

D  G  G  Y  F  D  V  W  G  Q  G  T  L  V  T  V  S  S

C. hAQC2 h2 heavy chain (pAND124)
1
GAGGTCCAGCTGGTCGAGTCAGGGGGAGGCTTAATCCAGCCTGGAGGGTCCCTGAGACTC    (SEQ ID NOs:43 and 44)

E  V  Q  L  V  E  S  G  G  G  L  I  Q  P  G  G  S  L  R  L

61
TCCTGTGCAGCCTCTGGATTCACCTTCAGTAGGTATACTATGTCTTGGGTTCGCCAGGCT

S  C  A  A  S  G  F  T  F  S  R  Y  T  M  S  W  V  R  Q  A

121
CCGGGGAAGGGGCTGGAGTGGGTCGCAACCATTAGTGGTGGTGGTCACACCTACTATCTA

P  G  K  G  L  E  W  V  A  T  I  S  G  G  G  H  T  Y  Y  L
```

-continued

```
181
GACAGTGTGAAGGGCCGATTCACCATCTCCAGAGACAATTCCAAGAACACCCTGTACCTG

D  S  V  K  G  R  F  T  I  S  R  D  N  S  K  N  T  L  Y  L

241
CAGATGAACAGTCTGAGGGCCGAGGACACAGCCGTGTATTACTGTACAAGAGGTTTTGGA

Q  M  N  S  L  R  A  E  D  T  A  V  Y  Y  C  T  R  G  F  G

301
GACGGGGGGTACTTCGATGTCTGGGGCCAAGGTACCCTGGTCACCGTCTCCTCAGG

D  G  G  Y  F  D  V  W  G  Q  G  T  L  V  T  V  S  S
```

D. hAQC2 c2 heavy chain (pAND121)

```
1
GAGGTCCAGCTGGTCGAGTCAGGGGGAGGCTTAGTCCAGCCTGGAGGGTCCCTGAGACTC    (SEQ ID NOs:45 AND 2)

E  V  Q  L  V  E  S  G  G  G  L  V  Q  P  G  G  S  L  R  L

61
TCCTGTGCAGCCTCTGGATTCACCTTCAGTAGGTATACTATGTCTTGGGTTCGCCAGGCT

S  C  A  A  S  G  F  T  F  S  R  Y  T  M  S  W  V  R  Q  A

121
CCGGGGAAGGGGCTGGAGTGGGTCGCAACCATTAGTGGTGGTGGTCACACCTACTATCTA

P  G  K  G  L  E  W  V  A  T  I  S  G  G  G  H  T  Y  Y  L

181
GACAGTGTGAAGGGCCGATTCACCATCTCCAGAGACAATTCCAAGAACACCCTGTACCTG

D  S  V  K  G  R  F  T  I  S  R  D  N  S  K  N  T  L  Y  L

241
CAGATGAACAGTCTGAGGGCCGAGGACACAGCCGTGTATTACTGTACAAGAGGTTTTGGA

Q  M  N  S  L  R  A  E  D  T  A  V  Y  Y  C  T  R  G  F  G

301
GACGGGGGGTACTTCGATGTCTGGGGCCAAGGTACCCTGGTCACCGTCTCCTCAGG

D  G  Y  F  D  V  W  G  Q  G  T  L  V  T  V  S  S
                                                           40
```

E. chAQC2 blocked light chain (Pand102) (SEQ ID NOs:46 and 1)

```
1
CAAATTGTTCTCACCCAGTTTCCAGCACTCATGTCTGCGTCTCCAGGGGAGAAGGTCACC

Q  I  V  L  T  Q  F  P  A  L  M  S  A  S  P  G  E  K  V  T

61
ATGACCTGCAGTGCCAGCTCAAGTGTAAATCACATGTTCTGGTATCAGCAGAAGCCAAAA

M  T  C  S  A  S  S  S  V  N  H  M  F  W  Y  Q  Q  K  P  K

121
TCCTCCCCCAAACCCTGGATTTATCTCACATCCAACCTGGCTTCTGGAGTCCCTGCTCGC

S  S  P  K  P  W  I  Y  L  T  S  N  L  A  S  G  V  P  A  R

181
TTCAGTGGCAGTGGGTCTGGGACCTCTTACTCTCTCACAATCAGCAGCATGGAGGCTGAA

F  S  G  S  G  S  G  T  S  Y  S  L  T  I  S  S  M  E  A  E

241
GATGCTGCCACTTATTACTGCCAGCAGTGGAGTGGTAACCCGTGGACGTTCGGTGGAGGC

D  A  A  T  Y  Y  C  Q  Q  W  S  G  N  P  W  T  F  G  G
```

```
301
ACCAAGCTGGAGATCAAA

T  K  L  E  I  K
```

F. hAQC2 h1 light chain (pAND117) (SEQ ID NOs:48 and 49)

```
1
CAAATTGTTCTCACCCAGTCTCCATCCTCCCTGTCTGCGTCTGTAGGGGACAGAGTCACC

Q  I  V  L  T  Q  S  P  S  S  L  S  A  S  V  G  D  R  V  T

61
ATCACATGCAGTGCCAGCTCAAGTGTAAATCACATGTTCTGGTATCAGCAGAAGCCCGGG

I  T  C  S  A  S  S  S  V  N  H  M  F  W  Y  Q  Q  K  P  G

121
AAAGCCCCCAAACCCTGGATTTATCTCACATCCAACCTGGCTTCTGGAGTCCCTTCACGC

K  A  P  K  P  W  I  Y  L  T  S  N  L  A  S  G  V  P  S  R

181
TTCAGTGGCAGTGGGTCTGGGACAGATTACACTCTCACAATCAGCAGCCTGCAACCTGAA

F  S  G  S  G  S  G  T  D  Y  T  L  T  I  S  S  L  Q  P  E

241
GATTTTGCCACTTATTACTGCCAGCAGTGGAGTGGTAACCCGTGGACGTTCGGTGGAGGC

D  F  A  T  Y  Y  C  Q  Q  W  S  G  N  P  W  T  F  G  G

301
ACTAAGGTGGAGATCAAA

T  K  V  E  I  K
```

G. hAQC2 h2 light chain (pAND120) (SEQ ID NOs:50 and 51)

```
1
CAAATTGTTCTCACCCAGTCTCCATCCTCCCTGTCTGCGTCTGTAGGGGACAGAGTCACC

Q  I  V  L  T  Q  S  P  S  S  L  S  A  S  V  G  D  R  V  T

61
ATCACATGCAGTGCCAGCTCAAGTGTAAATCACATGTTCTGGTATCAGCAGAAGCCCGGG

I  T  C  S  A  S  S  S  V  N  H  M  F  W  Y  Q  Q  K  P  G

121
AAAGCGCCCAAACTCCTGATTTATCTCACATCCAACCTGGCTTCTGGAGTCCCTTCACGC

K  A  P  K  L  L  I  Y  L  T  S  N  L  A  S  G  V  P  S  R

181
TTCAGTGGCAGTGGGTCTGGGACAGATTACACTCTCACAATCAGCAGCCTGCAACCTGAA

F  S  G  S  G  S  G  T  D  Y  T  L  T  I  S  S  L  Q  P  E

241
GATTTTGCCACTTATTACTGCCAGCAGTGGAGTGGTAACCCGTGGACGTTCGGTGGAGGC

D  F  A  T  Y  Y  C  Q  Q  W  S  G  N  P  W  T  F  G  G

301
ACTAAGGTGGAGATCAAA

T  K  V  E  I  K
```

H. hAQC2 c1 light chain (pAND122) (SEQ ID NOs:52 and 1)

```
1
CAAATTCAGCTCACCCAGTCTCCATCCTCCCTGTCTGCGTCTGTAGGGGACAGAGTCACC
    Q  I  Q  L  T  Q  S  P  S  S  L  S  A  S  V  G  D  R  V  T

61
ATCACATGCAGTGCCAGCTCAAGTGTAAATCACATGTTCTGGTATCAGCAGAAGCCCGGG
    I  T  C  S  A  S  S  S  V  N  H  M  F  W  Y  Q  Q  K  P  G

121
AAAGCCCCCAAACCCTGGATTTATCTCACATCCAACCTGGCTTCTGGAGTCCCTTCACGC
    K  A  P  K  P  W  I  Y  L  T  S  N  L  A  S  G  V  P  S  R

181
TTCAGTGGCAGTGGGTCTGGGACAGATTACACTCTCACAATCAGCAGCCTGCAACCTGAA
    F  S  G  S  G  S  G  T  D  Y  T  L  T  I  S  S  L  Q  P  E

241
GATTTTGCCACTTATTACTGCCAGCAGTGGAGTGGTAACCCGTGGACGTTCGGTCAGGGC
    D  F  A  T  Y  Y  C  Q  Q  W  S  G  N  P  W  T  F  G  Q  G

301
ACTAAGGTGGAGATCAAA
    T  K  V  E  I  K
```

I. hAQC2 c2 light chain (pAND123) (SEQ ID NOs:53 and 54)

```
1
CAAATTCAGCTCACCCAGTCTCCATCCTCCCTGTCTGCGTCTGTAGGGGACAGAGTCACC
    Q  I  Q  L  T  Q  S  P  S  S  L  S  A  S  V  G  D  R  V  T

61
ATCACATGCAGTGCCAGCTCAAGTGTAAATCACATGTTCTGGTATCAGCAGAAGCCCGGG
    I  T  C  S  A  S  S  S  V  N  H  M  F  W  Y  Q  Q  K  P  G

121
AAAGCGCCCAAACTCCTGATTTATCTCACATCCAACCTGGCTTCTGGAGTCCCTTCACGC
    K  A  P  K  L  L  I  Y  L  T  S  N  L  A  S  G  V  P  S  R

181
TTCAGTGGCAGTGGGTCTGGGACAGATTACACTCTCACAATCAGCAGCCTGCAACCTGAA
    F  S  G  S  G  S  G  T  D  Y  T  L  T  I  S  S  L  Q  P  E

241
GATTTTGCCACTTATTACTGCCAGCAGTGGAGTGGTAACCCGTGGACGTTCGGTCAGGGC
    D  F  A  T  Y  Y  C  Q  Q  W  S  G  N  P  W  T  F  G  Q  G

301
ACTAAGGTGGAGATCAAA
    T  K  V  E  I  K
```

J. chAQC2 unblocked light chain (pAND098) (SEQ ID NOs:55 and 56)

```
1
GAAATTGTTCTCACCCAGTTTCCAGCACTCATGTCTGCGTCTCCAGGGGAGAAGGTCACC
    E   I   V   L   T   Q   F   P   A   L   M   S   A   S   P   G   E   K   V   T
61
ATGACCTGCAGTGCCAGCTCAAGTGTAAATCACATGTTCTGGTATCAGCAGAAGCCAAAA
    M   T   C   S   A   S   S   S   V   N   H   M   F   W   Y   Q   Q   K   P   K
121
TCCTCCCCCAAACCCTGGATTTATCTCACATCCAACCTGGCTTCTGGAGTCCCTGCTCGC
    S   S   P   K   P   W   I   Y   L   T   S   N   L   A   S   G   V   P   A   R
181
TTCAGTGGCAGTGGGTCTGGGACCTCTTACTCTCTCACAATCAGCAGCATGGAGGCTGAA
    F   S   G   S   G   S   G   T   S   Y   S   L   T   I   S   S   M   E   A   E
241
GATGCTGCCACTTATTACTGCCAGCAGTGGAGTGGTAACCCGTGGACGTTCGGTGGAGGC
    D   A   A   T   Y   Y   C   Q   Q   W   S   G   N   P   W   T   F   G   G   G
301
ACCAAGCTGGAGATCAAA
    T   K   L   E   I   K
```

K. huAQC2 unblocked c1 light chain (pAND150) (SEQ ID NOs:57 and 58)

```
1
GATATCCAGCTCACCCAGTCTCCATCCTCCCTGTCTGCGTCTGTAGGGGACAGAGTCACC
    D   I   Q   L   T   Q   S   P   S   S   L   S   A   S   V   G   D   R   V   T
61
ATCACATGCAGTGCCAGCTCAAGTGTAAATCACATGTTCTGGTATCAGCAGAAGCCCGGG
    I   T   C   S   A   S   S   S   V   N   H   M   F   W   Y   Q   Q   K   P   G
121
AAAGCCCCCAAACCCTGGATTTATCTCACATCCAACCTGGCTTCTGGAGTCCCTTCACGC
    K   A   P   K   P   W   I   Y   L   T   S   N   L   A   S   G   V   P   S   R
181
TTCAGTGGCAGTGGGTCTGGGACAGATTACACTCTCACAATCAGCAGCCTGCAACCTGAA
    F   S   G   S   G   S   G   T   D   Y   T   L   T   I   S   S   L   Q   P   E
241
GATTTTGCCACTTATTACTGCCAGCAGTGGAGTGGTAACCCGTGGACGTTCGGTCAGGGC
    D   F   A   T   Y   Y   C   Q   Q   W   S   G   N   P   W   T   F   G   Q   G
301
ACTAAGGTGGAGATCAAA
    T   K   V   E   I   K
```

Example 22

This example describes the characterization of various AQC2 antibodies of the invention.

Solid-phase assay for α1 I domain binding. Fifty μl of 10 mg/ml α1 I domain-GST fusion protein was added to a CORNING COSTAR EASY WASH polystyrene 96-well plate (Gotwals et al., *Biochemistry*, 38, 8280-8 (1999)). Following incubation at 4° C. for 16 hrs, the plate was washed four times with 350 μl of 0.1% Tween-20 in PBS in a plate washer. The plate was blocked by addition of 180 μl of 3% BSA in TBS at 25° C. for 60 min, and then washed as above. Dilutions of antibodies (50 μl/well) in TBS containing 1 mg/ml BSA (assay buffer) were prepared in a 96-well roundbottom plate, transferred to the α1 I domain-coated plate, and incubated for 60 min at 25° C. Following a final wash, 100 μl/well of TMB reagent (Pierce) was added. After 10 min, 100 μl of 1 M sulfuric acid was added, and the absorbance at 450 nm was read on a UV-Vis 96-well spectrophotometer.

Electrochemiluminescence assays for binding of α1β1 integrin or α1 I domain to collagen. Tosyl-activated DYNA-BEADS M-280 (Dynal, Inc.) were coated with 100 μg/ml type IV collagen (Sigma) according to the manufacturer's instructions. Cell lysates from α1-transfected K562 cells were prepared as follows. Cells were collected by centrifugation, resuspended at $10^8$ cells/ml in a lysis buffer containing 25 mM Tris, pH 7.4, 1% NP-40, 1 mM $CaCl_2$, 1 mM $MnCl_2$, 1 mM $MgCl_2$, 2% BSA, and 1 mM PMSF, and incubated at 4° C. for 60 min. Cell debris was removed by centrifugation at 12,000 rpm for 30 min and the resulting supernatant was used in subsequent experiments. Anti-β1 activating antibody TS2/16 and polyclonal anti-GST antibody (Pharmacia) were labeled with TAG-NHS ester (IGEN International, Inc., Gaithersburg, Md.) according to the manufacturer's instructions. Labeled antibodies were purified by gel filtration chromatography on SEPHADEX G25M (Pharmacia).

To carry out the binding assay, collagen-coated beads (1 mg/ml) were blocked for 5 min with 8% Lewis rat plasma in an assay buffer containing 50 mM HEPES, pH 7.5, 150 mM NaCl, and 0.1% Triton X-100. For the α1β1 binding assay, serial dilutions of antibodies were incubated with 10 μg of beads, cell lysate prepared from $10^5$ α1-transfected K562 cells (supra), and 0.1 μg/ml of TAG-TS2/16 in an assay buffer containing 1 mM $MnCl_2$. For the α1 I domain binding assay, the antibodies were incubated with 10 μg of beads, 0.1 μg/ml α1 I domain GST fusion protein, and 1 μg/ml of TAG-anti-GST in an assay buffer containing 1 mM $MnCl_2$. After one to two hours of agitation at room temperature, 200 μl of the assay buffer was added and the samples were read on an ORIGEN 1.5 electrochemiluminescence detector (IGEN). Plots are presented with arbitrary electrochemiluminescence units (ECL) on the ordinate axis.

Biotinylated mAQC2 competition assay. A 96-well plate was coated with 50 μl of 5 μg/ml α1 I domain GST fusion protein and blocked with 3% BSA in TBS as described above. Dilutions of antibodies (60 μl/well) in the assay buffer were prepared in a 96-well roundbottom plate, and 60 μl of 0.1 μg/ml biotinylated murine AQC2 in the assay buffer was added. Fifty microliters from each well was transferred to the coated plate and incubated for 3 hrs at 25° C. The plate was then washed as above, 50 μl of 1 μg/ml peroxidase-conjugated EXTRAVIDIN (Sigma) was added, and the plate was incubated another 2 hrs at 25° C. After a final wash, 100 μl/well of TMB reagent (Pierce) was added. After 10 min, 100 μl of 1 M sulfuric acid was added, and the absorbance at 450 nm was read on a UV-Vis 96-well spectrophotometer.

Experimental results. The experimental results are shown in FIGS. 16A-D and Table 3. The ability of mAQC2, chAQC2, hAQC2, and hAQC2' (i.e., huAQC2-c4; differing from hAQC2 only in that residue 1 of the hAQC2' light chain was D instead of Q) to (1) bind to human α1-transfected K562 cells (by FACS); (2) bind to immobilized α1-I domain (by ELISA); (3) compete with mAQC2 for binding to α1-I domain (ELISA); (4) block α1-I domain binding to collagen (Electrochemiluminescence assay); or (5) block α1β1 integrin binding to collagen (Electrochemiluminescence assay) was determined. The results are shown in FIGS. 16A-D, and calculated IC50 (for inhibition) or EC50 (for binding) values are given in Table 3. In each assay, each of the humanized AQC2 forms showed a similar ability to either bind VLA1 (or the α1 domain) or block binding to collagen (Note that in panel C, the observed difference in intensity between mAQC2 and the humanized forms derives from the use of an anti-murine-IgG secondary antibody, instead of an anti-human-IgG).

TABLE 3

Summary of assay results (all values in nM)

| Antibody | FACS (EC50) | VLA1 Inhibition (IC50) | α1I Inhibition (IC50) | ELISA (EC50) | Competition with biotin-AQC2 (IC50) |
|---|---|---|---|---|---|
| mAQC2 | n.d. | 0.0726 (±0.014) | 0.029 (±0.011) | 0.061 (±0.015) | 38 (±8.7) |
| Chimera | 0.25 | 0.071 (±0.002) | 0.027 (±0.007) | 0.176 (±0.058) | 30 (±6.9) |
| hAQC2 | 0.29 | 0.129 (±0.005) | 0.035 (±0.005) | 0.190 (±0.010) | 65 (±2.2) |
| hAQC2' | 0.43 | 0.125 (±0.018) | 0.037 (±0.001) | 0.313 (±0.072) | 69 (±25.7) |

We next tested whether changes at certain conservative residues in the CDRs could preserve the VLA-1 binding activity of hAQC2. DNA constructs encoding variants of hAQC2 with the following mutations were made by site-directed mutagenesis: (1) G55S in the heavy chain CDR2; (2) S24N in the light chain CDR1 (introducing an occupied N-linked glycosylation site); (3) G92S in the light chain CDR3; (4) a combination of (1) and (2); and (5) a combination of (1) and (3). The DNA constructs encoding both the heavy and light chains were then co-transfected into 293-EBNA cells, and the conditioned medium of the transfectants was assayed for antibody expression by Western blot and ELISA. The results indicated that the hAQC2 variants were expressed as efficiently as cognate hAQC2. FACS analysis using VLA-1-expressing K562 cells further showed that the VLA-1-binding activities of these variants were similar to hAQC2 itself. In sum, the amino acid substitutions did not alter the VLA-1 binding activity of hAQC2. Indeed, X-ray crystal structure of the RΔH/hAQC2 Fab complex (infra) shows that S24 and G92 of the light chain and G55 of the heavy chain are not in the binding pocket that is in contact with the α1-I domain.

Example 23

The effector functions of an immunoglobulin couple the immunoglobulin's antigen-binding activity to the inflammatory, cytotoxic and stimulatory arms of the immune system. Effector functions may impair the safety and efficacy of an immunoglobulin therapeutic product. To reduce the potential effector functions of hAQC2, mutations of L234A and L235A were made to its heavy chain to generate hsAQC2. For the same reason, a single mutation of N298Q (numbering according to SEQ ID NO:5) was made in the heavy chain of hAQC2 to generate an aglycosylated form of hAQC2, named haAQC2. Studies can be done to compare their efficacy, residual effector function, stability and immunogenicity to cognate hAQC2. Unless otherwise indicated, residue position numbers in constant regions as used herein are designated in accordance with the EU numbering convention.

The heavy chain polypeptide sequence of haAQC2 is as follows (Plasmid: pAND161):
```
  1 EVQLVESGGG LVQPGGSLRL SCAASGFTFS RYTMSWVRQA PGKGLEWVAT   (SEQ ID NO:5)
 51 ISGGGHTYYL DSVKGRFTIS RDNSKNTLYL QMNSLRAEDT AVYYCTRGFG
101 DGGYFDVWGQ GTLVTVSSAS TKGPSVFPLA PSSKSTSGGT AALGCLVKDY
151 FPEPVTVSWN SGALTSGVHT FPAVLQSSGL YSLSSVVTVP SSSLGTQTYI
201 CNVNHKPSNT KVDKKVEPKS CDKTHTCPPC PAPELLGGPS VFLFPPKPKD
251 TLMISRTPEV TCVVVDVSHE DPEVKFNWYV DGVEVHNAKT KPREEQYQST
301 YRVVSVLTVL HQDWLNGKEY KCKVSNKALP APIEKTISKA KGQPREPQVY
351 TLPPSRDELT KNQVSLTCLV KGFYPSDIAV EWESNGQPEN NYKTTPPVLD
401 SDGSFFLYSK LTVDKSRWQQ GNVFSCSVMH EALHNHYTQK SLSLSPG
```

The heavy chain polypeptide sequence of hsAQC2 is as follows (Plasmid:pAND171):
```
  1 EVQLVESGGG LVQPGGSLRL SCAASGFTFS RYTMSWVRQA PGKGLEWVAT   (SEQ ID NO:6)
 51 ISGGGHTYYL DSVKGRFTIS RDNSKNTLYL QMNSLRAEDT AVYYCTRGFG
101 DGGYFDVWGQ GTLVTVSSAS TKGPSVFPLA PSSKSTSGGT AALGCLVKDY
151 FPEPVTVSWN SGALTSGVHT FPAVLQSSGL YSLSSVVTVP SSSLGTQTYI
201 CNVNHKPSNT KVDKKVEPKS CDKTHTCPPC PAPEAAGGPS VFLFPPKPKD
251 TLMISRTPEV TCVVVDVSHE DPEVKFNWYV DGVEVHNAKT KPREEQYNST
301 YRVVSVLTVL HQDWLNGKEY KCKVSNKALP APIEKTISKA KGQPREPQVY
351 TLPPSRDELT KNQVSLTCLV KGFYPSDIAV EWESNGQPEN NYKTTPPVLD
401 SDGSFFLYSK LTVDKSRWQQ GNVFSCSVMH EALHNHYTQK SLSLSPG
```

Example 24

This example describes a method for determining the crystal structure of the complex of a rat/human chimeric α1-I domain of the α1β1 integrin and the hAQC2 Fab fragment.

Preparation of the Protein Complex

The hAQC2 Fab fragment was prepared from hAQC2 antibody using a variation of the procedure of the IMMUNOPURE® Fab preparation kit (Cat# 44885, Pierce, Rockford, Ill.). The intact hAQC2 antibody was concentrated to 12 mg/ml in a buffer containing 20 mM phosphate, 10 mM EDTA and 25 mM cysteine (pH 7.0). Immobilized papain was added at an enzyme to substrate ratio of 1:50, and digestion was allowed to occur overnight at 37° C. The immobilized papain was removed and the crude digest was dialyzed against 20 mM sodium acetate buffer (pH 4.5). The Fab fragment was separated from residual intact antibody, dimeric Fab fragment, and Fc fragment by cation exchange chromatography using a S-column (Poros HS/M, PERSEPTIVE Biosytems #PO42M26) with a shallow salt gradient. The Fab fragment was then exchanged into 0.1 M Hepes buffer (pH 8.0).

The chimeric α1-I domain used in the present invention is a rat/human chimeric I domain construct (mutant RΔH) containing residues Thr145-Phe336 of the rat α1 integrin chain, where residues Gly217, Arg218, Gln219 and Leu222 (crystal numbering) have been substituted with equivalent human residues Val, Gln, Arg and Arg, respectively, in order to restore antibody binding. The amino acid sequences of chimeric RΔH, rat, and human α1-I domains are given below in SEQ ID NOs:59, 60 and 61, respectively. Recombinant α1-I domain was expressed in E. coli as a GST-fusion protein. The RΔH α1-I domain was cleaved with thrombin and purified from a Pichia pastoris clone as described previously (Gotwals et al., 1999, Biochemistry 38:8280-8288).

```
                                                           (SEQ ID NO:59)
145  TQLDIV
151  IVLDGSNSIY PWESVIAFLN DLLKRMDIGP KQTQVGIVQY
191  GENVTHEFNL NKYSSTEEVL VAANKIVQRG GRQTMTALGI
231  DTARKEAFTE ARGARRGVKK VMVIVTDGES HDNYRLKQVI
271  QDCEDENIQR FSIAILGHYN RGNLSTEKFV EEIKSIASEP
311  TEKHFFNVSD ELLALVTIVKA LGERIF (SEQ ID NO:60)
145  TQLDIV
```

```
151   IVLDGSNSIY PWESVIAFLN DLLKRMDIGP KQTQVGIVQY

191   GENVTHEFNL NKYSSTEEVL VAANKIGRQG GLQTMTALGI

231   DTARKEAFTE ARGARRGVKK VMVIVTDGES HDNYRLKQVI

271   QDCEDENIQR FSIAILGHYN RGNLSTEKFV EEIKSIASEP

311   TEKHFFNVSD ELALVTIVKA LGERIF (SEQ ID NO:61)
145   TQLDIV

151   IVLDGSNSIY PWDSVTAFLN DLLKRMDIGP KQTQVGIVQY

191   GENVTHEFNL NKYSSTEEVL VAAKKIVQRG GRQTMTALGI

231   DTARKEAFTE ARGARRGVKK VMVIVTDGES HDNHRLKKVI

271   QDCEDENIQR FSIAILGSYN RGNLSTEKFV EEIKSIASEP

311   TEKHFFNVSD EIALVTIVKT LGERIF
```

The hAQC2 Fab fragment was mixed with excess chimeric α1-I domain and incubated at 37° C. for 15 minutes. The saturated α1/Fab complexes were separated from uncomplexed α1-I domain by size exclusion chromatography using a S200 Sephacryl column (Pharmacia, Gibco). The complex was further concentrated to 11 mg/ml in a 20 mM Tris (pH 7.4), 150 mM NaCl, 1 mM $MnCl_2$, 5 mM β-mercaptoethanol.

Preparation of Crystals

Crystallization conditions were found using the CRYSTAL SCREEN™ KITs from Hampton Research (Laguna Niguel, Calif.). Crystals of the complex described above were grown at 20° C. by vapor diffusion using an equal amount of protein complex solution and a 20-30% PEG 1500 reservoir solution. Typically, 2 μL of protein complex was added to 2 μL of well solution to yield drops of 4 μL. Crystals grew in two to seven days as hexagonal rods with dimensions 0.8×0.05×0.05 $mm^3$. The presence of the α1-I domain and hAQC2 Fab fragment was confirmed by SDS-PAGE analysis of dissolved crystals. In order to reduce the inherent radiation damage during data collection, X-ray diffraction data was collected at approximately 100 K. To prepare the crystals for data collection at this low temperature, crystals were gradually equilibrated into a cryoprotectant solution containing 25% PEG 400 and 30% PEG 1500, and flash cooled in liquid nitrogen.

Structure Determination

Native X-ray diffraction data to 2.8 Å resolution were collected from a single crystal at about 100 K using an ADSC Quantum 4 charged-coupled device detector at beamline X4A of the Brookhaven National Laboratory (BNL) National Synchrotron Light Source (NSLS). Data was processed using the software programs DENZO and SCALEPACK (Otwinowski & Minor, 1997, *Methods in Enzymol.* 276:307-326). Crystals belonged to the space group $P6_1$ or its enantiomorph $P6_5$, with unit cell dimensions a=b=255.09 Å, c=38.64 Å. The data set was 96.6% complete and had an R-merge of 8.3%. The Matthews coefficient (Matthews, 1968, *J. Mol. Biol.* 33:491-497) was 2.59 $Å^3$ $Da^{-1}$ with a solvent content of 52.1%, which indicated that there were two complexes in the asymmetric unit. The two complexes in the asymmetric unit were related by non-crystallographic 2-fold symmetry. Data statistics are shown in Table 4.

Molecular replacement searches were done with the program AMoRe (Navaza, 1994, *Acta Cryst.* A50:157-163) from the CCP4 program package (Collaborative Computational Project No.4. The CCP4 Suite: programs for protein crystallography. 1994, *Acta Cyst.* D50:760-763), and molecular graphics manipulations were done with the program QUANTA. A single α1-I domain from the structure of the rat α1-I domain of α1β1 integrin (Protein Data Bank (PDB) accession number 1ck4; Nolte et al., 1999, *FEBS Lett.* 452:379-385) was used as a model or probe for rotation and translation searches. The translation function search indicated that the $1^{st}$ and $9^{th}$ highest peaks of the rotation function corresponded to the correct solutions for the two α1-I domains in the asymmetric unit (correlation coefficient (cc)=21.1%, R=53.1%) and that the space group was $P6_5$. Subsequently, searches for the hAQC2 Fab fragments were done, keeping the I domain solutions fixed and using a model of the Fv domain of the hAQC2 Fab as a search probe. A clear solution was found for one of the two Fv domains (cc=22.1%, R=52.6%), but the second Fv could not be located. The position of the second Fv was derived using the non-crystallographic 2-fold symmetry. Rigid body refinement of the two I domains and two Fv domains reduced the R-factor to 43.6% (R-free=42.7%). An 2Fo-Fc electron density map showed clear electron density for the constant domain (Fconst) of the first Fab fragment, but no density for the Fconst domain of the second Fab fragment. A model of the Fconst domain of the first Fab was manually fit in the observed electron density. Subsequent rigid body refinement with the software program CNX (Accelrys Inc., San Diego, Calif. ©2000; Brunger, 1998, *Acta Cryst.* D54: 905-921), using data in the 500-2.8 Å resolution range, optimized the position of all domains, reducing the R-factor to 39.7% (R-free=38.9%).

All subsequent refinement steps were carried out with the CNX program. To reduce model bias, partial models were used for 2Fo-Fc map calculation and model refinement. The initial partial model, was subjected to simulated annealing and grouped B-factor refinement with non-crystallographic symmetry restraints. The R-working and R-free factors dropped to 28.3% and 32.9%, respectively. Several cycles consisting of iterative model building, maximum likelihood positional refinement and B-factor refinement followed. Only model adjustments that resulted in a drop in the R-free factor were accepted. A bulk-solvent correction was employed after the complete model was built. The R-working and R-free factors of the final model are 21.3% and 27.2%, respectively for the data (F>2σ) in the 500-2.8 Å resolution range.

The final 2Fo-Fc electron density map is of good quality for most of the complex with the exception of amino acid residues 288-295 of one I domain fragment (molecule A in FIG. 19) that are associated with weak electron density and have not been included in the model. In addition, the entire constant domain of one Fab fragment has no visible electron density, which indicates that it is disordered. This appears to be consequence of the absence of crystal contacts for the constant domain of the Fab fragment due to its position within a large solvent channel. This domain was also not included in the final model that consists of 1030 amino acid residues, constituting 6 polypeptide chains, and 2 manganese ions. The r.m.s. positional deviation between equivalent residues from the two complexes in the asymmetric unit is small (0.37 Å for 1660 equivalent main chain atoms). Stereochemistry statistics were calculated with the software programs PROCHECK (Laskowski et al., 1993, *J. Appl. Cryst.* 26:283-291; Morris et al., 1992, *Proteins* 12:345-364)

and CNX. Hydrogen bonds (<3.6 Å) were found with the program CONTACT (Tadeusz Skarzynski, Imperial College, London, 1.12.88; Collaborative Computational Project No.4. The CCP4 Suite: programs for protein crystallography. 1994, *Acta Cryst. D*50, 760-763). All non-glycine residues (except residue Thr50 of the L chain that will be discussed below) are in the allowed regions of the Ramachandran diagram and 86% of the residues are in the most favored regions. The average-B-factor of the main chain atoms is 38.5 Å$^2$. Crystallographic analysis data are in Table 4.

TABLE 4

Summary of Data Statistics and Crystallographic Analysis

Data collection

| | |
|---|---|
| Cell dimensions a, b, c (Å) | 255.09, 255.09, 38.64 |
| Space group | P6$_5$ |
| Resolution (Å) | 500-2.8 (2.9-2.8)$^†$ |
| Unique reflections | 35275 |
| Completeness (%) | 96.6 (87.7)$^†$ |
| Average I/s | 11.92 (2.29)$^†$ |
| Rmerge*(%) | 8.3 (30.9)$^†$ |

Model

| | |
|---|---|
| Number of non-H atoms | 7950 |
| Number of protein residues | 1030 |
| Contents of asymmetric unit | 2 I domains, 1 Fab fragment, 1 Fv domain |
| Average B-factor (Å$^2$) | 38.5 |

Refinement

| | |
|---|---|
| Resolution range used (F > 2σ) | 500-2.8 |
| R-factor (R-working) (%) | 21.3 |
| R-free$^{††}$(%) | 27.2 |

Stereochemistry

| | |
|---|---|
| RMS deviations | |
| Bond lengths (Å) | 0.007 |
| Angles (°) | 1.43 |

*Rmerge = $\Sigma_h\Sigma_i|I_{hi}-I_h|/\Sigma_{hi}I_{hi}$
$^†$Values for the highest resolution shell given in parenthesis.
$^{††}$8% of the data were allocated for the calculation of R-free factor.

Example 25

This example describes the crystal structure of the complex of a rat/human chimeric α1-I domain of the α1β1 integrin and the hAQC2 Fab fragment.

Architecture of Crystal Structure

The crystal structure of the complex of the rat/human chimeric α1-I domain of the α1β1 integrin and the hAQC2 Fab fragment has an elongated shape (FIG. 20). The dimensions of the complex are 100 Å×50 Å×35 Å.

The Fab fragment exhibits the typical immunoglobulin fold. The light chain and heavy chains of the Fab fragment each form two broad sheets of anti-parallel β-strands which pack tightly together to form a scaffold for the complementarity determining region (CDR) loops which extend from the packed sheets. Both the light chain and the heavy chain contain three CDR loops. The light chain loops are called L1, L2 and L3, while the heavy chain loops are referred to as H1, H2 and H3. The complementarity determining region (CDR) loops correspond to canonical structure 1 for light chain L1, L2 and L3 loops and for heavy chain H1 and H2 loops (Chothia et al., 1989, *Nature* 342:877-883). The heavy chain H3 loop has a tight β-hairpin-like conformation that is stabilized by internal hydrogen bonds as well as two aromatic residues (Tyr104 and Phe105) that are packed against the light chain. Residue Thr50 of L2 adopts mainchain dihedral angles that fall in the disallowed regions of the Ramachandran diagram. The same observation for the corresponding residue has been made for other antibodies (Muller et al., 1998, *Structure* 6, pp. 1153-11567) which indicates that this is a natural characteristic of L2 loops.

The α1-I domain in the present invention has a structure very similar to the uncomplexed α1-I domain (PDB accession number 1ck4; Nolte et al., 1999, *FEBS Lett.* 452:379-385; PDB accession code 1qc5; Rich et al., 1999, *J. Biol. Chem.* 274:24906-24913). The I domain structure exhibits a "dinucleotide-binding" or "Rossman" fold (Rao & Rossman, 1973, *J. Mol. Biol.* 76:241-256) in which a central sheet of five parallel β-strands and one small antiparallel-strand is surrounded on both sides by a total of seven α-helices. The six β-strands of the structure in this invention will be referred to as βA, βB, βC, βD, βE, and βF and the seven α-helices are called α1, α2, α3, α4, α5, α6 and α7.

Three characteristic structural features exist for I domains. The first characteristic feature is the presence of an inserted small helix in the βE-α6 loop, termed as the C helix. Most of the C helix loop of molecule A (FIG. 19) in the present invention is associated with weak electron density, which suggests disorder. This appears to be a consequence of absence of crystal contacts or contacts with the Fab that would have stabilized the loop. However, the same loop in molecule B (FIG. 19) in the present invention has well-defined electron density and has been included in the model. The second characteristic feature of α1-I domains is the MIDAS or Metal-Ion-Dependent-Adhesion-Site where metal ions and ligands are implicated to bind to the I domain. Five key residues which form part of the MIDAS are referred to as the "DxSxS-T-D" motif. These residues, which are completely conserved among I domains, coordinate the metal ion (Gotwals et al., 1999, *Biochemistry* 38:8280-8288). The crystals in the present invention were grown in the presence of manganese and the MIDAS site of the I domain in this structure is observed to contain a Mn$^{+2}$ metal ion. The ion is directly coordinated by the side chains of residues Ser156, Ser158 and Thr224. The 2Fo-Fc electron density map shows no evidence that MIDAS residues Asp154 and Asp257 make water-mediated indirect coordination of the metal ion (FIG. 20). However, the apparent absence of water molecules could be a consequence of the limited resolution (2.8 Å) of the electron density map. The third feature of I domains is that all determined structures of I domains belong to one of two conformations called "open" and "closed". The differences between the open and closed conformation include a different mode of metal ion coordination and a significant (about 10 Å) positional shift of the C-terminal helix of the I domain. The I domain in the complex in the present invention is in the closed conformation.

In the structure of the complex in the present invention, the Fab fragment binds to its epitope on the front upper surface of the I domain with a footprint 35 Å by 30 Å. The total buried surface area in the antibody-antigen interface is 1534 Å$^2$ which is typical of other antibody-antigen complexes (Davies et al., 1996, *Proc. Natl. Acad. Sci. USA* 93:7-12; Jones & Thornton, 1996, *Proc. Natl. Acad. Sci. USA* 93:13-20). The surface is 25% hydrophobic and 75% hydrophilic in character. The heavy chain contributes 65% of the buried surface area for the complex, while the remaining 35% is contributed by the light chain. The antibody epitope consists of residues located in four loops of the I domain (Emsley et al., 2000, *Cell* 101:47-56). Three of the loops form the MIDAS site: loop 1 (βA-α1) which contains the conserved DXSXS sequence, loop 2 (α3-α4) which contains the MIDAS Thr224 and loop 3 (βD-α5) that contains MIDAS residue Asp257. The fourth loop is the C-helix loop and is involved in only in minor contacts.

The central feature of the antigen-antibody interaction is the coordination of the MIDAS site metal ion by Asp101 from the CDR H3 of the antibody (FIG. 20). The distance between the ion and Oδ1 of Asp101 is 2.4 Å. In addition, the Oδ2 atom of Asp101 is interacting with His261 of the I domain. Interestingly, the CDR H3 contains several glycine residues adjacent to Asp101 (sequence GFGDGGY)(SEQ ID NO:62), presumably to allow enough flexibility to the CDR loop to permit proper coordination of the metal ion. The CDR H3 sequence is essentially invariant in monoclonal antibodies that were raised against the same antigen and found to belong in the same class. Most of the antibody residues that are involved in antibody-antigen contacts are located in L3, H1, H2 and H3 CDR loops. A few residues from the L1 (Asn30) and L2 (Tyr48) loops appear to form minor Van Der Waals contacts. L3 primarily contributes to contacts through two large hydrophobic residues, Trp90 and Trp95. In addition, Asn93 from L3 forms hydrogen bonds with Gln223 of the I domain. The side chains of His56 and Tyr58 from the H2 loop form hydrogen bonds with main chain atoms of loop 2 of the I domain. Arg31 of H1 is in contact with Arg291 of loop 4 of the I domain. Arg222 from loop 2 of the I domain is sandwiched between several antibody residues including Tyr58, Trp95 and Asn93. This is the only residue out of the four mutated in the RΔH I domain, that is involved in contacts with the Fab. It is therefore likely to be the only residue responsible for restoring the binding of the antibody after the mutagenesis.

Comparison of the Crystal Structure of the Complex of a Rat/Human Chimeric α1-I Domain and the hAQC2 Fab Fragment with Other I Domain Structures The chimeric RΔH $\alpha$1-I domain has four sequence differences with the rat $\alpha$1-I domain (rat residues: 217G, 218R, 219Q and 222L), eight sequence differences with the human $\alpha$1-I domain (human residues: 163D, 166T, 214K, 264H, 268K, 288S, 322I and 380T), and ten sequence differences with the clone used in the crystal structure studies of human $\alpha$1-I domain (clone residues: 163D, 166T, 174E, 214K, 230I, 264H, 268K, 288S, 322 I and 380T). In the unliganded rat $\alpha1\beta1$ $\alpha$1-I domain crystal structure (PDB accession code 1ck4; Nolte et al., 1999, *FEBS Lett.* 452:379-385), the $\alpha$1-I domain contains no bound metal ions and adopts the "closed" conformation. In the unliganded human $\alpha$1-I domain crystal structure (accession code 1qc5; Rich et al., 1999, *J. Biol. Chem.* 274:24906-24913), the $\alpha$1-I domain contains bound $Mg^{+2}$ and similarly adopts the closed conformation. Superimposition of these two structures with the complexed chimeric $\alpha$1-I domain indicates that there are only minor conformational changes upon hAQC2 antibody binding. The r.m.s. positional deviation between the rat and chimeric $\alpha$1-I domain is 1.04 Å for all 768 main chain atoms. The r.m.s. positional deviation between the human and chimeric $\alpha$1-I domain is 0.69 Å for all 764 main chain atoms. The biggest differences (human and chimeric $\alpha$1-I domain pair) are observed in loop 1 (r.m.s. deviations 1.24 Å for main chain atoms of residues 154-161) and the loop 4 (C helix loop) of the $\alpha$1-I domain (r.m.s. deviations 1.55 Å for main chain atoms of residues 288-296). However, these differences can be more accurately described as shifts of the whole secondary structure elements rather than complex conformational changes. These are likely to be within the normal range of conformational flexibility of proteins. The r.m.s. positional deviation between the human and chimeric $\alpha$1-I domain for backbone atoms of amino acid residues Glu192, Gln218, Arg219, Gly220, and Gly221 (crystal numbering) is 0.33 Å. The r.m.s. positional deviation between the rat and chimeric $\alpha$1-I domain for backbone atoms of amino acid residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering) is 0.97 Å.

The I domain maintains the "closed" I domain conformation that has been observed only for unliganded I domains crystallized in the absence of ligands or pseudo-ligands bound to the MIDAS site. The r.m.s. positional deviation of the C-terminal helices of the human and chimeric I domains (calculated for the main chain atoms of residues 321-335) is 0.64 Å. A simulated annealing omit map calculated for the final refined model unambiguously confirms that the position of the C-terminal helix and adjacent structural elements are consistent with the closed conformation.

In order to investigate the effects of ligand binding to the modes of metal ion coordination, the structure of the present invention was superimposed with the structures of the unliganded $\alpha$2-I domain (PDB accession code 1aox; Emsley et al., 1997, *J Biol. Chem.* 272:28512-28517) and the $\alpha$2-I domain complexed with a collagen peptide (PDB accession code 1dzi; Emsley et al., 2000, *Cell* 101:47-56). The coordination of the metal ion by Asp101 from the antibody is remarkably similar to the coordination of the metal ion of the $\alpha$2-I domain by a glutamic acid from the collagen peptide. Another feature that is conserved is the simultaneous interaction of the acidic group with His261 (His258 in the $\alpha$2-I domain). All MIDAS residues of the I domain-Fab complex except Ser156 and Ser158 adopt conformations very similar to those observed in the unliganded I domain. In contrast, the side chains of Ser156 and Ser158, as well as the metal, adopt conformations similar with those of the liganded I domain. It is clear that the coordination of the metal ion by Asp101 does not allow the ion to maintain the position and coordination distances that are observed in the unliganded state. Thus, the metal ion is not directly coordinated by Asp257, a fact that permits the ion to maintain high electrophilicity.

Biological Implications

In the present invention, there is no direct coordination of the metal by Asp257, which may permit high affinity binding by lowering the energy barrier between a closed (no ligand bound) and open (ligand bound) conformation. However, the coordination of the metal by an aspartic acid from the antibody is not sufficient to induce the open conformation to the I domain in the present invention. The I domain-Fab complex structure indicates that it is possible to have strong binding to the I domain that adopts the closed conformation and that coordination of the metal ion by an acidic residue from the ligand may be necessary but not sufficient to induce a conformational change to the open state. Binding of the antibody is expected to stabilize the low affinity state of the integrin and prevent the outside-in signaling that would have accompanied integrin binding to collagen.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention.

What is claimed is:

1. An anti-VLA-1 antibody whose light chain complementarity determining regions are defined by amino acid residues 24 to 33, 49 to 55, and 88 to 96 of SEQ ID NO:1, and whose heavy chain complementarity determining regions are defined by amino acid residues 31 to 35, 50 to 65, and 98 to 107 of SEQ ID NO:2.

2. The antibody of claim 1, wherein the antibody comprises a light chain variable domain sequence of SEQ ID NO:1 and a heavy chain variable domain sequence of SEQ ID NO:2.

3. The antibody of claim 1, wherein the antibody comprises the same heavy and light chain polypeptide sequences as an antibody produced by hybridoma mAQC2 which is deopsited under ATCC accession number PTA3273.

4. The antibody of claim 1, wherein the antibody is a humanized antibody.

5. The antibody of claim 4, wherein the antibody comprises at least one of the following residues in its light chain: Q1, L4, P45, W46 and Y70 of SEQ ID NO:1; or at least one of the following residues in its heavy chain: D1, V12, S28, F29, A49, T96, and R97 of SEQ ID NO:2.

6. The antibody of claim 4, wherein the antibody comprises a light chain variable domain sequence defined by amino acid residues 1 to 106 of SEQ ID NO:3, and a heavy chain variable domain sequence defined by amino acid residues 1 to 118 of SEQ ID NO:4.

7. The antibody of claim 4, wherein the antibody comprises the same heavy and light chain polypeptide sequences as an antibody produced by cell line hAQC2 which is deposited under ATCC accession number PTA3275.

8. The antibody of claim 4, wherein the antibody comprises the same heavy and light polypeptide sequences as an antibody produced by cell line hsAQC2 which is deposited under ATCC accession number PTA3356.

9. The antibody of claim 4, wherein the antibody comprises the same heavy and light chain polypeptide sequences as an antibody produced by cell line haAQC2 which is deposited under ATCC accession number PTA3274.

10. A composition comprising an antibody of any one of claims 4, and a pharmaceutically acceptable carrier.

11. A cell of cell line hAQC2 which is deposited under ATCC accession number PTA3275.

12. A cell of cell line haAQC2 which is deposited under ATCC accession number PTA3274.

13. A cell of cell line hsAQC2 which is deposited under ATCC accession number PTA3356.

14. An antibody produced by the cell line hAQC2, which is deposited under ATCC accession number PTA3275.

15. An antibody produced by the cell line haAQC2, which is deposited under ATCC accession number PTA3274.

16. An antibody produced by the cell line hsAQC2, which is deposited under ATCC accession number PTA3356.

17. An antibody produced by the cell line mAQC2, which is deposited under ATCC accession number PTA3273.

18. The antibody of claim 4, wherein the antibody has a glutamine at amino acid position 298 as set forth in SEQ ID NO:5.

19. An antibody selected from the group consisting of:
an antibody comprising a light chain variable domain sequence of SEQ ID NO:49 and a heavy chain variable domain sequence of SEQ ID NO:42;
an antibody comprising a light chain variable domain sequence of SEQ ID NO:51 and a heavy chain variable domain sequence of SEQ ID NO:44;
an antibody comprising a light chain variable domain sequence of SEQ ID NO:66 and a heavy chain variable domain sequence of SEQ ID NO:42;
an antibody comprising a light chain variable domain sequence of SEQ ID NO:54 and a heavy chain variable domain sequence of SEQ ID NO:68;
an antibody comprising a light chain variable domain sequence of SEQ ID NO:54 and a heavy chain variable domain sequence of SEQ ID NO:42;
an antibody comprising a light chain variable domain sequence of SEQ ID NO:58 and a heavy chain variable domain sequence of SEQ ID NO:68;
an antibody comprising a light chain variable domain sequence of SEQ ID NO:70 and a heavy chain variable domain sequence of SEQ ID NO:68; and
an antibody comprising a light chain variable domain sequence of SEQ ID NO:47 and a heavy chain variable domain sequence of SEQ ID NO:68.

20. A composition comprising an antibody of claim 5, and a pharmaceutically acceptable carrier.

21. A composition comprising an antibody of claim 6, and a pharmaceutically acceptable carrier.

22. A composition comprising an antibody of claim 7, and a pharmaceutically acceptable carrier.

23. A composition comprising an antibody of claim 8, and a pharmaceutically acceptable carrier.

24. A composition comprising an antibody of claim 9, and a pharmaceutically acceptable carrier.

25. The antibody of claim 1, wherein the antibody is a chimeric antibody.

* * * * *

UNITED STATES PATENT AND TRADEMARK OFFICE
CERTIFICATE OF CORRECTION

PATENT NO. : 7,358,054 B2
APPLICATION NO. : 10/474832
DATED : April 15, 2008
INVENTOR(S) : Paul D. Lyne et al.

It is certified that error appears in the above-identified patent and that said Letters Patent is hereby corrected as shown below:

Column 123, lines 40-41, please change the wording in claim 10 from "an antibody of any one of claims 4, and a pharmaceutically acceptable carrier" to --an antibody of claim 4, and a pharmaceutically acceptable carrier--.

Signed and Sealed this

Third Day of February, 2009

JOHN DOLL
*Acting Director of the United States Patent and Trademark Office*